US008685896B2

(12) United States Patent
Enzelberger et al.

(10) Patent No.: US 8,685,896 B2
(45) Date of Patent: *Apr. 1, 2014

(54) COLLECTION AND METHODS FOR ITS USE

(75) Inventors: Markus Enzelberger, Planegg (DE);
Stefanie Urlnger, Munich (DE);
Thomas Tiller, Munich (DE); Josef Prassler, Germering (DE); Tanja Herrmann, Munich (DE)

(73) Assignee: MorphoSys AG, Martinsried (DE)

( * ) Notice: Subject to any disclaimer, the term of this patent is extended or adjusted under 35 U.S.C. 154(b) by 78 days.

This patent is subject to a terminal disclaimer.

(21) Appl. No.: 13/321,564

(22) PCT Filed: May 29, 2010

(86) PCT No.: PCT/EP2010/057507
§ 371 (c)(1),
(2), (4) Date: Nov. 21, 2011

(87) PCT Pub. No.: WO2010/136598
PCT Pub. Date: Dec. 2, 2010

(65) Prior Publication Data
US 2012/0077713 A1    Mar. 29, 2012

Related U.S. Application Data

(60) Provisional application No. 61/182,350, filed on May 29, 2009, provisional application No. 61/299,401, filed on Jan. 29, 2010.

(30) Foreign Application Priority Data

Jun. 15, 2009 (EP) .................................... 09162724

(51) Int. Cl.
*C40B 40/10* (2006.01)

(52) U.S. Cl.
USPC ........................................................ 506/18

(58) Field of Classification Search
None
See application file for complete search history.

(56) References Cited

U.S. PATENT DOCUMENTS

| 5,091,513 | A | 2/1992 | Huston |
| 5,223,409 | A | 6/1993 | Ladner |
| 5,403,484 | A | 4/1995 | Ladner |
| 5,476,786 | A | 12/1995 | Huston |
| 5,482,858 | A | 1/1996 | Huston |

(Continued)

FOREIGN PATENT DOCUMENTS

| EP | 0368684 | 5/1990 |
| EP | 2088432 | 8/2009 |

(Continued)

OTHER PUBLICATIONS

Meijer et. al. (2006) Journal of Molecular Biology vol. 358 pp. 764 to 772 Supplementary Data only.*

(Continued)

*Primary Examiner* — Christian Boesen
(74) *Attorney, Agent, or Firm* — Paul F. Wiegel

(57) ABSTRACT

The present disclosure enables methods of identifying the VH and VL class pairs in the human immune repertoire, determining the VH and VL class pairs that are most prevalent and those having favorable biophysical properties. More specifically, the collections of the present disclosure comprise the most prevalent and/or preferred VH and VL class pairings with highly diversified CDRs.

19 Claims, 66 Drawing Sheets

(56) References Cited

U.S. PATENT DOCUMENTS

| | | | |
|---|---|---|---|
| 5,565,332 | A | 10/1996 | Hoogenboom |
| 5,571,698 | A | 11/1996 | Ladner |
| 5,580,717 | A | 12/1996 | Dower |
| 5,693,493 | A | 12/1997 | Robinson |
| 5,780,225 | A | 7/1998 | Wigler |
| 5,837,500 | A | 11/1998 | Ladner |
| 5,840,479 | A | 11/1998 | Little |
| 5,855,885 | A | 1/1999 | Smith |
| 5,859,205 | A | 1/1999 | Adair |
| 5,885,793 | A | 3/1999 | Griffiths |
| 5,969,108 | A | 10/1999 | McCafferty |
| 5,977,322 | A | 11/1999 | Marks |
| 6,096,551 | A | 8/2000 | Barbas |
| 6,248,516 | B1 | 6/2001 | Winter |
| 6,291,158 | B1 | 9/2001 | Winter |
| 6,291,159 | B1 | 9/2001 | Winter |
| 6,291,160 | B1 | 9/2001 | Lerner |
| 6,291,161 | B1 | 9/2001 | Lerner |
| 6,297,053 | B1 | 10/2001 | Stemmer |
| 6,300,064 | B1 | 10/2001 | Knappik |
| 6,303,313 | B1 | 10/2001 | Wigler |
| 6,979,538 | B2 | 12/2005 | Ladner |
| 7,117,096 | B2 | 10/2006 | Luo |
| 7,118,879 | B2 | 10/2006 | Ladner |
| 7,208,293 | B2 | 4/2007 | Ladner |
| 7,244,592 | B2 | 7/2007 | Hoogenboom |
| 7,288,249 | B2 | 10/2007 | Carter |
| 2001/0049107 | A1 | 12/2001 | Sharon |
| 2004/0180327 | A1 | 9/2004 | Ladner |
| 2005/0037358 | A1 | 2/2005 | Muyldermans |
| 2006/0188896 | A1 | 8/2006 | Seul |
| 2008/0003566 | A1 | 1/2008 | Vaux |
| 2009/0082221 | A1 | 3/2009 | Wang |

FOREIGN PATENT DOCUMENTS

| | | | |
|---|---|---|---|
| WO | | 9002809 | 3/1990 |
| WO | | 9005144 | 5/1990 |
| WO | | 9014424 | 11/1990 |
| WO | | 9014430 | 11/1990 |
| WO | | 9014443 | 11/1990 |
| WO | | 9201047 | 1/1992 |
| WO | | 9215678 | 9/1992 |
| WO | | 9215679 | 9/1992 |
| WO | | 9306213 | 9/1992 |
| WO | | 9220791 | 11/1992 |
| WO | | 9303151 | 2/1993 |
| WO | | 9311236 | 6/1993 |
| WO | | 9319172 | 9/1993 |
| WO | | 9511998 | 5/1995 |
| WO | | 9708320 A | 3/1997 |
| WO | | 9906587 | 2/1999 |
| WO | | 9920749 | 4/1999 |
| WO | | 0105950 | 1/2001 |
| WO | | 03029456 | 4/2003 |
| WO | | 03052416 | 6/2003 |
| WO | | 2004013276 | 2/2004 |
| WO | | 2004094474 | 11/2004 |
| WO | | 2005023993 | 3/2005 |
| WO | | 2005042774 | 5/2005 |
| WO | | 2005094159 | 10/2005 |
| WO | | 2006014498 | 2/2006 |
| WO | | 2006084050 | 8/2006 |
| WO | | 2007056441 | 5/2007 |
| WO | | 2008053275 | 5/2008 |
| WO | | 2009024593 | 2/2009 |
| WO | | 2009036379 | 3/2009 |
| WO | | 2009085462 | 7/2009 |
| WO | | 2009100896 | 8/2009 |
| WO | | 2009114815 | 9/2009 |
| WO | | 2010028791 | 3/2010 |
| WO | | 2010054007 | 5/2010 |
| WO | | 2010136598 | 12/2010 |
| WO | | 2011092313 | 8/2011 |

OTHER PUBLICATIONS

Brezinschek H. P. et al. (1997) J. Clin. Invest. 99, 2488.
Chapal, Biotechniques, 23(3), Sep. 1, 1997, 518-524.
Coronella, Nucleic Acids Research, 28(20), Oct. 15, 2000, E85.
Database WPI Week 200656, Aug. 3, 2006.
de Wildt et al., J Mol Biol. 22;285(3):895-901 (Jan. 1999).
Demaison C. et al. (1995) Immunogenetics 42, 342.
Ewert, J. Mol. Biol. 325(3), Jan. 17, 2003, 531-553.
Ewert, Methods: A companion to methods in enzymology, 34(2), Oct. 1, 2004, 184-199.
Foster SJ. et al. (1997) J. Clin. Invest. 99, 1614.
Fuh et al., Expert Opin Biol Ther.,7(1 ):73-87 (Jan. 2007).
Glanville et al., Proc Natl Acad Sci 1 ;106(48):20216-21 (Dec. 2009).
Meijer et al., J Mol Biol., 358(3):764-72 (May 5, 2006).
Ponsel, Molecules. May 3, 2011;16(5):3675-700.
Scott, Phage Display, A Laboratory Manual, Jan. 1, 2001, pp. 2-1, figure 2.3.
Shi et al., J Mol Biol., 397(2):385-96 (Mar. 26, 2010).
Thirion, European Journal of Cancer Prevention, 5(6), Dec. 1, 1996, 507-511.
Wang, Journal of Immunogical Methods, 244(1-2), Oct. 20, 2000, 217-225.
Knappik A, Gel L, Honegger A, Pack P, Fischer M, Wellnhofer G, Hoess A, Mlle J, Plueckthun A, VirnekAs B, 'Fully synthetic human combinatorial antibody libraries (HuCAL) based on modular consensus frameworks and CDRs randomized with trinucleotides', J Mol Biol. Feb 11, 2000; 296(1):57-86.
Kruif Selection and Application of Human Chain scFv antibody fragments from a semi-synthetic Phage Antibody Display Library with Designed CDR3 regions, J. Mol. Biol. (1995) 248, 97-105.
Robert Schier et al., 'Identification of functional and structural amino-acid residues by parsimonious mutagenesis', Gene, 169, 1996, pp. 147-155.
Carlos F. Barbas, III, 'Semisynthetic combinatorial antibody libraries: A Chemical solution to the diversity problem', Proc. Natl. Acad. Sci. USA, vol. 89, May 1992, p. 4457-4461.
Winter Making antibodies by phage display technology, annual review of immunology, Annual Reviews Inc, US, vol. 12, 1994, pp. 433-455, XP000564245 ISSN: 0732-0582.
Collett A binarly plasmid system for shuffling combinatorial antibodies libraries PNAC, vol. 89, No. 21, Nov. 1, 1992, p. 10026-10030.
Knappik and Pluckthun Engineered turns of a recombinant antibody improve ist in vivo folding, Protein Engineering, 8(1), 81-89 (1995).
Cox A directory of human germ-line Vk segments reveals a strong bias in their usage, Eur. J. Immunol. 1994, 24:827-836.
Tomlinson The repertoire of human germline Vh sequences reveals about 50 groups of Vh segments with different hypervariable loops, J. Mol. Biol. (1992) 227, 776-799.
Foote Antibody framework residues affecting the conformation of the hypervariable loops, J. Mol. Biol. 224, 487-499 (1992).
Gram In vitro and affinity maturation of antibodies from a naive conbinatorial immunoglobulin library, PNAS, 89 (8), 3576-3580 (1992).
Waterhouse Combinatorial infection and in vivo recombination: as strategy for making large phage antibody repertoires, Nucl. Acids Res. 21(9), 2265-2266 (1993).
Williams Cloning and sequences of human Vlambda gene segments, Eur. J. Immunol. 23, 1456-1461 (1993).
Marks by passing immunization: building high affinity antibodies by chain shuffling, 1992 Biotechnology 10:779-783.
Hoogenboom, Building antibodies from their genes, 1992 Immunlogical review, 130: 41-68.
Griffiths isolation of high affinity human antibodies directly from large synthetic repertoires, 1994 EMBO J. 13:3245-3260.
Winter and Milstein, Man made antibodies, 1991 Nature 349:293-299.
Matsuda et al. (1998), "The complete nucleotide sequence of the human immunoglobulin heavy chain variable region locus" J Exp Med 188(11):2151-62.
Embleton et al in Nucleic Acid Res. 20, 3831-3837, 1992.

(56) References Cited

OTHER PUBLICATIONS

Marks 1991, J.Mol.Biol. 222, 581-597, By passing immunization, human abs from V-gene libraries.
Pini "Design and Use of Phage Display Library", Journal of BioChemistry 1998, vol. 273,No. 34, Issue of Aug. 21.
Söderlind 2000 Nature Biotechnology, 18; 852-856.
de Haard 1999vol. 274, No. 26, Issue of Jun. 25, pp. 18218-18230, 1999.
Sheets Proc. Natl. Acad. Sci. USA, vol. 95, pp. 6157-6162, May 1998, Cell Biology.
Ignotovich Mol. Biol. (1997) 268, 69±77.
Söderlind 2000 Nature Biotechnology, 18; 852-856 (2000).
European Examination Report dated Mar. 12, 2013 for EP 2 435 568.

* cited by examiner

Figure 4

| Ig | Heavy | Light |
|---|---|---|
| mm-JB | VH | Vκ |
| mm-JB1 | 3-23 | 3-20 |
| mm-JB4 | 3-15 | 3-20 |
| mm-JB14 | 3-23 | 4-1 |
| mm-JB15 | 4-39* | 2(D)-28 |
| mm-JB17 | 4-59 | 3-15 |
| mm-JB18# | 3-23 | 3-11 |
| mm-JB19 | 1-2 | 3-20 |
| mm-JB23# | 3-30 | 4-1 |
| mm-JB28 | 3-72 | 1-16 |
| mm-JB29 | 3-23 | 3-20 |
| mm-JB37 | 3-30 | 2-24 |
| mm-JB38 | 3-30* | 1(D)-8 |
| mm-JB40 | 3-23 | 3-20 |
| mm-JB43# | 3-53* | 1-27 |
| mm-JB50 | 4-59 | 4-1 |
| mm-JB52 | 3-33 | 3-11 |
| mm-JB56 | 3-15 | 3-20 |
| mm-JB57 | 4-34 | 1(D)-33 |
| mm-JB60# | 5-51 | 2-30 |
| mm-JB65# | 1-24 | 3-11 |
| mm-JB68# | 3-72 | 1-5 |
| mm-JB70# | 3-30* | 1-5* |
| mm-JB73# | 3-7 | 2-30 |
| mm-JB75 | 3-30 | 3-11 |
| mm-JB76# | 4-59 | 3-15 |
| mm-JB77# | 3-30* | 3-15 |
| mm-JB86 | 3-33 | 2-24 |
| mm-JB90+l | 3-30* | 2-30 |
| mm-JB | VH | Vλ |
| mm-JB13# | 3-7* | 3-1 |
| mm-JB16 | 3-11 | 3-1 |
| mm-JB33 | 1-3* | 2-23 |
| mm-JB48 | 3-33 | 1-47* |
| mm-JB62# | 3-15 | 7-43 |
| mm-JB64 | 3-15 | 2-18 |
| mm-JB80 | 3-72 | 1-51 |
| mm-JB81# | 3-11 | 2-14 |
| mm-JB82 | 3-53* | 2-14* |
| mm-JB87 | 3-11 | 2-8 |
| mm-JB88 | 3-30 | 1-44 |
| mm-JB93 | 4-39* | 2-18* |

Figure 5

| Ig | Heavy | Light |
|---|---|---|
| mm-GO | VH | Vk |
| mm-GO1# | 3-30* | 1-8 |
| mm-GO12 | 4-34 | 1-5 |
| mm-GO14 | 4-28 | 1-39 |
| mm-GO15# | 3-74 | 4-1 |
| mm-GO16# | 3-21 | 1-5 |
| mm-GO18 | 3-21 | 1-5 |
| mm-GO19# | 3-43 | 3-11 |
| mm-GO26 | 3-23 | 1-9* |
| mm-GO30 | 4-34 | 3-15 |
| mm-GO38 | 4-34 | 1-5 |
| mm-GO43# | 3-23 | 3-11 |
| mm-GO50 | 4-39 | 1-39* |
| mm-GO68# | 3-15 | 2D28 |
| mm-GO73# | 7-81* | 4-1 |
| mm-GO75# | 3-48 | 3-20 |
| mm-GO80 | 3-53* | 3-11 |
| mm-GO86 | 3-30 | 3(D)-20 |
| mm-GO89# | 3-7 | 1-5 |
| mm-GO93# | 3-7* | 2-30 |
| mm-5-GO1 | 3-11 | 3-15 |
| mm-5-GO2# | 3-23 | 1-5 |
| mm-5-GO14 | 3-7* | 1-5 |
| mm-5-GO20 | 5-51 | 1D-39* |
| mm-5-GO25# | 1-3 | 3-15 |
| mm-5-GO33 | 3-30* | 4-1 |
| mm-5-GO38 | 3-48 | 4-1 |
| mm-5-GO39 | 4-39 | 1-5 |
| mm-5-GO43 | 3-53 | 1-5 |
| mm-5-GO50 | 4-31* | 3-20 |
| mm-5-GO57 | 5-51 | 1-5 |
| mm-5-GO65 | 4-34 | 1-5 |
| mm-5-GO68# | 3-53 | 3-11 |
| mm-5-GO74 | 3-23 | 1(D)-13 |
| mm-5-GO77# | 3-23 | 4-1 |
| mm-5-GO85 | 4-59 | 3-20 |
| mm-5-GO86 | 3-7 | 3-15 |
| mm-5-GO87 | 3-30* | 1-8 |
| mm-5+GO13# | 1-2 | 1D-39 |
| mm-5+GO18# | 1-8 | 3-15 |
| mm-5+GO26# | 1-3 | 1-6 |
| mm-5+GO43 | 3-23 | 3-15 |
| mm-5+GO47# | 3-9 | 3-15 |
| mm-5+GO49# | 3-33 | 3-15 |
| mm-5+GO51# | 3-15 | 4-1 |
| mm-5+GO52# | 1-2 | 3-20 |
| mm-5+GO65# | 5-51 | 1D-39 |
| mm-5+GO66# | 3-7 | 2D-28 |
| mm-5+GO71# | 3-23 | 1-8 |
| mm-5+GO72 | 3-30 | 3-20 |

| mm-GO | VH | Vl |
|---|---|---|
| mm-GO2# | 3-23 | 1-51 |
| mm-GO9 | 3-7 | 2-14* |
| mm-GO61# | 4-31* | 2-14 |
| mm-GO79 | 3-11 | 4-69* |
| mm-GO85# | 3-9 | 4-60* |
| mm-GO88# | 4-39 | 2-8 |
| mm-GO90 | 1-18 | 1-44 |
| mm-GO91 | 4-28 | 1-51 |
| mm-5-GO30 | 3-11 | 2-14* |
| mm-5-GO37 | 3-11 | 1-44 |
| mm-5-GO41# | 3-48 | 2-14* |
| mm-5-GO44 | 3-74 | 2-14* |
| mm-5-GO47 | 3-48* | 2-11 |
| mm-5-GO49 | 4-31* | 2-14* |
| mm-5-GO61 | 3-15 | 7-46* |
| mm-5-GO64# | 3-7 | 1-47 |
| mm-5-GO84 | 3-15 | 1-40 |
| mm-5-GO91 | 3-23 | 1-40 |
| mm-5-GO94 | 3-23 | 1-36 |
| mm-5+GO3 | 1-69* | 1-44 |
| mm-5+GO25# | 4-59 | 2-14 |
| mm-5+GO27 | 4-39 | 2-14* |
| mm-5+GO39 | 3-23 | 1-44 |
| mm-5+GO57 | 3-23 | 2-14* |

Figure 6

| Ig | Heavy | Light |
|---|---|---|
| mm-JH | VH | Vk |
| mmJH.2 A1 | 4-59 | 1-27 |
| mmJH.2 A4# | 3-23 | 1-5* |
| mmJH.2 A9 | 4-59 | 1D-39 |
| mmJH.2 C5 | 3-23 | 3-20 |
| mmJH.2 C10# | 1-2 | 1D-39 |
| mmJH.2 C12 | 3-21 | 1D-39 |
| mmJH.2 D1 | 3-23 | 3-20 |
| mmJH.2 D4 | 7-81* | 1-5* |
| mmJH.2 D9 | 3-23 | 3-15 |
| mmJH.2 D11 | 3-74 | 1-5* |
| mmJH.2 E7 | 3-11 | 3-11 |
| mmJH.2 F1 | 7-81 | 2D-28 |
| mmJH.2 F7 | 3-23 | 3-15 |
| mmJH.2 G3 | 1-3* | 1D-39 |
| mmJH.2 H2 | 3-23 | 3-15 |
| mmJH.3 A1 | 3-74 | 3-11 |
| mmJH.3 A6 | 3-23 | 3-20 |
| mmJH.3 B1# | 3-23 | 4-1 |
| mmJH.3 B2 | 3-7* | 1-5 |
| mmJH.3 B3 | 3-33 | 3-11 |
| mmJH.3 B4 | 3-23 | 2D-28 |
| mmJH.3 D2 | 3-21 | 3-11 |
| mmJH.3 D4 | 1-18 | 3-11 |
| mmJH.3 D10 | 3-72 | 1-9 |
| mmJH.3 F2 | 4-59 | 1D-39 |
| mmJH.3 F3# | 3-15 | 1-9 |
| mmJH.3 G9 | 3-33 | 4-1 |
| mm-JH | VH | Vl |
| mmJH.2 B2 | 4-31* | 1-47* |
| mmJH.2 B11 | 4-59 | 1-44* |
| mmJH.2 C3 | 3-9 | 2-23 |
| mmJH.2 F2 | 3-23 | 2-18* |
| mmJH.2 F3 | 3-9 | 2-23 |
| mmJH.2 H3# | 3-15 | 3-1 |
| mmJH.3 A3 | 7-81* | 2-14* |
| mmJH.3 A5 | 3-9 | 2-8 |
| mmJH.3 D1-k | 4-4 | 3-1 |
| mmJH.3 D3 | 3-7* | 3-27 |
| mmJH.3 D9 | 3-15 | 7-43 |
| mmJH.3 E10 | 3-30 | 2-8 |
| mmJH.3 F1# | 3-23 | 2-14 |
| mmJH.3 F4# | 3-7 | 3-21* |
| mmJH.3 F9 | 4-39 | 1-47* |
| mmJH.3 G8 | 3-53 | 1-44* |

Figure 7

| Ig | Heavy | Light |
|---|---|---|
| m-JB | VH | Vk |
| m-JB 39+l | 4-39 | 3-15 |
| m-JB 49 | 1-2 | 3-20 |
| m-JB 63 | 4-39 | 3-20 |
| m-JB 74 | 3-48 | 3-20 |
| m-JB 77 | 5-51 | 1-39 |
| m-JB 86 | 4-39 | 3-15 |
| m-JB 87 | 3-30 | 1-9 |
| m-JB | VH | Vl |
| m-JB 8 | 1-69 | 2-8 |
| m-JB 17 | 3-30 | 9-49 |
| m-JB 29 | 4-39 | 3-1 |
| m-JB 38 | 3-48 | 2-14 |
| m-JB 39+k |  | 3-21 |
| m-JB 64 | 3-9 | 1-47 |
| m-JB 85 | 1-18 | 2-14 |
| m-JB 88 | 4-39 | 2-23 |

Figure 8

| Ig | Heavy | Light |
|---|---|---|
| m-GO | VH | Vκ |
| m-GO4 | 3-7 | 2D-28 |
| m-GO6 | 4-59 | 3-20 |
| m-GO13 | 3-43 | 1-5 |
| m-GO15 | 3-53 | 1-5 |
| m-GO21 | 3-15 | 1-5 |
| m-GO26 | 3-48 | 3-11 |
| m-GO40 | 4-34 | 3-20 |
| m-GO43 | 4-34 | 3-20 |
| m-GO53 | 4-39 | 3-15 |
| m-GO56 | 3-15 | 3-20 |
| m-GO64 | 3-30 | 1-39 |
| m-GO66 | 3-48 | 1-39 |
| m-GO75 | 1-18 | 1-33 |
| m-GO79 | 3-30 | 1-9 |
| m-GO86 | 4-34 | 3-20 |
| m-GO88 | 3-23 | 2D-28 |
| m-GO119 | 3-49 | 3-20 |
| m-GO126 | 1-46 | 1-39 |
| m-GO132 | 4-59 | 1-39 |
| m-GO162 | 1-69 | 1-39 |
| m-GO166 | 4-39 | 3-15 |
| m-GO186 | 1-46 | 1-9 |
| m-GO191 | 3-15 | 1-39 |
| m-GO193 | 3-48 | 3-15 |
| m-GO | VH | Vλ |
| m-GO3 | 4-28 | 1-44 |
| m-GO16 | 4-34 | 2-14 |
| m-GO19 | 3-74 | 3-21 |
| m-GO28 | 3-23 | 3-1 |
| m-GO67 | 3-48 | 2-14 |
| m-GO76 | 1-69 | 2-14 |
| m-GO77 | 4-39 | 1-40 |
| m-GO102 | 4-28 | 1-36 |
| m-GO113 | 1-2 | 1-40 |
| m-GO115 | 5-51 | 1-40 |
| m-GO152 | 3-9 | 1-44 |
| m-GO157 | 5-51 | 1-36 |
| m-GO163 | 4-34 | 2-23 |
| m-GO173 | 3-43 | 1-51 |
| m-GO189 | 1-8 | 2-14 |

Figure 9

| Ig | Heavy | Light |
|---|---|---|
| m-JH | VH | Vk |
| m-JH.1 D4 | 7-81 | 3-20 |
| m-JH.1 D12# | 4-4 | 3-15 |
| m-JH.1 E3 | 4-34 | 3-20 |
| m-JH.1 F5 | 3-30 | 3-15 |
| m-JH.1 F8 | 3-21 | 2D-28 |
| m-JH.1 G8 | 3-48 | 1D-12 |
| m-JH.1 G10 | 3-23 | 3-15 |
| m-JH.1 H5 | 4-59 | 3-20 |
| m-JH.1 H11 | 3-33 | 2D-28 |
| m-JH.2 A2 | 3-74 | 1D-39 |
| m-JH.2 A8 | 3-7 | 1-8 |
| m-JH.2 A9 | 4-31 | 3-11 |
| m-JH.2 A11 | 4-61 | 4-1 |
| m-JH.2 A12# | 3-9 | 1D-8 |
| m-JH.2 B5 | 7-81 | 3-20 |
| m-JH.2 C3 | 3-23 | 3-20 |
| m-JH.2 C6 | 3-23 | 1-9 |
| m-JH.2 C10 | 4-59 | 3-15 |
| m-JH.2 D6 | 3-49 | 1-17 |
| m-JH.2 D7 | 3-48 | 3-15 |
| m-JH.2 E3 | 1-18 | 3-20 |
| m-JH.2 E5 | 4-39 | 1D-39 |
| m-JH.2 E8 | 3-9 | 3-15 |
| m-JH.2 E10# | 3-48 | 3-11 |
| m-JH.2 F3 | 7-81 | 3-20 |
| m-JH.2 F9 | 5-51 | 3-20 |
| m-JH.2 H12# | 3-9 | 2D-28 |
| m-JH | VH | Vl |
| m-JH.1 B11 | 3-23 | 2-14 |
| m-JH.1 C12 | 4-59 | 1-40 |
| m-JH.1 D2 | 1-18 | 2-8 |
| m-JH.1 D10 | 4-59 | 2-14 |
| m-JH.1 F6 | 1-8 | 2-14 |
| m-JH.1 H6 | 3-9 | 2-11 |
| m-JH.1 H12# | 4-34 | 3-25 |
| m-JH.2 B12 | 3-23 | 2-14 |
| m-JH.2 C8# | 1-3 | 2-14 |
| m-JH.2 C12 | 4-4 | 2-14 |
| m-JH.2 D8 | 3-21 | 6-57 |
| m-JH.2 E6 | 3-33 | 2-11 |
| m-JH.2 F6 | 1-2 | 2-14 |
| m-JH.2 G12 | 5-51 | 2-14 |
| m-JH.2 H4 | 4-59 | 1-40 |
| m-JH.2 H12# |  | 2-14 |

Figure 10

| Ig | Heavy | Light |
|---|---|---|
| gmVB | VH | Vκ |
| VB1 | 4-59 | 4-1 |
| VB4 | 4-39 | 3-11 |
| VB7# | 3-74 | 3-15 |
| VB10# | 4-31* | 4-1 |
| VB11# | 4-34 | 2-28 |
| VB23# | 4-31* | 1-5* |
| VB26# | 3-30 | 1-13 |
| VB34 | 3-30 | 3-20 |
| VB41# | 3-15 | 3-20 |
| VB50 | 3-11 | 1-5* |
| VB52 | 3-53 | 1-39 |
| VB54# | 3-23 | 3-20 |
| VB56 | 3-7* | 3-15 |
| VB57 | 4-31* | 3-20 |
| VB58# | 4-31* | 1-5* |
| VB60 | 3-11 | 3-15 |
| VB65 | 3-74 | 1-39 |
| VB68# | 5-51 | 1-5 |
| VB72 | 3-30 | 2-28 |
| VB78# | 4-31* | 3-20 |
| VB83 | 4-34 | 1-39 |
| VB86 | 3-33 | 1-17 |
| VB92# | 1-24 | 1-39 |
| VB110 | 4-61 | 4-1 |
| VB111 | 3-48 | 4-1 |
| VB114# | 3-74 | 3-20 |
| VB120# | 3-49 | 1-39 |
| VB121# | 3-7* | 1-6 |
| VB126 | 4-39 | 3D-15 |
| VB129 | 3-23 | 1-39 |
| VB132 | 3-23 | 1-5* |
| VB137 | 3-30 | 1-5 |
| VB139# | 5-51 | 4-1 |
| VB140 | 3-21 | 3-15 |
| VB142 | 3-33 | 4-1 |
| VB148 | 3-33 | 1-16 |
| VB155 | 5-51 | 3-20 |
| VB161 | 4-61 | 3-11 |
| VB162 | 3-48 | 3-11 |
| VB165 | 3-30 | 3-20 |
| VB168 | 5-51 | 1-39 |
| VB171# | 3-33 | 3-20 |
| VB174 | 3-72 | 1-17 |
| VB176 | 3-74 | 3-20 |
| VB179# | 3-23 | 1-17 |

| gmVB | VH | Vλ |
|---|---|---|
| VB13 | 5-51 | 7-43 |
| VB18 | 1-46 | 1-51 |
| VB28 | 3-23 | 2-11 |
| VB43 | 1-69* | 2-11 |
| VB45 | 3-21 | 2-14 |
| VB53 | 5-51 | 2-14 |
| VB70 | 4-59 | 1-44 |
| VB73# | 3-53 | 7-46* |
| VB75 | 3-21 | 2-14 |
| VB90# | 3-21 | 4-69 |
| VB101 | 3-23 | 1-51 |
| VB102 | 4-31* | 2-11 |
| VB107# | 5-51 | 1-47 |
| VB108 | 3-64 | 7-43 |
| VB117# | 4-28 | 2-23 |
| VB138 | 3-7* | 7-46* |
| VB157 | 3-30 | 3-1 |
| VB164 | 3-7* | 1-51 |
| VB173 | 3-21 | 1-47 |

Figure 11

| Ig gmPN | Heavy VH | Light Vκ |
|---|---|---|
| PN1 | 1-46 | 3-15 |
| PN2# | 3-7 | 1-5* |
| PN4 | 5-51 | 1-9 |
| PN8 | 4-59 | 4-1 |
| PN13 | 3-43 | 2-28 |
| PN16 | 4-4 | 1-39 |
| PN30 | 1-46 | 1-5* |
| PN33 | 4-34 | 3-11 |
| PN40# | 3-48 | 1-16 |
| PN46 | 4-34 | 3-20 |
| PN49# | 3-48 | 1-39 |
| PN52 | 3-23 | 4-1 |
| PN53# | 3-23 | 3-11 |
| PN54 | 4-59 | 1-12 |
| PN56 | 3-23 | 3-20 |
| PN60 | 3-7 | 3-20 |
| PN64 | 3-23 | 3-20 |
| PN73 | 1-18 | 1-39 |
| PN75 | 5-51 | 3-15 |
| PN76# | 4-59 | 1-27 |
| PN79 | 1-46 | 1-5* |
| PN83# | 3-23 | 3-11 |
| PN84 | 3-23 | 1-5* |
| PN87 | 4-39 | 1-5* |
| PN89 | 3-74 | 2-30 |
| PN102 | 3-7 | 3-20 |
| PN116 | 4-34 | 1-39 |
| PN117# | 3-33 | 1-39 |
| PN119 | 1-69* | 1-5* |
| PN120# | 1-69 | 1-27 |
| PN123 | 1-46 | 3-11 |
| PN138 | 3-7 | 1-39 |
| PN140# | 1-8 | 3-20 |
| PN147# | 4-59 | 2D-30 |
| PN148 | 4-34 | 2-28 |
| PN156 | 1-69 | 2-28 |
| PN157 | 4-39 | 3-20 |
| PN158 | 3-9 | 1-17 |
| PN162 | 1-69* | 3-11 |
| PN164 | 1-69* | 3-11 |
| PN167 | 1-69* | 1-6 |
| PN169 | 3-13 | 1-9 |
| PN171 | 1-2 | 3-20 |
| PN175 | 1-46 | 1-9 |
| PN182 | 4-4 | 1-39 |
| PN184 | 4-39 | 1-5 |
| PN187 | 3-9 | 3-11 |
| PN189 | 3-11 | 1-5* |
| PN191 | 3-15 | 1-13 |

| gmPN | VH | Vλ |
|---|---|---|
| PN7 | 3-74 | 7-46 |
| PN14 | 4-4 | 1-40 |
| PN18# | 3-23 | 2-14 |
| PN42 | 3-7 | 2-8 |
| PN51 | 5-51 | 3-21 |
| PN57 | 4-34 | 1-40 |
| PN58 | 4-31* | 7-43 |
| PN67 | 4-59 | 1-47 |
| PN69 | 1-8 | 2-14 |
| PN88 | 3-15 | 1-51 |
| PN107 | 3-7 | 1-40 |
| PN115 | 3-7 | 1-51 |
| PN131 | 3-21 | 3-21 |
| PN134# | 1-2 | 1-40 |
| PN139 | 3-33 | 3-21 |
| PN153 | 3-9 | 1-40 |
| PN161 | 3-74 | 3-21 |
| PN192# | 3-21 | 1-44 |

Figure 12

| Ig | Heavy | Light |
|---|---|---|
| gmHW | VH | Vκ |
| HW 106# | 4-61 | 4-1 |
| HW 120 | 4-31 | 3-15 |
| HW 149 | 3-21 | 1-6 |
| HW 154 | 3-53 | 3-15 |
| HW 156 | 3-7 | 3-15 |
| HW 161 | 3-74 | 3-15 |
| HW 168 | 4-39 | 3-15 |
| HW 169 | 1-18 | 3-15 |
| HW 175 | 1-18 | 3-20 |
| HW 209# | 4-39 | 3-15 |
| HW 221 | 3-74 | 3-20 |
| HW 224 | 3-15 | 4-1 |
| HW 230 | 3-7 | 3-15 |
| HW 247 | 3-9 | 3-20 |
| HW 266 | 3-9 | 1-5* |
| HW 285 | 3-33 | 1D-39 |
| HW 290 | 3-15 | 1-5* |
| HW 307 | 4-39 | 1D-39 |
| HW 311 | 4-59 | 3-20 |
| HW 326 | 3-7 | 1-5* |
| HW 329 | 4-34 | 3-20 |
| HW 337 | 4-34 | 3-20 |
| HW 352 | 1-3* | 3-20 |
| HW 376 | 4-28 | 3-20 |
| HW 378 | 1-46 | 1-27 |
| HW 386# | 3-30 | 1D-39 |
| HW 387 | 1-46 | 3-20 |

| gmHW | VH | Vλ |
|---|---|---|
| HW 101# | 1-18 | 2-23* |
| HW 109 | 3-30 | 2-11 |
| HW 124 | 3-7 | 1-40 |
| HW 157# | 3-23 | 7-43 |
| HW 158 | 3-11 | 2-14 |
| HW 174 | 7-81 | 2-14* |
| HW 177 | 5-51 | 1-47* |
| HW 181 | 1-46 | 2-14* |
| HW 182 | 4-39 | 2-14* |
| HW 205 | 1-69 | 2-11 |
| HW 225 | 3-30 | 1-40 |
| HW 231 | 3-21 | 1-51* |
| HW 237 | 3-48 | 1-47* |
| HW 248 | 3-21 | 1-40 |
| HW 251 | 3-30 | 1-51 |
| HW 259 | 1-46 | 2-11 |
| HW 296 | 3-21 | 2-14* |
| HW 313 | 3-33 | 2-23* |
| HW 327# | 3-9 | 2-14* |
| HW 330 | 3-15 | 1-40 |
| HW 338# | 3-21 | 1-51 |
| HW 345 | 4-39 | 1-51* |
| HW 355 | 3-73 | 6-57 |
| HW 357# | 3-33 | 1-51 |
| HW 360 | 1-46 | 2-14* |

Figure 13

| Ig | Heavy | Light |
|---|---|---|
| gm/gp169 | VH | Vκ |
| gm169-3κ | 3-48 | 3-20 |
| gm169-15 | 1-24 | 3-11 |
| gm169-16κ | 1-8 | 1-33 |
| gm169-20κ | 3-7 | 4-1 |
| gm169-22κ | 3-23 | 3-15 |
| gm169-24κ | 4-4 | 2-28 |
| gm169-28κ | 3-33 | 1-5 |
| gm169-31κ | 3-66 | 1-39 |
| gm169-34κ# | 4-4 | 1-39 |
| gm169-38κ | 3-23 | 3-15 |
| gm169-42 | 3-33 | 1-5 |
| gm169-44 | 3-48 | 2-28 |
| gm169-46 | 4-39 | 1-39 |
| gm169-57 | 3-23 | 1-5 |
| gm169-60 | 3-43 | 1-33 |
| gm169-61 | 4-39 | 3-20 |
| gm169-64κ | 3-7 | 3-20 |
| gm169-68 | 4-34 | 1-5 |
| gm169-70κ | 3-13 | 1-39 |
| gm169-76κ | 3-11 | 2-28 |
| gm169-80κ | 4-39 | 2-28 |
| gm169-86 | 4-4 | 1-5 |
| gm169-94 | 3-30 | 4-1 |
| gm169-95 | 1-46 | 1-39 |
| gp169-8 | 1-24 | 3-15 |
| gp169-26κ | 3-33 | 4-1 |
| gp169-29 | 4-4 | 3-20 |
| gp169-53κ | 4-4 | 4-1 |
| gp169-64κ | 3-30 | 3-11 |
| gp169-66 | 4-4 | 3-20 |
| gp169-81 | 5-51 | 2-30 |
| gp169-87 | 4-39 | 3-15 |
| gp169-103κ | 4-39 | 4-1 |
| gp169-108 | 1-2 | 2-28 |
| gp169-117# | 4-59 | 1-5 |
| gp169-126 | 3-23 | 3-15 |
| gp169-127κ | 1-69 | 3-11 |
| gp169-129 | 5-51 | 1-12 |
| gp169-144κ | 4-4 | 1-6 |

| gm/gp169 | VH | Vλ |
|---|---|---|
| gm169-3λ | | 1-47 |
| gm169-4 | 3-11 | 2-23 |
| gm169-8 | 4-34 | 1-47 |
| gm169-11 | 1-2 | 1-44 |
| gm169-16λ# | | 2-11 |
| gm169-20λ | | 3-21 |
| gm169-22λ | | 3-21 |
| gm169-24λ | | 9-49 |
| gm169-28λ | | 2-14 |
| gm169-31λ | | 3-25 |
| gm169-33# | 4-34 | 2-14 |
| gm169-34λ | | 1-40 |
| gm169-38λ | | 3-21 |
| gm169-48 | 4-4 | 1-44 |
| gm169-64λ | | 1-40 |
| gm169-70λ# | | 1-40 |
| gm169-74 | 1-46 | 1-40 |
| gm169-76λ | | 2-11 |
| gm169-80λ | | 3-21 |
| gm169-83 | 3-74 | 2-11 |
| gm169-85 | 3-48 | 1-47 |
| gm169-88 | 3-30 | 3-1 |
| gp169-23# | 1-58 | 2-14 |
| gp169-26λ | | 1-44 |
| gp169-32 | 4-59 | 3-21 |
| gp169-43 | 4-4 | 1-40 |
| gp169-53λ | | 2-14 |
| gp169-64λ | | 6-57 |
| gp169-65 | 3-30 | 3-10 |
| gp169-71# | 1-18 | 1-51 |
| gp169-74 | 3-23 | 3-1 |
| gp169-77 | 3-33 | 6-57 |
| gp169-82# | 3-30 | 1-47 |
| gp169-83 | 3-23 | 2-14 |
| gp169-85 | 3-43 | 1-36 |
| gp169-86 | 3-30 | 3-10 |
| gp169-103λ | | 6-57 |
| gp169-113 | 1-69 | 3-21 |
| gp169-116 | 3-30 | 1-40 |
| gp169-122 | 4-4 | 2-11 |
| gp169-127λ | | 1-51 |
| gp169-142 | 5-51 | 1-44 |
| gp169-144λ# | | 2-8 |
| gp169-148# | 1-46 | 6-57 |

Figure 14

| Ig | Heavy | Light |
|---|---|---|
| gm174 | VH | Vk |
| 174-2 | 4-39 | 2-28 |
| 174-5 | 1-69 | 3-11 |
| 174-8 | 3-11 | 1-5 |
| 174-9 | 1-2 | 4-1 |
| 174-12# | 1-46 | 1-27 |
| 174-17# | 3-23 | 2-29 |
| 174-23 | 5-51 | 3-11 |
| 174-24# | 3-30 | 3-20 |
| 174-28 | 3-23 | 1-39 |
| 174-32 | 3-49 | 1-5 |
| 174-35 | 1-46 | 3-11 |
| 174-55# | 1-3 | 3-15 |
| 174-60 | 5-51 | 1-39 |
| 174-67 | 3-30 | 1-6 |
| 174-79# | 3-30 | 1-39 |
| 174-84 | 4-34 | 1-39 |
| 174-87 | 3-48 | 3-20 |
| 174-91# | 4-31 | 1-17 |
| 174-117# | 4-34 | 1-39 |
| 174-119 | 3-48 | 3-20 |
| 174-120k | 1-24 | 2-30 |
| 174-129 | 3-30 | 4-1 |
| 174-130 | 4-31 | 3-11 |
| 174-133 | 1-69 | 2-28 |
| 174-140 | 4-59 | 1-39 |
| 174-146# | 3-72 | 3-20 |
| 174-148# | 5-51 | 1-33 |
| 174-154 | 4-34 | 1-5 |
| 174-156 | 4-39 | 1-5 |
| 174-157# | 3-53 | 3-15 |
| 174-169# | 3-23 | 1-5 |
| 174-176 | 3-23 | 4-1 |
| 174-177 | 5-51 | 3-20 |
| 174-179# | 4-39 | 1-39 |
| 174-184# | 4-39 | 1-5 |
| 174-194# | 4-31 | 2-29 |
| 174-196 | 3-7 | 2-30 |

| gm174 | VH | Vl |
|---|---|---|
| 174-1 | 1-69 | 3-10 |
| 174-16 | 4-28 | 2-23 |
| 174-18# | 5-51 | 2-14 |
| 174-29 | 3-15 | 3-1 |
| 174-33 | 3-21 | 1-40 |
| 174-44 | 3-33 | 2-23 |
| 174-45 | 3-53 | 2-11 |
| 174-54 | 4-59 | 3-12 |
| 174-59 | 3-33 | 2-23 |
| 174-63 | 3-74 | 7-43 |
| 174-68 | 3-7 | 2-23 |
| 174-71 | 1-46 | 2-23 |
| 174-77 | 3-15 | 2-8 |
| 174-82 | 5-51 | 2-14 |
| 174-114 | 1-18 | 2-14 |
| 174-115# | 4-39 | 2-14 |
| 174-118 | 4-59 | 1-44 |
| 174-120l |  | 2-14 |
| 174-125# | 7-81 | 1-40 |
| 174-127 | 3-33 | 6-57 |
| 174-131 | 4-28 | 1-51 |
| 174-151 | 3-53 | 3-1 |
| 174-162# | 5-51 | 2-14 |
| 174-165 | 3-53 | 2-14 |
| 174-174 | 4-39 | 2-23 |
| 174-180 | 5-51 | 1-40 |
| 174-183# | 3-11 | 1-44 |

Figure 15

| Ig | Heavy | Light |
|---|---|---|
| gm175 | VH | Vk |
| 175-19 | 3-23 | 1-5 |
| 175-29 | 5-51 | 3-15 |
| 175-39# | 3-43 | 3-15 |
| 175-62 | 4-61 | 1-13 |
| 175-77 | 3-23 | 1-5 |
| 175-79 | 3-73 | 2-28 |
| 175-86# | 3-23 | 3-15 |
| 175-90 | 4-4 | 1-5 |
| 175-95# | 4-34 | 1-39 |
| 175-107 | 3-7 | 1-5 |
| 175-108 | 1-69 | 3-11 |
| 175-113# | 3-33 | 1-33 |
| 175-116 | 4-34 | 4-1 |
| 175-128 | 3-23 | 2-28 |
| 175-140 | 4-59 | 1D-43 |
| 175-150# | 1-18 | 3-15 |
| 175-153 | 3-7 | 3-11 |
| 175-157 | 3-23 | 1-9 |
| 175-162 | 3-33 | 1-5 |
| 175-217 | 1-8 | 4-1 |
| 175-229# | 3-30 | 3-20 |
| 175-233 | 3-15 | 2-30 |
| 175-240 | 1-2 | 1-39 |
| 175-241 | 4-31 | 1-27 |
| 175-250 | 1-2 | 3-20 |
| 175-258# | 3-23 | 1-16 |
| 175-260# | 3-30 | 4-1 |
| 175-263# | 1-8 | 3-15 |
| 175-264 | 3-33 | 3-15 |
| 175-265 | 3-23 | 3-11 |
| 175-266 | 3-15 | 3-20 |
| 175-269 | 1-3 | 3-20 |
| 175-276 | 1-24 | 2-40 |
| 175-277 | 3-21 | 1-5 |
| 175-285# | 3-9 | 2D-29 |
| 175-292# | 1-69 | 3-20 |

| gm175 | VH | Vl |
|---|---|---|
| 175-23 | 4-39 | 2-14 |
| 175-42 | 3-74 | 2-23 |
| 175-80 | 4-34 | 2-11 |
| 175-82# | 1-3 | 1-40 |
| 175-101# | 4-39 | 1-47 |
| 175-114# | 1-3 | 2-23 |
| 175-142# | 4-31 | 2-23 |
| 175-146# | 4-34 | 1-51 |
| 175-160 | 3-23 | 2-11 |
| 175-165 | 3-23 | 1-44 |
| 175-169 | 1-8 | 1-47 |
| 175-215 | 4-28 | 2-23 |
| 175-236# | 3-49 | 3-21 |
| 175-238 | 1-2 | 1-40 |
| 175-242 | 3-11 | 2-11 |
| 175-248# | 7-81 | 3-21 |
| 175-249# | 3-33 | 2-23 |
| 175-270# | 4-34 | 1-51 |
| 175-280 | 3-48 | 2-23 |
| 175-282 | 3-74 | 3-1 |
| 175-286 | 4-61 | 2-23 |
| 175-289 | 3-11 | 2-11 |
| 175-295 | 3-9 | 2-23 |

Figure 16

| Ig      | Heavy | Light |
|---------|-------|-------|
| gm176   | VH    | Vk    |
| 176-10  | 3-48  | 1-33  |
| 176-62  | 3-23  | 3-15  |
| 176-66  | 4-31  | 1-5   |
| 176-91# | 3-21  | 1-5   |
| 176-172#| 3-21  | 3-15  |
| 176-214 | 1-69  | 3-15  |
| 176-236#| 4-59  | 3-15  |
| 176-256 | 1-18  | 3-15  |
| 176-267 | 3-23  | 3-15  |
| 176-270 | 4-34  | 3-15  |
| 176-301 | 3-33  | 2-28  |
| 176-337 | 3-33  | 2-28  |
| 176-435 | 1-69  | 3-15  |
| 176-514 | 1-69  | 1-39  |
| 176-534 | 3-21  | 3-15  |
| 176-548 | 3-21  | 1-27  |
| 176-585 | 4-59  | 3-20  |
| 176-592#| 4-31  | 3-11  |
| 176-611 | 3-9   | 4-1   |
| 176-618 | 1-58  | 3-11  |
| 176-621 | 4-34  | 1-9   |
| 176-632 | 4-59  | 4-1   |
| 176-641 | 3-23  | 3-15  |
| 176-650k| 3-9   | 4-1   |
| 176-655 | 4-39  | 3-15  |
| 176-694 | 3-48  | 1-39  |

| gm176   | VH    | Vl    |
|---------|-------|-------|
| 176-29  | 3-48  | 2-14  |
| 176-130#| 4-4   | 1-44  |
| 176-223 | 4-34  | 1-40  |
| 176-226 | 1-46  | 1-51  |
| 176-229 | 3-21  | 1-44  |
| 176-241 | 3-9   | 2-14  |
| 176-253#| 4-39  | 1-40  |
| 176-272 | 4-39  | 3-9   |
| 176-275 | 1-8   | 1-51  |
| 176-287#| 1-2   | 1-40  |
| 176-290#| 4-34  | 2-14  |
| 176-310 | 3-7   | 1-47  |
| 176-318#| 5-51  | 1-40  |
| 176-323 | 1-69  | 2-14  |
| 176-365 | 4-31  | 3-21  |
| 176-392 | 4-4   | 2-14  |
| 176-393#| 4-61  | 2-14  |
| 176-395 | 4-59  | 3-21  |
| 176-428#| 1-18  | 2-14  |
| 176-447#| 4-59  | 2-14  |
| 176-508#| 4-4   | 2-23  |
| 176-523 | 3-30  | 1-51  |
| 176-535 | 3-11  | 2-23  |
| 176-536 | 1-2   | 2-23  |
| 176-540 | 3-30  | 1-51  |
| 176-558 | 3-48  | 1-47  |
| 176-614 | 4-39  | 1-44  |
| 176-616 | 3-9   | 1-44  |
| 176-620 | 3-9   | 2-8   |
| 176-627 | 3-30  | 1-44  |
| 176-650l#|      | 4-69  |
| 176-662#| 3-30  | 1-51  |

Figure 17

| Ig | Heavy | Light |
|---|---|---|
| gmJH | VH | Vκ |
| JH1 | 1-18 | 3-20 |
| JH5 | 3-30 | 3-20 |
| JH17 | 4-34 | 3-11 |
| JH19# | 4-59 | 3-20 |
| JH20 | 3-33 | 3-15 |
| JH22# | 1-24 | 1-39 |
| JH23# | 1-18 | 3-20 |
| JH-26# | 5-51 | 3-20 |
| JH35 | 3-21 | 1-6 |
| JH38 | 3-7 | 1-39 |
| JH39# | 3-30 | 1-39 |
| JH40# | 4-31 | 3-20 |
| JH55 | 3-30 | 3-20 |
| JH56# | 1-8 | 3-20 |
| JH57 | 4-59 | 1-39 |
| JH60 | 3-23 | 3-20 |
| JH65 | 1-18 | 1-39 |
| JH66 | 3-48 | 1-39 |
| JH69 | 3-7 | 4-1 |
| JH76# | 4-31 | 1-39 |
| JH78# | 1-8 | 3-15 |
| JH81# | 7-4 | 1-39 |
| JH82# | 3-48 | 1-9 |
| JH96 | 3-30 | 3-15 |
| JH101# | 1-69 | 3-20 |
| JH103 | 4-31 | 2-28 |
| JH113 | 3-33 | 1-5 |
| JH114# | 1-46 | 3-20 |
| JH117# | 3-23 | 3-20 |
| JH124# | 4-39 | 1-39 |
| JH125# | 3-9 | 1-12 |
| JH129 | 1-18 | 1-33 |
| JH131# | 3-7 | 1-5 |
| JH132 | 4-39 | 1-39 |
| JH135 | 1-18 | 1-39 |
| JH147# | 3-30 | 3-20 |
| JH148 | 3-23 | 1-5 |
| JH154 | 3-33 | 3-15 |
| JH156 | 3-7 | 1-27 |
| JH160# | 3-21 | 3-20 |
| JH162 | 3-15 | 1-33 |
| JH165 | 3-7 | 4-1 |
| JH167# | 4-59 | 3-20 |
| JH179 | 3-23 | 4-1 |
| JH183# | 3-11 | 3-20 |
| JH186 | 1-2 | 1-39 |
| JH188 | 3-30 | 1-17 |
| JH192 | 3-48 | 3-15 |
| JH194 | 7-4 | 1-5 |
| JH195 | 4-34 | 3-20 |

| gmJH | VH | Vλ |
|---|---|---|
| JH16 | 4-39 | 1-47 |
| JH21 | 3-15 | 1-44 |
| JH28# | 3-74 | 2-23 |
| JH42 | 7-4 | 1-51 |
| JH48# | 5-51 | 1-40 |
| JH50 | 4-31 | 2-23 |
| JH59# | 1-2 | 1-44 |
| JH63 | 4-34 | 1-47 |
| JH75 | 4-34 | 3-21 |
| JH79 | 4-31 | 2-14 |
| JH88 | 3-66 | 1-44 |
| JH91 | 3-21 | 2-8 |
| JH93 | 4-39 | 3-1 |
| JH95 | 4-59 | 1-47 |
| JH105# | 4-4 | 2-8 |
| JH107# | 3-23 | 2-14 |
| JH109# | 5-51 | 2-14 |
| JH128 | 4-59 | 6-57 |
| JH143# | 5-51 | 2-23 |
| JH171 | 4-39 | 2-23 |
| JH185# | 4-59 | 2-14 |

Figure 18

| S3 preB | | S4 ei | | S5 imm | |
|---|---|---|---|---|---|
| VH | Vk | VH | Vk | VH | Vk |
| 3-9 | 1-16 | 3-23 | 4-1 | 3-48 | 1-8 |
| 3-30 | 2D-30 | 3-23 | 1-8 | 3-15 | 1-9 |
| 3-48 | 1-33 | 4-34 | 1-16 | 4-39 | 1-39 |
| 4-59 | 1D-17 | 3-33 | 1-39 | 3-7 | 1-8 |
| 3-30 | 1D-8 | 3-30 | 3-20 | 3-33 | 1-5 |
| 1-2 | 1-5 | 4-34 | 2D-28 | 1-18 | 1-5 |
| 1-2 | 1-6 | 3-74 | 4-1 | 3-15 | 1-9 |
| 3-15 | 1D-43 | VH | VL | 3-23 | 1-8 |
| 3-30 | 2-30 | 3-21 | 1-47 | 4-34 | 1-39 |
| 3-30 | 3-11 | 3-23 | 1-36 | 3-30 | 1-39 |
| 3-11 | 1-6 | 3-48 | 3-25 | 3-15 | 1-39 |
| 4-59 | 2-30 | 4-39 | 1-44 | 7-81 | 1-39 |
| 3-30 | 3-20 | 1-69 | 3-1 | 3-15 | 1-33 |
| 1-3 | 2-30 | 4-59 | 1-40 | 3-23 | 3-15 |
| VH | VL | 4-34 | 1-44 | 4-39 | 3-11 |
| 3-21 | 1-51 | | | 4-34 | 3-15 |
| 3-21 | 7-46 | | | 3-11 | 1D-8 |
| 3-53 | 1-47 | | | 1-2 | 3-20 |
| 1-2 | 3-27 | | | 4-31 | 3-15 |
| 1-69 | 1-44 | | | 3-21 | 1-39 |
| 3-21 | 2-23 | | | 3-33 | 1-9 |
| | | | | 3-15 | 1-5 |
| | | | | 4-39 | 1-5 |
| | | | | 1-69 | 4-1 |
| | | | | 1-58 | 4-1 |
| | | | | VH | VL |
| | | | | 1-46 | 1-44 |
| | | | | 3-11 | 4-69 |
| | | | | 3-23 | 3-19 |
| | | | | 1-18 | 2-11 |
| | | | | 4-61 | 7-43 |
| | | | | 5-51 | 2-14 |
| | | | | 3-15 | 1-44 |
| | | | | 3-11 | 3-1 |
| | | | | 3-15 | 3-25 |
| | | | | 5-51 | 2-14 |
| | | | | 1-69 | 1-51 |
| | | | | 1-18 | 2-14 |
| | | | | 3-23 | 3-1 |

Figure 19

| S6 imm | | S7 ne | | S8 ne | |
|---|---|---|---|---|---|
| VH | Vk | VH | Vk | VH | Vk |
| 1-18 | 2-40 | 3-53 | 1-39 | 3-13 | 1-39 |
| 4-59 | 3-20 | 1-69 | 1-33 | 3-7 | 3-11 |
| 3-21 | 1-5 | 3-21 | 3-15 | 1-46 | 3-15 |
| 1-2 | 1-5 | 5-51 | 2D-28 | 3-48 | 3-11 |
| 1-18 | 1-33 | 3-13 | 1-5 | 3-48 | 3-20 |
| 4-34 | 1-39 | 1-69 | 1-8 | 1-46 | 1-33 |
| 1-8 | 2D-28 | 3-30 | 1-27 | 3-49 | 1-5 |
| 4-34 | 3-20 | 4-34 | 1-27 | 1-3 | 1-39 |
| 4-34 | 1-39 | 3-30 | 1-9 | 1-18 | 3-20 |
| 1-2 | 1-39 | 1-69 | 1-39 | 4-59 | 1-5 |
| 3-30 | 2-24 | 3-15 | 1-5 | 4-39 | 3-11 |
| 3-15 | 3-20 | 4-49 | 3-20 | 3-23 | 1-5 |
| 1-24 | 2-24 | 3-21 | 2D-28 | 4-39 | 1-33 |
| 1-3 | 1-39 | 4-39 | 3-15 | 1-69 | 3D-15 |
| 3-30 | 3-20 | 3-15 | 1-39 | 3-33 | 1-9 |
| 4-4 | 1D-8 | 3-74 | 3-20 | 1-3 | 3-15 |
| 3-21 | 3-15 | 3-30 | 2D-28 | 1-46 | 1-8 |
| 4-39 | 3-20 | 3-30 | 1-6 | 3-7 | 1-39 |
| 4-59 | 1-27 | 3-23 | 3D-20 | 5-51 | 1-5 |
| 3-9 | 1-8 | 3-30 | 3-11 | 3-33 | 3-15 |
| 3-7 | 3-15 | VH | VL | 4-34 | 1-39 |
| 3-33 | sD-28 | 5-51 | 1-40 | 3-53 | 1D-16 |
| 1-69 | 1-39 | 3-7 | 1-51 | 1-18 | 3-20 |
| 3-30 | 1-5 | 3-9 | 2-14 | 1-2 | 3-20 |
| 1-18 | 3-11 | 4-59 | 1-44 | 3-7 | 1-13 |
| 3-15 | 3-20 | 4-49 | 2-14 | VH | VL |
| 3-21 | 1-5 | 1-69 | 1-40 | 1-18 | 3-10 |
| 1-2 | 1-8 | 4-39 | 1-51 | 1-2 | 3-1 |
| 3-74 | 3-15 | 4-31 | 2-14 | 3-30 | 3-1 |
| 4-4 | 4-1 | 3-9 | 2-14 | 1-3 | 3-1 |
| VH | VL | 5-51 | 1-44 | 3-30 | 1-51 |
| 4-34 | 1-47 | 3-49 | 1-40 | 3-7 | 1-40 |
| 5-51 | 1-40 | 4-39 | 2-14 | 5-51 | 3-21 |
| 4-61 | 2-11 | 5-51 | 1-44 | 1-46 | 1-44 |
| 3-30 | 2-23 | | | 3-21 | 2-14 |
| 3-15 | 2-23 | | | 1-2 | 1-40 |
| 4-31 | 1-44 | | | 4-59 | 2-11 |
| 3-13 | 1-47 | | | 4-34 | 2-14 |
| 4-39 | 1-44 | | | 3-48 | 2-14 |
| 5-51 | 2-14 | | | 1-2 | 2-14 |
| 3-33 | 1-40 | | | 3-48 | 1-51 |
| 3-30 | 1-51 | | | 3-48 | 3-1 |
| 4-34 | 1-51 | | | | |
| 3-21 | 3-1 | | | | |
| 3-30 | 2-14 | | | | |
| 4-31 | 3-21 | | | | |

Figure 20

| S9 mn | |
|---|---|
| VH | Vk |
| 4-39 | 3-15 |
| 3-7 | 2D-28 |
| 4-59 | 3-20 |
| 3-43 | 1-5 |
| 3-53 | 1-5 |
| 3-15 | 1-5 |
| 1-24 | 1-39 |
| 3-48 | 3-11 |
| 4-39 | 3-15 |
| 4-34 | 3-20 |
| 4-34 | 3-20 |
| 3-43 | 1-5 |
| 4-39 | 3-15 |
| 3-15 | 3-20 |
| 1-3 | 1-39 |
| 3-30 | 1-39 |
| 3-48 | 1-39 |
| 3-48 | 1-9 |
| 1-69 | 2-30 |
| 1-18 | 1-33 |
| 3-30 | 1-9 |
| 3-21 | 3-11 |
| 4-34 | 3-20 |
| 3-23 | 2D-28 |
| 1-24 | 3-11 |
| 3-49 | 3-20 |
| 5-51 | 2D-28 |
| 1-46 | 1-39 |
| 4-59 | 1-39 |
| 1-69 | 1-39 |
| 3-15 | 1-33 |
| 4-34 | 3-15 |
| 3-48 | 1-39 |
| 1-69 | 1-39 |
| 4-39 | 3-15 |
| 3-74 | 1D-37 |
| 3-23 | 1-39 |
| 1-46 | 1-9 |
| 3-23 | 3-15 |
| 3-15 | 1-39 |
| 3-48 | 3-15 |

| VH | VL |
|---|---|
| 1-24 | 1-44 |
| 4-28 | 1-44 |
| 4-34 | 2-14 |
| 3-74 | 3-21 |
| 5-51 | 3-21 |
| 3-23 | 3-1 |
| 3-15 | 1-44 |
| 4-39 | 2-14 |
| 3-48 | 2-14 |
| 1-69 | 2-14 |
| 4-39 | 1-40 |
| 5-51 | 3-25 |
| 3-64 | 3-21 |
| 4-28 | 1-36 |
| 4-59 | 3-1 |
| 1-2 | 1-40 |
| 5-51 | 1-40 |
| 3-7 | 3-21 |
| 1-69 | 1-51 |
| 3-9 | 2-14 |
| 3-9 | 1-44 |
| 3-33 | 2-14 |
| 5-51 | 1-36 |
| 4-34 | 2-23 |
| 3-30 | 3-21 |
| 1-69 | 1-40 |
| 3-43 | 1-51 |
| 3-11 | 1-47 |
| 4-34 | 2-8 |
| 1-8 | 2-14 |

| S10 mn | |
|---|---|
| VH | Vk |
| 1-2 | 4-1 |
| 4-34 | 3-20 |
| 1-18 | 3-20 |
| 3-30 | 1-39 |
| 4-39 | 1-39 |
| 4-59 | 4-1 |
| 4-39 | 3-15 |
| 4-39 | 3-20 |
| 1-24 | 2-30 |
| 1-2 | 3-20 |
| 3-9 | 1-16 |
| 4-59 | 3-20 |
| 4-31 | 2-28 |
| 4-59 | 1-16 |
| 4-39 | 3-20 |
| 3-53 | 1-17 |
| 3-48 | 3-11 |
| 3-48 | 3-20 |
| 4-59 | 3-20 |
| 5-51 | 1-39 |
| 3-9 | 1-5 |
| 4-39 | 3-15 |
| 3-30 | 1-9 |
| 4-34 | 1-39 |
| VH | VL |
| 1-69 | 2-8 |
| 5-51 | 1-44 |
| 3-30 | 9-49 |
| 5-51 | 1-44 |
| 4-39 | 3-1 |
| 1-69 | 3-25 |
| 4-59 | 2-23 |
| 3-48 | 2-14 |
| 3-21 | 1-51 |
| 5-51 | 1-40 |
| 4-31 | 4-69 |
| 1-69 | 1-40 |
| 1-46 | 1-47 |
| 3-9 | 1-47 |
| 1-18 | 2-14 |
| 4-39 | 2-23 |
| 1-2 | 3-1 |

Figure 21

| S1 ne | | S2 mn | |
|---|---|---|---|
| VH | Vk | VH | Vk |
| 3-23 | 3-20 | 3-7 | 4-1 |
| 4-59 | 1-33 | 3-73 | 1-9 |
| 1-18 | 3-20 | 1-18 | 1-5 |
| 3-48 | 1-33 | 3-23 | 3-15 |
| 4-34 | 3-20 | 5-51 | 4-1 |
| 3-23 | 4-1 | 3-23 | 1-12 |
| 4-4 | 2D-29 | 3-9 | 1-39 |
| 3-11 | 1-5 | 3-33 | 4-1 |
| 3-53 | 1-5 | 3-53 | 1-12 |
| 3-9 | 1-39 | 4-39 | 3-20 |
| 3-7 | 1-27 | 3-23 | 3-20 |
| 3-48 | 4-1 | 3-72 | 3-15 |
| 5-51 | 4-1 | 3-48 | 1-33 |
| 3-30 | 3-20 | 5-51 | 3-15 |
| 3-53 | 3-20 | 5-51 | 4-1 |
| 3-30 | 1-39 | 5-51 | 3-20 |
| 3-30 | 4-1 | 1-2 | 3-15 |
| 3-7 | 1-5 | 3-21 | 4-1 |
| 7-81 | 1-39 | 3-11 | 1-39 |
| 3-9 | 4-1 | 1-2 | 3-20 |
| 5-51 | 3-15 | 3-48 | 4-1 |
| 3-23 | 4-1 | 4-39 | 1-5 |
| 1-2 | 1-39 | 4-39 | 1-39 |
| 4-59 | 3-20 | 1-2 | 1-27 |
| 4-34 | 4-1 | 4-31 | 1-39 |
| 3-33 | 1-8 | 4-59 | 1-39 |
| 3-48 | 1-33 | 4-39 | 1-33 |
| 5-51 | 3-15 | 4-39 | 1-6 |
| 3-15 | 2D-28 | 3-48 | 4-1 |
| 1-18 | 1-39 | 3-23 | 4-1 |
| 1-3 | 1-33 | 3-7 | 3-15 |
| 4-59 | 4-1 | 3-53 | 4-1 |
| 4-39 | 1-33 | 3-7 | 3-20 |
| 3-15 | 3-11 | VH | VL |
| 1-18 | 2-30 | 4-39 | 1-44 |
| 4-39 | 4-1 | 1-2 | 1-44 |
| 3-48 | 3D-20 | 1-69 | 2-8 |
| VH | VL | 4-59 | 3-1 |
| 3.23 | 2-8 | 4-39 | 2-8 |
| 4-39 | 2-14 | 3-23 | 1-40 |
| 3-23 | 3-21 | 4-31 | 1-51 |
| 3-33 | 3-27 | 4-34 | 1-51 |
| 5-51 | 1-40 | 3-49 | 2-14 |
| 7-81 | 3-21 | 4-31 | 1-47 |
| 4-4 | 1-44 | 1-18 | 1-40 |
| 1-2 | 2-14 | 4-31 | 2-14 |
| 4-4 | 1-44 | 4-39 | 1-51 |
| | | 4-39 | 2-14 |
| | | 3-48 | 7-46 |

| VH | Vk | VH | VL |
|---|---|---|---|
| 3-30 | 4-1 | 1-18 | 1-36 |
| 3-49 | 1-17 | 3-43 | 2-14 |
| 3-23 | 1-8 | 5-51 | 1-40 |
| 3-30 | 3-15 | 5-51 | 1-40 |
| 3-64 | 3-15 | 4-39 | 1-51 |
| 1-18 | 3-11 | 3-23 | 2-14 |
| 3-48 | 1-5 | 3-43 | 3-1 |
| 1-24 | 1-33 | 4-59 | 1-40 |
| 3-30 | 1-5 | 3-7 | 2-14 |
| 1-69 | 4-1 | 3-7 | 1-47 |
| 1-8 | 3-11 | 1-18 | 1-40 |
| 3-9 | 2D-29 | 4-61 | 3-1 |
| 1-18 | 2-28 | 3-30 | 1-44 |
| 3-30 | 3-15 | 4-61 | 2-14 |
| 3-23 | 4-1 | 3-33 | 2-14 |
| 1-8 | 3-15 | 1-18 | 1-40 |
| 4-39 | 1-5 | 4-59 | 1-40 |
| 4-31 | 1-6 | 1-24 | 2-11 |
| 3-23 | 1-5 | 5-51 | 1-47 |
| 3-33 | 3-20 | 4-34 | 2-14 |
| 3-53 | 1-8 | 1-8 | 9-49 |
| 3-53 | 1-8 | | |
| 3-7 | 1D-8 | | |
| 4-39 | 1-39 | | |
| 3-30 | 1-9 | | |
| 5-51 | 4-1 | | |
| 3-53 | 1-5 | | |
| 4-39 | 1-5 | | |
| 4-34 | 3-20 | | |
| 1-69 | 1-5 | | |
| 4-59 | 3-20 | | |
| 3-7 | 1-17 | | |
| 3-21 | 1-8 | | |
| 3-23 | 1-5 | | |
| 3-30 | 1-33 | | |
| 3-30 | 1-5 | | |
| 4-31 | 3-11 | | |
| 1-2 | 1-5 | | |
| 4-61 | 3-15 | | |
| 3-30 | 1-39 | | |
| 3-48 | 3-15 | | |
| 3-7 | 1-8 | | |
| 3-23 | 1-5 | | |

Figure 23

| S4 mn | | S5 ne | | S6 mn | |
|---|---|---|---|---|---|
| VH | Vk | VH | Vk | VH | Vk |
| 3-30 | 3-11 | 4-34 | 1-39 | 3-13 | 4-1 |
| 4-34 | 3-11 | 3-23 | 3-15 | 4-34 | 4-1 |
| 3-30 | 1-5 | 3-23 | 3-20 | 3-15 | 4-1 |
| 1-58 | 1-5 | 4-61 | 1-39 | 1-18 | 2-28 |
| 3-21 | 3-15 | 3-64 | 3-11 | 1-69 | 1-16 |
| 4-39 | 2-30 | 3-15 | 3-15 | 3-23 | 4-1 |
| 3-23 | 1-33 | 3-53 | 2-28 | 3-23 | 1-5 |
| 3-7 | 1-9 | 1-18 | 3-11 | 3-30 | 3-15 |
| 3-30 | 3-11 | 3-49 | 1-39 | 3-48 | 1-17 |
| 3-23 | 3-20 | 3-64 | 2D-29 | 3-23 | 1-33 |
| 4-34 | 1-5 | 3-21 | 3-15 | 3-23 | 1-16 |
| 4-34 | 1-17 | 4-59 | 1-33 | 3-53 | 3-15 |
| 3-53 | 1-33 | 3-53 | 3-11 | 3-48 | 2-28 |
| 3-21 | 3-20 | 3-23 | 3-15 | 3-7 | 1-9 |
| 4-31 | 1-33 | 3-9 | 1-27 | 3-30 | 3-11 |
| 4-34 | 1-39 | 3-13 | 2-30 | 3-30 | 4-1 |
| 1-18 | 3-20 | 4-4 | 3-11 | 3-43 | 3-11 |
| 3-53 | 1-5 | 3-33 | 3-20 | 1-18 | 2-28 |
| 4-61 | 1-39 | 5-51 | 2-28 | 3-30 | 4-1 |
| 3-21 | 1-39 | 3-7 | 3-20 | 5-51 | 3-11 |
| 5-51 | 1-27 | 3-23 | 2-40 | 3-23 | 2-28 |
| 5-51 | 4-1 | 4-31 | 1-39 | 1-2 | 3-15 |
| 3-30 | 2D-29 | 3-23 | 1-16 | 3-11 | 3-20 |
| 3-53 | 1-5 | 3-48 | 2-28 | 4-31 | 3-11 |
| 3-23 | 1-39 | 4-31 | 1-33 | 1-24 | 2D-28 |
| 5-51 | 4-1 | 4-31 | 1-27 | 1-46 | 3-20 |
| 3-11 | 3-20 | 3-48 | 3-20 | 5-51 | 1-17 |
| VH | VL | 3-53 | 4-1 | 1-58 | 3-20 |
| 4-59 | 1-51 | 4-4 | 2D-29 | 4-59 | 3-20 |
| 3-23 | 2-14 | 4-31 | 4-1 | 3-21 | 1-5 |
| 3-15 | 2-8 | 4-34 | 2-28 | 1-8 | 4-1 |
| 3-11 | 3-1 | 4-34 | 3-15 | 3-53 | 4-1 |
| 4-28 | 2-23 | 1-69 | 3-20 | 3-23 | 1-39 |
| 4-34 | 1-44 | 3-15 | 1-27 | 3-64 | 1-5 |
| 4-59 | 3-1 | 1-24 | 3-15 | 4-4 | 3-15 |
| 3-30 | 1-51 | 1-2 | 2D-26 | 1-46 | 4-1 |
| 3-30 | 3-27 | VH | VL | VH | VL |
| 4-39 | 2-18 | 1-3 | 3-1 | 3-64 | 2-14 |
| 5-51 | 1-40 | 1-69 | 2-11 | 3-23 | 1-40 |
| 5-51 | 1-47 | 3-33 | 3-9 | 3-74 | 2-8 |
| 4-39 | 2-8 | 4-31 | 1-51 | 4-34 | 1-40 |
| 3-33 | 1-47 | 4-59 | 3-1 | 5-51 | 2-14 |
| | | 1-46 | 1-44 | 3-21 | 1-51 |
| | | 4-4 | 2-23 | 3-11 | 1-51 |
| | | 4-39 | 2-8 | 1-8 | 1-47 |
| | | 1-3 | 2-14 | 3-48 | 1-19 |
| | | 3-15 | 1-47 | 1-69 | 2-14 |
| | | 3-48 | 3-21 | 3-23 | 2-11 |
| | | 3-21 | 2-14 | 3-23 | 1-40 |
| | | 3-11 | 3-21 | | |
| | | 3-30 | 2-14 | | |

Figure 24

| S1 mn | | S2 mn | | | |
|---|---|---|---|---|---|
| VH | Vk | VH | Vk | VH | VL |
| 4-4 | 3-11 | 3-7 | 3-11 | 5-51 | 2-23 |
| 1-18 | 3-20 | 3-23 | 3-11 | 1-46 | 1-51 |
| 3-74 | 2-30 | 4-4 | 4-1 | 3-48 | 3-1 |
| 5-51 | 3-11 | 4-59 | 1-12 | 3-30 | 1-40 |
| 3-30 | 1-5 | 4-39 | 1-5 | 1-46 | 1-51 |
| 3-21 | 3-20 | 1-3 | 1-5 | 3-30 | 1-40 |
| 3-23 | 2D-40 | 5-51 | 4-1 | 4-31 | 1-40 |
| 4-39 | 3-20 | 4-34 | 4-1 | 4-59 | 1-47 |
| 4-31 | 3-20 | 4-34 | 3-20 | 4-31 | 3-1 |
| 3-15 | 3-15 | 4-39 | 3-11 | 3-9 | 2-23 |
| 4-39 | 3-15 | 3-33 | 3-15 | 4-34 | 1-40 |
| 4-4 | 3-20 | 3-15 | 1-39 | 3-9 | 2-14 |
| 1-18 | 1-5 | 1-18 | 4-1 | 3-9 | 2-11 |
| 4-39 | 3-20 | 4-34 | 3-15 | 4-39 | 2-8 |
| 4-59 | 1D-39 | 4-31 | 3-15 | 1-18 | 1-51 |
| 3-30 | 3-20 | 1-2 | 1-33 | 4-59 | 1-51 |
| 3-33 | 1D-39 | 4-39 | 1-5 | 4-31 | 2-14 |
| 4-34 | 1-5 | 4-34 | 1-39 | 4-61 | 1-44 |
| 3-21 | 3-20 | 4-39 | 1-5 | 4-31 | 1-40 |
| 1-8 | 1-9 | 3-74 | 1-5 | 3-9 | 1-44 |
| 4-34 | 3-20 | 4-39 | 3-20 | 3-30 | 1-51 |
| 4-4 | 3-11 | 1-18 | 3-20 | 3-11 | 9-49 |
| 1-46 | 3-20 | 4-34 | 3-20 | 4-4 | 1-51 |
| 1-18 | 1-8 | 4-39 | 1-5 | 1-18 | 3-25 |
| 4-39 | 1-39 | 3-7 | 1D-17 | | |
| 4-59 | 1-8 | 5-51 | 2-28 | | |
| 3-7 | 3-15 | 3-53 | 1-27 | | |
| 3-53 | 1D-39 | 1-69 | 1D-16 | | |
| VH | VL | 4-34 | 3-11 | | |
| 3-33 | 1-47 | 3-53 | 1-39 | | |
| 3-30 | 3-21 | 1-69 | 1-5 | | |
| 4-59 | 1-51 | 4-31 | 3-20 | | |
| 3-15 | 6-57 | 4-31 | 1-33 | | |
| 4-39 | 2-14 | 3-15 | 3-20 | | |
| 3-73 | 1-51 | 3-48 | 3-20 | | |
| 5-51 | 3-25 | 5-51 | 1-5 | | |
| 3-53 | 1-51 | 4-59 | 3-11 | | |
| 3-48 | 3-1 | 3-30 | 1-39 | | |
| 4-39 | 7-46 | 3-11 | 1-39 | | |
| 4-39 | 6-57 | 3-33 | 3-15 | | |
| 1-18 | 1-40 | 4-59 | 3-11 | | |
| 4-34 | 2-8 | 4-34 | 3-11 | | |
| 5-51 | 1-40 | 3-30 | 1-5 | | |
| 4-39 | 2-8 | 4-39 | 1-27 | | |
| 4-39 | 1-40 | 3-30 | 3-11 | | |
| 4-39 | 2-8 | 4-34 | 2-28 | | |
| 1-18 | 2-8 | 3-33 | 3-20 | | |
| | | 3-30 | 3-11 | | |
| | | 4-34 | 3-15 | | |
| | | 4-39 | 1-39 | | |
| | | 3-48 | 1-27 | | |
| | | 4-34 | 3-20 | | |
| | | 4-4 | 3-20 | | |

| VH | Vk | VH | VL |
|---|---|---|---|
| 3-23 | 3-20 | 3-15 | 1-44 |
| 1-46 | 1-16 | 3-23 | 2-23 |
| 3-30 | 1-5 | 4-4 | 1-44 |
| 3-33 | 1D-33 | 3-15 | 3-21 |
| 3-7 | 1D-39 | 1-2 | 2-8 |
| 1-69 | 1D-39 | 3-30 | 2-11 |
| 4-34 | 3-20 | 4-31 | 2-23 |
| 3-74 | 3-11 | 3-49 | 2-28 |
| 3-15 | 1D-33 | 1-18 | 6-57 |
| 1-3 | 2D-29 | 3-11 | 1-44 |
| 1-18 | 1D-33 | 1-69 | 2-11 |
| 1-46 | 1-16 | 4-39 | 2-23 |
| 3-23 | 1-5 | 1-2 | 2-8 |
| 4-39 | 3-20 | 3-49 | 3-21 |
| 3-30 | 3-11 | 4-34 | 2-8 |
| 3-11 | 2D-28 | 3-9 | 2-11 |
| 3-7 | 4-1 | | |
| 3-23 | 1-5 | | |
| 3-15 | 1-5 | | |
| 3-72 | 3-15 | | |
| 3-11 | 3-11 | | |
| 3-21 | 2D-29 | | |
| 3-23 | 1-5 | | |
| 1-69 | 3-20 | | |
| 1-69 | 1D-39 | | |
| 1-69 | 3-20 | | |
| 3-11 | 1-16 | | |
| 3-23 | 1-27 | | |
| 4-34 | 2D-28 | | |
| 3-53 | 1-9 | | |
| 1-69 | 2D-30 | | |
| 1-8 | 2-29 | | |
| 3-7 | 3-15 | | |
| 3-53 | 1-5 | | |
| 3-23 | 1D-33 | | |
| 3-48 | 1D-33 | | |
| 3-15 | 3-11 | | |
| 4-31 | 2D-28 | | |
| 3-23 | 1D-39 | | |
| 3-23 | 2D-28 | | |
| 4-61 | 1-16 | | |
| 3-30 | 1D-39 | | |
| 4-34 | 3-15 | | |
| 3-33 | 4-1 | | |
| 3-21 | 1-5 | | |
| 3-49 | 3-15 | | |
| 5-51 | 3-20 | | |
| 4-31 | 1-17 | | |
| 4-34 | 1D-39 | | |
| 1-18 | 2D-28 | | |
| 3-53 | 1D-33 | | |
| 5-51 | 3-20 | | |
| 5-51 | 3-20 | | |
| 3-53 | 2-29 | | |

S4 mn

| VH | Vk | VH | VL |
|---|---|---|---|
| 1-69 | 1D-39 | 3-21 | 2-11 |
| 3-23 | 3-15 | 1-69 | 2-8 |
| 4-4 | 3-20 | 4-34 | 2-14 |
| 3-21 | 1-27 | 1-24 | 2-23 |
| 3-23 | 1-17 | 3-23 | 1-40 |
| 1-18 | 1D-39 | 4-34 | 1-40 |
| 3-23 | 3-20 | 3-48 | 1-44 |
| 4-4 | 1D-39 | 3-48 | 1-47 |
| 1-46 | 1D-39 | 3-73 | 1-47 |
| 3-7 | 1D-39 | 4-4 | 2-14 |
| 4-34 | 3-20 | 3-23 | 1-40 |
| 3-30 | 1-16 | | |
| 1-69 | 2D-28 | | |
| 1-69 | 3-20 | | |
| 3-53 | 1D-33 | | |
| 1-69 | 1D-39 | | |
| 4-31 | 3-11 | | |
| 3-21 | 1D-39 | | |
| 4-39 | 1-27 | | |
| 1-18 | 3-20 | | |
| 1-24 | 3-20 | | |
| 3-23 | 3-20 | | |
| 3-23 | 1-27 | | |
| 3-30 | 3-15 | | |
| 1-2 | 2D-28 | | |
| 4-61 | 3-15 | | |
| 3-15 | 1D-39 | | |
| 3-7 | 1D-39 | | |
| 1-18 | 1D-39 | | |
| 3-23 | 3-11 | | |
| 1-18 | 1D-39 | | |
| 3-23 | 2D-28 | | |
| 1-2 | 1-27 | | |
| 3-53 | 3-15 | | |
| 4-34 | 1-17 | | |
| 3-15 | 1D-39 | | |
| 3-53 | 1D-39 | | |
| 3-30 | 2D-28 | | |
| 3-11 | 1D-39 | | |
| 3-23 | 3-20 | | |
| 3-23 | 3-15 | | |

| VH | Vk | VH | VL |
|---|---|---|---|
| 4-39 | 1D-39 | 1-69 | 2-14 |
| 4-34 | 3-20 | 3-15 | 3-22 |
| 3-21 | 3-15 | 5-51 | 1-40 |
| 3-48 | 3-20 | 4-34 | 1-51 |
| 3-15 | 3-20 | 3-23 | 1-51 |
| 4-59 | 1-39 | 1-2 | 2-11 |
| 4-4 | 3-20 | 4-59 | 1-51 |
| 4-39 | 1-17 | 3-49 | 2-8 |
| 3-49 | 1-39 | 1-18 | 1-44 |
| 4-4 | 1-5 | 1-69 | 1-40 |
| 4-34 | 4-1 | 3-66 | 1-47 |
| 4-34 | 1-9 | 3-48 | 2-11 |
| 3-15 | 3-11 | 4-31 | 2-14 |
| 4-34 | 1-39 | 4-28 | 2-14 |
| 3-48 | 3-11 | 1-2 | 2-14 |
| 3-30 | 3-20 | 3-73 | 1-40 |
| 3-20 | 1-39 | 3-48 | 1-47 |
| 3-48 | 1-16 | 4-34 | 2-14 |
| 3-30 | 1-39 | 3-23 | 2-23 |
| 1-69 | 3-20 | 1-24 | 2-23 |
| 4-39 | 3-15 | | |
| 4-31 | 2-40 | | |
| 3-33 | 3-20 | | |
| 4-59 | 4-1 | | |
| 4-34 | 1-39 | | |
| 4-59 | 3-11 | | |
| 3-11 | 3-15 | | |
| 1-18 | 1-5 | | |
| 3-7 | 1-39 | | |
| 4-34 | 4-1 | | |

S6 mn

| VH | Vk | VH | VL |
|---|---|---|---|
| 1-18 | 3-20 | 1-8 | 2-8 |
| 4-59 | 1D-39 | 4-34 | 1-51 |
| 3-53 | 3-11 | 3-11 | 8-61 |
| 4-4 | 1-5 | 1-18 | 6-57 |
| 3-53 | 1D-33 | 4-34 | 2-14 |
| 3-9 | 1D-39 | 4-34 | 1-47 |
| 5-51 | 1D-39 | 1-2 | 2-14 |
| 3-11 | 1-9 | 3-21 | 4-69 |
| 3-7 | 3-11 | 3-74 | 1-47 |
| 1-18 | 4-1 | | |
| 3-48 | 1-6 | | |
| 4-59 | 1D-39 | | |
| 3-53 | 4-1 | | |
| 3-30 | 4-1 | | |
| 4-59 | 4-1 | | |
| 3-30 | 1-5 | | |
| 4-59 | 1D-39 | | |
| 3-7 | 2-30 | | |
| 4-59 | 1D-39 | | |
| 3-53 | 3-15 | | |
| 3-23 | 1-27 | | |
| 4-34 | 1D-39 | | |
| 1-2 | 1D-39 | | |
| 3-23 | 2-29 | | |
| 3-13 | 1D-33 | | |
| 4-59 | 3-20 | | |
| 3-21 | 4-1 | | |
| 3-7 | 3-20 | | |
| 3-21 | 3-15 | | |
| 1-8 | 1D-39 | | |
| 3-66 | 1D-39 | | |
| 3-23 | 3-20 | | |
| 3-21 | 1-8 | | |
| 3-13 | 1D-39 | | |
| 3-23 | 1-27 | | |
| 3-23 | 1-17 | | |
| 3-21 | 1D-39 | | |
| 1-18 | 2-28 | | |
| 4-34 | 1-5 | | |
| 4-54 | 3-11 | | |
| 3-49 | 1D-39 | | |
| 4-39 | 1D-39 | | |
| 3-48 | 2D-29 | | |
| 3-21 | 1D-39 | | |
| 3-64 | 1-9 | | |
| 3-23 | 3-20 | | |
| 3-53 | 3-20 | | |
| 4-34 | 3-20 | | |
| 3-23 | 1-17 | | |
| 4-4 | 1-27 | | |
| 4-34 | 1D-33 | | |
| 3-48 | 1-8 | | |
| 1-24 | 4-1 | | |
| 4-4 | 2-28 | | |

Figure 28

| | VH | Vk | Vl |
|---|---|---|---|
| ascTT_201 | 1-02*02 | | 1-44*01 |
| ascTT_65 | 1-02*02 | | 1-51*01 |
| ascTT_153 | 1-02*02 | | 2-14*04 |
| ascTT_316 | 1-02*02 | | 7-46*01 |
| ascTT_294 | 1-02*04 | | 2-14*03 |
| ascTT_307 | 1-08*01 | 1-05*03 | |
| ascTT_350 | 1-18*01 | 1-17*01 | |
| ascTT_06 | 1-18*01 | 3-20*01 | |
| ascTT_207 | 1-18*01 | | 1-51*01 |
| ascTT_164 | 1-58*01 | 3-20*01 | |
| ascTT_395 | 1-69*01 | 3-15*01 | |
| ascTT_138 | 1-69*01 | 3-20*01 | |
| ascTT_214 | 1-69*01 | 4-01*01 | |
| ascTT_51 | 1-69*01 | | 1-44*01 |
| ascTT_176 | 1-69*01 | | 1-44*01 |
| ascTT_212 | 1-69*01 | | 1-44*01 |
| ascTT_258 | 1-69*01 | | 1-44*01 |
| ascTT_327 | 1-69*01 | | 1-44*01 |
| ascTT_08 | 1-69*01 | | 2-11*01 |
| ascTT_310 | 1-69*06 | 1-27*01 | |
| ascTT_255 | 1-69*06 | 1-39*01 | |
| ascTT_178 | 1-69*06 | 3-11*01 | |
| ascTT_79 | 1-69*06 | 3-15*01 | |
| ascTT_334 | 1-69*06 | 3-15*01 | |
| ascTT_105 | 1-69*06 | 3D-15*01 | |
| ascTT_61 | 1-69*06 | 4-01*01 | |
| ascTT_231 | 1-69*06 | 4-01*01 | |
| ascTT_265 | 1-69*06 | | 1-47*01 |
| ascTT_179 | 1-69*06 | | 6-57*01 |
| ascTT_101 | 3-07*01 | 1-05*03 | |
| ascTT_42 | 3-07*01 | | 1-44*01 |
| ascTT_195 | 3-07*01 | | 1-44*01 |
| ascTT_390 | 3-09*01 | | 1-51*01 |
| ascTT_182 | 3-09*01 | | |
| ascTT_188 | 3-09*01 | | |
| ascTT_225 | 3-09*01 | | |
| ascTT_319 | 3-11*01 | 1-12*01 | |
| ascTT_29 | 3-11*01 | | 1-40*01 |
| ascTT_385 | 3-11*01 | | 7-46*01 |
| ascTT_87 | 3-11*03 | 1-39*01 | |
| ascTT_349 | 3-20*01 | | 2-14*03 |
| ascTT_156 | 3-21*01 | | 1-51*01 |
| ascTT_344 | 3-21*01 | | 3-21*01 |

Figure 29

| | VH | Vk | Vl |
|---|---|---|---|
| ascTT_31 | 3-23*01 | 1-05*03 | |
| ascTT_45 | 3-23*01 | 1-05*03 | |
| ascTT_59 | 3-23*01 | 1-05*03 | |
| ascTT_78 | 3-23*01 | 1-05*03 | |
| ascTT_88 | 3-23*01 | 1-05*03 | |
| ascTT_148 | 3-23*01 | 1-05*03 | |
| ascTT_292 | 3-23*01 | 1-05*03 | |
| ascTT_320 | 3-23*01 | 1-05*03 | |
| ascTT_348 | 3-23*01 | 1-05*03 | |
| ascTT_358 | 3-23*01 | 1-39*01 | |
| ascTT_365 | 3-23*01 | 1-39*01 | |
| ascTT_158 | 3-23*01 | 3-20*01 | |
| ascTT_204 | 3-23*01 | | 1-44*01 |
| ascTT_245 | 3-23*01 | | 1-44*01 |
| ascTT_275 | 3-23*01 | | 1-44*01 |
| ascTT_56 | 3-23*01 | | 2-14*04 |
| ascTT_278 | 3-23*01 | | 2-23*01 |
| ascTT_21 | 3-30*18 | 1-09*01 | |
| ascTT_335 | 3-30*18 | 3-11*01 | |
| ascTT_159 | 3-30*18 | 3-15*01 | |
| ascTT_274 | 3-30*18 | 3-15*01 | |
| ascTT_109 | 3-30*18 | | 1-40*01 |
| ascTT_27 | 3-30*18 | | 2-14*01 |
| ascTT_394 | 3-30*18 | | 3-21*03 |
| ascTT_193 | 3-33*01 | 3-15*01 | |
| ascTT_144 | 3-33*05 | | 4-69*02 |
| ascTT_162 | 3-43*01 | | 2-11*01 |
| ascTT_124 | 3-43*01 | | 9-49*01 |
| ascTT_57 | 3-48*01 | 3-20*01 | |
| ascTT_77 | 3-48*01 | 3-20*01 | |
| ascTT_01 | 3-53*01 | | 1-44*01 |
| ascTT_28 | 3-53*01 | | 1-44*01 |
| ascTT_36 | 3-53*01 | | 1-44*01 |
| ascTT_141 | 3-53*01 | | 1-44*01 |
| ascTT_229 | 3-53*01 | | 1-44*01 |
| ascTT_304 | 3-53*01 | | 1-44*01 |
| ascTT_341 | 3-53*01 | | 1-44*01 |
| ascTT_354 | 3-53*01 | | 1-44*01 |
| ascTT_134 | 3-64*05 | | 3-21*01 |
| ascTT_03 | 3-74*01 | | 2-23*01 |
| ascTT_259 | 4-30-2*01 | 4-01*01 | |
| ascTT_328 | 4-31*03 | 3-20*01 | |
| ascTT_306 | 4-31*03 | | 1-51*01 |

Figure 30

| | VH | Vk | Vl |
|---|---|---|---|
| ascTT_25 | 4-31*03 | | 2-08*01 |
| ascTT_85 | 4-31*03 | | 2-08*01 |
| ascTT_96 | 4-31*03 | | 2-08*01 |
| ascTT_185 | 4-31*03 | | 2-08*01 |
| ascTT_187 | 4-31*03 | | 2-08*01 |
| ascTT_312 | 4-31*03 | | 2-08*01 |
| ascTT_311 | 4-31*03 | | 2-08*01 |
| ascTT_313 | 4-31*03 | | 2-08*01 |
| ascTT_116 | 4-31*03 | | 2-08*01 |
| ascTT_196 | 4-39*01 | 1-06*01 | |
| ascTT_47 | 4-39*01 | 2-28*01 | |
| ascTT_295 | 4-39*01 | | 1-40*01 |
| ascTT_318 | 4-39*01 | | 1-44*01 |
| ascTT_337 | 4-39*01 | | 1-44*01 |
| ascTT_35 | 4-39*01 | | 3-21*03 |
| ascTT_40 | 4-39*01 | | 3-21*03 |
| ascTT_81 | 4-39*01 | | 3-21*03 |
| ascTT_93 | 4-39*01 | | 3-21*03 |
| ascTT_126 | 4-39*01 | | 3-21*03 |
| ascTT_166 | 4-39*01 | | 3-21*03 |
| ascTT_210 | 4-39*01 | | 3-21*03 |
| ascTT_224 | 4-39*01 | | 3-21*03 |
| ascTT_244 | 4-39*01 | | 3-21*03 |
| ascTT_370 | 4-39*01 | | 3-21*03 |
| ascTT_392 | 4-39*01 | | 3-21*03 |
| ascTT_232 | 4-39*01 | | 3-21*03 |
| ascTT_263 | 4-59*01 | | 2-08*01 |
| ascTT_15 | 4-59*01 | 1-39*01 | |
| ascTT_122 | 4-59*01 | 3-15*01 | |
| ascTT_276 | 4-59*01 | 3-15*01 | |
| ascTT_302 | 4-59*01 | 3-15*01 | |
| ascTT_110 | 4-59*03 | 1-39*01 | |
| ascTT_34 | 4-59*04 | 1-39*01 | |
| ascTT_173 | 4-61*01 | | 2-14*03 |
| ascTT_177 | 5-51*01 | 1-13*02 | |
| ascTT_190 | 5-51*01 | 1-13*02 | |
| ascTT_233 | 5-51*01 | 1-13*02 | |
| ascTT_84 | 5-51*01 | 1-13*02 | |
| ascTT_43 | 5-51*01 | 1-13*02 | |
| ascTT_147 | 5-51*01 | 1-13*02 | |
| ascTT_377 | 5-51*01 | 3-11*01 | |
| ascTT_82 | 5-51*01 | 3-15*01 | |

Figure 31

| | VH | Vk | Vl |
|---|---|---|---|
| mnTT_16 | 1-02*02 | 2-30*01 | |
| mnTT_125 | 1-02*02 | 3-20*01 | |
| mnTT_436 | 1-02*02 | 3-20*01 | |
| mnTT_507 | 1-02*02 | 3-20*01 | |
| mnTT_238 | 1-02*02 | | 1-44*01 |
| mnTT_260 | 1-02*02 | | 1-51*01 |
| mnTT_451 | 1-02*02 | | 1-51*01 |
| mnTT_284 | 1-02*02 | | 2-14*03 |
| mnTT_20 | 1-02*02 | | 2-23*01 |
| mnTT_278 | 1-02*02 | | 2-23*01 |
| mnTT_166 | 1-02*02 | | 3-21*02 |
| mnTT_170 | 1-02*02 | | 7-46*01 |
| mnTT_548 | 1-02*03 | 4-01*01 | |
| mnTT_70 | 1-02*03 | | 3-01*01 |
| mnTT_75 | 1-18*01 | 1-05*03 | |
| mnTT_149 | 1-18*01 | 1-12*02 | |
| mnTT_17 | 1-18*01 | 1-13*02 | |
| mnTT_06 | 1-18*01 | 1-16*02 | |
| mnTT_492 | 1-18*01 | 1-33*01 | 1-44*01 |
| mnTT_490 | 1-18*01 | 1-33*01 | |
| mnTT_321 | 1-18*01 | 1-39*01 | |
| mnTT_542 | 1-18*01 | 2-30*01 | |
| mnTT_318 | 1-18*01 | 3-15*01 | |
| mnTT_101 | 1-18*01 | 3-20*01 | |
| mnTT_29 | 1-18*01 | | 1-40*01 |
| mnTT_309 | 1-24*01 | 2-28*01 | |
| mnTT_220 | 1-24*01 | 3-11*01 | |
| mnTT_311 | 1-24*01 | 3-15*01 | |
| mnTT_145 | 1-24*01 | | 1-40*01 |
| mnTT_217 | 1-24*01 | | 3-21*02 |
| mnTT_119 | 1-46*01 | 1-05*03 | |
| mnTT_76 | 1-46*01 | 1-09*01 | |
| mnTT_230 | 1-46*01 | 1-39*01 | |
| mnTT_365 | 1-46*01 | 3-15*01 | |
| mnTT_328 | 1-46*01 | 3-20*01 | |
| mnTT_526 | 1-46*01 | 3-20*01 | |
| mnTT_457 | 1-46*01 | | 2-11*01 |
| mnTT_57 | 1-46*01 | | 2-14*03 |
| mnTT_88 | 1-46*01 | | 3-21*02 |
| mnTT_530 | 1-69*01 | 1-05*03 | |
| mnTT_263 | 1-69*01 | 1-33*01 | |
| mnTT_317 | 1-69*01 | 1-33*01 | |
| mnTT_61 | 1-69*01 | 1-39*01 | |
| mnTT_331 | 1-69*01 | 1-39*01 | |
| mnTT_395 | 1-69*01 | 1-39*01 | |
| mnTT_487 | 1-69*01 | 2D-29*01 | |
| mnTT_18 | 1-69*01 | 3-11*01 | |
| mnTT_234 | 1-69*01 | 3-15*01 | 2-23*01 |

Figure 32

| | VH | Vk | Vl |
|---|---|---|---|
| mnTT_379 | 1-69*01 | 3-15*01 | |
| mnTT_27 | 1-69*01 | 3-20*01 | |
| mnTT_90 | 1-69*01 | 3-20*01 | |
| mnTT_209 | 1-69*01 | 3-20*01 | |
| mnTT_351 | 1-69*01 | 3-20*01 | |
| mnTT_432 | 1-69*01 | 4-01*01 | |
| mnTT_545 | 1-69*01 | 4-01*01 | |
| mnTT_95 | 1-69*01 | | 1-40*01 |
| mnTT_279 | 1-69*01 | | 1-40*01 |
| mnTT_332 | 1-69*01 | | 1-40*02 |
| mnTT_147 | 1-69*01 | | 1-44*01 |
| mnTT_183 | 1-69*01 | | 1-51*01 |
| mnTT_01 | 1-69*01 | | 2-14*03 |
| mnTT_292 | 1-69*01 | | 2-14*03 |
| mnTT_244 | 1-69*01 | | 2-14*04 |
| mnTT_71 | 1-69*01 | | 2-23*01 |
| mnTT_525 | 1-69*01 | | 2-23*01 |
| mnTT_250 | 1-69*01 | | 3-01*01 |
| mnTT_136 | 1-69*01 | | 1-51*01 |
| mnTT_342 | 1-69*06 | 1-05*03 | |
| mnTT_163 | 1-69*06 | 1-08*01 | |
| mnTT_48 | 1-69*06 | 3-11*01 | |
| mnTT_255 | 1-69*06 | 4-01*01 | |
| mnTT_196 | 1-69*06 | | 1-47*01 |
| mnTT_226 | 1-69*06 | | 3-21*02 |
| mnTT_168 | 3-07*01 | 1-17*01 | |
| mnTT_281 | 3-07*01 | 1-39*01 | |
| mnTT_381 | 3-07*01 | 1-39*01 | |
| mnTT_518 | 3-07*01 | 1-39*01 | |
| mnTT_327 | 3-07*01 | | 1-44*01 |
| mnTT_64 | 3-07*02 | 1-05*03 | |
| mnTT_434 | 3-07*02 | 1-13*02 | |
| mnTT_303 | 3-09*01 | 1-37*01 | |
| mnTT_419 | 3-09*01 | | 1-47*01 |
| mnTT_144 | 3-09*01 | | 2-23*01 |
| mnTT_13 | 3-09*01 | | 2-23*03 |
| mnTT_39 | 3-09*01 | | 2-23*03 |
| mnTT_37 | 3-09*01 | | 3-21*02 |
| mnTT_405 | 3-09*01 | | 3-21*03 |
| mnTT_131 | 3-09*01 | 3-11*01 | |
| mnTT_121 | 3-11*01 | 1-05*03 | |
| mnTT_473 | 3-11*01 | 1-05*03 | |
| mnTT_385 | 3-11*01 | 1-17*01 | |
| mnTT_256 | 3-11*01 | 1-33*01 | |
| mnTT_382 | 3-11*01 | 3-20*01 | |
| mnTT_66 | 3-11*01 | 4-01*01 | |
| mnTT_111 | 3-11*01 | | 3-25*01 |
| mnTT_127 | 3-11*01 | 2-28*01 | |
| mnTT_49 | 3-11*03 | 1-39*01 | |

Figure 33

| | VH | Vk | Vl |
|---|---|---|---|
| mnTT_537 | 3-11*03 | 3-11*01 | |
| mnTT_246 | 3-11*03 | 3-15*01 | |
| mnTT_481 | 3-11*03 | 4-01*01 | |
| mnTT_272 | 3-11*03 | | 3-21*01 |
| mnTT_368 | 3-13*01 | 4-01*01 | |
| mnTT_252 | 3-15*01 | 1-05*03 | |
| mnTT_290 | 3-15*01 | 1-05*03 | |
| mnTT_259 | 3-15*01 | 2-28*01 | |
| mnTT_228 | 3-15*01 | 2D-29*01 | |
| mnTT_326 | 3-15*01 | 4-01*01 | |
| mnTT_192 | 3-15*01 | | 1-51*01 |
| mnTT_59 | 3-15*01 | | 2-14*04 |
| mnTT_12 | 3-15*01 | | 7-46*01 |
| mnTT_63 | 3-15*01 | | 7-46*01 |
| mnTT_233 | 3-21*01 | 1-05*03 | |
| mnTT_221 | 3-21*01 | 1-39*01 | |
| mnTT_41 | 3-21*01 | 3-20*01 | |
| mnTT_56 | 3-21*01 | 4-01*01 | |
| mnTT_383 | 3-21*01 | 4-01*01 | |
| mnTT_148 | 3-21*01 | | 1-47*01 |
| mnTT_182 | 3-21*01 | | 1-51*01 |
| mnTT_215 | 3-21*01 | | 1-51*01 |
| mnTT_369 | 3-21*01 | | 1-51*01 |
| mnTT_443 | 3-21*01 | | 2-11*01 |
| mnTT_350 | 3-21*01 | | 3-25*01 |
| mnTT_335 | 3-23*01 | 1-05*03 | |
| mnTT_15 | 3-23*01 | 1-17*01 | |
| mnTT_78 | 3-23*01 | 1-33*01 | 3-21*02 |
| mnTT_418 | 3-23*01 | 1-33*01 | |
| mnTT_520 | 3-23*01 | 1-33*01 | |
| mnTT_107 | 3-23*01 | 1-39*01 | |
| mnTT_466 | 3-23*01 | 1-39*01 | |
| mnTT_485 | 3-23*01 | 1-39*01 | |
| mnTT_488 | 3-23*01 | 1-39*01 | |
| mnTT_34 | 3-23*01 | 1D-12*01 | |
| mnTT_158 | 3-23*01 | 2-30*01 | |
| mnTT_176 | 3-23*01 | 2D-29*01 | |
| mnTT_315 | 3-23*01 | 2D-29*01 | |
| mnTT_116 | 3-23*01 | 3-11*01 | 2-23*01 |
| mnTT_87 | 3-23*01 | 3-11*01 | |
| mnTT_512 | 3-23*01 | 3-15*01 | |
| mnTT_393 | 3-23*01 | 3-20*01 | |
| mnTT_539 | 3-23*01 | 4-01*01 | |
| mnTT_480 | 3-23*01 | | 1-47*01 |
| mnTT_322 | 3-23*01 | | 2-11*01 |
| mnTT_329 | 3-23*01 | | 2-11*01 |
| mnTT_162 | 3-23*01 | | 2-14*03 |
| mnTT_258 | 3-23*01 | | 2-14*03 |
| mnTT_216 | 3-23*01 | | 2-14*04 |

Figure 34

| | VH | Vk | Vl |
|---|---|---|---|
| mnTT_108 | 3-23*01 | | 3-01*01 |
| mnTT_179 | 3-23*01 | | 3-21*02 |
| mnTT_195 | 3-23*01 | | 3-21*02 |
| mnTT_423 | 3-30*18 | 1-33*01 | |
| mnTT_468 | 3-30*18 | 1D-8*01 | |
| mnTT_153 | 3-30*18 | 2-28*01 | |
| mnTT_286 | 3-30*18 | 3-11*01 | |
| mnTT_242 | 3-30*18 | 4-01*01 | |
| mnTT_185 | 3-30*18 | | 1-44*01 |
| mnTT_547 | 3-30*18 | | 1-51*01 |
| mnTT_251 | 3-30*18 | | 2-14*03 |
| mnTT_126 | 3-30*18 | | 2-14*04 |
| mnTT_415 | 3-30*18 | | 2-14*04 |
| mnTT_440 | 3-30*18 | | 2-14*04 |
| mnTT_72 | 3-30*18 | | 2-23*01 |
| mnTT_267 | 3-33*01 | 1-39*01 | |
| mnTT_123 | 3-33*01 | 3-20*01 | |
| mnTT_493 | 3-33*01 | 4-01*01 | |
| mnTT_516 | 3-33*01 | | 1-47*01 |
| mnTT_184 | 3-33*01 | | 2-14*03 |
| mnTT_44 | 3-33*01 | | 3-21*01 |
| mnTT_156 | 3-33*01 | | 3-21*01 |
| mnTT_10 | 3-33*01 | | 9-49*01 |
| mnTT_140 | 3-33*01 | 1-39*01 | |
| mnTT_138 | 3-33*01 | | 3-01*01 |
| mnTT_81 | 3-33*01 | | 3-21*01 |
| mnTT_506 | 3-43*01 | 4-01*01 | |
| mnTT_08 | 3-48*01 | 1-08*01 | |
| mnTT_522 | 3-48*01 | 1-39*01 | |
| mnTT_106 | 3-48*01 | 4-01*01 | |
| mnTT_91 | 3-48*01 | | 1-40*01 |
| mnTT_79 | 3-48*02 | 1-17*01 | |
| mnTT_194 | 3-48*02 | 1-39*01 | |
| mnTT_130 | 3-48*02 | 3-15*01 | |
| mnTT_282 | 3-48*02 | | 9-49*01 |
| mnTT_426 | 3-49*03 | 3-11*01 | |
| mnTT_474 | 3-49*05 | 1-17*01 | |
| mnTT_270 | 3-49*05 | 2-28*01 | |
| mnTT_453 | 3-53*01 | 1-33*01 | |
| mnTT_305 | 3-53*01 | 3-15*01 | |
| mnTT_137 | 3-53*01 | | 2-08*01 |
| mnTT_65 | 3-53*01 | | 2-23*01 |
| mnTT_358 | 3-64*05 | 1-05*03 | |
| mnTT_53 | 3-64*05 | 3-11*01 | |
| mnTT_447 | 3-72*01 | 1-05*03 | |
| mnTT_283 | 3-72*01 | | 4-69*01 |
| mnTT_82 | 3-73*01 | | 2-11*01 |
| mnTT_177 | 3-74*01 | 1-05*03 | |
| mnTT_09 | 3-74*01 | 4-01*01 | |

Figure 35

| | VH | Vk | Vl |
|---|---|---|---|
| mnTT_143 | 3-74*01 | | 2-14*04 |
| mnTT_276 | 4-04*07 | 1-17*01 | |
| mnTT_102 | 4-04*07 | 3-15*01 | |
| mnTT_191 | 4-04*07 | | 1-44*01 |
| mnTT_467 | 4-04*07 | | 1-51*01 |
| mnTT_374 | 4-04*07 | | 3-25*01 |
| mnTT_132 | 4-04*07 | 1-39*01 | |
| mnTT_104 | 4-30-2*01 | 1-39*01 | |
| mnTT_408 | 4-30-2*01 | | 3-21*01 |
| mnTT_319 | 4-31*01 | 1-05*03 | |
| mnTT_323 | 4-31*01 | 3-15*01 | |
| mnTT_50 | 4-31*02 | 1-39*01 | |
| mnTT_188 | 4-31*02 | 3-11*01 | |
| mnTT_14 | 4-31*02 | | 2-14*03 |
| mnTT_77 | 4-31*02 | | 2-23*01 |
| mnTT_257 | 4-31*03 | | 1-40*01 |
| mnTT_533 | 4-31*03 | | 1-47*01 |
| mnTT_546 | 4-34*01 | 1-05*03 | |
| mnTT_02 | 4-34*01 | 1-08*01 | |
| mnTT_266 | 4-34*01 | 1-12*01 | |
| mnTT_380 | 4-34*01 | 1-16*01 | |
| mnTT_157 | 4-34*01 | 1-33*01 | |
| mnTT_146 | 4-34*01 | 1-39*01 | |
| mnTT_384 | 4-34*01 | 3-11*01 | |
| mnTT_73 | 4-34*01 | 3-20*01 | |
| mnTT_376 | 4-34*01 | 3-20*01 | |
| mnTT_236 | 4-34*01 | 4-01*01 | |
| mnTT_89 | 4-34*01 | | 1-36*01 |
| mnTT_68 | 4-34*01 | | 1-40*02 |
| mnTT_69 | 4-34*01 | | 1-47*01 |
| mnTT_367 | 4-34*01 | | 1-47*01 |
| mnTT_32 | 4-34*01 | | 1-51*01 |
| mnTT_225 | 4-34*01 | | 1-51*01 |
| mnTT_511 | 4-34*01 | | 1-51*01 |
| mnTT_441 | 4-34*01 | | 2-08*01 |
| mnTT_294 | 4-34*01 | | 2-14*03 |
| mnTT_219 | 4-34*01 | | 3-21*01 |
| mnTT_165 | 4-34*01 | | 3-25*01 |
| mnTT_241 | 4-34*01 | | 7-43*01 |
| mnTT_523 | 4-34*01 | | 9-49*01 |
| mnTT_273 | 4-39*01 | 1-05*03 | |
| mnTT_333 | 4-39*01 | 1-05*03 | |
| mnTT_262 | 4-39*01 | 1-06*01 | |
| mnTT_459 | 4-39*01 | 1-27*01 | 1-40*01 |
| mnTT_361 | 4-39*01 | 1-33*01 | |
| mnTT_84 | 4-39*01 | 1-39*01 | |
| mnTT_312 | 4-39*01 | 1-39*01 | |
| mnTT_141 | 4-39*01 | 2-28*01 | |
| mnTT_455 | 4-39*01 | 2-28*01 | |

Figure 36

| | VH | Vk | Vl |
|---|---|---|---|
| mnTT_458 | 4-39*01 | 2-30*01 | |
| mnTT_360 | 4-39*01 | 3-11*01 | |
| mnTT_544 | 4-39*01 | 3-11*01 | |
| mnTT_103 | 4-39*01 | 3-15*01 | |
| mnTT_110 | 4-39*01 | 3-15*01 | |
| mnTT_513 | 4-39*01 | 3-15*01 | |
| mnTT_316 | 4-39*01 | 3-20*01 | |
| mnTT_271 | 4-39*01 | 4-01*01 | |
| mnTT_448 | 4-39*01 | 4-01*01 | |
| mnTT_83 | 4-39*01 | | 1-44*01 |
| mnTT_05 | 4-39*01 | | 1-51*01 |
| mnTT_74 | 4-39*01 | | 2-08*01 |
| mnTT_254 | 4-39*01 | | 2-08*01 |
| mnTT_462 | 4-39*01 | | 2-18*02 |
| mnTT_171 | 4-39*01 | | 3-01*01 |
| mnTT_135 | 4-39*01 | | 2-08*01 |
| mnTT_340 | 4-59*01 | 1-05*03 | |
| mnTT_477 | 4-59*01 | 1-17*01 | |
| mnTT_28 | 4-59*01 | 1-39*01 | |
| mnTT_47 | 4-59*01 | 1-39*01 | |
| mnTT_353 | 4-59*01 | 3-11*01 | |
| mnTT_269 | 4-59*01 | 3-15*01 | |
| mnTT_338 | 4-59*01 | 4-01*01 | |
| mnTT_357 | 4-59*01 | 4-01*01 | |
| mnTT_118 | 4-59*01 | | 1-40*01 |
| mnTT_231 | 4-59*01 | | 1-40*01 |
| mnTT_337 | 4-59*01 | | 1-40*02 |
| mnTT_427 | 4-59*01 | | 2-11*01 |
| mnTT_519 | 4-59*01 | | 2-23*01 |
| mnTT_339 | 4-59*01 | | 3-01*01 |
| mnTT_442 | 4-59*01 | 1-39*01 | |
| mnTT_207 | 4-61*01 | 1-12*01 | |
| mnTT_218 | 4-61*01 | 1-39*01 | |
| mnTT_159 | 4-61*01 | 2-28*01 | |
| mnTT_211 | 4-61*01 | | 1-44*01 |
| mnTT_253 | 4-61*01 | | 1-44*01 |
| mnTT_521 | 4-61*01 | | 1-44*01 |
| mnTT_428 | 4-61*01 | | 3-21*01 |
| mnTT_151 | 4-61*07 | | 2-11*01 |
| mnTT_352 | 4-61*08 | 4-01*01 | |
| mnTT_407 | 4-61*08 | 4-01*01 | |
| mnTT_169 | 5-51*01 | 1-33*01 | |
| mnTT_62 | 5-51*01 | 3-11*01 | |
| mnTT_430 | 5-51*01 | 3-11*01 | |
| mnTT_295 | 5-51*01 | 3-15*01 | |
| mnTT_424 | 5-51*01 | 3-20*01 | |
| mnTT_444 | 5-51*01 | 3-20*01 | |
| mnTT_464 | 5-a*01 | 1D-33*01 | |
| mnTT_26 | 5-a*01 | | 2-14*03 |
| mnTT_210 | 5-a*01 | | 2-23*03 |

Figure 37

Summary 20 VH region genes

| | Heavy chain germline genes | CDR lengths Kabat CDR-H1 | CDR lengths Kabat CDR2-H2 | VNTI pI | Ranking pos | PTMs (w/o NxS/T) | NxS/T | Met in CDRs | Cysteine (to be removed) | Epibase check Deviations from germline | Epibase check Strong T-cell epitope | Aggresolve Theoretical aggregation propensity |
|---|---|---|---|---|---|---|---|---|---|---|---|---|
| 1 | hVH_1_2 | 5 | 17 | 9.4 | 14 | 2 | 0 | 1 | 0 | 0 | 0 | intermediate |
| 2 | hVH_1_18 | 5 | 17 | 9.2 | 9 | 2 | 0 | 0 | 0 | 0 | 0 | high |
| 3 | hVH_1_69 | 5 | 17 | 9.3 | 7 | 0 | 0 | 0 | 0 | 0 | 0 | intermediate |
| 4 | hVH_1_46 | 5 | 17 | 9.2 | 21 | 4 | 0 | 1 | 0 | 0 | 0 | n.d. |
| 5 | hVH_3_7 | 5 | 17 | 8.6 | 8 | 2 | 0 | 1 | 0 | 0 | 0 | low |
| 6 | hVH_3_11 | 5 | 17 | 9.0 | 17 | 3 | 0 | 1 | 0 | 0 | 0 | n.d. |
| 7 | hVH_3_15 | 5 | 19 | 9.0 | 12 | 3 | 0 | 1 | 0 | 0 | 0 | low |
| 8 | hVH_3_21 | 5 | 17 | 9.0 | 11 | 4 | 0 | 1 | 0 | 0 | 0 | intermediate |
| 9 | hVH_3_23 | 5 | 17 | 8.7 | 1 | 4 | 0 | 1 | 0 | 0 | 0 | intermediate |
| 10 | hVH_3_30 | 5 | 17 | 9.0 | 2 | 3 | 0 | 1 | 0 | 0 | 0 | intermediate |
| 11 | hVH_3_33 | 5 | 17 | 9.5 | 15 | 3 | 0 | 1 | 0 | 0 | 0 | n.d. |
| 12 | hVH_3_48 | 5 | 17 | 6.0 | 10 | 3 | 0 | 1 | 0 | 0 | 0 | intermediate |
| 13 | hVH_3_53 | 5 | 16 | 8.7 | 16 | 3 | 0 | 1 | 0 | 0 | 0 | intermediate |
| 14 | hVH_3_73 | 5 | 19 | 9.5 | 33 | 3 | 0 | 1 | 0 | 0 | 0 | n.d. |
| 15 | hVH_3_74 | 5 | 17 | 9.1 | 19 | 4 | 0 | 1 | 0 | 0 | 0 | n.d. |
| 16 | hVH_4_4 | 6 | 16 | 9.5 | 20 | 0 | 0 | 0 | 0 | 0 | 0 | n.d. |
| 17 | hVH_4_31 | 7 | 16 | 9.2 | 13 | 0 | 0 | 0 | 0 | 0 | 0 | n.d. |
| 18 | hVH_4_39 | 7 | 16 | 8.0 | 3 | 1 | 0 | 0 | 1 | 0 | 0 | n.d. |
| 19 | hVH_5_51 | 5 | 17 | 8.6 | 6 | 0 | 0 | 0 | 0 | 0 | 0 | intermediate |
| 20 | hVH_6_1 | 7 | 18 | 9.3 | 39 | 3 | 0 | 1 | 0 | 0 | 0 | n.d. |

Figure 38

Summary 20 VL region genes

| | Light chain germline genes | Kabat CDR-L1 | Kabat CDR-L2 | VNTI pI | Ranking pos | PTMs (w/o NxS/T) | NxS/T | Met in CDRs | Cysteine (to be removed) | Deviations from germline | Strong T-cell epitope | Theoretical aggregation propensity |
|---|---|---|---|---|---|---|---|---|---|---|---|---|
| 1 | hVL_1-40 | 14 | 7 | 4.9 | 2 | 1 | 0 | 0 | 0 | 0 | 0 | intermediate |
| 2 | hVL_1-47 | 13 | 7 | 5.0 | 5 | 0 | 0 | 0 | 0 | 0 | 0 | intermediate |
| 3 | hVL_1-51 | 13 | 7 | 6.2 | 4 | 0 | 0 | 0 | 0 | 1 | 0 | intermediate |
| 4 | hVL_2-11 | 14 | 7 | 6.7 | 8 | 0 | 0 | 0 | 0 | 0 | 0 | n.d. |
| 5 | hVL_2-23 | 14 | 7 | 6.7 | 6 | 0 | 0 | 0 | 0 | 0 | 0 | n.d. |
| 6 | hVL_2-14 | 14 | 7 | 5.6 | 9 | 0 | 0 | 0 | 0 | 0 | 0 | high |
| 7 | hVL_3-1 | 11 | 7 | 4.5 | 7 | 2 | 0 | 0 | 1 | 2 | 1* | n.d. |
| 8 | hVL_3-21 | 11 | 7 | 4.8 | 3 | 1 | 0 | 0 | 0 | 1 | 1* | high |
| 9 | hVK_1_5 | 11 | 7 | 5.0 | 16 | 0 | 0 | 0 | 0 | 0 | 0 | n.d. |
| 10 | hVK_1_6 | 11 | 7 | 8.0 | 20 | 0 | 0 | 0 | 0 | 0 | 0 | n.d. |
| 11 | hVK_1_9 | 11 | 7 | 8.0 | 15 | 0 | 0 | 0 | 0 | 0 | 0 | n.d. |
| 12 | hVK_1_12 | 11 | 7 | 8.0 | 14 | 0 | 0 | 0 | 0 | 0 | 0 | n.d. |
| 13 | hVK_1_16 | 11 | 7 | 8.7 | 11 | 0 | 0 | 0 | 0 | 0 | 0 | n.d. |
| 14 | hVK_1_17 | 11 | 7 | 8.7 | 12 | 0 | 0 | 0 | 0 | 0 | 0 | n.d. |
| 15 | hVK_1_27 | 11 | 7 | 8.9 | 2 | 0 | 0 | 0 | 0 | 0 | 0 | n.d. |
| 16 | hVK_1_39 | 11 | 7 | 8.0 | 10 | 2 | 0 | 0 | 0 | 0 | 0 | high |
| 17 | hVK_2_30 | 16 | 7 | 8.0 | 6 | 0 | 0 | 0 | 0 | 0 | 0 | n.d. |
| 18 | hVK_3_11 | 11 | 7 | 6.3 | 4 | 0 | 0 | 0 | 0 | 0 | 0 | intermediate |
| 19 | hVK_3_15 | 11 | 7 | 8.9 | 1 | 0 | 0 | 0 | 0 | 0 | 0 | intermediate |
| 20 | hVK_3_20 | 12 | 7 | 6.3 | 13 | 0 | 0 | 0 | 0 | 0 | 0 | (n.d.) |
| alt. | hVK_1_8 | 11 | 7 | 8.9 | 18 | 0 | 0 | 0 | 1 | n.d. | n.d. | n.d. |

| 779.0 | IGLV 2-14 | IGLV 1-40 | IGLV 1-44 | IGLV 1-51 | IGLV 1-47 | IGLV 2-23 | IGLV 3-21 | IGLV 2-11 | IGLV 3-1 | IGLV 2-8 | IGLV 6-57 | IGLV 1-36 | IGLV 3-25 | IGLV 4-69 | IGLV 7-43 | IGLV 7-46 | IGLV 2-18 | IGLV 3-27 | IGLV 9-49 | IGLV 3-10 | IGLV 3-9 | IGLV 8-61 | IGLV 3-12 | IGLV 3-19 | IGLV 3-22 | IGLV 4-60 |
|---|---|---|---|---|---|---|---|---|---|---|---|---|---|---|---|---|---|---|---|---|---|---|---|---|---|---|
| >VH3-23 | 13 | 6 | 5 | 3 | 1 | 4 | 6 | 5 | 5 | 1 | 0 | 2 | 0 | 0 | 1 | 0 | 1 | 0 | 0 | 0 | 0 | 0 | 1 | 0 | 0 | 0 |
| >VH3-30 | 7 | 5 | 4 | 9 | 1 | 2 | 3 | 2 | 3 | 1 | 1 | 0 | 0 | 0 | 0 | 0 | 0 | 1 | 2 | 2 | 0 | 0 | 0 | 0 | 0 | 0 |
| >VH4-39 | 10 | 6 | 7 | 5 | 3 | 5 | 13 | 0 | 2 | 10 | 2 | 0 | 0 | 0 | 1 | 3 | 0 | 0 | 0 | 1 | 0 | 0 | 0 | 0 | 0 | 0 |
| >VH4-59 | 4 | 8 | 4 | 4 | 3 | 2 | 2 | 2 | 5 | 1 | 1 | 0 | 0 | 0 | 0 | 0 | 0 | 0 | 0 | 0 | 0 | 1 | 0 | 0 | 0 | 0 |
| >VH4-34 | 10 | 6 | 2 | 9 | 6 | 2 | 2 | 1 | 0 | 4 | 0 | 1 | 2 | 0 | 1 | 0 | 0 | 0 | 1 | 0 | 0 | 0 | 0 | 0 | 0 | 0 |
| >VH5-51 | 11 | 14 | 5 | 0 | 4 | 3 | 3 | 0 | 0 | 0 | 0 | 2 | 2 | 0 | 1 | 0 | 0 | 0 | 0 | 0 | 0 | 0 | 0 | 0 | 0 | 0 |
| >VH1-69 | 8 | 7 | 8 | 5 | 2 | 3 | 2 | 5 | 2 | 4 | 1 | 0 | 1 | 0 | 0 | 0 | 0 | 0 | 0 | 1 | 0 | 0 | 0 | 0 | 0 | 0 |
| >VH3-7 | 2 | 4 | 3 | 3 | 3 | 1 | 3 | 0 | 1 | 1 | 0 | 0 | 0 | 0 | 1 | 0 | 1 | 0 | 0 | 0 | 0 | 0 | 0 | 0 | 0 | 0 |
| >VH1-18 | 5 | 5 | 3 | 3 | 0 | 1 | 0 | 1 | 0 | 2 | 2 | 1 | 1 | 0 | 0 | 0 | 0 | 0 | 1 | 0 | 0 | 0 | 0 | 0 | 0 | 0 |
| >VH3-48 | 6 | 1 | 1 | 1 | 6 | 1 | 1 | 2 | 3 | 0 | 0 | 0 | 1 | 0 | 1 | 0 | 0 | 1 | 0 | 0 | 0 | 0 | 0 | 0 | 0 | 0 |
| >VH3-21 | 5 | 2 | 2 | 9 | 3 | 1 | 2 | 2 | 1 | 1 | 1 | 0 | 1 | 2 | 0 | 1 | 0 | 0 | 0 | 0 | 0 | 0 | 0 | 0 | 0 | 0 |
| >VH3-15 | 1 | 2 | 4 | 2 | 1 | 1 | 1 | 0 | 2 | 2 | 1 | 0 | 1 | 0 | 2 | 3 | 1 | 0 | 0 | 0 | 0 | 0 | 0 | 0 | 1 | 0 |
| >VH4-31 | 9 | 3 | 1 | 3 | 3 | 4 | 2 | 1 | 1 | 0 | 0 | 0 | 0 | 1 | 1 | 0 | 0 | 0 | 0 | 0 | 0 | 0 | 0 | 0 | 0 | 0 |
| >VH1-2 | 5 | 6 | 5 | 3 | 0 | 3 | 1 | 1 | 3 | 2 | 0 | 0 | 0 | 0 | 2 | 0 | 1 | 0 | 0 | 0 | 0 | 0 | 0 | 0 | 0 | 0 |
| >VH3-33 | 4 | 1 | 1 | 1 | 4 | 4 | 4 | 1 | 1 | 0 | 2 | 0 | 0 | 1 | 0 | 0 | 0 | 1 | 1 | 0 | 1 | 0 | 0 | 0 | 0 | 0 |
| >VH3-53 | 2 | 0 | 5 | 1 | 1 | 1 | 0 | 1 | 1 | 1 | 0 | 0 | 0 | 0 | 1 | 0 | 0 | 0 | 0 | 0 | 0 | 0 | 0 | 0 | 0 | 0 |
| >VH3-11 | 3 | 1 | 3 | 1 | 1 | 2 | 2 | 3 | 3 | 1 | 0 | 0 | 1 | 2 | 0 | 1 | 0 | 0 | 1 | 0 | 0 | 1 | 0 | 0 | 0 | 0 |
| >VH3-9 | 6 | 1 | 4 | 1 | 3 | 2 | 2 | 3 | 0 | 2 | 0 | 0 | 0 | 1 | 0 | 0 | 0 | 0 | 0 | 0 | 0 | 0 | 0 | 0 | 0 | 1 |
| >VH3-74 | 2 | 0 | 0 | 0 | 1 | 3 | 3 | 1 | 1 | 1 | 0 | 0 | 0 | 0 | 1 | 1 | 0 | 0 | 0 | 0 | 0 | 0 | 0 | 0 | 0 | 0 |
| >VH4-4 | 4 | 3 | 6 | 2 | 0 | 2 | 0 | 1 | 1 | 2 | 0 | 0 | 1 | 0 | 0 | 0 | 0 | 1 | 0 | 0 | 0 | 0 | 0 | 0 | 0 | 0 |
| >VH1-46 | 3 | 1 | 3 | 4 | 1 | 1 | 1 | 2 | 0 | 0 | 1 | 0 | 0 | 0 | 0 | 0 | 0 | 0 | 0 | 0 | 0 | 0 | 0 | 0 | 0 | 0 |
| >VH4-61 | 3 | 0 | 4 | 0 | 0 | 1 | 1 | 2 | 1 | 0 | 0 | 0 | 0 | 1 | 0 | 0 | 0 | 0 | 0 | 0 | 0 | 0 | 0 | 0 | 0 | 0 |
| >VH1-8 | 4 | 0 | 0 | 1 | 2 | 0 | 0 | 1 | 0 | 1 | 0 | 0 | 0 | 0 | 0 | 0 | 1 | 0 | 0 | 0 | 0 | 0 | 0 | 0 | 0 | 0 |
| >VH1-24 | 1 | 1 | 1 | 0 | 0 | 2 | 1 | 1 | 0 | 0 | 0 | 0 | 0 | 0 | 0 | 0 | 0 | 0 | 0 | 0 | 0 | 0 | 0 | 0 | 0 | 0 |
| >VH1-3 | 2 | 1 | 0 | 0 | 0 | 2 | 0 | 0 | 2 | 0 | 0 | 0 | 0 | 0 | 0 | 0 | 0 | 0 | 0 | 0 | 0 | 0 | 0 | 0 | 0 | 0 |
| >VH3-49 | 1 | 1 | 0 | 0 | 0 | 1 | 2 | 0 | 0 | 1 | 0 | 0 | 0 | 0 | 0 | 0 | 0 | 0 | 0 | 0 | 0 | 0 | 0 | 0 | 0 | 0 |
| >VH4-28 | 1 | 0 | 2 | 2 | 0 | 4 | 0 | 0 | 0 | 0 | 0 | 2 | 0 | 0 | 0 | 0 | 0 | 0 | 0 | 0 | 0 | 0 | 0 | 0 | 0 | 0 |
| >VH3-43 | 1 | 0 | 0 | 2 | 0 | 0 | 0 | 1 | 1 | 0 | 0 | 1 | 0 | 0 | 0 | 0 | 1 | 0 | 0 | 0 | 0 | 0 | 0 | 0 | 0 | 0 |
| >VH3-64 | 1 | 0 | 0 | 0 | 0 | 0 | 2 | 0 | 0 | 0 | 0 | 0 | 0 | 1 | 0 | 0 | 0 | 0 | 0 | 0 | 0 | 0 | 0 | 0 | 0 | 0 |
| >VH7-81 | 2 | 1 | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 |
| >VH3-13 | 0 | 1 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-72 | 0 | 0 | 0 | 1 | 0 | 0 | 0 | 0 | 0 | 0 | 0 | 0 | 1 | 0 | 0 | 0 | 0 | 0 | 0 | 0 | 0 | 0 | 0 | 0 | 0 | 0 |
| >VH3-73 | 0 | 1 | 0 | 1 | 1 | 0 | 0 | 1 | 0 | 0 | 1 | 0 | 0 | 0 | 0 | 0 | 0 | 0 | 0 | 0 | 0 | 0 | 0 | 0 | 0 | 0 |
| >VH1-58 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-66 | 0 | 0 | 1 | 0 | 1 | 0 | 0 | 0 | 0 | 0 | 0 | 1 | 0 | 0 | 0 | 0 | 0 | 0 | 0 | 0 | 0 | 0 | 0 | 0 | 0 | 0 |
| >VH4-30.2 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 |
| >VH7-4.1 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH2-5 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH6-1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH4-30.4 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-20 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

Figure 41

| 888.0 | IGKV3-20 | IGKV1-39/1D-39 | IGKV1-5 | IGKV3-15 | IGKV4-1 | IGKV3-11 | IGKV2-28/2D-28 | IGKV1-33/1D-33 | IGKV1-9 | IGKV2-30 | IGKV1-17 | IGKV1-27 | IGKV1-8 | IGKV1-16 | IGKV1-12 | IGKV1-6 | IGKV2D-29 | IGKV1-13 | IGKV2-24 | IGKV1D-8 | IGKV2-29 | IGKV5-2 | IGKV3D-20 | IGKV1D-12 | IGKV2-40/2D-40 | IGKV1D-43 | IGKV2D-30 | IGKV1D-16 | IGKV3D-15 | IGKV1D-13 | IGKV1D-17 |
|---|---|---|---|---|---|---|---|---|---|---|---|---|---|---|---|---|---|---|---|---|---|---|---|---|---|---|---|---|---|---|---|
| >VH3-23 |  |  |  |  |  | 4 | 5 | 6 | 1 | 1 | 4 | 4 | 3 | 2 |  | 0 | 2 | 0 | 0 | 0 |  | 0 |  | 1 | 2 | 0 | 0 | 0 | 0 | 0 | 0 |
| >VH3-30 |  |  |  |  |  | 3 | 2 |  | 1 | 0 | 1 | 0 | 1 | 0 |  | 1 | 1 | 0 | 1 | 2 | 0 | 0 | 0 | 0 | 0 | 0 | 1 | 0 | 0 | 0 | 0 |
| >VH4-39 |  |  |  | 10 |  | 5 | 2 | 4 | 0 | 2 | 1 | 3 | 0 | 0 | 0 | 2 | 0 | 0 | 0 | 0 | 0 | 0 | 0 | 0 | 0 | 0 | 0 | 0 | 0 | 0 | 0 |
| >VH4-59 |  |  | 2 | 2 |  | 4 | 0 | 2 | 0 | 1 | 1 | 1 |  | 1 | 1 | 0 | 0 | 0 | 0 | 0 | 0 | 0 | 0 | 0 | 0 | 0 | 0 | 0 | 0 | 0 | 1 |
| >VH4-34 | 21 |  | 4 |  |  | 4 | 4 | 2 | 1 | 0 | 2 | 1 | 1 | 2 |  | 0 | 0 | 0 | 0 | 0 | 0 | 0 | 0 | 0 | 0 | 0 | 0 | 0 | 0 | 0 | 0 |
| >VH5-51 |  | 3 | 2 | 4 |  |  | 4 | 2 | 0 | 0 | 1 | 1 | 0 | 0 | 0 | 0 | 0 | 0 | 0 | 0 | 0 | 0 | 0 | 0 | 0 | 0 | 0 | 0 | 0 | 0 | 0 |
| >VH1-69 |  |  | 4 | 2 | 5 | 2 | 1 | 3 | 0 | 1 | 0 | 0 | 2 |  | 0 | 0 | 1 | 0 | 0 | 0 | 0 | 0 | 0 | 0 | 0 | 1 | 1 | 1 | 0 | 0 |
| >VH3-7 |  |  | 2 | 4 | 2 | 3 | 2 | 0 | 2 |  | 1 | 1 | 3 | 0 | 0 | 0 | 2 | 0 |  | 0 | 0 | 0 | 0 | 0 | 0 | 0 | 0 | 0 | 0 | 0 |
| >VH1-18 |  | 5 | 5 | 1 | 1 | 2 | 3 |  | 6 | 0 | 2 | 0 | 0 | 1 | 1 | 1 | 0 | 0 | 1 | 0 | 0 | 0 | 0 | 0 |  | 0 | 0 | 0 | 0 | 0 | 0 |
| >VH3-48 |  |  | 1 |  | 4 |  | 2 |  | 1 | 0 | 2 |  | 1 | 3 |  | 0 | 1 | 1 | 0 | 0 | 0 | 0 | 0 |  | 1 | 0 | 0 | 0 | 0 | 0 | 0 |
| >VH3-21 |  |  | 5 |  | 4 | 1 | 2 | 0 | 0 | 0 |  | 1 | 2 | 0 | 0 | 0 | 1 | 0 | 0 | 0 | 0 | 0 | 0 | 0 | 0 | 0 | 0 | 0 | 0 | 0 | 0 |
| >VH3-15 |  |  | 5 | 4 |  | 3 | 2 |  | 2 | 0 | 0 | 1 | 0 | 0 | 0 | 0 | 1 | 0 | 0 | 0 | 0 | 0 | 0 | 0 | 1 | 0 | 0 | 0 | 0 | 0 | 0 |
| >VH4-31 | 2 | 3 | 1 | 3 | 1 |  | 5 | 2 | 3 | 0 | 0 | 1 | 1 | 0 | 0 | 0 | 1 | 0 | 0 | 0 | 0 | 0 | 0 | 0 |  | 0 | 0 | 0 | 0 | 0 | 0 |
| >VH1-2 |  | 3 | 3 | 2 | 2 | 0 | 2 | 1 | 0 | 1 | 0 | 2 | 1 | 0 | 0 | 0 | 1 | 0 | 0 | 0 | 0 | 0 | 0 | 0 | 0 | 0 | 0 | 0 | 0 | 0 | 0 |
| >VH3-33 |  | 4 | 1 | 3 | 3 | 0 | 2 | 1 | 2 | 0 | 0 | 0 | 1 | 0 | 0 | 0 | 0 | 0 | 0 | 0 | 0 | 0 | 0 | 0 | 0 | 0 | 0 | 0 | 0 | 0 | 0 |
| >VH3-53 | 2 | 4 | 7 | 4 | 4 | 2 | 1 | 5 | 1 | 0 | 1 | 1 | 2 | 0 | 1 | 0 | 0 | 0 | 0 | 0 | 1 | 0 | 0 | 0 | 0 | 0 | 1 | 0 | 0 | 0 |
| >VH3-11 | 2 | 4 | 3 | 3 | 2 | 2 | 2 | 1 | 1 | 0 | 1 | 0 | 0 | 0 | 0 | 2 | 0 | 0 | 0 | 1 | 0 | 0 | 0 | 0 | 0 | 0 | 0 | 0 | 0 | 0 | 0 |
| >VH3-9 | 0 | 3 | 2 | 1 |  | 1 | 1 | 1 | 0 | 0 | 0 | 0 | 1 | 1 | 2 | 0 | 0 | 2 | 0 | 0 | 1 | 0 | 0 | 0 | 0 | 0 | 0 | 0 | 0 | 0 | 0 |
| >VH3-74 | 1 | 2 | 2 | 1 | 2 | 1 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH4-4 | 4 | 2 | 2 | 3 | 2 | 3 | 1 | 0 | 0 | 0 |  | 1 | 0 | 0 | 0 | 0 | 2 | 0 | 0 | 1 | 0 | 0 | 0 | 0 | 0 | 0 | 0 | 0 | 0 | 0 | 0 |
| >VH1-46 | 4 | 4 | 1 | 2 | 1 | 0 | 1 | 3 | 0 | 0 | 0 | 0 | 0 | 2 | 0 | 0 | 0 | 0 | 0 | 0 | 0 | 0 | 0 | 0 | 0 | 0 | 0 | 0 | 0 | 0 | 0 |
| >VH4-61 | 0 | 3 | 0 | 2 | 3 | 0 | 1 | 0 | 0 | 0 | 0 | 0 | 0 | 1 | 1 | 0 | 0 | 0 | 0 | 0 | 0 | 0 | 0 | 0 | 0 | 0 | 0 | 0 | 0 | 0 | 0 |
| >VH1-8 | 0 | 1 | 0 | 1 | 1 | 1 | 1 | 0 | 1 | 0 | 0 | 0 | 0 | 0 | 0 | 0 | 1 | 0 | 0 | 0 | 0 | 0 | 0 | 0 | 0 | 0 | 0 | 0 | 0 | 0 | 0 |
| >VH1-24 | 1 | 1 | 0 | 2 | 1 | 2 | 2 | 1 | 0 | 1 | 0 | 0 | 0 | 0 | 0 | 0 | 1 | 0 | 0 | 0 | 0 | 0 | 0 | 0 | 0 | 0 | 0 | 0 | 0 | 0 | 0 |
| >VH1-3 | 0 | 3 | 1 | 1 | 0 | 0 | 0 | 1 | 0 | 1 | 0 | 0 | 0 | 0 | 1 | 0 | 0 | 0 | 0 | 0 | 0 | 0 | 0 | 0 | 0 | 0 | 0 | 0 | 0 | 0 | 0 |
| >VH3-49 | 2 | 3 | 1 | 1 | 0 | 1 | 1 | 1 | 0 | 0 | 3 | 0 | 0 | 0 | 0 | 0 | 0 | 0 | 0 | 0 | 0 | 0 | 0 | 0 | 0 | 0 | 0 | 0 | 0 | 0 | 0 |
| >VH4-28 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-43 | 0 | 0 | 3 | 0 | 1 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-64 | 0 | 0 | 2 | 1 | 0 | 2 | 0 | 0 | 1 | 0 | 0 | 0 | 0 | 0 | 1 | 0 | 0 | 0 | 0 | 0 | 0 | 0 | 0 | 0 | 0 | 0 | 0 | 0 | 0 | 0 | 0 |
| >VH7-81 | 3 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-13 | 0 | 2 | 1 | 0 | 2 | 0 | 0 | 1 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-72 | 0 | 0 | 1 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-73 | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH1-58 | 1 | 0 | 1 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-66 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH4-30.2 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH7-4.1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH2-5 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH6-1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH4-30.4 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-20 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

Figure 42

| 457.0 | IGLV 2-14 | IGLV 1-40 | IGLV 1-44 | IGLV 1-51 | IGLV 1-47 | IGLV 2-23 | IGLV 3-21 | IGLV 2-11 | IGLV 3-1 | IGLV 2-8 | IGLV 6-57 | IGLV 1-36 | IGLV 3-25 | IGLV 4-69 | IGLV 7-43 | IGLV 7-46 | IGLV 2-18 | IGLV 3-27 | IGLV 9-49 | IGLV 3-10 | IGLV 3-9 | IGLV 8-61 | IGLV 3-12 | IGLV 3-19 | IGLV 3-22 |
|---|---|---|---|---|---|---|---|---|---|---|---|---|---|---|---|---|---|---|---|---|---|---|---|---|---|
| >VH3-23 | 7 | 5 | 0 | 1 | 1 | 3 | 4 | 3 | 4 | 1 | 0 | 1 | 0 | 0 | 0 | 0 | 0 | 0 | 0 | 0 | 0 | 0 | 0 | 1 | 0 |
| >VH3-30 | 6 | 2 | 2 | 5 | 0 | 2 | 2 | 1 | 1 | 0 | 0 | 0 | 0 | 0 | 0 | 0 | 1 | 2 | 0 | 0 | 0 | 0 | 0 | 0 | 0 |
| >VH4-39 | 5 | 4 | 4 | 4 | 0 | 3 | 0 | 0 | 1 | 9 | 1 | 0 | 0 | 0 | 0 | 1 | 2 | 0 | 0 | 0 | 0 | 0 | 0 | 0 | 0 |
| >VH4-59 | 1 | 8 | 1 | 4 | 1 | 2 | 0 | 2 | 5 | 0 | 0 | 0 | 0 | 0 | 0 | 0 | 0 | 0 | 0 | 0 | 0 | 0 | 0 | 0 | 0 |
| >VH4-34 | 8 | 4 | 2 | 7 | 4 | 2 | 1 | 0 | 0 | 4 | 0 | 1 | 2 | 0 | 1 | 0 | 0 | 0 | 1 | 0 | 0 | 0 | 0 | 0 | 0 |
| >VH5-51 | 6 | 11 | 4 | 0 | 2 | 2 | 2 | 0 | 0 | 0 | 0 | 2 | 2 | 0 | 1 | 0 | 0 | 0 | 0 | 0 | 0 | 0 | 0 | 0 | 0 |
| >VH1-69 | 7 | 7 | 2 | 4 | 1 | 3 | 1 | 2 | 2 | 4 | 0 | 0 | 1 | 0 | 0 | 0 | 0 | 0 | 0 | 0 | 0 | 0 | 0 | 0 | 0 |
| >VH3-7 | 1 | 1 | 1 | 1 | 1 | 0 | 1 | 0 | 0 | 0 | 0 | 0 | 0 | 0 | 0 | 0 | 0 | 0 | 0 | 0 | 0 | 0 | 0 | 0 | 0 |
| >VH1-18 | 3 | 5 | 2 | 1 | 0 | 0 | 0 | 1 | 0 | 2 | 2 | 1 | 0 | 1 | 0 | 0 | 0 | 0 | 0 | 0 | 1 | 0 | 0 | 0 | 0 |
| >VH3-48 | 5 | 1 | 1 | 1 | 2 | 0 | 1 | 1 | 3 | 0 | 0 | 0 | 1 | 0 | 0 | 1 | 0 | 0 | 1 | 0 | 0 | 0 | 0 | 0 | 0 |
| >VH3-21 | 2 | 0 | 0 | 8 | 2 | 1 | 0 | 2 | 1 | 0 | 1 | 0 | 1 | 1 | 0 | 1 | 0 | 0 | 0 | 0 | 0 | 0 | 0 | 0 | 0 |
| >VH3-15 | 1 | 0 | 3 | 1 | 1 | 1 | 1 | 0 | 0 | 1 | 1 | 0 | 1 | 0 | 0 | 2 | 0 | 0 | 0 | 0 | 0 | 0 | 0 | 0 | 1 |
| >VH4-31 | 5 | 3 | 1 | 2 | 2 | 2 | 1 | 0 | 1 | 0 | 0 | 0 | 0 | 1 | 0 | 0 | 0 | 0 | 0 | 0 | 0 | 0 | 0 | 0 | 0 |
| >VH1-2 | 6 | 3 | 2 | 2 | 0 | 2 | 1 | 1 | 3 | 2 | 0 | 0 | 0 | 0 | 1 | 0 | 1 | 0 | 0 | 0 | 0 | 0 | 0 | 0 | 0 |
| >VH3-33 | 3 | 1 | 0 | 0 | 3 | 0 | 3 | 1 | 1 | 0 | 0 | 0 | 0 | 0 | 0 | 0 | 1 | 1 | 0 | 1 | 0 | 0 | 0 | 0 | 0 |
| >VH3-53 | 0 | 0 | 0 | 1 | 1 | 1 | 0 | 0 | 1 | 0 | 0 | 0 | 0 | 0 | 0 | 0 | 0 | 0 | 0 | 0 | 0 | 0 | 0 | 0 | 0 |
| >VH3-11 | 0 | 0 | 1 | 1 | 1 | 0 | 2 | 0 | 2 | 0 | 0 | 1 | 1 | 0 | 0 | 0 | 1 | 0 | 0 | 1 | 0 | 0 | 0 | 0 | 0 |
| >VH3-9 | 4 | 0 | 3 | 0 | 3 | 4 | 2 | 3 | 0 | 0 | 0 | 0 | 0 | 0 | 0 | 0 | 0 | 0 | 0 | 0 | 0 | 0 | 0 | 0 | 0 |
| >VH3-74 | 1 | 0 | 0 | 0 | 1 | 0 | 2 | 0 | 1 | 0 | 0 | 0 | 0 | 0 | 0 | 0 | 0 | 0 | 0 | 0 | 0 | 0 | 0 | 0 | 0 |
| >VH4-4 | 2 | 0 | 4 | 2 | 0 | 1 | 0 | 0 | 0 | 0 | 1 | 0 | 0 | 0 | 0 | 0 | 0 | 0 | 0 | 0 | 0 | 0 | 0 | 0 | 0 |
| >VH1-46 | 1 | 0 | 3 | 2 | 1 | 0 | 1 | 1 | 0 | 0 | 0 | 0 | 0 | 0 | 0 | 0 | 0 | 0 | 0 | 0 | 0 | 0 | 0 | 0 | 0 |
| >VH4-61 | 1 | 0 | 4 | 0 | 0 | 0 | 1 | 2 | 1 | 0 | 0 | 0 | 0 | 1 | 0 | 0 | 0 | 0 | 0 | 0 | 0 | 0 | 0 | 0 | 0 |
| >VH1-8 | 3 | 0 | 0 | 0 | 1 | 0 | 0 | 0 | 0 | 1 | 0 | 0 | 0 | 0 | 0 | 0 | 0 | 0 | 1 | 0 | 0 | 0 | 0 | 0 | 0 |
| >VH1-24 | 0 | 1 | 1 | 0 | 0 | 2 | 1 | 1 | 0 | 0 | 0 | 0 | 0 | 0 | 0 | 0 | 0 | 0 | 0 | 0 | 0 | 0 | 0 | 0 | 0 |
| >VH1-3 | 2 | 0 | 0 | 0 | 0 | 0 | 0 | 0 | 2 | 0 | 0 | 0 | 0 | 0 | 0 | 0 | 0 | 0 | 0 | 0 | 0 | 0 | 0 | 0 | 0 |
| >VH3-49 | 1 | 1 | 0 | 0 | 0 | 1 | 1 | 0 | 1 | 0 | 0 | 0 | 0 | 0 | 0 | 0 | 0 | 0 | 0 | 0 | 0 | 0 | 0 | 0 | 0 |
| >VH4-28 | 1 | 0 | 2 | 0 | 0 | 1 | 0 | 0 | 0 | 0 | 2 | 0 | 0 | 0 | 0 | 0 | 0 | 0 | 0 | 0 | 0 | 0 | 0 | 0 | 0 |
| >VH3-43 | 1 | 0 | 0 | 2 | 0 | 0 | 0 | 0 | 1 | 0 | 0 | 0 | 0 | 0 | 0 | 0 | 0 | 0 | 0 | 0 | 0 | 0 | 0 | 0 | 0 |
| >VH3-64 | 1 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 |
| >VH7-81 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 |
| >VH3-13 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 |
| >VH3-72 | 0 | 0 | 0 | 0 | 0 | 0 | 0 | 0 | 0 | 0 | 0 | 0 | 1 | 0 | 0 | 0 | 0 | 0 | 0 | 0 | 0 | 0 | 0 | 0 | 0 |
| >VH3-73 | 0 | 1 | 0 | 1 | 1 | 0 | 0 | 1 | 0 | 0 | 0 | 0 | 0 | 0 | 0 | 0 | 0 | 0 | 0 | 0 | 0 | 0 | 0 | 0 | 0 |
| >VH1-58 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-66 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 |
| >VH4-30.2 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 |

| 322.0 | IGLV 2-14 | IGLV 1-40 | IGLV 1-44 | IGLV 1-51 | IGLV 1-47 | IGLV 2-23 | IGLV 3-21 | IGLV 2-11 | IGLV 3-1 | IGLV 2-8 | IGLV 6-57 | IGLV 1-36 | IGLV 3-25 | IGLV 4-69 | IGLV 7-43 | IGLV 7-46 | IGLV 2-18 | IGLV 3-27 | IGLV 9-49 | IGLV 3-10 | IGLV 3-9 | IGLV 8-61 | IGLV 3-12 | IGLV 3-19 | IGLV 3-22 | IGLV 4-60 |
|---|---|---|---|---|---|---|---|---|---|---|---|---|---|---|---|---|---|---|---|---|---|---|---|---|---|---|
| >VH3-23 | 6 | 1 | 5 | 2 | 0 | 1 | 2 | 2 | 1 | 0 | 0 | 1 | 0 | 0 | 1 | 0 | 1 | 0 | 0 | 0 | 0 | 0 | 0 | 0 | 0 | 0 |
| >VH3-30 | 1 | 3 | 2 | 4 | 1 | 0 | 1 | 1 | 2 | 1 | 1 | 0 | 0 | 0 | 0 | 0 | 0 | 0 | 0 | 2 | 0 | 0 | 0 | 0 | 0 | 0 |
| >VH4-39 | 5 | 2 | 3 | 1 | 3 | 2 | 13 | 0 | 1 | 1 | 1 | 0 | 0 | 0 | 0 | 0 | 1 | 0 | 0 | 0 | 1 | 0 | 0 | 0 | 0 | 0 |
| >VH4-59 | 3 | 0 | 3 | 0 | 2 | 0 | 2 | 0 | 0 | 1 | 1 | 0 | 0 | 0 | 0 | 0 | 0 | 0 | 0 | 0 | 0 | 0 | 1 | 0 | 0 | 0 |
| >VH4-34 | 2 | 2 | 0 | 2 | 2 | 0 | 1 | 1 | 0 | 0 | 0 | 0 | 0 | 0 | 0 | 0 | 0 | 0 | 0 | 0 | 0 | 0 | 0 | 0 | 0 | 0 |
| >VH5-51 | 5 | 3 | 1 | 0 | 2 | 1 | 1 | 0 | 0 | 0 | 0 | 0 | 0 | 0 | 1 | 0 | 0 | 0 | 0 | 0 | 0 | 0 | 0 | 0 | 0 | 0 |
| >VH1-69 | 1 | 0 | 6 | 1 | 1 | 0 | 1 | 3 | 0 | 0 | 1 | 0 | 0 | 0 | 0 | 0 | 0 | 0 | 1 | 0 | 0 | 0 | 0 | 0 | 0 | 0 |
| >VH3-7 | 1 | 3 | 2 | 2 | 2 | 1 | 2 | 0 | 1 | 1 | 0 | 0 | 0 | 0 | 1 | 0 | 1 | 0 | 0 | 0 | 0 | 0 | 0 | 0 | 0 | 0 |
| >VH1-18 | 2 | 0 | 1 | 2 | 0 | 1 | 0 | 0 | 0 | 0 | 0 | 0 | 0 | 0 | 0 | 0 | 0 | 0 | 0 | 0 | 0 | 0 | 0 | 0 | 0 | 0 |
| >VH3-48 | 1 | 0 | 0 | 0 | 4 | 1 | 0 | 1 | 0 | 0 | 0 | 0 | 0 | 0 | 0 | 0 | 0 | 0 | 0 | 0 | 0 | 0 | 0 | 0 | 0 | 0 |
| >VH3-21 | 3 | 2 | 2 | 3 | 1 | 0 | 2 | 0 | 0 | 1 | 0 | 0 | 1 | 0 | 0 | 0 | 0 | 0 | 0 | 0 | 0 | 0 | 0 | 0 | 0 | 0 |
| >VH3-15 | 0 | 2 | 1 | 1 | 0 | 0 | 0 | 0 | 2 | 1 | 0 | 0 | 0 | 0 | 2 | 1 | 1 | 0 | 0 | 0 | 0 | 0 | 0 | 0 | 0 | 0 |
| >VH4-31 | 3 | 0 | 0 | 1 | 1 | 2 | 1 | 1 | 0 | 0 | 0 | 0 | 0 | 0 | 1 | 0 | 0 | 0 | 0 | 0 | 0 | 0 | 0 | 0 | 0 | 0 |
| >VH1-2 | 2 | 3 | 3 | 1 | 0 | 1 | 0 | 0 | 0 | 0 | 0 | 0 | 0 | 0 | 0 | 1 | 0 | 0 | 0 | 0 | 0 | 0 | 0 | 0 | 0 | 0 |
| >VH3-33 | 1 | 0 | 1 | 1 | 1 | 4 | 1 | 0 | 0 | 0 | 2 | 0 | 0 | 1 | 0 | 0 | 0 | 0 | 0 | 0 | 0 | 0 | 0 | 0 | 0 | 0 |
| >VH3-53 | 2 | 0 | 1 | 0 | 0 | 0 | 0 | 1 | 1 | 0 | 0 | 0 | 0 | 0 | 0 | 1 | 0 | 0 | 0 | 0 | 0 | 0 | 0 | 0 | 0 | 0 |
| >VH3-11 | 3 | 1 | 2 | 0 | 0 | 2 | 0 | 3 | 1 | 1 | 0 | 0 | 0 | 0 | 1 | 0 | 1 | 0 | 0 | 0 | 0 | 0 | 0 | 0 | 0 | 0 |
| >VH3-9 | 2 | 1 | 1 | 1 | 0 | 3 | 0 | 0 | 0 | 2 | 0 | 0 | 0 | 1 | 0 | 0 | 0 | 0 | 0 | 0 | 0 | 0 | 0 | 0 | 0 | 1 |
| >VH3-74 | 1 | 0 | 0 | 0 | 0 | 3 | 1 | 1 | 1 | 0 | 0 | 0 | 0 | 0 | 1 | 1 | 0 | 0 | 0 | 0 | 0 | 0 | 0 | 0 | 0 | 0 |
| >VH4-4 | 2 | 3 | 2 | 0 | 0 | 1 | 0 | 1 | 1 | 2 | 0 | 0 | 0 | 0 | 0 | 0 | 0 | 0 | 1 | 0 | 0 | 0 | 0 | 0 | 0 | 0 |
| >VH1-46 | 2 | 1 | 0 | 2 | 0 | 1 | 0 | 1 | 0 | 0 | 1 | 0 | 0 | 0 | 0 | 0 | 0 | 0 | 0 | 0 | 0 | 0 | 0 | 0 | 0 | 0 |
| >VH4-61 | 2 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 |
| >VH1-8 | 1 | 0 | 0 | 1 | 1 | 0 | 0 | 1 | 0 | 0 | 0 | 0 | 0 | 0 | 0 | 0 | 0 | 0 | 0 | 0 | 0 | 0 | 0 | 0 | 0 | 0 |
| >VH1-24 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH1-3 | 0 | 1 | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 |
| >VH3-49 | 0 | 0 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 |
| >VH4-28 | 0 | 0 | 0 | 2 | 0 | 3 | 0 | 0 | 0 | 0 | 0 | 0 | 0 | 0 | 0 | 0 | 0 | 0 | 0 | 0 | 0 | 0 | 0 | 0 | 0 | 0 |
| >VH3-43 | 0 | 0 | 0 | 0 | 0 | 0 | 0 | 1 | 0 | 0 | 0 | 1 | 0 | 0 | 0 | 0 | 0 | 0 | 1 | 0 | 0 | 0 | 0 | 0 | 0 | 0 |
| >VH3-64 | 0 | 0 | 0 | 0 | 0 | 0 | 1 | 0 | 0 | 0 | 0 | 0 | 0 | 0 | 1 | 0 | 0 | 0 | 0 | 0 | 0 | 0 | 0 | 0 | 0 | 0 |
| >VH7-81 | 2 | 1 | 0 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 |
| >VH3-13 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-72 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-73 | 0 | 0 | 0 | 0 | 0 | 0 | 0 | 0 | 0 | 0 | 1 | 0 | 0 | 0 | 0 | 0 | 0 | 0 | 0 | 0 | 0 | 0 | 0 | 0 | 0 | 0 |
| >VH1-58 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-66 | 0 | 0 | 1 | 0 | 0 | 0 | 0 | 0 | 0 | 0 | 0 | 1 | 0 | 0 | 0 | 0 | 0 | 0 | 0 | 0 | 0 | 0 | 0 | 0 | 0 | 0 |
| >VH4-30.2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH7-4.1 | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH2-5 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH6-1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH4-30.4 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| >VH3-20 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

Figure 45A

| | Matsuda et al | Tomlinson et al | Protein sequence | SEQ ID NO |
|---|---|---|---|---|
| IGHV1-2 | VH 1-2 | DP-75 | QVQLVQSGAEVKKPGASVKVSCKASGYTFTGYYMHWVRQAPGQGLEWMG WINPNSGGTNYAQKFQGRVTMTRDTSISTAYMELSRLRSDDTAVYYCAR | 62 |
| IGHV1-3 | VH 1-3 | DP-25 | QVQLVQSGAEVKKPGASVKVSCKASGYTFTSYAMHWVRQAPGQRLEWMG WSNAGNGNTKYSQEFQGRVTITRDTSASTAYMELSSLRSEDMAVYYCAR | 63 |
| IGHV1-8 | VH 1-8 | DP-15 | QVQLVQSGAEVKKPGASVKVSCKASGYTFTSYDINWVRQATGQGLEWMGW MNPNSGNTGYAQKFQGRVTMTRNTSISTAYMELSSLRSEDTAVYYCARG | 64 |
| IGHV1-18 | VH 1-18 | DP-14 | QVQLVQSGAEVKKPGASVKVSCKASGYTFTSYGISWVRQAPGQGLEWMGW ISAYNGNTNYAQKLQGRVTMTTDTSTSTAYMELRSLRSDDTAVYYCAR | 65 |
| IGHV1-24 | VH 1-24 | DP-5 | QVQLVQSGAEVKKPGASVKVSCKVSGYTLTELSMHWVRQAPGKGLEWMG GFDPEDGETIYAQKFQGRVTMTEDTSTDTAYMELSSLRSEDTAVYYCAT | 66 |
| IGHV1-45 | VH 1-45 | -- | QMQLVQSGAEVKKTGSSVKVSCKASGYTFTYRYLHWVRQAPGQALEWMG WITPFNGNTNYAQKFQDRVTITRDRSMSTAYMELSSLRSEDTAMYYCAR | 67 |
| IGHV1-46 | VH 1-46 | DP-7 | QVQLVQSGAEVKKPGASVKVSCKASGYTFTSYYMHWVRQAPGQGLEWMGI INPSGGSTSYAQKFQGRVTMTRDTSTSTVYMELSSLRSEDTAVYYCAR | 68 |
| IGHV1-58 | VH 1-58 | DP-2 | QMQLVQSGPEVKKPGTSVKVSCKASGFTFTSSAMQWVRQARGQRLEWIGW IVVGSGNTNYAQKFQERVTITRDMSTSTAYMELSSLRSEDTAVYYCAA | 69 |
| IGHV1-69*01 | VH 1-69 | DP-10 | QVQLVQSGAEVKKPGSSVKVSCKASGGTFSSYAISWVRQAPGQGLEWMGG IIPIFGTANYAQKFQGRVTITADESTSTAYMELSSLRSEDTAVYYCAR | 70 |
| IGHV1-69*06, IGHV1-e | VH 1-69 | DP-88 | QVQLVQSGAEVKKPGSSVKVSCKASGGTFSSYAISWVRQAPGQGLEWMGG IIPIFGTANYAQKFQGRVTITADKSTSTAYMELSSLRSEDTAVYYCAR | 71 |
| IGHV1-c | -- | -- | KSGASVKVSCSFSGFTITSYGIHWVQQSPGQGLEWMGWINPGNGSPSYAKK FQGRFTMTRDMSTTTAYTDLSSLTSEDMAVYYYAR | 72 |
| IGHV1-f | -- | DP-3 | EVQLVQSGAEVKKPGATVKISCKVSGYTFTDYYMHWVQQAPGKGLEWMGL VDPEDGETIYAEKFQGRVTITADTSTDTAYMELSSLRSEDTAVYYCAT | 73 |
| IGHV2-5 | VH 2-5 | DP-76 | QITLKESGPTLVKPTQTLTLTCTFSGFSLSTSGVGVGWIRQPPGKALEWLALI YWNDDKRYSPSLKSRLTITKDTSKNQVVLTMTNMDPVDTATYYCAHR | 74 |
| IGHV2-26 | VH 2-26 | DP-26 | QVTLKESGPVLVKPTETLTLTCTVSGFSLSNARMGVSWIRQPPGKALEWLAH IFSNDEKSYSTSLKSRLTISKDTSKSQVVLTMTNMDPVDTATYYCARI | 75 |
| IGHV2-70 | VH 2-70 | DP-27 | QVTLRESGPALVKPTQTLTLTCTFSGFSLSTSGMCVSWIRQPPGKALEWLALI DWDDDKYYSTSLKTRLTISKDTSKNQVVLTMTNMDPVDTATYYCARI | 76 |
| IGHV3-7 | VH 3-7 | DP-54 | EVQLVESGGGLVQPGGSLRLSCAASGFTFSSYWMSWVRQAPGKGLEWVA NIKQDGSEKYYVDSVKGRFTISRDNAKNSLYLQMNSLRAEDTAVYYCAR | 77 |
| IGHV3-9 | VH 3-9 | DP-31 | EVQLVESGGGLVQPGRSLRLSCAASGFTFDDYAMHWVRQAPGKGLEWVSG ISWNSGSIGYADSVKGRFTISRDNAKNSLYLQMNSLRAEDTALYYCAKD | 78 |

Figure 45B

| | Matsuda et al | Tominson et al | Protein sequence | SEQ ID NO |
|---|---|---|---|---|
| IGHV3-11 | VH 3-11 | DP-35 | QVQLVESGGGLVKPGGSLRLSCAASGFTFSDYYMSWIRQAPGKGLEWVSYI SSSGSTIYYADSVKGRFTISRDNAKNSLYLQMNSLRAEDTAVYYCAR | 79 |
| IGHV3-13 | VH 3-13 | DP-48 | EVQLVESGGGLVQPGGSLRLSCAASGFTFSSYDMHWVRQATGKGLEWVSA IGTAGDTYYPGSVKGRFTISRENAKNSLYLQMNSLRAGDTAVYYCAR | 80 |
| IGHV3-15 | VH 3-15 | DP-38 | EVQLVESGGGLVKPGGSLRLSCAASGFTFSNAWMSWVRQAPGKGLEWVG RIKSKTDGGTTDYAAPVKGRFTISRDDSKNTLYLQMNSLKTEDTAVYYCTT | 81 |
| IGHV3-16 | VH 3-16 | | EVQLVESGGGLVQPGGSLRLSCAASGFTFSNSDMNWARKAPGKGLEWVSG VSWNGSRTHYVDSVK.RRFIISRDNSRNSLYLQKNRRRAEDMAVYYCVR | 82 |
| IGHV3-20 | VH 3-20 | DP-32 | EVQLVESGGGVVRPGGSLRLSCAASGFTFDDYGMSWVRQAPGKGLEWVS GINWNGGSTGYADSVKGRFTISRDNAKNSLYLQMNSLRAEDTALYHCAR | 83 |
| IGHV3-21 | VH 3-21 | DP-77 | EVQLVESGGGLVKPGGSLRLSCAASGFTFSSYSMNWVRQAPGKGLEWVSSI SSSSSYIYYADSVKGRFTISRDNAKNSLYLQMNSLRAEDTAVYYCAR | 84 |
| IGHV3-23 | VH 3-23 | DP-47 | EVQLLESGGGLVQPGGSLRLSCAASGFTFSSYAMSWVRQAPGKGLEWVSAI SGSGGSTYYADSVKGRFTISRDNSKNTLYLQMNSLRAEDTAVYYCAK | 85 |
| IGHV3-30 | VH 3-30 | DP-49 | QVQLVESGGGVVQPGRSLRLSCAASGFTFSSYGMHWVRQAPGKGLEWVA VISYDGSNKYYADSVKGRFTISRDNSKNTLYLQMNSLRAEDTAVYYCAR | 86 |
| IGHV3-30-3 | -- | DP-46 | QVQLVESGGGVVQPGRSLRLSCAASGFTFSSYAMHWVRQAPGKGLEWVAV ISYDGSNKYYADSVKGRFTISRDNSKNTLYLQMNSLRAEDTAVYYCAR | 87 |
| IGHV3-30-5 | -- | -- | QVQLVESGGGVVQPGRSLRLSCAASGFTFSSYGMHWVRQAPGKGLEWVA VISYDGSNKYYADSVKGRFTISRDNSKNTLYLQMNSLRAEDTAVYYCAK | 88 |
| IGHV3-33 | VH 3-33 | DP-50 | QVQLVESGGGVVQPGRSLRLSCAASGFTFSSYGMHWVRQAPGKGLEWVA VIWYDGSNKYYADSVKGRFTISRDNSKNTLYLQMNSLRAEDTAVYYCAR | 89 |
| IGHV3-35 | VH 3-35 | DP-59 | EVQLVESGGGLVQPGGSLRLSCAASGFTFSNSDMNWVHQAPGKGLEWVSG VSWNGSRTHYADSVKGRFIISRDNSRNTLYLQTNSLRAEDTAVYYCVR | 90 |
| IGHV3-38 | VH 3-38P | -- | EVQLVESGGGLVQPRGSLRLSCAASGFTVSSNEMSWIRQAPGKGLEWVSSI SGGSTYYADSRKGRFTISRDNSKNTLYLQMNNLRAEGTAAYYCARY | 91 |
| IGHV3-43 | VH 3-43 | DP-33 | EVQLVESGGVVVQPGGSLRLSCAASGFTFDDYTMHWVRQAPGKGLEWVSLI SWDGGSTYYADSVKGRFTISRDNSKNSLYLQMNSLRTEDTALYYCAKD | 92 |
| IGHV3-48 | VH 3-48 | DP-51 | EVQLVESGGGLVQPGGSLRLSCAASGFTFSSYSMNWVRQAPGKGLEWVSY ISSSSSTIYYADSVKGRFTISRDNAKNSLYLQMNSLRDEDTAVYYCAR | 93 |
| IGHV3-49 | VH 3-49 | 3-49RB | EVQLVESGGGLVQPGRSLRLSCTASGFTFGDYAMSWFRQAPGKGLEWVGF IRSKAYGGTTEYAASVKGRFTISRDDSKSIAYLQMNSLKTEDTAVYYCTR | 94 |
| IGHV3-53 | VH 3-53 | DP-42 | EVQLVESGGGLIQPGGSLRLSCAASGFTVSSNYMSWVRQAPGKGLEWVSVI YSGGSTYYADSVKGRFTISRDNSKNTLYLQMNSLRAEDTAVYYCAR | 95 |
| IGHV3-64 | VH 3-64 | DP-61 | EVQLVESGEGLVQPGGSLRLSCAASGFTFSSYAMHWVRQAPGKGLEYVSAI SSNGGSTYYADSVKGRFTISRDNSKNTLYLQMGSLRAEDMAVYYCAR | 96 |
| IGHV3-66 | VH 3-66 | DP-86 | EVQLVESGGGLIQPGGSLRLSCAASGFTVSSNYMSWVRQAPGKGLEWVSVI YSCGSTYYADSVKGRFTISRDNSKNTLYLQMNSLRAEDTAVYYCAR | 97 |
| IGHV3-72 | VH 3-72 | DP-29 | EVQLVESGGGLVQPGGSLRLSCAASGFTFSDHYMDWVRQAPGKGLEWVG RTRNKANSYTTEYAASVKGRFTISRDDSKNSLYLQMNSLKTEDTAVYYCAR | 98 |
| IGHV3-73 | VH 3-73 | DA-11 | EVQLVESGGGLVQPGGSLKLSCAASGFTFSGSAMHWVRQASGKGLEWVGR IRSKANSYATAYAASVKGRFTISRDDSKNTAYLQMNSLKTEDTAVYYCTR | 99 |
| IGHV3-74 | VH 3-74 | DP-53 | EVQLVESGGGLVQPGGSLRLSCAASGFTFSSYWMHWVRQAPGKGLVWVS RINSDGSSTSYADSVKGRFTISRDNAKNTLYLQMNSLRAEDTAVYYCAR | 100 |

Figure 45C

| | Matsuda et al | Tomlinson et al | Protein sequence | SEQ ID NO |
|---|---|---|---|---|
| IGHV3-d | -- | -- | EVQLVESRGVLVQPGGSLRLSCAASGFTVSSNEMSWVRQAPGKGLEWVSSI SGGSTYYADSRKGRFTISRDNSKNTLHLQMNSLRAEDTAVYYCKK | 101 |
| IGHV4-4 | VH 4-4 | DP-70 | QVQLQESGPGLVKPSETLSLTCTVSGGSISSYYWSWIRQPAGKGLEWIGRIY TSGSTNYNPSLKSRVTMSVDTSKNQFSLKLSSVTAADTAVYYCAR | 102 |
| IGHV4-28 | VH 4-28 | DP-68 | QVQLQESGPGLVKPSDTLSLTCAVSGYSISSSNWWGWIRQPFGKGLEWIGYI YYSGSTYYNPSLKSRVTMSVDTSKNQFSLKLSSVTAVDTAVYYCAR | 103 |
| IGHV4-30-1 | -- | -- | QVQLQESGPGLVKPSQTLSLTCTVSGGSISSGGYYWSWIRQHPGKGLEWIG YIYYSGSTYYNPSLKSRVTISVDTSKNQFSLKLSSVTAADTAVYYCAR | 104 |
| IGHV4-30-2 | -- | DP-64 | QLQLQESGSGLVKPSQTLSLTCAVSGGSISSGGYSWSWIRQPPGKGLEWIG YIYHSGSTYYNPSLKSRVTISVDRSKNQFSLKLSSVTAADTAVYYCAR | 105 |
| IGHV4-30-4 | -- | DP-78 | QVQLQESGPGLVKPSQTLSLTCTVSGGSISSGDYYWSWIRQPPGKGLEWIG YIYYSGSTYYNPSLKSRVTISVDTSKNQFSLKLSSVTAADTAVYYCAR | 106 |
| IGHV4-31 | VH 4-31 | DP-65 | QVQLQESGPGLVKPSQTLSLTCTVSGGSISSGGYYWSWIRQHPGKGLEWIG YIYYSGSTYYNPSLKSRVTISVDTSKNQFSLKLSSVTAADTAVYYCAR | 107 |
| IGHV4-34 | VH 4-34 | DP-63 | QVQLQQWGAGLLKPSETLSLTCAVYGGSFSGYYWSWIRQPPGKGLEWIGEI NHSGSTNYNPSLKSRVTISVDTSKNQFSLKLSSVTAADTAVYYCARG | 108 |
| IGHV4-39 | VH 4-39 | DP-79 | QLQLQESGPGLVKPSETLSLTCTVSGGSISSSSYYWGWIRQPPGKGLEWIGS IYYSGSTYYNPSLKSRVTISVDTSKNQFSLKLSSVTAADTAVYYCAR | 109 |
| IGHV4-59 | VH 4-59 | DP-71 | QVQLQESGPGLVKPSETLSLTCTVSGGSISSYYWSWIRQPPGKGLEWIGYIY YSGSTNYNPSLKSRVTISVDTSKNQFSLKLSSVTAADTAVYYCAR | 110 |
| IGHV4-61 | VH 4-61 | DP-66 | QVQLQESGPGLVKPSETLSLTCTVSGGSVSSGGYYWSWIRQPPGKGLEWIG YIYYSGSTNYNPSLKSRVTISVDTSKNQFSLKLSSVTAADTAVYYCAR | 111 |
| IGHV4-b | -- | DP-67 | QVQLQESGPGLVKPSETLSLTCAVSGYSISSGYYWGWIRQPPGKGLEWIGSI YHSGSTYYNPSLKSRVTISVDTSKNQFSLKLSSVTAADTAVYYCAR | 112 |
| IGHV5-51 | VH 5-51 | DP-73 | EVQLVQSGAEVKKPGESLKISCKGSGYSFTSYWIGWVRQMPGKGLEWMGII YPGDSDTRYSPSFQGQVTISADKSISTAYLQWSSLKASDTAMYYCAR | 113 |
| IGHV5-a | -- | -- | EVQLVQSGAEVKKPGESLRISCKGSGYSFTSYWISWVRQMPGKGLEWMGRI DPSDSYTNYSPSFQGHVTISADKSISTAYLQWSSLKASDTAMYYCAR | 114 |
| IGHV6-1 | VH 6-1 | DP-74 | QVQLQQSGPGLVKPSQTLSLTCAISGDSVSSNSAAWNWIRQSPSRGLEWLG RTYYRSKWYNDYAVSVKSRITINPDTSKNQFSLQLNSVTPEDTAVYYCAR | 115 |
| IGHV7-4-1 | -- | DP-21 | QVQLVQSGSELKKPGASVKVSCKASGYTFTSYAMNWVRQAPGQGLEWMG WINTNTGNPTYAQGFTGRFVFSLDTSVSTAYLQICSLKAEDTAVYYCAR | 116 |
| IGHV7-81 | VH 7-81 | -- | QVQLVQSGHEVKQPGASVKVSCKASGYSFTTYGMNWVPQAPGQGLEWMG WFNTYTGNPTYAQGFTGRFVFSMDTSASTAYLQISSLKAEDMAMYYCAR | 117 |

Figure 46A

| | Zachau | Protein sequence | SEQ ID NO |
|---|---|---|---|
| IGKV1-5 | L12 | DIQMTQSPSTLSASVGDRVTITCRASQSISSWLAWYQQKPGKAPKLLIYDASS LESGVPSRFSGSGSGTEFTLTISSLQPDDFATYYCQQYNSYS | 118 |
| IGKV1-6 | L11 | AIQMTQSPSSLSASVGDRVTITCRASQGIRNDLGWYQQKPGKAPKLLIYAASS LQSGVPSRFSGSGSGTDFTLTISSLQPEDFATYYCLQDYNYP | 119 |
| IGKV1-8 | L9 | AIRMTQSPSSFSASTGDRVTITCRASQGISSYLAWYQQKPGKAPKLLIYAASTL QSGVPSRFSGSGSGTDFTLTISCLQSEDFATYYCQQYYSYP | 120 |
| IGKV1-9 | L8 | DIQLTQSPSFLSASVGDRVTITCRASQGISSYLAWYQQKPGKAPKLLIYAASTL QSGVPSRFSGSGSGTEFTLTISSLQPEDFATYYCQQLNSYP | 121 |
| IGKV1-12 | L5 | DIQMTQSPSSVSASVGDRVTITCRASQGISSWLAWYQQKPGKAPKLLIYAASS LQSGVPSRFSGSGSGTDFTLTISSLQPEDFATYYCQQANSFP | 122 |
| IGKV1-13 | L4/18a | AIQLTQSPSSLSASVGDRVTITCRASQGISSALAWYQQKPGKAPKLLIYDASSL ESGVPSRFSGSGSGTDFTLTISSLQPEDFATYYCQQFNSYP | 123 |
| IGKV1-16 | L1 | DIQMTQSPSSLSASVGDRVTITCRASQGISNYLAWFQQKPGKAPKSLIYAASS LQSGVPSRFSGSGSGTDFTLTISSLQPEDFATYYCQQYNSYP | 124 |
| IGKV1-17 | A30 | DIQMTQSPSSLSASVGDRVTITCRASQGIRNDLGWYQQKPGKAPKRLIYAASS LQSGVPSRFSGSGSGTEFTLTISSLQPEDFATYYCLQHNSYP | 125 |
| IGKV1-27 | A20 | DIQMTQSPSSLSASVGDRVTITCRASQGISNYLAWYQQKPGKVPKLLIYAASTL QSGVPSRFSGSGSGTDFTLTISSLQPEDVATYYCQKYNSAP | 126 |
| IGKV1-33 | O18 | DIQMTQSPSSLSASVGDRVTITCQASQDISNYLNWYQQKPGKAPKLLIYDASN LETGVPSRFSGSGSGTDFTFTISSLQPEDIATYYCQQYDNLP | 127 |
| IGKV1-37 | O14 | DIQLTQSPSSLSASVGDRVTITCRVSQGISSYLNWYRQKPGKVPKLLIYSASNL QSGVPSRFSGSGSGTDFTLTISSLQPEDVATYYGQRTYNAPP | 128 |
| IGKV1-39 | O12 | DIQMTQSPSSLSASVGDRVTITCRASQSISSYLNWYQQKPGKAPKLLIYAASSL QSGVPSRFSGSGSGTDFTLTISSLQPEDFATYYCQQSYSTP | 129 |
| IGKV1D-08 | L24 | VIWMTQSPSLLSASTGDRVTISCRMSQGISSYLAWYQQKPGKAPELLIYAAST LQSGVPSRFSGSGSGTDFTLTISCLQSEDFATYYCQQYYSFP | 130 |
| IGKV1D-12 | L19 | DIQMTQSPSSVSASVGDRVTITCRASQGISSWLAWYQQKPGKAPKLLIYAASS LQSGVPSRFSGSGSGTDFTLTISSLQPEDFATYYCQQANSFP | 131 |
| IGKV1D-13 | L18 | AIQLTQSPSSLSASVGDRVTITCRASQGISSALAWYQQKPGKAPKLLIYDASSL ESGVPSRFSGSGSGTDFTLTISSLQPEDFATYYCQQFNNYP | 132 |
| IGKV1D-16 | L15 | DIQMTQSPSSLSASVGDRVTITCRASQGISSWLAWYQQKPEKAPKSLIYAASS LQSGVPSRFSGSGSGTDFTLTISSLQPEDFATYYCQQYNSYP | 133 |
| IGKV1D-17 | L14 | NIQMTQSPSAMSASVGDRVTITCRARQGISNYLAWFQQKPGKVPKHLIYAASS LQSGVPSRFSGSGSGTEFTLTISSLQPEDFATYYCLQHNSYP | 134 |
| IGKV1D-33 | O8 | DIQMTQSPSSLSASVGDRVTITCQASQDISNYLNWYQQKPGKAPKLLIYDASN LETGVPSRFSGSGSGTDFTFTISSLQPEDIATYYCQQYDNLP | 135 |
| IGKV1D-37 | O4 | DIQLTQSPSSLSASVGDRVTITCRVSQGISSYLNWYRQKPGKVPKLLIYSASNL QSGVPSRFSGSGSGTDFTLTISSLQPEDVATYYGQRTYNAPP | 136 |

Figure 46B

| | Zachau | Protein sequence | SEQ ID NO |
|---|---|---|---|
| IGKV1D-39 | O2 | DIQMTQSPSSLSASVGDRVTITCRASQSISSYLNWYQQKPGKAPKLLIYAASSL QSGVPSRFSGSGSGTDFTLTISSLQPEDFATYYCQQSYSTP | 137 |
| IGKV1D-42 | L22 | DIQMIQSPSFLSASVGDRVSIICWASEGISSNLAWYLQKPGKSPKLFLYDAKDL HPGVSSRFSGRGSGTDFTLTIISLKPEDFAAYYCKQDFSYPP | 138 |
| IGKV1D-43 | L23 | AIRMTQSPFSLSASVGDRVTITCWASQGISSYLAWYQQKPAKAPKLFIYYASSL QSGVPSRFSGSGSGTDYTLTISSLQPEDFATYYCQQYYSTP | 139 |
| IGKV2-24 | A23 | DIVMTQTPLSSPVTLGQPASISCRSSQSLVHSDGNTYLSWLQQRPGQPPRLLI YKISNRFSGVPDRFSGSGAGTDFTLKISRVEAEDVGVYYCMQATQFP | 140 |
| IGKV2-28 | A19 | DIVMTQSPLSLPVTPGEPASISCRSSQSLLHSNGYNYLDWYLQKPGQSPQLLI YLGSNRASGVPDRFSGSGSGTDFTLKISRVEAEDVGVYYCMQALQTP | 141 |
| IGKV2-29 | A18b | DIVMTQTPLSLSVTPGQPASISCKSSQSLLHSDGKTYLYWYLQKPGQSPQLLI YEVSSRFSGVPDRFSGSGSGTDFTLKISRVEAEDVGVYYCMQGIHLP | 142 |
| IGKV2-30 | A17 | DVVMTQSPLSLPVTLGQPASISCRSSQSLVYSDGNTYLNWFQQRPGQSPRR LIYKVSNRDSGVPDRFSGSGSGTDFTLKISRVEAEDVGVYYCMQGTHWP | 143 |
| IGKV2-40 | O11 | DIVMTQTPLSLPVTPGEPASISCRSSQSLLDSDDGNTYLDWYLQKPGQSPQLL IYTLSYRASGVPDRFSGSGSGTDFTLKISRVEAEDVGVYYCMQRIEFP | 144 |
| IGKV2D-24 | A7 | DIVMTQTPLSSPVTLGQPASISFRSSQSLVHSDGNTYLSWLQQRPGQPPRLLI YKVSNRFSGVPDRFSGSGAGTDFTLKISRVEAEDVGVYYCTQATQFP | 145 |
| IGKV2D-26 | A5 | EIVMTQTPLSLSITPGEQASISCRSSQSLLHSDGYTYLYWFLQKARPVSTLLIYE VSNRFSGVPDRFSGSGSGTDFTLKISRVEAEDFGVYYCMQDAQDPP | 146 |
| IGKV2D-28 | A3 | DIVMTQSPLSLPVTPGEPASISCRSSQSLLHSNGYNYLDWYLQKPGQSPQLLI YLGSNRASGVPDRFSGSGSGTDFTLKISRVEAEDVGVYYCMQALQTP | 147 |
| IGKV2D-29 | A2 | DIVMTQTPLSLSVTPGQPASISCKSSQSLLHSDGKTYLYWYLQKPGQPPQLLI YEVSNRFSGVPDRFSGSGSGTDFTLKISRVEAEDVGVYYCMQSIQLP | 148 |
| IGKV2D-30 | A1 | DVVMTQSPLSLPVTLGQPASISCRSSQSLVYSDGNTYLNWFQQRPGQSPRR LIYKVSNWDSGVPDRFSGSGSGTDFTLKISRVEAEDVGVYYCMQGTHWP | 149 |
| IGKV2D-40 | O1 | DIVMTQTPLSLPVTPGEPASISCRSSQSLLDSDDGNTYLDWYLQKPGQSPQLL IYTLSYRASGVPDRFSGSGSGTDFTLKISRVEAEDVGVYYCMQRIEFP | 150 |
| IGKV3-7 | L10 | EIVMTQSPPTLSLSPGERVTLSCRASQSVSSSYLTWYQQKPGQAPRLLIYGAS TRATSIPARFSGSGSGTDFTLTISSLQPEDFAVYYCQQDHNLPP | 151 |
| IGKV3-11 | L6 | EIVLTQSPATLSLSPGERATLSCRASQSVSSYLAWYQQKPGQAPRLLIYDASN RATGIPARFSGSGSGTDFTLTISSLEPEDFAVYYCQQRSNWP | 152 |
| IGKV3-15 | L2 | EIVMTQSPATLSVSPGERATLSCRASQSVSSNLAWYQQKPGQAPRLLIYGAS TRATGIPARFSGSGSGTEFTLTISSLQSEDFAVYYCQQYNNWP | 153 |

Figure 46C

| | Zachau | Protein sequence | SEQ ID NO |
|---|---|---|---|
| IGKV3-20 | A27 | EIVLTQSPGTLSLSPGERATLSCRASQSVSSSYLAWYQQKPGQAPRLLIYGAS SRATGIPDRFSGSGSGTDFTLTISRLEPEDFAVYYCQQYGSSP | 154 |
| IGKV3D-07 | L25 | EIVMTQSPATLSLSPGERATLSCRASQSVSSSYLSWYQQKPGQAPRLLIYGAS TRATGIPARFSGSGSGTDFTLTISSLQPEDFAVYYCQQDYNLP | 155 |
| IGKV3D-11 | L20 | EIVLTQSPATLSLSPGERATLSCRASQGVSSYLAWYQQKPGQAPRLLIYDASN RATGIPARFSGSGPGTDFTLTISSLEPEDFAVYYCQQRSNWH | 156 |
| IGKV3D-15 | L16 | EIVMTQSPATLSVSPGERATLSCRASQSVSSNLAWYQQKPGQAPRLLIYGAS TRATGIPARFSGSGSGTEFTLTISSLQSEDFAVYYCQQYNNWP | 157 |
| IGKV3D-20 | A11 | EIVLTQSPATLSLSPGERATLSCGASQSVSSSYLAWYQQKPGLAPRLLIYDAS SRATGIPDRFSGSGSGTDFTLTISRLEPEDFAVYYCQQYGSSP | 158 |
| IGKV4-1 | B3 | DIVMTQSPDSLAVSLGERATINCKSSQSVLYSSNNKNYLAWYQQKPGQPPKL LIYWASTRESGVPDRFSGSGSGTDFTLTISSLQAEDVAVYYCQQYYSTP | 159 |
| IGKV5-2 | B2 | ETTLTQSPAFMSATPGDKVNISCKASQDIDDDMNWYQQKPGEAAIFIIQEATTL VPGIPPRFSGSGYGTDFTLTINNIESEDAAYYFCLQHDNFP | 160 |
| IGKV6-21 | A26 | EIVLTQSPDFQSVTPKEKVTITCRASQSIGSSLHWYQQKPDQSPKLLIKYASQS FSGVPSRFSGSGSGTDFTLTINSLEAEDAATYYCHQSSSLP | 161 |
| IGKV6D-21 | A10 | EIVLTQSPDFQSVTPKEKVTITCRASQSIGSSLHWYQQKPDQSPKLLIKYASQS FSGVPSRFSGSGSGTDFTLTINSLEAEDAATYYCHQSSSLP | 162 |
| IGKV6D-41 | A14 | DVVMTQSPAFLSVTPGEKVTITCQASEGIGNYLYWYQQKPDQAPKLLIKYASQ SISGVPSRFSGSGSGTDFTFTISSLEAEDAATYYCQQGNKHP | 163 |

Figure 47A

| | Kawasaki et al | Frippiat et al | Protein sequence | SEQ ID NO |
|---|---|---|---|---|
| IGLV1-36 | VL 1-11 | 1a | QSVLTQPPSVSEAPRQRVTISCSGSSSNIGNNAVNWYQQLPGKAPKLLIYY DDLLPSGVSDRFSGSKSGTSASLAISGLQSEDEADYYCAAWDDSLNGP | 164 |
| IGLV1-40 | VL 1-13 | 1e | QSVLTQPPSVSGAPGQRVTISCTGSSSNIGAGYDVHWYQQLPGTAPKLLIY GNSNRPSGVPDRFSGSKSGTSASLAITGLQAEDEADYYCQSYDSSLSGS | 165 |
| IGLV1-44 | VL 1-16 | 1c | QSVLTQPPSASGTPGQRVTISCSGSSSNIGSNTVNWYQQLPGTAPKLLIYS NNQRPSGVPDRFSGSKSGTSASLAISGLQSEDEADYYCAAWDDSLNGP | 166 |
| IGLV1-47 | VL 1-17 | 1g | QSVLTQPPSASGTPGQRVTISCSGSSSNIGSNYVYWYQQLPGTAPKLLIYS NNQRPSGVPDRFSGSKSGTSASLAISGLRSEDEADYYCAAWDDSLSGP | 167 |
| IGLV1-50 | VL 1-18 | 1f | QSVLTQPPSVSGAPGQRVTISCTGSSSNIGAGYVVHWYQQLPGTAPKLLIY GNSNRPSGVPDQFSGSKSGTSASLAITGLQSEDEADYYCKAWDNSLNA | 168 |
| IGLV1-51 | VL 1-19 | 1b | QSVLTQPPSVSAAPGQKVTISCSGSSSNIGNNYVSWYQQLPGTAPKLLIYD NNKRPSGIPDRFSGSKSGTSATLGITGLQTGDEADYYCGTWDSSLSAG | 169 |
| IGLV2-08 | VL 1-2 | 2c | QSALTQPPSASGSPGQSVTISCTGTSSDVGGYNYVSWYQQHPGKAPKLMI YEVSKRPSGVPDRFSGSKSGNTASLTVSGLQAEDEADYYCSSYAGSNNF | 170 |
| IGLV2-11 | VL 1-3 | 2e | QSALTQPRSVSGSPGQSVTISCTGTSSDVGGYNYVSWYQQHPGKAPKLMI YDVSKRPSGVPDRFSGSKSGNTASLTISGLQAEDEADYYCCSYAGSYTF | 171 |
| IGLV2-14 | VL 1-4 | 2a2 | QSALTQPASVSGSPGQSITISCTGTSSDVGGYNYVSWYQQHPGKAPKLMIY EVSNRPSGVSNRFSGSKSGNTASLTISGLQAEDEADYYCSSYTSSSTL | 172 |
| IGLV2-18 | VL 1-5 | 2d | QSALTQPPSVSGSPGQSVTISCTGTSSDVGSYNRVSWYQQPPGTAPKLMI YEVSNRPSGVPDRFSGSKSGNTASLTISGLQAEDEADYYCSLYTSSSTF | 173 |
| IGLV2-23 | VL 1-7 | 2b2 | QSALTQPASVSGSPGQSITISCTGTSSDVGSYNLVSWYQQHPGKAPKLMIY EGSKRPSGVSNRFSGSKSGNTASLTISGLQAEDEADYYCCSYAGSSTF | 174 |
| IGLV2-33 | VL 1-9 | 2f | QSALTQPPFVSGAPGQSVTISCTGTSSDVGDYDHVFWYQKRLSTTSRLLIY NVNTRPSGISDLFSGSKSGNMASLTISGLKSEVEANYHCSLYSSSYTF | 175 |
| IGLV3-1 | VL 2-1 | 3r | SYELTQPPSVSVSPGQTASITCSGDKLGDKYACWYQQKPGQSPVLVIYQD SKRPSGIPERFSGSNSGNTATLTISGTQAMDEADYYCQAWDSSTA | 176 |
| IGLV3-9 | VL 2-6 | 3j | SYELTQPLSVSVALGQTARITCGGNNIGSKNVHWYQQKPGQAPVLVIYRDS NRPSGIPERFSGSNSGNTATLTISRAQAGDEADYYCQVWDSSTA | 177 |
| IGLV3-10 | VL 2-7 | 3p | SYELTQPPSVSVSPGQTARITCSGDALPKKYAYWYQQKSGQAPVLVIYEDS KRPSGIPERFSGSSSGTMATLTISGAQVEDEADYYCYSTDSSGNH | 178 |
| IGLV3-12 | VL 2-8 | 3i | SYELTQPHSVSVATAQMARITCGGNNIGSKAVHWYQQKPGQDPVLVIYSDS NRPSGIPERFSGSNPGNTATLTISRIEAGDEADYYCQVWDSSSDHP | 179 |
| IGLV3-16 | VL 2-11 | 3a | SYELTQPPSVSVSLGQMARITCSGEALPKKYAYWYQQKPGQFPVLVIYKDS ERPSGIPERFSGSSSGTIVTLTISGVQAEDEADYYCLSADSSGTYP | 180 |
| IGLV3-19 | VL 2-13 | 3l | SSELTQDPAVSVALGQTVRITCQGDSLRSYYASWYQQKPGQAPVLVIYGKN NRPSGIPDRFSGSSSGNTASLTITGAQAEDEADYYCNSRDSSGNHL | 181 |
| IGLV3-21 | VL 2-14 | 3h | SYVLTQPPSVSVAPGQTARITCGGNNIGSKSVHWYQQKPGQAPVLVVYDD SDRPSGIPERFSGSNSGNTATLTISRVEAGDEADYYCQVWDSSSDHP | 182 |
| IGLV3-22 | VL 2-15 | 3e | SYELTQLPSVSVSPGQTARITCSGDVLGENYADWYQQKPGQAPELVIYEDS ERYPGIPERFSGSTSGNTTTLTISRVLTEDEADYYCLSGDEDNP | 183 |
| IGLV3-25 | VL 2-17 | 3m | SYELTQPPSVSVSPGQTARITCSGDALPKQYAYWYQQKPGQAPVLVIYKDS ERPSGIPERFSGSSSGTTVTLTISGVQAEDEADYYCQSADSSGTYP | 184 |
| IGLV3-27 | VL 2-19 | -- | SYELTQPSSVSVSPGQTARITCSGDVLAKKYARWFQQKPGQAPVLVIYKDS ERPSGIPERFSGSSSGTTVTLTISGAQVEDEADYYCYSAADNNL | 185 |

Figure 47B

| | Kawasaki et al | Frippiat et al | Protein sequence | SEQ ID NO |
|---|---|---|---|---|
| IGLV3-32 | VL 2-23P | 3i1 | SSGPTQVPAVSVALGQMARITCQGDSMEGSYEHWYQQKPGQAPVLVIYDSS DRPSRIPERFSGSKSGNTTTLTITGAQAEDEADYYYQLIDNHA | 186 |
| IGLV4-3 | VL 5-1 | 4c | LPVLTQPPSASALLGASIKLTCTLSSEHSTYTIEWYQQRPGRSPQYIMKVKSD GSHSKGDGIPDRFMGSSSGADRYLTFSNLQSDDEAEYHCGESHTIDGQVG | 187 |
| IGLV4-60 | VL 5-4 | 4a | QPVLTQSSSASASLGSSVKLTCTLSSGHSSYIIAWHQQQPGKAPRYLMKLEG SGSYNKGSGVPDRFSGSSSGADRYLTISNLQFEDEADYYCETWDSNT | 188 |
| IGLV4-69 | VL 5-6 | 4b | QLVLTQSPSASASLGASVKLTCTLSSGHSSYAIAWHQQQPEKGPRYLMKLNS DGSHSKGDGIPDRFSGSSSGAERYLTISSLQSEDEADYYCQTWGTG | 189 |
| IGLV5-37 | VL 4-1 | 5e | QPVLTQPPSSSASPGESARLTCTLPSDINVGSYNIYWYQQKPGSPPRYLLYYY SDSDKGQGSGVPSRFSGSKDASANTGILLISGLQSEDEADYYCMIWPSNAS | 190 |
| IGLV5-39 | -- | 5a | QPVLTQPTSLSASPGASARFTCTLRSGINVGTYRIYWYQQKPGSLPRYLLRYK SDSDKQQGSGVPSRFSGSKDASTNAGLLLISGLQSEDEADYYCAIWYSSTS | 191 |
| IGLV5-45 | VL 4-2 | 5c | QAVLTQPSSLSASPGASASLTCTLRSGINVGTYRIYWYQQKPGSPPQYLLRYK SDSDKQQGSGVPSRFSGSKDASANAGILLISGLQSEDEADYYCMIWHSSAS | 192 |
| IGLV5-48 | VL 4-3 | 5d | QPVLTQPTSLSASPGASARLTCTLRSGINLGSYRIFWYQQKPESPPRYLLSYY SDSSKHQGSGVPSRFSGSKDASSNAGILVISGLQSEDEADYYCMIWHSSAS | 193 |
| IGLV5-52 | VL 4-4 | 5b | QPVLTQPSSHSASSGASVRLTCMLSSGFSVGDFWIRWYQQKPGNPPRYLLY YHSDSNKGQGSGVPSRFSGSNDASANAGILRISGLQPEDEADYYCGTWHSN SKT | 194 |
| IGLV6-57 | VL 1-22 | 6a | NFMLTQPHSVSESPGKTVTISCTRSSGSIASNYVQWYQQRPGSSPTTVIYEDN QRPSGVPDRFSGSIDSSSNSASLTISGLKTEDEADYYCQSYDSSN | 195 |
| IGLV7-43 | VL 3-2 | 7a | QTVVTQEPSLTVSPGGTVTLTCASSTGAVTSGYYPNWFQQKPGQAPRALIYS TSNKHSWTPARFSGSLLGGKAALTLSGVQPEDEAEYYCLLYYGGAQ | 196 |
| IGLV7-46 | VL 3-3 | 7b | QAVVTQEPSLTVSPGGTVTLTCGSSTGAVTSGHYPYWFQQKPGQAPRTLIYD TSNKHSWTPARFSGSLLGGKAALTLLGAQPEDEAEYYCLLSYSGAR | 197 |
| IGLV8-61 | VL 3-4 | 8a | QTVVTQEPSFSVSPGGTVTLTCGLSSGSVSTSYYPSWYQQTPGQAPRTLIYS TNTRSSGVPDRFSGSILGNKAALTITGAQADDESDYYCVLYMGSGIS | 198 |
| IGLV9-49 | VL 5-2 | 9a | QPVLTQPPSASASLGASVTLTCTLSSGYSNYKVDWYQQRPGKGPRFVMRVG TGGIVGSKGDGIPDRFSVLGSGLNRYLTIKNIQEEDESDYHCGADHGSGSNFV | 199 |
| IGLV10-54 | VL 1-20 | 10a | QAGLTQPPSVSKGLRQTATLTCTGNSNIVGNQGAAWLQQHQGHPPKLLSYR NNNRPSGISERFSASRSGNTASLTITGLQPEDEADYYCSALDSSLSA | 200 |
| IGLV11-55 | VL 4-6 | -- | RPVLTQPPSLSASPGATARLPCTLSSDLSVGGKNMFWYQQKPGSSPRLFLYH YSDSDKQLGPGVPSRVSGSKETSSNTAFLLISGLQPEDEADYYCQVYESSAN | 201 |

Figure 55

| Relative Fab Display in ELISA (pJPd1) | | hVK_1_05 | hVK_1_06 | hVK_1_09 | hVK_1_12 | hVK_1_16 | hVK_1_17 | hVK_1_27 | hVK_1_39 | hVK_2_30 | hVK_3_11 | hVK_3_15 | hVK_3_20 | hVL_1_40 | hVL_1_47 | hVL_1_51 | hVL_2_11 | hVL_2_14 | hVL_2_23 | hVL_3_1 | hVL_3_21 |
|---|---|---|---|---|---|---|---|---|---|---|---|---|---|---|---|---|---|---|---|---|---|
| 1 | hVH_1_2 | 0.1 | 0.1 | 0.0 | 0.0 | 0.1 | 0.0 | 0.0 | 0.0 | | 0.0 | 0.0 | | | 0.0 | 0.0 | 0.1 | 0.1 | 0.0 | 0.4 | 0.0 |
| 2 | hVH_1_18 | 2.0 | 0.6 | 3.0 | 1.6 | 2.0 | 1.3 | 1.2 | 3.7 | 1.9 | | 2.6 | 2.2 | 2.4 | | 5.7 | 1.9 | 2.5 | 4.3 | 4.4 | 3.4 |
| 3 | hVH_1_46 | | 2.9 | | 2.1 | 1.3 | | | 2.5 | | | 3.0 | | | | | 1.6 | | 2.7 | 4.3 | 5.2 |
| 4 | hVH_1_69*01 | 2.1 | | | | 1.2 | 0.9 | 0.2 | 3.5 | | | 1.6 | | | | | 0.8 | 11.3 | 1.8 | 3.4 | 4.6 |
| 5 | hVH_3_07 | 5.5 | 4.3 | 6.7 | 10.6 | 7.0 | 10.5 | 14.5 | 27.3 | 13.0 | | 14.5 | | 8.2 | 6.3 | | | 8.4 | 6.9 | 5.0 | 9.8 |
| 6 | hVH_3_11 | 8.1 | 11.7 | 6.7 | 8.2 | 10.3 | 6.4 | 6.0 | 29.0 | | 0.0 | 4.6 | | 12.4 | 8.1 | 11.0 | 10.5 | 6.4 | 8.9 | 9.4 | 9.2 |
| 7 | hVH_3_15 | 10.0 | 16.1 | 10.0 | 11.5 | 14.5 | 5.0 | 7.8 | 14.2 | | 19.4 | 12.1 | 8.9 | 16.7 | 13.0 | | 13.6 | 9.7 | 10.1 | 4.6 | 11.8 |
| 8 | hVH_3_21 | | | | 11.3 | | | 8.7 | 11.6 | 4.1 | | | | | 0.0 | | | 6.5 | 8.8 | 8.8 | 7.4 |
| 9 | hVH_3_23 | | | 6.1 | 5.4 | 8.4 | | 17.1 | 10.8 | | | | 13.3 | | | 10.2 | | 9.1 | 7.4 | | 16.6 |
| 10 | hVH_3_30 | | | | | | | 9.1 | 13.1 | | | 12.3 | | | 10.3 | | | | 9.5 | 6.0 | |
| 11 | hVH_3_33 | 11.1 | | | | | | | | | | 12.1 | | | | | | | 17.1 | 5.1 | |
| 12 | hVH_3_48 | | | 8.3 | 14.8 | 10.7 | 2.9 | 8.9 | | 1.3 | | 9.6 | | | | 6.4 | 7.2 | | 9.3 | | 0.4 |
| 13 | hVH_3_53 | 0.4 | 0.3 | 0.3 | 0.3 | 0.3 | 0.1 | 3.6 | 0.2 | | 0.5 | 0.2 | | | 0.0 | 0.3 | 0.2 | | 6.3 | 0.0 | 1.8 |
| 14 | hVH_3_73 | 6.4 | 9.5 | 8.7 | 8.4 | 8.0 | 5.0 | 5.0 | 8.7 | 0.3 | | 10.0 | | 8.8 | 3.2 | 7.1 | | 4.7 | 0.8 | 7.0 | 5.2 |
| 15 | hVH_3_74 | | | 4.5 | | 3.2 | 0.7 | | | | | | | | 8.3 | | | | | 2.2 | |
| 16 | hVH_4_04*03 | 0.0 | | | | | | | | | | | | 0.0 | 0.0 | | | 0.0 | | | |
| 17 | hVH_4_31 | | 1.6 | 2.6 | 1.8 | 1.3 | | 0.4 | 2.1 | 0.9 | | | | 0.6 | | | 0.0 | 2.0 | 0.9 | 3.6 | 1.4 |
| 18 | hVH_4_39 | | | | | | | | 3.7 | | | 1.9 | | | | | | 2.1 | 3.0 | 3.8 | |
| 19 | hVH_5_51 | | 3.3 | 5.9 | 1.5 | | | | | | | | | 7.2 | | | 1.0 | | 2.1 | | |
| 20 | hVH_6_1 | | | | | | | | | | | | | | | | | | | | 0.4 |

Values illustrate Fab display compared to control; higher numbers indicate higher display levels

Figure 56

| | Relative Fab Expression in ELISA and BEL (pJPx1) | | hVK_1_05 | hVK_1_06 | hVK_1_09 | hVK_1_12 | hVK_1_16 | hVK_1_17 | hVK_1_27 | hVK_1_39 | hVK_2_30 | hVK_3_11 | hVK_3_15 | hVK_3_20 | hVL_1_40 | hVL_1_47 | hVL_1_51 | hVL_2_11 | hVL_2_14 | hVL_2_23 | hVL_3_1 | hVL_3_21 |
|---|---|---|---|---|---|---|---|---|---|---|---|---|---|---|---|---|---|---|---|---|---|---|
| | | | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| 1 | hVH_1_2 | | 0.0 | 0.2 | 0.0 | 0.0 | 0.0 | 0.0 | 0.1 | 0.0 | 0.0 | 0.0 | 0.0 | 0.0 | | | 0.0 | 0.0 | 0.0 | 0.0 | 0.0 | 0.0 |
| 2 | hVH_1_18 | | 0.4 | 0.5 | 0.6 | 0.5 | | 0.5 | 0.4 | 0.3 | 0.5 | 0.6 | 0.5 | 0.9 | | 0.8 | | | 0.6 | 0.7 | 0.6 | 0.6 |
| 3 | hVH_1_46 | | 0.4 | | 0.3 | 0.4 | 0.6 | 0.3 | | 0.4 | 0.2 | | 0.7 | 0.5 | 1.0 | | | | 0.8 | 1.0 | | |
| 4 | hVH_1_69*01 | | 0.5 | 0.9 | | 0.9 | | 0.5 | 0.3 | 0.1 | | 0.7 | 0.5 | | 1.0 | 1.2 | 1.0 | 0.7 | 0.8 | 0.8 | 0.7 | 0.7 |
| 5 | hVH_3_07 | | 0.7 | 0.6 | 0.4 | | 0.7 | 0.5 | 0.5 | 0.3 | 0.4 | | 0.7 | | | 0.8 | 1.1 | | 0.9 | 1.0 | 0.5 | 0.7 |
| 6 | hVH_3_11 | | 0.5 | | 0.5 | 0.6 | 0.9 | 0.6 | 0.6 | | | | | | | | 1.1 | | | | 0.5 | |
| 7 | hVH_3_15 | | 0.5 | 0.6 | | 0.7 | 0.7 | 0.6 | 0.5 | 0.4 | 0.3 | | 0.6 | | 0.9 | 1.2 | 1.1 | 0.9 | 0.8 | 1.0 | 0.3 | 0.8 |
| 8 | hVH_3_21 | | | 1.0 | 0.8 | 0.6 | 0.9 | | 0.6 | 0.5 | 0.6 | | 0.8 | | 1.0 | 1.2 | | 0.9 | 0.9 | 1.0 | 0.7 | 0.9 |
| 9 | hVH_3_23 | | 0.8 | 0.7 | | 0.9 | 0.6 | 0.6 | | 0.3 | 0.3 | | 0.7 | 0.8 | | | 1.1 | | | 0.9 | 0.4 | 0.8 |
| 10 | hVH_3_30 | | | 1.0 | | 0.8 | | | 0.7 | | | | | | 0.8 | 1.1 | 1.2 | 0.7 | 0.8 | 1.0 | 0.6 | 0.8 |
| 11 | hVH_3_33 | | 0.3 | | 0.7 | 0.2 | | | 0.6 | | | 0.4 | 0.7 | 0.3 | 1.1 | 1.1 | 1.3 | 0.5 | 0.9 | | 0.2 | 0.8 |
| 12 | hVH_3_48 | | | | | | | | | | | | 0.6 | 1.0 | 0.1 | 0.3 | 0.2 | | 0.9 | 0.5 | 0.1 | 0.2 |
| 13 | hVH_3_53 | | 0.7 | 0.7 | 0.9 | 0.7 | 0.0 | 0.5 | 0.4 | 0.6 | 0.3 | 0.8 | 0.7 | 0.3 | 0.4 | 1.2 | 1.1 | 0.6 | 1.0 | 1.1 | 0.6 | 0.6 |
| 14 | hVH_3_73 | | 0.2 | 0.2 | 0.1 | 0.1 | 0.2 | 0.1 | 0.1 | 0.2 | 0.1 | | 0.1 | | 1.0 | | | 1.0 | | | 0.1 | 0.7 |
| 15 | hVH_3_74 | | | 0.9 | 0.6 | 0.6 | | 0.6 | 0.6 | 0.2 | 0.4 | 0.6 | 0.8 | 0.7 | 0.6 | | | 0.5 | | | 0.6 | 0.6 |
| 16 | hVH_4_04*03 | | 0.8 | 0.8 | | 0.7 | 0.2 | 0.4 | 0.4 | | 0.5 | | 0.6 | 1.1 | 1.0 | 0.7 | 0.9 | 1.0 | 0.7 | 1.0 | 0.6 | 0.7 |
| 17 | hVH_4_31 | | 0.0 | | 0.1 | 0.1 | 0.0 | 0.0 | 0.0 | 0.8 | 0.0 | 0.6 | 0.1 | | 0.6 | | 0.9 | | | 0.0 | 0.3 | 0.4 |
| 18 | hVH_4_39 | | 0.3 | | 0.5 | | | 0.3 | | 0.3 | 0.2 | 0.3 | 0.6 | 0.6 | 0.9 | 0.7 | 0.8 | 0.5 | 0.6 | 0.7 | 0.5 | 0.6 |
| 19 | hVH_5_51 | | 0.5 | 0.5 | 0.5 | 0.8 | | 0.5 | 0.2 | 0.3 | 0.2 | 1.0 | | 0.9 | 1.0 | 1.0 | 1.1 | 0.7 | | 1.0 | 0.7 | 0.7 |
| 20 | hVH_6_1 | | 0.7 | 0.6 | | 0.0 | | 0.5 | 0.5 | 0.3 | 0.3 | | 0.7 | | | 1.1 | 1.1 | 1.0 | 0.6 | 0.8 | 0.5 | 0.8 |

Values display Fab expression compared to control; higher numbers indicate higher Fab expression levels

Figure 57

Relative Fab temperature stability in ELISA and BEL (pJPx1)

| # | VH | hVK_1_05 | hVK_1_06 | hVK_1_09 | hVK_1_12 | hVK_1_16 | hVK_1_17 | hVK_1_27 | hVK_1_39 | hVK_2_30 | hVK_3_11 | hVK_3_15 | hVK_3_20 | hVL_1_40 | hVL_1_47 | hVL_1_51 | hVL_2_11 | hVL_2_14 | hVL_2_23 | hVL_3_1 | hVL_3_21 |
|---|---|---|---|---|---|---|---|---|---|---|---|---|---|---|---|---|---|---|---|---|---|
| 1 | hVH_1_2 | bg | 60 | bg | bg | bg | bg | bg | bg | bg | bg | bg | bg |  | 4 | 4 | 4 | 4 | 4 | 4 | 4 |
| 2 | hVH_1_18 | 60 | 60 | 60 | 60 | 60 |  | 70 | 60 | 60 | 60 | 70 | 60 |  | 60 |  |  | 60 | 60 | 60 | 60 |
| 3 | hVH_1_46 | 60 |  | 60 | 60 | 60 |  |  | 60 | 4 | 60 | 60 | 60 | 60 |  | 60 | 60 | 60 | 60 |  |  |
| 4 | hVH_1_69*01 | 60 | 60 | 60 | 70 |  | 4 | 70 | 4 |  |  | 70 |  | 60 | 60 | 60 |  |  |  | 60 | 60 |
| 5 | hVH_3_07 | 60 | 60 | 60 | 60 | 60 | 4 | 70 | 60 | 4 |  | 60 |  |  | 60 | 60 | 60 | 60 | 60 | 60 | 60 |
| 6 | hVH_3_11 | 60 | 60 | 70 | 60 | 60 |  |  |  | 4 |  | 70 |  |  | 60 | 60 | 60 |  | 60 | 4 | 60 |
| 7 | hVH_3_15 |  | 60 |  | 70 | 60 | 4 | 70 | 60 | 4 | 60 | 60 | 60 | 60 | 60 | 60 | 60 | 60 | 60 |  | 60 |
| 8 | hVH_3_21 |  |  | 60 | 60 | 60 |  | 60 |  | 4 |  | 70 | 60 | 60 | 60 |  |  | 4 |  |  | 60 |
| 9 | hVH_3_23 | 60 | 60 | 70 | 60 |  | 4 | 60 | bg | bg | 60 | 60 | 60 |  | 60 | 60 | 60 |  | 60 | 60 | 60 |
| 10 | hVH_3_30 |  | 60 | 60 | 60 | bg | 4 | 60 | 60 | 4 | 60 | 60 | 4 | 4 |  | 60 | 60 | 60 | 60 | 60 | 60 |
| 11 | hVH_3_33 | 4 |  | 60 | 60 | 60 |  | 60 | 60 | bg | 60 | 60 | 60 | 60 | 4 | 60 | 4 | 60 | 60 | 60 | 60 |
| 12 | hVH_3_48 |  | 60 | 60 | 60 | bg | 4 | bg | bg | 4 | bg | bg | 60 | 4 |  | 60 | 60 | 60 |  | 60 | 60 |
| 13 | hVH_3_53 | 60 |  | 60 | 60 | 60 |  | 60 | 60 | 4 | 60 | 60 |  | 60 | 60 | 60 | 60 |  | 60 | 60 | 60 |
| 14 | hVH_3_73 | bg |  | bg | 60 |  | bg | bg | bg | bg |  | bg |  | 60 |  | 60 |  | 60 | 60 | 60 | 60 |
| 15 | hVH_3_74 | 60 | 60 | 60 | 60 |  | 60 | 70 |  |  | 60 | 70 | 60 | 4 | 60 | 60 | 60 | 60 | 60 | 60 | 60 |
| 16 | hVH_4_04*03 | 60 |  | 60 | 60 | 60 | 4 | 60 | 60 | 4 |  | 60 |  | 60 | 70 | 60 |  |  | 60 | 60 | 60 |
| 17 | hVH_4_31 | bg |  | bg | 60 |  | bg | bg | bg | bg | bg | bg |  |  | 60 |  |  | 60 | 60 | 60 | 60 |
| 18 | hVH_4_39 | 60 | 60 | 4 |  |  | 4 | 60 | 60 | 4 | 60 | 60 | 60 | 60 | 60 | 60 | 60 | 60 |  | 60 | 60 |
| 19 | hVH_5_51 | 60 | 60 | 60 |  |  | 60 | 60 | 60 | 4 | 60 | 70 |  | 60 | 60 | 60 |  |  | 60 | 60 | 60 |
| 20 | hVH_6_1 | 60 | 60 | 60 | bg | 60 | 60 | 70 | 60 | 4 | 60 | 70 | 60 | 60 | 60 | 60 | 60 | 60 | 60 | 60 | 60 |

The numbers 60 and 70 indicate VH/VL pairs which are stable for 45 min at 60 or 70 °C in the tested set-up. The number 4 indicates temperature-instable pairs and bg (background) indicates low expression levels.

Figure 58

| | Relative Fab bovine serum stability in ELISA and BEL (pJPx1) | hVK_1_05 | hVK_1_06 | hVK_1_09 | hVK_1_12 | hVK_1_16 | hVK_1_17 | hVK_1_27 | hVK_1_39 | hVK_2_30 | hVK_3_11 | hVK_3_15 | hVK_3_20 | hVL_1_40 | hVL_1_47 | hVL_1_51 | hVL_2_11 | hVL_2_14 | hVL_2_23 | hVL_3_1 | hVL_3_21 |
|---|---|---|---|---|---|---|---|---|---|---|---|---|---|---|---|---|---|---|---|---|---|
| 1 | hVH_1_2 | S | S | S | S | S | S | S | S | S | S | S | S | | S | U | S | U | U | U | U |
| 2 | hVH_1_18 | S | S | | S | | S | S | S | S | S | S | S | | S | | | | S | S | S |
| 3 | hVH_1_46 | S | | U | S | S | S | S | S | S | | S | S | S | | | S | S | S | S | S |
| 4 | hVH_1_69*01 | S | S | S | S | U | S | S | S | | | | | S | | S | | | | S | S |
| 5 | hVH_3_07 | S | S | S | S | S | U | S | S | S | | S | | | S | S | S | | S | S | S |
| 6 | hVH_3_11 | S | S | | S | S | U | | S | U | S | S | | S | S | S | S | S | | S | S |
| 7 | hVH_3_15 | S | | S | S | S | | | | S | | S | | | | | | | | S | S |
| 8 | hVH_3_21 | | S | | S | S | | S | S | S | | S | S | | S | S | S | S | S | S | S |
| 9 | hVH_3_23 | S | | S | S | S | | S | | | | S | S | | S | | | | | S | S |
| 10 | hVH_3_30 | S | | S | S | U | S | S | | U | | S | S | | | S | S | S | | S | S |
| 11 | hVH_3_33 | S | S | S | S | S | | S | S | S | | S | S | S | S | S | S | S | S | S | S |
| 12 | hVH_3_48 | S | S | S | S | S | S | S | S | S | S | S | U | S | S | S | S | S | | S | S |
| 13 | hVH_3_53 | S | S | S | S | S | S | S | S | S | S | S | | S | S | S | S | | | S | S |
| 14 | hVH_3_73 | S | | S | S | S | S | S | S | S | | S | | S | | S | S | | | S | S |
| 15 | hVH_3_74 | S | S | S | S | S | | S | S | S | S | S | U | S | S | S | S | S | S | S | S |
| 16 | hVH_4_04*03 | S | S | S | S | S | | | | S | | | | S | | | | | | S | S |
| 17 | hVH_4_31 | | | | S | S | bg | | | | | | | | | | | | | | |
| 18 | hVH_4_39 | S | S | S | S | S | S | S | S | | | | | S | S | S | S | S | S | S | S |
| 19 | hVH_5_51 | S | S | S | S | | S | S | S | S | S | S | | | S | S | S | | S | S | S |
| 20 | hVH_6_1 | S | | | | | | S | S | | | S | S | | S | S | S | S | S | S | S |

S stands for stable and U for unstable at the tested conditions; bg (background)

Figure 59

| Relative Fab mouse serum stability in ELISA and BEL (pJPx1) | | hVK_1_05 | hVK_1_06 | hVK_1_09 | hVK_1_12 | hVK_1_16 | hVK_1_17 | hVK_1_27 | hVK_1_39 | hVK_2_30 | hVK_3_11 | hVK_3_15 | hVK_3_20 | hVL_1_40 | hVL_1_47 | hVL_1_51 | hVL_2_11 | hVL_2_14 | hVL_2_23 | hVL_3_1 | hVL_3_21 |
|---|---|---|---|---|---|---|---|---|---|---|---|---|---|---|---|---|---|---|---|---|---|
| 1 | hVH_1_2 | U | S | U | S | S | S | S | S | S | S | U | S | | U | U | S | U | U | U | U |
| 2 | hVH_1_18 | S | S | S | S | S | S | S | S | S | S | S | S | S | S | S | | S | S | S | S |
| 3 | hVH_1_46 | S | | S | S | | S | S | S | U | S | S | | S | | S | | S | S | S | S |
| 4 | hVH_1_69*01 | S | S | S | S | S | S | S | S | S | S | S | S | S | S | S | S | S | | S | S |
| 5 | hVH_3_07 | S | S | S | S | S | | S | S | S | S | S | | S | S | S | S | S | S | S | S |
| 6 | hVH_3_11 | S | | S | S | S | S | S | S | S | | S | S | S | S | | S | S | S | S | S |
| 7 | hVH_3_15 | S | S | S | S | S | | S | S | S | S | S | S | S | S | S | S | S | S | S | S |
| 8 | hVH_3_21 | | | S | S | S | | S | U | S | S | S | S | | S | | S | S | S | S | S |
| 9 | hVH_3_23 | S | | | | | S | S | S | S | | S | | S | S | S | S | | S | S | S |
| 10 | hVH_3_30 | S | | S | S | S | | S | S | S | S | S | S | S | S | S | S | S | S | S | S |
| 11 | hVH_3_33 | U | | S | S | bg | S | S | S | S | S | S | S | S | S | S | S | S | S | S | S |
| 12 | hVH_3_48 | S | S | S | S | S | | S | | S | | S | S | S | S | S | S | S | S | S | S |
| 13 | hVH_3_53 | S | S | S | | S | S | S | S | S | S | S | S | S | S | S | S | S | S | S | S |
| 14 | hVH_3_73 | S | | S | S | S | U | S | S | S | S | S | S | S | | S | S | | S | S | S |
| 15 | hVH_3_74 | S | S | S | S | | S | S | S | S | S | S | S | S | S | S | S | S | S | S | S |
| 16 | hVH_4_04*03 | S | S | S | | S | S | S | S | S | S | S | S | S | S | S | S | S | S | S | S |
| 17 | hVH_4_31 | S | | S | S | | S | S | S | S | | S | S | S | S | S | S | | S | S | S |
| 18 | hVH_4_39 | S | S | S | | S | S | S | S | S | S | S | | S | S | S | | S | S | S | S |
| 19 | hVH_5_51 | S | S | S | | | S | S | S | S | S | S | S | | S | S | | | S | S | S |
| 20 | hVH_6_1 | S | | | U | | | S | S | S | S | S | | | | | | | | S | S |

S stands for stable and U for unstable at the tested conditions; bg (background)

Figure 60

| Relative IgG Expression in ELISA to MOR03080 | | hVK_1_05 | hVK_1_06 | hVK_1_09 | hVK_1_12 | hVK_1_16 | hVK_1_17 | hVK_1_27 | hVK_1_39 | hVK_2_30 | hVK_3_11 | hVK_3_15 | hVK_3_20 | hVL_1_40 | hVL_1_47 | hVL_1_51 | hVL_2_11 | hVL_2_14 | hVL_2_23 | hVL_3_1 | hVL_3_21 |
|---|---|---|---|---|---|---|---|---|---|---|---|---|---|---|---|---|---|---|---|---|---|
| 1 | hVH_1_2 | 0.0 | 0.0 | 0.0 | 0.0 | 0.0 | 0.0 | 0.0 | 0.0 | 0.0 | 0.0 | 0.0 | 0.0 | 0.3 | 0.0 | 0.4 | 0.3 | 0.1 | 0.0 | 0.0 | 0.0 |
| 2 | hVH_1_18 | 0.4 | 0.2 | 0.1 | 0.1 | 0.2 | 0.3 | 0.5 | 0.1 | 0.0 | 0.0 | 0.3 | 0.0 | 0.5 | 0.4 | 0.5 | 0.5 | 0.5 | 0.4 | 0.2 | 0.2 |
| 3 | hVH_1_46 | 0.9 | 0.9 | 0.4 | 0.2 | 0.3 | 0.5 | 0.6 | 0.5 | 0.0 | 0.1 | 0.4 | 0.1 | 0.9 | 0.6 | 0.3 | 0.3 | 0.3 | 0.3 | 0.4 | 0.3 |
| 4 | hVH_1_69*01 | 0.9 | 0.5 | 0.4 | 0.3 | 0.4 | 0.3 | 0.4 | 0.4 | 0.0 | 0.0 | 0.5 | 0.0 | 0.2 | 0.2 | 0.3 | 0.2 | 0.3 | 0.3 | 0.2 | 0.1 |
| 5 | hVH_3_07 | 0.9 | 1.3 | 1.5 | 0.9 | 1.5 | 0.9 | 1.8 | 1.2 | 0.3 | 0.4 | 1.8 | 0.4 | 0.3 | 0.8 | 0.9 | 1.2 | 0.8 | 0.7 | 1.2 | 0.3 |
| 6 | hVH_3_11 | 0.5 | 1.4 | 0.9 | 0.9 | 1.2 | 0.9 | 1.7 | 1.8 | 1.1 | 0.6 | 1.6 | 0.2 | 0.3 | 1.3 | 1.9 | 1.1 | 0.4 | 0.4 | 1.6 | 0.3 |
| 7 | hVH_3_15 | 0.4 | 0.8 | 0.9 | 0.7 | 1.5 | 0.8 | 1.7 | 1.8 | 0.6 | 0.8 | 1.9 | 0.5 | 0.1 | 0.2 | 0.9 | 0.8 | 0.9 | 0.4 | 1.0 | 0.3 |
| 8 | hVH_3_21 | 0.8 | 0.9 | 0.4 | 0.5 | 0.0 | 0.0 | 0.5 | 0.8 | 0.1 | 0.2 | 0.3 | 0.2 | 0.5 | 0.3 | 0.9 | 0.7 | 1.2 | 0.9 | 0.4 | 0.2 |
| 9 | hVH_3_23 | 0.2 | 0.2 | 0.1 | 0.1 | 0.2 | 0.1 | 0.2 | 0.3 | 0.0 | 0.0 | 0.4 | 0.4 | 0.1 | 0.1 | 0.2 | 0.1 | 0.3 | 0.3 | 0.1 | 0.1 |
| 10 | hVH_3_30 | 0.7 | 0.6 | 0.3 | 0.3 | 0.4 | 0.5 | 0.5 | 1.0 | 0.3 | 0.1 | 0.9 | 0.3 | 0.8 | 0.3 | 0.4 | 0.4 | 1.0 | 0.5 | 0.5 | 0.2 |
| 11 | hVH_3_33 | 0.0 | 0.6 | 0.2 | 0.2 | 0.5 | 0.5 | 0.2 | 0.8 | 0.3 | 0.6 | 0.9 | 0.4 | 1.0 | 0.4 | 0.6 | 0.5 | 0.9 | 0.5 | 0.7 | 0.5 |
| 12 | hVH_3_48 | 0.6 | 0.7 | 0.4 | 0.3 | 0.3 | 0.5 | 0.9 | 0.5 | 0.3 | 0.7 | 0.3 | 0.3 | 0.6 | 0.4 | 0.7 | 0.6 | 0.6 | 0.5 | 0.5 | 0.3 |
| 13 | hVH_3_53 | 0.8 | 0.7 | 0.9 | 0.2 | 0.5 | 0.5 | 0.2 | 0.2 | 0.0 | 0.3 | 0.5 | 0.4 | 1.2 | 0.2 | 0.4 | 0.3 | 0.8 | 0.6 | 0.5 | 0.5 |
| 14 | hVH_3_73 | 1.1 | 1.0 | 0.9 | 0.5 | 1.1 | 1.0 | 0.9 | 0.8 | 0.7 | 0.2 | 0.1 | 0.3 | 0.9 | 0.8 | 0.7 | 0.8 | 0.4 | 0.1 | 1.0 | 1.1 |
| 15 | hVH_3_74 | 0.6 | 1.0 | 0.5 | 0.0 | 0.8 | 0.2 | 1.1 | 0.3 | 0.2 | 0.1 | 1.0 | 0.6 | 1.2 | 0.6 | 1.2 | 0.8 | 0.6 | 1.0 | 0.3 | 0.3 |
| 16 | hVH_4_04*03 | 0.6 | 1.1 | 0.6 | 0.8 | 0.4 | 0.8 | 0.9 | 1.0 | 0.0 | 0.3 | 1.1 | 1.1 | 1.3 | 0.4 | 0.6 | 0.7 | 0.4 | 0.7 | 1.3 | 0.5 |
| 17 | hVH_4_31 | 0.0 | 0.2 | 0.6 | 0.4 | 0.0 | 0.2 | 0.0 | 0.5 | 0.2 | 0.0 | 0.1 | 0.4 | 0.9 | 0.1 | 0.3 | 0.2 | 0.5 | 0.3 | 0.5 | 0.4 |
| 18 | hVH_4_39 | 0.3 | 0.8 | 0.7 | 0.9 | 0.5 | 1.0 | 1.0 | 1.2 | 0.0 | 0.2 | 1.0 | 1.2 | 0.8 | 0.3 | 0.5 | 0.3 | 0.5 | 0.4 | 1.3 | 0.6 |
| 19 | hVH_5_51 | 0.4 | 0.9 | 0.5 | 0.8 | 0.5 | 0.6 | 0.9 | 1.1 | 0.7 | 0.6 | 1.0 | 0.4 | 1.3 | 0.8 | 0.5 | 0.3 | 0.8 | 0.7 | 0.9 | 0.7 |
| 20 | hVH_6_1 | 0.0 | 1.2 | 1.3 | 1.1 | 1.4 | 1.3 | 1.2 | 1.1 | 0.3 | 0.9 | 1.2 | 1.3 | 1.4 | 0.2 | 0.5 | 0.2 | 0.4 | 0.4 | 1.4 | 0.5 |

Values illustrate IgG expression compared to control; higher numbers indicate higher expression levels

Figure 61

| | Relative IgG bovine serum stability in ELISA after 14 days incubation at 37°C | hVK_1_05 | hVK_1_06 | hVK_1_09 | hVK_1_12 | hVK_1_16 | hVK_1_17 | hVK_1_27 | hVK_1_39 | hVK_2_30 | hVK_3_11 | hVK_3_15 | hVK_3_20 | hVL_1_40 | hVL_1_47 | hVL_1_51 | hVL_2_11 | hVL_2_14 | hVL_2_23 | hVL_3_1 | hVL_3_21 |
|---|---|---|---|---|---|---|---|---|---|---|---|---|---|---|---|---|---|---|---|---|---|
| | | bg | bg | bg | bg | bg | bg | bg | bg | bg | bg | bg | bg | bg | bg | bg | bg | bg | bg | bg | bg |
| 1 | hVH_1_2 | S | S | S | bg | S | S | S | S | S | S | S | S | S | U | S | S | U | S | U | S |
| 2 | hVH_1_18 | S | S | S | bg | S | S | S | S | S | S | S | S | S | U | S | S | U | S | S | S |
| 3 | hVH_1_46 | S | S | S | S | S | S | S | U | S | S | S | S | S | U | S | S | U | S | S | S |
| 4 | hVH_1_69*01 | U | S | S | S | S | S | S | S | S | S | S | S | S | U | S | S | U | S | S | S |
| 5 | hVH_3_07 | S | S | S | S | S | S | S | S | S | S | S | S | S | S | S | S | U | S | S | S |
| 6 | hVH_3_11 | S | S | S | S | S | S | S | S | S | S | S | S | S | S | S | S | S | S | S | S |
| 7 | hVH_3_15 | S | S | S | S | S | S | S | S | U | S | S | S | S | S | S | S | S | S | S | S |
| 8 | hVH_3_21 | S | S | S | S | S | S | S | S | S | bg | S | S | S | S | S | S | S | S | S | S |
| 9 | hVH_3_23 | S | S | S | S | S | S | S | S | U | S | S | S | S | S | S | S | S | S | S | S |
| 10 | hVH_3_30 | S | S | S | S | S | S | S | S | bg | S | S | S | S | S | S | S | S | S | S | S |
| 11 | hVH_3_33 | S | S | S | S | S | S | S | S | S | S | S | S | S | S | S | S | S | S | S | S |
| 12 | hVH_3_48 | S | S | S | S | S | S | S | S | bg | S | S | S | S | S | S | S | S | S | S | S |
| 13 | hVH_3_53 | S | S | S | S | S | S | S | S | U | S | S | S | S | S | S | S | S | S | S | bg |
| 14 | hVH_3_73 | S | S | S | S | S | S | bg | S | bg | S | S | S | S | S | S | S | S | S | S | S |
| 15 | hVH_3_74 | S | S | S | S | S | S | S | S | S | S | S | S | S | S | S | S | S | S | S | S |
| 16 | hVH_4_04*03 | S | bg | S | S | bg | bg | bg | S | bg | bg | S | S | S | S | S | S | S | S | bg | bg |
| 17 | hVH_4_31 | S | S | S | S | S | S | S | S | U | S | S | S | S | S | S | S | S | S | S | S |
| 18 | hVH_4_39 | S | S | S | S | S | S | S | S | bg | S | S | S | S | S | S | S | S | S | S | S |
| 19 | hVH_5_51 | S | S | S | S | S | S | S | S | S | S | S | S | S | S | S | S | S | S | S | S |
| 20 | hVH_6_1 | S | S | S | S | S | S | S | S | S | S | S | S | S | S | S | S | S | S | S | S |

S stands for stable and U for unstable at the tested conditions; bg (background)

```
                            SEQUENCE LISTING

<160> NUMBER OF SEQ ID NOS: 202

<210> SEQ ID NO 1
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Trp Gly Gly Asp Gly Phe Tyr Ala Met Asp Tyr
1               5                   10

<210> SEQ ID NO 2
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Gln Gln His Tyr Thr Thr Pro Pro Thr
1               5

<210> SEQ ID NO 3
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gln Ser Tyr Asp Ser Ser Leu Ser Gly Val Val
1               5                   10

<210> SEQ ID NO 4
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Tyr Phe Asp Tyr Trp Gly Gln Gly Thr Leu Val Thr Val Ser Ser
1               5                   10                  15

<210> SEQ ID NO 5
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 5

Trp Thr Phe Gly Gln Gly Thr Lys Val Glu Ile Lys
1               5                   10

<210> SEQ ID NO 6
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Val Val Phe Gly Gly Gly Thr Lys Leu Thr Val Leu
1               5                   10

<210> SEQ ID NO 7
<211> LENGTH: 63
<212> TYPE: DNA
<213> ORGANISM: Escherichia coli
<220> FEATURE:
<221> NAME/KEY: CDS
<222> LOCATION: (1)..(63)

<400> SEQUENCE: 7 atg aaa cag agc acc att gcc ctg gcc ctg ctg ccg ctg ctg ttt acc      48
Met Lys Gln Ser Thr Ile Ala Leu Ala Leu Leu Pro Leu Leu Phe Thr
1               5                   10                  15 cca gtg acc aaa gcc                                                  63
Pro Val Thr Lys Ala
            20

<210> SEQ ID NO 8
<211> LENGTH: 21
<212> TYPE: PRT
<213> ORGANISM: Escherichia coli

<400> SEQUENCE: 8

Met Lys Gln Ser Thr Ile Ala Leu Ala Leu Leu Pro Leu Leu Phe Thr
1               5                   10                  15

Pro Val Thr Lys Ala
            20

<210> SEQ ID NO 9
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: CDS
<222> LOCATION: (1)..(63)

<400> SEQUENCE: 9 atg aaa cag agc acc att gcc ctg gcc ctg ctg ccg ctg ctg ttt acc      48
Met Lys Gln Ser Thr Ile Ala Leu Ala Leu Leu Pro Leu Leu Phe Thr
1               5                   10                  15 cca gtg gtg cta gcc                                                  63
Pro Val Val Leu Ala
            20

<210> SEQ ID NO 10
<211> LENGTH: 21
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Met Lys Gln Ser Thr Ile Ala Leu Ala Leu Leu Pro Leu Leu Phe Thr
1               5                   10                  15

Pro Val Val Leu Ala
            20

<210> SEQ ID NO 11
<211> LENGTH: 63
<212> TYPE: DNA
<213> ORGANISM: Escherichia coli
<220> FEATURE:
<221> NAME/KEY: CDS
<222> LOCATION: (1)..(63)

<400> SEQUENCE: 11 atg aaa aaa acc gcc att gcc att gcc gtg gcc ctg gca ggc ttt gcc     48
Met Lys Lys Thr Ala Ile Ala Ile Ala Val Ala Leu Ala Gly Phe Ala
1               5                   10                  15 acc gtg gcg cag gcc                                                 63
Thr Val Ala Gln Ala
            20

<210> SEQ ID NO 12
<211> LENGTH: 21
<212> TYPE: PRT
<213> ORGANISM: Escherichia coli

<400> SEQUENCE: 12

Met Lys Lys Thr Ala Ile Ala Ile Ala Val Ala Leu Ala Gly Phe Ala
1               5                   10                  15

Thr Val Ala Gln Ala
            20

<210> SEQ ID NO 13
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: CDS
<222> LOCATION: (1)..(63)

<400> SEQUENCE: 13 atg aaa aaa acc gcc att gcc att gcc gtg gcc ctg gca ggc ttt gcc     48
Met Lys Lys Thr Ala Ile Ala Ile Ala Val Ala Leu Ala Gly Phe Ala
1               5                   10                  15 acc gtg gca tat gcc                                                 63
Thr Val Ala Tyr Ala
            20

<210> SEQ ID NO 14
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

-continued

```
<400> SEQUENCE: 14

Met Lys Lys Thr Ala Ile Ala Ile Ala Val Ala Leu Ala Gly Phe Ala
1               5                   10                  15

Thr Val Ala Tyr Ala
            20

<210> SEQ ID NO 15
<211> LENGTH: 57
<212> TYPE: DNA
<213> ORGANISM: Homo sapiens
<220> FEATURE:
<221> NAME/KEY: CDS
<222> LOCATION: (1)..(57)

<400> SEQUENCE: 15 atg aaa cac ctg tgg ttc ttc ctc ctg ctg gtg gca gct ccc aga tgg       48
Met Lys His Leu Trp Phe Phe Leu Leu Leu Val Ala Ala Pro Arg Trp
1               5                   10                  15 gtc ctg tcc                                                           57
Val Leu Ser <210> SEQ ID NO 16
<211> LENGTH: 19
<212> TYPE: PRT
<213> ORGANISM: Homo sapiens

<400> SEQUENCE: 16

Met Lys His Leu Trp Phe Phe Leu Leu Leu Val Ala Ala Pro Arg Trp
1               5                   10                  15

Val Leu Ser

<210> SEQ ID NO 17
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: CDS
<222> LOCATION: (1)..(57)

<400> SEQUENCE: 17 atg aag cac ctg tgg ttc ttt ctg ctg ctg gtg gcc gct ccc cgg tgg       48
Met Lys His Leu Trp Phe Phe Leu Leu Leu Val Ala Ala Pro Arg Trp
1               5                   10                  15 gtg cta gcc                                                           57
Val Leu Ala <210> SEQ ID NO 18
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Met Lys His Leu Trp Phe Phe Leu Leu Leu Val Ala Ala Pro Arg Trp
1               5                   10                  15

Val Leu Ala

<210> SEQ ID NO 19
```

```
<211> LENGTH: 60
<212> TYPE: DNA
<213> ORGANISM: Homo sapiens
<220> FEATURE:
<221> NAME/KEY: CDS
<222> LOCATION: (1)..(60)

<400> SEQUENCE: 19 atg gtg ttg cag acc cag gtc ttc att tct ctg ttg ctc tgg atc tct      48
Met Val Leu Gln Thr Gln Val Phe Ile Ser Leu Leu Leu Trp Ile Ser
1               5                   10                  15 ggt gcc tac ggg                                                      60
Gly Ala Tyr Gly
            20

<210> SEQ ID NO 20
<211> LENGTH: 20
<212> TYPE: PRT
<213> ORGANISM: Homo sapiens

<400> SEQUENCE: 20

Met Val Leu Gln Thr Gln Val Phe Ile Ser Leu Leu Leu Trp Ile Ser
1               5                   10                  15

Gly Ala Tyr Gly
            20

<210> SEQ ID NO 21
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: CDS
<222> LOCATION: (1)..(60)

<400> SEQUENCE: 21 atg gtg ctc cag acc cag gtg ttc atc agc ctg ctg ctg tgg atc agc      48
Met Val Leu Gln Thr Gln Val Phe Ile Ser Leu Leu Leu Trp Ile Ser
1               5                   10                  15 ggc gca tat gcg                                                      60
Gly Ala Tyr Ala
            20

<210> SEQ ID NO 22
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Met Val Leu Gln Thr Gln Val Phe Ile Ser Leu Leu Leu Trp Ile Ser
1               5                   10                  15

Gly Ala Tyr Ala
            20

<210> SEQ ID NO 23
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic primer"

<400> SEQUENCE: 23
acaggtgccc actcccaggt gcag                                              24

<210> SEQ ID NO 24
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
aaggtgtcca gtgtgargtg cag                                               23

<210> SEQ ID NO 25
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 25
cccagatggg tcctgtccca ggtgcag                                           27

<210> SEQ ID NO 26
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
caaggagtct gttccgaggt gcag                                              24

<210> SEQ ID NO 27
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
gggaattctc acaggagacg a                                                 21

<210> SEQ ID NO 28
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
ggaaggtgtg cacgccgctg gtc                                               23

<210> SEQ ID NO 29
<211> LENGTH: 38
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
ctgcaaccgg tgtacattcc caggtgcagc tggtgcag                     38

<210> SEQ ID NO 30
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
ctgcaaccgg tgtacattcc gaggtgcagc tggtgcag                     38

<210> SEQ ID NO 31
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
ctgcaaccgg tgtacattct gaggtgcagc tggtggag                     38

<210> SEQ ID NO 32
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
ctgcaaccgg tgtacattct gaggtgcagc tgttggag                     38

<210> SEQ ID NO 33
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 33
ctgcaaccgg tgtacattcc caggtgcagc tgcaggag                     38

<210> SEQ ID NO 34
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
ctgcaaccgg tgtacattcc caggtgcagc tacagcagtg                   40
```

```
<210> SEQ ID NO 35
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 35
tgcgaagtcg acgctgagga gacggtgacc ag                                32

<210> SEQ ID NO 36
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36
tgcgaagtcg acgctgaaga gacggtgacc attg                              34

<210> SEQ ID NO 37
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37
tgcgaagtcg acgctgagga gacggtgacc gtg                               33

<210> SEQ ID NO 38
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38
gttcggggaa gtagtccttg ac                                           22

<210> SEQ ID NO 39
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 39
atgaggstcc cygctcagct gctgg                                        25

<210> SEQ ID NO 40
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

```
<210> SEQ ID NO 41
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 41
atttctctgt tgctctggat ctctg                                          25

<210> SEQ ID NO 42
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 42
gtttctcgta gtctgctttg ctca                                           24

<210> SEQ ID NO 43
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43
atgacccagw ctccabycwc cctg                                           24

<210> SEQ ID NO 44
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 44
gtgctgtcct tgctgtcctg ct                                             22

<210> SEQ ID NO 45
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 45
ggtcctgggc ccagtctgtg ctg                                            23

<210> SEQ ID NO 46
<211> LENGTH: 23
<212> TYPE: DNA
<213> ORGANISM: Artificial Sequence
<220> FEATURE:
```

SEQUENCE: 40 ctcttcctcc tgctactctg gctcccag                                       28

```
<221> NAME/KEY: source
<223> OTHER INFORMATION: /note="Description of Artificial Sequence:
      Synthetic primer"

<400> SEQUENCE: 46
ggtcctgggc ccagtctgcc ctg                                              23

<210> SEQ ID NO 47
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 47
gctctgtgac tcctatgag ctg                                               23

<210> SEQ ID NO 48
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 48
ggtctctctc scagcytgtg ctg                                              23

<210> SEQ ID NO 49
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 49
gttcttgggc caattttatg ctg                                              23

<210> SEQ ID NO 50
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
ggtccaattc ycaggctgtg gtg                                              23

<210> SEQ ID NO 51
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 51
gagtggattc tcagactgtg gtg                                              23

<210> SEQ ID NO 52
```

```
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 52
caccagtgtg gccttgttgg cttg                                              24

<210> SEQ ID NO 53
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 53
ctgctaccgg ttcctgggcc cagtctgtgc tgackcag                               38

<210> SEQ ID NO 54
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 54
ctgctaccgg ttcctgggcc cagtctgccc tgactcag                               38

<210> SEQ ID NO 55
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
ctgctaccgg ttctgtgacc tcctatgagc tgacwcag                               38

<210> SEQ ID NO 56
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 56
ctgctaccgg ttctctctcs cagcytgtgc tgactca                                37

<210> SEQ ID NO 57
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 57
```

```
ctgctaccgg ttcttgggcc aattttatgc tgactcag                         38
```

<210> SEQ ID NO 58
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 58

```
ctgctaccgg ttccaattcy cagrctgtgg tgacycag                         38
```

<210> SEQ ID NO 59
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 59

```
ctcctcactc gagggygggga acagagtg                                   28
```

<210> SEQ ID NO 60
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Asn Ile Tyr Ser Asp Gly Ser Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Met Tyr Arg Trp Pro Phe His Tyr Phe Phe Asp Tyr Trp
            100                 105                 110

Gly Gln Gly Thr Leu Val Thr Val Ser Ser
        115                 120

<210> SEQ ID NO 61
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Lys Tyr Val
            20                  25                  30

Ser Trp Tyr Gln Gln Lys Pro Gly Gln Ala Pro Val Val Val Ile Tyr
            35                  40                  45

Gly Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Tyr Asp Ser Ser Tyr Phe Val
                85                  90                  95

Phe Gly Gly Gly Thr Lys Leu Thr Val Leu Gly Gln
                100                 105

<210> SEQ ID NO 62
<211> LENGTH: 98
<212> TYPE: PRT
<213> ORGANISM: Homo sapiens

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 63
<211> LENGTH: 98
<212> TYPE: PRT
<213> ORGANISM: Homo sapiens

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
            35                  40                  45

Gly Trp Ser Asn Ala Gly Asn Gly Asn Thr Lys Tyr Ser Gln Glu Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Met Ala Val Tyr Tyr Cys
                85                  90                  95

Ala Arg

<210> SEQ ID NO 64
<211> LENGTH: 99
<212> TYPE: PRT
<213> ORGANISM: Homo sapiens

<400> SEQUENCE: 64

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Asp Ile Asn Trp Val Arg Gln Ala Thr Gly Gln Gly Leu Glu Trp Met
        35                  40                  45
Gly Trp Met Asn Pro Asn Ser Gly Asn Thr Gly Tyr Ala Gln Lys Phe
    50                  55                  60
Gln Gly Arg Val Thr Met Thr Arg Asn Thr Ser Ile Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly

<210> SEQ ID NO 65
<211> LENGTH: 98
<212> TYPE: PRT
<213> ORGANISM: Homo sapiens

<400> SEQUENCE: 65

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Asn Gly Asn Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg

<210> SEQ ID NO 66
<211> LENGTH: 98
<212> TYPE: PRT
<213> ORGANISM: Homo sapiens

<400> SEQUENCE: 66

Gln Val Gln Leu Val Gln Ser Gly Ala Glu Val Lys Lys Pro Gly Ala
1               5                   10                  15
Ser Val Lys Val Ser Cys Lys Val Ser Gly Tyr Thr Leu Thr Glu Leu
            20                  25                  30
Ser Met His Trp Val Arg Gln Ala Pro Gly Lys Gly Leu Glu Trp Met
        35                  40                  45
Gly Gly Phe Asp Pro Glu Asp Gly Glu Thr Ile Tyr Ala Gln Lys Phe
    50                  55                  60
Gln Gly Arg Val Thr Met Thr Glu Asp Thr Ser Thr Asp Thr Ala Tyr
65                  70                  75                  80
Met Glu Leu Ser Ser Leu Arg Ser Glu Asp Thr Ala Val Tyr Tyr Cys
                85                  90                  95
Ala Thr

```
<210> SEQ ID NO 67
<211> LENGTH: 98
<212> TYPE: PRT
<213> ORGANISM: Homo sapiens

<400> SEQUENCE: 67

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Tyr Arg
            20                  25                  30

Tyr Leu His Trp Val Arg Gln Ala Pro Gly Gln Ala Leu Glu Trp Met
        35                  40                  45

Gly Trp Ile Thr Pro Phe Asn Gly Asn Thr Asn Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg

<210> SEQ ID NO 68
<211> LENGTH: 98
<212> TYPE: PRT
<213> ORGANISM: Homo sapiens

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 69
<211> LENGTH: 98
<212> TYPE: PRT
<213> ORGANISM: Homo sapiens

<400> SEQUENCE: 69

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Ser Ser
            20                  25                  30

Ala Met Gln Trp Val Arg Gln Ala Arg Gly Gln Arg Leu Glu Trp Ile
        35                  40                  45

Gly Trp Ile Val Val Gly Ser Gly Asn Thr Asn Tyr Ala Gln Lys Phe
    50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Ala

<210> SEQ ID NO 70
<211> LENGTH: 98
<212> TYPE: PRT
<213> ORGANISM: Homo sapiens

<400> SEQUENCE: 70

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 71
<211> LENGTH: 98
<212> TYPE: PRT
<213> ORGANISM: Homo sapiens

<400> SEQUENCE: 71

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 72
<211> LENGTH: 86
<212> TYPE: PRT
<213> ORGANISM: Homo sapiens

<400> SEQUENCE: 72

Lys Ser Gly Ala Ser Val Lys Val Ser Cys Ser Phe Ser Gly Phe Thr
1               5                   10                  15

Ile Thr Ser Tyr Gly Ile His Trp Val Gln Gln Ser Pro Gly Gln Gly
            20                  25                  30

Leu Glu Trp Met Gly Trp Ile Asn Pro Gly Asn Gly Ser Pro Ser Tyr
        35                  40                  45

Ala Lys Lys Phe Gln Gly Arg Phe Thr Met Thr Arg Asp Met Ser Thr
    50                  55                  60

Thr Thr Ala Tyr Thr Asp Leu Ser Ser Leu Thr Ser Glu Asp Met Ala

```
                65                  70                  75                  80
Val Tyr Tyr Tyr Ala Arg
                85

<210> SEQ ID NO 73
<211> LENGTH: 98
<212> TYPE: PRT
<213> ORGANISM: Homo sapiens

<400> SEQUENCE: 73

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 74
<211> LENGTH: 100
<212> TYPE: PRT
<213> ORGANISM: Homo sapiens

<400> SEQUENCE: 74

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg
            100

<210> SEQ ID NO 75
<211> LENGTH: 100
<212> TYPE: PRT
<213> ORGANISM: Homo sapiens

<400> SEQUENCE: 75

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
```

```
                  50                  55                  60

Leu Lys Ser Arg Leu Thr Ile Ser Lys Asp Thr Ser Lys Ser Gln Val
 65                  70                  75                  80

Val Leu Thr Met Thr Asn Met Asp Pro Val Asp Thr Ala Thr Tyr Tyr
                 85                  90                  95

Cys Ala Arg Ile
            100

<210> SEQ ID NO 76
<211> LENGTH: 100
<212> TYPE: PRT
<213> ORGANISM: Homo sapiens

<400> SEQUENCE: 76

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
                 20                  25                  30

Gly Met Cys Val Ser Trp Ile Arg Gln Pro Pro Gly Lys Ala Leu Glu
             35                  40                  45

Trp Leu Ala Leu Ile Asp Trp Asp Asp Asp Lys Tyr Tyr Ser Thr Ser
 50                  55                  60

Leu Lys Thr Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile
            100

<210> SEQ ID NO 77
<211> LENGTH: 98
<212> TYPE: PRT
<213> ORGANISM: Homo sapiens

<400> SEQUENCE: 77

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Trp Met Ser Trp Val Arg Gln Ala Pro Gly Lys Gly Leu Glu Trp Val
             35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 78
<211> LENGTH: 99
<212> TYPE: PRT
<213> ORGANISM: Homo sapiens

<400> SEQUENCE: 78

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
```

-continued

```
                    20                  25                  30
Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp
```

<210> SEQ ID NO 79
<211> LENGTH: 98
<212> TYPE: PRT
<213> ORGANISM: Homo sapiens

<400> SEQUENCE: 79

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 80
<211> LENGTH: 97
<212> TYPE: PRT
<213> ORGANISM: Homo sapiens

<400> SEQUENCE: 80

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Asp Met His Trp Val Arg Gln Ala Thr Gly Lys Gly Leu Glu Trp Val
            35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg
```

<210> SEQ ID NO 81
<211> LENGTH: 100
<212> TYPE: PRT
<213> ORGANISM: Homo sapiens

<400> SEQUENCE: 81

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 82
<211> LENGTH: 98
<212> TYPE: PRT
<213> ORGANISM: Homo sapiens

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Asp Met Asn Trp Ala Arg Lys Ala Pro Gly Lys Gly Leu Glu Trp Val
        35                  40                  45

Ser Gly Val Ser Trp Asn Gly Ser Arg Thr His Tyr Val Asp Ser Val
    50                  55                  60

Lys Arg Arg Phe Ile Ile Ser Arg Asp Asn Ser Arg Asn Ser Leu Tyr
65                  70                  75                  80

Leu Gln Lys Asn Arg Arg Ala Glu Asp Met Ala Val Tyr Tyr Cys
                85                  90                  95

Val Arg

<210> SEQ ID NO 83
<211> LENGTH: 98
<212> TYPE: PRT
<213> ORGANISM: Homo sapiens

<400> SEQUENCE: 83

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg

<210> SEQ ID NO 84
<211> LENGTH: 98
```

```
<212> TYPE: PRT
<213> ORGANISM: Homo sapiens

<400> SEQUENCE: 84

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 85
<211> LENGTH: 98
<212> TYPE: PRT
<213> ORGANISM: Homo sapiens

<400> SEQUENCE: 85

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 86
<211> LENGTH: 98
<212> TYPE: PRT
<213> ORGANISM: Homo sapiens

<400> SEQUENCE: 86

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 87
<211> LENGTH: 98
<212> TYPE: PRT
<213> ORGANISM: Homo sapiens

<400> SEQUENCE: 87

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Ala Met His Trp Val Arg Gln Ala Pro Gly Lys Gly Leu Glu Trp Val
        35                  40                  45
Ala Val Ile Ser Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg
```

<210> SEQ ID NO 88
<211> LENGTH: 98
<212> TYPE: PRT
<213> ORGANISM: Homo sapiens

<400> SEQUENCE: 88

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Ser Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys
```

<210> SEQ ID NO 89
<211> LENGTH: 98
<212> TYPE: PRT
<213> ORGANISM: Homo sapiens

<400> SEQUENCE: 89

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Trp Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg

<210> SEQ ID NO 90
<211> LENGTH: 98
<212> TYPE: PRT
<213> ORGANISM: Homo sapiens

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Asp Met Asn Trp Val His Gln Ala Pro Gly Lys Gly Leu Glu Trp Val
        35                  40                  45

Ser Gly Val Ser Trp Asn Gly Ser Arg Thr His Tyr Ala Asp Ser Val
    50                  55                  60

Lys Gly Arg Phe Ile Ile Ser Arg Asp Asn Ser Arg Asn Thr Leu Tyr
65                  70                  75                  80

Leu Gln Thr Asn Ser Leu Arg Ala Glu Asp Thr Ala Val Tyr Tyr Cys
                85                  90                  95

Val Arg

<210> SEQ ID NO 91
<211> LENGTH: 97
<212> TYPE: PRT
<213> ORGANISM: Homo sapiens

<400> SEQUENCE: 91

Glu Val Gln Leu Val Glu Ser Gly Gly Gly Leu Val Gln Pro Arg Gly
1               5                   10                  15

Ser Leu Arg Leu Ser Cys Ala Ala Ser Gly Phe Thr Val Ser Ser Asn
            20                  25                  30

Glu Met Ser Trp Ile Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Lys Asn Thr Leu Tyr Leu Gln
65                  70                  75                  80

Met Asn Asn Leu Arg Ala Glu Gly Thr Ala Ala Tyr Tyr Cys Ala Arg
                85                  90                  95

Tyr

<210> SEQ ID NO 92
<211> LENGTH: 99
<212> TYPE: PRT
<213> ORGANISM: Homo sapiens

<400> SEQUENCE: 92

Glu Val Gln Leu Val Glu Ser Gly Gly Val Val Val Pro Gly Gly
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Leu Ile Ser Trp Asp Gly Ser Thr Tyr Tyr Ala Asp Ser Val
    50                  55                  60
```

-continued

```
Lys Gly Arg Phe Thr Ile Ser Arg Asp Asn Ser Lys Asn Ser Leu Tyr
 65                  70                  75                  80

Leu Gln Met Asn Ser Leu Arg Thr Glu Asp Thr Ala Leu Tyr Tyr Cys
                 85                  90                  95

Ala Lys Asp

<210> SEQ ID NO 93
<211> LENGTH: 98
<212> TYPE: PRT
<213> ORGANISM: Homo sapiens

<400> SEQUENCE: 93

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Gly Leu Glu Trp Val
         35                  40                  45

Ser Tyr Ile Ser Ser Ser Ser Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Arg

<210> SEQ ID NO 94
<211> LENGTH: 100
<212> TYPE: PRT
<213> ORGANISM: Homo sapiens

<400> SEQUENCE: 94

Glu Val Gln Leu Val Glu Ser Gly Gly Gly Leu Val Gln Pro Gly Arg
 1               5                  10                  15

Ser Leu Arg Leu Ser Cys Thr Ala Ser Gly Phe Thr Phe Gly Asp Tyr
             20                  25                  30

Ala Met Ser Trp Phe Arg Gln Ala Pro Gly Lys Gly Leu Glu Trp Val
         35                  40                  45

Gly Phe Ile Arg Ser Lys Ala Tyr Gly Gly Thr Thr Glu Tyr Ala Ala
     50                  55                  60

Ser Val Lys Gly Arg Phe Thr Ile Ser Arg Asp Asp Ser Lys Ser Ile
 65                  70                  75                  80

Ala Tyr Leu Gln Met Asn Ser Leu Lys Thr Glu Asp Thr Ala Val Tyr
                 85                  90                  95

Tyr Cys Thr Arg
            100

<210> SEQ ID NO 95
<211> LENGTH: 97
<212> TYPE: PRT
<213> ORGANISM: Homo sapiens

<400> SEQUENCE: 95

Glu Val Gln Leu Val Glu Ser Gly Gly Gly Leu Ile Gln Pro Gly Gly
 1               5                  10                  15

Ser Leu Arg Leu Ser Cys Ala Ser Gly Phe Thr Val Ser Ser Asn
             20                  25                  30
```

```
Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 96
<211> LENGTH: 98
<212> TYPE: PRT
<213> ORGANISM: Homo sapiens

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg

<210> SEQ ID NO 97
<211> LENGTH: 97
<212> TYPE: PRT
<213> ORGANISM: Homo sapiens

<400> SEQUENCE: 97

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Cys Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 98
<211> LENGTH: 100
<212> TYPE: PRT
<213> ORGANISM: Homo sapiens

<400> SEQUENCE: 98

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg
            100

<210> SEQ ID NO 99
<211> LENGTH: 100
<212> TYPE: PRT
<213> ORGANISM: Homo sapiens

<400> SEQUENCE: 99

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 100
<211> LENGTH: 98
<212> TYPE: PRT
<213> ORGANISM: Homo sapiens

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 101
<211> LENGTH: 96
<212> TYPE: PRT

<213> ORGANISM: Homo sapiens

<400> SEQUENCE: 101

```
Glu Val Gln Leu Val Glu Ser Arg Gly Val Leu Val Gln Pro Gly Gly
1               5                   10                  15

Ser Leu Arg Leu Ser Cys Ala Ala Ser Gly Phe Thr Val Ser Ser Asn
            20                  25                  30

Glu Met Ser Trp Val Arg Gln Ala Pro Gly Lys Gly Leu Glu Trp Val
        35                  40                  45

Ser Ser Ile Ser Gly Gly Ser Thr Tyr Tyr Ala Asp Ser Arg Lys Gly
    50                  55                  60

Arg Phe Thr Ile Ser Arg Asp Asn Ser Lys Asn Thr Leu His Leu Gln
65                  70                  75                  80

Met Asn Ser Leu Arg Ala Glu Asp Thr Ala Val Tyr Tyr Cys Lys Lys
                85                  90                  95
```

<210> SEQ ID NO 102
<211> LENGTH: 97
<212> TYPE: PRT
<213> ORGANISM: Homo sapiens

<400> SEQUENCE: 102

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg
```

<210> SEQ ID NO 103
<211> LENGTH: 98
<212> TYPE: PRT
<213> ORGANISM: Homo sapiens

<400> SEQUENCE: 103

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Ser
            20                  25                  30

Asn Trp Trp Gly Trp Ile Arg Gln Pro Pro Gly Lys Gly Leu Glu Trp
        35                  40                  45

Ile Gly Tyr Ile Tyr Tyr Ser Gly Ser Thr Tyr Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg
```

<210> SEQ ID NO 104

```
<211> LENGTH: 99
<212> TYPE: PRT
<213> ORGANISM: Homo sapiens

<400> SEQUENCE: 104

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg

<210> SEQ ID NO 105
<211> LENGTH: 99
<212> TYPE: PRT
<213> ORGANISM: Homo sapiens

<400> SEQUENCE: 105

Gln Leu Gln Leu Gln Glu Ser Gly Ser Gly Leu Val Lys Pro Ser Gln
1               5                   10                  15

Thr Leu Ser Leu Thr Cys Ala Val Ser Gly Gly Ser Ile Ser Ser Gly
            20                  25                  30

Gly Tyr Ser Trp Ser Trp Ile Arg Gln Pro Pro Gly Lys Gly Leu Glu
        35                  40                  45

Trp Ile Gly Tyr Ile Tyr His Ser Gly Ser Thr Tyr Tyr Asn Pro Ser
50                  55                  60

Leu Lys Ser Arg Val Thr Ile Ser Val Asp Arg Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg

<210> SEQ ID NO 106
<211> LENGTH: 99
<212> TYPE: PRT
<213> ORGANISM: Homo sapiens

<400> SEQUENCE: 106

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95
```

Cys Ala Arg

<210> SEQ ID NO 107
<211> LENGTH: 99
<212> TYPE: PRT
<213> ORGANISM: Homo sapiens

<400> SEQUENCE: 107

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 108
<211> LENGTH: 98
<212> TYPE: PRT
<213> ORGANISM: Homo sapiens

<400> SEQUENCE: 108

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly

<210> SEQ ID NO 109
<211> LENGTH: 99
<212> TYPE: PRT
<213> ORGANISM: Homo sapiens

<400> SEQUENCE: 109

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

```
Ser Leu Lys Leu Ser Ser Val Thr Ala Ala Asp Thr Ala Val Tyr Tyr
            85                  90                  95

Cys Ala Arg

<210> SEQ ID NO 110
<211> LENGTH: 97
<212> TYPE: PRT
<213> ORGANISM: Homo sapiens

<400> SEQUENCE: 110

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 111
<211> LENGTH: 99
<212> TYPE: PRT
<213> ORGANISM: Homo sapiens

<400> SEQUENCE: 111

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 112
<211> LENGTH: 98
<212> TYPE: PRT
<213> ORGANISM: Homo sapiens

<400> SEQUENCE: 112

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
```

```
            50                  55                  60
Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg

<210> SEQ ID NO 113
<211> LENGTH: 98
<212> TYPE: PRT
<213> ORGANISM: Homo sapiens

<400> SEQUENCE: 113

Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
                 20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
         50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg

<210> SEQ ID NO 114
<211> LENGTH: 98
<212> TYPE: PRT
<213> ORGANISM: Homo sapiens

<400> SEQUENCE: 114

Glu Val Gln Leu Val Gln Ser Gly Ala Glu Val Lys Lys Pro Gly Glu
  1               5                  10                  15

Ser Leu Arg Ile Ser Cys Lys Gly Ser Gly Tyr Ser Phe Thr Ser Tyr
                 20                  25                  30

Trp Ile Ser Trp Val Arg Gln Met Pro Gly Lys Gly Leu Glu Trp Met
             35                  40                  45

Gly Arg Ile Asp Pro Ser Asp Ser Tyr Thr Asn Tyr Ser Pro Ser Phe
         50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg

<210> SEQ ID NO 115
<211> LENGTH: 101
<212> TYPE: PRT
<213> ORGANISM: Homo sapiens

<400> SEQUENCE: 115

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
                 20                  25                  30
```

```
Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg
            100

<210> SEQ ID NO 116
<211> LENGTH: 98
<212> TYPE: PRT
<213> ORGANISM: Homo sapiens

<400> SEQUENCE: 116

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg

<210> SEQ ID NO 117
<211> LENGTH: 98
<212> TYPE: PRT
<213> ORGANISM: Homo sapiens

<400> SEQUENCE: 117

Gln Val Gln Leu Val Gln Ser Gly His Glu Val Lys Gln Pro Gly Ala
1               5                   10                  15

Ser Val Lys Val Ser Cys Lys Ala Ser Gly Tyr Ser Phe Thr Thr Tyr
            20                  25                  30

Gly Met Asn Trp Val Pro Gln Ala Pro Gly Gln Gly Leu Glu Trp Met
        35                  40                  45

Gly Trp Phe Asn Thr Tyr Thr Gly Asn Pro Thr Tyr Ala Gln Gly Phe
    50                  55                  60

Thr Gly Arg Phe Val Phe Ser Met Asp Thr Ser Ala Ser Thr Ala Tyr
65                  70                  75                  80

Leu Gln Ile Ser Ser Leu Lys Ala Glu Asp Met Ala Met Tyr Tyr Cys
                85                  90                  95

Ala Arg

<210> SEQ ID NO 118
<211> LENGTH: 95
<212> TYPE: PRT
<213> ORGANISM: Homo sapiens

<400> SEQUENCE: 118

Asp Ile Gln Met Thr Gln Ser Pro Ser Thr Leu Ser Ala Ser Val Gly
```

```
                1               5                  10                 15
Asp Arg Val Thr Ile Thr Cys Arg Ala Ser Gln Ser Ile Ser Ser Trp
                20                 25                 30

Leu Ala Trp Tyr Gln Gln Lys Pro Gly Lys Ala Pro Lys Leu Leu Ile
        35                 40                 45

Tyr Asp Ala Ser Ser Leu Glu Ser Gly Val Pro Ser Arg Phe Ser Gly
    50                 55                 60

Ser Gly Ser Gly Thr Glu Phe Thr Leu Thr Ile Ser Ser Leu Gln Pro
65                 70                 75                 80

Asp Asp Phe Ala Thr Tyr Tyr Cys Gln Gln Tyr Asn Ser Tyr Ser
                85                 90                 95
```

<210> SEQ ID NO 119
<211> LENGTH: 95
<212> TYPE: PRT
<213> ORGANISM: Homo sapiens

<400> SEQUENCE: 119

```
Ala Ile Gln Met Thr Gln Ser Pro Ser Ser Leu Ser Ala Ser Val Gly
1               5                  10                 15

Asp Arg Val Thr Ile Thr Cys Arg Ala Ser Gln Gly Ile Arg Asn Asp
                20                 25                 30

Leu Gly Trp Tyr Gln Gln Lys Pro Gly Lys Ala Pro Lys Leu Leu Ile
        35                 40                 45

Tyr Ala Ala Ser Ser Leu Gln Ser Gly Val Pro Ser Arg Phe Ser Gly
    50                 55                 60

Ser Gly Ser Gly Thr Asp Phe Thr Leu Thr Ile Ser Ser Leu Gln Pro
65                 70                 75                 80

Glu Asp Phe Ala Thr Tyr Tyr Cys Leu Gln Asp Tyr Asn Tyr Pro
                85                 90                 95
```

<210> SEQ ID NO 120
<211> LENGTH: 95
<212> TYPE: PRT
<213> ORGANISM: Homo sapiens

<400> SEQUENCE: 120

```
Ala Ile Arg Met Thr Gln Ser Pro Ser Ser Phe Ser Ala Ser Thr Gly
1               5                  10                 15

Asp Arg Val Thr Ile Thr Cys Arg Ala Ser Gln Gly Ile Ser Ser Tyr
                20                 25                 30

Leu Ala Trp Tyr Gln Gln Lys Pro Gly Lys Ala Pro Lys Leu Leu Ile
        35                 40                 45

Tyr Ala Ala Ser Thr Leu Gln Ser Gly Val Pro Ser Arg Phe Ser Gly
    50                 55                 60

Ser Gly Ser Gly Thr Asp Phe Thr Leu Thr Ile Ser Cys Leu Gln Ser
65                 70                 75                 80

Glu Asp Phe Ala Thr Tyr Tyr Cys Gln Gln Tyr Tyr Ser Tyr Pro
                85                 90                 95
```

<210> SEQ ID NO 121
<211> LENGTH: 95
<212> TYPE: PRT
<213> ORGANISM: Homo sapiens

<400> SEQUENCE: 121

```
Asp Ile Gln Leu Thr Gln Ser Pro Ser Phe Leu Ser Ala Ser Val Gly
1               5                  10                 15
```

-continued

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro
                85                  90                  95

<210> SEQ ID NO 122
<211> LENGTH: 95
<212> TYPE: PRT
<213> ORGANISM: Homo sapiens

<400> SEQUENCE: 122

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro
                85                  90                  95

<210> SEQ ID NO 123
<211> LENGTH: 95
<212> TYPE: PRT
<213> ORGANISM: Homo sapiens

<400> SEQUENCE: 123

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro
                85                  90                  95

<210> SEQ ID NO 124
<211> LENGTH: 95
<212> TYPE: PRT
<213> ORGANISM: Homo sapiens

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

```
Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95

<210> SEQ ID NO 125
<211> LENGTH: 95
<212> TYPE: PRT
<213> ORGANISM: Homo sapiens

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro
                85                  90                  95

<210> SEQ ID NO 126
<211> LENGTH: 95
<212> TYPE: PRT
<213> ORGANISM: Homo sapiens

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro
                85                  90                  95

<210> SEQ ID NO 127
<211> LENGTH: 95
<212> TYPE: PRT
<213> ORGANISM: Homo sapiens

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
```

```
                35                  40                  45
Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro
                 85                  90                  95

<210> SEQ ID NO 128
<211> LENGTH: 96
<212> TYPE: PRT
<213> ORGANISM: Homo sapiens

<400> SEQUENCE: 128

Asp Ile Gln Leu Thr Gln Ser Pro Ser Ser Leu Ser Ala Ser Val Gly
  1               5                  10                  15

Asp Arg Val Thr Ile Thr Cys Arg Val Ser Gln Gly Ile Ser Ser Tyr
                 20                  25                  30

Leu Asn Trp Tyr Arg Gln Lys Pro Gly Lys Val Pro Lys Leu Leu Ile
             35                  40                  45

Tyr Ser Ala Ser Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Gly Gln Arg Thr Tyr Asn Ala Pro Pro
                 85                  90                  95

<210> SEQ ID NO 129
<211> LENGTH: 95
<212> TYPE: PRT
<213> ORGANISM: Homo sapiens

<400> SEQUENCE: 129

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro
                 85                  90                  95

<210> SEQ ID NO 130
<211> LENGTH: 95
<212> TYPE: PRT
<213> ORGANISM: Homo sapiens

<400> SEQUENCE: 130

Val Ile Trp Met Thr Gln Ser Pro Ser Leu Leu Ser Ala Ser Thr Gly
  1               5                  10                  15

Asp Arg Val Thr Ile Ser Cys Arg Met Ser Gln Gly Ile Ser Ser Tyr
                 20                  25                  30

Leu Ala Trp Tyr Gln Gln Lys Pro Gly Lys Ala Pro Glu Leu Leu Ile
             35                  40                  45
```

Tyr Ala Ala Ser Thr Leu Gln Ser Gly Val Pro Ser Arg Phe Ser Gly
                50                  55                  60

Ser Gly Ser Gly Thr Asp Phe Thr Leu Thr Ile Ser Cys Leu Gln Ser
 65                  70                  75                  80

Glu Asp Phe Ala Thr Tyr Tyr Cys Gln Gln Tyr Tyr Ser Phe Pro
                85                  90                  95

<210> SEQ ID NO 131
<211> LENGTH: 95
<212> TYPE: PRT
<213> ORGANISM: Homo sapiens

<400> SEQUENCE: 131

Asp Ile Gln Met Thr Gln Ser Pro Ser Ser Val Ser Ala Ser Val Gly
 1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
                35                  40                  45

Tyr Ala Ala Ser Ser Leu Gln Ser Gly Val Pro Ser Arg Phe Ser Gly
                50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro
                85                  90                  95

<210> SEQ ID NO 132
<211> LENGTH: 95
<212> TYPE: PRT
<213> ORGANISM: Homo sapiens

<400> SEQUENCE: 132

Ala Ile Gln Leu Thr Gln Ser Pro Ser Ser Leu Ser Ala Ser Val Gly
 1               5                   10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
                35                  40                  45

Tyr Asp Ala Ser Ser Leu Glu Ser Gly Val Pro Ser Arg Phe Ser Gly
                50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Asn Tyr Pro
                85                  90                  95

<210> SEQ ID NO 133
<211> LENGTH: 95
<212> TYPE: PRT
<213> ORGANISM: Homo sapiens

<400> SEQUENCE: 133

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
                35                  40                  45

Tyr Ala Ala Ser Ser Leu Gln Ser Gly Val Pro Ser Arg Phe Ser Gly
                50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                 85                  90                  95
```

<210> SEQ ID NO 134
<211> LENGTH: 95
<212> TYPE: PRT
<213> ORGANISM: Homo sapiens

<400> SEQUENCE: 134

```
Asn Ile Gln Met Thr Gln Ser Pro Ser Ala Met Ser Ala Ser Val Gly
  1               5                  10                  15

Asp Arg Val Thr Ile Thr Cys Arg Ala Arg Gln Gly Ile Ser Asn Tyr
                 20                  25                  30

Leu Ala Trp Phe Gln Gln Lys Pro Gly Lys Val Pro Lys His Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro
                 85                  90                  95
```

<210> SEQ ID NO 135
<211> LENGTH: 95
<212> TYPE: PRT
<213> ORGANISM: Homo sapiens

<400> SEQUENCE: 135

```
Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
         50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro
                 85                  90                  95
```

<210> SEQ ID NO 136
<211> LENGTH: 96
<212> TYPE: PRT
<213> ORGANISM: Homo sapiens

<400> SEQUENCE: 136

```
Asp Ile Gln Leu Thr Gln Ser Pro Ser Ser Leu Ser Ala Ser Val Gly
  1               5                  10                  15

Asp Arg Val Thr Ile Thr Cys Arg Val Ser Gln Gly Ile Ser Ser Tyr
                 20                  25                  30

Leu Asn Trp Tyr Arg Gln Lys Pro Gly Lys Val Pro Lys Leu Leu Ile
             35                  40                  45

Tyr Ser Ala Ser Asn Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
```

-continued

```
                65                  70                  75                  80
Glu Asp Val Ala Thr Tyr Tyr Gly Gln Arg Thr Tyr Asn Ala Pro Pro
                    85                  90                  95

<210> SEQ ID NO 137
<211> LENGTH: 95
<212> TYPE: PRT
<213> ORGANISM: Homo sapiens

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 138
<211> LENGTH: 96
<212> TYPE: PRT
<213> ORGANISM: Homo sapiens

<400> SEQUENCE: 138

Asp Ile Gln Met Ile Gln Ser Pro Ser Phe Leu Ser Ala Ser Val Gly
1               5                   10                  15

Asp Arg Val Ser Ile Ile Cys Trp Ala Ser Glu Gly Ile Ser Ser Asn
            20                  25                  30

Leu Ala Trp Tyr Leu Gln Lys Pro Gly Lys Ser Pro Lys Leu Phe Leu
        35                  40                  45

Tyr Asp Ala Lys Asp Leu His Pro Gly Val Ser Ser Arg Phe Ser Gly
    50                  55                  60

Arg Gly Ser Gly Thr Asp Phe Thr Leu Thr Ile Ile Ser Leu Lys Pro
65                  70                  75                  80

Glu Asp Phe Ala Ala Tyr Tyr Cys Lys Gln Asp Phe Ser Tyr Pro Pro
                85                  90                  95

<210> SEQ ID NO 139
<211> LENGTH: 95
<212> TYPE: PRT
<213> ORGANISM: Homo sapiens

<400> SEQUENCE: 139

Ala Ile Arg Met Thr Gln Ser Pro Phe Ser Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Ala Lys Ala Pro Lys Leu Phe Ile
        35                  40                  45

Tyr Tyr Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80
```

```
Glu Asp Phe Ala Thr Tyr Tyr Cys Gln Gln Tyr Tyr Ser Thr Pro
                85                  90                  95

<210> SEQ ID NO 140
<211> LENGTH: 100
<212> TYPE: PRT
<213> ORGANISM: Homo sapiens

<400> SEQUENCE: 140

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro
            100

<210> SEQ ID NO 141
<211> LENGTH: 100
<212> TYPE: PRT
<213> ORGANISM: Homo sapiens

<400> SEQUENCE: 141

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100

<210> SEQ ID NO 142
<211> LENGTH: 100
<212> TYPE: PRT
<213> ORGANISM: Homo sapiens

<400> SEQUENCE: 142

Asp Ile Val Met Thr Gln Thr Pro Leu Ser Leu Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60
```

```
Asp Arg Phe Ser Gly Ser Gly Ser Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro
            100
```

<210> SEQ ID NO 143
<211> LENGTH: 100
<212> TYPE: PRT
<213> ORGANISM: Homo sapiens

<400> SEQUENCE: 143

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
                20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
            100
```

<210> SEQ ID NO 144
<211> LENGTH: 101
<212> TYPE: PRT
<213> ORGANISM: Homo sapiens

<400> SEQUENCE: 144

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
                20                  25                  30

Asp Asp Gly Asn Thr Tyr Leu Asp Trp Tyr Leu Gln Lys Pro Gly Gln
            35                  40                  45

Ser Pro Gln Leu Leu Ile Tyr Thr Leu Ser Tyr Arg Ala Ser Gly Val
        50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro
            100
```

<210> SEQ ID NO 145
<211> LENGTH: 100
<212> TYPE: PRT
<213> ORGANISM: Homo sapiens

<400> SEQUENCE: 145

```
Asp Ile Val Met Thr Gln Thr Pro Leu Ser Ser Pro Val Thr Leu Gly
1               5                   10                  15

Gln Pro Ala Ser Ile Ser Phe Arg Ser Ser Gln Ser Leu Val His Ser
```

```
                20                  25                  30
Asp Gly Asn Thr Tyr Leu Ser Trp Leu Gln Gln Arg Pro Gly Gln Pro
            35                  40                  45

Pro Arg Leu Leu Ile Tyr Lys Val Ser Asn Arg Phe Ser Gly Val Pro
 50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Thr Gln Ala
                85                  90                  95

Thr Gln Phe Pro
            100
```

<210> SEQ ID NO 146
<211> LENGTH: 101
<212> TYPE: PRT
<213> ORGANISM: Homo sapiens

<400> SEQUENCE: 146

```
Glu Ile Val Met Thr Gln Thr Pro Leu Ser Leu Ser Ile Thr Pro Gly
 1               5                  10                  15

Glu Gln Ala Ser Ile Ser Cys Arg Ser Ser Gln Ser Leu Leu His Ser
                20                  25                  30

Asp Gly Tyr Thr Tyr Leu Tyr Trp Phe Leu Gln Lys Ala Arg Pro Val
            35                  40                  45

Ser Thr Leu Leu Ile Tyr Glu Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Phe Gly Val Tyr Tyr Cys Met Gln Asp
                85                  90                  95

Ala Gln Asp Pro Pro
            100
```

<210> SEQ ID NO 147
<211> LENGTH: 100
<212> TYPE: PRT
<213> ORGANISM: Homo sapiens

<400> SEQUENCE: 147

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                85                  90                  95

Leu Gln Thr Pro
            100
```

<210> SEQ ID NO 148
<211> LENGTH: 100
<212> TYPE: PRT
<213> ORGANISM: Homo sapiens

<400> SEQUENCE: 148

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro
            100

<210> SEQ ID NO 149
<211> LENGTH: 100
<212> TYPE: PRT
<213> ORGANISM: Homo sapiens

<400> SEQUENCE: 149

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
            100

<210> SEQ ID NO 150
<211> LENGTH: 101
<212> TYPE: PRT
<213> ORGANISM: Homo sapiens

<400> SEQUENCE: 150

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro

```
                    100

<210> SEQ ID NO 151
<211> LENGTH: 97
<212> TYPE: PRT
<213> ORGANISM: Homo sapiens

<400> SEQUENCE: 151

Glu Ile Val Met Thr Gln Ser Pro Pro Thr Leu Ser Leu Ser Pro Gly
1               5                   10                  15

Glu Arg Val Thr Leu Ser Cys Arg Ala Ser Gln Ser Val Ser Ser Ser
            20                  25                  30

Tyr Leu Thr Trp Tyr Gln Gln Lys Pro Gly Gln Ala Pro Arg Leu Leu
        35                  40                  45

Ile Tyr Gly Ala Ser Thr Arg Ala Thr Ser Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp His Asn Leu Pro
                85                  90                  95

Pro

<210> SEQ ID NO 152
<211> LENGTH: 95
<212> TYPE: PRT
<213> ORGANISM: Homo sapiens

<400> SEQUENCE: 152

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 153
<211> LENGTH: 95
<212> TYPE: PRT
<213> ORGANISM: Homo sapiens

<400> SEQUENCE: 153

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
```

85                  90                  95

<210> SEQ ID NO 154
<211> LENGTH: 96
<212> TYPE: PRT
<213> ORGANISM: Homo sapiens

<400> SEQUENCE: 154

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Pro
                85                  90                  95

<210> SEQ ID NO 155
<211> LENGTH: 96
<212> TYPE: PRT
<213> ORGANISM: Homo sapiens

<400> SEQUENCE: 155

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

<210> SEQ ID NO 156
<211> LENGTH: 95
<212> TYPE: PRT
<213> ORGANISM: Homo sapiens

<400> SEQUENCE: 156

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp His
                85                  90                  95

<210> SEQ ID NO 157
<211> LENGTH: 95
<212> TYPE: PRT
<213> ORGANISM: Homo sapiens

<400> SEQUENCE: 157

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro
                85                  90                  95

<210> SEQ ID NO 158
<211> LENGTH: 96
<212> TYPE: PRT
<213> ORGANISM: Homo sapiens

<400> SEQUENCE: 158

Glu Ile Val Leu Thr Gln Ser Pro Ala Thr Leu Ser Leu Ser Pro Gly
1               5                   10                  15

Glu Arg Ala Thr Leu Ser Cys Gly Ala Ser Gln Ser Val Ser Ser Ser
            20                  25                  30

Tyr Leu Ala Trp Tyr Gln Gln Lys Pro Gly Leu Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 159
<211> LENGTH: 101
<212> TYPE: PRT
<213> ORGANISM: Homo sapiens

<400> SEQUENCE: 159

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro
            100

<210> SEQ ID NO 160
<211> LENGTH: 95
<212> TYPE: PRT
<213> ORGANISM: Homo sapiens

<400> SEQUENCE: 160

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro
                85                  90                  95

<210> SEQ ID NO 161
<211> LENGTH: 95
<212> TYPE: PRT
<213> ORGANISM: Homo sapiens

<400> SEQUENCE: 161

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95

<210> SEQ ID NO 162
<211> LENGTH: 95
<212> TYPE: PRT
<213> ORGANISM: Homo sapiens

<400> SEQUENCE: 162

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro
                85                  90                  95

```
<210> SEQ ID NO 163
<211> LENGTH: 95
<212> TYPE: PRT
<213> ORGANISM: Homo sapiens

<400> SEQUENCE: 163

Asp Val Val Met Thr Gln Ser Pro Ala Phe Leu Ser Val Thr Pro Gly
1               5                   10                  15

Glu Lys Val Thr Ile Thr Cys Gln Ala Ser Glu Gly Ile Gly Asn Tyr
            20                  25                  30

Leu Tyr Trp Tyr Gln Gln Lys Pro Asp Gln Ala Pro Lys Leu Leu Ile
        35                  40                  45

Lys Tyr Ala Ser Gln Ser Ile Ser Gly Val Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Lys His Pro
                85                  90                  95

<210> SEQ ID NO 164
<211> LENGTH: 99
<212> TYPE: PRT
<213> ORGANISM: Homo sapiens

<400> SEQUENCE: 164

Gln Ser Val Leu Thr Gln Pro Pro Ser Val Ser Glu Ala Pro Arg Gln
1               5                   10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro

<210> SEQ ID NO 165
<211> LENGTH: 100
<212> TYPE: PRT
<213> ORGANISM: Homo sapiens

<400> SEQUENCE: 165

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser
```

-continued

<210> SEQ ID NO 166
<211> LENGTH: 99
<212> TYPE: PRT
<213> ORGANISM: Homo sapiens

<400> SEQUENCE: 166

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro

<210> SEQ ID NO 167
<211> LENGTH: 99
<212> TYPE: PRT
<213> ORGANISM: Homo sapiens

<400> SEQUENCE: 167

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Pro

<210> SEQ ID NO 168
<211> LENGTH: 99
<212> TYPE: PRT
<213> ORGANISM: Homo sapiens

<400> SEQUENCE: 168

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Gln Phe
    50                  55                  60

Ser Gly Ser Lys Ser Gly Thr Ser Ala Ser Leu Ala Ile Thr Gly Leu
65                  70                  75                  80

```
Gln Ser Glu Asp Glu Ala Asp Tyr Tyr Cys Lys Ala Trp Asp Asn Ser
                85                  90                  95

Leu Asn Ala

<210> SEQ ID NO 169
<211> LENGTH: 99
<212> TYPE: PRT
<213> ORGANISM: Homo sapiens

<400> SEQUENCE: 169

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly

<210> SEQ ID NO 170
<211> LENGTH: 99
<212> TYPE: PRT
<213> ORGANISM: Homo sapiens

<400> SEQUENCE: 170

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Phe

<210> SEQ ID NO 171
<211> LENGTH: 99
<212> TYPE: PRT
<213> ORGANISM: Homo sapiens

<400> SEQUENCE: 171

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Lys Arg Pro Ser Gly Val Pro Asp Arg Phe
```

```
                50                  55                  60
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Tyr Thr Phe

<210> SEQ ID NO 172
<211> LENGTH: 99
<212> TYPE: PRT
<213> ORGANISM: Homo sapiens

<400> SEQUENCE: 172

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                 20                  25                  30

Asn Tyr Val Ser Trp Tyr Gln Gln His Pro Gly Lys Ala Pro Lys Leu
             35                  40                  45

Met Ile Tyr Glu Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Leu

<210> SEQ ID NO 173
<211> LENGTH: 99
<212> TYPE: PRT
<213> ORGANISM: Homo sapiens

<400> SEQUENCE: 173

Gln Ser Ala Leu Thr Gln Pro Pro Ser Val Ser Gly Ser Pro Gly Gln
 1               5                  10                  15

Ser Val Thr Ile Ser Cys Thr Gly Thr Ser Ser Asp Val Gly Ser Tyr
                 20                  25                  30

Asn Arg Val Ser Trp Tyr Gln Gln Pro Pro Gly Thr Ala Pro Lys Leu
             35                  40                  45

Met Ile Tyr Glu Val Ser Asn Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Leu Tyr Thr Ser Ser
                 85                  90                  95

Ser Thr Phe

<210> SEQ ID NO 174
<211> LENGTH: 99
<212> TYPE: PRT
<213> ORGANISM: Homo sapiens

<400> SEQUENCE: 174

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ser Tyr
                 20                  25                  30
```

```
Asn Leu Val Ser Trp Tyr Gln Gln His Pro Gly Lys Ala Pro Lys Leu
             35                  40                  45

Met Ile Tyr Glu Gly Ser Lys Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Tyr Ala Gly Ser
                 85                  90                  95

Ser Thr Phe

<210> SEQ ID NO 175
<211> LENGTH: 99
<212> TYPE: PRT
<213> ORGANISM: Homo sapiens

<400> SEQUENCE: 175

Gln Ser Ala Leu Thr Gln Pro Pro Phe Val Ser Gly Ala Pro Gly Gln
 1               5                  10                  15

Ser Val Thr Ile Ser Cys Thr Gly Thr Ser Ser Asp Val Gly Asp Tyr
             20                  25                  30

Asp His Val Phe Trp Tyr Gln Lys Arg Leu Ser Thr Thr Ser Arg Leu
             35                  40                  45

Leu Ile Tyr Asn Val Asn Thr Arg Pro Ser Gly Ile Ser Asp Leu Phe
 50                  55                  60

Ser Gly Ser Lys Ser Gly Asn Met Ala Ser Leu Thr Ile Ser Gly Leu
 65                  70                  75                  80

Lys Ser Glu Val Glu Ala Asn Tyr His Cys Ser Leu Tyr Ser Ser Ser
                 85                  90                  95

Tyr Thr Phe

<210> SEQ ID NO 176
<211> LENGTH: 95
<212> TYPE: PRT
<213> ORGANISM: Homo sapiens

<400> SEQUENCE: 176

Ser Tyr Glu Leu Thr Gln Pro Pro Ser Val Ser Val Ser Pro Gly Gln
 1               5                  10                  15

Thr Ala Ser Ile Thr Cys Ser Gly Asp Lys Leu Gly Asp Lys Tyr Ala
             20                  25                  30

Cys Trp Tyr Gln Gln Lys Pro Gly Gln Ser Pro Val Leu Val Ile Tyr
             35                  40                  45

Gln Asp Ser Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Ala Trp Asp Ser Ser Thr Ala
                 85                  90                  95

<210> SEQ ID NO 177
<211> LENGTH: 95
<212> TYPE: PRT
<213> ORGANISM: Homo sapiens

<400> SEQUENCE: 177

Ser Tyr Glu Leu Thr Gln Pro Leu Ser Val Ser Val Ala Leu Gly Gln
 1               5                  10                  15

Thr Ala Arg Ile Thr Cys Gly Gly Asn Asn Ile Gly Ser Lys Asn Val
```

-continued

```
                    20                  25                  30

His Trp Tyr Gln Gln Lys Pro Gly Gln Ala Pro Val Leu Val Ile Tyr
            35                  40                  45

Arg Asp Ser Asn Arg Pro Ser Gly Ile Pro Glu Arg Phe Ser Gly Ser
        50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Thr Ala
                85                  90                  95

<210> SEQ ID NO 178
<211> LENGTH: 96
<212> TYPE: PRT
<213> ORGANISM: Homo sapiens

<400> SEQUENCE: 178

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
                    20                  25                  30

Tyr Trp Tyr Gln Gln Lys Ser Gly Gln Ala Pro Val Leu Val Ile Tyr
            35                  40                  45

Glu Asp Ser Lys Arg Pro Ser Gly Ile Pro Glu Arg Phe Ser Gly Ser
        50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Gly Asn His
                85                  90                  95

<210> SEQ ID NO 179
<211> LENGTH: 97
<212> TYPE: PRT
<213> ORGANISM: Homo sapiens

<400> SEQUENCE: 179

Ser Tyr Glu Leu Thr Gln Pro His Ser Val Ser Val Ala Thr Ala Gln
1               5                   10                  15

Met Ala Arg Ile Thr Cys Gly Gly Asn Asn Ile Gly Ser Lys Ala Val
                    20                  25                  30

His Trp Tyr Gln Gln Lys Pro Gly Gln Asp Pro Val Leu Val Ile Tyr
            35                  40                  45

Ser Asp Ser Asn Arg Pro Ser Gly Ile Pro Glu Arg Phe Ser Gly Ser
        50                  55                  60

Asn Pro Gly Asn Thr Ala Thr Leu Thr Ile Ser Arg Ile Glu Ala Gly
65                  70                  75                  80

Asp Glu Ala Asp Tyr Tyr Cys Gln Val Trp Asp Ser Ser Ser Asp His
                85                  90                  95

Pro

<210> SEQ ID NO 180
<211> LENGTH: 97
<212> TYPE: PRT
<213> ORGANISM: Homo sapiens

<400> SEQUENCE: 180

Ser Tyr Glu Leu Thr Gln Pro Pro Ser Val Ser Val Ser Leu Gly Gln
1               5                   10                  15

Met Ala Arg Ile Thr Cys Ser Gly Glu Ala Leu Pro Lys Lys Tyr Ala
```

```
                20                  25                  30
Tyr Trp Tyr Gln Gln Lys Pro Gly Gln Phe Pro Val Leu Val Ile Tyr
            35                  40                  45
Lys Asp Ser Glu Arg Pro Ser Gly Ile Pro Glu Arg Phe Ser Gly Ser
        50                  55                  60
Ser Ser Gly Thr Ile Val Thr Leu Thr Ile Ser Gly Val Gln Ala Glu
65                  70                  75                  80
Asp Glu Ala Asp Tyr Tyr Cys Leu Ser Ala Ser Ser Gly Thr Tyr
                85                  90                  95
Pro

<210> SEQ ID NO 181
<211> LENGTH: 97
<212> TYPE: PRT
<213> ORGANISM: Homo sapiens

<400> SEQUENCE: 181

Ser Ser Glu Leu Thr Gln Asp Pro Ala Val Ser Val Ala Leu Gly Gln
1               5                   10                  15
Thr Val Arg Ile Thr Cys Gln Gly Asp Ser Leu Arg Ser Tyr Tyr Ala
                20                  25                  30
Ser Trp Tyr Gln Gln Lys Pro Gly Gln Ala Pro Val Leu Val Ile Tyr
            35                  40                  45
Gly Lys Asn Asn Arg Pro Ser Gly Ile Pro Asp Arg Phe Ser Gly Ser
        50                  55                  60
Ser Ser Gly Asn Thr Ala Ser Leu Thr Ile Thr Gly Ala Gln Ala Glu
65                  70                  75                  80
Asp Glu Ala Asp Tyr Tyr Cys Asn Ser Arg Asp Ser Ser Gly Asn His
                85                  90                  95
Leu

<210> SEQ ID NO 182
<211> LENGTH: 97
<212> TYPE: PRT
<213> ORGANISM: Homo sapiens

<400> SEQUENCE: 182

Ser Tyr Val Leu Thr Gln Pro Pro Ser Val Ser Val Ala Pro Gly Gln
1               5                   10                  15
Thr Ala Arg Ile Thr Cys Gly Gly Asn Asn Ile Gly Ser Lys Ser Val
                20                  25                  30
His Trp Tyr Gln Gln Lys Pro Gly Gln Ala Pro Val Leu Val Val Tyr
            35                  40                  45
Asp Asp Ser Asp Arg Pro Ser Gly Ile Pro Glu Arg Phe Ser Gly Ser
        50                  55                  60
Asn Ser Gly Asn Thr Ala Thr Leu Thr Ile Ser Arg Val Glu Ala Gly
65                  70                  75                  80
Asp Glu Ala Asp Tyr Tyr Cys Gln Val Trp Asp Ser Ser Ser Asp His
                85                  90                  95
Pro

<210> SEQ ID NO 183
<211> LENGTH: 95
<212> TYPE: PRT
<213> ORGANISM: Homo sapiens

<400> SEQUENCE: 183
```

-continued

Ser Tyr Glu Leu Thr Gln Leu Pro Ser Val Ser Val Ser Pro Gly Gln
1               5                   10                  15

Thr Ala Arg Ile Thr Cys Ser Gly Asp Val Leu Gly Glu Asn Tyr Ala
            20                  25                  30

Asp Trp Tyr Gln Gln Lys Pro Gly Gln Ala Pro Glu Leu Val Ile Tyr
        35                  40                  45

Glu Asp Ser Glu Arg Tyr Pro Gly Ile Pro Glu Arg Phe Ser Gly Ser
    50                  55                  60

Thr Ser Gly Asn Thr Thr Leu Thr Ile Ser Arg Val Leu Thr Glu
65                  70                  75                  80

Asp Glu Ala Asp Tyr Tyr Cys Leu Ser Gly Glu Asp Asn Pro
                85                  90                  95

<210> SEQ ID NO 184
<211> LENGTH: 97
<212> TYPE: PRT
<213> ORGANISM: Homo sapiens

<400> SEQUENCE: 184

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Pro

<210> SEQ ID NO 185
<211> LENGTH: 95
<212> TYPE: PRT
<213> ORGANISM: Homo sapiens

<400> SEQUENCE: 185

Ser Tyr Glu Leu Thr Gln Pro Ser Ser Val Ser Val Ser Pro Gly Gln
1               5                   10                  15

Thr Ala Arg Ile Thr Cys Ser Gly Asp Val Leu Ala Lys Lys Tyr Ala
            20                  25                  30

Arg Trp Phe Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Ala Gln Val Glu
65                  70                  75                  80

Asp Glu Ala Asp Tyr Tyr Cys Tyr Ser Ala Ala Asp Asn Asn Leu
                85                  90                  95

<210> SEQ ID NO 186
<211> LENGTH: 94
<212> TYPE: PRT
<213> ORGANISM: Homo sapiens

<400> SEQUENCE: 186

-continued

Ser Ser Gly Pro Thr Gln Val Pro Ala Val Ser Val Ala Leu Gly Gln
1               5                   10                  15

Met Ala Arg Ile Thr Cys Gln Gly Asp Ser Met Glu Gly Ser Tyr Glu
                20                  25                  30

His Trp Tyr Gln Gln Lys Pro Gly Gln Ala Pro Val Leu Val Ile Tyr
            35                  40                  45

Asp Ser Ser Asp Arg Pro Ser Arg Ile Pro Glu Arg Phe Ser Gly Ser
        50                  55                  60

Lys Ser Gly Asn Thr Thr Thr Leu Thr Ile Thr Gly Ala Gln Ala Glu
65                  70                  75                  80

Asp Glu Ala Asp Tyr Tyr Tyr Gln Leu Ile Asp Asn His Ala
                85                  90

<210> SEQ ID NO 187
<211> LENGTH: 103
<212> TYPE: PRT
<213> ORGANISM: Homo sapiens

<400> SEQUENCE: 187

Leu Pro Val Leu Thr Gln Pro Ser Ala Ser Ala Leu Leu Gly Ala
1               5                   10                  15

Ser Ile Lys Leu Thr Cys Thr Leu Ser Ser Glu His Ser Thr Tyr Thr
                20                  25                  30

Ile Glu Trp Tyr Gln Gln Arg Pro Gly Arg Ser Pro Gln Tyr Ile Met
            35                  40                  45

Lys Val Lys Ser Asp Gly Ser His Ser Lys Gly Asp Gly Ile Pro Asp
        50                  55                  60

Arg Phe Met Gly Ser Ser Ser Gly Ala Asp Arg Tyr Leu Thr Phe Ser
65                  70                  75                  80

Asn Leu Gln Ser Asp Asp Glu Ala Glu Tyr His Cys Gly Glu Ser His
                85                  90                  95

Thr Ile Asp Gly Gln Val Gly
            100

<210> SEQ ID NO 188
<211> LENGTH: 99
<212> TYPE: PRT
<213> ORGANISM: Homo sapiens

<400> SEQUENCE: 188

Gln Pro Val Leu Thr Gln Ser Ser Ser Ala Ser Ala Ser Leu Gly Ser
1               5                   10                  15

Ser Val Lys Leu Thr Cys Thr Leu Ser Ser Gly His Ser Ser Tyr Ile
                20                  25                  30

Ile Ala Trp His Gln Gln Gln Pro Gly Lys Ala Pro Arg Tyr Leu Met
            35                  40                  45

Lys Leu Glu Gly Ser Gly Ser Tyr Asn Lys Gly Ser Gly Val Pro Asp
        50                  55                  60

Arg Phe Ser Gly Ser Ser Ser Gly Ala Asp Arg Tyr Leu Thr Ile Ser
65                  70                  75                  80

Asn Leu Gln Phe Glu Asp Glu Ala Asp Tyr Tyr Cys Glu Thr Trp Asp
                85                  90                  95

Ser Asn Thr

<210> SEQ ID NO 189
<211> LENGTH: 98
<212> TYPE: PRT
<213> ORGANISM: Homo sapiens

<400> SEQUENCE: 189

Gln Leu Val Leu Thr Gln Ser Pro Ser Ala Ser Leu Gly Ala
1               5                   10                  15

Ser Val Lys Leu Thr Cys Thr Leu Ser Ser Gly His Ser Ser Tyr Ala
                20                  25                  30

Ile Ala Trp His Gln Gln Pro Glu Lys Gly Pro Arg Tyr Leu Met
            35                  40                  45

Lys Leu Asn Ser Asp Gly Ser His Ser Lys Gly Asp Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gln Thr Trp Gly
                85                  90                  95

Thr Gly

<210> SEQ ID NO 190
<211> LENGTH: 104
<212> TYPE: PRT
<213> ORGANISM: Homo sapiens

<400> SEQUENCE: 190

Gln Pro Val Leu Thr Gln Pro Pro Ser Ser Ala Ser Pro Gly Glu
1               5                   10                  15

Ser Ala Arg Leu Thr Cys Thr Leu Pro Ser Asp Ile Asn Val Gly Ser
                20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser Asp Lys Gly Gln Gly Ser Gly Val
        50                  55                  60

Pro Ser Arg Phe Ser Gly Ser Lys Asp Ala Ser Ala Asn Thr Gly Ile
65                  70                  75                  80

Leu Leu Ile Ser Gly Leu Gln Ser Glu Asp Glu Ala Asp Tyr Tyr Cys
                85                  90                  95

Met Ile Trp Pro Ser Asn Ala Ser
            100

<210> SEQ ID NO 191
<211> LENGTH: 104
<212> TYPE: PRT
<213> ORGANISM: Homo sapiens

<400> SEQUENCE: 191

Gln Pro Val Leu Thr Gln Pro Thr Ser Leu Ser Ala Ser Pro Gly Ala
1               5                   10                  15

Ser Ala Arg Phe Thr Cys Thr Leu Arg Ser Gly Ile Asn Val Gly Thr
                20                  25                  30

Tyr Arg Ile Tyr Trp Tyr Gln Gln Lys Pro Gly Ser Leu Pro Arg Tyr
            35                  40                  45

Leu Leu Arg Tyr Lys Ser Asp Ser Asp Lys Gln Gln Gly Ser Gly Val
        50                  55                  60

Pro Ser Arg Phe Ser Gly Ser Lys Asp Ala Ser Thr Asn Ala Gly Leu
65                  70                  75                  80

Leu Leu Ile Ser Gly Leu Gln Ser Glu Asp Glu Ala Asp Tyr Tyr Cys
                85                  90                  95

Ala Ile Trp Tyr Ser Ser Thr Ser
            100

<210> SEQ ID NO 192
<211> LENGTH: 104
<212> TYPE: PRT
<213> ORGANISM: Homo sapiens

<400> SEQUENCE: 192

Gln Ala Val Leu Thr Gln Pro Ser Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Ser Ala Ser
            100

<210> SEQ ID NO 193
<211> LENGTH: 104
<212> TYPE: PRT
<213> ORGANISM: Homo sapiens

<400> SEQUENCE: 193

Gln Pro Val Leu Thr Gln Pro Thr Ser Leu Ser Ala Ser Pro Gly Ala
1               5                   10                  15

Ser Ala Arg Leu Thr Cys Thr Leu Arg Ser Gly Ile Asn Leu Gly Ser
            20                  25                  30

Tyr Arg Ile Phe Trp Tyr Gln Gln Lys Pro Glu Ser Pro Pro Arg Tyr
        35                  40                  45

Leu Leu Ser Tyr Tyr Ser Asp Ser Ser Lys His Gln Gly Ser Gly Val
    50                  55                  60

Pro Ser Arg Phe Ser Gly Ser Lys Asp Ala Ser Ser Asn Ala Gly Ile
65                  70                  75                  80

Leu Val Ile Ser Gly Leu Gln Ser Glu Asp Glu Ala Asp Tyr Tyr Cys
                85                  90                  95

Met Ile Trp His Ser Ser Ala Ser
            100

<210> SEQ ID NO 194
<211> LENGTH: 102
<212> TYPE: PRT
<213> ORGANISM: Homo sapiens

<400> SEQUENCE: 194

Gln Pro Val Leu Thr Gln Pro Ser Ser His Ser Ala Ser Ser Gly Ala
1               5                   10                  15

Ser Val Arg Leu Thr Cys Met Leu Ser Ser Gly Phe Ser Val Gly Asp
            20                  25                  30

Phe Trp Ile Arg Trp Tyr Gln Gln Lys Pro Gly Asn Pro Pro Arg Tyr
        35                  40                  45

Leu Leu Tyr Tyr His Ser Asp Ser Asn Lys Gly Gln Gly Ser Gly Val
    50                  55                  60

Pro Ser Arg Phe Ser Gly Ser Asn Asp Ala Ser Ala Asn Ala Gly Ile

```
                65                  70                  75                  80
Leu Arg Ile Ser Gly Leu Gln Pro Glu Asp Glu Ala Asp Tyr Tyr Cys
                    85                  90                  95
Gly Thr Trp His Ser Asn
            100

<210> SEQ ID NO 195
<211> LENGTH: 98
<212> TYPE: PRT
<213> ORGANISM: Homo sapiens

<400> SEQUENCE: 195

Asn Phe Met Leu Thr Gln Pro His Ser Val Ser Glu Ser Pro Gly Lys
1               5                   10                  15
Thr Val Thr Ile Ser Cys Thr Arg Ser Ser Gly Ser Ile Ala Ser Asn
                20                  25                  30
Tyr Val Gln Trp Tyr Gln Gln Arg Pro Gly Ser Ser Pro Thr Thr Val
            35                  40                  45
Ile Tyr Glu Asp Asn Gln Arg Pro Ser Gly Val Pro Asp Arg Phe Ser
        50                  55                  60
Gly Ser Ile Asp Ser Ser Ser Asn Ser Ala Ser Leu Thr Ile Ser Gly
65                  70                  75                  80
Leu Lys Thr Glu Asp Glu Ala Asp Tyr Tyr Cys Gln Ser Tyr Asp Ser
                85                  90                  95
Ser Asn

<210> SEQ ID NO 196
<211> LENGTH: 98
<212> TYPE: PRT
<213> ORGANISM: Homo sapiens

<400> SEQUENCE: 196

Gln Thr Val Val Thr Gln Glu Pro Ser Leu Thr Val Ser Pro Gly Gly
1               5                   10                  15
Thr Val Thr Leu Thr Cys Ala Ser Ser Thr Gly Ala Val Thr Ser Gly
                20                  25                  30
Tyr Tyr Pro Asn Trp Phe Gln Gln Lys Pro Gly Gln Ala Pro Arg Ala
            35                  40                  45
Leu Ile Tyr Ser Thr Ser Asn Lys His Ser Trp Thr Pro Ala Arg Phe
        50                  55                  60
Ser Gly Ser Leu Leu Gly Gly Lys Ala Ala Leu Thr Leu Ser Gly Val
65                  70                  75                  80
Gln Pro Glu Asp Glu Ala Glu Tyr Tyr Cys Leu Leu Tyr Tyr Gly Gly
                85                  90                  95
Ala Gln

<210> SEQ ID NO 197
<211> LENGTH: 98
<212> TYPE: PRT
<213> ORGANISM: Homo sapiens

<400> SEQUENCE: 197

Gln Ala Val Val Thr Gln Glu Pro Ser Leu Thr Val Ser Pro Gly Gly
1               5                   10                  15
Thr Val Thr Leu Thr Cys Gly Ser Ser Thr Gly Ala Val Thr Ser Gly
                20                  25                  30
His Tyr Pro Tyr Trp Phe Gln Gln Lys Pro Gly Gln Ala Pro Arg Thr
            35                  40                  45
```

-continued

```
Leu Ile Tyr Asp Thr Ser Asn Lys His Ser Trp Thr Pro Ala Arg Phe
         50                  55                  60

Ser Gly Ser Leu Leu Gly Gly Lys Ala Ala Leu Thr Leu Leu Gly Ala
 65                  70                  75                  80

Gln Pro Glu Asp Glu Ala Glu Tyr Tyr Cys Leu Leu Ser Tyr Ser Gly
                 85                  90                  95

Ala Arg

<210> SEQ ID NO 198
<211> LENGTH: 99
<212> TYPE: PRT
<213> ORGANISM: Homo sapiens

<400> SEQUENCE: 198

Gln Thr Val Val Thr Gln Glu Pro Ser Phe Ser Val Ser Pro Gly Gly
 1               5                  10                  15

Thr Val Thr Leu Thr Cys Gly Leu Ser Ser Gly Ser Val Ser Thr Ser
                 20                  25                  30

Tyr Tyr Pro Ser Trp Tyr Gln Gln Thr Pro Gly Gln Ala Pro Arg Thr
             35                  40                  45

Leu Ile Tyr Ser Thr Asn Thr Arg Ser Ser Gly Val Pro Asp Arg Phe
         50                  55                  60

Ser Gly Ser Ile Leu Gly Asn Lys Ala Ala Leu Thr Ile Thr Gly Ala
 65                  70                  75                  80

Gln Ala Asp Asp Glu Ser Asp Tyr Tyr Cys Val Leu Tyr Met Gly Ser
                 85                  90                  95

Gly Ile Ser

<210> SEQ ID NO 199
<211> LENGTH: 104
<212> TYPE: PRT
<213> ORGANISM: Homo sapiens

<400> SEQUENCE: 199

Gln Pro Val Leu Thr Gln Pro Pro Ser Ala Ser Ala Ser Leu Gly Ala
 1               5                  10                  15

Ser Val Thr Leu Thr Cys Thr Leu Ser Ser Gly Tyr Ser Asn Tyr Lys
                 20                  25                  30

Val Asp Trp Tyr Gln Gln Arg Pro Gly Lys Gly Pro Arg Phe Val Met
             35                  40                  45

Arg Val Gly Thr Gly Gly Ile Val Gly Ser Lys Gly Asp Gly Ile Pro
 50                  55                  60

Asp Arg Phe Ser Val Leu Gly Ser Gly Leu Asn Arg Tyr Leu Thr Ile
 65                  70                  75                  80

Lys Asn Ile Gln Glu Glu Asp Glu Ser Asp Tyr His Cys Gly Ala Asp
                 85                  90                  95

His Gly Ser Gly Ser Asn Phe Val
            100

<210> SEQ ID NO 200
<211> LENGTH: 98
<212> TYPE: PRT
<213> ORGANISM: Homo sapiens

<400> SEQUENCE: 200

Gln Ala Gly Leu Thr Gln Pro Pro Ser Val Ser Lys Gly Leu Arg Gln
 1               5                  10                  15
```

-continued

```
Thr Ala Thr Leu Thr Cys Thr Gly Asn Ser Asn Ile Val Gly Asn Gln
                20                  25                  30

Gly Ala Ala Trp Leu Gln Gln His Gln Gly His Pro Pro Lys Leu Leu
            35                  40                  45

Ser Tyr Arg Asn Asn Asn Arg Pro Ser Gly Ile Ser Glu Arg Phe Ser
 50                          55                  60

Ala Ser Arg Ser Gly Asn Thr Ala Ser Leu Thr Ile Thr Gly Leu Gln
 65                  70                      75                  80

Pro Glu Asp Glu Ala Asp Tyr Tyr Cys Ser Ala Leu Asp Ser Ser Leu
                85                  90                  95

Ser Ala

<210> SEQ ID NO 201
<211> LENGTH: 103
<212> TYPE: PRT
<213> ORGANISM: Homo sapiens

<400> SEQUENCE: 201

Arg Pro Val Leu Thr Gln Pro Pro Ser Leu Ser Ala Ser Pro Gly Ala
 1               5                  10                  15

Thr Ala Arg Leu Pro Cys Thr Leu Ser Ser Asp Leu Ser Val Gly Gly
                20                  25                  30

Lys Asn Met Phe Trp Tyr Gln Gln Lys Pro Gly Ser Ser Pro Arg Leu
            35                  40                  45

Phe Leu Tyr His Tyr Ser Asp Ser Asp Lys Gln Leu Gly Pro Gly Val
 50                          55                  60

Pro Ser Arg Val Ser Gly Ser Lys Glu Thr Ser Ser Asn Thr Ala Phe
 65                  70                      75                  80

Leu Leu Ile Ser Gly Leu Gln Pro Glu Asp Glu Ala Asp Tyr Tyr Cys
                85                  90                  95

Gln Val Tyr Glu Ser Ser Ala
                100

<210> SEQ ID NO 202
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 202

His His His His His His
 1               5
```

COLLECTION AND METHODS FOR ITS USE

CROSS REFERENCE TO RELATED APPLICATIONS

This application claims the benefit of U.S. provisional application Ser. No. 61/299,401 filed Jan. 29, 2010, and U.S. provisional application Ser. No. 61/182,350 filed May 29, 2009, which are both incorporated by reference in their entireties.

BACKGROUND

Advances in pharmaceutical development, especially in the field of therapeutic antibodies, are rapidly enabling and/or improving the treatment of many diseases. These advances by reaching novel target spaces and providing novel mechanisms of action are increasingly improving the quality of lives of patients even with the most severe and challenging diseases. One challenge for the health care system in general and patients in particular is that the costs of new drugs, enabled by of these pharmaceutical advances, are also rapidly increasing. The high costs are a result of the investments required for the development of pharmaceuticals, especially of antibodies, which currently exceed one billion dollars per marketed product. The high risk of failure in development and very long developmental timelines make these investments inevitable. It may take over fifteen years from the time of identification of a potential therapeutic antibody until it reaches the market and can benefit patients. Each stage of development, from identification, pre-clinical, clinical to market entry is riddled with challenges and risks. Pharmaceutical companies are constantly assessing to determine how to reduce developmental costs by reducing timelines and risks of failure in order to get the most effective medicines into the hands of patients quickly and in order to make them affordable.

The following disclosure provides a valuable advance which allows for faster identification of the optimal therapeutic antibodies for the treatment of arguably any disease. Therapeutic antibody candidates must fulfill a number of development criteria in order to make it to the market, such as, long term stability and high expression yields. The disclosed advance increases the probability and speed of identifying an antibody that can fulfill all of the rigorous development criteria right from the start. The resultant antibody will be less expensive to produce and will be effective and safe in the treatment of numerous diseases.

A well known method of identifying therapeutic antibodies is through the use of phage display technology. Phage display utilizes virus-like particles that are grown in bacteria to display antibodies. One benefit of this technology is that the libraries used are massive, with up to $1 \times 10^{10}$ antibodies, which can quickly be tested for binding to any target relevant for any disease. See, for example, Knappik et al., (2000), "Fully synthetic human combinatorial antibody libraries (HuCAL) based on modular consensus frameworks and CDRs randomized with trinucleotides," *J. Mol. Biol.* 11; 296 (1):57-86. The benefit of working with such large numbers is that the output of a screening against a target may result in hundreds of antibodies that bind to the therapeutic target, all of which could be therapeutically relevant. A problem, though, is that often only a few of these antibodies are developable, meaning that they can meet all of the rigorous criteria required in order to make it to the market.

In order for a new phage display library to rapidly shorten the identification timelines and reduce the inherent risks, the library should comprise antibodies having the properties which are necessary for selection and clinical development and which will result in safe and effective treatment in patients. Such properties include: 1) high phage display rates, so that each and every antibody of the collection can be tested against the target of interest; 2) high expression levels, so that the antibody or fragment can be reproduced efficiently; 3) high thermal stability, so that the antibody can reach patients in an effective form; 4) high stability in serum, so that the antibody can survive within the body for a therapeutically relevant time; 5) low risk of immunogenicity, thereby increasing safety, and 5) high diversity, so that one library can be used to identify antibodies against any therapeutic target.

A library, which in essential ways imitates the human immune system, should be highly valuable, or even the optimal solution. The human immune system is composed of antibodies encoded by germline genes. Antibodies, in part, comprise of a variable heavy chain and variable light chains. There are approximately 50 variable heavy chain germline genes and approximately 50 variable light chain germline genes, combined providing about 2,500 combinations of different variable heavy and light chain pairs. In humans, all 2500 of these combinations are believed to be produced. It has been found, though, that certain variable heavy chains, variable light chains and/or variable heavy and light chain combinations (pairs) are expressed at a higher level than others. It was hypothesized that there must be some reason that some are expressed more than others, and if so, that the highly expressed germline genes may have favorable functional properties. Therefore, one way of providing a library of antibodies having favorable functional properties is to generate a library comprising the abundant variable heavy chain, variable light chain, and/or variable heavy chain and variable light chain germline pairs from the human immune repertoire.

In addition, the germline gene sequences present in humans are thought to have very low immunogenicity, for obvious reasons, therefore these sequences can be imitated in recombinant antibodies in order to lower the risk of immunogenicity.

Approaches to evaluate the variable heavy and light chain germline gene pairings prevalent in the human immune repertoire have been undertaken. See de Wildt et al., Analysis of heavy and light chain pairings indicates that receptor editing shapes the human antibody repertoire, J Mol. Biol. 22; 285 (3):895-901 (January 1999), which is incorporated by reference in its entirety. Wildt et al. took blood samples from human donors, sorted the IgG+ B cells, which had undergone somatic hypermutation, PCR amplified the cDNAs, sequenced each cDNA, and aligned each sequence to the known human variable domain germline genes. Wildt et al. observed that only a few germline genes dominated the immune repertoire and that the frequently expressed heavy and light chain gene segments are often paired.

Attempts at maintaining the heavy and light chain variable domain pairings of individual B cells have also been undertaken. For example, libraries of variable domain "cognate pairs" have been disclosed. See Meijer et al., Isolation of human antibody repertoires with preservation of the natural heavy and light chain pairing, J Mol. Biol., 358(3):764-72 (May 5, 2006); and WO2005042774. Libraries according to the techniques described in Meijer et al. have been generated from individual B cells from an immunized host. Generally, the B cells are sorted, by FACS so that $CD38^{HI}$ B cells, which represent somatically hypermutated cells, are selected, their cDNAs are PCR amplified, and the antibody gene products are inserted into Fab vectors for selection. Such cognate pair libraries are not without their limitations. For example, the hosts providing the B cells typically are immunized; and the B cell populations sorted have been hypermutated, therefore, the resulting libraries are biased towards a particular immunogen.

Additionally, attempts at utilizing prominent variable heavy chain or variable light chains for library generation have been undertaken. For example, in Shi et al., "De Novo Selection of High-Affinity Antibodies from Synthetic Fab Libraries Displayed on Phage as pIX Fusion Proteins; J Mol. Biol., 397(2):385-96 (Mar. 26, 2010) (which is not admitted to be prior art with respect to the present invention), and the respective patent application WO2009085462; and WO2006014498, variable heavy chain or variable light chain germline protein sequences were incorporated into libraries based upon their frequency of use in the human immune repertoire.

Additional attempts have also been undertaken, which incorporate a specific germline pair into a library. For example, WO1999020749 describes a library where its members comprise heavy chains having the canonical structure of a hypervariable loop encoded by the human germline heavy chain gene segment DP-47 (IGHV3-23) and/or framework regions encoded by the germline gene, and/or light chains having the canonical structure of a hypervariable loop encoded by the human germline light chain gene segment O2/O12 (IGKV1-39/1D-39) and/or framework regions encoded by the germline gene.

Additional approaches have generated libraries directly from or derived from B cells. For example, Glanville et al., Precise Determination of the Diversity of a Combinatorial Antibody Library Gives Insight into the Human Immunoglobulin Repertoire, Proc Natl Acad Sci 1; 106(48):20216-21 (December 2009) (which is not admitted to be prior art with respect to the present invention), which describes an antibody library built from the diversity of 654 human donor Immunoglobulin M (IgM) repertoires. Specifically, the heavy and light chain V-gene cDNAs from 654 human donors were separately PCR amplified (separating the variable heavy and light chain pair) and the heavy and light chain domains were then randomly reassociated. WO2003052416 describes the isolation of B cells from a host exhibiting a pronounced response to a pathogen of interest, resulting from either an infection by a micro-organism or treatment with a vaccine. In WO2003052416, the cDNA encoding the CDR3 region of the variable regions was sequenced and antibody fragments comprising the dominant CDR3s were designed. WO2009100896 describes the isolation of B cells from an immunized host, where the cDNAs encoding the variable heavy and light chain regions were sequenced and the abundance of the unparied variable heavy and variable light chain sequences was determined. In WO2009100896 (which is not admitted to be prior art with respect to the present invention), libraries were synthesized comprising the randomly recombined variable heavy and variable light chains, wherein the antibodies were specific for one immunogen. A summary of these and additional approaches is found in Fuh et al., Synthetic antibodies as therapeutics, Expert Opin Biol Ther., 7(1):73-87 (January 2007).

There is, therefore, a high need for a collection of antibodies or fragments thereof that incorporate the variable heavy and variable light germline gene pairs expressed in the human immune repertoire that have favorable biophysical properties, which lead to readily developable antibodies that are safe and effective in patients. These and other needs are satisfied by the present invention.

SUMMARY

The present disclosure provides a valuable solution to the problem of efficiently identifying antibodies against any target that are developable and safe and effective in patients. In its most general sense, the inventors began with the idea that an antibody library that imitates the human immune system in essential ways may be advantageous. On one level, the inventors decided to imitate the human immune system by incorporating the optimal germline gene sequences from the human immune repertoire into antibodies. As such, in some embodiments, the antibodies of the library comprise portions, for example, framework regions, that are germline in sequence. Using the germline sequences should dramatically decrease the risk of immunogenicity of recombinant antibodies for therapeutic use in patients.

In addition, the inventors worked from their hypothesis that the variable heavy chain and variable light chain germline gene pairs abundant in the human immune repertoire likely have favorable biophysical properties that would lead to more efficient clinical development and increase the safety and efficacy of the resulting antibodies in patients. As background, each B cell encodes one antibody, and each antibody comprises a variable heavy chain and variable light chain. Each of the variable heavy chain and variable light chains of an antibody can be aligned with germline sequences in order to determine the origin of the antibody, meaning from which germline gene the variable heavy chain and variable light chain are encoded. Therefore, for each antibody the variable heavy chain and variable light chain comprise a germline pair, for example, VH3-23 paired with VK1-5.

In order to prove the hypothesis that the prominent germline gene pairs likely have favorable biophysical properties, the first step was to identify the variable heavy chain and variable light chain germline gene pairs present in the human immune repertoire. This was done by extensively searching publically available literature and by sampling B cells from a human host. As a next step, the raw data was pooled, analyzed and the variable heavy chain and variable light chain germline pairs present in the human immune repertoire were ranked in terms of their incidence. From this data it was clear that certain variable heavy chain and variable light chain germline gene pairs were present more frequently than others in the human immune repertoire.

Additionally the inventors thought that certain variable heavy chain and variable light chain germline gene pairs may be differentially expressed in naïve B cells (antigen inexperienced) versus antigen experienced B cells, therefore, the pooled data was analyzed based on the development or differentiation of the sampled B cells. From our analysis it is clear that certain germline gene pairs are differentially expressed in naïve B cell populations versus in antigen experienced B cells populations.

As a next step, it had to be determined which germline protein pairs were to be tested, as there are ~2500 pairs in the human immune repertoire. One way would be to test the variable heavy chain and variable light chain germline protein pairs that occur most prominently in the human immune repertoire, for example see Table 18. One could, for example, select the top four hundred pairs for testing, or select the variable heavy chain and variable light chain germline gene pairs expressed above a certain threshold concentration. This approach would require the synthesis and testing of a large number of variable heavy chain and variable light chain germline protein pair sequences; therefore, such an approach may not be very efficient.

As an alternative approach, the inventors selected a subset of the variable heavy chain and variable light chain germline pairs that are representative of, accurately reproduce, or cover the majority of the prominently expressed pairs from the human immune repertoire. This approach was based, in part, upon the observation that a small number of variable heavy, variable κ light chain, and variable λ light chain germline genes are dominant in the human immune repertoire. Wildt et al. at 895-896 describes this phenomenon. Wildt et al. also states that the frequently expressed heavy and light chain gene segments are often paired, and observed that half of the pairings sampled correspond to only five germline pairs. Therefore, a small number of the prominently expressed heavy and light chain germline genes (unpaired) can be combined to generate a group of pairs that are representative of the human immune repertoire.

This approach was undertaken in the following way. The pooled data and additional data (identifying only VH or VL expression, not linked pairs) was analyzed to determine the variable heavy chain, variable κ light chain, and variable λ light chain germline gene expression in the human immune repertoire. As a next step the prominently expressed variable heavy chain, variable κ light chain, and variable λ light chain germline protein sequences (not pairs) were evaluated to determine their biophysical properties relevant to development. The variable heavy chain, variable κ light chain, and variable λ light chain germline protein sequences were evaluated in silico for the following properties: (i) CDR length, (ii) isoelectric point (pI) (the preferred isoelectric point is 8 or above as this is should provide stability in a neutral formulation buffer), (iii) post translational modifications (PTM's) (specifically, N-linked glycosylation sites (NxS or NxT) or chemical modifications such as Asp cleavage (often at a DP), (iv) Asp isomerization (DD, DG), (v) deamidation (NS, NG) which can occur in vivo (in serum) or upon storage in formulation buffer and lead to loss of antibody binding), (vi) the presence of Methionines in the CDRs (can be oxidized when exposed to solvent), (vii) the presence of unpaired Cysteines (will form disulfide bonds with any other unpaired cysteine, thus leading to crosslinking of proteins and/or lower expression levels), (viii) deviations from germline, (ix) the presence of possible T-cell epitopes, and (x) theoretical aggregation propensity.

As a next step the variable heavy chain, variable κ light chain, and variable λ light chain germline pairs having favorable biophysical characteristics were combined to form variable heavy chain and variable light chain pairs. This subset of pairs is representative of, accurately reproduce, or cover the majority of the prominently expressed pairs from the human immune repertoire as shown in Table 23. This was done by synthesizing the variable heavy and light chain germline genes, combining them into pairs, expressing the pairs as protein and testing each to identify their biophysical properties. The following properties were tested: (i) relative display rate on phage in the Fab format, (ii) relative expression level in the Fab format, e.g., in *E. coli*; (iii) thermal stability in the Fab format; (iv) stability in bovine or mouse serum in the Fab format; (v) relative expression level in the IgG format; (vi) stability in bovine serum in the IgG format.

Once the germline protein pairs having favorable biophysical properties were identified, then collections were designed to include these pairs. An aspect of the present disclosure is a collection of antibodies or functional fragments comprising the variable heavy and light chain germline gene pairs having advantageous properties that enhance developability, but excluding variable heavy and light chain germline gene pairs not having such properties, even if they are prominently expressed in the human immune repertoire. In this way, the collection was designed to exclude the variable heavy and light chain combinations or pairs that occur in nature (out of the 2,500 pairs) which fail to have advantageous functional properties. For example, VH4-34 is frequently occurring in the human immune repertoire as shown in Table 20, but it is also known that antibodies derived from this heavy chain germline gene are B cell cytotoxic, therefore, antibodies derived from this gene could be excluded from a library design. See Bhat et al., Rapid cytotoxicity of human B lymphocytes induced by VH4-34 (VH4.21) gene-encoded monoclonal antibodies, Clin Exp Immunol., 105(1):183-90 (July 1996).

In some embodiments, the present collections include antibodies comprising a large number of functionally advantageous variable heavy and light chain combinations or pairs, so that the antibodies of the collections are quite diverse, thus providing a collection that can be used to identify antibodies against any therapeutic target.

Such collections overcome many of the problems of the prior art. For example, a cognate library derived from B cells does not incorporate this concept, as the VH and VL class pairings present in such a library are identical to the class pairings present in the sample of B cells. If a large enough sample of B cells is taken, each of the approximately 50 VH and 50 VL class pairing combinations (2500) will be present. The extensive testing of VH and VL pairs in the present disclosure shows that many of the VH and VL germline gene pairs fail to have properties that would allow for the developability in the clinic. Therefore, such cognate libraries comprise many VH and VL pairs that are likely not developable. Therefore, it may be desirable to generate libraries of large diversity comprising only the VH and VL class pairs having advantageous functional properties, but with a cognate library approach, this is not possible.

In addition, in some embodiments, the germline gene pairs comprised in the collection are based on samples of naïve or antigen inexperienced B cells, therefore, the germline gene pairs represented are not biased towards a particular immunogen and the collections may be superior in screening against any immunogen.

DESCRIPTION OF THE DRAWINGS

FIGS. 4-9 show the VH/VL germline gene pairs of B cells isolated and described in Tsuiji M. et al. (2006).

FIGS. 10-12 show the VH/VL germline gene pairs of the B cells isolated and described in Tiller T. et al. (2007).

FIGS. 13-17 show the VH/VL germline gene pairs of the B cells isolated in and described Mietzner B. et al. (2008).

FIGS. 18-20 show the VH/VL germline gene pairs of the B cells isolated and described in Wardemann H. et al. (2003).

FIGS. 21-23 show the VH/VL germline gene pairs of the B cells isolated and described in Yurasov S. et al. (2005).

FIGS. 24-26 show the VH/VL germline gene pairs of the B cells isolated and described in Yurasov S. et al. (2006).

FIGS. 28-36 show the VH/VL pairs of the B cells isolated from a human sample as described in detail in Example 2.2.

FIG. 37 shows the 20 VH germline genes selected for synthesis, combination and functional characterization, as described in detail in Examples 4-4.1. The figure also shows the results of the in silico analysis of each germline gene, where pI represents isoelectric point, PTMs are post translational modifications in the complementarity determining regions, as described herein, NxS/T are N-linked glycosylation sites, and Met in CDR are methionines.

FIG. 38 shows the 8 Vλ and 12 Vκ germline genes selected for synthesis, combination and functional characterization, as described in detail in Examples 4-4.1. The figure also shows the results of the in silico analysis of each germline gene, where pI represents isoelectric point, PTMs are post translational modifications in the complementarity determining regions, as described herein, NxS/T are N-linked glycosylation sites, and Met in CDR are methionines.

FIG. 39 shows the VH/κ pairs of the pooled data from Examples 2.1 shown in FIGS. 4-26 and Example 2.2 shown in FIGS. 28-36. The numerical entries represent the number of each VH/Vκ germline gene pair from an individual B cell identified in the pooled data. The Y axis shows the VH germline genes ranked from top (VH3-23) to bottom (VH3-20) in terms of frequency of expression in the pooled data. The X axis shows the Vκ germline genes ranked from left (IGKV3-20) to right (IGKV1D-17) in terms of frequency of expression in the pooled data. The number 1358 is the number of B cells sampled.

FIG. 40 shows the VH/Vλ pairs of the pooled data from Examples 2.1 shown in FIGS. 4-26 and Example 2.2 shown in FIGS. 28-36. The numerical entries represent the number of each VH/Vλ germline gene pair from an individual B cell identified in the pooled data. The Y axis shows the VH germline genes ranked from top (VH3-23) to bottom (VH3-20) in terms of frequency of expression in the pooled data. The X axis shows the Vλ germline genes ranked from left (IGLV2-14) to right (IGLV4-60) in terms of frequency of expression in the pooled data. The number 779 is the number of B cells sampled.

FIG. 41 shows the VH/Vκ pairs of the pooled data from Examples 2.1 shown in FIGS. 4-26 and Example 2.2 shown in FIGS. 28-36, but including only the antigen inexperienced B cells populations of immature B cells, new emigrant B cells, and mature naïve B cells in order to identify the VH/Vκ pairs prominent in the naïve human immune repertoire. The numerical entries represent the number of each VH/VL germline gene pair from an individual B cell identified in the pooled data. The Y axis shows the VH germline genes ranked from top (VH3-23) to bottom (VH3-20) in terms of frequency of expression in the pooled data. The X axis shows the Vκ germline genes ranked from left (IGKV3-20) to right (IGKV1D-17) in terms of frequency of expression in the pooled data. The number 888 is the number of B cells sampled.

FIG. 42 shows the VH/Vλ pairs of the pooled data from Examples 2.1 shown in FIGS. 4-26 and Example 2.2 shown in FIGS. 28-36, but including only the antigen inexperienced B cells populations of immature B cells, new emigrant B cells, and mature naïve B cells in order to identify the VH/Vλ pairs prominent in the naïve human immune repertoire. The numerical entries represent the number of each VH/Vλ germline gene pair from an individual B cell identified in the pooled data. The Y axis shows the VH germline genes ranked from top (VH3-23) to bottom (VH3-20) in terms of frequency of expression in the pooled data. The X axis shows the Vλ germline genes ranked from left (IGLV2-14) to right (IGLV4-60) in terms of frequency of expression in the pooled data. The number 457 is the number of B cells sampled.

FIG. 43 shows the VH/Vκ pairs of the pooled data from Examples 2.1 shown in FIGS. 4-26 and Example 2.2 shown in FIGS. 28-36, but including only the antigen experienced B cells populations of IgG antibody secreting cells, and IgM and IgG memory B cells. The numerical entries represent the number of each VH/Vκ germline gene pair from an individual B cell identified in the pooled data. The Y axis shows the VH germline genes ranked from top (VH3-23) to bottom (VH3-20) in terms of frequency of expression in the pooled data. The X axis shows the Vκ germline genes ranked from left (IGKV3-20) to right (IGKV1D-17) in terms of frequency of expression in the pooled data. The number 470 is the number of B cells sampled.

FIG. 44 shows the VH/Vλ pairs of the pooled data from Examples 2.1 shown in FIGS. 4-26 and Example 2.2 shown in FIGS. 28-36, but including only the antigen experienced B cells populations of IgG antibody secreting cells, and IgM and IgG memory B cells. The numerical entries represent the number of each VH/Vλ germline gene pair from an individual B cell identified in the pooled data. The Y axis shows the VH germline genes ranked from top (VH3-23) to bottom (VH3-20) in terms of frequency of expression in the pooled data. The X axis shows the Vλ germline genes ranked from left (IGLV2-14) to right (IGLV4-60) in terms of frequency of expression in the pooled data. The number 322 is the number of B cells sampled.

FIGS. 45A-C show the amino acid sequences encoded by the VH germline genes, as described in Tomlinson et al., (1992), "The Repertoire of Human Germline Vh Sequences Reveals about Fifty Groups of Vh Segments with Different Hypervariable Loop" J. Moi. Biol. 227, 776-798; Matsuda et al, (1998), "The complete nucleotide sequence of the human immunoglobulin heavy chain variable region locus" J Exp Med 188(11):2151-62; and LeFranc MP (2001) "Nomenclature of the human immunoglobulin heavy (IGH) genes." Exp Clin Immunogenet. 18(2):100-16. FIG. 45A discloses SEQ ID NOS 62-78, respectively, in order of appearance. FIG. 45B discloses SEQ ID NOS 79-100, respectively, in order of appearance. FIG. 45C discloses, SEQ ID NOS 101-117, respectively, in order of appearance.

FIGS. 46A-C show the amino acid sequences encoded by the Vκ germline genes, as described in Schäble and Zachau (1993), "The variable genes of the human immunoglobulin kappa locus," Biol. Chem Hoppe Seyler. 374(11):1001-22; Brensing-Küppers et al, (1997), "The human immunoglobulin kappa locus on yeast artificial chromosomes (YACs)"

Gene. 191(2):173-81; Kawasaki et al. (2001), "Evolutionary dynamics of the human immunoglobulin kappa locus and the germline repertoire of the Vkappa genes" Eur J Immunol 31(4):1017-28; and Lefranc (2001) "Nomenclature of the human immunoglobulin kappa (IGK) genes38 Exp Clin Immunogenet., 18, 161-174. FIG. 46A discloses SEQ ID NOS 118-136, respectively, in order of appearance. FIG. 46B discloses SEQ ID NOS 137-153, respectively, in order of appearance. FIG. 46C discloses SEQ ID NOS 154-163, respectively, in order of appearence.

FIGS. 47A-B show the amino acid sequences encoded by the Vλ germline genes, as described in Kawasaki et al., (1997) "One-Megabase Sequence Analysis of the Human immunoglobulin lambda Gene Locus" Genome Research 7(3):250-61; Frippiat et at, (1995) "Organization of the human immunoglobulin lambda tight-chain locus on chromosome 22q11.2" Hum. Mol. Genet., 4, 983-991; and LeFranc MP (2001) "Nomenclature of the human immunoglobulin lambda (IGL) genes. Exp Clin Immunogenet.; 18:242-254. FIG. 47A discloses SEQ ID NOS 164-185 respectively, in order of appearance. FIG. 47B discloses SEQ ID NOS 186-201, respectively, in order of appearance.

FIG. 49 discloses 'His6' as SEQ ID NO: 202.

FIG. 55 shows the relative Fab display rates for the 400 VH/VL germline gene pairs tested. Higher numbers indicate higher display levels.

FIG. 56 shows the relative Fab expression levels for the 400 VH/VL germline gene pairs tested. Higher numbers indicate higher Fab expression levels.

FIG. 57 shows the temperature stability data of the 400 VH/VL germline gene pairs tested in Fab format. The numbers 60 and 70 indicate VH/VL pairs which are stable for 45 min at 60 or 70° C. in the tested set-up. The number 4 indicates temperature-instable pairs and bg indicates low expression levels.

FIG. 58 shows the stability data in bovine serum of the 400 VH/VL germline gene pairs tested in Fab format. S stands for stable and U for unstable at the tested conditions.

FIG. 59 shows the stability data in mouse serum of the 400 VH/VL germline gene pairs tested in Fab format. S stands for stable and U for unstable at the tested conditions.

FIG. 60 shows the relative IgG expression rates for the 400 VH/VL germline gene pairs tested. Higher numbers indicate higher IgG1 expression levels.

FIG. 61 shows the serum stability data of the 400 VH/VL germline gene pairs tested in IgG format. S stands for stable and U for unstable at the tested conditions.

DETAILED DESCRIPTION

Definitions

Figure 1:
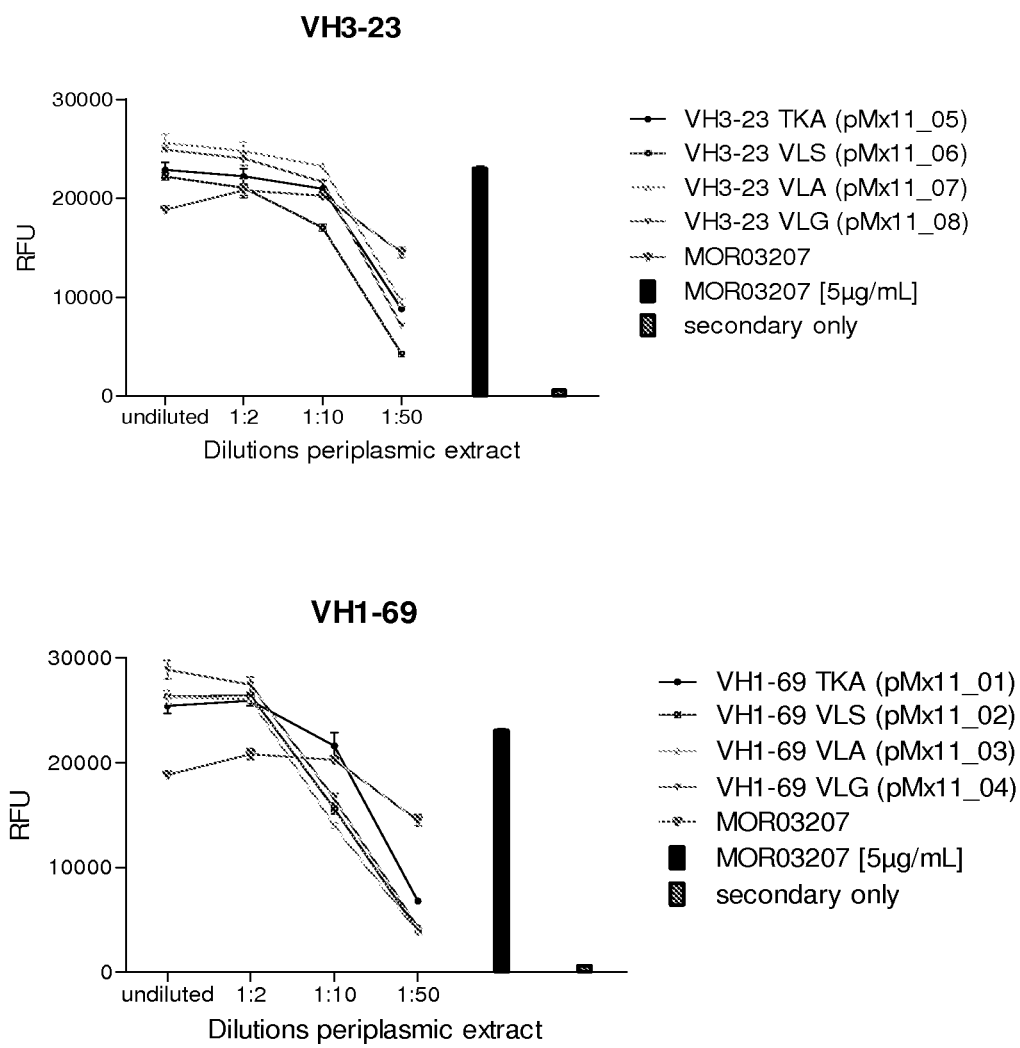
FIG. 1 shows the results of an Anti-Fd expression ELISA after periplasmic extraction of an antibody with the VH3-23 heavy chain (upper panel) and the VH1-69 heavy chain (lower panel), each antibody carrying one of the three modified phoA signal sequences comprising the C-terminal restriction sites AflIII (VLS), NheI (VLA), and AvrII (VLG) as compared to the wildtype (TKA) signal sequence. In the VH3-23 group, all the modified phoA signal sequences maintained expression levels in the range of wildtype (TKA).

To facilitate understanding of the invention, the following definitions and illustrations are provided.

General Terms

The terms "about" or "approximately" in the context of numerical values and ranges refers to values or ranges that approximate or are close to the recited values or ranges such that the invention can perform as intended, such as having a desired number or percentage of sequence homology, as is apparent to the skilled person from the teachings contained herein. This is due, at least in part, to the varying culture conditions and the variability of biological systems. Thus, these terms encompass values beyond those resulting from systematic error. These terms make explicit what is implicit. Typically, "about" encompasses±10% of the stated value. The term "about" can be used to describe a range, therefore.

All ranges set forth herein in the summary and description of the invention include all numbers or values thereabout or there between of the numbers of the range. The ranges of the invention expressly denominate and set forth all integers, decimals and fractional values in the range.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "treating" includes the administration of compositions or antibodies to prevent or delay the onset of the symptoms, complications, or biochemical indicia of a disease, alleviating the symptoms or arresting or inhibiting further development of the disease, condition, or disorder. Treating therefore encompasses, but is not limited to "cure." Treatment may be prophylactic (to prevent or delay the onset of the disease, or to prevent or slow the manifestation of clinical or subclinical symptoms thereof) or therapeutic suppression or alleviation of symptoms after the manifestation of the disease.

"Database or readable medium" as used herein, refers to any format for storing sequence data and thus any collection of information, such as a database file, a lookup table, an Excel spreadsheet or the like. In certain embodiments the database is stored in electronic form, such as a computer readable memory device. This includes media such as a server, a client, a hard disk, a CD, a DVD, a personal digital assistant such as a Palm Pilot, a tape, a zip disk, the computer's internal ROM (read-only-memory) or the internet or worldwide web. Other media for the storage of files accessible by a computer will be obvious to one skilled in the art.

"In silico" refers to manipulations, analysis, and designs performed on a computer, but may also be likewise performed on paper or mentally.

Antibodies and their Properties

The term "antibody" as used herein includes whole antibodies. An antibody may be polyclonal, affinity-purified polyclonal, monoclonal, fully human, murine or rodent, chimeric, camelid or humanized antibodies. An antibody may belong to any of the antibody classes, such as IgG, IgG1, IgG2, IgG3, IgG4, IgA (including human subclasses IgA1 and IgA2), IgD, IgE, IgG, or IgM. A naturally occurring "antibody" is a glycoprotein comprising at least two heavy (H) chains and two light (L) chains inter-connected by disulfide bonds.

The term "functional fragment thereof" as used herein includes any antigen binding fragment, such as Fab, F(ab')2, Fab', Fv, scFv, single chains which include an Fc portion, nanobodies and other antibody like structures having scaffolds other than variable framework regions. The term "functional fragment thereof" includes, but is not limited to any functional portion of an antibody, where function includes binding of an immunogen or effector function.

As used herein, the term "affinity" refers to the strength of interaction between antibody and antigen at antigenic sites. Within each antigenic site, the variable region of the antibody "arm" interacts through non-covalent forces with an antigen at numerous sites; the more interactions, the stronger the affinity. As used herein, the term "high affinity" for an antibody or functional fragment thereof, such as an IgG antibody, refers to an antibody having a KD of $10^{-8}$ M or less, $10^{-9}$ M or less, or $10^{-19}$ M or less, or $10^{-11}$ M or less for a target antigen. However, "high affinity" binding can vary for other antibody isotypes. For example, "high affinity" binding for an IgM isotype refers to an antibody having a KD of $10^{-7}$ M or less, or $10^{-8}$ M or less.

The term "Kassoc" or "Ka", as used herein, is intended to refer to the association rate of a particular antibody-antigen interaction, whereas the term "Kdis" or "Kd," as used herein, is intended to refer to the dissociation rate of a particular antibody-antigen interaction. The term "KD", as used herein, is intended to refer to the dissociation constant, which is obtained from the ratio of Kd to Ka (i.e. Kd/Ka) and is expressed as a molar concentration (M). KD values for antibodies can be determined using methods well established in the art. A method for determining the KD of an antibody is by using surface plasmon resonance, or using a biosensor system such as a Biacore® system.

The terms "cross-block", "cross-blocked" and "cross-blocking" are used interchangeably herein to mean the ability of an antibody or other binding agent to interfere with the binding of other antibodies or binding agents to the same target in a standard competitive binding assay. The ability or extent to which an antibody or other binding agent is able to interfere with the binding of another antibody or binding molecule to the same target, and therefore whether it can be said to cross-block according to the invention, can be determined using standard competition binding assays. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-blocking uses an ELISA-based approach.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

The term "chimeric antibody" is an antibody molecule in which (a) the constant region, or a portion thereof, is altered, replaced or exchanged so that the antigen binding site (variable region) is linked to a constant region of a different or altered class, effector function and/or species.

The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors.

The term "germline" means the nucleic acid sequence encoding antibodies or functional fragments thereof that are passed down from parent to offspring.

The term "germline protein sequence" means a) the amino acid sequence of a variable region of antibody or functional fragment thereof encoded by a germline gene, b) the amino acid sequence encoded by a modified nucleic acid sequence encoding a variable region of antibody or functional fragment thereof having the same amino acid sequence a variable region of an antibody or functional fragment thereof encoded by a germline gene, wherein the nucleic acid sequence is modified by, for example, codon optimization, the addition of desired restriction sites, optimized GC content, the removal of undesired splice sites or the removal of mRNA instability motifs, or c) an amino acid sequence encoded by a germline gene, but with point mutations in the amino acid sequence, such as, for the purpose of removing of an undesired cysteine, or introduction of desired restriction sites, e.g. Bbsl, or that result from errors in synthesis, amplification or cloning.

The term "germline gene sequence" means a) the nucleic acid sequence of a germline gene encoding a variable region of an antibody or functional fragment thereof, or b) a modified nucleic acid sequence encoding a variable region of an antibody or functional fragment thereof having the same amino acid sequence as a variable region of an antibody encoded by a germline gene, wherein the nucleic acid sequence is modified by, for example, codon optimization, the addition of desired restriction sites, optimized GC content, the removal of undesired splice sites or the removal of mRNA instability motifs.

The term "germline gene pair(s)" means the pair of nucleic acid sequences, and their corresponding germline gene, encoding a variable heavy chain and a variable light chain of an antibody or functional fragment thereof. For example, a germline gene pair could be VH3-23/Vκ1-5, where the antibody encoded by VH3-23/Vκ1-5 comprises a variable heavy chain, or a portion thereof, encoded by germline gene VH3-23 and a variable light chain, or portion thereof, encoded by germline gene Vκ1-5.

Figure 3:
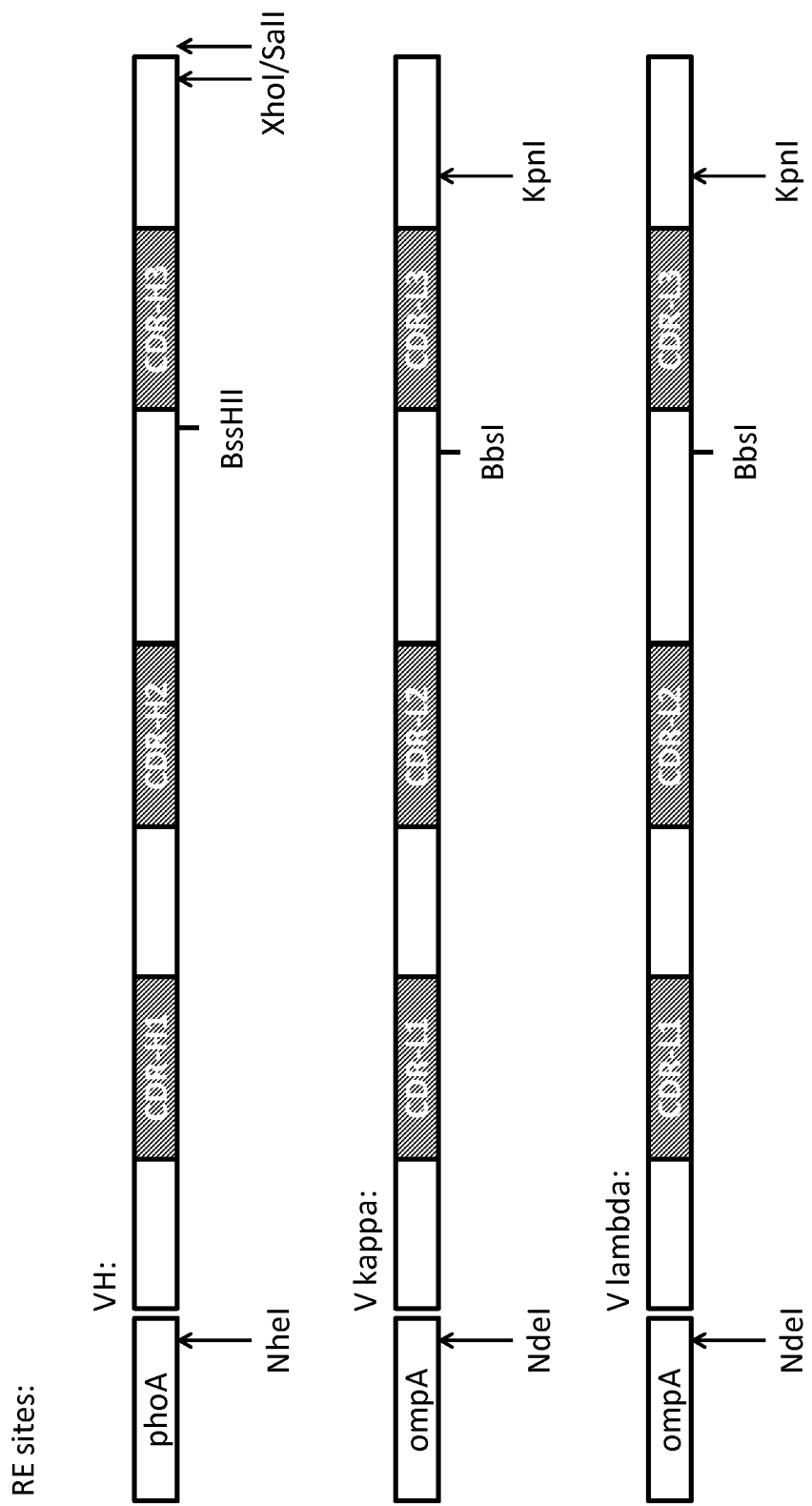
FIG. 3 shows the restriction sites selected for incorporation into the C-terminus of the phoA and ompA *E. coli* signal sequences, as described in detail in Examples 1-1.3, and includes the signal sequences around CDR 3 and their respective orientations. This figure, while displaying the *E. coli* signal sequences, also represents the C-terminal restriction sites selected for incorporation in the human heavy chain and kappa chain leader sequences for use in IgG expression, as described in detail in Example 1.5.

The term "germline protein pair" means an antibody or functional fragment thereof, wherein the variable heavy chain, or portion thereof and the variable light chain, or portion thereof, a) are each encoded by a specific germline gene, or b) are each encoded by a modified nucleic acid sequence encoding a variable region of an antibody or functional fragment thereof having the same amino acid sequence as a variable region of an antibody encoded by the specific germline gene, wherein the nucleic acid sequence is modified by, for example, codon optimization, the addition of desired restriction sites, optimized GC content, the removal of undesired splice sites or the removal of mRNA instability motifs, or c) each comprise an amino acid sequence encoded by a germline gene, but with point mutations in the amino acid sequence, such as, for the purpose of removing of an undesired cysteine, or introduction of desired restriction sites, e.g. Bbsl, or that result from errors in synthesis, amplification or cloning. For example, a germline protein pair could be the antibody or functional fragment encoded by VH3-23/Vκ1-5, where the antibody comprises a variable heavy chain, or a portion thereof, encoded by germline gene VH3-23 and a variable light chain, or portion thereof, encoded by germline gene Vκ1-5. A "germline protein pair" includes the constructs as prepared in Example 5, which comprise a) for VH: leader sequence (modified phoA incorporating a NheI RE site as shown in FIG. 3); germline FR1, CDR1, FR2, CDR2 and FR3 (incorporating a BssHII RE site as shown in FIG. 3); CDR-H3 (WGGDGFYAMDY (SEQ ID NO: 1)) of the 4D5 antibody as used in Ewert S. et al., J. Mol. Biol. (2003) 325, 531-553; and the JH4 FR4 (incorporating a XhoI/SalI RE site as shown in FIG. 3);

b) for Vk: leader sequence (ompA incorporating the NdeI RE site as shown in FIG. 3); germline FR1, CDR1, FR2, CDR2 and FR3 (incorporating a Bbsl RE site as shown in FIG. 3), kappa-like CDR-L3 (QQHYTTPPT (SEQ ID NO:

2)) according to Ewert S. et al., J. Mol. Biol. (2003) 325, 531-553; and the Jk1 FR4 (incorporating a KpnI RE site as shown in FIG. 3);

c) for Vλ: leader sequence (ompA incorporating the NdeI RE site as shown in FIG. 3); germline FR1, CDR1, FR2, CDR2 and FR3 (incorporating a BbsI RE site as shown in FIG. 3), lambda-like CDR-L3 (QSYDSSLSGVV (SEQ ID NO: 3)) according to Ewert S. et al., J. Mol. Biol. (2003) 325, 531-553; and the J12/3 FR4 (incorporating a KpnI RE site as shown in FIG. 3).

Each of these constructs were synthesized, expressed and tested as Fab and IgG, as described in Examples 6 and 7 for the following functional properties: a) relative display after phage production and phage ELISA in Fab format; b) relative Fab expression levels after Fab production in *E. coli, E. coli* cell lysis and ELISA detection of produced Fab; c) temperature stability of Fab after Fab production in *E. coli, E. coli* cell lysis and ELISA detection of non-denatured Fab after incubation at increased temperatures; d) bovine/mouse serum stability of Fab from *E. coli* lysates by ELISA detection of non-denatured Fab after incubation in bovine/mouse serum; e) relative human IgG1 expression levels after IgG1 production in mammalian cells and ELISA detection of secreted IgG1 from cell culture supernatants; and f) bovine serum stability of human IgG1 by ELISA detection of non-denatured Fab after incubation in bovine/mouse serum.

The term "substantially germline protein sequence" means an amino acid sequence encoded by a germline gene, but with point mutations in the amino acid sequence, such as, for the purpose of removing of an undesired cysteine, or introduction of desired restriction sites, e.g. BbsI, or that result from errors in synthesis, amplification or cloning.

The "germline genes" are the nucleic acids of the germline genes encoding antibodies or functional fragments thereof disclosed in the following publications, for VH: Tomlinson et al., (1992), "The Repertoire of Human Germline Vh Sequences Reveals about Fifty Groups of Vh Segments with Different Hypervariable Loop" J. Mol. Biol. 227, 776-798; Matsuda et al. (1998), "The complete nucleotide sequence of the human immunoglobulin heavy chain variable region locus" J Exp Med 188(11):2151-62; and LeFranc M P (2001) "Nomenclature of the human immunoglobulin heavy (IGH) genes." Exp Clin Immunogenet. 18(2):100-16; for VA: Kawasaki et al., (1997) "One-Megabase Sequence Analysis of the Human immunoglobulin lambda Gene Locus" Genome Research 7(3):250-61; Frippiat et al., (1995) "Organization of the human immunoglobulin lambda light-chain locus on chromosome 22q11.2" Hum. Mol. Genet., 4, 983-991; and LeFranc MP (2001) "Nomenclature of the human immunoglobulin lambda (IGL) genes. Exp Clin Immunogenet.; 18:242-254; and for VK: Schäble and Zachau (1993), "The variable genes of the human immunoglobulin kappa locus," Biol. Chem. Hoppe Seyler. 374(11):1001-22; Brensing-Küppers et al. (1997), "The human immunoglobulin kappa locus on yeast artificial chromosomes (YACs)" Gene. 191(2):173-81; Kawasaki et al. (2001), "Evolutionary dynamics of the human immunoglobulin kappa locus and the germline repertoire of the Vkappa genes" Eur J Immunol 31(4):1017-28; and Lefranc MP (2001) "Nomenclature of the human immunoglobulin kappa (IGK) genes" Exp Clin Immunogenet., 18, 161-174, which are all hereby incorporated by reference in their entireties.

The sequences of the JH4 for variable heavy chain, Jκ1 for variable κ light chain, and Jλ2/3 for variable κ light chain regions are described within the following publications: Scaviner et al., (1999), "Protein displays of the human immunoglobulin heavy, kappa and lambda variable and joining regions" Exp Clin Immunogenet. 16(4):234-40; for JH: Ravetch et al., (1981), "Structure of the human immunoglobulin mu locus: characterization of embryonic and rearranged and D genes," Cell 27 (3 pt 2): 583-91; for Hieter et at (1982), "Evolution of human immunoglobulin kappa J region genes." Biol Chem 257(3):1516-22; for JL: Kawasaki et al., (1997) "One-Megabase Sequence Analysis of the Human immunoglobulin lambda Gene Locus" Genome Research 7(3):250-61, which are all incorporated by reference herein in their entireties. The JH4 sequence is (YFDYWGQGTLVTVSS (SEQ ID NO: 4)); the Jκ1 sequence is (WTFGQGTKVEIK (SEQ ID NO: 5)); and the Jλ2/3 sequence is (VVFGGGTKLTVL (SEQ ID NO: 6)).

The term "position-dependent amino-acid usage" refers to the likelihood of occurrence of a particular amino acid sequence at a given position in a polypeptide. In the present invention, the position-dependent amino acid usage was determined for the re-arranged amino acid sequences classified by the individual germline gene. This enables the individual, precise design of the a CDR within its natural germline context.

The term "variable domain/region (VH or VL)" means the region of an immunoglobulin that comprises one or more Ig domains substantially encoded by any of the VL (including Vk and Vλ), VH, JL (including Jk and Jλ), and JH nucleic acids that make up the light chain (including κ and λ) and heavy chain immunoglobulin genetic loci respectively. A light or heavy chain variable region (VL and VH) is made up of a "framework" or "FR" region interspersed by three hypervariable regions referred to as "complementarity determining regions" or "CDRs." The extent of the framework region and CDRs have been precisely defined (see Kabat, 1991, *J. Immunol.*, 147, 915-920; Chothia & Lesk, 1987, *J. Mol. Biol.* 196: 901-917; Chothia et al., 1989, *Nature* 342: 877-883; Al-Lazikani et al., 1997, *J. Mol. Biol.* 273: 927-948). The framework regions of an antibody, that is, the combined framework regions of the constituent light and heavy chains, serves to position and align the CDRs, which are primarily responsible for binding to an antigen.

The term "framework region" means an antibody variable domain as defined by Kabat et al. (1991) as the part of the variable domain which serves as a scaffold for the antigen binding loops of this variable domain. Examples of the framework regions include FR1, FR2, FR3, and FR4 of either the variable heavy or variable light chains The term "complementarity determining region" or "CDR" means an antibody's antigen binding loops, as defined by Kabat et al. (1991). Each of the two variable domains of an antibody Fv fragment contains three CDRs. The complementarity determining regions include CDR1, CDR2, and CDR3 of either the variable heavy or variable light chains The "preferred VH and VL class pair" means those VH and VL class pairs that are preferred in an immune repertoire, for example the human immune repertoire according to a threshold set of criteria. For example, VH-VL pairs that are abundant; or have favorable biophysical properties, such as, low immunogenicity; stability; are readily displayed and/or expressed or VH-VL pairs that appear at a concentration of at least 0.05% in a sample of ~2500 human B cells. The VH and VL class pairs preferred in the human immune repertoire may have preferred characteristics over other VH and VL class pairs.

The term "naïve" means antigen inexperienced.

The term "naive B cell" means a B cell, wherein the nucleic acids encoding the antibodies or functional fragments thereof have not undergone somatic hypermutation, therefore, are considered to comprise the nucleic acids of the germline genes, with the occurrence of V(D)J gene segment rearrangement. The populations of B-cells considered naïve are immature B cells, new emigrant B cells, and mature naïve B cells.

The term "naïve human immune repertoire" means a repertoire of the nucleic acids isolated from antigen inexperienced B cells from the immune system of a human, wherein the nucleic acids encoding the antibodies or functional fragments thereof have not undergone somatic hypermutation, therefore, are considered to comprise the nucleic acids of the germline genes, with the occurrence of V(D)J gene segment rearrangement. A repertoire may be that of an individual, or a population. The present invention is amenable to the determination of an immune repertoire from a single individual, provided sufficient B-cells are obtained. Preferably, the immune repertoire is obtained from multiple individuals to avoid sample biases.

The term "human immune repertoire" means a repertoire of the nucleic acids isolated from B cells from the immune system of a human. A repertoire may be that of an individual, or a population, and may come from naïve B cells and/or antigen experienced B cells. The present invention is amenable to the determination of an immune repertoire from a single individual, provided sufficient B-cells are obtained. Preferably, the immune repertoire is obtained from multiple individuals to avoid sample biases.

An "antigen" and "immunogen" are defined as any molecule that is bound specifically by an antibody.

The term "specific for an immunogen" means the specific association between an antibody and a corresponding molecule.

"CDR diversification" or "diversified CDR" as used herein is the modification of amino acid sequences with the CDRs by any suitable method. CDRs are generally known to be the immunogen binding regions, therefore having collections comprising members representing a large diversity within the CDRs increases the possibility that a collection will comprise antibodies or fragments thereof having specificity, and optimal properties for any immunogen. Diversity is obtained by varying the amino acid composition of one or more CDRs. This can be achieved by any methods known to one of skill in the art, including the methods described herein.

A "collection of synthetic nucleic acids encoding antibodies or fragments thereof" means that all nucleic acids that encode the antibody or fragment thereof are synthetic, but does not refer to other nucleic acids, such as vectors, that may be operably linked with such synthetic nucleic acids.

Terms Used in the Context of Molecular Biology

The term "synthesis" or "synthesized" means gene synthesis, where nucleic acid sequences are synthesized into physical DNA, comprising polynucleotides. Standard DNA synthesis comprises single nucleotide synthesis, where single-stranded oligo-nucleotides are generated and then the overlapping oligonucleotides are ligated using a PCR-like assembly. Companies, such as, Sloning (Puchheim, Germany), Geneart (Regensburg, Germany), DNA2.0 (Menlo Park, Calif. USA), and Genscript (Piscataway, N.J. USA) provide gene synthesis technology. Sloning, for example, utilizes a set of pre-made double stranded triplet nucleotides, which are annealed and subsequently ligated.

The term "synthetic" describes a molecule that is made by synthesis or synthesized.

The term "collection" or "library" means at least two members. The term "member" includes, but is not limited to nucleic acids encoding antibodies or fragments thereof or the antibodies or fragments thereof themselves.

The term "host" refers to any host including mammal, such as human, murine, or rodent, mice, rats, squirrels, chipmunks, gophers, porcupines, beavers, hamsters, gerbils, guinea pigs, rabbits, dogs, cats, cows, or horses.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid. Examples of such analogs include, without limitation, phosphorothioates, phosphoramidates, methyl phosphonates, chiral-methyl phosphonates, 2-O-methyl ribonucleotides, and peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., *Nucleic Acid Res.* 19:5081, 1991; Ohtsuka et al., *J. Biol. Chem.* 260:2605-2608, 1985; and Rossolini et al., *Mol. Cell. Probes* 8:91-98, 1994).

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, the term, "codon optimized" or "codon optimization" means that a nucleotide sequence has been altered to encode an amino acid sequence using codons that are preferred in the production cell or organism. The optimized nucleotide sequence is engineered to retain the amino acid sequence originally encoded by the starting nucleotide sequence. In addition the nucleotide sequence may be designed to be completely or as much as possible devoid of inhibitory motifs, splice sites, mRNA instability motifs and undesired restriction sites. It can also be optimized for GC content, desired restriction sites and other parameters. Sequences may be optimized for expression in different hosts, including bacterial or eukaryotic cells. The amino acid sequences encoded by optimized nucleotide sequences are also referred to as optimized.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. Unless otherwise indicated, a particular polypeptide sequence also implicitly encompasses conservatively modified variants thereof.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch, *J. Mol. Biol.* 48:443, 1970, by the search for similarity method of Pearson and Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., *Current Protocols in Molecular Biology*, John Wiley & Sons, Inc. (2003)).

Two examples of algorithms that are suitable for determining percent sequence identity and sequence similarity are the BLAST and BLAST 2.0 algorithms, which are described in Altschul et al., *Nucl. Acids Res.* 25:3389-3402, 1977; and Altschul et al., *J. Mol. Biol.* 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci.* USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller (*Comput. Appl. Biosci.*, 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453, 1970) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Typical host cells are prokaryotic (such as bacterial, including but not limited to *E. coli*) or eukaryotic (which includes yeast, mammalian cells, and more)

The term "vector" is intended to refer to a polynucleotide molecule capable of transporting another polynucleotide to which it has been linked. Preferred vectors are those capable of autonomous replication and/or expression of nucleic acids to which they are linked. Vectors capable of directing the expression of nucleic acids to which they are operatively linked are referred to herein as "expression vectors." One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Vectors typically include a prokaryotic replicon which may include a prokaryotic promoter capable of directing the expression (transcription and translation) of the VH- and/or VL-coding homologs in a bacterial host cell, such as *Escherichia coli* transformed therewith. A promoter is an expression control element formed by a DNA sequence that permits binding of RNA polymerase and transcription to occur. Promoter sequences compatible with bacterial hosts are typically provided in plasmid vectors containing convenience restriction sites for insertion of a DNA segment. Examples of such vector plasmids include pUC8, pUC9, pBR322, and pBR329, pPL and pKK223, available commercially.

A "display vector" includes a DNA sequence having the ability to direct replication and maintenance of the recombinant DNA molecule extra chromosomally in a host cell, such as a bacterial host cell, transformed therewith. Such DNA sequences are well known in the art. Display vectors can for example be phage vectors or phagemid vectors originating from the class of fd, M13, or fl filamentous bacteriophage. Such vectors are capable of facilitating the display of a protein including, for example, a binding protein or a fragment thereof, on the surface of a filamentous bacteriophage. Display vectors suitable for display on phage, ribosomes, DNA, bacterial cells or eukaryotic cells, for example yeast or mammalian cells are also known in the art, for example, as are viral vectors or vectors encoding chimeric proteins.

Restriction sites that are "unique" are restriction sites that exist or appear only once on a given nucleic acid molecule.

Collections and Methods of Producing and Using the Same

The present disclosure enables collections of antibodies or functional fragments thereof that can be used in the identification of a therapeutic antibody against any target, where the antibodies are clinically developable and safe and effective in patients. As background, the inventors assumed that the variable heavy chain and variable light chain germline gene pairs abundant in the human immune repertoire likely have favorable biophysical properties that would lead to more efficient development and increase the safety and efficacy of the resulting antibodies in patients. Each B cell encodes one antibody, and each antibody comprises a variable heavy chain and variable light chain. Each of the variable heavy chain and variable light chains of an antibody can be aligned with a germline gene sequence in order to determine the origin of the antibody, meaning from which germline gene the variable heavy chain and variable light chain were formed. Therefore, for each antibody, it can be said, that the variable heavy chain and variable light chain comprise a germline gene pair, for example, VH3-23 paired with VK1-5. Such favorable biophysical properties could include: a) high relative display rate in Fab format; b) high relative Fab expression levels; c) temperature stability of Fab; d) bovine/mouse serum stability of Fab; e) high relative human IgG1 expression levels; and f) bovine serum stability of human IgG1.

In order to prove the hypothesis that the germline gene pairs likely have favorable biophysical properties, the first step was to identify the variable heavy chain and variable light chain germline gene pairs expressed in the human immune repertoire. In some aspects, the present invention comprises a method of producing a collection of synthetic antibodies or functional fragments thereof comprising the step of obtaining data comprising the variable heavy chain and variable light chain germline gene pairs present in the human immune repertoire. In some embodiments the data is obtained from publically available literature that provides variable heavy chain and variable light chain germline gene pairs. Generally, in the relevant publically available literature, the following methods were followed: B cells were isolated from human donors, the B cells were sorted in order to determine their stage of development or differentiation, cDNAs were generated and amplified representing the DNA encoding the antibody from each B cell, the cDNAs were sequenced, cDNAs encoding the variable heavy chain and variable light chains were aligned to the known germline gene sequences, and the germline gene pair from each B cell was determined. In some embodiments the data was obtained from the sampling and isolation of human B cells, which comprised a method similar to that used in the literature. In these aspects the method of producing a collection of synthetic antibodies or functional fragments thereof comprises the step of obtaining data comprising the variable heavy chain and variable light chain germline gene pairs present in the human immune repertoire; wherein the obtaining step further comprises the steps of aa) isolating human B cells from a sample; ab) generating cDNA from the B cells; ac) PCR amplifying the cDNA from the B cells; ad) sequencing the PCR products; and ae) identifying the germline genes of the PCR products. Both sets of data provided the variable heavy chain and variable light chain germline gene pairs that are present in the human immune repertoire.

As a next step, the raw data was pooled, analyzed and the variable heavy chain and variable light chain germline gene pairs present in the human immune repertoire were ranked in terms of level of expression. In these aspects, the present invention comprises a method of producing a collection of antibodies or functional fragments thereof comprising identifying the variable heavy chain and variable light chain germline gene pairs that are prominently expressed in the human immune repertoire.

Germline Gene Pairs Prominently Expressed in the Human Immune Repertoire

From this data it was clear that certain variable heavy chain and variable light chain germline gene pairs were present more frequently than others in the human immune repertoire. As these prominent pairs were expected to have superior biophysical properties, aspects of the present invention comprise collections of synthetic antibodies or functional fragments thereof derived from the germline gene pairs that are prominent in the human immune repertoire, where in some embodiments, one or more of the framework regions and/or the complementarity determining regions of the antibodies or functional fragments thereof are derived from the germline gene pairs that are prominent in the human immune repertoire. In other aspects, the present invention comprises collections of synthetic antibodies or functional fragments thereof comprising substantially germline protein sequences of the germline gene pairs that are prominently expressed in the human immune repertoire, where in some embodiments, one or more of the framework regions and/or the complementarity determining regions of the antibodies or functional fragments thereof comprise substantially germline protein sequences of the germline gene pairs that are prominently expressed in the human immune repertoire. In other aspects, the present invention comprises collections of synthetic antibodies or functional fragments thereof comprising germline protein sequences of the germline gene pairs that are prominently expressed in the human immune repertoire, where in some embodiments, one or more of the framework regions and/or the complementarity determining regions of the antibodies or functional fragments thereof comprise germline protein sequences of the germline gene pairs that are prominently expressed in the human immune repertoire. In some aspects, the present invention comprises a collection of synthetic antibodies or functional fragments thereof, comprising variable heavy chain and variable light chain framework regions, wherein said framework regions comprise germline protein sequences of a germline protein pairs, wherein said germline genes are prominently expressed in the human immune repertoire.

In some embodiments, the present invention comprises a collection of synthetic antibodies or functional fragments thereof, wherein said variable heavy chain and variable light chain framework regions consist essentially of germline protein sequences of the germline gene pairs that are prominently expressed in the human immune repertoire. In some embodiments, the antibodies or functional fragments thereof consist essentially of the germline gene pairs that are prominently expressed in the human immune repertoire, where in some embodiments one or more CDRs consist essentially of the germline protein sequences of the germline gene pairs that are prominently expressed in the human immune repertoire. In some embodiments, the present invention comprises a collection of synthetic antibodies or functional fragments thereof, wherein said variable heavy chain and variable light chain framework regions consist of germline protein sequences of the germline gene pairs that are prominently expressed in the human immune repertoire. In some embodiments, the antibodies or functional fragments thereof consist of the germline protein pairs that are encoded by the germline protein pairs prominently expressed in the human immune repertoire where in some embodiments one or more CDRs consist essentially of the germline protein sequences of the germline gene pairs that are prominently expressed in the human immune repertoire. In some embodiments, the majority of or substantially all of the antibodies or functional fragments thereof of the collections comprise germline protein sequences of the germline gene pairs that are prominently expressed in the human immune repertoire.

In some embodiments, the germline gene pairs that are abundant or prominently expressed in the human immune repertoire are expressed at a concentration of at least 0.05% in the human immune repertoire, at least 0.09% in the human immune repertoire; at least 0.14% in the human immune repertoire; at least 0.19% in the human immune repertoire; at least 0.23% in the human immune repertoire; at least 0.28% in the human immune repertoire; at least 0.33% in the human immune repertoire; at least 0.37% in the human immune repertoire; at least 0.42% in the human immune repertoire; at least 0.47% in the human immune repertoire; at least 0.51% in the human immune repertoire; at least 0.56% in the human immune repertoire; at least 0.61% in the human immune repertoire; at least 0.66% in the human immune repertoire; at least 0.70% in the human immune repertoire; at least 0.84% in the human immune repertoire; at least 0.89% in the human immune repertoire; at least 0.94% in the human immune repertoire; at least 1.03% in the human immune repertoire; at least 1.12% in the human immune repertoire; at least 1.17% in the human immune repertoire; or at least 1.26% in the human immune repertoire.

An additional aspect to the present invention is the ability of the collections to be useful in identifying antibodies or functional fragments thereof against any immunogen. It was thought that generating collections with at least two variable heavy chain and variable light chain germline protein pairs that are prominently expressed in the human immune repertoire would provide diversity within the collection, especially within the complementarity determining regions of the antibodies of the collection, in terms of CDR length and diversity in conformations or canonical structures. This allows the collections of the present invention to be useful in identifying antibodies or functional fragments thereof against any immunogen. Therefore, some aspects of the invention comprise collections comprising antibodies or functional fragments thereof comprising at least two different germline protein pairs; at least three different germline protein pairs; at least four different germline protein pairs; at least five different germline protein pairs; at least six different germline protein pairs; at least seven different germline protein pairs; at least eight different germline protein pairs; at least nine different germline protein pairs; at least ten different germline protein pairs; at least eleven different germline protein pairs; at least twelve different germline protein pairs; at least thirteen different germline protein pairs; at least fourteen different germline protein pairs; at least fifteen different germline protein pairs; at least sixteen different germline protein pairs; at least seventeen different germline protein pairs; at least eighteen different germline protein pairs; at least nineteen different germline protein pairs; at least twenty different germline protein pairs; at least 21 different germline protein pairs; at least 22 different germline protein pairs; at least 23 different germline protein pairs; at least 24 different germline protein pairs; at least 25 different germline protein pairs; at least 26 different germline protein pairs; at least 27 different germline protein pairs; at least 28 different variable heavy chain germline protein; at least 29 different germline protein pairs sequences; at least 30 different germline protein pairs; at least 31 different germline protein pairs; at least 32 different germline protein pairs; at least 33 different germline protein pairs; at least 34 different germline protein pairs; at least 35 different germline protein pairs; at least 36 different germline protein pairs; at least 37 different germline protein pairs; at least 38 different germline protein pairs; at least 39 different germline protein pairs; at least 40 different germline protein pairs; at least 41 different germline protein pairs; at least 42 different germline protein pairs; at least 43 different germline protein pairs; at least 44 different variable heavy chain germline protein; at least 45 different germline protein sequences; at least 46 different germline protein pairs; at least 47 different germline protein pairs; at least 48 different germline protein pairs; at least 49 different germline protein pairs; or at least 50 different germline protein pairs selected from the prominently expressed germline protein pairs of the human immune repertoire.

In some embodiments, the collections comprise variable heavy and variable light chain framework regions comprising one or more germline protein pairs selected from the germline gene pairs shown in Table 18.

In some embodiments, the present invention comprises an isolated antibody or functional fragment thereof, comprising a variable heavy chain domain and variable light chain domain comprising a FR1, CDR1, FR2, CDR2, and FR3 comprising germline protein sequences of a germline gene pair, wherein the germline gene pair is selected from the germline gene pairs of Table 18.

Germline Gene Pairs Prominently Expressed in the Naïve Human Immune Repertoire

It was also contemplated that certain variable heavy chain and variable light chain germline gene pairs may be differentially expressed in naïve B cells (antigen inexperienced) versus antigen experienced B cells, therefore, the data was analyzed based on the development or differentiation of the sampled B cells. Collections comprising germline protein pairs of the germline gene pairs differentially expressed in naïve B cells may be advantageous in selecting for antibodies or functional fragments thereof against any immunogen. Therefore aspects of the present invention comprise collections of synthetic antibodies or functional fragments thereof, derived from the germline gene pairs that are prominently expressed in the naïve human immune repertoire, where in some embodiments, one or more of the framework regions and/or the complementarity determining regions of the antibodies or functional fragments thereof are derived from the germline gene pairs that are prominently expressed in the naïve human immune repertoire. In other aspects, the present invention comprises collections of synthetic antibodies or functional fragments thereof comprising substantially germline protein sequences of the germline gene pairs that are prominently expressed in the naïve human immune repertoire, where in some embodiments, one or more of the framework regions and/or the complementarity determining regions of the antibodies or functional fragments thereof comprise substantially germline protein sequences of the germline gene pairs that are prominently expressed in the naïve human immune repertoire. In other aspects, the present invention comprises collections of synthetic antibodies or functional fragments thereof comprising germline protein sequences of the germline gene pairs that are prominently expressed in the naïve human immune repertoire, where in some embodiments, one or more of the framework regions and/or the complementarity determining regions of the antibodies or functional fragments thereof comprise germline protein sequences of the germline gene pairs that are prominently expressed in the naïve human immune repertoire. In some aspects, the present invention comprises a collection of synthetic antibodies or functional fragments thereof, comprising variable heavy chain and variable light chain framework regions, wherein said framework regions comprise germline protein sequences, wherein said germline protein sequences comprise variable heavy chain and variable light chain germline protein pairs, wherein said germline protein pairs are encoded by germline gene pairs are prominently expressed in the naïve human immune repertoire.

In some embodiments, the present invention comprises a collection of synthetic antibodies or functional fragments thereof, wherein said variable heavy chain and variable light chain framework regions consist essentially of germline protein sequences of the germline gene pairs that are prominently expressed in the naïve human immune repertoire. In some embodiments, the antibodies or functional fragments thereof consist essentially of the germline protein pairs encoded by the germline gene pairs that are prominently expressed in the naïve human immune repertoire. In some embodiments, the present invention comprises a collection of synthetic antibodies or functional fragments thereof, wherein said variable heavy chain and variable light chain framework regions consist of germline protein sequences of the germline gene pairs that are prominently expressed in the naïve human immune repertoire. In some embodiments, the antibodies or functional fragments thereof consist of the germline protein pairs that are encoded by the germline gene pairs prominently expressed in the naïve human immune repertoire. In some embodiments, the majority of or substantially all of the antibodies or functional fragments thereof of the collections comprise germline protein sequences of the germline gene pairs that are prominently expressed in the naïve human immune repertoire.

In some embodiments, the germline gene pairs that are abundant or prominently expressed in the naïve human immune repertoire are expressed at a concentration of at least 0.07% in the naïve human immune repertoire, at least 0.15% in the naïve human immune repertoire; at least 0.22% in the naïve human immune repertoire; at least 0.30% in the naïve human immune repertoire; at least 0.37% in the naïve human immune repertoire; at least 0.45% in the naïve human immune repertoire; at least 0.52% in the naïve human immune repertoire; at least 0.59% in the naïve human immune repertoire; at least 0.67% in the naïve human immune repertoire; at least 0.74% in the naïve human immune repertoire; at least 0.82% in the naïve human immune repertoire; at least 0.89% in the naïve human immune repertoire; at least 0.97% in the naïve human immune repertoire; at least 1.19% in the naïve human immune repertoire; or at least 1.56% in the naïve human immune repertoire.

An additional aspect to the present invention is the ability of the collections to be useful in identifying antibodies or functional fragments thereof against any immunogen. It was thought that generating collections with at least two variable heavy chain and variable light chain germline protein pairs that are encoded by germline gene pairs prominently expressed in the naïve human immune repertoire would provide diversity within the collection, especially within the complementarity determining regions of the antibodies of the collection, in terms of CDR length and diversity in conformations or canonical structures. This allows the collections of the present invention to be useful in identifying antibodies or functional fragments thereof against any immunogen. Therefore, some aspects of the invention comprise collections comprising antibodies or functional fragments thereof comprising at least two different germline protein pairs; at least three different germline protein pairs; at least four different germline protein pairs; at least five different germline protein pairs; at least six different germline protein pairs; at least seven different germline protein pairs; at least eight different germline protein pairs; at least nine different germline protein pairs; at least ten different germline protein pairs; at least eleven different germline protein pairs; at least twelve different germline protein pairs; at least thirteen different germline protein pairs; at least fourteen different germline protein pairs; at least fifteen different germline protein pairs; at least sixteen different germline protein pairs; at least seventeen different germline protein pairs; at least eighteen different germline protein pairs; at least nineteen different germline protein pairs; at least twenty different germline protein pairs; at least 21 different germline protein pairs; at least 22 different germline protein pairs; at least 23 different germline protein pairs; at least 24 different germline protein pairs; at least 25 different germline protein pairs; at least 26 different germline protein pairs; at least 27 different germline protein pairs; at least 28 different variable heavy chain germline protein; at least 29 different germline protein pairs sequences; at least 30 different germline protein pairs; at least 31 different germline protein pairs; at least 32 different germline protein pairs; at least 33 different germline protein pairs; at least 34 different germline protein pairs; at least 35 different germline protein pairs; at least 36 different germline protein pairs; at least 37 different germline protein pairs; at least 38 different germline protein pairs; at least 39 different germline protein pairs; at least 40 different germline protein pairs; at least 41 different germline protein pairs; at least 42 different germline protein pairs; at least 43 different germline protein pairs; at least 44 different variable heavy chain germline protein; at least 45 different germline protein pairs sequences; at least 46 different germline protein pairs; at least 47 different germline protein pairs; at least 48 different germline protein pairs; at least 49 different germline protein pairs; at least 49 different germline protein pairs; or at least 50 different germline protein pairs.

In some embodiments, the collections comprise variable heavy and variable light chain framework regions comprising one or more germline protein pairs selected from the germline gene pairs of Table 19.

In some embodiments, the present invention comprises an isolated antibody or functional fragment thereof, comprising a variable heavy chain domain and variable light chain domain comprising a FR1, CDR1, FR2, CDR2, and FR3 comprising germline protein sequences comprising a germline protein pair, wherein the germline protein pair is selected from the germline gene pairs of Table 19.

Variable Heavy Chain, Variable κ Light Chain, and Variable λ Light Chain Germline Genes Prominently Expressed in the Human Immune Repertoire As a next step, the pooled data and additional data was analyzed to determine the variable heavy chain, variable κ light chain, and variable λ light chain germline gene expression in the human immune repertoire. Therefore, additional aspects of the present invention comprise methods of producing a collection of antibodies or functional fragments thereof comprising the step of identifying the variable heavy chain, variable κ light chain, and variable A light chain germline genes that are prominently expressed in the human immune repertoire. One way of doing this is to rank the variable heavy chain, variable κ light chain, and variable A light chain germline genes based upon their level of expression.

Antibodies comprising the variable heavy chain or variable light chain germline protein sequences encoded by the germline genes prominently expressed in the human immune repertoire likely have favorable biophysical properties that enhance development and safety and efficacy in patients. Therefore aspects of the present invention comprise collections of synthetic antibodies or functional fragments thereof derived from the variable heavy chain or variable light chain germline genes that are prominently expressed in the human immune repertoire, where in some embodiments, one or more of the framework regions and/or the complementarity determining regions of the antibodies or functional fragments thereof are derived from the variable heavy chain or variable light chain germline genes that are prominently expressed in the human immune repertoire. In other aspects, the present invention comprises collections of synthetic antibodies or functional fragments thereof comprising substantially germline protein sequences of the variable heavy chain or variable light chain germline genes that are prominently expressed in the human immune repertoire, where in some embodiments, one or more of the framework regions and/or the complementarity determining regions of the antibodies or functional fragments thereof comprise substantially germline protein sequences of the variable heavy chain or variable light chain germline genes that are prominently expressed in the naïve human immune repertoire. In other aspects, the present invention comprises collections of synthetic antibodies or functional fragments thereof comprising germline protein sequences of the variable heavy chain or variable light chain germline genes that are prominently expressed in the human immune repertoire, where in some embodiments, one or more of the framework regions and/or the complementarity determining regions of the antibodies or functional fragments thereof comprise germline protein sequences of the variable heavy chain or variable light chain germline genes that are prominently expressed in the human immune repertoire. In some aspects, the present invention comprises a collection of synthetic antibodies or functional fragments thereof, comprising variable heavy chain and variable light chain framework regions, wherein said framework regions comprise germline protein sequences, wherein said germline protein sequences are encoded by the variable heavy chain or variable light chain germline genes that are prominently expressed in the human immune repertoire.

In some embodiments, the present invention comprises a collection of synthetic antibodies or functional fragments thereof, wherein said variable heavy chain and variable light chain framework regions consist essentially of germline protein sequences of the variable heavy chain or variable light chain germline genes that are prominently expressed in the human immune repertoire. In some embodiments, the antibodies or functional fragments thereof consist essentially of the variable heavy chain or variable light chain germline protein sequences encoded by the germline genes that are prominently expressed in the naïve human immune repertoire. In some embodiments, the present invention comprises a collection of synthetic antibodies or functional fragments thereof, wherein said variable heavy chain and variable light chain framework regions consist of germline protein sequences of the variable heavy chain or variable light chain germline genes that are prominently expressed in the human immune repertoire. In some embodiments, the antibodies or functional fragments thereof consist of the variable heavy chain or variable light chain germline protein sequences encoded by the germline genes that are prominently expressed in the human immune repertoire. In some embodiments, the majority of or substantially all of the antibodies or functional fragments thereof of the collections comprise germline protein sequences encoded by the germline genes that are prominently expressed in the naïve human immune repertoire.

In some embodiments, the variable heavy chain germline genes that are abundant or prominently expressed in the human immune repertoire are expressed at a concentration of at least 0.1% in the human immune repertoire; at least 0.2% in the human immune repertoire; at least 0.3% in the human immune repertoire; at least 0.4% in the human immune repertoire; at least 0.5% in the human immune repertoire; at least 0.6% in the human immune repertoire; at least 1.0% in the human immune repertoire; at least 1.6% in the human immune repertoire; at least 2.1% in the human immune repertoire; at least 2.2% in the human immune repertoire; at least 2.6% in the human immune repertoire; at least 2.7% in the human immune repertoire; at least 3.0% in the human immune repertoire; at least 3.2% in the human immune repertoire; at least 3.3% in the human immune repertoire; at least 4.0% in the human immune repertoire; at least 4.1% in the human immune repertoire; at least 4.5% in the human immune repertoire; at least 4.6% in the human immune repertoire; at least 5.3% in the human immune repertoire; at least 5.8% in the human immune repertoire; at least 6.8% in the human immune repertoire; at least 7.6% in the human immune repertoire; at least 8.0% in the human immune repertoire or at least 10.6% in the human immune repertoire.

In some embodiments, the variable κ light chain germline genes that are abundant or prominently expressed in the human immune repertoire are expressed at a concentration of at least 0.1% in the human immune repertoire; at least 0.2% in the human immune repertoire; at least 0.3% in the human immune repertoire; at least 0.4% in the human immune repertoire; at least 0.5% in the human immune repertoire; at least 0.7% in the human immune repertoire; at least 1.0% in the human immune repertoire; at least 1.1% in the human immune repertoire; at least 1.3% in the human immune repertoire; at least 1.9% in the human immune repertoire; at least 2.2% in the human immune repertoire; at least 2.4% in the human immune repertoire; at least 2.6% in the human immune repertoire; at least 4.6% in the human immune repertoire; at least 6.0% in the human immune repertoire; at least 7.6% in the human immune repertoire; at least 8.5% in the human immune repertoire; at least 11.1% in the human immune repertoire; at least 11.2% in the human immune repertoire; at least 14.2% in the human immune repertoire; or at least 16.2% in the human immune repertoire.

In some embodiments, the variable λ light chain germline genes that are abundant or prominently expressed in the human immune repertoire are expressed at a concentration of at least 0.1% in the human immune repertoire; at least 0.3% in the human immune repertoire; at least 0.5% in the human immune repertoire; at least 0.6% in the human immune repertoire; at least 1.0% in the human immune repertoire; at least 1.2% in the human immune repertoire; at least 1.5% in the human immune repertoire; at least 1.7% in the human immune repertoire; at least 4.5% in the human immune repertoire; at least 5.1% in the human immune repertoire; at least 5.3% in the human immune repertoire; at least 6.5% in the human immune repertoire; at least 8.1% in the human immune repertoire; at least 10.0% in the human immune repertoire; at least 11.3% in the human immune repertoire; or at least 18.1% in the human immune repertoire.

An additional aspect to the present invention is the ability of the collections to be useful in identifying antibodies or functional fragments thereof against any immunogen. It was thought that generating collections with one or more of the variable heavy chain, variable κ light chain, and variable λ light chain germline genes prominently expressed in the human immune repertoire would generate diversity within the collection, especially in CDR length and conformations or canonical structures thus enabling the collection to be useful in identifying an antibodies or functional fragments thereof against any immunogen. Embodiments of the present invention comprise collections comprising antibodies or functional fragments thereof comprising at least two different variable heavy chain germline protein sequences; at least three different variable heavy chain germline protein sequences; at least four different variable heavy chain germline protein sequences; at least five different variable heavy chain germline protein sequences; at least six different variable heavy chain germline protein sequences; at least seven different variable heavy chain germline protein sequences; at least eight different variable heavy chain germline protein sequences; at least nine different variable heavy chain germline protein sequences; at least ten different variable heavy chain germline protein sequences; at least eleven different variable heavy chain germline protein sequences; at least twelve different variable heavy chain germline protein sequences; at least thirteen different variable heavy chain germline protein sequences; at least fourteen different variable heavy chain germline protein sequences; at least fifteen different variable heavy chain germline protein sequences; at least sixteen different variable heavy chain germline protein sequences; at least seventeen different variable heavy chain germline protein sequences; at least eighteen different variable heavy chain germline protein sequences; at least nineteen different variable heavy chain germline protein sequences; at least twenty different variable heavy chain germline protein sequences; at least 21 different variable heavy chain germline protein sequences; at least 22 different variable heavy chain germline protein sequences; at least 23 different variable heavy chain germline protein sequences; at least 24 different variable heavy chain germline protein sequences; at least 25 different variable heavy chain germline protein sequences; at least 26 different variable heavy chain germline protein sequences; at least 27 different variable heavy chain germline protein sequences; at least 28 different variable heavy chain germline protein; at least 29 different variable heavy chain germline protein sequences; at least 30 different variable heavy chain germline protein sequences; at least 31 different variable heavy chain germline protein sequences; at least 32 different variable heavy chain germline protein sequences; at least 33 different variable heavy chain germline protein sequences; at least 34 different variable heavy chain germline protein sequences; at least 35 different variable heavy chain germline protein sequences; at least 36 different variable heavy chain germline protein sequences; at least 37 different variable heavy chain germline protein sequences; at least 38 different variable heavy chain germline protein sequences; at least 39 different variable heavy chain germline protein sequences; at least 40 different variable heavy chain germline protein sequences; at least 41 different variable heavy chain germline protein sequences; at least 42 different variable heavy chain germline protein sequences; at least 43 different variable heavy chain germline protein sequences; at least 44 different variable heavy chain germline protein; at least 45 different variable heavy chain germline protein sequences; at least 46 different variable heavy chain germline protein sequences; at least 47 different variable heavy chain germline protein sequences; at least 48 different variable heavy chain germline protein sequences; at least 49 different variable heavy chain germline protein sequences.

Embodiments of the present invention comprise collections comprising antibodies or functional fragments thereof comprising at least two variable κ light chain germline protein sequences; at least three different variable κ light chain germline protein sequences; at least four different variable κ light chain germline protein sequences; at least five different variable κ light chain germline protein sequences; at least six different variable κ light chain germline protein sequences; at least seven different variable κ light chain germline protein sequences; at least eight different variable κ light chain germline protein sequences; at least nine different variable κ light chain germline protein sequences; at least ten different variable κ light chain germline protein sequences; at least eleven different variable κ light chain germline protein sequences; at least twelve different variable κ light chain germline protein sequences; at least thirteen different variable κ light chain germline protein sequences; at least fourteen different variable κ light chain germline protein sequences; at least fifteen different variable κ light chain germline protein sequences; at least sixteen different variable κ light chain germline protein sequences; at least seventeen different variable κ light chain germline protein sequences; at least eighteen different variable κ light chain germline protein sequences; at least nineteen different variable κ light chain germline protein sequences; at least twenty different variable κ light chain germline protein sequences; at least 21 different variable κ light chain germline protein sequences; at least 22 different variable κ light chain germline protein sequences; at least 23 different variable κ light chain germline protein sequences; at least 24 different variable κ light chain germline protein sequences; at least 25 different variable κ light chain germline protein sequences; at least 26 different variable κ light chain germline protein sequences; at least 27 different variable κ light chain germline protein sequences; at least 28 different variable κ light chain germline protein; at least 29 different variable κ light chain germline protein sequences; at least 30 different variable κ light chain germline protein sequences; at least 31 different variable κ light chain germline protein sequences; at least 32 different variable κ light chain germline protein sequences; at least 33 different variable κ light chain germline protein sequences; at least 34 different variable κ light chain germline protein sequences; at least 35 different variable κ light chain germline protein sequences.

Embodiments of the present invention comprise collections comprising antibodies or functional fragments thereof comprising at least two different variable λ light chain germline protein sequences; at least three different variable λ light chain germline protein sequences; at least four different variable λ light chain germline protein sequences; at least five different variable λ light chain germline protein sequences; at least six different variable λ light chain germline protein sequences; at least seven different variable λ light chain germline protein sequences; at least eight different variable λ light chain germline protein sequences; at least nine different variable λ light chain germline protein sequences; at least ten different variable λ light chain germline protein sequences; at least eleven different variable λ light chain germline protein sequences; at least twelve different variable λ light chain germline protein sequences; at least thirteen different variable λ light chain germline protein sequences; at least fourteen different variable λ light chain germline protein sequences; at least fifteen different variable λ light chain germline protein sequences; at least sixteen different variable λ light chain germline protein sequences; at least seventeen different variable λ light chain germline protein sequences; at least eighteen different variable λ light chain germline protein sequences; at least nineteen different variable λ light chain germline protein sequences; at least twenty different variable λ light chain germline protein sequences; at least 21 different variable λ light chain germline protein sequences; at least 22 different variable λ light chain germline protein sequences; at least 23 different variable λ light chain germline protein sequences; at least 24 different variable λ light chain germline protein sequences; at least 25 different variable λ light chain germline protein sequences; at least 26 different variable λ light chain germline protein sequences; at least 27 different variable λ light chain germline protein sequences; at least 28 different variable λ light chain germline protein; at least 29 different variable λ light chain germline protein sequences; at least 30 different variable λ light chain germline protein sequences; at least 31 different variable λ light chain germline protein sequences; at least 32 different variable λ light chain germline protein sequences; at least 33 different variable λ A light chain germline protein sequences In some embodiments, the collections comprise antibodies or functional fragments thereof comprising variable heavy and variable light chain framework regions wherein said framework regions comprise one or more variable heavy chain germline protein sequences selected from the group consisting of: IGHV3-23; IGHV3-30; IGHV4-39; IGHV4-34; IGHV4-59; IGHV1-69; IGHV5-51; IGHV3-7; IGHV1-18; IGHV3-48; IGHV3-15; IGHV3-21; IGHV1-2; IGHV3-33; IGHV4-31; IGHV3-53; IGHV3-11; IGHV3-9; IGHV4-4; IGHV1-46; IGHV3-74; IGHV1-24; IGHV4-61; IGHV1-8; IGHV1-3; IGHV3-49; IGHV3-43; IGHV4-28; IGHV3-64; and IGHV7-81.

In some embodiments, the collections comprise antibodies or functional fragments thereof comprising variable heavy and variable light chain framework regions wherein said framework regions comprise one or more variable κ light chain germline protein sequences selected from the group consisting of: IGKV3-20; IGKV1-39/1D-39; IGKV1-5; IGKV3-15; IGKV3-11; IGKV4-1; IGKV2-28/2D-28; IGKV1-33/1D-33; IGKV2-30; IGKV1-9; IGKV1-17; IGKV1-27; IGKV1-8; IGKV1-16; IGKV1-6; IGKV1-12; IGKV2D-29; IGKV1-13; IGKV1D-8; and IGKV2-24.

In some embodiments, the collections comprise antibodies or functional fragments thereof comprising variable heavy and variable light chain framework regions wherein said framework regions comprise one or more variable λ light chain germline protein sequences selected from the group consisting of: IGLV2-14; IGLV1-40; IGLV1-44; IGLV1-51; IGLV2-23; IGLV3-21; IGLV1-47; IGLV3-1; IGLV2-11; IGLV2-8; IGLV6-57; IGLV3-25; IGLV7-46; IGLV1-36; IGLV7-43; IGLV9-49; IGLV4-69; IGLV2-18; IGLV3-10; and IGLV3-27.

In some embodiments, the present invention comprises an isolated antibody or functional fragment thereof, comprising a FR1, CDR1, FR2, CDR2, and FR3 comprising germline protein sequences selected from the group consisting of: IGHV3-23; IGHV3-30; IGHV4-39; IGHV4-34; IGHV4-59; IGHV1-69; IGHV5-51; IGHV3-7; IGHV1-18; IGHV3-48; IGHV3-15; IGHV3-21; IGHV1-2; IGHV3-33; IGHV4-31; IGHV3-53; IGHV3-11; IGHV3-9; IGHV4-4; IGHV1-46; IGHV3-74; IGHV1-24; IGHV4-61; IGHV1-8; IGHV1-3; IGHV3-49; IGHV3-43; IGHV4-28; IGHV3-64; IGHV7-81; IGKV3-20; IGKV1-39/1D-39; IGKV1-5; IGKV3-15; IGKV4-1; IGKV3-11; IGKV2-28/2D-28; IGKV1-33/1D-33; IGKV2-30; IGKV1-9; IGKV1-17; IGKV1-27; IGKV1-8; IGKV1-16; IGKV1-6; IGKV1-12; IGKV2D-29; IGKV1-13; IGKV1D-8; IGKV2-24; IGLV2-14; IGLV1-40; IGLV1-44; IGLV1-51; IGLV2-23; IGLV3-21; IGLV1-47; IGLV3-1; IGLV2-11; IGLV2-8; IGLV6-57; IGLV3-25; IGLV7-46; IGLV1-36; IGLV7-43; IGLV9-49; IGLV4-69; IGLV2-18; IGLV3-10; and IGLV3-27.

Variable Heavy Chain, Variable κ Light Chain, and Variable λ Light Chain Germline Genes Having Favorable Biophysical Properties As a next step the prominent variable heavy chain, variable κ light chain, and variable λ light chain germline protein sequences were evaluated to determine their biophysical properties relevant to development. The variable heavy chain, variable κ light chain, and variable λ light chain germline protein sequences were evaluated in silico for the following properties: CDR length, isoelectric point (pI) the preferred isoelectric point is 7.5 or above as this is should provide stability in a standard pH 5.5 to pH 7 formulation buffer, post translational modifications in the complementarity determining regions (PTM's) (specifically, N-linked glycosylation sites (NxS or NxT) or chemical modifications such as Asp cleavage (often at a DP), Asp isomerization (DD, DG), deamidation (NS, NG) which can occur in vivo (in serum) or upon storage in formulation buffer and lead to loss of antibody binding), the presence of Methionines in the CDRs (can be oxidized when exposed to solvent), the presence of unpaired Cysteines (will form disulfide bonds with any other unpaired cysteine, thus leading to crosslinking of proteins and/or lower expression levels), deviations from germline, the presence of potential T-cell epitopes, and theoretical aggregation propensity.

In some embodiments the present invention comprises a method of producing the collection of synthetic antibodies or functional fragments thereof comprises the steps of a) identifying the variable heavy chain and/or variable light chain germline protein sequences comprising the following properties: i) four or less post translational modifications in the complementarity determining regions; ii) two or less methionines in the complementarity determining regions; iii) one or less unpaired cysteines; iv) one or less potential T-cell epitopes; v) an intermediate or low propensity for aggregation; and vi) an isoelectric point of at least 7.5; and b) generating a collection of antibodies or functional fragments thereof comprising the variable heavy chain and/or variable light chain germline gene sequences identified in a).

Aspects of the present invention comprise collections of synthetic antibodies or functional fragments thereof derived from the variable heavy chain and/or variable light chain germline protein sequences comprising one or more of the following properties: i) four or less post translational modifications in the complementarity determining regions; ii) two or less methionines in the complementarity determining regions; iii) one or less unpaired cysteines; iv) one or less potential T-cell epitopes; v) an intermediate or low propensity for aggregation; or vi) an isoelectric point of at least 7.5, where in some embodiments, one or more of the framework regions and/or the complementarity determining regions of the antibodies or functional fragments thereof are derived from the variable heavy chain and/or variable light chain germline protein sequences having such properties.

Aspects of the present invention comprise collections of synthetic antibodies or functional fragments thereof comprising substantially germline protein sequences of the variable heavy chain and/or variable light chain germline protein sequences comprising one or more of the following properties: i) four or less post translational modifications in the complementarity determining regions; ii) two or less methionines in the complementarity determining regions; iii) one or less unpaired cysteines; iv) one or less potential T-cell epitopes; v) an intermediate or low propensity for aggregation; or vi) an isoelectric point of at least 7.5, where in some embodiments, one or more of the framework regions and/or the complementarity determining regions of the antibodies or functional fragments thereof comprise substantially germline protein sequences from the variable heavy chain and/or variable light chain germline protein sequences having such properties.

Aspects of the present invention comprise collections of synthetic antibodies or functional fragments thereof comprising germline protein sequences of the variable heavy chain and/or variable light chain germline protein sequences comprising one or more of the following properties: i) four or less post translational modifications in the complementarity determining regions; ii) two or less methionines in the complementarity determining regions; iii) one or less unpaired cysteines; iv) one or less potential T-cell epitopes; v) an intermediate or low propensity for aggregation; or vi) an isoelectric point of at least 7.5, where in some embodiments, one or more of the framework regions and/or the complementarity determining regions of the antibodies or functional fragments thereof comprising germline protein sequences of the variable heavy chain and/or variable light chain germline protein having such properties.

Aspects of the present invention comprise collections of synthetic antibodies or functional fragments thereof comprising the variable heavy chain and/or variable light chain germline protein sequences comprising no unpaired cysteines.

Aspects of the present invention comprise collections of synthetic antibodies or functional fragments thereof comprising the variable heavy chain and/or variable light chain germline protein sequences comprising four or less post translational modifications in the complementarity determining regions; three or less post translational modifications in the complementarity determining regions; two or less post translational modifications in the complementarity determining regions; one or less post translational modifications in the complementarity determining regions, or no post translational modifications in the complementarity determining regions.

Aspects of the present invention comprise collections of synthetic antibodies or functional fragments thereof derived from the variable heavy chain and/or variable light chain germline protein sequences comprising an isoelectric point of at least 7.5; of at least 8.0; of at least 8.5; of at least 9; or of at least 9.5.

Aspects of the present invention comprise collections of synthetic antibodies or functional fragments thereof, comprising variable heavy chain and variable light chain framework regions, wherein said framework regions comprise variable heavy chain and/or variable light chain germline protein sequences comprising one or more of the following properties: i) four or less post translational modifications in the complementarity determining regions; ii) two or less methionines in the complementarity determining regions; iii) one or less unpaired cysteines; iv) one or less potential T-cell epitopes; v) an intermediate or low propensity for aggregation; or vi) an isoelectric point of at least 7.5.

In some embodiments the collections of synthetic antibodies or functional fragments thereof, comprise variable heavy chain and/or variable light chain germline protein sequences comprising at least two of the following properties: i) four or less post translational modifications in the complementarity determining regions; ii) two or less methionines in the complementarity determining regions; iii) one or less unpaired cysteines; iv) one or less potential T-cell epitopes; v) an intermediate or low propensity for aggregation; or vi) an isoelectric point of at least 7.5.

In some embodiments the collections of synthetic antibodies or functional fragments thereof, comprise variable heavy chain and/or variable light chain germline protein sequences comprising at least four of the following properties: i) four or less post translational modifications in the complementarity determining regions; ii) two or less methionines in the complementarity determining regions; iii) one or less unpaired cysteines; iv) one or less potential T-cell epitopes; v) an intermediate or low propensity for aggregation; or vi) an isoelectric point of at least 7.5.

In some embodiments the collections of synthetic antibodies or functional fragments thereof, comprise variable heavy chain and/or variable light chain germline protein sequences comprising at least four of the following properties: i) four or less post translational modifications in the complementarity determining regions; ii) two or less methionines in the complementarity determining regions; iii) one or less unpaired cysteines; iv) one or less potential T-cell epitopes; v) an intermediate or low propensity for aggregation; or vi) an isoelectric point of at least 7.5.

In some embodiments the collections of synthetic antibodies or functional fragments thereof, comprise variable heavy chain and/or variable light chain germline protein sequences comprising at least five of the following properties: i) four or less post translational modifications in the complementarity determining regions; ii) two or less methionines in the complementarity determining regions; iii) one or less unpaired cysteines; iv) one or less potential T-cell epitopes; v) an intermediate or low propensity for aggregation; or vi) an isoelectric point of at least 7.5.

In some embodiments the collections of synthetic antibodies or functional fragments thereof, comprise variable heavy chain and/or variable light chain germline protein sequences comprising the following properties: i) four or less post translational modifications in the complementarity determining regions; ii) two or less methionines in the complementarity determining regions; iii) one or less unpaired cysteines; iv) one or less potential T-cell epitopes; v) an intermediate or low propensity for aggregation; and vi) an isoelectric point of at least 7.5.

In some embodiments, the collections of synthetic antibodies or functional fragments thereof, comprise variable heavy chain and variable light chain framework regions, wherein the framework regions consist essentially of the variable heavy chain and/or variable light chain germline protein sequences comprising one or more of the following properties: i) four or less post translational modifications in the complementarity determining regions; ii) two or less methionines in the complementarity determining regions; iii) one or less unpaired cysteines; iv) one or less potential T-cell epitopes; v) an intermediate or low propensity for aggregation; or vi) an isoelectric point of at least 7.5.

In some embodiments, the antibodies or functional fragments thereof consist essentially of the variable heavy chain and/or variable light chain germline protein sequences comprising one or more of the following properties: i) four or less post translational modifications in the complementarity determining regions; ii) two or less methionines in the complementarity determining regions; iii) one or less unpaired cysteines; iv) one or less potential T-cell epitopes; v) an intermediate or low propensity for aggregation; or vi) an isoelectric point of at least 7.5.

In some embodiments, the collections of synthetic antibodies or functional fragments thereof, comprise variable heavy chain and variable light chain framework regions, wherein the framework regions consist of variable heavy chain and/or variable light chain germline protein sequences comprising one or more of the following properties: i) four or less post translational modifications in the complementarity determining regions; ii) two or less methionines in the complementarity determining regions; iii) one or less unpaired cysteines; iv) one or less potential T-cell epitopes; v) an intermediate or low propensity for aggregation; or vi) an isoelectric point of at least 7.5.

In some embodiments, the antibodies or functional fragments thereof consist of the variable heavy chain and/or variable light chain germline protein sequences comprising one or more of the following properties: i) four or less post translational modifications in the complementarity determining regions; ii) two or less methionines in the complementarity determining regions; iii) one or less unpaired cysteines; iv) one or less potential T-cell epitopes; v) an intermediate or low propensity for aggregation; or vi) an isoelectric point of at least 7.5.

In some embodiments, the majority of or substantially all of the antibodies or functional fragments thereof of the collections comprise the variable heavy chain and/or variable light chain germline protein sequences comprising one or more of the following properties: i) four or less post translational modifications in the complementarity determining regions; ii) two or less methionines in the complementarity determining regions; iii) one or less unpaired cysteines; iv) one or less potential T-cell epitopes; v) an intermediate or low propensity for aggregation; or vi) an isoelectric point of at least 7.5.

Some embodiments, comprise a collection of synthetic antibodies or functional fragments thereof, comprising variable heavy chain and variable light chain framework regions, wherein said framework regions comprise germline protein sequences, wherein said germline protein sequences comprise the following properties: i) four or less post translational modifications in the complementarity determining regions in the complementarity determining regions; ii) two or less methionines in the complementarity determining regions; iii) one or less unpaired cysteines; iv) one or less potential T-cell epitopes; and v) an isoelectric point of at least 7.5.

Some embodiments comprise a collection of synthetic antibodies or functional fragments thereof, comprising variable heavy chain and variable light chain framework regions, wherein said framework regions comprise germline protein sequences, wherein said germline protein sequences comprise the following property: i) one or less unpaired cysteines.

Some embodiments comprise a collection of synthetic antibodies or functional fragments thereof, comprising variable heavy chain and variable light chain framework regions, wherein said framework regions comprise germline protein sequences, wherein said germline protein sequences comprise the following properties: i) one or less unpaired cysteines; ii) one or less potential T-cell epitopes.

Some embodiments comprise a collection of synthetic antibodies or functional fragments thereof, comprising variable heavy chain and variable light chain framework regions, wherein said framework regions comprise germline protein sequences, wherein said germline protein sequences comprise the following properties: i) one or less unpaired cysteines; ii) one or less potential T-cell epitopes; and iii) an isoelectric point of at least 7.5.

Some embodiments comprise a collection of synthetic antibodies or functional fragments thereof, comprising variable heavy chain and variable light chain framework regions, wherein said framework regions comprise germline protein sequences, wherein said germline protein sequences comprise the following properties: i) two or less methionines in the complementarity determining regions; ii) one or less unpaired cysteines; iii) one or less potential T-cell epitopes; and iv) an isoelectric point of at least 7.5.

An additional aspect of the present invention is the ability of the collections to be useful in identifying antibodies or functional fragments thereof against any immunogen. It was thought that generating collections with one or more variable heavy chain, variable κ light chain, and variable λ light chain germline protein sequences would generate diversity within the collection, especially in CDR length and conformations or canonical structures thus enabling the collection to be useful in identifying antibodies or functional fragments thereof against any immunogen.

Embodiments of the present invention comprise collections comprising antibodies or functional fragments thereof comprising at least two different variable heavy chain germline protein sequences; at least three different variable heavy chain germline protein sequences; at least four different variable heavy chain germline protein sequences; at least five different variable heavy chain germline protein sequences; at least six different variable heavy chain germline protein sequences; at least seven different variable heavy chain germline protein sequences; at least eight different variable heavy chain germline protein sequences; at least nine different variable heavy chain germline protein sequences; at least ten different variable heavy chain germline protein sequences; at least eleven different variable heavy chain germline protein sequences; at least twelve different variable heavy chain germline protein sequences; at least thirteen different variable heavy chain germline protein sequences; at least fourteen different variable heavy chain germline protein sequences; at least fifteen different variable heavy chain germline protein sequences; at least sixteen different variable heavy chain germline protein sequences; at least seventeen different variable heavy chain germline protein sequences; at least eighteen different variable heavy chain germline protein sequences; at least nineteen different variable heavy chain germline protein sequences; or at least twenty different variable heavy chain germline protein sequences comprising the following properties: i) four or less post translational modifications in the complementarity determining regions; ii) two or less methionines in the complementarity determining regions; iii) one or less unpaired cysteines; iv) one or less potential T-cell epitopes; v) an intermediate or low propensity for aggregation; or vi) an isoelectric point of at least 7.5.

Embodiments of the present invention comprise collections comprising antibodies or functional fragments thereof comprising at least two different variable κ light chain germline protein sequences; at least three different variable κ light chain germline protein sequences; at least four different variable κ light chain germline protein sequences; at least five different variable κ light chain germline protein sequences; at least six different variable κ light chain germline protein sequences; at least seven different variable κ light chain germline protein sequences; at least eight different variable κ light chain germline protein sequences; at least nine different variable κ light chain germline protein sequences; at least ten different variable κ light chain germline protein sequences; at least eleven different variable κ light chain germline protein sequences; at least twelve different variable κ light chain germline protein sequences comprising the following properties: i) four or less post translational modifications in the complementarity determining regions; ii) two or less methionines in the complementarity determining regions; iii) one or less unpaired cysteines; iv) one or less potential T-cell epitopes; v) an intermediate or low propensity for aggregation; or vi) an isoelectric point of at least 7.5.

Embodiments of the present invention comprise collections comprising antibodies or functional fragments thereof comprising at least two different variable λ light chain germline protein sequences; at least three different variable λ light chain germline protein sequences; at least four different variable λ light chain germline protein sequences; at least five different variable λ light chain germline protein sequences; at least six different variable λ light chain germline protein sequences; at least seven different variable λ light chain germline protein sequences; at least eight different variable λ light chain germline protein sequences comprising the following properties: i) four or less post translational modifications in the complementarity determining regions; ii) two or less methionines in the complementarity determining regions; iii) one or less unpaired cysteines; iv) one or less potential T-cell epitopes; v) an intermediate or low propensity for aggregation; or vi) an isoelectric point of at least 7.5.

In some embodiments, the collections comprise antibodies or functional fragments thereof comprising variable heavy and variable light chain framework regions wherein said framework regions comprise one or more variable heavy chain germline protein sequences selected from the group consisting of: IGHV1-2; IGHV1-18; IGHV1-69; IGHV1-46; IGHV3-7; IGHV3-11; IGHV3-15; IGHV3-21; IGHV3-23; IGHV3-30; IGHV3-33; IGHV3-48; IGHV3-53; IGHV3-73; IGH3-74; IGHV4-4; IGHV4-31; IGHV4-39; IGHV 5-51 and IGHV6-1.

In some embodiments, the collections comprise antibodies or functional fragments thereof comprising variable heavy and variable light chain framework regions wherein said framework regions comprise one or more variable κ light chain germline protein sequences selected from the group consisting of: IGKV1-5; IGKV1-6; IGKV1-9; IGKV1-12; IGKV1-16; IGKV1-17; IGKV1-27; IGKV1-39; IGKV2-30; IGKV3-11; IGKV3-15; and IGKV3-20.

In some embodiments, the collections comprise antibodies or functional fragments thereof comprising variable heavy and variable light chain framework regions wherein said framework regions comprise one or more variable λ light chain germline protein sequences selected from the group consisting of: IGLV1-40; IGLV1-47; IGLV1-51; IGLV2-11; IGLV2-23; IGLV2-14; IGLV3-1 and IGLV3-21.

In some embodiments, the present invention comprises an isolated antibody or functional fragment thereof, comprising a FR1, CDR1, FR2, CDR2, and FR3 comprising germline protein sequences selected from the group consisting of: IGHV1-2; IGHV1-18; IGHV1-69; IGHV1-46; IGHV3-7; IGHV3-11; IGHV3-15; IGHV3-21; IGHV3-23; IGHV3-30; IGHV3-33; IGHV3-48; IGHV3-53; IGHV3-73; IGH3-74; IGHV4-4; IGHV4-31; IGHV4-39; IGHV 5-51; IGHV6-1; IGKV1-5; IGKV1-6; IGKV1-9; IGKV1-12; IGKV1-16; IGKV1-17; IGKV1-27; IGKV1-39; IGKV2-30; IGKV3-11; IGKV3-15; IGKV3-20; IGLV1-40; IGLV1-47; IGLV1-51; IGLV2-11; IGLV2-23; IGLV2-14; IGLV3-1 and IGLV3-21.

Germline Gene Pairs Having Favorable Biophysical Properties

As a next step, it had to be determined which germline protein pairs were to be tested, as there are ~2500 pairs in the human immune repertoire. One way would be to test the variable heavy chain and variable light chain germline protein pairs that occur most prominently in the human immune repertoire, for example see Table 18. One could, for example, select the top four hundred pairs for testing, or select the variable heavy chain and variable light chain germline protein pairs expressed above a certain threshold concentration. Therefore, aspects of the present invention comprise methods producing the collection of synthetic antibodies or functional fragments thereof wherein the step of producing further comprises the step of identifying the variable heavy chain and variable light chain germline gene pairs expressed at a concentration of at least 0.05% in the human immune repertoire; generating antibodies or functional fragments thereof comprising the germline protein pairs identified; and evaluating the following properties of said germline protein pairs: i) relative display rate in Fab format; ii) expression level in Fab format; iii) thermal stability at 60° C. or more in Fab format for at least 45 minutes; iv) stability in bovine serum in Fab format for greater than ten days at 37° C.; v) expression level in IgG format; and vi) stability in bovine serum in IgG format for fourteen days at 37° C.

This approach would require the synthesis and testing of a large number of variable heavy chain and variable light chain germline protein pair sequences; therefore, such an approach would not be very efficient.

As an alternative approach, the inventors selected a subset of the variable heavy chain and variable light chain germline pairs that are representative of, accurately reproduce, or cover the majority of the prominently expressed pairs from the human immune repertoire. This approach was based, in part, upon the observation that a small number of variable heavy, variable κ light chain, and variable λ light chain germline genes are dominant in the human immune repertoire. Wildt et al. at 895-896 describes this phenomenon. Wildt et al. also states that the frequently expressed heavy and light chain gene segments are often paired, and observed that half of the pairings sampled correspond to only five germline pairs. Therefore, a small number of the prominently expressed heavy and light chain germline genes (unpaired) can be combined to generate a group of pairs that are representative of the human immune repertoire.

Therefore, aspects of the present invention comprise collections of antibodies or fragments thereof comprising germline protein pairs representative of, that accurately reproduce or cover the majority of the prominently expressed variable heavy chain and variable light chain germline gene pairs of the human immune repertoire or naïve human immune repertoire. As described below, our approach leads to collections comprising antibodies or fragments thereof that are fully developable, as the variable heavy chain and variable light chain germline protein pairs are first tested for favorable biophysical properties and then collections are designed to include the germline protein pairs comprising one or more of these favorable biophysical properties.

Aspects of the present invention comprise methods of producing a collection of antibodies or functional fragments thereof comprising the step of identifying the variable heavy chain and variable light chain germline protein pairs comprising one or more of the following properties: i) a relative display rate in Fab format comprising a value within the top 75% of Fabs sampled; ii) an expression level in Fab format of at least 0.4 as compared to Fab pMx11_FH VH1-69 VLA_Vl1-40 AYA; iii) thermal stability at 60° C. or more for at least 45 minutes in Fab format; iv) stability in bovine or mouse serum in Fab format for greater than ten days at 37° C.; v) an expression level in IgG format of at least 0.4 as compared to MOR03080; and vi) stability in bovine serum in IgG format for fourteen days at 37° C.

In some aspects, the present invention comprises methods of producing a collection of antibodies or functional fragments thereof comprising generating a collection of antibodies or functional fragments thereof comprising variable heavy chain and variable light chain framework regions, wherein said one or more framework regions comprise germline protein sequences of a germline protein pairs, wherein said germline protein pair comprise one or more the following properties: i) a relative display rate in Fab format comprising a value within the top 75% of Fabs sampled; ii) an expression level in Fab format of at least 0.4 as compared to Fab VH1-69 VLA_Vl1-40 AYA; iii) thermal stability at 60° C. or more for at least 45 minutes in Fab format; iv) stability in bovine or mouse serum in Fab format for greater than ten days at 37° C.; v) an expression level in IgG format of at least 0.4 as compared to MOR03080; and vi) stability in bovine serum in IgG format for fourteen days at 37° C. In some embodiments, the FR1, FR2, and FR3 regions comprise germline protein sequences.

In some embodiments, the FR1, FR2, and FR3 regions comprise germline protein sequences of a germline protein pair. In some embodiments, the antibodies or functional fragments thereof comprise one or more complementarity determining regions comprising germline protein sequences. In some embodiments, the antibodies or functional fragments thereof comprise one or more complementarity determining regions comprising germline protein sequences of a germline protein pair. In some embodiments, the CDR1 and CDR2 regions comprise germline protein sequences. In some embodiments, the CDR1 and CDR2 regions comprise germline protein sequences of a germline protein pair. In some embodiments, the FR1, CDR1, FR2, CDR2, and FR3 regions comprise germline protein sequences. In some embodiments, the FR1, CDR1, FR2, CDR2, and FR3 regions comprise germline protein sequences of a germline protein pair. In some embodiments, the FR4 region comprises the JH4 heavy chain region. In some embodiments, the FR4 region comprises the JK1 light chain region. In some embodiments, the FR4 region comprises the Jλ2/3 light chain region.

In other embodiments the present invention comprises methods of producing collections of antibodies or functional fragments thereof comprising generating a collection, wherein generating further comprises the steps of synthesizing the nucleic acids encoding the antibodies or functional fragments thereof; cloning the nucleic acids into a vector; and expressing the antibodies or functional fragments thereof.

Once the prominently expressed or representative group thereof of variable heavy chain and variable light chain germline protein pairs were synthesized and tested, then collections could be designed to include germline protein pairs comprising favorable biophysical properties.

Aspects of the present invention comprise collections of synthetic antibodies or functional fragments thereof derived from the germline protein pairs comprising one or more of the following properties: i) a relative display rate in Fab format comprising a value within the top 75% of Fabs sampled; ii) an expression level in Fab format of at least 0.4 as compared to Fab VH1-69 VLA_Vl1-40 AYA; iii) thermal stability at 60° C. or more for at least 45 minutes in Fab format; iv) stability in bovine or mouse serum in Fab format for greater than ten days at 37° C.; v) an expression level in IgG format of at least 0.4 as compared to MOR03080; and vi) stability in bovine serum in IgG format for fourteen days at 37° C., where in some embodiments, one or more of the framework regions and/or the complementarity determining regions of the antibodies or functional fragments thereof are derived from the germline protein pairs having such properties.

Aspects of the present invention comprise collections of synthetic antibodies or functional fragments thereof comprising substantially germline protein sequences of the germline protein pairs comprising one or more of the following properties: i) a relative display rate in Fab format comprising a value within the top 75% of Fabs sampled; ii) an expression level in Fab format of at least 0.4 as compared to Fab VH1-69 VLA_Vl1-40 AYA; iii) thermal stability at 60° C. or more for at least 45 minutes in Fab format; iv) stability in bovine or mouse serum in Fab format for greater than ten days at 37° C.; v) an expression level in IgG format of at least 0.4 as compared to MOR03080; and vi) stability in bovine serum in IgG format for fourteen days at 37° C., where in some embodiments, one or more of the framework regions and/or the complementarity determining regions of the antibodies or functional fragments thereof comprise substantially germline protein sequences of the germline protein pairs having such properties.

Aspects of the present invention comprise collections of synthetic antibodies or functional fragments thereof comprising germline protein sequences of the germline protein pairs comprising one or more of the following properties: i) a relative display rate in Fab format comprising a value within the top 75% of Fabs sampled; ii) an expression level in Fab format of at least 0.4 as compared to Fab VH1-69 VLA_Vl1-40 AYA; iii) thermal stability at 60° C. or more for at least 45 minutes in Fab format; iv) stability in bovine or mouse serum in Fab format for greater than ten days at 37° C.; v) an expression level in IgG format of at least 0.4 as compared to MOR03080; and vi) stability in bovine serum in IgG format for fourteen days at 37° C., where in some embodiments, one or more of the framework regions and/or the complementarity determining regions of the antibodies or functional fragments thereof comprise germline protein sequences of the germline protein pairs having such properties.

In some aspects, the collections of synthetic antibodies or functional fragments thereof, comprise variable heavy chain and variable light chain framework regions, wherein the framework regions comprise germline protein sequences of a germline protein pair comprising one or more of the following properties: i) a relative display rate in Fab format comprising a value within the top 75% of Fabs sampled; ii) an expression level in Fab format of at least 0.4 as compared to Fab VH1-69 VLA_Vl1-40 AYA; iii) thermal stability at 60° C. or more for at least 45 minutes in Fab format; iv) stability in bovine or mouse serum in Fab format for greater than ten days at 37° C.; v) an expression level in IgG format of at least 0.4 as compared to MOR03080; and vi) stability in bovine serum in IgG format for fourteen days at 37° C.

In some embodiments, the framework regions comprising germline protein sequences of a germline protein pair comprise FR1, FR2, and FR3 regions. In some embodiments, the antibodies or functional fragments thereof comprise one or more complementarity determining regions comprising germline protein sequences. In some embodiments, the antibodies or functional fragments thereof comprise one or more complementarity determining regions comprising germline protein sequences of a germline protein pair. In some embodiments, the CDR1 and CDR2 regions comprise germline protein sequences. In some embodiments, the CDR1 and CDR2 regions comprise germline protein sequences of a germline protein pair. In some embodiments, the FR1, CDR1, FR2, CDR2, and FR3 regions comprise germline protein sequences. In some embodiments, the FR1, CDR1, FR2, CDR2, and FR3 regions comprise germline protein sequences of a germline protein pair. In some embodiments, the FR4 region comprises the JH4 heavy chain region. In some embodiments, the FR4 region comprises the JK1 light chain region. In some embodiments, the FR4 region comprises the Jλ2/3 light chain region.

In some embodiments, the collections of synthetic antibodies or functional fragments thereof, comprise variable heavy chain and variable light chain framework regions, wherein the framework regions comprise germline protein sequences of a germline protein pair comprising at least two of the following properties: i) a relative display rate in Fab format comprising a value within the top 75% of Fabs sampled; ii) an expression level in Fab format of at least 0.4 as compared to Fab VH1-69 VLA_Vl1-40 AYA; iii) thermal stability at 60° C. or more for at least 45 minutes in Fab format; iv) stability in bovine or mouse serum in Fab format for greater than ten days at 37° C.; v) an expression level in IgG format of at least 0.4 as compared to MOR03080; and vi) stability in bovine serum in IgG format for fourteen days at 37° C.

In some embodiments, the collections of synthetic antibodies or functional fragments thereof, comprise variable heavy chain and variable light chain framework regions, wherein the framework regions comprise germline protein sequences of a germline protein pair comprising at least three of the following properties: i) a relative display rate in Fab format comprising a value within the top 75% of Fabs sampled; ii) an expression level in Fab format of at least 0.4 as compared to Fab VH1-69 VLA_Vl1-40 AYA; iii) thermal stability at 60° C. or more for at least 45 minutes in Fab format; iv) stability in bovine or mouse serum in Fab format for greater than ten days at 37° C.; v) an expression level in IgG format of at least 0.4 as compared to MOR03080; and vi) stability in bovine serum in IgG format for fourteen days at 37° C.

In some embodiments, the collections of synthetic antibodies or functional fragments thereof, comprise variable heavy chain and variable light chain framework regions, wherein the framework regions comprise germline protein sequences of a germline protein pair comprising at least four of the following properties: i) a relative display rate in Fab format comprising a value within the top 75% of Fabs sampled; ii) an expression level in Fab format of at least 0.4 as compared to Fab VH1-69 VLA_Vl1-40 AYA; iii) thermal stability at 60° C. or more for at least 45 minutes in Fab format; iv) stability in bovine or mouse serum in Fab format for greater than ten days at 37° C.; v) an expression level in IgG format of at least 0.4 as compared to MOR03080; and vi) stability in bovine serum in IgG format for fourteen days at 37° C.

In some embodiments, the collections of synthetic antibodies or functional fragments thereof, comprise variable heavy chain and variable light chain framework regions, wherein the framework regions comprise germline protein sequences of a germline protein pair comprising at least five of the following properties: i) a relative display rate in Fab format comprising a value within the top 75% of Fabs sampled; ii) an expression level in Fab format of at least 0.4 as compared to Fab VH1-69 VLA_Vl1-40 AYA; iii) thermal stability at 60° C. or more for at least 45 minutes in Fab format; iv) stability in bovine or mouse serum in Fab format for greater than ten days at 37° C.; v) an expression level in IgG format of at least 0.4 as compared to MOR03080; and vi) stability in bovine serum in IgG format for fourteen days at 37° C.

In some embodiments, the collections of synthetic antibodies or functional fragments thereof, comprise variable heavy chain and variable light chain framework regions, wherein the framework regions comprise germline protein sequences of a germline protein pair comprising the following properties: i) a relative display rate in Fab format comprising a value within the top 75% of Fabs sampled; ii) an expression level in Fab format of at least 0.4 as compared to Fab VH1-69 VLA_Vl1-40 AYA; iii) thermal stability at 60° C. or more for at least 45 minutes in Fab format; iv) stability in bovine or mouse serum in Fab format for greater than ten days at 37° C.; v) an expression level in IgG format of at least 0.4 as compared to MOR03080; and vi) stability in bovine serum in IgG format for fourteen days at 37° C.

In some embodiments, the collections of synthetic antibodies or functional fragments thereof, comprise variable heavy chain and variable light chain framework regions, wherein the framework regions consist essentially of germline protein sequences of a germline protein pair comprising one or more of the following properties: i) a relative display rate in Fab format comprising a value within the top 75% of Fabs sampled; ii) an expression level in Fab format of at least 0.4 as compared to Fab VH1-69 VLA_Vl1-40 AYA; iii) thermal stability at 60° C. or more for at least 45 minutes in Fab format; iv) stability in bovine or mouse serum in Fab format for greater than ten days at 37° C.; v) an expression level in IgG format of at least 0.4 as compared to MOR03080; and vi) stability in bovine serum in IgG format for fourteen days at 37° C.

In some embodiments, the antibodies or functional fragments thereof consist essentially of germline protein sequences of a germline protein pair comprising one or more of the following properties: i) a relative display rate in Fab format comprising a value within the top 75% of Fabs sampled; ii) an expression level in Fab format of at least 0.4 as compared to Fab VH1-69 VLA_Vl1-40 AYA; iii) thermal stability at 60° C. or more for at least 45 minutes in Fab format; iv) stability in bovine or mouse serum in Fab format for greater than ten days at 37° C.; v) an expression level in IgG format of at least 0.4 as compared to MOR03080; and vi) stability in bovine serum in IgG format for fourteen days at 37° C.

In some embodiments, the collections of synthetic antibodies or functional fragments thereof, comprise variable heavy chain and variable light chain framework regions, wherein the framework regions consist of germline protein sequences of a germline protein pair comprising one or more of the following properties: i) a relative display rate in Fab format comprising a value within the top 75% of Fabs sampled; ii) an expression level in Fab format of at least 0.4 as compared to Fab VH1-69 VLA_Vl1-40 AYA; iii) thermal stability at 60° C. or more for at least 45 minutes in Fab format; iv) stability in bovine or mouse serum in Fab format for greater than ten days at 37° C.; v) an expression level in IgG format of at least 0.4 as compared to MOR03080; and vi) stability in bovine serum in IgG format for fourteen days at 37° C.

In some embodiments, the antibodies or functional fragments thereof consist of germline protein sequences of a germline protein pair comprising one or more of the following properties: i) a relative display rate in Fab format comprising a value within the top 75% of Fabs sampled; ii) an expression level in Fab format of at least 0.4 as compared to Fab VH1-69 VLA_Vl1-40 AYA; iii) thermal stability at 60° C. or more for at least 45 minutes in Fab format; iv) stability in bovine or mouse serum in Fab format for greater than ten days at 37° C.; v) an expression level in IgG format of at least 0.4 as compared to MOR03080; and vi) stability in bovine serum in IgG format for fourteen days at 37° C.

In some embodiments, the majority of or substantially all of the antibodies or functional fragments thereof of the collections comprise germline protein sequences of a germline protein pair comprising one or more of the following properties: i) a relative display rate in Fab format comprising a value within the top 75% of Fabs sampled; ii) an expression level in Fab format of at least 0.4 as compared to Fab VH1-69 VLA_Vl1-40 AYA; iii) thermal stability at 60° C. or more for at least 45 minutes in Fab format; iv) stability in bovine or mouse serum in Fab format for greater than ten days at 37° C.; v) an expression level in IgG format of at least 0.4 as compared to MOR03080; and vi) stability in bovine serum in IgG format for fourteen days at 37° C.

In some aspects, the antibodies or functional fragments thereof of the collection comprise the germline protein sequences of the germline protein pairs comprising one or more of the following properties: i) a relative display rate in Fab format comprising a value within the top 75% of Fabs sampled; ii) an expression level in Fab format of at least 0.4 as compared to Fab VH1-69 VLA_Vl1-40 AYA; iii) thermal stability at 60° C. or more for at least 45 minutes in Fab format; iv) stability in bovine or mouse serum in Fab format for greater than ten days at 37° C.; v) an expression level in IgG format of at least 0.4 as compared to MOR03080; and vi) stability in bovine serum in IgG format for fourteen days at 37° C.

In some embodiments, the antibodies or functional fragments thereof consist essentially of germline protein sequences of a germline protein pair comprising the following properties: i) a relative display rate in Fab format comprising a value within the top 75% of Fabs sampled; ii) an expression level in Fab format of at least 0.4 as compared to Fab VH1-69 VLA_Vl1-40 AYA; iii) thermal stability at 60° C. or more for at least 45 minutes in Fab format; iv) stability in bovine or mouse serum in Fab format for greater than ten days at 37° C.; v) an expression level in IgG format of at least 0.4 as compared to MOR03080; and vi) stability in bovine serum in IgG format for fourteen days at 37° C.

In some embodiments, the antibodies or functional fragments thereof consist of germline protein sequences of a germline protein pair comprising the following properties: i) a relative display rate in Fab format comprising a value within the top 75% of Fabs sampled; ii) an expression level in Fab format of at least 0.4 as compared to Fab VH1-69 VLA_Vl1-40 AYA; iii) thermal stability at 60° C. or more for at least 45 minutes in bovine or mouse serum in Fab format for greater than ten days at 37° C.; v) an expression level in IgG format of at least 0.4 as compared to MOR03080; and vi) stability in bovine serum in IgG format for fourteen days at 37° C.

In some embodiments, the collection of synthetic antibodies or functional fragments thereof, comprising variable heavy chain and variable light chain framework regions, wherein said variable heavy chain framework regions and variable light chain framework regions comprise germline protein sequences of a germline protein pair, wherein said germline protein pair comprises the following properties: i) thermal stability at 60° C. or more for at least 45 minutes in Fab format; and ii) stability in serum in IgG format for fourteen days at 37° C.

In some embodiments, the collection of synthetic antibodies or functional fragments thereof, comprising variable heavy chain and variable light chain framework regions, wherein said variable heavy chain framework regions and variable light chain framework regions comprise germline protein sequences of a germline protein pair, wherein said germline protein pair comprises the following properties: i) thermal stability at 60° C. or more for at least 45 minutes in Fab format; ii) stability in bovine or mouse serum in Fab format for greater than ten days at 37° C.; iii) stability in serum in IgG format for fourteen days at 37° C.

In some embodiments, a collection of synthetic antibodies or functional fragments thereof, comprising variable heavy chain and variable light chain framework regions, wherein said variable heavy chain framework regions and variable light chain framework regions comprise germline protein sequences of a germline protein pair, wherein said germline protein pair comprises the following properties: i) a relative display rate in Fab format comprising a value within the top 75% of Fabs sampled; ii) thermal stability at 60° C. or more for at least 45 minutes in Fab format; iii) stability in bovine or mouse serum in Fab format for greater than ten days at 37° C.; and iv) stability in serum in IgG format for fourteen days at 37° C.

In some embodiments, a collection of synthetic antibodies or functional fragments thereof comprises variable heavy chain and variable light chain framework regions, wherein said variable heavy chain framework regions and variable light chain framework regions comprise germline protein sequences of a germline protein pair, wherein said germline protein pair comprises the following properties: i) an expression level in Fab format of at least 0.4 as compared to Fab VH1-69 VLA_Vl1-40 AYA; ii) thermal stability at 60° C. or more for at least 45 minutes in Fab format; iii) stability in bovine or mouse serum in Fab format for greater than ten days at 37° C.; iv) an expression level in IgG format of at least 0.4 as compared to MOR003080; and v) stability in serum in IgG format for fourteen days at 37° C.

In other embodiments the collections of the present invention comprise a collection of synthetic antibodies or functional fragments thereof, comprising variable heavy chain and variable light chain framework regions, wherein said variable heavy chain framework regions and variable light chain framework regions comprise germline protein sequences of a germline protein pair, wherein said germline protein pair comprises the following properties: i) thermal stability at 60° C. or more for at least 45 minutes in Fab format; ii) stability in bovine or mouse serum in Fab format for greater than ten days at 37° C.; iii) an expression level in IgG format of at least 0.4 as compared to MOR003080; and iv) stability in serum in IgG format for fourteen days at 37° C.

In other embodiments the collections of the present invention and/or methods of producing such collections comprise antibodies or functional fragments thereof comprise variable heavy chain and variable light chain framework regions, wherein said framework regions comprise germline protein sequences of a germline protein pair comprising a relative display rate in Fab format of at least 0.1 as compared to control; of at least 0.2 as compared to control; of at least 0.3 as compared to control; of at least 0.4 as compared to control; of at least 0.5 as compared to control; of at least 0.6 as compared to control; of at least 0.7 as compared to control; of at least 0.8 as compared to control; of at least 0.9 as compared to control; of at least 1.0 as compared to control; of at least 1.1 as compared to control; of at least 1.2 as compared to control; of at least 1.3 as compared to control; of at least 1.4 as compared to control; of at least 1.5 as compared to control; of at least 1.6 as compared to control; of at least 1.7 as compared to control; of at least 1.8 as compared to control; of at least 1.9 as compared to control; of at least 2.0 as compared to control; of at least 2.1 as compared to control; of at least 2.2 as compared to control; of at least 2.3 as compared to control; of at least 2.4 as compared to control; of at least 2.5 as compared to control; of at least 2.6 as compared to control; of at least 2.7 as compared to control; of at least 2.8 as compared to control; of at least 2.9 as compared to control; of at least 3.0 as compared to control; of at least 3.2 as compared to control; of at least 3.3 as compared to control; of at least 3.4 as compared to control; of at least 3.5 as compared to control; of at least 3.6 as compared to control; of at least 3.7 as compared to control; of at least 3.8 as compared to control; of at least 4.1 as compared to control; of at least 4.3 as compared to control; of at least 4.4 as compared to control; of at least 4.5 as compared to control; of at least 4.6 as compared to control; of at least 4.7 as compared to control; of at least 5.0 as compared to control; of at least 5.1 as compared to control; of at least 5.2 as compared to control; of at least 5.4 as compared to control; of at least 5.5 as compared to control; of at least 5.7 as compared to control; of at least 5.9 as compared to control; of at least 6.0 as compared to control; of at least 6.1 as compared to control; of at least 6.3 as compared to control; of at least 6.4 as compared to control; of at least 6.7 as compared to control; of at least 6.9 as compared to control; of at least 7.0 as compared to control; of at least 7.1 as compared to control; of at least 7.2 as compared to control; of at least 7.3 as compared to control; of at least 7.4 as compared to control; of at least 8.1 as compared to control; of at least 8.2 as compared to control; of at least 8.3 as compared to control; of at least 8.4 as compared to control; of at least 8.5 as compared to control; of at least 8.6 as compared to control; of at least 8.7 as compared to control; of at least 8.8 as compared to control; of at least 8.9 as compared to control; of at least 9.1 as compared to control; of at least 9.2 as compared to control; of at least 9.3 as compared to control; of at least 9.4 as compared to control; of at least 9.5 as compared to control; of at least 9.7 as compared to control; of at least 9.8 as compared to control; of at least 10.0 as compared to control; of at least 10.2 as compared to control; of at least 10.3 as compared to control; of at least 10.5 as compared to control; of at least 10.6 as compared to control; of at least 10.7 as compared to control; of at least 10.8 as compared to control; of at least 11.0 as compared to control; of at least 11.2 as compared to control; of at least 11.3 as compared to control; of at least 11.5 as compared to control; of at least 11.7 as compared to control; of at least 11.8 as compared to control; of at least 12.1 as compared to control; of at least 12.3 as compared to control; of at least 12.4 as compared to control; of at least 12.9 as compared to control; of at least 13.0 as compared to control; of at least 13.6 as compared to control; of at least 14.4 as compared to control; of at least 14.5 as compared to control; of at least 16.1 as compared to control; of at least 16.6 as compared to control; of at least 16.7 as compared to control; of at least 17.1 as compared to control; of at least 19.4 as compared to control; of at least 27.3 as compared to control; or of at least 29.0 as compared to control.

In some embodiments, the collection of synthetic antibodies or functional fragments thereof, comprise variable heavy chain and variable light chain framework regions, wherein said variable heavy chain framework regions and variable light chain framework regions comprise germline protein sequences of a germline protein pair, wherein said germline protein pair comprises a relative display rate in Fab format comprising a value within the top 10% of Fabs sampled; a value within the top 15% of Fabs sampled; a value within the top 20% of Fabs sampled; a value within the top 25% of Fabs sampled; a value within the top 30% of Fabs sampled; a value within the top 35% of Fabs sampled; a value within the top 40% of Fabs sampled; a value within the top 45% of Fabs sampled; a value within the top 50% of Fabs sampled; a value within the top 55% of Fabs sampled; a value within the top 60% of Fabs sampled; a value within the top 65% of Fabs sampled; a value within the top 70% of Fabs sampled; a value within the top 75% of Fabs sampled; a value within the top 80% of Fabs sampled; a value within the top 85% of Fabs sampled; or a value within the top 90% of Fabs sampled.

In other embodiments the collections of the present invention and/or methods of producing such collections comprise antibodies or functional fragments thereof comprising variable heavy chain and variable light chain framework regions, wherein said framework regions comprise germline protein sequences of a germline protein pair comprising a relative expression level in Fab format of at least 0.1 as compared to Fab VH1-69 VLA_Vl1-40 AYA; of at least 0.2 as compared to Fab VH1-69 VLA_Vl1-40 AYA; of at least 0.3 as compared to Fab VH1-69 VLA_Vl1-40 AYA; of at least 0.4 as compared to Fab VH1-69 VLA_Vl1-40 AYA; of at least 0.5 as compared to Fab VH1-69 VLA_Vl1-40 AYA; of at least 0.6 as compared to Fab VH1-69 VLA_Vl1-40 AYA; of at least 0.7 as compared to Fab VH1-69 VLA_Vl1-40 AYA; of at least 0.8 as compared to Fab VH1-69 VLA_Vl1-40 AYA; of at least 0.9 as compared to Fab VH1-69 VLA_Vl1-40 AYA; of at least 1.0 as compared to Fab VH1-69 VLA_Vl1-40 AYA; of at least 1.1 as compared to Fab VH1-69 VLA_Vl1-40 AYA; of at least 1.2 as compared to Fab VH1-69 VLA_Vl1-40 AYA; or of at least 1.3 as compared to Fab VH1-69 VLA_Vl1-40 AYA.

In other embodiments the collections of the present invention and/or methods of producing such collections comprise antibodies or functional fragments thereof comprising variable heavy chain and variable light chain framework regions, wherein said framework regions comprise germline protein sequences of a germline protein pair comprising thermal stability at 70° C. or more for at least 45 minutes in Fab format; or comprising thermal stability at 80° C. or more for at least 45 minutes in Fab format.

In other embodiments the collections of the present invention and/or methods of producing such collections comprise antibodies or functional fragments thereof comprise variable heavy chain and variable light chain framework regions, wherein said framework regions comprise germline protein sequences of a germline protein pair comprising a relative expression level in IgG format of at least 0.1 as compared to MOR03080; of at least 0.2 as compared to MOR03080; of at least 0.3 as compared to MOR03080; of at least 0.4 as compared to MOR03080; of at least 0.5 as compared to MOR03080; of at least 0.6 as compared to MOR03080; of at least 0.7 as compared to MOR03080; of at least 0.8 as compared to MOR03080; of at least 0.9 as compared to MOR03080; of at least 1.0 as compared to MOR03080; of at least 1.1 as compared to MOR03080; of at least 1.2 as compared to MOR03080; of at least 1.3 as compared to MOR03080; of at least 1.4 as compared to MOR03080 of at least 1.5 as compared to MOR03080; of at least 1.6 as compared to MOR03080; of at least 1.7 as compared to MOR03080; of at least 1.8 as compared to MOR03080; of at least 1.9 as compared to MOR03080.

In certain aspects the present invention comprises collections and methods of producing or using the collections of antibodies or functional fragments thereof comprising one or more complementarity determining regions comprising germline protein sequences, substantially germline sequences or sequences derived from the germline protein sequences. In certain embodiments, the antibodies or functional fragments thereof comprise a CDR1 and CDR2 comprising germline protein sequences. In certain embodiments, the antibodies or functional fragments thereof comprise a CDR1 and CDR2 comprising the germline protein sequences of the germline protein pair.

In some aspects, one or more framework regions comprise germline protein sequences of the germline protein pair. As in some aspects, FR4 is selected from the group consisting of JH4, Jκ1, and Jλ2/3. As shown in FIGS. 45A-47B the germline protein sequences comprise only FR1-FR3. Therefore in certain aspects, when said variable heavy chain framework regions and variable light chain framework regions comprise germline protein sequences, the FR1, FR2 and/or FR3 comprise germline protein sequences. In some aspects, one or more framework regions comprise germline protein sequences, allowing for the diversification of one or more complementarity determining regions. In some embodiments, the present invention comprises collections and methods of producing and making said collections of synthetic antibodies or functional fragments thereof, comprising a diversified HCDR3 region. In some embodiments, the present invention comprises collections and methods of producing and using said collections of synthetic antibodies or functional fragments thereof, comprising a diversified LCDR3 region.

An additional aspect to the present invention is the ability of the collections to be useful in identifying antibodies or functional fragments thereof against any immunogen. It was thought that generating collections with at least two variable heavy chain and variable light chain germline protein pairs comprising the above functional properties would provide diversity within the collection, especially within the complementarity determining regions of the antibodies of the collection, in terms of CDR length and diversity in conformations or canonical structures. This allows the collections of the present invention to be useful in identifying antibodies or functional fragments thereof against any immunogen.

Some embodiments of the invention comprise collections comprising antibodies or functional fragments thereof comprising variable heavy chain and variable light chain framework regions, wherein the framework regions comprise germline protein sequence of a germline gene pair comprising the following properties: i) a relative display rate in Fab comprising a value within the top 75% of Fabs sampled; ii) an expression level in Fab format of at least 0.4 as compared to Fab VH1-69 VLA_Vl1-40 AYA; iii) thermal stability at 60° C. or more for at least 45 minutes in Fab format; iv) stability in bovine or mouse serum in Fab format for greater than ten days at 37° C.; v) an expression level in IgG format of at least 0.4 as compared to MOR03080; and vi) stability in bovine serum in IgG format for fourteen days at 37° C., wherein said collection comprises antibodies of functional fragments thereof comprising at least two different germline protein pairs; at least different three germline protein pairs; at least four different germline protein pairs; at least five different germline protein pairs; at least six different germline protein pairs; at least seven different germline protein pairs; at least eight different germline protein pairs; at least nine different germline protein pairs; at least ten different germline protein pairs; at least eleven different germline protein pairs; at least twelve different germline protein pairs; at least thirteen different germline protein pairs; at least fourteen different germline protein pairs; at least fifteen different germline protein pairs; at least sixteen different germline protein pairs; at least seventeen different germline protein pairs; at least eighteen different germline protein pairs; at least nineteen different germline protein pairs; at least twenty different germline protein pairs; at least 21 different germline protein pairs; at least 22 different germline protein pairs; at least 23 different germline protein pairs; at least 24 different germline protein pairs; at least 25 different germline protein pairs; at least 26 different germline protein pairs; at least 27 different germline protein pairs; at least 28 different variable heavy chain germline protein; at least 29 different germline protein pairs sequences; at least 30 different germline protein pairs; at least 31 different germline protein pairs; at least 32 different germline protein pairs; at least 33 different germline protein pairs; at least 34 different germline protein pairs; at least 35 different germline protein pairs; at least 36 different germline protein pairs; at least 37 different germline protein pairs; at least 38 different germline protein pairs; at least 39 different germline protein pairs; at least 40 different germline protein pairs; at least 41 different germline protein pairs; at least 42 different germline protein pairs; at least 43 different germline protein pairs; at least 44 different variable heavy chain germline protein; at least 45 different germline protein pairs sequences; at least 46 different germline protein pairs; at least 47 different germline protein pairs; at least 48 different germline protein pairs; at least 49 different germline protein pairs or at least 50 different germline protein pairs.

Antibodies or Functional Fragments Thereof Comprising Germline Gene Sequences Additionally, it was thought that utilizing germline protein sequences should lower the immunogenicity risk of the antibodies when administered to patients. Therefore, aspects of the present invention comprise collections and methods of producing and using said collections of synthetic antibodies or functional fragments thereof, comprising variable heavy chain and variable light chain framework regions, wherein said framework regions comprise germline protein sequences. In some embodiments, the variable heavy chain and variable light chain framework regions of the antibodies or functional fragments thereof comprise substantially germline sequences. In some embodiments, the variable heavy chain and variable light chain framework regions of the antibodies or functional fragments thereof are derived from germline sequences. In some embodiments, said antibodies or functional fragments thereof comprise FR1, FR2, FR3 and FR4 regions comprising germline protein sequences, substantially germline sequences or are derived from the germline protein sequences. In certain embodiments said antibodies or functional fragments thereof comprise FR1, FR2, FR3 comprising the germline protein sequences of the representative germline protein pair. In some embodiments, the FR4 region that is used is JH4 for variable heavy chain, Jκ1 for variable κ light chain, and Jλ2/3 for variable λ light chain.

Again as utilizing germline protein sequences should lower the immunogenicity risk of the antibodies when administered in patients, certain aspects of the present invention comprise collections and methods of producing or using the collections of antibodies or functional fragments thereof comprising one or more complementarity determining regions comprising germline protein sequences, substantially germline sequences or are derived from the germline protein sequences. In certain embodiments, the antibodies or functional fragments thereof comprise a CDR1 and CDR2 comprising germline protein sequences. In certain embodiments, the antibodies or functional fragments thereof comprise a CDR1 and CDR2 comprising the germline protein sequences of the germline protein pair.

In some aspects, one or more framework regions comprise germline protein sequences, allowing for the diversification of one or more complementarity determining regions. In some embodiments, the present invention comprises collections and methods of producing and making said collections of synthetic antibodies or functional fragments thereof, comprising a diversified HCDR3 region. In some embodiments, the present invention comprises collections and methods of producing and using said collections of synthetic antibodies or functional fragments thereof, comprising a diversified LCDR3 region. CDRs can be designed by methods well known in the art including those disclosed in Knappik et al. 2000; WO 97/08320; WO2008053275; WO2009036379 WO2007056441; WO2009114815, all of which are incorporated by reference in their entireties.

Additionally, in order to generate collections comprising antibodies or functional fragments thereof having a low risk of immunogenicity, in certain aspects the collection of the present invention and methods of producing and using the same, comprise antibodies or functional fragments thereof comprising human sequences.

In some aspects, the collection of the invention comprises at least $1 \times 10^4$; at least $1 \times 10^5$; at least $1 \times 10^6$; at least $1 \times 10^7$; at least $1 \times 10^8$; at least $1 \times 10^9$; at least $1 \times 10^{10}$; or at least $1 \times 10^{11}$ nucleic acid sequences encoding antibodies or functional fragments thereof or antibodies or functional fragments thereof.

In some aspects, the antibodies or functional fragments thereof of the collections are synthetic.

In some aspects, the collections comprise nucleic acids encoding the antibodies or functional fragments thereof.

Additional Embodiments of the Present Invention

In some aspects, the present invention comprises a collection of synthetic antibodies or functional fragments thereof, comprising variable heavy chain and variable light chain framework regions, wherein said variable heavy chain framework regions and variable light chain framework regions comprise germline protein sequences of a germline protein pair, wherein said germline protein pair comprises the following properties:
i) a relative display rate in Fab format comprising a value within the top 75% of Fabs sampled;
ii) an expression level in Fab format of at least 0.4 as compared to Fab VH1-69 VLA_Vl1-40 AYA;
iii) thermal stability at 60° C. or more for at least 45 minutes in Fab format;
iv) stability in bovine or mouse serum in Fab format for greater than ten days at 37° C.;
v) an expression level in IgG format of at least 0.4 as compared to MOR03080; and
vi) stability in serum in IgG format for fourteen days at 37° C.;
wherein said collection of antibodies or functional fragments thereof comprises germline protein sequences of at least two different germline protein pairs, and
wherein said germline protein pair is encoded by a germline gene pair.

In some embodiments, the present invention comprises a collection synthetic antibodies or functional fragments thereof, wherein said variable heavy chain and variable light chain framework regions consist essentially of germline protein sequences of the germline protein pairs comprising the following properties: i) a relative display rate in Fab format comprising a value within the top 75% of Fabs sampled;
ii) an expression level in Fab format of at least 0.4 as compared to Fab VH1-69 VLA_Vl1-40 AYA;
iii) thermal stability at 60° C. or more for at least 45 minutes in Fab format;
iv) stability in bovine or mouse serum in Fab format for greater than ten days at 37° C.;
v) an expression level in IgG format of at least 0.4 as compared to MOR03080; and
vi) stability in bovine serum in IgG format for fourteen days at 37° C.

In some embodiments, the present invention comprises a collection of synthetic antibodies or functional fragments thereof, wherein said variable heavy chain and variable light chain framework regions consist of germline protein sequences of the germline protein pairs comprising the following properties: i) a relative display rate in Fab format comprising a value within the top 75% of Fabs sampled;
ii) an expression level in Fab format of at least 0.4 as compared to Fab VH1-69 VLA_Vl1-40 AYA;
iii) thermal stability at 60° C. or more for at least 45 minutes in Fab format;
iv) stability in bovine or mouse serum in Fab format for greater than ten days at 37° C.;
v) an expression level in IgG format of at least 0.4 as compared to MOR03080; and
vi) stability in bovine serum in IgG format for fourteen days at 37° C.

In some embodiments, said germline gene pairs are present at a concentration of at least 0.05% in the human immune repertoire. In some embodiments, said germline gene pairs are present at a concentration of at least 0.23% in the human immune repertoire. In some embodiments, said germline gene pairs are present at a concentration of at least 0.51% in the human immune repertoire. In some embodiments, said germline gene pairs are present at a concentration of at least 0.07% in the naïve human immune repertoire. In some embodiments, said germline gene pairs are present at a concentration of at least 0.52% in the naïve human immune repertoire. In some embodiments, said germline gene pairs are present at a concentration of at least 0.88% in the naïve human immune repertoire. In some embodiments, said antibodies or functional fragments thereof comprise human sequences. In some embodiments, said collection of antibodies or functional fragments thereof comprises germline protein sequences of at least seventeen different germline protein pairs.

In some embodiments, said antibodies or functional fragments thereof comprise one or more complementarity determining regions comprising germline protein sequences. In some embodiments, said antibodies or functional fragments thereof comprise FR1, CDR1, FR2, CDR2, and FR3 regions comprising germline protein sequences. In some embodiments, said antibodies or functional fragments thereof comprise a FR4 region selected from the group consisting of: JH4, Jκ1, and Jλ2/3. In some embodiments, said antibodies or functional fragments thereof comprise a diversified HCDR3 region. In some embodiments, said antibodies or functional fragments thereof comprise a diversified LCDR3 region.

In some embodiments, the collection comprises $1 \times 10^4$ antibodies or functional fragments thereof. In some embodiments, said germline protein pairs comprise a relative display rate in Fab format comprising a value within the top 60% of Fabs sampled. In some embodiments, said germline protein pairs comprise an expression level in Fab format of at least 0.6 as compared to Fab VH1-69 VLA_Vl1-40 AYA. In some embodiments, said germline protein pairs comprise thermal stability at 70° C. or more for at least 45 minutes in Fab format. In some embodiments, said germline protein pairs comprise an expression level in IgG format of at least 0.6 as compared to MOR03080.

In some embodiments, the variable heavy and variable light chain framework regions comprise germline protein sequences of a germline protein pair selected from the group consisting of: IGHV3-23/IGKV1-5; IGHV3-23/IGKV3-20; IGHV4-39/IGKV3-15; IGHV3-23/IGKV3-15; IGHV4-39/IGKV1-39/1D-39; IGHV1-18/IGKV3-20; IGHV3-30/IGKV3-20; IGHV4-39/IGKV1-5; IGHV1-69/IGKV1-39/1D-39; IGHV5-51/IGLV1-40; IGHV4-39/IGKV3-20; IGHV3-23/IGLV 2-14; IGHV4-39/IGLV 3-21; IGHV3-23/IGKV1-39/1D-39; IGHV3-30/IGKV1-39/1D-39; IGHV1-69/IGKV3-20; IGHV3-48/IGKV3-20; IGHV1-2/IGKV3-20; IGHV3-30/IGKV4-1; IGHV5-51/IGLV 2-14; IGHV5-51/IGKV3-20; IGHV3-7/IGKV1-39/1D-39; IGHV3-7/IGKV1-5; IGHV3-15/IGKV3-20; IGHV4-39/IGLV 2-14; IGHV3-23/IGKV3-11; IGHV3-30/IGKV1-5; IGHV3-30/IGKV3-15; IGHV3-21/IGKV1-5; IGHV3-21/IGKV3-15; IGHV3-30/IGLV 1-51; IGHV3-21/IGLV 1-51; and IGHV1-69/IGKV3-11.

In some embodiments, said functional fragments of said antibodies are selected from the group consisting of Fab, F(ab')2, Fab', Fv, and scFv.

In some aspects, the present invention comprises a collection of nucleic acids encoding the disclosed collections of antibodies. In some aspects, the present invention comprises a vector comprising the nucleic acids encoding the disclosed collections of antibodies. In some aspects, the present invention comprises a recombinant host cell comprising the nucleic acids encoding the disclosed collections of antibodies. In some embodiments, the recombinant host cell is prokaryotic or eukaryotic. In some embodiments, the recombinant host cell is *E. coli* or mammalian.

In some aspects, the present invention comprises a collection of synthetic antibodies or functional fragments thereof, comprising variable heavy chain and variable light chain framework regions,
wherein said framework regions comprise germline protein sequences,
wherein said germline protein sequences comprise the following properties:
  i) four or less post translational modifications in the complementarity determining regions;
  ii) two or less methionines in the complementarity determining regions;
  iii) one or less unpaired cysteines;
  iv) one or less potential T-cell epitopes;
  v) an intermediate or low propensity for aggregation; and
  vi) an isoelectric point of at least 7.5; and
wherein said collection of antibodies or functional fragments thereof comprises at least two different variable heavy chain germline protein sequences,
wherein said germline protein sequence is encoded by a germline gene sequence.

In some embodiments, said variable heavy chain or variable light chain germline gene sequences are present at a concentration of at least 0.5% in the human immune repertoire. In some embodiments, said collection of antibodies or functional fragments thereof comprises at least five different variable heavy chain germline protein sequences. In some embodiments, said antibodies or functional fragments thereof comprise human sequences. In some embodiments, said variable heavy chain or variable light chain germline gene sequences are present at a concentration of at least 5.0% in the human immune repertoire. In some embodiments, said antibodies or functional fragments thereof comprise one or more complementarity determining regions comprising germline protein sequences. In some embodiments, said antibodies or functional fragments thereof comprise FR1, CDR1, FR2, CDR2, and FR3 comprising germline protein sequences. In some embodiments, said antibodies or functional fragments thereof comprise a FR4 region selected from the group consisting of: JH4, Jκ1, and Jλ2/3. In some embodiments, said antibodies or functional fragments thereof further comprise a diversified HCDR3 region. In some embodiments, said antibodies or functional fragments thereof further comprise a diversified LCDR3 region. In some embodiments, the collection comprises $1 \times 10^4$ antibodies or functional fragments thereof.

In some embodiments, said variable heavy chain germline protein sequences are selected from the group consisting of: IGHV3-23; IGHV3-30; IGHV4-39; IGHV4-34; IGHV4-59; IGHV1-69; IGHV5-51; IGHV3-7; IGHV1-18; IGHV3-48; IGHV3-15; IGHV3-21; IGHV1-2; IGHV3-33; IGHV4-31; IGHV3-53; IGHV3-11; IGHV3-9; IGHV4-4; IGHV1-46; IGHV3-74; IGHV1-24; IGHV4-61; IGHV1-8; IGHV1-3; IGHV3-49; IGHV3-43; IGHV4-28; IGHV3-64; and IGHV7-81.

In some embodiments, the variable κ light chain germline protein sequences are selected from the group consisting of: IGKV3-20; IGKV1-39/1D-39; IGKV1-5; IGKV3-15; IGKV4-1; IGKV3-11; IGKV2-28/2D-28; IGKV1-33/1D-33; IGKV2-30; IGKV1-9; IGKV1-17; IGKV1-27; IGKV1-8; IGKV1-16; IGKV1-6; IGKV1-12; IGKV2-29; IGKV1-13; IGKV1D-8; and IGKV2-24.

In some embodiments, the variable λ light chain germline protein sequences are selected from the group consisting of: IGLV2-14; IGLV1-40; IGLV1-44; IGLV1-51; IGLV2-23; IGLV3-21; IGLV1-47; IGLV3-1; IGLV2-11; IGLV2-8; IGLV6-57; IGLV3-25; IGLV7-46; IGLV1-36; IGLV7-43; IGLV9-49; IGLV4-69; IGLV2-18; IGLV3-10; and IGLV3-27.

In some aspects, the present invention comprises a method of producing the disclosed collections of synthetic antibodies or functional fragments thereof. In some embodiments, the steps of producing further comprises generating a collection of antibodies or functional fragments thereof comprising variable heavy chain and variable light chain framework regions,
wherein said variable heavy chain framework regions and variable light chain framework regions comprise germline protein sequences of a germline protein pair,
wherein said germline protein pair comprises the following properties:
  i) a relative display rate in Fab format comprising a value within the top 75% of Fabs sampled;
  ii) an expression level in Fab format of at least 0.4 as compared to Fab VH1-69 VLA_Vl1-40 AYA;
  iii) thermal stability at 60° C. or more for at least 45 minutes in Fab format;
  iv) stability in bovine or mouse serum in Fab format for greater than ten days at 37° C.;
  v) an expression level in IgG format of at least 0.4 as compared to MOR03080; and
  vi) stability in bovine serum in IgG format for fourteen days at 37° C.; and
wherein said collection of antibodies or functional fragments thereof comprises at least two different germline protein pairs.

In some embodiments, the step of producing further comprises the steps of
a) obtaining data comprising the variable heavy chain and variable light chain germline gene pairs present in the human immune repertoire;
b) identifying the variable heavy chain and variable light chain germline protein pairs comprising the following properties:
  i) a relative display rate in Fab format comprising a value within the top 75% of Fabs sampled;
  ii) an expression level in Fab format of at least 0.4 as compared to Fab pMx11_FH VH1-69 VLA_Vl1-40 AYA;
  iii) thermal stability at 60° C. or more for at least 45 minutes in Fab format;
  iv) stability in bovine or mouse serum in Fab format for greater than ten days at 37° C.;
  v) an expression level in IgG format of at least 0.4 as compared to MOR3080; and
  vi) stability in bovine serum in IgG format for fourteen days at 37° C.; and
c) generating a collection of antibodies or functional fragments thereof comprising the variable heavy chain and variable light chain germline protein sequences of the germline protein pairs identified in step b).

In some embodiments, step b) further comprises the steps of
ba) identifying the variable heavy chain and variable light chain germline gene pairs present at a concentration of at least 0.05% in the human immune repertoire;
bb) generating antibodies or functional fragments thereof comprising the germline protein pairs identified in step ba); and
bc) evaluating the following properties of said germline protein pairs:

i) relative display rate in Fab format;
ii) expression level in Fab format;
iii) thermal stability at 60° C. or more in Fab format;
iv) stability in bovine or mouse serum in Fab format for greater than ten days at 37° C.;
v) expression level in IgG format; and
vi) stability in bovine serum in IgG format for fourteen days at 37° C.

In some embodiments, step a) further comprises the following steps:
aa) isolating human B cells from a sample;
ab) generating cDNAs from the B cells;
ac) PCR amplifying the cDNAs from the B cells;
ad) sequencing the PCR products;
ae) identifying the germline genes of each PCR product.

In some embodiments, the step of generating a collection further comprises the following steps: ca) synthesizing the nucleic acids encoding the antibodies or functional fragments thereof; cb) cloning the nucleic acids into a vector; cc) expressing the antibodies or functional fragments thereof.

In some embodiments, said germline gene pairs are present at a concentration of at least 0.05% in the human immune repertoire. In some embodiments, said germline gene pairs are present at a concentration of at least 0.23% in the human immune repertoire. In some embodiments, said germline gene pairs are present at a concentration of at least 0.51% in the human immune repertoire. In some embodiments, said germline gene pairs are present at a concentration of at least 0.07% in the naïve human immune repertoire. In some embodiments, said germline gene pairs are present at a concentration of at least 0.52% in the naïve human immune repertoire. In some embodiments, said germline gene pairs are present at a concentration of at least 0.88% in the naïve human immune repertoire. In some embodiments, said antibodies or functional fragments thereof comprise human sequences. In some embodiments, said antibodies or functional fragments thereof comprise germline protein sequences of at least seventeen different germline protein pairs. In some embodiments, said antibodies or functional fragments thereof comprise one or more complementarity determining regions comprising germline protein sequences.

In some embodiments, said antibodies or functional fragments thereof comprise FR1, CDR1, FR2, CDR2, and FR3 comprising germline protein sequences. In some embodiments, said antibodies or functional fragments thereof comprise a FR4 region selected from the group consisting of: JH4, Jκ1, and Jλ2/3. In some embodiments, the antibodies or functional fragments thereof comprise a diversified HCDR3 region. In some embodiments, the antibodies or functional fragments thereof comprise a diversified LCDR3 region. In some embodiments, the collection comprises $1\times10^4$ antibodies or functional fragments thereof.

In some embodiments, said germline protein pairs comprise a relative display in Fab format comprising a value within the top 60% of Fabs sampled. In some embodiments, said germline protein pairs comprise an expression level in Fab format of at least 0.6 as compared to Fab VH1-69 VLA_Vl1-40 AYA. In some embodiments, said germline protein pairs comprise thermal stability at 70° C. or more for at least 45 minutes in Fab format. In some embodiments, said germline protein pairs comprise an expression level in IgG format of at least 0.6 as compared to MOR03080.

In some embodiments, the variable heavy and light chain framework regions comprise germline protein sequences of a germline protein pair selected from the group consisting of: IGHV3-23/IGKV1-5; IGHV3-23/IGKV3-20; IGHV4-39/IGKV3-15; IGHV3-23/IGKV3-15; IGHV4-59/IGKV1-39/1D-39; IGHV4-39/IGKV1-39/1D-39; IGHV4-59/IGKV3-20; IGHV1-18/IGKV3-20; IGHV3-30/IGKV3-20; IGHV4-39/IGKV1-5; IGHV1-69/IGKV1-39/1D-39; IGHV5-51/IGLV 1-40; IGHV3-23/IGKV4-1; IGHV4-39/IGKV3-20; IGHV3-23/IGLV 2-14; IGHV4-39/IGLV 3-21; IGHV3-23/IGKV1-39/1D-39; IGHV3-30/IGKV1-39/1D-39; IGHV3-30/IGKV3-11; IGHV1-69/IGKV3-20; IGHV3-48/IGKV3-20; IGHV1-2/IGKV3-20; IGHV3-30/IGKV4-1; IGHV5-51/IGLV 2-14; IGHV4-59/IGKV4-1; IGHV5-51/IGKV3-20; IGHV3-7/IGKV1-39/1D-39; IGHV3-7/IGKV1-5; IGHV3-15/IGKV3-20; IGHV4-39/IGLV 2-14; IGHV4-39/IGLV 2-8; IGHV3-23/IGKV3-11; IGHV3-30/IGKV1-5; IGHV3-30/IGKV3-15; IGHV3-21/IGKV1-5; IGHV3-21/IGKV3-15; IGHV3-30/IGLV 1-51; IGHV3-21/IGLV 1-51; IGHV3-53/IGLV 1-44; IGHV4-59/IGKV3-15; IGHV5-51/IGKV4-1; IGHV1-69/IGKV4-1; and IGHV1-69/IGKV3-11.

In some aspects, said functional fragments of said antibodies are selected from the group consisting of Fab, F(ab')2, Fab', Fv, and scFv.

In some aspects, the present invention comprises an isolated nucleic acid encoding a signal or leader sequence comprising a C-terminal restriction site. In some embodiments, the restriction site is NheI. In some embodiments, the signal or leader sequence comprises phoA or a human heavy chain leader sequence. In some embodiments, the restriction site is NdeI. In some embodiments, the signal sequence comprises ompA or a human kappa leader sequence.

In some aspects, the present invention comprises a vector comprising the nucleic acids encoding the signal or leader sequence comprising a C-terminal restriction site. In some aspects, the present invention comprises a host cell comprising the vector. In some embodiments, the host cell is prokaryotic or eukaryotic. In some embodiments, the host cell is *E. coli*. In some embodiments, the host cell is mammalian.

In some aspects, the present invention comprises an isolated antibody or functional fragment thereof, comprising a FR1, CDR1, FR2, CDR2, and FR3 comprising germline protein sequences of a germline protein pair, wherein the germline protein pair is selected from the group consisting of: IGHV3-23/IGKV1-5; IGHV3-23/IGKV3-20; IGHV4-39/IGKV3-15; IGHV3-23/IGKV3-15; IGHV4-39/IGKV1-39/1D-39; IGHV1-18/IGKV3-20; IGHV3-30/IGKV3-20; IGHV4-39/IGKV1-5; IGHV1-69/IGKV1-39/1D-39; IGHV5-51/IGLV 1-40; IGHV4-39/IGKV3-20; IGHV3-23/IGLV 2-14; IGHV4-39/IGLV 3-21; IGHV3-23/IGKV1-39/1D-39; IGHV3-30/IGKV1-39/1D-39; IGHV1-69/IGKV3-20; IGHV3-48/IGKV3-20; IGHV1-2/IGKV3-20; IGHV3-30/IGKV4-1; IGHV5-51/IGLV 2-14; IGHV5-51/IGKV3-20; IGHV3-7/IGKV1-39/1D-39; IGHV3-7/IGKV1-5; IGHV3-15/IGKV3-20; IGHV4-39/IGLV 2-14; IGHV3-23/IGKV3-11; IGHV3-30/IGKV1-5; IGHV3-30/IGKV3-15; IGHV3-21/IGKV1-5; IGHV3-21/IGKV3-15; IGHV3-30/IGLV 1-51; IGHV3-21/IGLV 1-51; and IGHV1-69/I.

In one aspect, the present disclosure describes collections of antibodies comprising variable heavy and light chain framework regions comprising germline sequences, specifically FR1. It is expected that having germline framework regions shall lower the immunogenicity risk of the antibodies when administered to patients. Restriction sites, however, must be used in order to enable standard cloning of the nucleic acids encoding the collections of antibodies into display and/or expression vectors so that the antibodies can be screened against immunogens. In the past, restriction sites utilized for cloning were often located within the framework regions, thus modifying the nucleic acid sequence away from germline. In order to ensure that at least the framework 1 (FR1) region of each of the antibodies of the present disclosure maintain a germline sequence, there should not be any non-naturally occurring restriction sites within FR1. Therefore, an aspect of the present disclosure is the incorporation of a restriction site within the C-terminus of prokaryotic signal sequences and a human leader sequence, specifically within the three C-terminal residues. Additionally, the signal sequence and leader sequence comprising a restriction site must be functional and allow for good display and expression levels of the antibodies or fragments thereof in both prokaryotic and mammalian expression systems.

In some aspects, the present invention comprises an isolated nucleic acid encoding a signal or leader sequence comprising a C-terminal restriction site. In some embodiments the restriction site is NheI or NdeI. In some embodiments the signal or leader sequence comprises phoA or a human heavy chain leader sequence. In some embodiments the signal or leader sequence comprises ompA or a human kappa leader sequence. In some aspects, the present invention comprises a vector comprising the isolated nucleic acid encoding a signal or leader sequence comprising a C-terminal restriction site. In some aspects, the present invention comprises a host cell comprising the isolated nucleic acid encoding a signal or leader sequence comprising a C-terminal restriction site or the vector comprising the isolated nucleic acid encoding a signal or leader sequence comprising a C-terminal restriction site. In some embodiments, the host cell according is prokaryotic, e.g. E. coli, or eukaryotic, e.g. mammalian.

The present disclosure is the first to disclose the concept that the VH and VL class pairs that are most prevalent in a naïve human immune repertoire likely have preferred characteristics, such as, greater stability, and lower immunogenicity. The present disclosure is also first to incorporate this concept into collection design and utilize total gene synthesis to generate such collections. The present disclosure enables methods of identifying the VH and VL class pairs in the naïve and antigen-experienced human immune repertoires, determining the VH and VL class pairs that are most prevalent and then generating collections comprising those VH and VL class pairs. More specifically, the collections of the present disclosure comprise the most prevalent and/or preferred VH and VL class pairings with highly diversified CDRs. This strategy increases the probability that the collections comprise antibodies or fragments thereof against any immunogen that are stable, have low immunogenicity and high affinity for the specific antigen. The result is a dramatically increased probability that the collections comprise highly efficacious antibodies or fragments thereof against any immunogen that can be used for therapeutic or diagnostic purposes.

Accordingly, nucleic acid sequences (or a selected portion thereof) encoding antibodies or fragments thereof obtained from the naïve B cells from human hosts can be sequenced. From these sequence data, germline family VH/VL chain class pairings represented in the immune repertoire can be identified. Based upon certain criteria, such as prevalence and/or favorable biophysical properties, the heavy and light chain class pairs are selected for incorporation into collections. The collections can be then synthesized by gene synthesis. In some embodiments, the synthetic collections comprise substantially germline VH and VL framework regions, wherein the CDRs are diversified, or only one CDR of a VH and/or VL is diversified.

Using the DNA sequences obtained from naïve B cells of human hosts as a "template," the present disclosure enables methods of identifying the most prevalent VH and VL pairs. Once, the relative abundance of VH and VL class pairings have been elucidated, a highly diverse collection of antibodies or fragments thereof comprising the most prevalent and/or preferred VH and VL class pairings can be generated. Using this information, the skilled worker can generate a high degree of diversity without sacrificing the key benefits attributable to the most prevalent and/or preferred VH and VL class pair combinations. Prior to the present disclosure, no one has elucidated the most prevalent and/or preferred VH and VL class pairings or attempted to harness that knowledge into library generation techniques. This approach, therefore, provides comprehensive collections of nucleic acids encoding antibodies or fragments thereof that represent the naïve, human immune system.

Utilizing the collection design and display methods disclosed herein, large diversity collections can be generated, as some embodiments comprise collections of at least $1 \times 10^{10}$ members.

In some aspects, the present disclosure enables vectors and host cells comprising the disclosed collections of nucleic acids.

In some aspects, the present disclosure enables methods of producing such collections.

In some embodiments, the naïve DNA sequences representative of the human immune repertoire are obtained in a separate step, and stored in a database; therefore, the collection design can be readily modified, optimized and customized in silico, allowing for a level of customization that can typically be realized in a synthetic library.

In some aspects, the present disclosure enables methods of identifying antibodies or fragments thereof using the disclosed collections.

In some aspects, the present invention is directed to collections or libraries encoding antibodies, or fragments thereof, comprising the germline protein sequences encoded by the VH and VL germline families and/or genes that are abundant and/or preferred in the immune repertoire. In some embodiments, the nucleic acids encoding antibodies or fragments thereof are germline, substantially germline, or codon-optimized variants thereof. Such collections or libraries may comprise the VH and VL germline families and/or genes having advantageous biophysical properties, including highly displayed on phage; high expression in E. coli in Fab format; high expression in mammalian cells in IgG format; high thermal stability; serum stability; low tendency for aggregation (i.e. high solubility); and low risk of immunogenicity. In some embodiments, the collections or libraries may comprise the VH and VL germline families and/or genes that exist in the naïve human immune repertoire. Related embodiments include methods of making and using such collections.

In some aspects, the present invention is directed to collections or libraries encoding antibodies, or fragments thereof, comprising the germline protein sequences encoded by the VH and VL germline families and/or genes that are abundant and/or preferred in the immune repertoire along with the VH/VL class pairs that are abundant and/or preferred in the immune repertoire. In some embodiments, the nucleic acids encoding antibodies or fragments thereof are germline, substantially germline, or codon-optimized variants thereof. Such collections or libraries may comprise the germline protein sequences encoded by the VH and VL germline families and/or genes and/or the VH/VL class pairs having advantageous biophysical properties, including highly displayed on phage; high expression in E. coli in Fab format; high expression in mammalian cells in IgG format; high thermal stability; serum stability; low tendency for aggregation (i.e. high solubility); and low risk of immunogenicity. In some embodiments, the collections or libraries may comprise the germline protein sequences encoded by the VH and VL germline families and/or genes and/or the VH/VL class pairs that exist in the naïve human immune repertoire. Related embodiments include methods of making and using such collections.

Accordingly, the present invention includes collections of nucleic acids encoding antibodies or fragments thereof substantially representative of an immune repertoire, wherein each antibody or fragment thereof comprises a VH/VL class pair, wherein substantially representative of an immune repertoire is such that each VH/VL class pair present in the collection is a VH/VL class pair present at a concentration of at least 0.05%, at least 1%, or at least 2% of the VH/VL class pairs in the immune repertoire. The immune repertoire may be of an individual, or population, and may be naïve. Such an immune repertoire may be determined as that of the VH/VL class pairs in at least $1\times10^5$ B cells from an individual; the VH/VL class pairs in at least $1\times10^5$ B cells from a population of individuals; or the VH/VL class pairs present in at least $1\times10^5$ antibodies, for example. The immune repertoire may be that of naïve B cells or of antigen experienced B cells. The individual or population may be human. The immune repertoire may be determined by analyzing publically available databases and/or literature.

In some embodiments, the nucleic acids encoding antibodies or fragments thereof are synthetic, such as, generated by total gene synthesis. In related embodiments, the nucleic acids are germline sequences; substantially germline sequences; or codon optimized variants of germline or substantially germline sequences. In some embodiments at least one of the CDRs is highly diversified.

In some embodiments, the collection of the present disclosure comprises antibodies or fragments thereof wherein FR1, FR2 and FR3 of both the VH and VL comprise the germline protein sequences of the VH and VL class pairs having preferred characteristics. Most preferably, the collection of the present disclosure comprises antibodies or fragments thereof wherein FR1, FR2 and FR3 of both the VH and VL comprise the germline protein sequences of the VH and VL class pairs having preferred characteristics, wherein the CDR3 of both VH and VL are highly diversified.

In related embodiments, the collection of said nucleic acids encoding antibodies or fragments thereof is cloned into a vector. Suitable vectors are known in the art, and include displays vector, such as phage display vectors, plasmid vectors, a phagemid vectors, expression vectors, including bacterial or mammalian expression vector. In further related embodiments, the collection, or the collection cloned into vectors, are transformed into host cells. Thus, the invention includes a collection of host cells. Suitable host cells include prokaryotic host cells (such as *E. coli*) and eukaryotic host cells (such as mammalian host cells).

In another embodiment, the invention is a database comprising VH/VL class pairs from ~1345 naïve human B cells or from publically available sequences on a readable medium. Such a database is useful for the design and construction of the collection and libraries of the invention.

The invention also includes methods of producing a collection of nucleic acids encoding antibodies or fragments thereof substantially representative of an immune repertoire. The immune repertoire may be that of naïve B cells or of antigen experienced B cells of a human or humans. Such a method may comprise the following steps: (a) identifying VH/VL class pairs present at a concentration of at least 0.05%, at least 1%, or at least 2% of the VH/VL class pairs in the immune repertoire; (b) synthesizing a collection of nucleic acids encoding antibodies or fragments thereof comprising VH/VL class pairs present at a concentration of at least 0.05%, at least 1%, or at least 2% of the VH/VL class pairs in the immune repertoire.

The step of identifying may be carried out in different ways. For example, identifying VH/VL class pairs may comprise isolating naive B-cells from one or more human hosts and determining the VH/VL class pairs in each B-cell by isolating and sequencing the DNA, mRNA or cDNA encoding the VH/VL class pairs, or by probing with one or more nucleic acid probes specific for each VH and VL, and then analyzing the VH/VL class pairs. In an alternative or complementary embodiment, the VH/VL class pairs may be determined from pre-existing databases, such as databases of antibody sequences. In an alternative or complementary embodiment, the VH/VL class pairs may be identified from literature. Thus, in one embodiment, the invention comprises obtaining antibody nucleic acid sequences (either pre-existing or generated de novo), determining the VH/VL class pairs by sequence alignment, and collating such sequences from to identify VH/VL class pairs present in the immune repertoire.

In some embodiments, the method is used to create collections in which the majority of members have favorable biophysical properties that facilitate production and expression of antibodies or fragments thereof (such as on phage, or from cells), and produce antibodies that are soluble, thermally stable. More particularly, such properties include: (i) efficiently displayed on phage; (ii) efficiently displayed on mammalian cells (iii) well expressed in *E. coli* in Fab format; (iv) well expressed in mammalian cells in an IgG format; (v) thermal stability; (vi) solubility; and (vii) low immunogenicity. By determining the VH/VL class pairs having some, or all of these properties, one may then construct a collection in which the majority of members have such biophysical properties, such as by synthesizing only those nucleic acids with such properties. Accordingly, the invention includes such a collection, and methods of making such a collection.

In some embodiments, the nucleic acids synthesized are germline, substantially germline, or codon-optimized variants thereof. Variation may be introduced into at least one complementarity determining region (CDR). Any CDR is appropriate, especially CDR3. Preferably, the sequence variation added to the CDR is limited to sequences in frame and free from cysteines and stop codons, thus ensuring that all members of the library are correctly expressed.

Once the nucleic acids have been synthesized, they may be cloned into a vector (such as a display vector, a phage display vector; a phagemid vector; or a mammalian expression vector), and may be transformed into a host cell. Suitable host cells include prokaryotic host cells (e.g. *E. coli*) and eukaryotic host cells (e.g. mammalian host cells).

In further embodiments, the invention provides methods of identifying an antibody specific for an immunogen. Such a method may comprise, in one embodiment, identifying VH/VL class pairs present at a concentration of at least 0.05%, at least 1%, or at least 2% of the VH/VL class pairs in the immune repertoire; synthesizing a collection of nucleic acids encoding antibodies or fragments thereof comprising VH/VL class pairs present at a concentration of at least 0.05%, at least 1%, or at least 2% of the VH/VL class pairs in the immune repertoire; displaying or expressing the antibody or fragment thereof from the collection; screening the collection against a specific immunogen; and selecting at least one antibody or fragment thereof specific for said immunogen. Because the methods and collections of the invention may be constructed with regard to favorable biophysical properties, the present invention is particularly useful for identifying an antibody or antibody fragment thereof for the treatment of a disease or condition, by making a collection of nucleic acids encoding antibodies or fragments thereof with such favorable properties, and screening against a specific immunogen to identify antibodies binding to such an immunogen.

In some aspects, the invention is directed to collections or libraries of antibodies or fragments thereof comprising VH/VL pairs. In some embodiments, the collections or libraries of antibodies or fragments thereof comprise the germline protein sequences encoded by the VH and VL germline families and/or genes that are abundant in an immune repertoire. In some embodiments, the invention is directed to collections or libraries of antibodies or fragments thereof comprising the germline protein sequences encoded by the VH and VL germline families and/or genes having certain favorable biophysical characteristics. In some embodiments, the VH and VL germline families and/or genes are those that naturally occur in the immune repertoire, and are among the more abundant or prevalent in the repertoire. In some embodiments, the collections or libraries of antibodies or fragments thereof comprise the germline protein sequences encoded by the VH and VL germline families and/or genes. In some embodiments, the collections or libraries of antibodies or fragments thereof comprise the framework regions and/or CDR regions from the germline, substantially germline, or codon optimized the VH and VL germline families and/or genes. In some embodiments, the collections or libraries of antibodies or fragments thereof comprise the germline protein sequences encoded by the VH and VL germline families and/or genes that are synthetic, being constructed by total gene synthesis. In some embodiments, the collections or libraries of antibodies or fragments thereof comprise portions of the VH and VL germline families and/or genes that are synthetic, being constructed by total gene synthesis. In some embodiments, the collections or libraries of antibodies or fragments thereof comprise the germline protein sequences encoded by the VH and VL germline families and/or genes having favorable biophysical properties that aid in the screening and further development of the antibodies, especially in the therapeutic context. The favorable biophysical properties include, but are not limited to (i) they are well displayed on phage in the Fab-format, (ii) they are well displayed on mammalian cells in the IgG format (iii) they are expressed in high amounts in Fab-format, e.g., in E. Coli, and IgG formats, e.g., in mammalian cells, (iv) are thermodynamically stable; (v) have high serum stability, (vi) have a low tendency for aggregation (i.e. high solubility); and (vii) have a low risk of immunogenicity.

In other aspects, the collections of the present disclosure comprise antibodies or fragments thereof comprising the germline protein sequences of the preferred VH and VL class pairs. The collections of the present disclosure preferably comprise antibodies or fragments thereof, wherein one or more framework regions comprise the germline protein sequences encoded by the VH and VL class pairs having preferred characteristics, especially wherein FR1, FR2 and FR3 of both the VH and VL comprise the germline protein sequences of the VH and VL class pairs having preferred characteristics. The CDRs may be highly diversified. Preferably, the CDR3 of both VH and VL are highly diversified. In some embodiments, the CDR1 and CDR2 of the VH and/or VL are germline or substantially germline in sequence.

This strategy increases the probability that the collections of the present disclosure comprise antibodies or fragments thereof against any immunogen that are able to be developed for therapeutic use, as the majority of the antibodies or fragments thereof present in the collections comprise the germline sequences of the VH and VL pairs having the above preferred characteristics. The selected antibodies also will have low immunogenicity and high affinity for the specific antigen. The result is a dramatically increased probability that antibodies or fragments thereof that are selected from the disclosed collections are highly efficacious against any immunogen and can be developed for therapeutic or diagnostic purposes.

Such collections overcome many of the problems of the prior art. For example, in a cognate library derived from B cells the VH and VL class pairings present in the library are dependent upon the class pairings present in the sample. If a large enough sample of B cells is taken, each of the approximately 50 VH and 50 VL class pairing combinations (~2500) will be present. The presence of so many VH and VL class pairs can be analogized to background noise. It may be desirable to generate libraries of large diversity comprising only the most prevalent VH and VL class pairs, but with a cognate library approach, this is not possible.

In addition, in some embodiments, the DNA sequences from which the collections are based are obtained from samples of naïve B cells that are antigen inexperienced, therefore, the expressed members are not biased towards a particular immunogen and the collections can be used to screen against any immunogen.

Accordingly, nucleic acid sequences (or a selected portion thereof) encoding antibodies or fragments thereof obtained from the naïve (antigen inexperienced) B cells from human hosts can be sequenced. From these sequence data, germline family VH/VL chain class pairings predominantly represented in the immune repertoire can be identified. Based upon certain criteria, such as prevalence, the heavy and light chain class pairs are selected for incorporation into collections. The collections can be then synthesized by gene synthesis. In some embodiments, the synthetic collections comprise substantially germline VH and VL framework regions, wherein the CDRs are diversified.

Using the DNA sequences obtained from, for example, naïve (antigen inexperienced) B cells from human hosts or from publically available databases or literature as a "template," the present disclosure enables methods of identifying the most prevalent VH and VL germline families and/or genes and/or class pairs. Once, the relative abundance of the VH and VL germline families and/or genes and/or class pairs have been elucidated, antibodies or fragments thereof comprising the germline protein sequences encoded by the VH and VL germline families and/or genes and/or class pairs can be tested for the following preferred characteristics: (i) they are well displayed on phage in the Fab-format, (ii) they are expressed in high amounts and in soluble form in Fab-format, and IgG formats, (iii) and they are thermodynamically stable. By testing the germline protein sequences encoded by the most prevalent VH and VL germline families and/or genes and/or class pairs, those having preferred characteristics can be identified. Using this information, the skilled worker can generate a high degree of diversity without sacrificing the key benefits attributable to the most prevalent VH and VL germline families and/or genes and/or class pair combinations.

Utilizing the collection design and display methods disclosed herein, large diversity collections can be generated, as some embodiments comprise collections of at least $1\times10^{10}$ members.

The present disclosure relates generally to synthetic antibody collections comprising the VH and VL class pair having the most preferred characteristics. In some embodiments, the collections comprise the germline protein sequences encoded by the VH and VL families represented by the class pair.

The present disclosure relates generally to synthetic antibody collections comprising one or more VH and VL class pairs having the preferred characteristics. In some aspects, the collections comprise the germline protein sequences encoded by the VH and VL families represented by the class pair.

In some aspect, the present disclosure enables methods of identifying the VH and VL germline genes that are most prevalent in an immune repertoire, testing the antibodies having the sequences of the most prevalent VH and VL germline genes to identify the VH and VL germline genes having preferred characteristics and then generating collections comprising the preferred VH and VL classes. The present disclosure enables methods of identifying the VH and VL class pairs in the human immune repertoire, which may be naïve, determining the VH and VL class pairs that are most prevalent, testing the VH and VL class pairs to identify VH and VL class pairs having preferred characteristics and then generating collections comprising the preferred VH and VL class pairs and/or antibodies derived from the preferred VH and VL germline genes. Once the VH and VL's and/or VH and VL class pairs are identified then their respective germline sequences are identified, so that the germline sequences can be incorporated into the collection design.

In some aspects, the present disclosure enables vectors and host cells comprising the disclosed collections of nucleic acids.

In some aspects, the present disclosure enables methods of producing such collections.

In some embodiments, the DNA sequences representative of the human immune repertoire are obtained in a separate step, and stored in a database; therefore, the collection design can be readily modified, optimized and customized in silico, allowing for a level of customization that can typically be realized in a synthetic library.

In some aspects, the present disclosure enables methods of identifying antibodies or fragments thereof using the disclosed collections.

Methods, Nucleic Acids, Proteins, Vector, Host Cell

In one aspect, the present disclosure enables collections of nucleic acids produced by total gene synthesis. Gene synthesis technology has advanced considerably in the recent years and very large collections of nucleic acids can be generated. The following companies provide such synthesis services: Entelechon (Regensburg, Germany), Geneart (Regensburg, Germany) and Sloning Biotechnology (Puchheim, Germany). In order for a gene synthesis company to generate a collection, the sequences of each member of the collection may be provided.

In some embodiments, the present disclosure enables a collection of synthetic nucleic acids encoding antibodies or fragments thereof comprising VH and VL class pairs present at a concentration of at least 0.05% of the VH and VL class pairs existing in a sample of at least $1\times10^5$ B cells. In other embodiments, the collections of the present disclosure comprise VH and VL class pairs present at a concentration of at least 1% of the VH and VL class pairs existing in a sample of at least $1\times10^5$ B cells. In other embodiments, the collections of the present disclosure comprise VH and VL class pairs present at a concentration of at least 1.5% of the VH and VL class pairs existing in a sample of at least $1\times10^5$ B cells. In other embodiments, the collections of the present disclosure comprise VH and VL class pairs present at a concentration of at least 2% of the VH and VL class pairs existing in a sample of at least $1\times10^5$ B cells. In other embodiments, the collections of the present disclosure comprise VH and VL class pairs present at a concentration of at least 3% of the VH and VL class pairs existing in a sample of at least $1\times10^5$ B cells. In other embodiments, the collections of the present disclosure comprise VH and VL class pairs present at a concentration of at least 4% of the VH and VL class pairs existing in a sample of at least $1\times10^5$ B cells. In other embodiments, the collections of the present disclosure comprise VH and VL class pairs present at a concentration of at least 5% of the VH and VL class pairs existing in a sample of at least $1\times10^5$ B cells.

In some embodiments, the present disclosure enables collections, wherein the VH and VL class pairs are identified from B cells isolated from a human host. In some embodiments, the B cells are naive. In some embodiments, the collections of nucleic acids encode antibodies or fragments thereof comprising germline VH and VL framework regions. In a preferred embodiment collections of nucleic acids are synthesized to include germline VH and VL framework regions with diversified CDRs. Germline frameworks regions are desirable as antibodies or fragments thereof comprising germline framework regions are not likely to be immunogenic.

Utilizing the collection design and display methods disclosed herein, large diversity collections can be generated, as some embodiments comprise collections of at least $1\times10^4$ nucleic acid sequences, some embodiments comprise collections of at least $1\times10^5$, $10^6$, $10^7$, $10^8$, $10^9$, $10^{10}$ $10^{11}$ or $10^{12}$ nucleic acid sequences. Such diversity is generated by synthesizing collections comprising members comprising the prevalent VH and VL class pairs with diversified CDRs.

The collections of the present disclosure are designed from sequence data substantially representative of an immune repertoire. In some embodiments, the sequence data is obtained by searching publically available immunoglobulin sequence listings. For example, NCBI can be searched using Ig-Blast or publically available literature can be searched. As of 2005 the database contained at least 25,000 rearranged human antibody sequences in FASTA format. Of the 22,500 entries, 13,235 represented VH sequences, 1,506 represented Vκ and 2,259 represented Vλ. From the sequences the VH, Vκ and Vλ can be categorized into their respective germline families and/or genes. As some of Ig-Blast includes full antibody sequences, the correct germline families and/or genes of each VH and VL domain class pairings can be determined from the database sequences. If this approach is utilized, the prominence of each VH and VL germline family and/or gene, and/or the germline family and/or gene of each VH and VL domain class pair can readily be determined by one of skill in the art. The selection of which VH and VL's and/or VH and VL class pairs to incorporate into the library can be accomplished in a number of ways. In some embodiments, the VH and VL's of highest prevalence are selected for incorporation into the collection or library. In some embodiments, the VH and VL's having favorable biophysical properties are selected for incorporation into the collection or library. In some embodiments, the VH and VL class pairs having the highest prevalence are selected for incorporation into the collection or library. In some embodiments, the VH and VL class pairs having favorable biophysical properties are selected for incorporation into the collection or library. In some embodiments, both the VH and VL's having the highest prevalence and/or favorable biophysical properties and/or the VH and VL class pairs having the highest prevalence and/or VH and VL class pairs having favorable biophysical properties are selected for incorporation into the collection or library.

One of the drawbacks of this approach is that the publically available databases are often populated with sequences of antibodies generated against specific immunogens, therefore the sequences are biased. In addition, in most of the databases the sequences of the heavy and light chain are not linked, therefore the VH and VL class pairing cannot be identified.

In some embodiments, the nucleic acid sequences are obtained by harvesting B-cells from one or more hosts; isolating the DNA from the B-cells and preferably sequencing the DNA. Preferably, the B cells are naïve. Samples of B cells are harvested from one or more human donors. The following is a technique that can be used to isolate B-cells. Resting B lymphocytes (B cells) are isolated from spleens by using negative selection against other cell types with anti-CD43 and anti-Mac-1/CD11b monoclonal antibodies, e.g. via magnetic microbeads. This strategy depletes non-B cells from a mixed population of splenocytes and relies on the fact that most mature leukocytes, with the exception of resting splenic B cells, express CD43 (in fact, expression of CD43 has been demonstrated on immature B cells, plasma cells, and some mature cells, in addition to granulocytes, monocytes, macrophages, platelets, natural killer (NK) cells, thymocytes, and peripheral CD8+ and most CD4+ T cells). Anti-Mac-1/CD11b microbeads are included in the negative selection to improve the removal of myeloid cells. B-cell isolation may be automated by using an AutoMACS automatic magnetic bead cell sorter (Miltenyi Biotec). As assessed by fluorescence analysis of B220+ cells, such isolation routinely yields approximately 4×10e7 B cells per spleen that are >95% pure. See also Miltenyi S, Muller W, Weichel W, and Radbruch A. (1990) Cytometry 11(2), 231-238.

The number of B cells harvested substantially represents the immune repertoire. In some embodiments at least $1 \times 10^4$ B cells are isolated from a host, more preferably at least $10^5$ B-cells; more preferably at least $10^6$ B cells; most preferably $10^7$ B cells are isolated from a host.

The DNA encoding antibodies and fragments thereof from each B cell are isolated, and amplified e.g., the heavy and light chain are linked by a PCR reaction. The DNA is preferably sequenced. The DNA sequenced may be cDNA generated from B cell mRNA. mRNA extraction from eukaryotic cells, such as B cells, is a well know technological procedure. Numerous protocols exist and commercial kits are available. Such as the PolyATtract® mRNA Isolation System (Promega, Madison, Wis., USA) or various RNeasy and Oligotex DirectmRNA kits (both from Qiagen, Hilden, Germany). Many of these techniques make use of the polyA tail of the eukaryotic mRNA, e.g. via affinity purification to oligo (dT) matrices, such as oligo (dT) cellulose.

cDNA can be selectively amplified from the isolated mRNA via reverse transcription using specific primers, followed by conventional PCR. Specific primers are used to amplify variable heavy and light chain domain nucleic acids. See *Cancer Surv.* 1997; 30:21-44, *J. Clin. Pathol.* 1994; 47:493-6, *J. Clin. Pathol.* 1990; 43:888-90 or *Mol. Pathol.* 2002 April; 55(2): 98-101.

The DNA coding for both the variable and light chain domains from one B cell are maintained together so that the variable domain heavy and light chain class pairing can be identified. Techniques for the isolation of nucleic acids encoding variable domain pairings from individual B cells are well known in the art. See for example, WO01/92291; WO92/15678; WO93/03151, WO2005/042774; Mullinax R L et al., 1992 *Biotechniques* 12:6 864-868; Chapal, N. et al. 1997 *Biotechniques* 23, 518-524, Embleton M J et al., 1992 *Nucleic Acids Res.* 20:15, 3831-3837; Coronella, J. A. et al. 2000 *Nucleic Acids Res.* 28:20, E85; Thirion S et al., 1996 *European Journal of Cancer Prevention* 5:6 507-511; and Wang, X et al. 2000 *J. Immunol. Methods* 20, 217-225.

These techniques can be used alone or in combination with other methods. For example, if a variable heavy and light chain domain sequences of a large sample are not successfully identified together from their respective B cells, then the following method can be completed, in order to identify the correct variable heavy and variable light domain class pairs. Single-cell PCR of each individual B cell is completed.

Preferably, the DNA from each of the B cells is sequenced. Various companies exist which are able to sequence entire genomes, such as Helicos BioSciences Corporation (Cambridge, Mass., USA). With its True Single Molecule Sequencing™ technology, Helicos is able to directly sequence single molecules of DNA or RNA at high speed and efficiency. Other companies able to perform similar sequence endeavors include Illumina (San Diego, Calif., USA; Solexa system) and Roche (Basel, CH; 454 system). No cloning steps are required prior to sequencing.

In another aspect, the disclosure enables methods of identifying the germline family of the heavy and light chain variable domain pairs present in the immune repertoire. All antibodies or fragments thereof can be traced back to their germline family using methods known to one of skill in the art. By analyzing the sequence of a nucleic acid encoding an antibody or fragment thereof, the germline family of both the VH and VL can be determined by methods known to one of skill in the art. For example, Wildt et. al, (1999) sampled B cells from 3 patients and identified 365 VH and VL class pairings. The RNA from each B cell was used for cDNA synthesis and the cDNA encoding the VH and VL regions was PCR amplified and sequenced. As shown in FIG. 1 of Wildt, certain VH and VLs classes paired more frequently than others, for example, VH3-8 with Vκ3-1, Vκ3-19, Vκ4-1, Vλ2-3, or Vλ1-2, and VH3-9 with Vκ3-1, Vκ3-3 or Vλ1-5.

In another aspect, the disclosure enables methods of designing diversified complementarity determining regions prior to synthesizing the collection. CDRs can be designed by methods well known in the art including those disclosed in Knappik et al. 2000; WO 97/08320.

In another aspect, the disclosure enables methods of selecting the variable domain class pairings desired to be included in the collections of nucleic acids encoding antibodies or fragments thereof. In some embodiments, a collection of nucleic acids is synthesized comprising all of the VH and VL domain class pairs identified by the disclosed methods.

In addition, the prevalence of the VH and VL class pairs may be determined by various statistical tests. In its easiest form the individual VH and VL class pairs are simply counted. More sophisticated statistical tests may take various other parameters into account. By way of non-limiting examples, the following statistical tests and references may guide as examples of the numerous approaches that have been made in such, or similar, analysis: Bayesian Shrinkage Estimation (see e.g. Biometrics 59 (2003): 476-486), DADA (Digital Analysis of cDNA Abundance, see e.g. BMC Genomics 2002, 3:7), linear modeling (Pacific Symposium on Biocomputing, 1999, 4:41-52) and various clustering methods (BMC Bioinformatics 2006, 7:397, Fourth IEEE International Conference on Data Mining (ICDM'04), pp. 403-406).

In other aspects, the present disclosure enables a collection of vectors comprising the collections of nucleic acids encoding antibodies or fragments thereof. In some embodiments, the vectors comprise expression vectors, display vectors, phage display vectors, or phagemid vectors.

Eukaryotic expression vectors are well known in the art and also are available commercially. Typically, such vectors are provided containing convenient restriction sites for insertion of the desired DNA. Examples of such vectors include pSVL and pKSV-10, pBPV-1/PML2d, and pTDT1 (ATCC, No. 31255).

In other aspects, the present disclosure enables a collection of host cells transformed with the disclosed collection of vectors. Host cells can be either prokaryotic or eukaryotic. Bacterial cells are preferred prokaryotic host cells and typically are a strain of *Escherichia coli* (*E. coli*) such as, for example, the *E. coli* strain DH5 available from Bethesda Research Laboratories, Inc., Bethesda, Md. Preferred eukaryotic host cells include yeast and mammalian cells including murine and rodents, preferably vertebrate cells such as those from a mouse, rat, monkey or human cell line.

The introduction of vectors into host cells may be accomplished by a number of transformation or transfection methods known to those skilled in the art, including calcium phosphate precipitation, electroporation, microinjection, liposome fusion, RBC ghost fusion, protoplast fusion, viral infection and the like. The production of monoclonal full-length antibodies, Fab fragments, Fv fragments and scFv fragments is well known.

Transformation of appropriate cell hosts with a recombinant DNA molecule is accomplished by methods that typically depend on the type of vector used. With regard to transformation of prokaryotic host cells, see, for example, Cohen et al., *Proceedings National Academy of Science*, USA, Vol. 69, P. 2110 (1972); and Maniatis et al., *Molecular Cloning, a Laboratory Manual*, Cold spring Harbor Laboratory, Cold Spring Harbor, N.Y. (1982). With regard to the transformation of vertebrate cells with retroviral vectors containing rDNAs, see for example, Sorge et al., *Mol. Cell. Biol.*, 4:1730-1737 (1984); Graham et al., *Virol.*, 52:456 (1973); and Wigler et al., *Proceedings National Academy of Sciences, USA*, Vol. 76, P. 1373-1376 (1979).

In another aspect, the disclosure enables a kit, or database, comprising sequence data illustrating nucleic acids encoding antibodies or fragments thereof comprising nucleic acids present in a sample of at least $1 \times 10^5$ naïve human B cells, wherein said sequence data are on a readable medium.

In another aspect, the disclosure enables a method of producing a collection of synthetic nucleic acids encoding antibodies or fragments thereof, comprising synthesizing a collection of nucleic acids encoding antibodies or fragments thereof comprising VH and VL class pairs present in a concentration of at least 0.05% of the VH and VL class pairs existing in a sample of at least 2500 B cells. In some embodiments, the disclosure enables a method of producing a collection of nucleic acids encoding antibodies or fragments thereof substantially representative of an immune repertoire comprising: (a) identifying VH/VL class pairs present in a concentration of at least 0.05%, at least 1%, or at least 2% of the VH/VL class pairs in the immune repertoire; (b) synthesizing a collection of nucleic acids encoding antibodies or fragments thereof comprising VH/VL class pairs in a concentration of at least 0.05%, at least 1%, or at least 2% of the VH/VL class pairs in the immune repertoire. In some embodiments, identifying VH/VL class pairs comprises: (i) isolating B-cells from one or more human hosts; (ii) determining the VH/VL class pairs in each B-cell by a process selected from: (A) isolating and sequencing the DNA, mRNA or cDNA encoding the VH/VL class pairs; or (B) probing with one or more nucleic acid probes specific for each VH and VL; and (iii) analyzing the VH/VL class pairs. In some embodiments, identifying VH/VL class pairs comprises: (i) obtaining antibody nucleic acid sequences; (ii) determining VH/VL class pairs by sequence alignment; (iii) collating such sequences from at least 100 antibodies, to identify VH/VL class pairs present in the immune repertoire. In some embodiments, the methods comprise selecting VH/VL class pairs exhibiting at least one biophysical property selected from the group consisting of: (i) efficiently displayed on phage; (ii) efficiently displayed on mammalian cells; (iii) well expressed in *E. coli* in Fab format; (iv) well expressed in mammalian cells in an IgG format; (v) thermal stability; (vi) solubility; and (vii) low immunogenicity; and synthesizing of a collection of nucleic acids encoding antibodies or fragments thereof exhibiting a least one of the biophysical properties. In some embodiments, the collection of nucleic acids encoding antibodies or fragments thereof is germline, substantially germline, or codon-optimized variants of germline nucleic acids. In some embodiments, during the synthesizing a collection of nucleic acids encoding antibodies or fragments thereof comprising VH/VL class pairs, sequence variation is introduced into at least one complementarity determining region (CDR). In some embodiments, the sequence variation is limited to sequences free from stop codons. In some embodiments, the methods further comprise cloning the collection of nucleic acids into a vector. In some embodiments, the vector is selected from the group consisting of: (i) a display vector, (ii) a phage display vector; (iii) a phagemid vector; and (iv) a mammalian expression vector. In some embodiments, the methods further comprise transformation into a host cell. In some embodiments, the host cells are selected from the group consisting of: (i) prokaryotic host cells; (ii) eukaryotic host cells: (iii) *E. coli* host cells; and (iv) mammalian host cells.

Some embodiments, further comprise inserting said nucleic acids into a collection of vectors and transforming/transfecting into a host cell and displaying the antibodies or fragments thereof. In some embodiments the vectors are expression vectors, display vectors, such as a phagemid vector. Some embodiments, further comprise transfecting said vectors into a suitable host cell. In some embodiments, the host cell is prokaryotic, such as *E Coli*, or eukaryotic, such as mammalian.

In another aspect, the disclosure enables a method of identifying an antibody or antibody fragments thereof specific for an immunogen, comprising the steps of synthesizing a collection of nucleic acids encoding antibodies or fragments thereof comprising VH and VL class pairs present in a concentration of at least 0.05% of the VH and VL class pairs existing in a sample of at least ~2500 B cells; screening the collection against a specific immunogen; and selecting one or more antibodies or fragments thereof specific for said immunogen. Some embodiments comprise, a method of identifying an antibody or antibody fragment thereof specific for an immunogen, comprising the steps of: (a) identifying VH/VL class pairs present in a concentration of at least 0.05%, at least 1%, or at least 2% of the VH/VL class pairs in the immune repertoire; (b) synthesizing a collection of nucleic acids encoding antibodies or fragments thereof comprising VH/VL class pairs present in a concentration of at least 0.05%, at least 1%, or at least 2% of the VH/VL class pairs in the immune repertoire; (c) displaying or expressing the antibody or fragment thereof from the collection; (d) screening the collection against a specific immunogen; and (e) selecting at least one antibodies or fragment thereof specific for said immunogen. Some embodiments comprise, a method of identifying an antibody or antibody fragment thereof for the treatment of a disease or condition, comprising the steps of: (a) identifying VH/VL class pairs present in a concentration of at least 0.05%, in at least 1%, or at least 2% of the VH/VL class pairs in the immune repertoire; (b) identifying VH/VL class pairs exhibiting at least one biophysical property selected from the group consisting of: (i) efficiently displayed on phage; (ii)

efficiently displayed on mammalian cells; (iii) well expressed in *E. coli* in Fab format; (iv) well expressed in mammalian cells in an IgG format; (v) thermal stability; (vi) solubility; and (vii) low immunogenicity; (c) synthesizing a collection of nucleic acids encoding antibodies or fragments thereof comprising VH/VL class pairs present in a concentration of at least 0.05%, in at least 1%, or at least 2% of the VH/VL class pairs in the immune repertoire and displaying the at least one biophysical property of (i)-(vii); (d) displaying or expressing the antibody or fragment thereof from the collection; (e) screening the collection against a specific immunogen associated with the disease or condition; and (f) selecting at least one antibodies or fragment thereof specific for said immunogen.

In some embodiments, the B cells are isolated from a human host. In some embodiments, the B cells are naive. In some embodiments, the VH and VL class pairs existing in a sample of at least 1×~2500 B cells are identified by a method comprising harvesting naïve B-cells from one or more human hosts; isolating the DNA from the B-cells harvested; and analyzing the DNA isolated. In some embodiments, the step of analyzing the DNA comprises sequencing the DNA. In some embodiments, the step of analyzing the DNA further comprises identifying the frequency that each VH and VL class pair exists in the sample.

Some embodiments further comprise inserting said nucleic acids into a collection of vectors and transforming/transfecting into a host cell, and displaying the antibodies or fragments thereof.

In another aspect, the disclosure enables a method of identifying an antibody or antibody fragments thereof specific for an immunogen, comprising the steps of synthesizing a collection of nucleic acids encoding antibodies or fragments thereof comprising VH and VL class pairs present in a concentration of at least 0.05% of the VH and VL class pairs existing in a sample of at least ~2500 B cells; screening the collection against a specific immunogen; and selecting one or more antibodies or fragments thereof specific for said immunogen.

In some embodiments, the B cells are isolated from a human host. In some embodiments, the B cells are naive. In some embodiments, the VH and VL class pairs in a sample of at least ~2500 B cells are identified by a method comprising harvesting B-cells from one or more human hosts; isolating the DNA from the B-cells harvested; and analyzing the DNA isolated. In some embodiments, the step of analyzing the DNA comprises sequencing the DNA. In some embodiments, the step of analyzing the DNA further comprises identifying the frequency that each VH and VL class pair exists in the sample.

In some embodiments a collection is displayed before testing/screening using phage, yeast, ribosomal, bacterial or eukaryotic display. In some embodiments, a collection is displayed on prokaryotic or eukaryotic cells. In some embodiments, a collection is displayed in Fab or IgG format or other format known to one of skill in the art.

Screening may be performed by using one of the methods well known in the art, such as phage-display, selectively infective phage, polysome technology to screen for binding, and assay systems for enzymatic activity or protein stability. Many such methods are known to the skilled artisan and as exemplary references the following are provided: Valle R P, Curr. Opin. Drug Discov. Devel. 2003 March; 6(2):197-203; Ackermann B L Expert Rev. Proteomics. 2007 April; 4(2): 175-86; and Anderson K S J Proteome Res. 2005 July-August; 4(4):1123-33.

In one embodiment, screening assays are carried out such that the binding of ligand by the antibody produces a detectable signal, either directly or indirectly. Such signals include, for example, the production of a complex, formation of a catalytic reaction product, the release or uptake of energy, and the like. Cells from a population subjected to transformation with a subject recombinant DNA can be cloned to produce monoclonal colonies, for example. Cells form those colonies can be harvested, lysed and their DNA content examined for the presence of the recombinant DNA using a method known in the art, for example, as described in Southern, J. Mol. Biol., 98:503 (1975) or Berent et al., Biotech. 3:208 (1985).

Biophysical Properties

The invention also includes collections, and methods of making such collections, in which the VH/VL class pairs have desirable biophysical properties. Favourable and desired biophysical properties include higher stability, higher expression levels and a low tendency for aggregation.

Suitable biophysical properties facilitate the use of the collection at different stages. For example, screening of the collection is facilitated if antibodies or fragments thereof are soluble and do not aggregate, and are well expressed in the screening background, such as phage. Later development of an antibody, such as for animal testing and therapeutic uses, are facilitated by properties such as antibody solubility, heat stability, high levels of expression (especially as IgG in mammalian cells), and low immunogenicity.

To ensure that all, or at least the majority, of antibodies or fragments thereof have such favorable biophysical properties, VH/VL class pairs may be screened in advance to identify which class pairs exhibit which of the properties. The library is then constructed by synthesizing nucleic acids encoding only those antibodies with such favorable biophysical properties.

Of course, not all VH/VL class pairs will exhibit all biophysical properties in the same degree, and the person of ordinary skill will determine which properties are more relevant and/or the balance of each properties in advance of determining which VH/VL class pairs are to be synthesized.

Thus, in certain aspects the present invention provides a synthetic antibody library selected for VH/VL combinations are efficiently displayed, such as on the surface of phage, or in other display technologies. Preferably all, essentially all, or substantially all VH/VL combinations are efficiently displayed. Efficiency of display can be measured by sandwich phage ELISA as described in the present invention.

In other aspects, the present invention provides a synthetic antibody library selected for VH-VL combinations that are well expressed in *E. coli* in Fab format. Preferably all, essentially all, or substantially all VH/VL combinations are well expressed in *E. coli* in Fab format. Expression in Fab format in *E. coli* can be quantified and is preferably more than 2 mg/L, more than 5 mg/L, more than 10 mg/L, or more than 15 mg/L in a bacterial culture. In certain aspects, all VH-VL are expressed at more than 2 mg/L, essentially all VH-VL combinations are expressed at levels of more than 5 mg/L, most VH-VL combinations are expressed at levels of more than 10 mg/L in a bacterial culture, and/or at least two, at least three, at least four or at least five VH-VL combinations are expressed at levels of more than 15 mg/L in a bacterial culture.

In certain aspects the present invention provides a synthetic antibody library selected for VH-VL combinations well expressed in a mammalian system in IgG format. The vast majority of antibody-based therapeutic biologicals currently on the market are in IgG-format for a variety of reasons: (i) the half-life of IgG molecules in the human body is very high (about 3 weeks) due to the interaction of the IgG with the neonatal receptor (FcRn); (ii) IgG molecules are highly soluble, thermodynamically stable and relatively resistant to proteases in blood; and (iii) IgG possess ADCC (antibody-dependent cell-mediated cytotoxicity) and/or CDC (complement-dependent cytotoxicity) activity, which are required for elimination of tumor cells. Expression of a particular VL/VH-combination in Fab-format does not necessarily correlate with the expression of the same VL/VH-combination in IgG-format, and so expression and solubility of VL/VH combinations in IgG formats are also important independent factors.

The mammalian system may include, for example, a mammalian suspension culture, a mammalian adherent cell culture, HKB11 cells, PERC.6 cells, or CHO cells. Preferably all, essentially all, or substantially all VH/VL combinations are well expressed in a mammalian system in IgG format. In certain aspects the present invention provides a synthetic human antibody library wherein all VH-VL combinations are expressed at levels of more than 10 mg/L in a mammalian system in IgG format wherein essentially all VH-VL combinations are expressed at levels of more than 15 mg/L in a mammalian system in IgG format; wherein most VH-VL combinations are expressed at levels of more than 20 mg/L in a mammalian system in IgG format; and/or at least three, at least four or at least five VH-VL combinations are expressed at levels of more than 25 mg/L in a mammalian system in IgG format.

In certain aspects the present invention provides a synthetic antibody library selected for VH/VL combinations that are thermally stable. Preferably all, essentially all, or substantially all combinations are thermally stable with Tm of at least 68, 70, 72, 74 or 76° C. Thermal stability can be measured as described herein. In certain aspects the present invention provides a synthetic human antibody library wherein essentially all VH-VL combinations have a Tm of more than 68° C.; essentially all VH-VL combinations have a Tm of more than 70° C., or of more than 72° C.; most VH-VL combinations have a Tm of more than 74° C.; and/or many VH-VL combinations have a Tm of more than 76° C. In certain aspects at least three, at least four or at least five VH-VL combinations have a Tm of more than 70° C.

In certain aspects the present invention provides a synthetic antibody library selected for VH-VL combinations that are soluble, i.e. do not tend to aggregate. Solubility may be determined, for example, by favorable folding and expression characteristics of tested Fab in a bacterial host or IgG1 in a eukaryotic host or aggregation after purification as determined by analytical size exclusion chromotography.

Low immunogenicity may be predicted or tested directly by methods known in the art, but may also be inferred by the fact that given VH/VL class pairs are the most abundant in the repertoire and used protein sequences are substantially germline protein sequences.

As described herein, antibody sequence data can be obtained from B-cells, for example, naïve B cells, publically available databases and/or literature. Each of the antibody sequences can be aligned to the closest germline family and/or gene. From this data, one can determine the VH and VL germline families and/or genes and/or the VH/VL class pairs that are abundant.

Once the VH and VL germline families and/or genes and/or VH/VL class pairs that are abundant are determined, one can select which VH and VL germline family and/or genes and/or VH/VL class pairs to be tested for favorable biophysical properties. One approach, would be to rank the VH and VL germline families and/or genes according to abundance and then test the VH and VL germline families and/or genes that are most abundant, for example, the top 20 most abundant VH and VL germline families and/or genes. In addition, one can combine the top 20 most abundant VH and VL germline families and/or genes, resulting, for example, in 400 combinations of VH and VL's and test them for favorable biophysical properties. In addition or complementarily, one can test the VH/VL class pairs that are most abundant for favorable biophysical properties.

The favorable biophysical properties include, but are not limited to: (i) they are well displayed on phage in the Fab-format, (ii) they are well displayed on mammalian cells in the IgG-format, (iii) they are expressed in high amounts in Fab-format, e.g., in $E.\ Coli$, and IgG formats, e.g., in mammalian cells, (iv) are thermodynamically stable; (v) have high serum stability, (vi) have a low tendency for aggregation (i.e. high solubility); and (vii) have a low risk of immunogenicity.

In some aspects, the present invention comprises a collection of synthetic nucleic acids encoding antibodies or fragments thereof comprising VH and VL class pairs present at a concentration of at least 0.5% of the VH and VL class pairs existing in a sample of at least $1\times10^5$ B cells. In some embodiments, the VH and VL class pairs are present at a concentration of at least 1% of the VH and VL class pairs existing in a sample of at least $1\times10^5$ B cells. In some embodiments, the VH and VL class pairs are present at a concentration of at least 2% of the VH and VL class pairs existing in a sample of at least $1\times10^5$ B cells. In some embodiments, the B cells are isolated from a human host. In some embodiments, the B cells are naive. In some aspects, the collection comprises nucleic acids encoding antibodies or fragments thereof comprising germline VH and VL framework regions. In some embodiments the collection comprises at least $1\times10^4$ nucleic acid sequences, at least $1\times10^6$ nucleic acid sequences; at least $1\times10^8$ nucleic acid sequences, at least $1\times10^{10}$ nucleic acid sequences, or at least $1\times10^{11}$ nucleic acid sequences.

In some aspect, the present invention comprises a kit comprising sequence data illustrating nucleic acids encoding antibodies or fragments thereof comprising nucleic acids present in a sample of at least $1\times10^5$ naïve human B cells, wherein said sequence data are on a readable medium. In some embodiments, the invention comprises the collection of nucleic acids encoding antibodies of functional fragments thereof. In some embodiments, the vector is a phage display vector. In some embodiments, the vector is a phagemid vector. In some aspects, the present invention comprises host cells transformed with the collection vectors comprises the collection of nucleic acids encoding antibodies of functional fragments thereof. In some embodiments, the host cells are prokaryotic. In some embodiments, the host cells are $E.\ coli$. In some embodiments, the host cells are eukaryotic. In some embodiments, the host cells are mammalian.

In some aspects the present invention comprises a method of producing a collection of synthetic nucleic acids encoding antibodies or fragments thereof, comprising: synthesizing a collection of nucleic acids encoding antibodies or fragments thereof comprising VH and VL class pairs present in a concentration of at least 0.5% of the VH and VL class pairs existing in a sample of at least $1\times1\ 0^5$ B cells. In some embodiments, the B cells are isolated from a human host. In some embodiments, the B cells are naive. In some embodiments, the VH and VL class pairs existing in a sample of at least $1\times10^5$ B cells are identified by a method comprising aa) harvesting naïve B-cells from one or more human hosts;

ab) isolating the DNA from the B-cells harvested in step aa); and ac) analyzing the DNA isolated in step ab).

In some embodiments, the step of analyzing the DNA comprises sequencing the DNA. In some embodiments, the step of analyzing the DNA further comprises identifying the frequency that each VH and VL class pair exists in the sample. In some embodiments, the methods further comprise inserting the nucleic acids into a collection of vectors. In some embodiments, the vector is an expression vector. In some embodiments, the vector is a display vector. In some embodiments, the display vector is a phagemid vector. In some embodiments, the method further comprising transfecting said vectors into a suitable host cell. In some embodiments, the host cell is prokaryotic. In some embodiments, the host cell is E. coli. In some embodiments, the host cell is eukaryotic. In some embodiments, the host cell is mammalian.

In some aspects, the present invention comprises a method of identifying an antibody or antibody fragments thereof specific for an immunogen, comprising the steps of: a) synthesizing a collection of nucleic acids encoding antibodies or fragments thereof comprising VH and VL class pairs present in a concentration of at least 0.5% of the VH and VL class pairs existing in a sample of at least $1 \times 10^5$ B cells; b) screening the collection against a specific immunogen; and c) selecting one or more antibodies or fragments thereof specific for said immunogen. In some embodiments, the B cells are isolated from a human host. In some embodiments, B cells are naive. In some embodiments, the VH and VL class pairs existing in a sample of at least $1 \times 10^5$ B cells are identified by a method comprising aa) harvesting naïve B-cells from one or more human hosts;

ab) isolating the DNA from the B-cells harvested in step aa); and ac) analyzing the DNA isolated in step ab).

In some embodiments, the step of analyzing the DNA comprises sequencing the DNA. In some embodiments, the step of analyzing the DNA further comprises identifying the frequency that each VH and VL class pair exists in the sample. In some embodiments, the step of synthesizing the collection further comprises inserting said nucleic acids into a collection of vectors. In some embodiments, the method further comprises transfecting said vectors into a suitable host cell. In some embodiments, the method further comprises displaying said collection.

EXAMPLES

Example 1

Generation of Restriction Sites in the C-Terminus of a Prokaryotic Signal Sequence and Human Leader Sequence, Providing for Fully Germline Fr1 Regions In one aspect, the present disclosure describes collections of antibodies comprising framework regions comprising germline protein sequences, specifically FR1. It is expected that having germline sequences shall lower the immunogenicity risk of the antibodies when administered in humans. Compatible restriction sites, however, must be used in order to enable standard cloning of the nucleic acids encoding the collections of antibodies into display and/or expression vectors so that the antibodies can be screened against immunogens. In the past, restriction sites utilized for cloning were often located within the framework regions, thus modifying the nucleic acid and/or amino acid sequence away from germline. In order to ensure that at least the framework 1 (FR1) region of each of the antibodies of the present disclosure maintain a germline protein sequence, there should not be any non-naturally occurring restriction sites within FR1. Therefore, an aspect of the present disclosure is the incorporation of an identical or at least compatible restriction site within the C-terminus of prokaryotic signal sequences and a human leader sequence, specifically within the three C-terminal residues. Additionally, the signal sequence and leader sequence comprising an identical or compatible restriction site must be functional and allow for good display and expression levels of the antibodies or fragments thereof in both prokaryotic and mammalian expression systems.

Example 1.1

Analysis of Abundant Amino Acid Residues at the C-Terminus of E. coli Signal Sequences The following describes the selection of restriction sites to be incorporated into the C-terminus of a signal sequence, both the E. coli ompA and phoA, and the evaluation of the functionality of the resulting signal sequences.

As a first step, the common amino acid residues at the C-terminal three amino acids of signal sequences (−3 to −1) were analyzed and a consensus sequence was generated, as shown in Table 1. See Chou et al., Prediction of protein signal sequences, Protein Pept. Sci. 3(6):615-22 (December 2002).

TABLE 1

Consensus sequences of the three C-terminal amino acids of signal sequences

| −3 | −2 | −1 |
|---|---|---|
| A | L | A |
| S | A | G |
| V | S | S |
| T | Q | |

At position −3, predominantly A, S, V, and T amino acids were observed. At position −2, predominantly L, A, S, and Q amino acids were observed. At position −1, predominantly A, G, and S were observed.

Example 1.2

Selection of a Restriction Site for Heavy Chain E. coli Signal Sequence (phoA)

After comparing the consensus sequences shown in Table 1 to known restriction sites, the following three restriction sites: AflIII, NheI, and AvrII were selected for incorporation into the phoA C-terminus and subsequently studied for expression levels. It is important to note what by changing the wildtype nucleotide sequences to modified nucleotide sequences, also the amino acid sequences are change. The nucleic acids sequences of the selected restriction sites and corresponding amino acids sequences are shown in Table 2.

TABLE 2

| | | | |
|---|---|---|---|
| AflII | V | L | S |
| | GTC | TTA | AGY |
| NheI | V | L | A |
| | GTG | CTA | GCN |
| AvrII | V | L | G |
| | GTC | CTA | GGN |

As a control, the wild type phoA signal sequence was studied for expression levels. The nucleic acid and amino acid sequences of the wild type phoA signal sequence, including the 3 C-terminal sequences are shown in Table 3.

TABLE 3

Wildtype *E. coli* phoA signal sequence (C-terminal amino acid sequence from position -3 to -1 is TKA without restriction-site)
(SEQ ID NOS 8 and 7, respectively):

```
  M   K   Q   S   T   I   A   L   A   L   L   P   L   L   F   T   P   V   T   K   A
ATGAAACAGAGCACCATTGCCCTGGCCCTGCTGCCGCTGCTGTTTACCCCAGTGACCAAAGCC

PhoA wild type C-terminus                                       T   K   A
                                                              ACC AAA GCC
```

Figure 50:
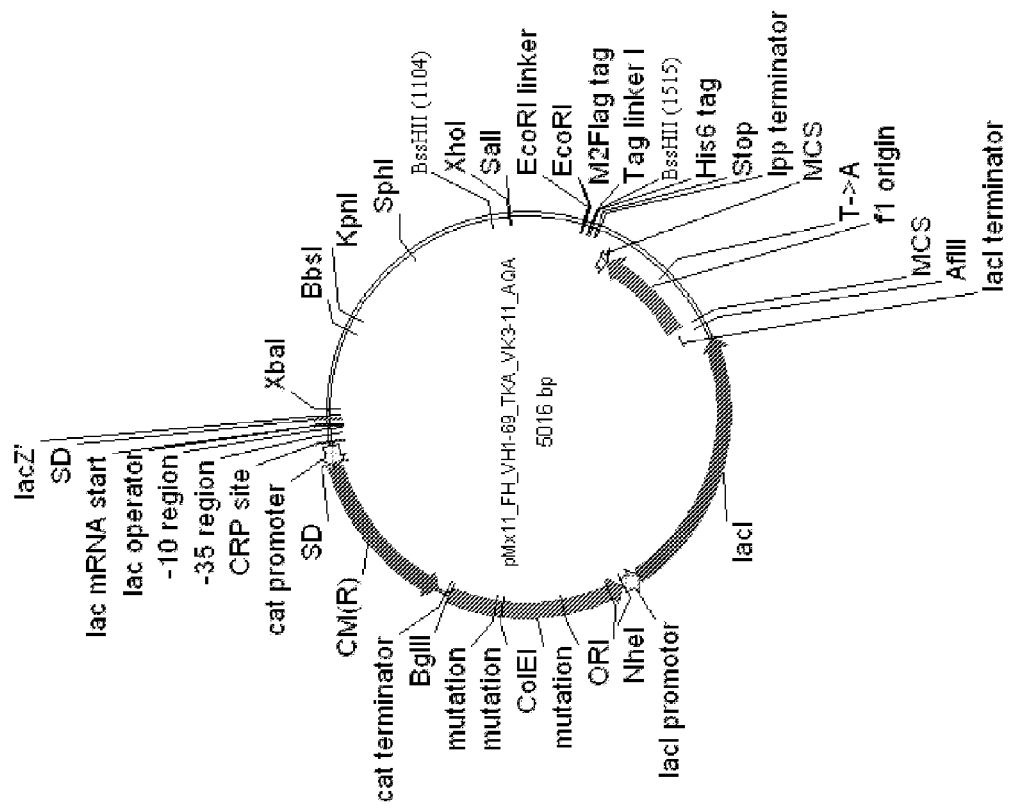
FIG. 50 shows the pMx11 (pMORPHX11) Fab expression vector, FIG. 50 discloses 'His6' as SEQ ID NO: 202.

In order to evaluate expression levels, the restriction sites shown in Table 2 were incorporated into the phoA signal sequence thereby also modifying the wildtype amino acid sequence. The resulting signal sequences were used to express Fab fragments comprising either a) the VH3-23 or b) VH1-69 germline protein sequences. These germline genes were selected as they are known to be stable and well expressed. Into both the VH3-23 and VH1-69 germline gene sequences, the CDR-H3 (WGGDGFYAMDY (SEQ ID NO: 1)) of the 4D5 antibody was incorporated, and the JH4 germline gene sequence was used for FR4. The 4D5 antibody is disclosed in (PDB entry 1FVC; Carter, P., Presta, L., Gorman, C. M., Ridgway, J. B., Henner, D., Wong, W. L. et al, (1992); Humanization Biophysical Properties of Human Antibody Domains 551 of an anti-p185HER2 antibody for human cancer therapy. Proc. Natl Acad. Sci. USA, 89, 4285-4289. pMORPHX11 (shown in FIG. 50) based plasmids were generated comprising a) phnA signal sequences comprising the C-terminal restriction sites and amino acid sequences of Table 2, b) the VH sequences of VH3-23 and VH1-69, incorporating the CDR-H3 and JH4, as described above, and c) the stable and well expressing light chain from MOR03207. All genes were generated at Geneart (Regensburg, Germany).

Expression and periplasmic transport were checked by performing anti-Fd ELISA after periplasmic extraction. The results of the Anti-Fd expression ELISA after periplasmic extraction using BBS buffer are shown in FIG. 1. As shown, in the VH3-23 group, the signal sequences including the C-terminal restriction sites, AflII (VLS), NheI (VLA), and AvrII (VLG), maintained expression levels in the range of wildtype (TKA), with NheI (VLA) performing better than wildtype (TKA).

Additionally, Fab expression in *E. coli* was performed after overnight culture in shake flasks and Fab production levels were determined after Fab purification by affinity chromatography and buffer exchange. The results are shown in Table 4.

TABLE 4

Fab expression using signal sequences including the C-terminal restriction sites AflII (VLS), NheI (VLA), and AvrII (VLG), as compared to wildtype (TKA)

| Fab Construct | Expression rate (mg/L) |
|---|---|
| VH3-23 TKA | 11.0 |
| VH3-23 VLS | 2.0 |
| VH3-23 VLA | 11.0 |
| VH3-23 VLG | 9.0 |
| VH1-69 TKA | 7.5 |
| VH1-69 VLS | 5.0 |
| VH1-69 VLA | 2.5 |
| VH1-69 VLG | 3.5 |

As shown, signal sequences including the C-terminal restriction sites AflII (VLS), NheI (VLA), and AvrII (VLG), as compared to wildtype (TKA) express similar amounts of Fab.

Based upon the above data, the NheI (VLA) restriction site was selected for incorporation into the heavy chain signal sequences (phoA). The nucleic acid and amino acid sequences of the modified NheI (VLA) phoA signal sequence are shown in Table 5.

TABLE 5

Modified *E. coli* phoA signal sequence with C-terminal VLA and NheI restriction site (= GCTAGC)(SEQ ID NOS and 9, respectively):

```
  M   K   Q   S   T   I   A   L   A   L   L   P   L   L   F   T   P   V   V   L   A
ATGAAACAGAGCACCATTGCCCTGGCCCTGCTGCCGCTGCTGTTTACCCCAGTGGTGCTAGCC
```

Example 1.3

Selection of a Restriction Site for Kappa and Lambda Light Chain E. coli Signal Sequence (ompA)

A similar method to that described in Examples 1.2 was used for the selection of the restriction sites to be incorporated into the C-termini of the light chain signal sequences (ompA) for both kappa and lambda.

After comparing the consensus sequences shown in Table 1 to known restriction sites, the following restriction sites: NdeI (AYG), NdeI (AYA) and BsiWI (TYA) were selected for incorporation into the ompA C-terminus, thereby also modifying the amino acid sequences, and subsequently studied for expression levels. The sequences of the selected restriction sites are shown in Table 6.

TABLE 6

| NdeI | A | Y | G |
| | GCA | TAT | GGN |
| NdeI | A | Y | A |
| | GCA | TAT | GCN |
| BsiWI | T | Y | A |
| | ACG | TAC | GCN |

As a control, the wild type ompA signal sequence was studied for expression levels. The nucleic acid and amino acid sequences of the wild type ompA signal sequence, including the 3 C-terminal sequences are shown in Table 7.

TABLE 7

Wildtype E. coli ompA signal sequence (C-terminal amino acid sequence from position −3 to −1 is AQA without restriction-site)

(SEQ ID NOS 12 and 11, respectively):

```
 M   K   K   T   A   I   A   I   A   V   A   L   A   G   F   A   T   V   A   Q   A
ATGAAAAAAACCGCCATTGCCATTGCCGTGGCCCTGGCAGGCTTTGCCACCGTGGCGCAGGCC

OmpA wild type C-terminus              A   Q   A
                                      GCG CAG GCC
```

In order to evaluate expression levels, the restriction sites shown in Table 6 were incorporated into the ompA signal sequences. The resulting modified signal sequences were used to express Fab fragments comprising a) the Kappa1 O12 (IGKV1-39), b) Kappa3 L6 (IGKV3-11), or c) Lambda1 V1-13 (IGLV1-40) germline gene sequences, These germline genes were selected as they are known to be stable and well expressed. In a) Kappa1 O12 (IGKV1-39) and b) Kappa3 L6 (IGKV3-11), the CDR-L3 region: QQHYTTPPT (SEQ ID NO: 2) (for kappa) was incorporated, in c) Lambda1 V1-13 (IGLV1-40) the CDR-L3 region: QSYDSSLSCIVV (SEQ ID NO: 3) (for lambda) was incorporated, and in a)-c), Jk1 germline gene sequence was used as FR4 for kappa light chain; and Jl2/3 germline gene sequence was used as FR4 for lambda light chain. pMORPHX11 (shown in FIG. 50) plasmids were generated comprising a) ompA signal sequences comprising the C-terminal restriction sites of Table 6, b) the VL germline sequences of Kappa1 O12 (IGKV1-39), b) Kappa3 L6 (IGKV3-11), or c) Lambda1 V1-13 (IGLV1-40), incorporating the CDR-L3 and FR4, as described above, and c) the IGHVH3-23 TKA construct, as heavy chain, described in Example 1.2. All genes were generated at Geneart (Regensburg, Germany).

Figure 2:
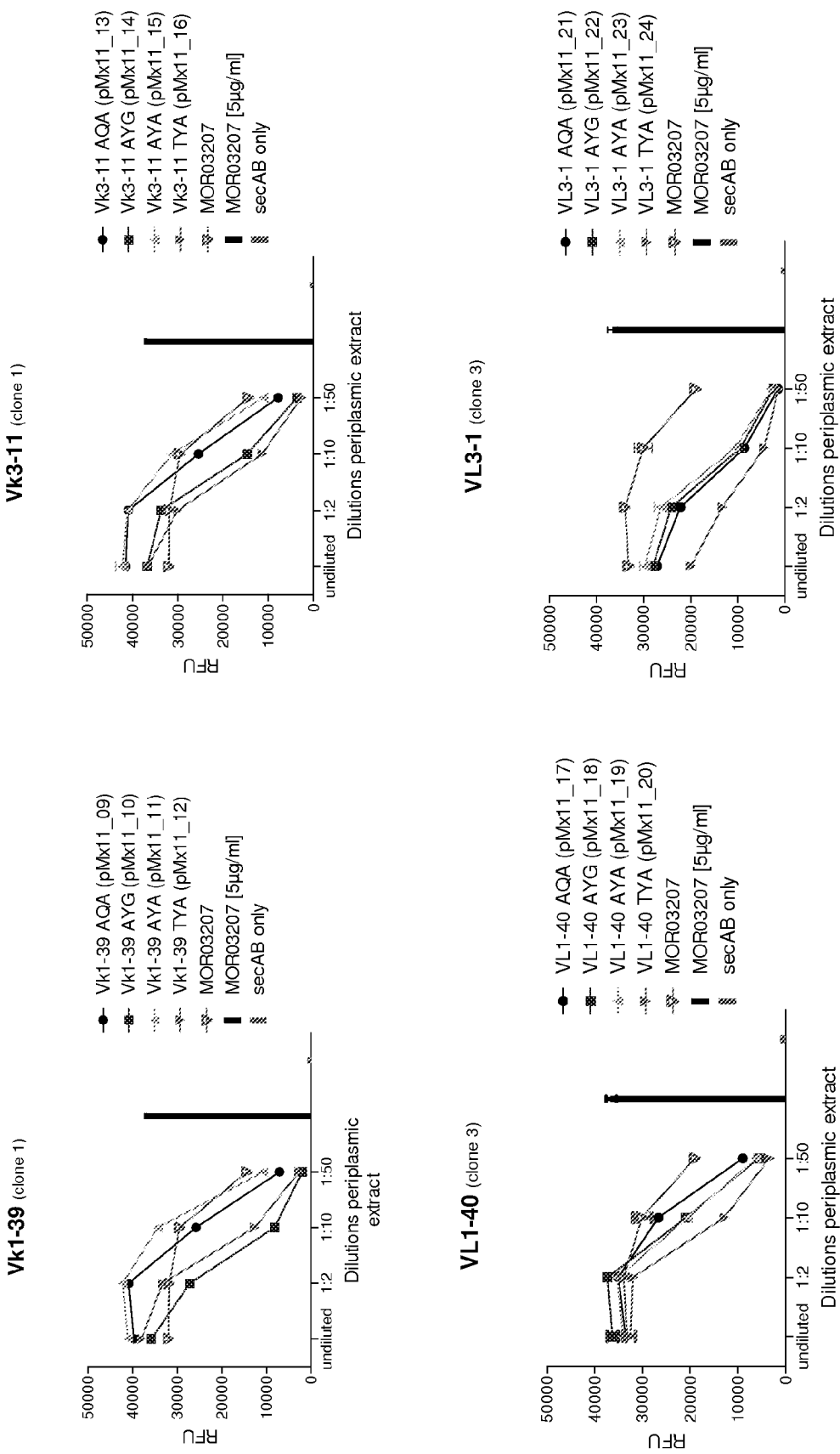
FIG. 2 shows the results of an Anti-Fd expression ELISA after periplasmic extraction of an antibody with the VK1-39 light chain (left upper panel), VK3-11 light chain (right upper panel), VL1-40 light chain (left lower panel) and VL3-1 light chain (right lower panel), each antibody carrying one of the three modified ompA signal sequences comprising the C-terminal restriction sites NdeI (AYG), NdeI (AYA) and BsiWI (TYA) as compared to the wildtype (AQA) signal sequence. The modified ompA signal sequences comprising the C-terminal restriction sites and wildtype signal sequence were tested using both VK and VA Fab fragments. The signal sequence including NdeI (AYA) shows consistently as good as or better expression than wildtype (AQA).

Expression and periplasmic transport were checked by performing overnight Fab production in E. coli, periplasmic extraction, and anti-Fd ELISA after periplasmic extraction. The results of the Anti-Fd expression ELISA after periplasmic extraction using BBS buffer are shown in FIG. 2. As shown, the signal sequence including NdeI (AYA) shows as good as or better expression than wildtype (AQA).

Additionally, Fab expression in E. coli was performed after overnight culture in shake flasks and Fab production levels were determined after Fab purification by affinity chromatography and buffer exchange. The results are shown in Table 8.

TABLE 8

Fab expression using signal sequences including the C-terminal restriction sites NdeI (AYA) as compared to wild type (AQA).

| Construct | Expression rate (mg/L) |
| --- | --- |
| VK1-39 AQA | 8.5 |
| VK1-39 AYA | 5.5 |
| VK3-11 AQA | 7.0 |

TABLE 8-continued

Fab expression using signal sequences including the C-terminal restriction sites NdeI (AYA) as compared to wild type (AQA).

| Construct | Expression rate (mg/L) |
| --- | --- |
| VK3-11 AYA | 9.5 |
| VL1-40 AQA | 5.0 |
| VL1-40 AYA | 5.0 |

Based upon the above data, the NdeI (AYA) restriction site was selected for incorporation into the kappa and lambda signal sequences (ompA). The nucleic acid and amino acid sequences of the modified NdeI (AYA) ompaA signal sequence are shown in Table 9.

TABLE 9

Modified *E. coli* ompA signal sequence with C-terminal AYA and NdeI restriction site (= CATATG)(SEQ ID NOS 14 and 13, respectively):

M K K T A I A I A V A L A G F A T V A Y A
ATGAAAAAAACCGCCATTGCCATTGCCGTGGCCCTGGCAGGCTTTGCCACCGTGGCATATGCC

Example 1.4

Evaluation of Efficiency of Display of Fab Fragments by Signal Sequences in Phage Display As described in Examples 1.2 and 1.3, the following restriction sites were selected for incorporation into the C-termini of the Fab signal sequences and IgG leader sequences: Heavy chain variable regions (phoA and heavy chain leader): NheI (VLA)
Light chain variable regions (K and A) (ompA and kappa leader): NdeI (AYA)

FIG. 3 shows the selected restriction sites and corresponding amino acid sequences.

Figure 48:
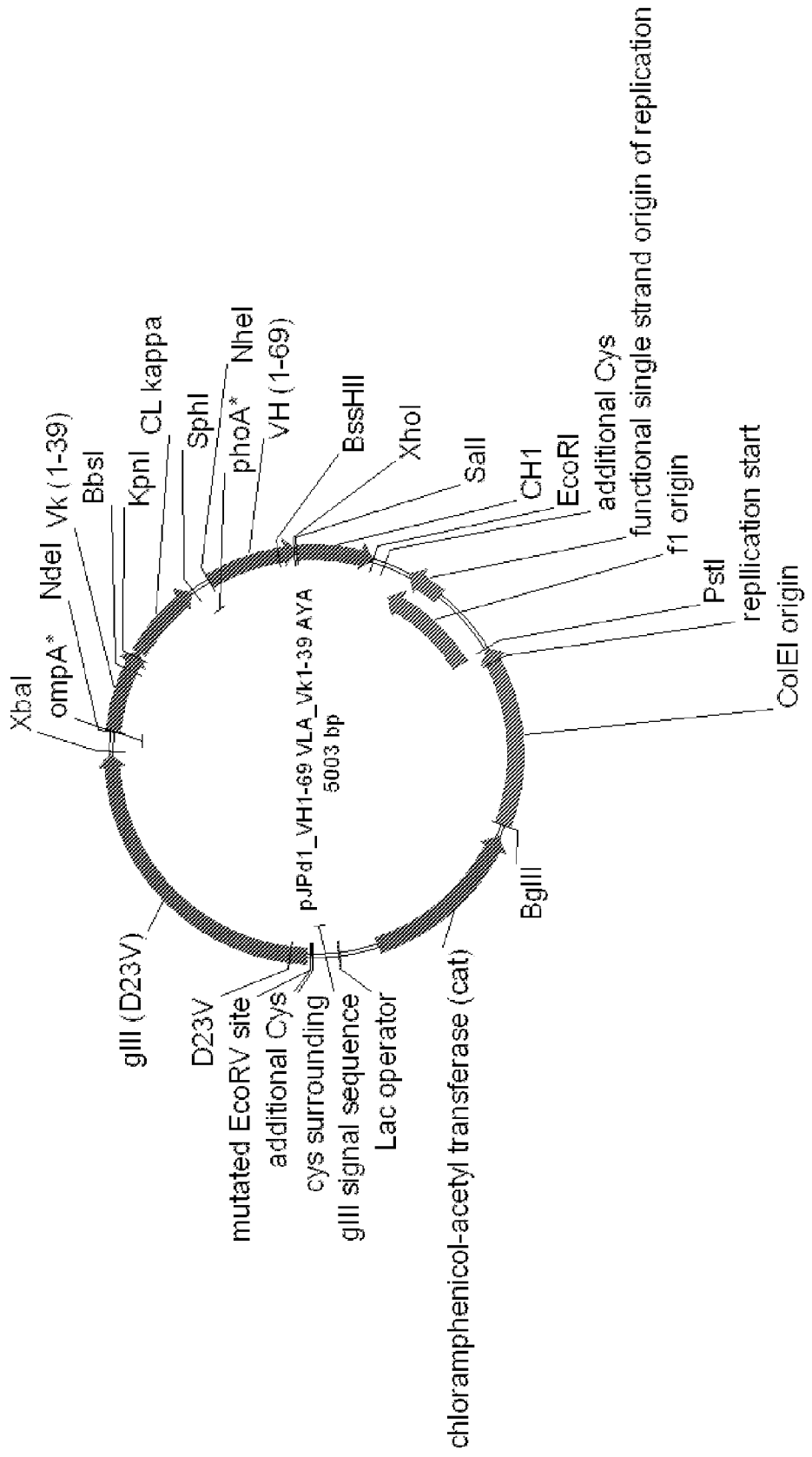
FIG. 48 shows the pJPd1 tricistronic phage display vector.

In order to show that these modified signal sequences mediate efficient transport and production of Fab fragments, vector constructs were generated incorporating the selected signal sequences into tricistronic display vectors, which encode a VH, VL and pIII (phage coat protein pIII used for phage display). This was done in order to confirm that such vectors, comprising the selected signal sequences, were able to provide useful phage display rates. pJPd1 (shown in FIG. 48) tricistronic vector constructs were generated comprising the VH of VH3-23 or VH1-69 germline genes, or the VL of VL1-40, VK3-11, or VK1-39 germline genes, and the selected heavy chain (phoA) restriction sites: NheI (VLA), and wildtype phoA (TKA) as a control, or the selected light chain (ompA) restriction sites: NdeI(AYA) and wildtype ompA (AQA), as a control. In addition, pMORPH30 (shown in FIG. 51) tricistronic vector constructs comprising the same were generated as controls. The relative display rates are shown in Table 10.

TABLE 10

| | | Rel. Display Rate | |
|---|---|---|---|
| Vector | Signal Sequence | VCSM13 | Hyperphage |
| pMORPH30 | VH1-69__TKA VL1-40__AQA | 0.6/0.7/0.9 | 0.7/1.0/1.6 |
| pMORPH30 | VH1-69__VLA VL1-40__AYA | 0.4/0.2/0.4 | 0.7/0.4/0.7 |
| pJPd1 | VH1-69__TKA VL1-40__AQA | 0.6/0.5/0.7 | 4.8/5.7/5.5 |
| pJPd1 | VH1-69__VLA VL1-40__AYA | 0.6/0.4/0.7 | 3.2/2.9/2.9 |
| pMORPH30 | VH1-69__TKA Vk3-11__AQA | 0.8 | 0.9 |
| pMORPH30 | VH1-69__VLA Vk3-11__AYA | 0.1 | 0.4 |
| pJPd1 | VH1-69__TKA Vk3-11__AQA | 0.3 | 1.8 |
| pJPd1 | VH1-69__VLA Vk3-11__AYA | 0.1 | 1.2 |
| pMORPH30 | VH1-69__TKA Vk1-39__AQA | not done | not done |
| pMORPH30 | VH1-69__VLA Vk1-39__AYA | 0.3 | 0.4 |
| pJPd1 | VH1-69__TKA Vk1-39__AQA | not done | not done |
| pJPd1 | VH1-69__VLA Vk1-39__AYA | 0.2 | 1.3 |
| pMORPH30 | VH3-23__TKA VL1-40__AQA | 0.6 | 1.6 |
| pMORPH30 | VH3-23__VLA VL1-40__AYA | 0.5 | 1.2 |
| pJPd1 | VH3-23__TKA VL1-40__AQA | 0.5 | 7.3 |
| pJPd1 | VH3-23__VLA VL1-40__AYA | 0.4 | 4.8 |
| pMORPH30 | VH3-23__TKA Vk1-39__AQA | not done | not done |
| pMORPH30 | VH3-23__VLA Vk1-39__AYA | 0.5 | 1.6 |
| pJPd1 | VH3-23__TKA Vk1-39__AQA | not done | not done |
| pJPd1 | VH3-23__VLA Vk1-39__AYA | 0.6 | 5.5 |
| pMORPH30 | VH3-23__TKA Vk3-11__AQA | 0.7 | 2.0 |
| pMORPH30 | VH3-23__VLA Vk3-11__AYA | 1.1 | 2.8 |
| pJPd1 | VH3-23__TKA Vk3-11__AQA | 0.5 | 3.9 |
| pJPd1 | VH3-23__VLA Vk3-11__AYA | 0.4 | 5.7 |

As shown, the pJPd1 vectors incorporating the selected signal sequences produced comparable relative display rates as the pMORPH30 vectors; and superior relative display rates compared to the pMORPH30 vectors were detected, when hyperphage were used as helper phage for phage production. Therefore, the pJPd1 vectors including the modified signal sequences should work well for phage display selection of antibodies or functional fragments thereof against target antigens.

Examples 1.2-1.4, describe the necessary tools to generate, express and display the collections of antibodies or functional fragments of the present disclosure, as they describe the signal sequences and leader sequences comprising restriction sites, which allow for FR1 regions with germline protein sequences, and describe the vector backbones useful for incorporating the disclosed collections of antibodies or functional fragments thereof into a phage display selection system, or mammalian expression system for the identification of antibodies against any immunogen. Moreover, the signal sequences carry restriction sites which allow full compatibility with both the Fab phage display and expression plasmids and corresponding IgG expression plasmids.

Example 1.5

Testing of Human Heavy Chain and Kappa Leader Sequences for IgG Expression Comprising the Selected C-terminal Restriction Sites In order to allow an easy switch from *E. coli* expressed Fab to mammalian expressed IgG formats, the human leader sequences for the IgG light chain (human kappa leader) and IgG heavy chain (human heavy chain leader) were generated to contain the same restriction sites as the C-termini of the ompA (NdeI (AYA)) and phoA (NheI (VLA)) signal sequences thereby modifying also some of the three C-terminal amino acid sequences.

The transfer of the VH from the *E. coli*-based Fab expression plasmid into the mammalian IgG expression vector can be performed using the described NheI restriction site which is located (a) in the C-terminus of the phoA signal sequence as well as (b) at the corresponding position in the C-terminus of the human heavy chain leader. In order to provide for this, the three final amino acids of the phoA signal sequence were modified (from TKA to VLA), and the C-terminus of the human heavy chain leader was adapted, by changing the wildtype amino acid sequence (−3 to −1) from VLS to the phoA compatible VLA.

The transfer of the VL from the *E. coli*-based Fab expression plasmid into the mammalian IgG expression vector can be performed by using the described NdeI restriction site which is located (a) in the C-terminus of the ompA signal sequence as well as (b) at the corresponding position in the C-terminus of the human kappa leader. In order to provide for this, the three final amino acids of the ompA signal sequence were modified (from AQA to AYA) and the C-terminus of the human kappa leader was adapted, by changing the wildtype amino acid sequence (−3 to −1) from AYG to the ompA compatible AYA. The wildtype and modified human heavy chain leader and human kappa leader sequences are shown in Table 11.

TABLE 11

Heavy chain leader

A)

Wildtype human heavy chain leader (C-terminal amino acid sequence
from position -3 to -1 is VLS without restriction site)
(SEQ ID NOS 16 and 15, respectively):
  M   K   H   L   W   F   F   L   L   L   V   A   A   P   R   W   V   L   S
ATGAAACACCTGTGGTTCTTCCTCCTGCTGGTGGCAGCTCCCAGATGGGTCCTGTCC Wild type Heavy chain leader C-terminus       V   L   S
                                             GTC CTG TCC

B)

Modified human heavy chain leader with C-terminal VLA and NheI
restriction site (= GCTAGC)(SEQ ID NOS 18 and 17, respectively):
  M   K   H   L   W   F   F   L   L   L   V   A   A   P   R   W   V   L   A
ATGAAGCACCTGTGGTTCTTTCTGCTGCTGGTGGCCGCTCCCCGGTGGGTGCTAGCC

C)

Wildtype human kappa leader (C-terminal amino acid sequence
from position -3 to -1 is AYG without restriction site)
(SEQ ID NOS 20 and 19, respectively):
  M   V   L   Q   T   Q   V   F   I   S   L   L   L   W   I   S   G   A   Y   G
ATGGTGTTGCAGACCCAGGTCTTCATTTCTCTGTTGCTCTGGATCTCTGGTGCCTACGGG Kappa leader C-terminus                       A   Y   G
                                             GCC TAC GGG

D)

Figure 53:
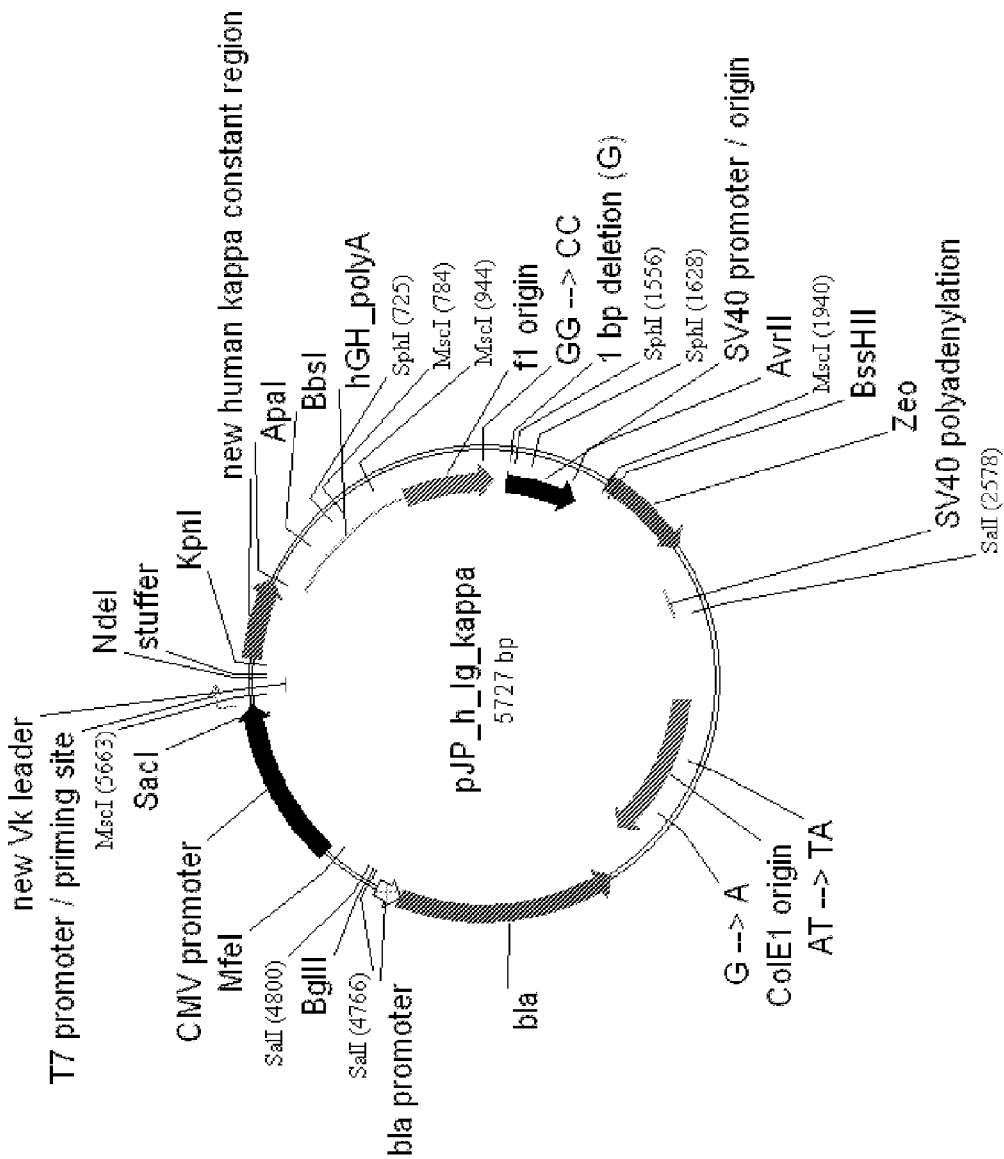
FIG. 53 shows the pJP_h_Ig_kappa variable κ light chain IgG expression vector.
Figure 54:
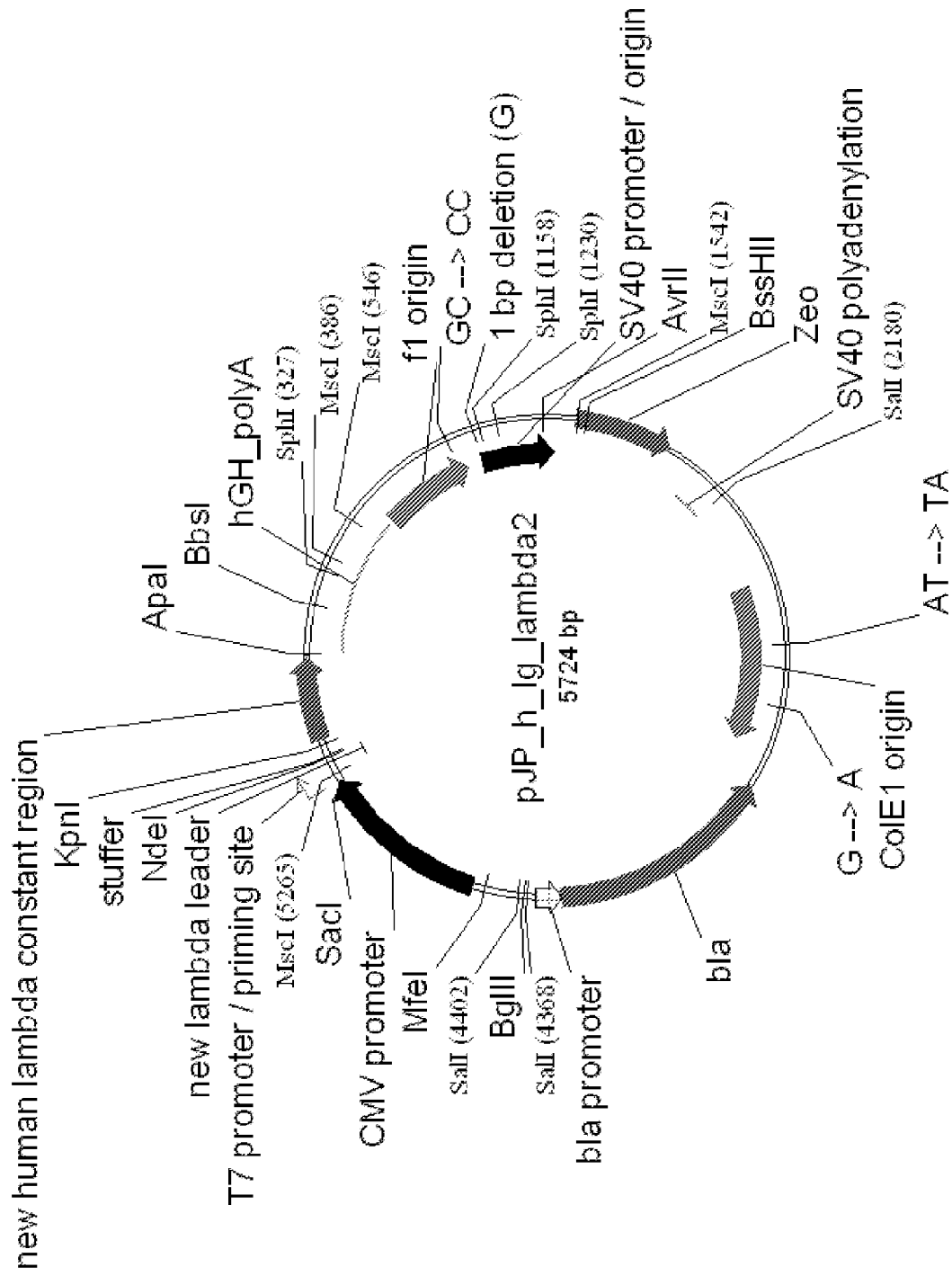
FIG. 54 shows the pJP_h_Ig_lambda2 variable λ light chain IgG expression vector.

Modified human kappa leader with C-terminal AYA and NdeI
restriction site (= CATATG)(SEQ ID NOS 22 and 21, respectively):
  M   V   L   Q   T   Q   V   F   I   S   L   L   L   W   I   S   G   A   Y   A
ATGGTGCTCCAGACCCAGGTGTTCATCAGCCTGCTGCTGTGGATCAGCGGCGCATATGCG In order to show that these modified signal/leader sequences mediate efficient transport and production of human IgG1 protein, both the modified human heavy chain leader and the modified human kappa leader were cloned into the pJP_Ig plasmids (shown in FIGS. 52-54) for mammalian expression of full length human IgG1, replacing the wildtype leader sequences. The resulting expression vectors containing the modified leader sequences, variable region genes as shown in Table 12 and constant regions for either kappa or lambda light chains and heavy chains were transfected into HKB11 cells and the human IgG1 was purified from cell culture supernatants several days post transfection by using Protein A chromatography. The IgG1 content was determined after purification and buffer exchange. The expression yields are shown in Table 12.

TABLE 12

| VH | VL | Human IgG1 expression |
|---|---|---|
| >hVH_1_69*01 | >hVL_3-1 | 36.4 mg/L |
| >hVH_1_69*01 | >hVL_3-21 | 34.5 mg/L |
| >hVH_3_23 | >hVL_3-1 | 40.0 mg/L |
| >hVH_3_23 | >hVL_3-21 | 34.5 mg/L |
| >hVH_3_30 | >hVK_3_20 | 25.6 mg/L |

All of the tested constructs express high amounts of human IgG1 indicating that the modified leader sequences maintain expression levels. The selected modified leader sequences (a) result in high yields of IgG protein according to the vector system used, (b) provide full compatibility for switching antibody formats, vectors and expression systems between prokaryotic and mammalian systems and (c) are located in the signal/leader sequences thereby maintaining the full germline sequences of FR1.

Example 2

Identification of the Most Abundant VH/VL Pairs in the Human Repertoire

An aspect of the present disclosure is a collection or library of antibodies or functional fragments thereof comprises germline protein sequences of the germline gene pairs most abundant in the human immune repertoire, wherein each antibody or functional fragments thereof comprises germline protein sequences of the respective germline protein pair, and wherein the germline protein pairs selected for incorporation into the collection comprise biophysical properties that increase the likelihood that each of the antibodies or functional fragments thereof selected from the collection will be clinically developable and commercially successful. In order to generate such a collection, many criteria had to be evaluated. Generally, the following steps were taken: the predominant germline gene pairs from the human immune repertoire were identified; the cDNAs of the predominant germline gene pairs from the human immune repertoire were synthesized and cloned into various vector backgrounds and antibodies or functional fragments thereof were produced; antibodies or functional fragments thereof comprising the germline protein sequences of the predominant germline gene pairs were functionally tested to determine their biophysical properties; and the biophysical properties of the antibodies or functional fragments thereof comprising the respective germline protein pairs were compared; then a subset of the germline protein pairs were selected for incorporation into a collection. In some embodiments, the germline protein sequences of the selected germline protein pairs act as scaffolds. In those embodiments, the scaffolds comprise the germline protein sequences of the selected germline protein pairs, wherein both the VH and VL comprise germline protein sequences of the respective pair in at least FR1, CDR1, FR2, CDR2, and FR3. In specific embodiments, CDR3 can be diversified. In specific embodiments, FR4 is fixed, for example, for VH the JH4 sequence can be used, for kappa VL, the Jk1 sequence can be used, and for lambda VL, the Jl2/3 can be used.

Example 2.1

Determination of VH/VL Pair Germline Gene Usage

In order to identify the predominant VH/VL germline gene pairs from the human immune repertoire, publically available data was analyzed and human B cells were sampled. As a first step, publically available data was reviewed to identify articles describing the VH/VL germline gene pairs isolated from B cells. As mentioned, many publically available databases provide antibody sequences, however, many provide only the sequences of either variable domain, VH or VL, but seldom provide the linkage of VH/VL germline gene pairs. The following articles were identified and analyzed in detail: Wardemann H. et al. (2003) Science 301, 1374-1377 and any supporting tables; Yurasov S. et al. (2005) J. Exp. Med. 201, 703-712 and any supporting tables; Tsuiji M. et al. (2006) J. Exp. Med. 203, 393-401 and any supporting tables; Yurasov S. et al. (2006) J. Exp. Med. 203, 2255-2262 and any supporting tables, Tiller T. et al. (2007) Immunity 26, 205-213 and any supporting tables, and Mietzner B. et al. (2008) PNAS 105, 9727-9732 and any supporting tables.

FIGS. 4-9 show the VH/VL pairs of the B cells isolated in Tsuiji M. et al. (2006).
FIGS. 10-12 show the VH/VL pairs of the B cells isolated in Tiller T. et al. (2007)
FIGS. 13-17 show the VH/VL pairs of the B cells isolated in Mietzner B. et al. (2008)
FIGS. 18-20 show the VH/VL pairs of the B cells isolated in Wardemann H. et al. (2003).
FIGS. 21-23 show the VH/VL pairs of the B cells isolated in identified in Yurasov S. et al. (2005).
FIGS. 24-26 show the VH/VL pairs of the B cells isolated in Yurasov S. et al. (2006)

Additional VH/VL pair data was identified from a sample of human B cells, as described below.

Example 2.2

Determination of VH/VL Pair Gene Usage from a Human Sample

In order to obtain additional VH/VL germline gene pair usage data, PBMCs were isolated from a human host. The PBMCs were sorted, the cDNAs of the B cells were amplified using PCR, the DNA from the B cells was sequenced and then the sequences were blasted with IgBLAST (NCBI) to identify the VH/VL germline gene pairs from each B cell.

Example 2.2(a)

Isolation and Sorting of Human Peripheral Blood Mononuclear Cells (PBMCs)

General methods of isolating and sorting human PBMCs from venous blood and mononuclear cells from bone marrow are described in Tiller et al. JIM 2008. The PBMCs were isolated as follows. 40 ml venous blood was collected from a human donor (7 days after Pandemrix™ vaccination (H1N1 vaccine GlaxoSmithKline)) into 4× Li-Heparin blood collection tubes (Sarstedt) (10 ml each). The contents of each monovette were combined into a single 50 ml Falcon (40 ml total) and then 100 µl RosetteSep (StemCell technologies) (2.5 µl/ml) was added, mixed well on a rotator (5 rpm) and incubated at room temperature for 30 min. The blood/RosettaSep combination was diluted with an equal volume of 1×PBS (Invitrogen). 15 ml of FicollPaque (GE Healthcare) was added to new 50 ml conical tubes and 20 ml of diluted blood was layered over the FicollPaque, totaling (4 tubes: each with 15 ml FicollPaque+20 ml blood). The tubes were spun on a centrifuge for 30 min at 400 g (1400 rpm on sigma laboratory centrifuge) at room temperature with no brake. After centrifugation the enriched PBMCs formed a band at the interface between the plasma and the FicollPaque. The PBMCs were removed from each tube with a pipette and transferred to a new 50 ml tube. The PBMCs were washed by diluting to 40 ml with FACS buffer (PBS, 3% FCS), and spinning on a centrifuge for 10 min at 1250 rpm at 4° C. The PBMCs were counted with Trypan Blue (10 µA sample+90 µA Trypan Blue (1:10 diluted with PBS)).

The PBMCs were stained by resuspending in ~5 ml ice cold FACS buffer. Aliquots of cells were prepared for staining. The fluorophore was prepared to be tested. The aliquots were spun down at 1250 rpm, 4° C. and the supernatant was discarded. Antibodies for staining were added to the cell pellets, according to the scheme described in Table 13.

TABLE 13

|  | 1 unstained | 2 APC | 3 FITC | 4 PE | 5 PE-Cy7 | 6 ASC | 7 mn Bcells |
|---|---|---|---|---|---|---|---|
| volume | 1.3. ml | 250 µl | 250 µl | 250 µl | 250 µl | 1.3 ml | 1.3 ml |
| cell number [×10e6] | ~2.7 | ~0.5 | ~0.5 | ~0.5 | ~0.5 | ~2.7 | ~2.7 |
| CD19-APC | — | 15 µl | — | — | — | 15 µl | 15 µl |
| CD27-FITC | — | — | 30 µl | — | — | 30 µl | 30 µl |
| CD38-PE | — | — | — | 15 µl | — | 15 µl | — |
| CD20-Biotin | — | — | — | — | 2 µl | 2 µl | — |
| CD10-PE | — | — | — | — | — | — | 15 µl |
| IgM-Biotin | — | — | — | — | — | — | 2 µl | incubate 20 min at 4° C. in the dark (here 30 min)
wash with 1 ml of FACS buffer, 1250 rpm, 4° C., 5 min, discard supernatant

|  |  |  |  |  | 100 µl | 200 µl | 200 µl |
|---|---|---|---|---|---|---|---|
| SA-PE-Cy7 (1:500) |  |  |  |  | (~1:1500) | (~1:5000) | (~1:5000) | incubate 20 min at 4° C. in the dark
wash twice with 1 ml of FACS buffer, 1250 rpm, 4° C., 5 min, discard supernatant
resuspend stained cell pellet in 500 µl FACS buffer The cells were then passed through a cell strainer on FACS tubes (Eppendorf) to avoid clogs in the cytometer. The cells were put on ice, and kept in the dark.

The cells were single sorted according to the cell surface marker of the phenotype of interest. For example, antibody secreting cells are CD19$^+$CD20$^{low}$CD27$^{hi}$CD38$^{hi}$ and mature naïve B cells are CD19$^+$CD27$^{neg}$CD10$^{neg}$IgM$^+$. The presence of the cell surface markers was identified using mouse anti-human antibodies (AbD: CD19, CD27, CD38, CD-20, and CD10) (Becton Dickinson: IgM). The cells were sorted on forward versus side scatter (live cell gate with double discrimination) into single cell 96 well PCR plates (Eppendorf) containing 4 µl of 0.5×PBS, 10 mM DTT, 8 U RNAsin (Promega) using a FACS Aria.

The PCR plates were prepared as shown in Table 14.

TABLE 14

| H$_2$0 nuclease free | 3200 µl |
|---|---|
| 10×PBS | 200 µl |

TABLE 14-continued

| 0.1M DTT | 400 µl |
|---|---|
| RNAsin (40 U/µl, Promega) | 200 µl |
| total | 4000 µl |

After sorting, each plate was immediately sealed with a microseal foil (BioRad) and placed on dry ice. Once the cell sorting was finished all plates were frozen at −80° C.

Example 2.2(b)

PCR Amplification of Human B Cell DNA

PBMCs were isolated and sorted as described in Example 2.2(a). Ig gene transcripts of the single sorted mature naïve (mn) B cells and antibody secreting cells (asc) were then PCR amplified for determination of the VH/VL germline gene pairings. General methods of PCR amplifying cDNA of B cells and the primers useful for the same are described in Tiller et. al. J Immunol Methods, 2008.

Figure 27:
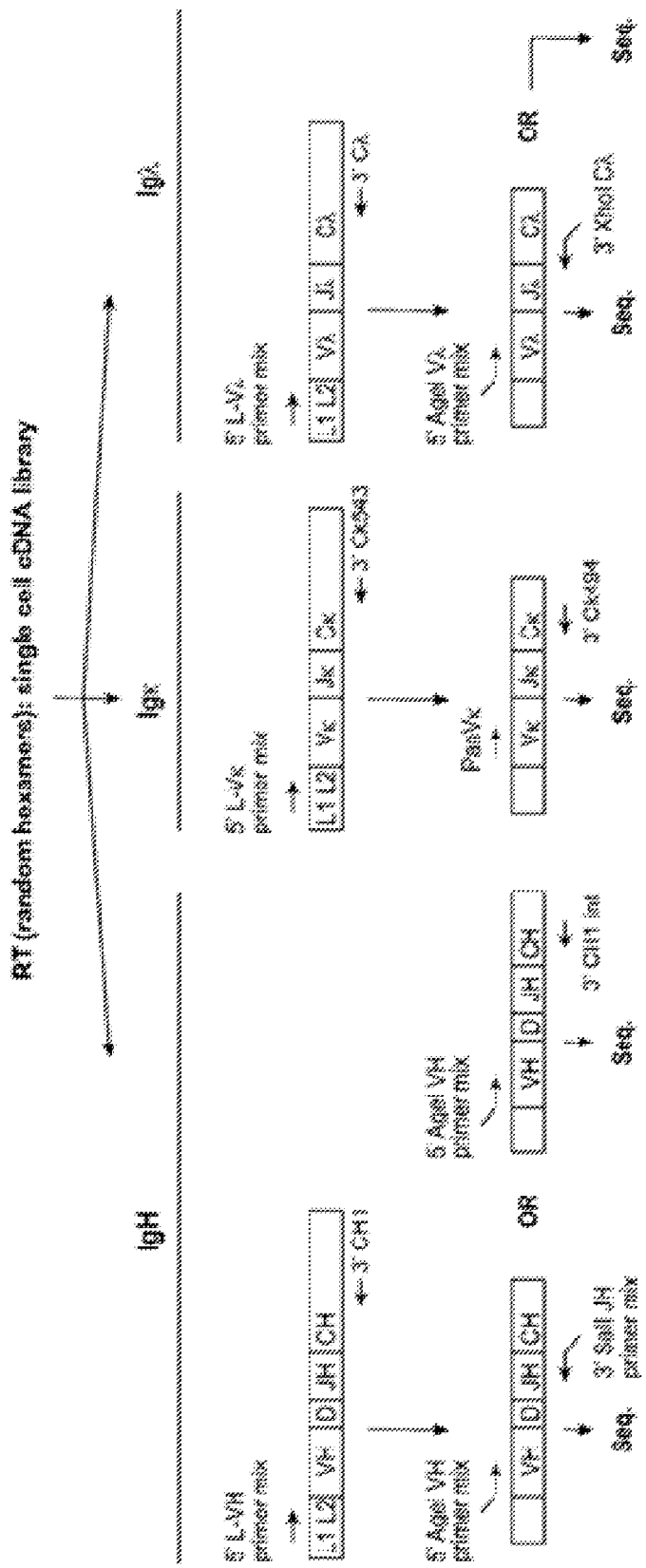
FIG. 27 shows the PCR strategy used for amplifying the cDNAs of the single sorted mature naïve (mn) B cells and antibody secreting cells (asc) isolated from a human host, as described in detail in Example 2.2.

The overall PCR strategy is shown in FIG. 27. The specific primers (SEQ ID NOS 23-59, Respectively, in order of appearance) used are shown in Table 15.

TABLE 15

| for µ or γ heavy chain PCR: | | |
|---|---|---|
| HC 1st PCR | | |
| 5' L-VH 1 | ACAGGTGCCCACTCCCAGGTGCAG | 24 |
| 5' L-VH 3 | AAGGTGTCCAGTGTGARGTGCAG | 23 |
| 5' L-VH 4/6 | CCCAGATGGGTCCTGTCCCAGGTGCAG | 27 |
| 5' L-VH 5 | CAAGGAGTCTGTTCCGAGGTGCAG | 24 |
| 3' Cµ CH1 (mu) | GGGAATTCTCACAGGAGACGA | 21 |
| 3' Cg CH1 (gamma) | GGAAGGTGTGCACGCCGCTGGTC | 23 |
| HC 2nd PCR | | |
| 5' AgeI VH1 | CTGCAACCGGTGTACATTCCCAGGTGCAGCTGGTGCAG | 38 |
| 5' AgeI VH1/5 | CTGCAACCGGTGTACATTCCGAGGTGCAGCTGGTGCAG | 38 |
| 5' AgeI VH3 | CTGCAACCGGTGTACATTCTGAGGTGCAGCTGGTGGAG | 38 |
| 5' AgeI VH3-23 | CTGCAACCGGTGTACATTCTGAGGTGCAGCTGTTGGAG | 38 |

TABLE 15-continued

| | | |
|---|---|---|
| 5' AgeI VH4 | CTGCAACCGGTGTACATTCCCAGGTGCAGCTGCAGGAG | 38 |
| 5' AgeI VH 4-34 | CTGCAACCGGTGTACATTCCCAGGTGCAGCTACAGCAGTG | 40 |
| 3' SaII JH 1/2/4/5 | TGCGAAGTCGACGCTGAGGAGACGGTGACCAG | 32 |
| 3' SaII JH 3 | TGCGAAGTCGACGCTGAAGAGACGGTGACCATTG | 34 |
| 3' SaII JH 6 | TGCGAAGTCGACGCTGAGGAGACGGTGACCGTG | 33 |
| 3' IgG (internal) | GTTCGGGGAAGTAGTCCTTGAC | 22 | for kappa light chain PCR:

k LC 1st PCR

| | | |
|---|---|---|
| 5' L-Vk 1/2 | ATGAGGSTCCCYGCTCAGCTGCTGG | 25 |
| 5' L-Vk 3 | CTCTTCCTCCTGCTACTCTGGCTCCCAG | 28 |
| 5' L-Vk 4 | ATTTCTCTGTTGCTCTGGATCTCTG | 25 |
| 3' Ck 543 | GTTTCTCGTAGTCTGCTTTGCTCA | 24 | k LC 2nd PCR

| | | |
|---|---|---|
| 5' Pan Vk | ATGACCCAGWCTCCABYCWCCCTG | 24 |
| 3' Ck 494 | GTGCTGTCCTTGCTGTCCTGCT | 22 | for lambda light chain PCR:

( LC 1st PCR

| | | |
|---|---|---|
| 5' L-Vl 1 | GGTCCTGGGCCCAGTCTGTGCTG | 23 |
| 5' L-Vl 2 | GGTCCTGGGCCCAGTCTGCCCTG | 23 |
| 5' L-Vl 3 | GCTCTGTGACCTCCTATGAGCTG | 23 |
| 5' L-Vl 4/5 | GGTCTCTCTCSCAGCYTGTGCTG | 23 |
| 5' L-Vl 6 | GTTCTTGGGCCAATTTTATGCTG | 23 |
| 5' L-Vl 7 | GGTCCAATTCYCAGGCTGTGGTG | 23 |
| 5' L-Vl 8 | GAGTGGATTCTCAGACTGTGGTG | 23 |
| 3' Cl | CACCAGTGTGGCCTTGTTGGCTTG | 24 |

( LC 2nd PCR

| | | |
|---|---|---|
| 5'AgeI Vl 1 | CTGCTACCGGTTCCTGGGCCCAGTCTGTGCTGACKCAG | 38 |
| 5'AgeI Vl 2 | CTGCTACCGGTTCCTGGGCCCAGTCTGCCCTGACTCAG | 38 |
| 5'AgeI Vl 3 | CTGCTACCGGTTCTGTGACCTCCTATGAGCTGACWCAG | 38 |
| 5'AgeI Vl 4/5 | CTGCTACCGGTTCTCTCSCAGCYTGTGCTGACTCA | 37 |
| 5'AgeI Vl 6 | CTGCTACCGGTTCTTGGGCCAATTTTATGCTGACTCAG | 38 |
| 5'AgeI Vl 7/8 | CTGCTACCGGTTCCAATTCYCAGRCTGTGGTGACYCAG | 38 |
| 3' XhoI Cl | CTCCTCACTCGAGGGYGGGAACAGAGTG | 28 | cDNAs of the single sorted mature naïve (mn) B cells and antibody secreting cells (asc) were synthesized as follows. First the RHP-Mix, RT-Mix and RT-Mix were prepared on ice. The RHP-Mix was prepared with the following: 115 μl of Random Hexamer Primers (Roche) (300 ng/μl), 115 μl NP-40 (Sigma) (10%), 35 μl RNAsin and 542 μl water. The RT-Mix was prepared with the following: 660 μl of 5×RT buffer, 110 μl of dNTP (Invitrogen) (25 mM each), 450 μl of water, 220μ of 0.1 M DTT, 44 μl of RNAsin (Promega), 55 μl Superscript III (reverse Transcriptase) (Invitrogen).

Next, a plate was put on dry ice, and 3.5 μl of RHP-Mix was added. The plate was covered with foil and incubated at 68° C. in a water bath for 1 min. The plate was then placed on regular ice. Then 7 μl of RT-Mix was added and the wells were closed with aluminium foil. The RT-Amplification-Program was run at the following temperatures and for the following durations: 42° C. for 5', 25° C. for 10', 50° C. for 60', 94° C. for 5', and 4° C. and held. The cDNA was stored at −20° C.

Nested PCR was conducted as follows. Human IgH, Igk and IgL V gene transcripts were PCR amplified independently. 3.5 μl cDNA was used as a template. All PCR reactions were performed in 96 well plates in a total volume of 40 μl per well. For each plate, 3 reaction tubes were prepared each with: 1154 μl of water, 150 μl of 10× buffer, 16 μl of dNTPs, 5 μl of 5' primer mix, 5 μl 3' primer, and 7 μl HotStar Taq (Qiagen). All nested PCR reactions with gene-specific primers or primer mixes were performed with 3.5 μl of unpurified first PCR product. Each round of PCR was performed as shown in Table 16.

TABLE 16

PCR program for amplification of human Ig gene transcripts

| Step | Temperature | Length of time | |
|---|---|---|---|
| Activation of HotStar Taq | 94° C. | 15 min | |
| Denaturation | 94° C. | 30 sec | ⎫ |
| Annealing | 58° C. (IgH/Igk) 60° C. (IgL) | 30 sec | ⎬ 50 cycles |
| Elongation | 72° C. | 55 sec (1$^{st}$ PCR) 45 sec (2$^{nd}$ PCR) | ⎭ |
| Final Elongation | 72° C. | 10 min | |
| Hold | 4° C. | ∞ | |

Next, 3 μl aliquots of the second PCRs were run on a 2% agarose gel containing ethidium bromide in 1×TBE buffer with an equal amount of loading buffer for 45 min at 150 V.

DNA bands were visualized under UV light. The expected PCR product sizes were approximately 450 by for Igγ, 510 bp for Igκ and 405 by for Igλ.

4 μl of VH, VK and VL PCR products (w/matching corresponding VH or VL product) were combined w/16 μl ddH$_2$O into 96 well plates and submitted to Eurofins MWG Operon, Ebersberg, Germany for plate sequencing. The sequencing primers were provided at 10 pmol/μl (stock 50 pmol/μl, 1:5 dilution) and are shown in Table 17.

TABLE 17

| | |
|---|---|
| μHC: | 5' Age VH-Mix |
| γHC: | 3' IgGinternal |
| VK: | 5' Pan-VK |
| VL: | 5' VL-Mix |

The sequencing results were blasted with IgBLAST (NCBIO) to identify the VH, VK, and VL germline genes, shown in FIGS. 28A-C (28-36).

Example 2.3

VH/VL Germline Gene Pairs Identified in the Human Immune Repertoire

The VH/VL germline gene pair data identified from the publically available literature as described in Example 2.1 and shown in FIGS. 4-26 was pooled with the data identified from a human sample as described in Example 2.2 and shown in FIGS. 28-36.

The pooled data was analyzed and is shown as a ranking in Table 18, i.e. the ranking of the concentration (%) of the VH/VL germline gene pairs identified in the human immune repertoire.

TABLE 18

Frequency of the VH/VL germline gene pair usage in the human immune repertoire
N = 2137

| pos | V heavy | V light | % |
|---|---|---|---|
| 1 | IGHV3-23 | IGKV1-5 | 1.26 |
| 2 | IGHV4-34 | IGKV3-20 | 1.17 |
| 3 | IGHV3-23 | IGKV3-20 | 1.12 |
| 4 | IGHV4-39 | IGKV3-15 | 1.03 |
| 5 | IGHV3-23 | IGKV3-15 | 0.94 |
| 6 | IGHV4-59 | IGKV1-39/1D-39 | 0.89 |
| 7 | IGHV4-39 | IGKV1-39/1D-39 | 0.84 |
|   | IGHV4-34 | IGKV1-39/1D-39 | 0.84 |
| 8 | IGHV4-59 | IGKV3-20 | 0.70 |
|   | IGHV1-18 | IGKV3-20 | 0.70 |
| 9 | IGHV3-30 | IGKV3-20 | 0.66 |
|   | IGHV4-39 | IGKV1-5 | 0.66 |
|   | IGHV1-69 | IGKV1-39/1D-39 | 0.66 |
|   | IGHV5-51 | IGLV 1-40 | 0.66 |
| 10 | IGHV3-23 | IGKV4-1 | 0.61 |
|   | IGHV4-39 | IGKV3-20 | 0.61 |
|   | IGHV3-23 | IGLV 2-14 | 0.61 |
|   | IGHV4-39 | IGLV 3-21 | 0.61 |
| 11 | IGHV3-23 | IGKV1-39/1D-39 | 0.56 |
|   | IGHV3-30 | IGKV1-39/1D-39 | 0.56 |
|   | IGHV3-30 | IGKV3-11 | 0.56 |
|   | IGHV1-69 | IGKV3-20 | 0.56 |
|   | IGHV3-48 | IGKV3-20 | 0.56 |
|   | IGHV1-2 | IGKV3-20 | 0.56 |
| 12 | IGHV3-30 | IGKV4-1 | 0.51 |
|   | IGHV5-51 | IGLV 2-14 | 0.51 |
| 13 | IGHV4-59 | IGKV4-1 | 0.47 |
|   | IGHV5-51 | IGKV3-20 | 0.47 |
|   | IGHV3-7 | IGKV1-39/1D-39 | 0.47 |
|   | IGHV3-7 | IGKV1-5 | 0.47 |

TABLE 18-continued

Frequency of the VH/VL germline gene pair usage in the human immune repertoire
N = 2137

| pos | V heavy | V light | % |
|---|---|---|---|
|   | IGHV3-15 | IGKV3-20 | 0.47 |
|   | IGHV4-39 | IGLV 2-14 | 0.47 |
|   | IGHV4-39 | IGLV 2-8 | 0.47 |
|   | IGHV4-34 | IGLV 2-14 | 0.47 |
| 14 | IGHV3-23 | IGKV3-11 | 0.42 |
|   | IGHV3-30 | IGKV1-5 | 0.42 |
|   | IGHV3-30 | IGKV3-15 | 0.42 |
|   | IGHV4-34 | IGKV1-5 | 0.42 |
|   | IGHV3-21 | IGKV1-5 | 0.42 |
|   | IGHV3-21 | IGKV3-15 | 0.42 |
|   | IGHV3-30 | IGLV 1-51 | 0.42 |
|   | IGHV4-34 | IGLV 1-51 | 0.42 |
|   | IGHV3-21 | IGLV 1-51 | 0.42 |
|   | IGHV3-53 | IGLV 1-44 | 0.42 |
| 15 | IGHV4-59 | IGKV3-15 | 0.37 |
|   | IGHV4-34 | IGKV3-15 | 0.37 |
|   | IGHV5-51 | IGKV4-1 | 0.37 |
|   | IGHV1-69 | IGKV4-1 | 0.37 |
|   | IGHV1-69 | IGKV3-11 | 0.37 |
|   | IGHV3-7 | IGKV3-15 | 0.37 |
|   | IGHV1-18 | IGKV1-39/1D-39 | 0.37 |
|   | IGHV3-48 | IGKV1-39/1D-39 | 0.37 |
|   | IGHV3-33 | IGKV3-15 | 0.37 |
|   | IGHV3-53 | IGKV1-5 | 0.37 |
|   | IGHV4-59 | IGLV 1-40 | 0.37 |
|   | IGHV1-69 | IGLV 2-14 | 0.37 |
|   | IGHV1-69 | IGLV 1-44 | 0.37 |
|   | IGHV4-31 | IGLV 2-14 | 0.37 |
|   | IGHV1-2 | IGLV 2-14 | 0.37 |
| 16 | IGHV3-23 | IGKV2-28/2D-28 | 0.33 |
|   | IGHV3-30 | IGKV1-9 | 0.33 |
|   | IGHV4-34 | IGKV4-1 | 0.33 |
|   | IGHV5-51 | IGKV1-39/1D-39 | 0.33 |
|   | IGHV5-51 | IGKV3-15 | 0.33 |
|   | IGHV1-69 | IGKV3-15 | 0.33 |
|   | IGHV1-18 | IGKV1-33/1D-33 | 0.33 |
|   | IGHV3-48 | IGKV3-11 | 0.33 |
|   | IGHV3-21 | IGKV1-39/1D-39 | 0.33 |
|   | IGHV4-31 | IGKV3-20 | 0.33 |
|   | IGHV4-31 | IGKV3-11 | 0.33 |
|   | IGHV3-30 | IGLV 2-14 | 0.33 |
|   | IGHV4-39 | IGLV 1-44 | 0.33 |
|   | IGHV1-69 | IGLV 1-40 | 0.33 |
|   | IGHV3-9 | IGLV 2-23 | 0.33 |
| 17 | IGHV3-23 | IGKV1-33/1D-33 | 0.28 |
|   | IGHV4-39 | IGKV3-11 | 0.28 |
|   | IGHV4-34 | IGKV3-11 | 0.28 |
|   | IGHV4-34 | IGKV2-28/2D-28 | 0.28 |
|   | IGHV5-51 | IGKV3-11 | 0.28 |
|   | IGHV5-51 | IGKV1-13 | 0.28 |
|   | IGHV3-7 | IGKV3-20 | 0.28 |
|   | IGHV3-48 | IGKV3-15 | 0.28 |
|   | IGHV3-48 | IGKV4-1 | 0.28 |
|   | IGHV3-48 | IGKV1-33/1D-33 | 0.28 |
|   | IGHV3-15 | IGKV1-39/1D-39 | 0.28 |
|   | IGHV3-15 | IGKV1-5 | 0.28 |
|   | IGHV1-2 | IGKV1-39/1D-39 | 0.28 |
|   | IGHV3-33 | IGKV3-20 | 0.28 |
|   | IGHV3-33 | IGKV1-39/1D-39 | 0.28 |
|   | IGHV3-33 | IGKV4-1 | 0.28 |
|   | IGHV3-53 | IGKV3-15 | 0.28 |
|   | IGHV3-11 | IGKV1-5 | 0.28 |
|   | IGHV4-4 | IGKV3-20 | 0.28 |
|   | IGHV1-46 | IGKV3-20 | 0.28 |
|   | IGHV3-23 | IGLV 1-40 | 0.28 |
|   | IGHV3-23 | IGLV 3-21 | 0.28 |
|   | IGHV4-39 | IGLV 1-40 | 0.28 |
|   | IGHV4-34 | IGLV 1-40 | 0.28 |
|   | IGHV4-34 | IGLV 1-47 | 0.28 |
|   | IGHV3-48 | IGLV 2-14 | 0.28 |
|   | IGHV3-48 | IGLV 1-47 | 0.28 |
|   | IGHV1-2 | IGLV 1-40 | 0.28 |
|   | IGHV3-9 | IGLV 2-14 | 0.28 |
|   | IGHV4-4 | IGLV 1-44 | 0.28 |

TABLE 18-continued

Frequency of the VH/VL germline gene pair usage in the human immune repertoire
N = 2137

| pos | V heavy | V light | % |
|---|---|---|---|
| 18 | IGHV3-23 | IGKV1-17 | 0.23 |
| | IGHV4-39 | IGKV4-1 | 0.23 |
| | IGHV4-39 | IGKV2-28/2D-28 | 0.23 |
| | IGHV1-69 | IGKV1-5 | 0.23 |
| | IGHV3-7 | IGKV4-1 | 0.23 |
| | IGHV1-18 | IGKV1-5 | 0.23 |
| | IGHV1-18 | IGKV2-28/2D-28 | 0.23 |
| | IGHV3-21 | IGKV3-20 | 0.23 |
| | IGHV3-33 | IGKV1-5 | 0.23 |
| | IGHV3-53 | IGKV1-39/1D-39 | 0.23 |
| | IGHV3-53 | IGKV1-33/1D-33 | 0.23 |
| | IGHV3-11 | IGKV1-39/1D-39 | 0.23 |
| | IGHV3-11 | IGKV3-15 | 0.23 |
| | IGHV4-4 | IGKV1-39/1D-39 | 0.23 |
| | IGHV1-46 | IGKV1-39/1D-39 | 0.23 |
| | IGHV4-61 | IGKV4-1 | 0.23 |
| | IGHV3-23 | IGLV 1-44 | 0.23 |
| | IGHV3-23 | IGLV 2-11 | 0.23 |
| | IGHV3-23 | IGLV 3-1 | 0.23 |
| | IGHV3-30 | IGLV 1-40 | 0.23 |
| | IGHV4-39 | IGLV 1-51 | 0.23 |
| | IGHV4-39 | IGLV 2-23 | 0.23 |
| | IGHV4-59 | IGLV 3-1 | 0.23 |
| | IGHV5-51 | IGLV 1-44 | 0.23 |
| | IGHV1-69 | IGLV 1-51 | 0.23 |
| | IGHV1-69 | IGLV 2-11 | 0.23 |
| | IGHV1-18 | IGLV 2-14 | 0.23 |
| | IGHV1-18 | IGLV 1-40 | 0.23 |
| | IGHV3-21 | IGLV 2-14 | 0.23 |
| | IGHV1-2 | IGLV 1-44 | 0.23 |
| 19 | IGHV3-23 | IGKV1-27 | 0.19 |
| | IGHV3-23 | IGKV1-8 | 0.19 |
| | IGHV3-30 | IGKV2-28/2D-28 | 0.19 |
| | IGHV4-39 | IGKV1-33/1D-33 | 0.19 |
| | IGHV4-39 | IGKV1-27 | 0.19 |
| | IGHV4-59 | IGKV3-11 | 0.19 |
| | IGHV5-51 | IGKV1-5 | 0.19 |
| | IGHV5-51 | IGKV2-28/2D-28 | 0.19 |
| | IGHV3-7 | IGKV3-11 | 0.19 |
| | IGHV3-7 | IGKV2-30 | 0.19 |
| | IGHV1-18 | IGKV3-15 | 0.19 |
| | IGHV1-18 | IGKV3-11 | 0.19 |
| | IGHV3-21 | IGKV4-1 | 0.19 |
| | IGHV3-15 | IGKV3-15 | 0.19 |
| | IGHV3-15 | IGKV4-1 | 0.19 |
| | IGHV3-15 | IGKV1-33/1D-33 | 0.19 |
| | IGHV4-31 | IGKV1-39/1D-39 | 0.19 |
| | IGHV4-31 | IGKV1-5 | 0.19 |
| | IGHV4-31 | IGKV3-15 | 0.19 |
| | IGHV4-31 | IGKV2-28/2D-28 | 0.19 |
| | IGHV3-33 | IGKV2-28/2D-28 | 0.19 |
| | IGHV3-53 | IGKV4-1 | 0.19 |
| | IGHV3-53 | IGKV3-11 | 0.19 |
| | IGHV3-74 | IGKV3-20 | 0.19 |
| | IGHV4-4 | IGKV1-5 | 0.19 |
| | IGHV1-46 | IGKV1-9 | 0.19 |
| | IGHV1-8 | IGKV3-15 | 0.19 |
| | IGHV1-24 | IGKV3-11 | 0.19 |
| | IGHV1-3 | IGKV1-39/1D-39 | 0.19 |
| | IGHV3-49 | IGKV1-39/1D-39 | 0.19 |
| | IGHV3-23 | IGLV 2-23 | 0.19 |
| | IGHV3-30 | IGLV 1-44 | 0.19 |
| | IGHV4-59 | IGLV 2-14 | 0.19 |
| | IGHV4-59 | IGLV 1-44 | 0.19 |
| | IGHV4-59 | IGLV 1-51 | 0.19 |
| | IGHV4-34 | IGLV 2-8 | 0.19 |
| | IGHV5-51 | IGLV 1-47 | 0.19 |
| | IGHV1-69 | IGLV 2-8 | 0.19 |
| | IGHV3-7 | IGLV 1-40 | 0.19 |
| | IGHV3-15 | IGLV 1-44 | 0.19 |
| | IGHV4-31 | IGLV 2-23 | 0.19 |
| | IGHV3-33 | IGLV 2-14 | 0.19 |
| | IGHV3-33 | IGLV 1-47 | 0.19 |
| | IGHV3-33 | IGLV 2-23 | 0.19 |
| | IGHV3-33 | IGLV 3-21 | 0.19 |
| | IGHV3-9 | IGLV 1-44 | 0.19 |
| | IGHV4-4 | IGLV 2-14 | 0.19 |
| | IGHV1-46 | IGLV 1-51 | 0.19 |
| | IGHV4-61 | IGLV 1-44 | 0.19 |
| | IGHV1-8 | IGLV 2-14 | 0.19 |
| | IGHV4-28 | IGLV 2-23 | 0.19 |
| 20 | IGHV3-23 | IGKV1-9 | 0.14 |
| | IGHV3-23 | IGKV1-16 | 0.14 |
| | IGHV4-39 | IGKV1-6 | 0.14 |
| | IGHV4-59 | IGKV1-5 | 0.14 |
| | IGHV4-59 | IGKV1-27 | 0.14 |
| | IGHV4-34 | IGKV1-33/1D-33 | 0.14 |
| | IGHV5-51 | IGKV1-33/1D-33 | 0.14 |
| | IGHV1-69 | IGKV2-28/2D-28 | 0.14 |
| | IGHV1-69 | IGKV1-33/1D-33 | 0.14 |
| | IGHV3-7 | IGKV2-28/2D-28 | 0.14 |
| | IGHV3-7 | IGKV1-8 | 0.14 |
| | IGHV3-48 | IGKV2-28/2D-28 | 0.14 |
| | IGHV3-48 | IGKV1-8 | 0.14 |
| | IGHV3-15 | IGKV3-11 | 0.14 |
| | IGHV3-15 | IGKV2-28/2D-28 | 0.14 |
| | IGHV3-15 | IGKV1-9 | 0.14 |
| | IGHV4-31 | IGKV1-33/1D-33 | 0.14 |
| | IGHV1-2 | IGKV1-5 | 0.14 |
| | IGHV1-2 | IGKV4-1 | 0.14 |
| | IGHV3-11 | IGKV3-20 | 0.14 |
| | IGHV3-11 | IGKV3-11 | 0.14 |
| | IGHV3-11 | IGKV2-28/2D-28 | 0.14 |
| | IGHV3-9 | IGKV1-39/1D-39 | 0.14 |
| | IGHV3-9 | IGKV1-5 | 0.14 |
| | IGHV3-9 | IGKV4-1 | 0.14 |
| | IGHV3-9 | IGKV2D-29 | 0.14 |
| | IGHV3-74 | IGKV1-39/1D-39 | 0.14 |
| | IGHV3-74 | IGKV1-5 | 0.14 |
| | IGHV3-74 | IGKV3-15 | 0.14 |
| | IGHV3-74 | IGKV4-1 | 0.14 |
| | IGHV4-4 | IGKV3-15 | 0.14 |
| | IGHV4-4 | IGKV4-1 | 0.14 |
| | IGHV4-4 | IGKV3-11 | 0.14 |
| | IGHV1-46 | IGKV1-5 | 0.14 |
| | IGHV1-46 | IGKV3-15 | 0.14 |
| | IGHV4-61 | IGKV1-39/1D-39 | 0.14 |
| | IGHV1-24 | IGKV1-39/1D-39 | 0.14 |
| | IGHV1-24 | IGKV3-15 | 0.14 |
| | IGHV1-3 | IGKV3-15 | 0.14 |
| | IGHV3-49 | IGKV1-17 | 0.14 |
| | IGHV3-43 | IGKV1-5 | 0.14 |
| | IGHV7-81 | IGKV3-20 | 0.14 |
| | IGHV3-13 | IGKV1-39/1D-39 | 0.14 |
| | IGHV3-23 | IGLV 1-51 | 0.14 |
| | IGHV3-30 | IGLV 3-21 | 0.14 |
| | IGHV3-30 | IGLV 3-1 | 0.14 |
| | IGHV4-39 | IGLV 1-47 | 0.14 |
| | IGHV4-39 | IGLV 2-18 | 0.14 |
| | IGHV4-59 | IGLV 1-47 | 0.14 |
| | IGHV5-51 | IGLV 2-23 | 0.14 |
| | IGHV5-51 | IGLV 3-21 | 0.14 |
| | IGHV1-69 | IGLV 2-23 | 0.14 |
| | IGHV3-7 | IGLV 1-44 | 0.14 |
| | IGHV3-7 | IGLV 1-51 | 0.14 |
| | IGHV3-7 | IGLV 1-47 | 0.14 |
| | IGHV3-7 | IGLV 3-21 | 0.14 |
| | IGHV1-18 | IGLV 1-44 | 0.14 |
| | IGHV1-18 | IGLV 1-51 | 0.14 |
| | IGHV3-48 | IGLV 3-1 | 0.14 |
| | IGHV3-21 | IGLV 1-47 | 0.14 |
| | IGHV3-15 | IGLV 7-46 | 0.14 |
| | IGHV4-31 | IGLV 1-40 | 0.14 |
| | IGHV4-31 | IGLV 1-51 | 0.14 |
| | IGHV4-31 | IGLV 1-47 | 0.14 |
| | IGHV1-2 | IGLV 1-51 | 0.14 |
| | IGHV1-2 | IGLV 2-23 | 0.14 |
| | IGHV1-2 | IGLV 3-1 | 0.14 |

TABLE 18-continued

Frequency of the VH/VL germline gene pair usage in the human immune repertoire
N = 2137

| pos | V heavy | V light | % |
|---|---|---|---|
|  | IGHV3-11 | IGLV 2-14 | 0.14 |
|  | IGHV3-11 | IGLV 1-44 | 0.14 |
|  | IGHV3-11 | IGLV 2-11 | 0.14 |
|  | IGHV3-11 | IGLV 3-1 | 0.14 |
|  | IGHV3-9 | IGLV 1-47 | 0.14 |
|  | IGHV3-9 | IGLV 2-11 | 0.14 |
|  | IGHV3-74 | IGLV 2-23 | 0.14 |
|  | IGHV3-74 | IGLV 3-21 | 0.14 |
|  | IGHV4-4 | IGLV 1-40 | 0.14 |
|  | IGHV1-46 | IGLV 2-14 | 0.14 |
|  | IGHV1-46 | IGLV 1-44 | 0.14 |
|  | IGHV4-61 | IGLV 2-14 | 0.14 |
| 21 | IGHV3-23 | IGKV2D-29 | 0.09 |
|  | IGHV3-23 | IGKV2-29 | 0.09 |
|  | IGHV3-23 | IGKV2-40/2D-40 | 0.09 |
|  | IGHV3-30 | IGKV1-33/1D-33 | 0.09 |
|  | IGHV3-30 | IGKV2-30 | 0.09 |
|  | IGHV3-30 | IGKV1-8 | 0.09 |
|  | IGHV3-30 | IGKV1-6 | 0.09 |
|  | IGHV3-30 | IGKV2-24 | 0.09 |
|  | IGHV3-30 | IGKV1D-8 | 0.09 |
|  | IGHV4-39 | IGKV2-30 | 0.09 |
|  | IGHV4-59 | IGKV1-33/1D-33 | 0.09 |
|  | IGHV4-59 | IGKV1-12 | 0.09 |
|  | IGHV4-34 | IGKV1-9 | 0.09 |
|  | IGHV4-34 | IGKV1-17 | 0.09 |
|  | IGHV4-34 | IGKV1-16 | 0.09 |
|  | IGHV5-51 | IGKV2-30 | 0.09 |
|  | IGHV1-69 | IGKV1-27 | 0.09 |
|  | IGHV1-69 | IGKV1-8 | 0.09 |
|  | IGHV1-69 | IGKV3D-15 | 0.09 |
|  | IGHV3-7 | IGKV1-9 | 0.09 |
|  | IGHV3-7 | IGKV1-17 | 0.09 |
|  | IGHV3-7 | IGKV1-27 | 0.09 |
|  | IGHV3-7 | IGKV1-13 | 0.09 |
|  | IGHV1-18 | IGKV4-1 | 0.09 |
|  | IGHV1-18 | IGKV2-30 | 0.09 |
|  | IGHV3-48 | IGKV1-9 | 0.09 |
|  | IGHV3-48 | IGKV1-17 | 0.09 |
|  | IGHV3-48 | IGKV1-16 | 0.09 |
|  | IGHV3-21 | IGKV3-11 | 0.09 |
|  | IGHV3-21 | IGKV2-28/2D-28 | 0.09 |
|  | IGHV3-21 | IGKV1-27 | 0.09 |
|  | IGHV3-21 | IGKV1-8 | 0.09 |
|  | IGHV3-21 | IGKV1-6 | 0.09 |
|  | IGHV4-31 | IGKV4-1 | 0.09 |
|  | IGHV4-31 | IGKV1-17 | 0.09 |
|  | IGHV4-31 | IGKV1-27 | 0.09 |
|  | IGHV1-2 | IGKV3-15 | 0.09 |
|  | IGHV1-2 | IGKV2-28/2D-28 | 0.09 |
|  | IGHV1-2 | IGKV1-27 | 0.09 |
|  | IGHV3-33 | IGKV3-11 | 0.09 |
|  | IGHV3-33 | IGKV1-33/1D-33 | 0.09 |
|  | IGHV3-33 | IGKV1-9 | 0.09 |
|  | IGHV3-53 | IGKV3-20 | 0.09 |
|  | IGHV3-53 | IGKV1-27 | 0.09 |
|  | IGHV3-53 | IGKV1-8 | 0.09 |
|  | IGHV3-11 | IGKV4-1 | 0.09 |
|  | IGHV3-11 | IGKV1-6 | 0.09 |
|  | IGHV3-9 | IGKV3-15 | 0.09 |
|  | IGHV3-9 | IGKV3-11 | 0.09 |
|  | IGHV3-9 | IGKV1-16 | 0.09 |
|  | IGHV3-74 | IGKV3-11 | 0.09 |
|  | IGHV3-74 | IGKV2-30 | 0.09 |
|  | IGHV4-4 | IGKV2-28/2D-28 | 0.09 |
|  | IGHV4-4 | IGKV2D-29 | 0.09 |
|  | IGHV1-46 | IGKV3-11 | 0.09 |
|  | IGHV1-46 | IGKV1-27 | 0.09 |
|  | IGHV1-46 | IGKV1-16 | 0.09 |
|  | IGHV4-61 | IGKV3-15 | 0.09 |
|  | IGHV1-8 | IGKV3-20 | 0.09 |
|  | IGHV1-8 | IGKV4-1 | 0.09 |
|  | IGHV1-24 | IGKV2-28/2D-28 | 0.09 |
|  | IGHV1-24 | IGKV2-30 | 0.09 |
|  | IGHV1-3 | IGKV3-20 | 0.09 |
|  | IGHV3-49 | IGKV3-20 | 0.09 |
|  | IGHV3-49 | IGKV1-5 | 0.09 |
|  | IGHV3-43 | IGKV3-11 | 0.09 |
|  | IGHV3-64 | IGKV1-5 | 0.09 |
|  | IGHV3-64 | IGKV3-11 | 0.09 |
|  | IGHV7-81 | IGKV1-39/1D-39 | 0.09 |
|  | IGHV3-13 | IGKV4-1 | 0.09 |
|  | IGHV3-72 | IGKV1-5 | 0.09 |
|  | IGHV3-72 | IGKV3-15 | 0.09 |
|  | IGHV1-58 | IGKV3-20 | 0.09 |
|  | IGHV3-66 | IGKV1-39/1D-39 | 0.09 |
|  | IGHV3-23 | IGLV 1-36 | 0.09 |
|  | IGHV3-30 | IGLV 2-23 | 0.09 |
|  | IGHV3-30 | IGLV 2-11 | 0.09 |
|  | IGHV3-30 | IGLV 9-49 | 0.09 |
|  | IGHV3-30 | IGLV 3-10 | 0.09 |
|  | IGHV4-39 | IGLV 3-1 | 0.09 |
|  | IGHV4-39 | IGLV 6-57 | 0.09 |
|  | IGHV4-59 | IGLV 2-23 | 0.09 |
|  | IGHV4-59 | IGLV 3-21 | 0.09 |
|  | IGHV4-59 | IGLV 2-11 | 0.09 |
|  | IGHV4-34 | IGLV 1-44 | 0.09 |
|  | IGHV4-34 | IGLV 2-23 | 0.09 |
|  | IGHV4-34 | IGLV 3-21 | 0.09 |
|  | IGHV4-34 | IGLV 3-25 | 0.09 |
|  | IGHV5-51 | IGLV 1-36 | 0.09 |
|  | IGHV5-51 | IGLV 3-25 | 0.09 |
|  | IGHV1-69 | IGLV 1-47 | 0.09 |
|  | IGHV1-69 | IGLV 3-21 | 0.09 |
|  | IGHV1-69 | IGLV 3-1 | 0.09 |
|  | IGHV3-7 | IGLV 2-14 | 0.09 |
|  | IGHV1-18 | IGLV 2-8 | 0.09 |
|  | IGHV1-18 | IGLV 6-57 | 0.09 |
|  | IGHV3-48 | IGLV 2-11 | 0.09 |
|  | IGHV3-21 | IGLV 1-40 | 0.09 |
|  | IGHV3-21 | IGLV 1-44 | 0.09 |
|  | IGHV3-21 | IGLV 3-21 | 0.09 |
|  | IGHV3-21 | IGLV 2-11 | 0.09 |
|  | IGHV3-21 | IGLV 4-69 | 0.09 |
|  | IGHV3-15 | IGLV 1-40 | 0.09 |
|  | IGHV3-15 | IGLV 1-51 | 0.09 |
|  | IGHV3-15 | IGLV 3-1 | 0.09 |
|  | IGHV3-15 | IGLV 2-8 | 0.09 |
|  | IGHV3-15 | IGLV 7-43 | 0.09 |
|  | IGHV4-31 | IGLV 3-21 | 0.09 |
|  | IGHV1-2 | IGLV 2-8 | 0.09 |
|  | IGHV1-2 | IGLV 7-46 | 0.09 |
|  | IGHV3-33 | IGLV 6-57 | 0.09 |
|  | IGHV3-53 | IGLV 2-14 | 0.09 |
|  | IGHV3-11 | IGLV 2-23 | 0.09 |
|  | IGHV3-11 | IGLV 3-21 | 0.09 |
|  | IGHV3-11 | IGLV 4-69 | 0.09 |
|  | IGHV3-9 | IGLV 3-21 | 0.09 |
|  | IGHV3-9 | IGLV 2-8 | 0.09 |
|  | IGHV3-74 | IGLV 2-14 | 0.09 |
|  | IGHV4-4 | IGLV 1-51 | 0.09 |
|  | IGHV4-4 | IGLV 2-23 | 0.09 |
|  | IGHV4-4 | IGLV 2-8 | 0.09 |
|  | IGHV1-46 | IGLV 2-11 | 0.09 |
|  | IGHV4-61 | IGLV 2-11 | 0.09 |
|  | IGHV1-8 | IGLV 1-47 | 0.09 |
|  | IGHV1-24 | IGLV 2-23 | 0.09 |
|  | IGHV1-3 | IGLV 2-14 | 0.09 |
|  | IGHV1-3 | IGLV 2-23 | 0.09 |
|  | IGHV1-3 | IGLV 3-1 | 0.09 |
|  | IGHV3-49 | IGLV 3-21 | 0.09 |
|  | IGHV4-28 | IGLV 1-44 | 0.09 |
|  | IGHV4-28 | IGLV 1-51 | 0.09 |
|  | IGHV4-28 | IGLV 1-36 | 0.09 |
|  | IGHV3-43 | IGLV 1-51 | 0.09 |
|  | IGHV3-64 | IGLV 3-21 | 0.09 |
|  | IGHV7-81 | IGLV 2-14 | 0.09 |
|  | IGHV7-81 | IGLV 3-21 | 0.09 |

TABLE 18-continued

Frequency of the VH/VL germline gene pair usage in the human immune repertoire
N = 2137

| pos | V heavy | V light | % |
|---|---|---|---|
| 22 | IGHV3-23 | IGKV2-30 | 0.05 |
| | IGHV3-23 | IGKV1-12 | 0.05 |
| | IGHV3-23 | IGKV3D-20 | 0.05 |
| | IGHV3-23 | IGKV1D-12 | 0.05 |
| | IGHV3-23 | IGKV1D-13 | 0.05 |
| | IGHV3-30 | IGKV1-17 | 0.05 |
| | IGHV3-30 | IGKV1-27 | 0.05 |
| | IGHV3-30 | IGKV1-16 | 0.05 |
| | IGHV3-30 | IGKV2D-29 | 0.05 |
| | IGHV3-30 | IGKV1-13 | 0.05 |
| | IGHV3-30 | IGKV5-2 | 0.05 |
| | IGHV3-30 | IGKV2D-30 | 0.05 |
| | IGHV4-39 | IGKV1-17 | 0.05 |
| | IGHV4-39 | IGKV3D-15 | 0.05 |
| | IGHV4-59 | IGKV2-30 | 0.05 |
| | IGHV4-59 | IGKV1-17 | 0.05 |
| | IGHV4-59 | IGKV1-8 | 0.05 |
| | IGHV4-59 | IGKV1-16 | 0.05 |
| | IGHV4-59 | IGKV1D-43 | 0.05 |
| | IGHV4-59 | IGKV2D-30 | 0.05 |
| | IGHV4-59 | IGKV1D-17 | 0.05 |
| | IGHV4-34 | IGKV1-27 | 0.05 |
| | IGHV4-34 | IGKV1-8 | 0.05 |
| | IGHV4-34 | IGKV1-12 | 0.05 |
| | IGHV5-51 | IGKV1-9 | 0.05 |
| | IGHV5-51 | IGKV1-17 | 0.05 |
| | IGHV5-51 | IGKV1-27 | 0.05 |
| | IGHV5-51 | IGKV1-12 | 0.05 |
| | IGHV1-69 | IGKV2-30 | 0.05 |
| | IGHV1-69 | IGKV1-16 | 0.05 |
| | IGHV1-69 | IGKV1-6 | 0.05 |
| | IGHV1-69 | IGKV2D-29 | 0.05 |
| | IGHV1-69 | IGKV2D-30 | 0.05 |
| | IGHV1-69 | IGKV1D-16 | 0.05 |
| | IGHV3-7 | IGKV1-6 | 0.05 |
| | IGHV3-7 | IGKV1D-8 | 0.05 |
| | IGHV3-7 | IGKV1D-17 | 0.05 |
| | IGHV1-18 | IGKV1-17 | 0.05 |
| | IGHV1-18 | IGKV1-8 | 0.05 |
| | IGHV1-18 | IGKV1-16 | 0.05 |
| | IGHV1-18 | IGKV1-12 | 0.05 |
| | IGHV1-18 | IGKV1-13 | 0.05 |
| | IGHV1-18 | IGKV2-40/2D-40 | 0.05 |
| | IGHV3-48 | IGKV1-5 | 0.05 |
| | IGHV3-48 | IGKV1-27 | 0.05 |
| | IGHV3-48 | IGKV1-6 | 0.05 |
| | IGHV3-48 | IGKV2D-29 | 0.05 |
| | IGHV3-48 | IGKV3D-20 | 0.05 |
| | IGHV3-48 | IGKV1D-12 | 0.05 |
| | IGHV3-21 | IGKV2D-29 | 0.05 |
| | IGHV3-15 | IGKV2-30 | 0.05 |
| | IGHV3-15 | IGKV1-27 | 0.05 |
| | IGHV3-15 | IGKV2D-29 | 0.05 |
| | IGHV3-15 | IGKV1-13 | 0.05 |
| | IGHV3-15 | IGKV1D-43 | 0.05 |
| | IGHV4-31 | IGKV1-6 | 0.05 |
| | IGHV4-31 | IGKV2-29 | 0.05 |
| | IGHV4-31 | IGKV2-40/2D-40 | 0.05 |
| | IGHV1-2 | IGKV1-33/1D-33 | 0.05 |
| | IGHV1-2 | IGKV2-30 | 0.05 |
| | IGHV1-2 | IGKV1-8 | 0.05 |
| | IGHV1-2 | IGKV1-6 | 0.05 |
| | IGHV3-33 | IGKV1-17 | 0.05 |
| | IGHV3-33 | IGKV1-8 | 0.05 |
| | IGHV3-33 | IGKV1-16 | 0.05 |
| | IGHV3-33 | IGKV2-24 | 0.05 |
| | IGHV3-53 | IGKV2-28/2D-28 | 0.05 |
| | IGHV3-53 | IGKV1-9 | 0.05 |
| | IGHV3-53 | IGKV1-17 | 0.05 |
| | IGHV3-53 | IGKV1-12 | 0.05 |
| | IGHV3-53 | IGKV2-29 | 0.05 |
| | IGHV3-53 | IGKV1D-16 | 0.05 |
| | IGHV3-11 | IGKV1-33/1D-33 | 0.05 |
| | IGHV3-11 | IGKV1-9 | 0.05 |
| | IGHV3-11 | IGKV1-17 | 0.05 |
| | IGHV3-11 | IGKV1-12 | 0.05 |
| | IGHV3-11 | IGKV1D-8 | 0.05 |
| | IGHV3-9 | IGKV3-20 | 0.05 |
| | IGHV3-9 | IGKV2-28/2D-28 | 0.05 |
| | IGHV3-9 | IGKV1-17 | 0.05 |
| | IGHV3-9 | IGKV1-27 | 0.05 |
| | IGHV3-9 | IGKV1-8 | 0.05 |
| | IGHV3-9 | IGKV1-12 | 0.05 |
| | IGHV3-9 | IGKV1D-8 | 0.05 |
| | IGHV4-4 | IGKV1-17 | 0.05 |
| | IGHV4-4 | IGKV1-27 | 0.05 |
| | IGHV4-4 | IGKV1-6 | 0.05 |
| | IGHV4-4 | IGKV1D-8 | 0.05 |
| | IGHV1-46 | IGKV4-1 | 0.05 |
| | IGHV1-46 | IGKV1-33/1D-33 | 0.05 |
| | IGHV1-46 | IGKV1-8 | 0.05 |
| | IGHV4-61 | IGKV3-11 | 0.05 |
| | IGHV4-61 | IGKV2-28/2D-28 | 0.05 |
| | IGHV4-61 | IGKV1-16 | 0.05 |
| | IGHV4-61 | IGKV1-12 | 0.05 |
| | IGHV4-61 | IGKV1-13 | 0.05 |
| | IGHV1-8 | IGKV1-39/1D-39 | 0.05 |
| | IGHV1-8 | IGKV1-5 | 0.05 |
| | IGHV1-8 | IGKV3-11 | 0.05 |
| | IGHV1-8 | IGKV2-28/2D-28 | 0.05 |
| | IGHV1-8 | IGKV1-33/1D-33 | 0.05 |
| | IGHV1-8 | IGKV1-9 | 0.05 |
| | IGHV1-8 | IGKV2-29 | 0.05 |
| | IGHV1-24 | IGKV3-20 | 0.05 |
| | IGHV1-24 | IGKV4-1 | 0.05 |
| | IGHV1-24 | IGKV1-33/1D-33 | 0.05 |
| | IGHV1-24 | IGKV2-24 | 0.05 |
| | IGHV1-24 | IGKV2-40/2D-40 | 0.05 |
| | IGHV1-3 | IGKV1-5 | 0.05 |
| | IGHV1-3 | IGKV1-33/1D-33 | 0.05 |
| | IGHV1-3 | IGKV2-30 | 0.05 |
| | IGHV1-3 | IGKV1-6 | 0.05 |
| | IGHV1-3 | IGKV2D-29 | 0.05 |
| | IGHV3-49 | IGKV3-15 | 0.05 |
| | IGHV3-49 | IGKV3-11 | 0.05 |
| | IGHV3-49 | IGKV2-28/2D-28 | 0.05 |
| | IGHV4-28 | IGKV3-20 | 0.05 |
| | IGHV4-28 | IGKV1-39/1D-39 | 0.05 |
| | IGHV3-43 | IGKV3-15 | 0.05 |
| | IGHV3-43 | IGKV4-1 | 0.05 |
| | IGHV3-43 | IGKV2-28/2D-28 | 0.05 |
| | IGHV3-43 | IGKV1-33/1D-33 | 0.05 |
| | IGHV3-64 | IGKV3-15 | 0.05 |
| | IGHV3-64 | IGKV1-9 | 0.05 |
| | IGHV3-64 | IGKV2D-29 | 0.05 |
| | IGHV7-81 | IGKV1-5 | 0.05 |
| | IGHV7-81 | IGKV4-1 | 0.05 |
| | IGHV7-81 | IGKV2-28/2D-28 | 0.05 |
| | IGHV3-13 | IGKV1-5 | 0.05 |
| | IGHV3-13 | IGKV1-33/1D-33 | 0.05 |
| | IGHV3-13 | IGKV1-9 | 0.05 |
| | IGHV3-13 | IGKV2-30 | 0.05 |
| | IGHV3-72 | IGKV3-20 | 0.05 |
| | IGHV3-72 | IGKV1-9 | 0.05 |
| | IGHV3-72 | IGKV1-17 | 0.05 |
| | IGHV3-72 | IGKV1-16 | 0.05 |
| | IGHV3-73 | IGKV2-28/2D-28 | 0.05 |
| | IGHV3-73 | IGKV1-9 | 0.05 |
| | IGHV1-58 | IGKV1-5 | 0.05 |
| | IGHV1-58 | IGKV4-1 | 0.05 |
| | IGHV1-58 | IGKV3-11 | 0.05 |
| | IGHV4-30.2 | IGKV1-39/1D-39 | 0.05 |
| | IGHV4-30.2 | IGKV4-1 | 0.05 |
| | IGHV7-4.1 | IGKV1-39/1D-39 | 0.05 |
| | IGHV7-4.1 | IGKV1-5 | 0.05 |
| | IGHV3-20 | IGKV1-39/1D-39 | 0.05 |

TABLE 18-continued

Frequency of the VH/VL germline gene pair usage in the human immune repertoire
N = 2137

| pos | V heavy | V light | % |
|---|---|---|---|
| | IGHV3-23 | IGLV 1-47 | 0.05 |
| | IGHV3-23 | IGLV 2-8 | 0.05 |
| | IGHV3-23 | IGLV 7-43 | 0.05 |
| | IGHV3-23 | IGLV 2-18 | 0.05 |
| | IGHV3-23 | IGLV 3-19 | 0.05 |
| | IGHV3-30 | IGLV 1-47 | 0.05 |
| | IGHV3-30 | IGLV 2-8 | 0.05 |
| | IGHV3-30 | IGLV 6-57 | 0.05 |
| | IGHV3-30 | IGLV 3-27 | 0.05 |
| | IGHV4-39 | IGLV 7-46 | 0.05 |
| | IGHV4-39 | IGLV 3-9 | 0.05 |
| | IGHV4-59 | IGLV 2-8 | 0.05 |
| | IGHV4-59 | IGLV 6-57 | 0.05 |
| | IGHV4-59 | IGLV 3-12 | 0.05 |
| | IGHV4-34 | IGLV 2-11 | 0.05 |
| | IGHV4-34 | IGLV 1-36 | 0.05 |
| | IGHV4-34 | IGLV 7-43 | 0.05 |
| | IGHV4-34 | IGLV 9-49 | 0.05 |
| | IGHV5-51 | IGLV 7-43 | 0.05 |
| | IGHV1-69 | IGLV 6-57 | 0.05 |
| | IGHV1-69 | IGLV 3-25 | 0.05 |
| | IGHV1-69 | IGLV 3-10 | 0.05 |
| | IGHV3-7 | IGLV 2-23 | 0.05 |
| | IGHV3-7 | IGLV 3-1 | 0.05 |
| | IGHV3-7 | IGLV 2-8 | 0.05 |
| | IGHV3-7 | IGLV 7-46 | 0.05 |
| | IGHV3-7 | IGLV 3-27 | 0.05 |
| | IGHV1-18 | IGLV 2-23 | 0.05 |
| | IGHV1-18 | IGLV 2-11 | 0.05 |
| | IGHV1-18 | IGLV 1-36 | 0.05 |
| | IGHV1-18 | IGLV 3-25 | 0.05 |
| | IGHV1-18 | IGLV 3-10 | 0.05 |
| | IGHV3-48 | IGLV 1-40 | 0.05 |
| | IGHV3-48 | IGLV 1-44 | 0.05 |
| | IGHV3-48 | IGLV 1-51 | 0.05 |
| | IGHV3-48 | IGLV 2-23 | 0.05 |
| | IGHV3-48 | IGLV 3-21 | 0.05 |
| | IGHV3-48 | IGLV 3-25 | 0.05 |
| | IGHV3-48 | IGLV 7-46 | 0.05 |
| | IGHV3-48 | IGLV 9-49 | 0.05 |
| | IGHV3-21 | IGLV 2-23 | 0.05 |
| | IGHV3-21 | IGLV 3-1 | 0.05 |
| | IGHV3-21 | IGLV 2-8 | 0.05 |
| | IGHV3-21 | IGLV 6-57 | 0.05 |
| | IGHV3-21 | IGLV 3-25 | 0.05 |
| | IGHV3-21 | IGLV 7-46 | 0.05 |
| | IGHV3-15 | IGLV 2-14 | 0.05 |
| | IGHV3-15 | IGLV 1-47 | 0.05 |
| | IGHV3-15 | IGLV 2-23 | 0.05 |
| | IGHV3-15 | IGLV 3-21 | 0.05 |
| | IGHV3-15 | IGLV 6-57 | 0.05 |
| | IGHV3-15 | IGLV 3-25 | 0.05 |
| | IGHV3-15 | IGLV 2-18 | 0.05 |
| | IGHV3-15 | IGLV 3-22 | 0.05 |
| | IGHV4-31 | IGLV 1-44 | 0.05 |
| | IGHV4-31 | IGLV 2-11 | 0.05 |
| | IGHV4-31 | IGLV 3-1 | 0.05 |
| | IGHV4-31 | IGLV 4-69 | 0.05 |
| | IGHV4-31 | IGLV 7-43 | 0.05 |
| | IGHV1-2 | IGLV 3-21 | 0.05 |
| | IGHV1-2 | IGLV 2-11 | 0.05 |
| | IGHV1-2 | IGLV 3-27 | 0.05 |
| | IGHV3-33 | IGLV 1-40 | 0.05 |
| | IGHV3-33 | IGLV 1-44 | 0.05 |
| | IGHV3-33 | IGLV 1-51 | 0.05 |
| | IGHV3-33 | IGLV 2-11 | 0.05 |
| | IGHV3-33 | IGLV 3-1 | 0.05 |
| | IGHV3-33 | IGLV 4-69 | 0.05 |
| | IGHV3-33 | IGLV 3-27 | 0.05 |
| | IGHV3-33 | IGLV 9-49 | 0.05 |
| | IGHV3-33 | IGLV 3-9 | 0.05 |
| | IGHV3-53 | IGLV 1-51 | 0.05 |
| | IGHV3-53 | IGLV 1-47 | 0.05 |
| | IGHV3-53 | IGLV 2-23 | 0.05 |
| | IGHV3-53 | IGLV 2-11 | 0.05 |
| | IGHV3-53 | IGLV 3-1 | 0.05 |
| | IGHV3-53 | IGLV 2-8 | 0.05 |
| | IGHV3-53 | IGLV 7-46 | 0.05 |
| | IGHV3-11 | IGLV 1-40 | 0.05 |
| | IGHV3-11 | IGLV 1-51 | 0.05 |
| | IGHV3-11 | IGLV 1-47 | 0.05 |
| | IGHV3-11 | IGLV 2-8 | 0.05 |
| | IGHV3-11 | IGLV 3-25 | 0.05 |
| | IGHV3-11 | IGLV 7-46 | 0.05 |
| | IGHV3-11 | IGLV 9-49 | 0.05 |
| | IGHV3-11 | IGLV 8-61 | 0.05 |
| | IGHV3-9 | IGLV 1-40 | 0.05 |
| | IGHV3-9 | IGLV 1-51 | 0.05 |
| | IGHV3-9 | IGLV 4-69 | 0.05 |
| | IGHV3-9 | IGLV 4-60 | 0.05 |
| | IGHV3-74 | IGLV 1-47 | 0.05 |
| | IGHV3-74 | IGLV 2-11 | 0.05 |
| | IGHV3-74 | IGLV 3-1 | 0.05 |
| | IGHV3-74 | IGLV 2-8 | 0.05 |
| | IGHV3-74 | IGLV 7-43 | 0.05 |
| | IGHV3-74 | IGLV 7-46 | 0.05 |
| | IGHV4-4 | IGLV 2-11 | 0.05 |
| | IGHV4-4 | IGLV 3-1 | 0.05 |
| | IGHV4-4 | IGLV 3-25 | 0.05 |
| | IGHV4-4 | IGLV 9-49 | 0.05 |
| | IGHV1-46 | IGLV 1-40 | 0.05 |
| | IGHV1-46 | IGLV 1-47 | 0.05 |
| | IGHV1-46 | IGLV 2-23 | 0.05 |
| | IGHV1-46 | IGLV 3-21 | 0.05 |
| | IGHV1-46 | IGLV 6-57 | 0.05 |
| | IGHV4-61 | IGLV 2-23 | 0.05 |
| | IGHV4-61 | IGLV 3-21 | 0.05 |
| | IGHV4-61 | IGLV 3-1 | 0.05 |
| | IGHV4-61 | IGLV 7-43 | 0.05 |
| | IGHV1-8 | IGLV 1-51 | 0.05 |
| | IGHV1-8 | IGLV 2-11 | 0.05 |
| | IGHV1-8 | IGLV 2-8 | 0.05 |
| | IGHV1-8 | IGLV 9-49 | 0.05 |
| | IGHV1-24 | IGLV 2-14 | 0.05 |
| | IGHV1-24 | IGLV 1-40 | 0.05 |
| | IGHV1-24 | IGLV 1-44 | 0.05 |
| | IGHV1-24 | IGLV 3-21 | 0.05 |
| | IGHV1-24 | IGLV 2-11 | 0.05 |
| | IGHV1-3 | IGLV 1-40 | 0.05 |
| | IGHV3-49 | IGLV 2-14 | 0.05 |
| | IGHV3-49 | IGLV 1-40 | 0.05 |
| | IGHV3-49 | IGLV 2-23 | 0.05 |
| | IGHV3-49 | IGLV 2-8 | 0.05 |
| | IGHV4-28 | IGLV 2-14 | 0.05 |
| | IGHV3-43 | IGLV 2-14 | 0.05 |
| | IGHV3-43 | IGLV 2-11 | 0.05 |
| | IGHV3-43 | IGLV 3-1 | 0.05 |
| | IGHV3-43 | IGLV 1-36 | 0.05 |
| | IGHV3-43 | IGLV 9-49 | 0.05 |
| | IGHV3-64 | IGLV 2-14 | 0.05 |
| | IGHV3-64 | IGLV 7-43 | 0.05 |
| | IGHV7-81 | IGLV 1-40 | 0.05 |
| | IGHV3-13 | IGLV 1-40 | 0.05 |
| | IGHV3-13 | IGLV 1-47 | 0.05 |
| | IGHV3-72 | IGLV 1-51 | 0.05 |
| | IGHV3-72 | IGLV 4-69 | 0.05 |
| | IGHV3-73 | IGLV 1-40 | 0.05 |
| | IGHV3-73 | IGLV 1-51 | 0.05 |
| | IGHV3-73 | IGLV 1-47 | 0.05 |
| | IGHV3-73 | IGLV 2-11 | 0.05 |
| | IGHV3-73 | IGLV 6-57 | 0.05 |
| | IGHV1-58 | IGLV 2-14 | 0.05 |
| | IGHV3-66 | IGLV 1-44 | 0.05 |
| | IGHV3-66 | IGLV 1-47 | 0.05 |
| | IGHV3-66 | IGLV 3-25 | 0.05 |
| | IGHV4- | IGLV 3-21 | 0.05 |

TABLE 18-continued

Frequency of the VH/VL germline gene pair
usage in the human immune repertoire
N = 2137

| pos | V heavy | V light | % |
|---|---|---|---|
| 30.2 | | | |
| | IGHV7-4.1 | IGLV 1-51 | 0.05 |
| | IGHV3-20 | IGLV 2-14 | 0.05 |

Pos: represents the position of relative ranking of the VH/VL pairs as determined by the percentage (%) of each VH/VL pair from the total sample.

Example 2.4

VH/VL Germline Gene Pair Usage in the "Naïve" Human Immune Repertoire

Additionally, the pooled data comprising the VH/VL germline gene pair data identified from the publically available literature as described in Example 2.1 and shown in FIGS. 4-26 and the VH/VL germline gene pair data identified from a human sample as described in Example 2.2 and shown in FIGS. 28-36 were analyzed in order to identify the germline gene usage in the naïve human repertoire. It is important to differentiate between the naïve, antigen inexperienced, and the antigen experienced B cell populations. Naïve, antigen inexperienced B cells include, but are not limited to immature B cells, new emigrant B cells, and mature naïve B cells, wherein the antibody sequences are still germline. Antigen experienced B cells include, but are not limited to, IgG antibody secreting cells, and IgM and IgG memory B cells, wherein the majority of the antibodies comprise somatic hypermutations.

It is believed that different germline gene pairs are overrepresented between the two B cell populations, of naïve, antigen inexperienced, B cells, and as compared to antigen experienced B cell populations. An aspect of the present disclosure is to generate a collection of antibodies or functional fragments thereof that can be used to identify antibodies or functional fragments thereof against any immunogen, therefore, it may be preferable to produce a collection comprising the VH/VL germline protein pairs predominantly expressed in the naïve, antigen inexperienced, immune repertoire.

In order to identify the VH/VL germline gene pairs predominanty expressed in the naïve, antigen inexperienced, immune repertoire, the pooled data from the publically available literature as described in Example 2.1 and shown in FIGS. 4-26 and the VH/VL germline gene pair data identified from a human sample as described in Example 2.2 and shown in FIGS. 28-36 was analyzed to separate the antigen inexperienced B cells populations of immature B cells, new emigrant B cells, and mature naïve B cells, from the antigen experienced B cell populations. The ranking of VH/VL germline gene pairs representative of the naïve human immune repertoire is shown in Table 19.

TABLE 19

N = 1345

| pos | V heavy | V light | % |
|---|---|---|---|
| 1 | IGHV4-34 | IGKV3-20 | 1.56 |
| 2 | IGHV4-39 | IGKV3-15 | 1.19 |
| 3 | IGHV4-34 | IGKV1-39/1D-39 | 0.97 |

TABLE 19-continued

N = 1345

| pos | V heavy | V light | % |
|---|---|---|---|
| 4 | IGHV3-23 | IGKV3-20 | 0.89 |
| | IGHV4-59 | IGKV1-39/1D-39 | 0.89 |
| | IGHV1-69 | IGKV1-39/1D-39 | 0.89 |
| 5 | IGHV4-39 | IGKV1-39/1D-39 | 0.82 |
| | IGHV1-18 | IGKV3-20 | 0.82 |
| | IGHV5-51 | IGLV1-40 | 0.82 |
| 6 | IGHV4-39 | IGKV3-20 | 0.74 |
| | IGHV4-39 | IGKV1-5 | 0.74 |
| | IGHV4-59 | IGKV3-20 | 0.74 |
| 7 | IGHV3-23 | IGKV1-5 | 0.67 |
| | IGHV3-23 | IGKV3-15 | 0.67 |
| | IGHV3-30 | IGKV1-39/1D-39 | 0.67 |
| | IGHV3-30 | IGKV3-11 | 0.67 |
| | IGHV1-69 | IGKV3-20 | 0.67 |
| | IGHV4-39 | IGLV2-8 | 0.67 |
| 8 | IGHV3-23 | IGKV1-39/1D-39 | 0.59 |
| | IGHV3-30 | IGKV1-5 | 0.59 |
| | IGHV3-7 | IGKV1-39/1D-39 | 0.59 |
| | IGHV1-2 | IGKV3-20 | 0.59 |
| | IGHV4-59 | IGLV1-40 | 0.59 |
| | IGHV4-34 | IGLV2-14 | 0.59 |
| 9 | IGHV3-23 | IGKV4-1 | 0.52 |
| | IGHV5-51 | IGKV3-20 | 0.52 |
| | IGHV5-51 | IGKV4-1 | 0.52 |
| | IGHV3-53 | IGKV1-5 | 0.52 |
| | IGHV3-23 | IGLV2-14 | 0.52 |
| | IGHV4-34 | IGLV1-51 | 0.52 |
| | IGHV1-69 | IGLV2-14 | 0.52 |
| | IGHV1-69 | IGLV1-40 | 0.52 |
| 10 | IGHV3-23 | IGKV1-33/1D-33 | 0.45 |
| | IGHV3-30 | IGKV3-20 | 0.45 |
| | IGHV3-30 | IGKV4-1 | 0.45 |
| | IGHV3-30 | IGKV1-9 | 0.45 |
| | IGHV4-59 | IGKV4-1 | 0.45 |
| | IGHV4-34 | IGKV3-15 | 0.45 |
| | IGHV4-34 | IGKV4-1 | 0.45 |
| | IGHV1-18 | IGKV1-33/1D-33 | 0.45 |
| | IGHV3-48 | IGKV3-20 | 0.45 |
| | IGHV3-48 | IGKV3-11 | 0.45 |
| | IGHV3-21 | IGKV1-39/1D-39 | 0.45 |
| | IGHV3-21 | IGKV3-15 | 0.45 |
| | IGHV3-15 | IGKV3-20 | 0.45 |
| | IGHV3-15 | IGKV1-39/1D-39 | 0.45 |
| | IGHV3-30 | IGLV2-14 | 0.45 |
| | IGHV5-51 | IGLV2-14 | 0.45 |
| | IGHV3-21 | IGLV1-51 | 0.45 |
| | IGHV1-2 | IGLV2-14 | 0.45 |
| 11 | IGHV3-23 | IGKV2-28/2D-28 | 0.37 |
| | IGHV3-30 | IGKV3-15 | 0.37 |
| | IGHV4-39 | IGKV3-11 | 0.37 |
| | IGHV1-69 | IGKV4-1 | 0.37 |
| | IGHV1-18 | IGKV1-39/1D-39 | 0.37 |
| | IGHV1-18 | IGKV1-5 | 0.37 |
| | IGHV1-18 | IGKV2-28/2D-28 | 0.37 |
| | IGHV3-48 | IGKV1-39/1D-39 | 0.37 |
| | IGHV3-48 | IGKV3-15 | 0.37 |
| | IGHV3-48 | IGKV1-33/1D-33 | 0.37 |
| | IGHV3-21 | IGKV1-5 | 0.37 |
| | IGHV3-15 | IGKV1-5 | 0.37 |
| | IGHV4-31 | IGKV3-11 | 0.37 |
| | IGHV3-33 | IGKV3-20 | 0.37 |
| | IGHV3-53 | IGKV1-33/1D-33 | 0.37 |
| | IGHV3-23 | IGLV1-40 | 0.37 |
| | IGHV3-30 | IGLV1-51 | 0.37 |
| | IGHV4-39 | IGLV2-14 | 0.37 |
| | IGHV4-59 | IGLV3-1 | 0.37 |
| | IGHV1-18 | IGLV1-40 | 0.37 |
| | IGHV3-48 | IGLV2-14 | 0.37 |
| | IGHV4-31 | IGLV2-14 | 0.37 |
| 12 | IGHV3-23 | IGKV3-11 | 0.30 |
| | IGHV3-23 | IGKV1-17 | 0.30 |
| | IGHV3-23 | IGKV1-27 | 0.30 |
| | IGHV4-39 | IGKV1-33/1D-33 | 0.30 |
| | IGHV4-59 | IGKV3-11 | 0.30 |
| | IGHV4-34 | IGKV1-5 | 0.30 |
| | IGHV4-34 | IGKV3-11 | 0.30 |

TABLE 19-continued

N = 1345

| pos | V heavy | V light | % |
|---|---|---|---|
| | IGHV4-34 | IGKV2-28/2D-28 | 0.30 |
| | IGHV5-51 | IGKV3-15 | 0.30 |
| | IGHV5-51 | IGKV3-11 | 0.30 |
| | IGHV5-51 | IGKV2-28/2D-28 | 0.30 |
| | IGHV1-69 | IGKV1-5 | 0.30 |
| | IGHV3-7 | IGKV3-15 | 0.30 |
| | IGHV3-48 | IGKV4-1 | 0.30 |
| | IGHV3-21 | IGKV3-20 | 0.30 |
| | IGHV3-21 | IGKV4-1 | 0.30 |
| | IGHV3-15 | IGKV3-15 | 0.30 |
| | IGHV3-33 | IGKV1-39/1D-39 | 0.30 |
| | IGHV3-53 | IGKV1-39/1D-39 | 0.30 |
| | IGHV3-53 | IGKV3-15 | 0.30 |
| | IGHV3-53 | IGKV4-1 | 0.30 |
| | IGHV3-11 | IGKV1-39/1D-39 | 0.30 |
| | IGHV4-4 | IGKV3-20 | 0.30 |
| | IGHV1-46 | IGKV3-20 | 0.30 |
| | IGHV1-46 | IGKV1-39/1D-39 | 0.30 |
| | IGHV3-23 | IGLV3-21 | 0.30 |
| | IGHV3-23 | IGLV3-1 | 0.30 |
| | IGHV4-39 | IGLV1-40 | 0.30 |
| | IGHV4-39 | IGLV1-44 | 0.30 |
| | IGHV4-39 | IGLV1-51 | 0.30 |
| | IGHV4-59 | IGLV1-51 | 0.30 |
| | IGHV4-34 | IGLV1-40 | 0.30 |
| | IGHV4-34 | IGLV1-47 | 0.30 |
| | IGHV4-34 | IGLV2-8 | 0.30 |
| | IGHV5-51 | IGLV1-44 | 0.30 |
| | IGHV1-69 | IGLV1-51 | 0.30 |
| | IGHV1-69 | IGLV2-8 | 0.30 |
| | IGHV3-9 | IGLV2-14 | 0.30 |
| | IGHV3-9 | IGLV2-23 | 0.30 |
| | IGHV4-4 | IGLV1-44 | 0.30 |
| | IGHV4-61 | IGLV1-44 | 0.30 |
| 13 | IGHV3-23 | IGKV1-8 | 0.22 |
| | IGHV3-30 | IGKV2-28/2D-28 | 0.22 |
| | IGHV4-39 | IGKV4-1 | 0.22 |
| | IGHV4-39 | IGKV1-27 | 0.22 |
| | IGHV5-51 | IGKV1-39/1D-39 | 0.22 |
| | IGHV1-69 | IGKV1-33/1D-33 | 0.22 |
| | IGHV3-7 | IGKV3-20 | 0.22 |
| | IGHV3-7 | IGKV3-11 | 0.22 |
| | IGHV3-7 | IGKV1-8 | 0.22 |
| | IGHV1-18 | IGKV3-11 | 0.22 |
| | IGHV3-48 | IGKV1-8 | 0.22 |
| | IGHV3-15 | IGKV3-11 | 0.22 |
| | IGHV3-15 | IGKV1-33/1D-33 | 0.22 |
| | IGHV4-31 | IGKV1-39/1D-39 | 0.22 |
| | IGHV4-31 | IGKV3-15 | 0.22 |
| | IGHV4-31 | IGKV1-33/1D-33 | 0.22 |
| | IGHV1-2 | IGKV1-39/1D-39 | 0.22 |
| | IGHV1-2 | IGKV1-5 | 0.22 |
| | IGHV3-33 | IGKV3-15 | 0.22 |
| | IGHV3-33 | IGKV4-1 | 0.22 |
| | IGHV3-11 | IGKV1-5 | 0.22 |
| | IGHV3-11 | IGKV3-15 | 0.22 |
| | IGHV3-9 | IGKV1-39/1D-39 | 0.22 |
| | IGHV4-4 | IGKV3-15 | 0.22 |
| | IGHV4-4 | IGKV3-11 | 0.22 |
| | IGHV1-46 | IGKV1-9 | 0.22 |
| | IGHV4-61 | IGKV1-39/1D-39 | 0.22 |
| | IGHV4-61 | IGKV4-1 | 0.22 |
| | IGHV1-3 | IGKV1-39/1D-39 | 0.22 |
| | IGHV3-49 | IGKV1-39/1D-39 | 0.22 |
| | IGHV3-49 | IGKV1-17 | 0.22 |
| | IGHV3-43 | IGKV1-5 | 0.22 |
| | IGHV7-81 | IGKV3-20 | 0.22 |
| | IGHV3-23 | IGLV2-23 | 0.22 |
| | IGHV3-23 | IGLV2-11 | 0.22 |
| | IGHV4-39 | IGLV2-23 | 0.22 |
| | IGHV1-69 | IGLV2-23 | 0.22 |
| | IGHV1-18 | IGLV2-14 | 0.22 |
| | IGHV3-48 | IGLV3-1 | 0.22 |
| | IGHV3-15 | IGLV1-44 | 0.22 |
| | IGHV4-31 | IGLV1-40 | 0.22 |
| | IGHV1-2 | IGLV1-40 | 0.22 |
| | IGHV1-2 | IGLV3-1 | 0.22 |
| | IGHV3-33 | IGLV2-14 | 0.22 |
| | IGHV3-33 | IGLV1-47 | 0.22 |
| | IGHV3-33 | IGLV3-21 | 0.22 |
| | IGHV3-9 | IGLV1-44 | 0.22 |
| | IGHV3-9 | IGLV1-47 | 0.22 |
| | IGHV3-9 | IGLV2-11 | 0.22 |
| | IGHV1-46 | IGLV1-44 | 0.22 |
| | IGHV1-8 | IGLV2-14 | 0.22 |
| 14 | IGHV3-23 | IGKV1-16 | 0.15 |
| | IGHV3-23 | IGKV2D-29 | 0.15 |
| | IGHV3-23 | IGKV2-40/2D-40 | 0.15 |
| | IGHV3-30 | IGKV1-33/1D-33 | 0.15 |
| | IGHV3-30 | IGKV1D-8 | 0.15 |
| | IGHV4-39 | IGKV2-28/2D-28 | 0.15 |
| | IGHV4-39 | IGKV2-30 | 0.15 |
| | IGHV4-39 | IGKV1-6 | 0.15 |
| | IGHV4-59 | IGKV1-5 | 0.15 |
| | IGHV4-59 | IGKV3-15 | 0.15 |
| | IGHV4-59 | IGKV1-33/1D-33 | 0.15 |
| | IGHV4-34 | IGKV1-33/1D-33 | 0.15 |
| | IGHV4-34 | IGKV1-17 | 0.15 |
| | IGHV4-34 | IGKV1-16 | 0.15 |
| | IGHV5-51 | IGKV1-5 | 0.15 |
| | IGHV5-51 | IGKV1-33/1D-33 | 0.15 |
| | IGHV1-69 | IGKV3-15 | 0.15 |
| | IGHV1-69 | IGKV3-11 | 0.15 |
| | IGHV1-69 | IGKV1-8 | 0.15 |
| | IGHV3-7 | IGKV1-5 | 0.15 |
| | IGHV3-7 | IGKV4-1 | 0.15 |
| | IGHV3-7 | IGKV2-28/2D-28 | 0.15 |
| | IGHV3-7 | IGKV1-9 | 0.15 |
| | IGHV3-7 | IGKV1-17 | 0.15 |
| | IGHV3-7 | IGKV1-13 | 0.15 |
| | IGHV1-18 | IGKV4-1 | 0.15 |
| | IGHV1-18 | IGKV2-30 | 0.15 |
| | IGHV3-48 | IGKV2-28/2D-28 | 0.15 |
| | IGHV3-48 | IGKV1-17 | 0.15 |
| | IGHV3-21 | IGKV2-28/2D-28 | 0.15 |
| | IGHV3-21 | IGKV1-8 | 0.15 |
| | IGHV3-15 | IGKV4-1 | 0.15 |
| | IGHV3-15 | IGKV2-28/2D-28 | 0.15 |
| | IGHV3-15 | IGKV1-9 | 0.15 |
| | IGHV4-31 | IGKV3-20 | 0.15 |
| | IGHV4-31 | IGKV2-28/2D-28 | 0.15 |
| | IGHV1-2 | IGKV3-15 | 0.15 |
| | IGHV1-2 | IGKV4-1 | 0.15 |
| | IGHV1-2 | IGKV1-27 | 0.15 |
| | IGHV3-33 | IGKV2-28/2D-28 | 0.15 |
| | IGHV3-33 | IGKV1-9 | 0.15 |
| | IGHV3-53 | IGKV3-20 | 0.15 |
| | IGHV3-53 | IGKV3-11 | 0.15 |
| | IGHV3-53 | IGKV1-8 | 0.15 |
| | IGHV3-11 | IGKV3-20 | 0.15 |
| | IGHV3-11 | IGKV4-1 | 0.15 |
| | IGHV3-11 | IGKV3-11 | 0.15 |
| | IGHV3-11 | IGKV2-28/2D-28 | 0.15 |
| | IGHV3-11 | IGKV1-6 | 0.15 |
| | IGHV3-9 | IGKV1-5 | 0.15 |
| | IGHV3-9 | IGKV1-16 | 0.15 |
| | IGHV3-9 | IGKV2D-29 | 0.15 |
| | IGHV3-74 | IGKV1-39/1D-39 | 0.15 |
| | IGHV3-74 | IGKV1-5 | 0.15 |
| | IGHV3-74 | IGKV4-1 | 0.15 |
| | IGHV4-4 | IGKV1-39/1D-39 | 0.15 |
| | IGHV4-4 | IGKV1-5 | 0.15 |
| | IGHV4-4 | IGKV4-1 | 0.15 |
| | IGHV4-4 | IGKV2D-29 | 0.15 |
| | IGHV1-46 | IGKV3-15 | 0.15 |
| | IGHV1-46 | IGKV1-16 | 0.15 |
| | IGHV4-61 | IGKV3-15 | 0.15 |
| | IGHV1-24 | IGKV3-15 | 0.15 |
| | IGHV1-24 | IGKV3-11 | 0.15 |
| | IGHV1-24 | IGKV2-28/2D-28 | 0.15 |
| | IGHV3-49 | IGKV3-20 | 0.15 |
| | IGHV3-64 | IGKV1-5 | 0.15 |
| | IGHV1-2 | IGLV3-1 | 0.22 |
| | IGHV3-33 | IGLV2-14 | 0.22 |
| | IGHV3-33 | IGLV1-47 | 0.22 |
| | IGHV3-33 | IGLV3-21 | 0.22 |
| | IGHV3-9 | IGLV1-44 | 0.22 |
| | IGHV3-9 | IGLV1-47 | 0.22 |
| | IGHV3-9 | IGLV2-11 | 0.22 |
| | IGHV1-46 | IGLV1-44 | 0.22 |
| | IGHV1-8 | IGLV2-14 | 0.22 |

TABLE 19-continued

N = 1345

| pos | V heavy | V light | % |
|---|---|---|---|
| | IGHV3-64 | IGKV3-11 | 0.15 |
| | IGHV7-81 | IGKV1-39/1D-39 | 0.15 |
| | IGHV3-13 | IGKV1-39/1D-39 | 0.15 |
| | IGHV3-13 | IGKV4-1 | 0.15 |
| | IGHV3-72 | IGKV3-15 | 0.15 |
| | IGHV3-30 | IGLV1-40 | 0.15 |
| | IGHV3-30 | IGLV1-44 | 0.15 |
| | IGHV3-30 | IGLV2-23 | 0.15 |
| | IGHV3-30 | IGLV3-21 | 0.15 |
| | IGHV3-30 | IGLV9-49 | 0.15 |
| | IGHV4-39 | IGLV2-18 | 0.15 |
| | IGHV4-59 | IGLV2-23 | 0.15 |
| | IGHV4-59 | IGLV2-11 | 0.15 |
| | IGHV4-34 | IGLV1-44 | 0.15 |
| | IGHV4-34 | IGLV2-23 | 0.15 |
| | IGHV4-34 | IGLV3-25 | 0.15 |
| | IGHV5-51 | IGLV1-47 | 0.15 |
| | IGHV5-51 | IGLV2-23 | 0.15 |
| | IGHV5-51 | IGLV3-21 | 0.15 |
| | IGHV5-51 | IGLV1-36 | 0.15 |
| | IGHV5-51 | IGLV3-25 | 0.15 |
| | IGHV1-69 | IGLV1-44 | 0.15 |
| | IGHV1-69 | IGLV2-11 | 0.15 |
| | IGHV1-69 | IGLV3-1 | 0.15 |
| | IGHV1-18 | IGLV1-44 | 0.15 |
| | IGHV1-18 | IGLV2-8 | 0.15 |
| | IGHV1-18 | IGLV6-57 | 0.15 |
| | IGHV3-48 | IGLV1-47 | 0.15 |
| | IGHV3-21 | IGLV2-14 | 0.15 |
| | IGHV3-21 | IGLV1-47 | 0.15 |
| | IGHV3-21 | IGLV2-11 | 0.15 |
| | IGHV3-15 | IGLV7-46 | 0.15 |
| | IGHV4-31 | IGLV1-51 | 0.15 |
| | IGHV4-31 | IGLV1-47 | 0.15 |
| | IGHV4-31 | IGLV2-23 | 0.15 |
| | IGHV1-2 | IGLV1-44 | 0.15 |
| | IGHV1-2 | IGLV1-51 | 0.15 |
| | IGHV1-2 | IGLV2-23 | 0.15 |
| | IGHV1-2 | IGLV2-8 | 0.15 |
| | IGHV3-11 | IGLV3-21 | 0.15 |
| | IGHV3-11 | IGLV3-1 | 0.15 |
| | IGHV3-9 | IGLV3-21 | 0.15 |
| | IGHV3-74 | IGLV3-21 | 0.15 |
| | IGHV4-4 | IGLV2-14 | 0.15 |
| | IGHV4-4 | IGLV1-51 | 0.15 |
| | IGHV1-46 | IGLV1-51 | 0.15 |
| | IGHV4-61 | IGLV2-11 | 0.15 |
| | IGHV1-24 | IGLV2-23 | 0.15 |
| | IGHV1-3 | IGLV2-14 | 0.15 |
| | IGHV1-3 | IGLV3-1 | 0.15 |
| | IGHV4-28 | IGLV1-44 | 0.15 |
| | IGHV4-28 | IGLV1-36 | 0.15 |
| | IGHV3-43 | IGLV1-51 | 0.15 |
| 15 | IGHV3-23 | IGKV1-9 | 0.07 |
| | IGHV3-23 | IGKV2-30 | 0.07 |
| | IGHV3-23 | IGKV1-12 | 0.07 |
| | IGHV3-23 | IGKV2-29 | 0.07 |
| | IGHV3-23 | IGKV3D-20 | 0.07 |
| | IGHV3-23 | IGKV1D-12 | 0.07 |
| | IGHV3-30 | IGKV2-30 | 0.07 |
| | IGHV3-30 | IGKV1-27 | 0.07 |
| | IGHV3-30 | IGKV1-16 | 0.07 |
| | IGHV3-30 | IGKV1-6 | 0.07 |
| | IGHV3-30 | IGKV2D-29 | 0.07 |
| | IGHV3-30 | IGKV2-24 | 0.07 |
| | IGHV3-30 | IGKV2D-30 | 0.07 |
| | IGHV4-39 | IGKV1-17 | 0.07 |
| | IGHV4-59 | IGKV2-30 | 0.07 |
| | IGHV4-59 | IGKV1-17 | 0.07 |
| | IGHV4-59 | IGKV1-27 | 0.07 |
| | IGHV4-59 | IGKV1-8 | 0.07 |
| | IGHV4-59 | IGKV1-16 | 0.07 |
| | IGHV4-59 | IGKV1-12 | 0.07 |
| | IGHV4-59 | IGKV1D-17 | 0.07 |
| | IGHV4-34 | IGKV1-9 | 0.07 |
| | IGHV4-34 | IGKV1-27 | 0.07 |
| | IGHV4-34 | IGKV1-8 | 0.07 |
| | IGHV4-34 | IGKV1-12 | 0.07 |
| | IGHV5-51 | IGKV1-17 | 0.07 |
| | IGHV5-51 | IGKV1-27 | 0.07 |
| | IGHV1-69 | IGKV2-28/2D-28 | 0.07 |
| | IGHV1-69 | IGKV2-30 | 0.07 |
| | IGHV1-69 | IGKV1-16 | 0.07 |
| | IGHV1-69 | IGKV2D-29 | 0.07 |
| | IGHV1-69 | IGKV2D-30 | 0.07 |
| | IGHV1-69 | IGKV1D-16 | 0.07 |
| | IGHV1-69 | IGKV3D-15 | 0.07 |
| | IGHV3-7 | IGKV2-30 | 0.07 |
| | IGHV3-7 | IGKV1-27 | 0.07 |
| | IGHV3-7 | IGKV1D-8 | 0.07 |
| | IGHV3-7 | IGKV1D-17 | 0.07 |
| | IGHV1-18 | IGKV3-15 | 0.07 |
| | IGHV1-18 | IGKV1-8 | 0.07 |
| | IGHV1-18 | IGKV1-16 | 0.07 |
| | IGHV1-18 | IGKV1-12 | 0.07 |
| | IGHV1-18 | IGKV1-13 | 0.07 |
| | IGHV1-18 | IGKV2-40/2D-40 | 0.07 |
| | IGHV3-48 | IGKV1-5 | 0.07 |
| | IGHV3-48 | IGKV1-9 | 0.07 |
| | IGHV3-48 | IGKV1-27 | 0.07 |
| | IGHV3-48 | IGKV1-16 | 0.07 |
| | IGHV3-48 | IGKV1-6 | 0.07 |
| | IGHV3-48 | IGKV2D-29 | 0.07 |
| | IGHV3-48 | IGKV3D-20 | 0.07 |
| | IGHV3-48 | IGKV1D-12 | 0.07 |
| | IGHV3-21 | IGKV3-11 | 0.07 |
| | IGHV3-21 | IGKV1-27 | 0.07 |
| | IGHV3-21 | IGKV2D-29 | 0.07 |
| | IGHV3-15 | IGKV1-27 | 0.07 |
| | IGHV3-15 | IGKV2D-29 | 0.07 |
| | IGHV3-15 | IGKV1D-43 | 0.07 |
| | IGHV4-31 | IGKV1-5 | 0.07 |
| | IGHV4-31 | IGKV4-1 | 0.07 |
| | IGHV4-31 | IGKV1-17 | 0.07 |
| | IGHV4-31 | IGKV1-27 | 0.07 |
| | IGHV4-31 | IGKV1-6 | 0.07 |
| | IGHV4-31 | IGKV2-40/2D-40 | 0.07 |
| | IGHV1-2 | IGKV2-28/2D-28 | 0.07 |
| | IGHV1-2 | IGKV1-33/1D-33 | 0.07 |
| | IGHV1-2 | IGKV2-30 | 0.07 |
| | IGHV1-2 | IGKV1-8 | 0.07 |
| | IGHV1-2 | IGKV1-6 | 0.07 |
| | IGHV3-33 | IGKV1-5 | 0.07 |
| | IGHV3-33 | IGKV1-33/1D-33 | 0.07 |
| | IGHV3-33 | IGKV1-8 | 0.07 |
| | IGHV3-53 | IGKV2-28/2D-28 | 0.07 |
| | IGHV3-53 | IGKV1-9 | 0.07 |
| | IGHV3-53 | IGKV1-17 | 0.07 |
| | IGHV3-53 | IGKV1-27 | 0.07 |
| | IGHV3-53 | IGKV1-12 | 0.07 |
| | IGHV3-53 | IGKV2-29 | 0.07 |
| | IGHV3-53 | IGKV1D-16 | 0.07 |
| | IGHV3-11 | IGKV1-33/1D-33 | 0.07 |
| | IGHV3-11 | IGKV1-9 | 0.07 |
| | IGHV3-11 | IGKV1-17 | 0.07 |
| | IGHV3-11 | IGKV1D-8 | 0.07 |
| | IGHV3-9 | IGKV3-15 | 0.07 |
| | IGHV3-9 | IGKV4-1 | 0.07 |
| | IGHV3-9 | IGKV3-11 | 0.07 |
| | IGHV3-9 | IGKV2-28/2D-28 | 0.07 |
| | IGHV3-9 | IGKV1-27 | 0.07 |
| | IGHV3-9 | IGKV1-8 | 0.07 |
| | IGHV3-9 | IGKV1D-8 | 0.07 |
| | IGHV3-74 | IGKV3-20 | 0.07 |
| | IGHV3-74 | IGKV3-15 | 0.07 |
| | IGHV3-74 | IGKV3-11 | 0.07 |
| | IGHV3-74 | IGKV2-30 | 0.07 |
| | IGHV4-4 | IGKV2-28/2D-28 | 0.07 |
| | IGHV4-4 | IGKV1-17 | 0.07 |
| | IGHV4-4 | IGKV1-27 | 0.07 |
| | IGHV4-4 | IGKV1D-8 | 0.07 |
| | IGHV1-46 | IGKV1-5 | 0.07 |

TABLE 19-continued

N = 1345

| pos | V heavy | V light | % |
|---|---|---|---|
| | IGHV1-46 | IGKV4-1 | 0.07 |
| | IGHV1-46 | IGKV1-33/1D-33 | 0.07 |
| | IGHV1-46 | IGKV1-8 | 0.07 |
| | IGHV4-61 | IGKV2-28/2D-28 | 0.07 |
| | IGHV4-61 | IGKV1-16 | 0.07 |
| | IGHV4-61 | IGKV1-12 | 0.07 |
| | IGHV1-8 | IGKV1-39/1D-39 | 0.07 |
| | IGHV1-8 | IGKV3-15 | 0.07 |
| | IGHV1-8 | IGKV4-1 | 0.07 |
| | IGHV1-8 | IGKV3-11 | 0.07 |
| | IGHV1-8 | IGKV2-28/2D-28 | 0.07 |
| | IGHV1-8 | IGKV1-9 | 0.07 |
| | IGHV1-8 | IGKV2-29 | 0.07 |
| | IGHV1-24 | IGKV3-20 | 0.07 |
| | IGHV1-24 | IGKV1-39/1D-39 | 0.07 |
| | IGHV1-24 | IGKV4-1 | 0.07 |
| | IGHV1-24 | IGKV1-33/1D-33 | 0.07 |
| | IGHV1-24 | IGKV2-30 | 0.07 |
| | IGHV1-24 | IGKV2-24 | 0.07 |
| | IGHV1-3 | IGKV1-5 | 0.07 |
| | IGHV1-3 | IGKV3-15 | 0.07 |
| | IGHV1-3 | IGKV1-33/1D-33 | 0.07 |
| | IGHV1-3 | IGKV2-30 | 0.07 |
| | IGHV1-3 | IGKV2D-29 | 0.07 |
| | IGHV3-49 | IGKV1-5 | 0.07 |
| | IGHV3-49 | IGKV3-15 | 0.07 |
| | IGHV3-49 | IGKV3-11 | 0.07 |
| | IGHV3-49 | IGKV2-28/2D-28 | 0.07 |
| | IGHV3-43 | IGKV4-1 | 0.07 |
| | IGHV3-43 | IGKV3-11 | 0.07 |

Example 3

Determining the VH and VL Germline Gene Usage

A review of Tables 18-19 from Examples 2.3-4, show that a small number of VH, VK, and VA germline genes are dominant in the human immune repertoire, and in the naïve human immune repertoire as compared to the total number of germline genes. Wildt et al. at 895-896 also described this phenomenon. Wildt et al. also described that the frequently expressed heavy and light chain gene segments are often paired, and observed that half of the pairings sampled corresponded to only five VH/VL germline gene pairs.

Additionally, the pooled data was evaluated to identify the VH, Vκ, and Vλ germline genes that are independently highly expressed in the human immune repertoire. Therefore, the data comprising the VH/VL germline gene pairs identified from the publically available literature as described in Example 2.1 and shown in FIGS. 4-26; the VH/VL germline gene pairs identified from a human sample as described in Example 2.2 and shown in FIGS. 28-36, and additional literature references, which included unpaired VH and/or VL germline gene expression, (see Brezinschek H. P. et al. (1997) J. Clin. Invest. 99, 2488, Demaison C. et al. (1995) Immunogenetics 42, 342, and Foster S. J. et al. (1997) J. Clin. Invest. 99, 1614, which articles are both incorporated by reference in their entireties) were pooled and ranked, in order to determine which VH, Vκ, and Vλ germline genes were the most highly expressed in the human immune repertoire. Table 20 shows the ranking of the prevalence of VH, Vλ and Vκ germline genes.

TABLE 20

Unpaired VH, Vκ, and Vλ germline gene usage in the human immune repertoire

| | VH n = 2463 | |
|---|---|---|
| 1 | IGHV3-23 | 10.6 |
| 2 | IGHV3-30 | 8.0 |
| 3 | IGHV4-39 | 7.6 |
| 4 | IGHV4-34 | 6.8 |
| 5 | IGHV4-59 | 5.8 |
| 6 | IGHV1-69 | 5.3 |
| 7 | IGHV5-51 | 4.6 |
| 8 | IGHV3-7 | 4.5 |
| 9 | IGHV1-18 | 4.1 |
| 10 | IGHV3-48 | 4.0 |
| 11 | IGHV3-15 | 3.3 |
| 12 | IGHV3-21 | 3.3 |
| 13 | IGHV1-2 | 3.2 |
| 14 | IGHV3-33 | 3.0 |
| 15 | IGHV4-31 | 3.0 |
| 16 | IGHV3-53 | 2.7 |
| 17 | IGHV3-11 | 2.6 |
| 18 | IGHV3-9 | 2.2 |
| 19 | IGHV4-4 | 2.1 |
| 20 | IGHV1-46 | 2.1 |
| 21 | IGHV3-74 | 1.6 |
| 22 | IGHV1-24 | 1.1 |
| 23 | IGHV4-61 | 1.1 |
| 24 | IGHV1-8 | 1.1 |
| 25 | IGHV1-3 | 1.0 |
| 26 | IGHV3-49 | 1.0 |
| 27 | IGHV3-43 | 0.6 |
| 28 | IGHV4-28 | 0.6 |
| 29 | IGHV3-64 | 0.5 |
| 30 | IGHV7-81 | 0.5 |
| 31 | IGHV3-13 | 0.4 |
| 32 | IGHV3-72 | 0.4 |
| 33 | IGHV1-58 | 0.3 |
| 34 | IGHV3-73 | 0.3 |
| 35 | IGHV3-66 | 0.2 |
| 36 | IGHV7-4.1 | 0.2 |
| 37 | IGHV2-5 | 0.1 |
| 38 | IGHV4-30.2 | 0.1 |
| 39 | IGHV3-20 | 0.1 |
| 40 | IGHV6-1 | 0.0 |
| 41 | IGHV1-e | 0.0 |
| 42 | IGHV1-f | 0.0 |
| 43 | IGHV1-45 | 0.0 |
| 44 | IGHV2-26 | 0.0 |
| 45 | IGHV2-70 | 0.0 |
| 46 | IGHV3-d | 0.0 |
| 47 | IGHV4-b | 0.0 |
| 48 | IGHV4-30.4 | 0.0 |
| 49 | IGHV5-a | 0.0 |
| | Vκ n = 1656 | |
| 1 | IGKV3-20 | 16.2 |
| 2 | IGKV1-39/1D-39 | 14.2 |
| 3 | IGKV1-5 | 11.2 |
| 4 | IGKV3-15 | 11.1 |
| 5 | IGKV4-1 | 8.5 |
| 6 | IGKV3-11 | 7.6 |
| 7 | IGKV2-28/2D-28 | 6.0 |
| 8 | IGKV1-33/1D-33 | 4.6 |
| 9 | IGKV2-30 | 2.6 |
| 10 | IGKV1-9 | 2.4 |
| 11 | IGKV1-17 | 2.4 |
| 12 | IGKV1-27 | 2.2 |
| 13 | IGKV1-8 | 1.9 |
| 14 | IGKV1-16 | 1.3 |
| 15 | IGKV1-6 | 1.1 |
| 16 | IGKV1-12 | 1.1 |
| 17 | IGKV2D-29 | 1.0 |
| 18 | IGKV1-13 | 0.7 |
| 19 | IGKV1D-8 | 0.5 |
| 20 | IGKV2-24 | 0.5 |
| 21 | IGKV5-2 | 0.4 |
| 22 | IGKV1D-12 | 0.3 |

TABLE 20-continued

Unpaired VH, Vκ, and Vλ germline gene usage in the human immune repertoire

| | | |
|---|---|---|
| 23 | IGKV2-40/2D-40 | 0.3 |
| 24 | IGKV3D-20 | 0.3 |
| 25 | IGKV1D-43 | 0.2 |
| 26 | IGKV2D-30 | 0.2 |
| 27 | IGKV3D-11 | 0.2 |
| 28 | IGKV3D-15 | 0.2 |
| 29 | IGKV2-29 | 0.2 |
| 30 | IGKV1D-16 | 0.1 |
| 31 | IGKV1D-17 | 0.1 |
| 32 | IGKV3D-7 | 0.1 |
| 33 | IGKV6-21/6D-21 | 0.1 |
| 34 | IGKV6D-41 | 0.1 |
| 35 | IGKV1D-13 | 0.0 |
| | Vλ n = 780 | |
| 1 | IGLV2-14 | 18.1 |
| 2 | IGLV1-40 | 11.3 |
| 3 | IGLV1-44 | 11.3 |
| 4 | IGLV1-51 | 10.0 |
| 5 | IGLV2-23 | 8.1 |
| 6 | IGLV3-21 | 8.1 |
| 7 | IGLV1-47 | 6.5 |
| 8 | IGLV3-1 | 5.3 |
| 9 | IGLV2-11 | 5.1 |
| 10 | IGLV2-8 | 4.5 |
| 11 | IGLV6-57 | 1.7 |
| 12 | IGLV3-25 | 1.5 |
| 13 | IGLV7-46 | 1.5 |
| 14 | IGLV1-36 | 1.2 |
| 15 | IGLV7-43 | 1.2 |
| 16 | IGLV9-49 | 1.2 |
| 17 | IGLV4-69 | 1.0 |
| 18 | IGLV2-18 | 0.6 |
| 19 | IGLV3-10 | 0.5 |
| 20 | IGLV3-27 | 0.5 |
| 21 | IGLV3-9 | 0.3 |
| 22 | IGLV3-12 | 0.1 |
| 23 | IGLV3-19 | 0.1 |
| 24 | IGLV3-22 | 0.1 |
| 25 | IGLV4-60 | 0.1 |
| 26 | IGLV8-61 | 0.1 |
| 27 | IGLV3-16 | 0.0 |
| 28 | IGLV4-3 | 0.0 |
| 29 | IGLV5-37 | 0.0 |
| 30 | IGLV5-39 | 0.0 |
| 31 | IGLV5-45 | 0.0 |
| 32 | IGLV5-52 | 0.0 |
| 33 | IGLV10-54 | 0.0 |

In comparing Table 20, showing the unlinked VH, VA and VK germline gene prevalence and Tables 18-19, showing the linked VH/VL pair germline gene prevalence within the human immune repertoire and the naïve human immune repertoire, it was apparent that many of the VH, Vλ and Vκ germline genes that are highly represented when evaluated independent of linkage or pairing were also highly represented when evaluated in the VH/VL pairings.

Figure 39:
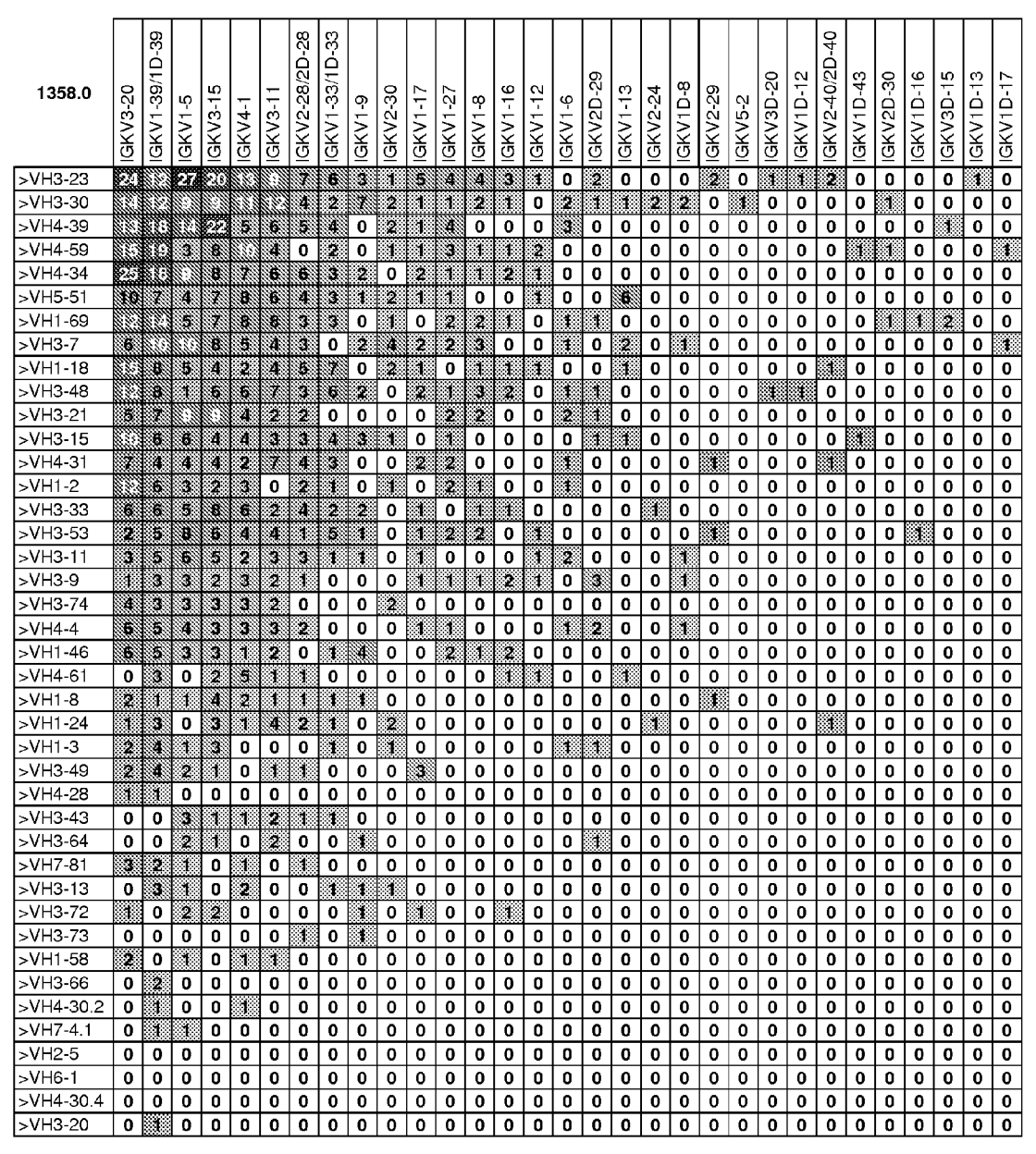

This observation is confirmed by the plots shown in FIGS. 39-40, which show the VH/VL germline gene pairs of the human immune repertoire and FIGS. 41-42, which show the VH/VL germline gene pairs of the naïve human immune repertoire. The Figs. show the actual number of each VH/VL germline gene pair identified from the pooled data, plotted on a matrix, where the Y axis includes the ranking of the VH germline genes, and the X axis includes the ranking of the VL germline genes.

Example 4

Selecting the VH/VL Germline Gene Pairings for Further Evaluation of their Biophysical Properties As a next step, it had to be determined which germline protein pairs were to be tested, as there are ~2500 pairs in the human immune repertoire and the inventors goal was to identify which of the germline protein pairs comprises favorable biophysical properties which would aid in selection and development. One way would be to to test the variable heavy chain and variable light chain germline protein pairs that occur most prominently in the human immune repertoire, for example see Table 18. One could, for example, select the top four hundred pairs for testing, or select the variable heavy chain and variable light chain germline gene pairs expressed above a certain threshold concentration. This approach would require the synthesis and testing of a large number of variable heavy chain and variable light chain germline protein pair sequences; therefore, such an approach may not be very efficient.

As an alternative approach, the inventors selected a subset of the variable heavy chain and variable light chain germline pairs that are representative of, accurately reproduce, or cover the majority of the prominently expressed pairs from the human immune repertoire. This approach was based, in part, upon the above observation that a small number of variable heavy, variable κ light chain, and variable λ light chain germline genes are dominant in the human immune repertoire. Therefore, a small number of the prominently expressed heavy and light chain germline genes (unpaired) can be combined to generate a group of pairs that are representative of the human immune repertoire.

This approach was undertaken in the following way. In Example 3, the variable heavy chain, variable κ light chain, and variable λ light chain germline gene expression was determined. As a next step, an in silico analysis was completed of the prominent VH, Vλ and Vκ germline genes, where at least the following factors were evaluated: CDR length, isoelectric point (pl) (the preferred isoelectric point is 7.5 or above as this is should provide stability in a standard pH 5.5 to pH 7 formulation buffer), post translational modifications (PTM's) (specifically, N-linked glycosylation sites (NxS or NxT) or chemical modifications such as Asp cleavage (often at a DP), Asp isomerization (DD, DG), deamidation (NS, NG) which can occur in vivo (in serum) or upon storage in formulation buffer and lead to loss of antibody binding), the presence of Methionines in the CDRs (can be oxidized when exposed to solvent), the presence of unpaired Cysteines (will form disulfide bonds with any other unpaired cysteine, thus leading to crosslinking of proteins and/or lower expression levels), deviations from germline, the presence of possible T-cell epitopes, and theoretical aggregation propensity. Selected data from the in silico analysis is shown in FIGS. 37-38.

Based upon the in silico analysis of the most prominent VH, Vλ and Vκ germline genes, a subset of these were selected for synthesis, combination and subsequent functional testing, this subset is shown in FIGS. 37-38. As shown, not all of the most prominent VH, Vλ and Vκ germline genes were selected for further testing. Of the most prominent VH germline genes, as shown in Table 20, IGHV4-34, IGHV4-59, and IGHV3-9 were not selected. Instead, as shown in FIG. 37-38, and Table 21, IGHV3-74, IGHV3-73, and IGHV6-1 were selected. In total, 20 VH germline genes were selected. Of the most prominent Vκ germline genes, as shown in Table 20, IGKV4-1, IGKV2-28/2D-28, IGKV1-33/1D-33, and IGKV1-8 were not selected. In total, 12 Vκ germline genes were selected. Of the most prominent VH germline genes as shown in Table 20, IGLV1-44 was not selected. In total, 8 VA germline genes were selected.

Table 21 shows again the ranking of the VH, VK, and VA germline gene usage from the human immune repertoire and bolds and underlines the germline genes that were selected for further functional testing.

TABLE 21

Ranking of the prevalence of VH, Vλ and Vκ germline genes from publically available data and a human B cell sample and identification of VH, Vλ and Vκ germline genes that were selected for further functional testing are bold and underlined.

VH
n = 2463

| | | |
|---|---|---|
| 1 | IGHV3-23 | 10.6 |
| 2 | IGHV3-30 | 8.0 |
| 3 | IGHV4-39 | 7.6 |
| 4 | IGHV4-34 | 6.8 |
| 5 | IGHV4-59 | 5.8 |
| 6 | IGHV1-69 | 5.3 |
| 7 | IGHV5-51 | 4.6 |
| 8 | IGHV3-7 | 4.5 |
| 9 | IGHV1-18 | 4.1 |
| 10 | IGHV3-48 | 4.0 |
| 11 | IGHV3-15 | 3.3 |
| 12 | IGHV3-21 | 3.3 |
| 13 | IGHV1-2 | 3.2 |
| 14 | IGHV3-33 | 3.0 |
| 15 | IGHV4-31 | 3.0 |
| 16 | IGHV3-53 | 2.7 |
| 17 | IGHV3-11 | 2.6 |
| 18 | IGHV3-9 | 2.2 |
| 19 | IGHV4-4 | 2.1 |
| 20 | IGHV1-46 | 2.1 |
| 21 | IGHV3-74 | 1.6 |
| 22 | IGHV1-24 | 1.1 |
| 23 | IGHV4-61 | 1.1 |
| 24 | IGHV1-8 | 1.1 |
| 25 | IGHV1-3 | 1.0 |
| 26 | IGHV3-49 | 1.0 |
| 27 | IGHV3-43 | 0.6 |
| 28 | IGHV4-28 | 0.6 |
| 29 | IGHV3-64 | 0.5 |
| 30 | IGHV7-81 | 0.5 |
| 31 | IGHV3-13 | 0.4 |
| 32 | IGHV3-72 | 0.4 |
| 33 | IGHV1-58 | 0.3 |
| 34 | IGHV3-73 | 0.3 |
| 35 | IGHV3-66 | 0.2 |
| 36 | IGHV7-4.1 | 0.2 |
| 37 | IGHV2-5 | 0.1 |
| 38 | IGHV4-30.2 | 0.1 |
| 39 | IGHV3-20 | 0.1 |
| 40 | IGHV6-1 | 0.0 |
| 41 | IGHV1-e | 0.0 |
| 42 | IGHV1-f | 0.0 |
| 43 | IGHV1-45 | 0.0 |
| 44 | IGHV2-26 | 0.0 |
| 45 | IGHV2-70 | 0.0 |
| 46 | IGHV3-d | 0.0 |
| 47 | IGHV4-b | 0.0 |
| 48 | IGHV4-30.4 | 0.0 |
| 49 | IGHV5-a | 0.0 |

Vκ
n = 1656

| | | |
|---|---|---|
| 1 | IGKV3-20 | 16.2 |
| 2 | IGKV1-39/1D-39 | 14.2 |
| 3 | IGKV1-5 | 11.2 |
| 4 | IGKV3-15 | 11.1 |
| 5 | IGKV4-1 | 8.5 |
| 6 | IGKV3-11 | 7.6 |
| 7 | IGKV2-28/2D-28 | 6.0 |
| 8 | IGKV1-33/1D-33 | 4.6 |
| 9 | IGKV2-30 | 2.6 |

TABLE 21-continued

Ranking of the prevalence of VH, Vλ and Vκ germline genes from publically available data and a human B cell sample and identification of VH, Vλ and Vκ germline genes that were selected for further functional testing are bold and underlined.

| | | |
|---|---|---|
| 10 | IGKV1-9 | 2.4 |
| 11 | IGKV1-17 | 2.4 |
| 12 | IGKV1-27 | 2.2 |
| 13 | IGKV1-8 | 1.9 |
| 14 | IGKV1-16 | 1.3 |
| 15 | IGKV1-6 | 1.1 |
| 16 | IGKV1-12 | 1.1 |
| 17 | IGKV2D-29 | 1.0 |
| 18 | IGKV1-13 | 0.7 |
| 19 | IGKV1D-8 | 0.5 |
| 20 | IGKV2-24 | 0.5 |
| 21 | IGKV5-2 | 0.4 |
| 22 | IGKV1D-12 | 0.3 |
| 23 | IGKV2-40/2D-40 | 0.3 |
| 24 | IGKV3D-20 | 0.3 |
| 25 | IGKV1D-43 | 0.2 |
| 26 | IGKV2D-30 | 0.2 |
| 27 | IGKV3D-11 | 0.2 |
| 28 | IGKV3D-15 | 0.2 |
| 29 | IGKV2-29 | 0.2 |
| 30 | IGKV1D-16 | 0.1 |
| 31 | IGKV1D-17 | 0.1 |
| 32 | IGKV3D-7 | 0.1 |
| 33 | IGKV6-21/6D-21 | 0.1 |
| 34 | IGKV6D-41 | 0.1 |
| 35 | IGKV1D-13 | 0.0 |

Vλ
n = 780

| | | |
|---|---|---|
| 1 | IGLV2-14 | 18.1 |
| 2 | IGLV1-40 | 11.3 |
| 3 | IGLV1-44 | 11.3 |
| 4 | IGLV1-51 | 10.0 |
| 5 | IGLV2-23 | 8.1 |
| 6 | IGLV3-21 | 8.1 |
| 7 | IGLV1-47 | 6.5 |
| 8 | IGLV3-1 | 5.3 |
| 9 | IGLV2-11 | 5.1 |
| 10 | IGLV2-8 | 4.5 |
| 11 | IGLV6-57 | 1.7 |
| 12 | IGLV3-25 | 1.5 |
| 13 | IGLV7-46 | 1.5 |
| 14 | IGLV1-36 | 1.2 |
| 15 | IGLV7-43 | 1.2 |
| 16 | IGLV9-49 | 1.2 |
| 17 | IGLV4-69 | 1.0 |
| 18 | IGLV2-18 | 0.6 |
| 19 | IGLV3-10 | 0.5 |
| 20 | IGLV3-27 | 0.5 |
| 21 | IGLV3-9 | 0.3 |
| 22 | IGLV3-12 | 0.1 |
| 23 | IGLV3-19 | 0.1 |
| 24 | IGLV3-22 | 0.1 |
| 25 | IGLV4-60 | 0.1 |
| 26 | IGLV8-61 | 0.1 |
| 27 | IGLV3-16 | 0.0 |
| 28 | IGLV4-3 | 0.0 |
| 29 | IGLV5-37 | 0.0 |
| 30 | IGLV5-39 | 0.0 |
| 31 | IGLV5-45 | 0.0 |
| 32 | IGLV5-52 | 0.0 |
| 33 | IGLV10-54 | 0.0 |

Example 4.1

Recombination of Abundant VH, Vκ, and Vλ Germline Genes to Yield Representation of VH/VL Most Prominent Pairs in the Human Immune Repertoire As discussed above, and shown in Tables 21, and FIGS. 39-40, 41-42, the 20 VH, 12 Vκ and 8 Vλ selected, when combined accurately reproduce or cover the majority of the prominently expressed VH/VL germline gene pairs from the human immune repertoire and the naïve human immune repertoire.

As a next step, the 20 VH, 12 Vκ and 8 Vλ selected VH, Vκ, and Vλ germline genes were synthesized and combined to generate 400 VH/VL germline gene pairs that accurately reproduce or cover the majority of the prominently expressed VH/VL germline gene pairs in the human immune repertoire. The 400 VH/VL germline gene pairs were then tested for their biophysical properties.

Table 22 shows the selected VH, Vκ, and Vλ germline genes to be combined to generate the 400 VH/VL germline gene pairs.

TABLE 22

| VH | Vκ | Vλ |
|---|---|---|
| 1. IGHV3-23 | 1. IGKV3-20 | 1. IGLV2-14 |
| 2. IGHV3-30 | 2. IGKV1-39/1D-39 | 2. IGLV1-40 |
| 3. IGHV4-39 | 3. IGKV1-5 | 3. IGLV1-51 |
| 4. IGHV1-69 | 4. IGKV3-15 | 4. IGLV2-23 |
| 5. IGHV5-51 | 5. IGKV3-11 | 5. IGLV3-21 |
| 6. IGHV3-7 | 6. IGKV2-30 | 6. IGLV1-47 |
| 7. IGHV1-18 | 7. IGKV1-9 | 7. IGLV3-1 |
| 8. IGHV3-48 | 8. IGKV1-17 | 8. IGLV2-11 |
| 9. IGHV3-15 | 9. IGKV1-27 | |
| 10. IGHV3-21 | 10. IGKV1-16 | |
| 11. IGHV1-2 | 11. IGKV1-6 | |
| 12. IGHV3-33 | 12. IGKV1-12 | |
| 13. IGHV4-31 | | |
| 14. IGHV3-53 | | |
| 15. IGHV3-11 | | |
| 16. IGHV4-4 | | |
| 17. IGHV1-46 | | |
| 18. IGHV3-74 | | |
| 19. IGHV3-73 | | |
| 20. IGHV6-1 | | |

To show that the 400 VH/VL germline gene pairs generated for functional testing do, in fact, accurately reproduce or cover the majority of the prominently expressed VH/VL germline gene pairs in the human immune repertoire, Table 18 is reproduced below as Table 23, wherein the 400 VH/VL pairs that were tested are bolded and underlined.

TABLE 23

The 400 VH/VL germline gene pairs functional tested are representative of the VH/VL germline gene pairs identified in the human immune repertoire

| pos | V heavy | V light | % |
|---|---|---|---|
| 1 | IGHV3-23 | IGKV1-5 | 1.26 |
| 2 | IGHV4-34 | IGKV3-20 | 1.17 |
| 3 | IGHV3-23 | IGKV3-20 | 1.12 |
| 4 | IGHV4-39 | IGKV3-15 | 1.03 |
| 5 | IGHV3-23 | IGKV3-15 | 0.94 |
| 6 | IGHV4-59 | IGKV1-39/1D-39 | 0.89 |
| 7 | IGHV4-39 | IGKV1-39/1D-39 | 0.84 |
| | IGHV4-34 | IGKV1-39/1D-39 | 0.84 |
| 8 | IGHV4-59 | IGKV3-20 | 0.70 |
| | IGHV1-18 | IGKV3-20 | 0.70 |
| 9 | IGHV3-30 | IGKV3-20 | 0.66 |
| | IGHV4-39 | IGKV1-5 | 0.66 |
| | IGHV1-69 | IGKV1-39/1D-39 | 0.66 |
| | IGHV5-51 | IGLV1-40 | 0.66 |
| 10 | IGHV3-23 | IGKV4-1 | 0.61 |
| | IGHV4-39 | IGKV3-20 | 0.61 |
| | IGHV3-23 | IGLV2-14 | 0.61 |
| | IGHV4-39 | IGLV3-21 | 0.61 |
| 11 | IGHV3-23 | IGKV1-39/1D-39 | 0.56 |
| | IGHV3-30 | IGKV1-39/1D-39 | 0.56 |

TABLE 23-continued

The 400 VH/VL germline gene pairs functional tested are representative of the VH/VL germline gene pairs identified in the human immune repertoire

| pos | V heavy | V light | % |
|---|---|---|---|
| | IGHV3-30 | IGKV3-11 | 0.56 |
| | IGHV1-69 | IGKV3-20 | 0.56 |
| | IGHV3-48 | IGKV3-20 | 0.56 |
| | IGHV1-2 | IGKV3-20 | 0.56 |
| 12 | IGHV3-30 | IGKV4-1 | 0.51 |
| | IGHV5-51 | IGLV2-14 | 0.51 |
| 13 | IGHV4-59 | IGKV4-1 | 0.47 |
| | IGHV5-51 | IGKV3-20 | 0.47 |
| | IGHV3-7 | IGKV1-39/1D-39 | 0.47 |
| | IGHV3-7 | IGKV1-5 | 0.47 |
| | IGHV3-15 | IGKV3-20 | 0.47 |
| | IGHV4-39 | IGLV2-14 | 0.47 |
| | IGHV4-39 | IGLV2-8 | 0.47 |
| | IGHV4-34 | IGLV2-14 | 0.47 |
| 14 | IGHV3-23 | IGKV3-11 | 0.42 |
| | IGHV3-30 | IGKV1-5 | 0.42 |
| | IGHV3-30 | IGKV3-15 | 0.42 |
| | IGHV4-34 | IGKV1-5 | 0.42 |
| | IGHV3-21 | IGKV1-5 | 0.42 |
| | IGHV3-21 | IGKV3-15 | 0.42 |
| | IGHV3-30 | IGLV1-51 | 0.42 |
| | IGHV4-34 | IGLV1-51 | 0.42 |
| | IGHV3-21 | IGLV1-51 | 0.42 |
| | IGHV3-53 | IGLV1-44 | 0.42 |
| 15 | IGHV4-59 | IGKV3-15 | 0.37 |
| | IGHV4-34 | IGKV3-15 | 0.37 |
| | IGHV5-51 | IGKV4-1 | 0.37 |
| | IGHV1-69 | IGKV4-1 | 0.37 |
| | IGHV1-69 | IGKV3-11 | 0.37 |
| | IGHV3-7 | IGKV3-15 | 0.37 |
| | IGHV1-18 | IGKV1-39/1D-39 | 0.37 |
| | IGHV3-48 | IGKV1-39/1D-39 | 0.37 |
| | IGHV3-33 | IGKV3-15 | 0.37 |
| | IGHV3-53 | IGKV1-5 | 0.37 |
| | IGHV4-59 | IGLV1-40 | 0.37 |
| | IGHV1-69 | IGLV2-14 | 0.37 |
| | IGHV1-69 | IGLV1-44 | 0.37 |
| | IGHV4-31 | IGLV2-14 | 0.37 |
| | IGHV1-2 | IGLV2-14 | 0.37 |
| 16 | IGHV3-23 | IGKV2-28/2D-28 | 0.33 |
| | IGHV3-30 | IGKV1-9 | 0.33 |
| | IGHV4-34 | IGKV4-1 | 0.33 |
| | IGHV5-51 | IGKV1-39/1D-39 | 0.33 |
| | IGHV5-51 | IGKV3-15 | 0.33 |
| | IGHV1-69 | IGKV3-15 | 0.33 |
| | IGHV1-18 | IGKV1-33/1D-33 | 0.33 |
| | IGHV3-48 | IGKV3-11 | 0.33 |
| | IGHV3-21 | IGKV1-39/1D-39 | 0.33 |
| | IGHV4-31 | IGKV3-20 | 0.33 |
| | IGHV4-31 | IGKV3-11 | 0.33 |
| | IGHV3-30 | IGLV2-14 | 0.33 |
| | IGHV4-39 | IGLV1-44 | 0.33 |
| | IGHV1-69 | IGLV1-40 | 0.33 |
| | IGHV3-9 | IGLV2-23 | 0.33 |
| 17 | IGHV3-23 | IGKV1-33/1D-33 | 0.28 |
| | IGHV4-39 | IGKV3-11 | 0.28 |
| | IGHV4-34 | IGKV3-11 | 0.28 |
| | IGHV4-34 | IGKV2-28/2D-28 | 0.28 |
| | IGHV5-51 | IGKV3-11 | 0.28 |
| | IGHV5-51 | IGKV1-13 | 0.28 |
| | IGHV3-7 | IGKV3-20 | 0.28 |
| | IGHV3-48 | IGKV3-15 | 0.28 |
| | IGHV3-48 | IGKV4-1 | 0.28 |
| | IGHV3-48 | IGKV1-33/1D-33 | 0.28 |
| | IGHV3-15 | IGKV1-39/1D-39 | 0.28 |
| | IGHV3-15 | IGKV1-5 | 0.28 |
| | IGHV1-2 | IGKV1-39/1D-39 | 0.28 |
| | IGHV3-33 | IGKV3-20 | 0.28 |
| | IGHV3-33 | IGKV1-39/1D-39 | 0.28 |
| | IGHV3-33 | IGKV4-1 | 0.28 |
| | IGHV3-53 | IGKV3-15 | 0.28 |
| | IGHV3-11 | IGKV1-5 | 0.28 |
| | IGHV4-4 | IGKV3-20 | 0.28 |
| | IGHV1-46 | IGKV3-20 | 0.28 |

TABLE 23-continued

The 400 VH/VL germline gene pairs functional tested are representative of the VH/VL germline gene pairs identified in the human immune repertoire

| pos | V heavy | V light | % |
|---|---|---|---|
|  | IGHV3-23 | IGLV1-40 | 0.28 |
|  | IGHV3-23 | IGLV3-21 | 0.28 |
|  | IGHV4-39 | IGLV1-40 | 0.28 |
|  | IGHV4-34 | IGLV1-40 | 0.28 |
|  | IGHV4-34 | IGLV1-47 | 0.28 |
|  | IGHV3-48 | IGLV2-14 | 0.28 |
|  | IGHV3-48 | IGLV1-47 | 0.28 |
|  | IGHV1-2 | IGLV1-40 | 0.28 |
|  | IGHV3-9 | IGLV2-14 | 0.28 |
|  | IGHV4-4 | IGLV1-44 | 0.28 |
| 18 | IGHV3-23 | IGKV1-17 | 0.23 |
|  | IGHV4-39 | IGKV4-1 | 0.23 |
|  | IGHV4-39 | IGKV2-28/2D-28 | 0.23 |
|  | IGHV1-69 | IGKV1-5 | 0.23 |
|  | IGHV3-7 | IGKV4-1 | 0.23 |
|  | IGHV1-18 | IGKV1-5 | 0.23 |
|  | IGHV1-18 | IGKV2-28/2D-28 | 0.23 |
|  | IGHV3-21 | IGKV3-20 | 0.23 |
|  | IGHV3-33 | IGKV1-5 | 0.23 |
|  | IGHV3-53 | IGKV1-39/1D-39 | 0.23 |
|  | IGHV3-53 | IGKV1-33/1D-33 | 0.23 |
|  | IGHV3-11 | IGKV1-39/1D-39 | 0.23 |
|  | IGHV3-11 | IGKV3-15 | 0.23 |
|  | IGHV4-4 | IGKV1-39/1D-39 | 0.23 |
|  | IGHV1-46 | IGKV1-39/1D-39 | 0.23 |
|  | IGHV4-61 | IGKV4-1 | 0.23 |
|  | IGHV3-23 | IGLV1-44 | 0.23 |
|  | IGHV3-23 | IGLV2-11 | 0.23 |
|  | IGHV3-23 | IGLV3-1 | 0.23 |
|  | IGHV3-30 | IGLV1-40 | 0.23 |
|  | IGHV4-39 | IGLV1-51 | 0.23 |
|  | IGHV4-39 | IGLV2-23 | 0.23 |
|  | IGHV4-59 | IGLV3-1 | 0.23 |
|  | IGHV5-51 | IGLV1-44 | 0.23 |
|  | IGHV1-69 | IGLV1-51 | 0.23 |
|  | IGHV1-69 | IGLV2-11 | 0.23 |
|  | IGHV1-18 | IGLV2-14 | 0.23 |
|  | IGHV1-18 | IGLV1-40 | 0.23 |
|  | IGHV3-21 | IGLV2-14 | 0.23 |
|  | IGHV1-2 | IGLV1-44 | 0.23 |
| 19 | IGHV3-23 | IGKV1-27 | 0.19 |
|  | IGHV3-23 | IGKV1-8 | 0.19 |
|  | IGHV3-30 | IGKV2-28/2D-28 | 0.19 |
|  | IGHV4-39 | IGKV1-33/1D-33 | 0.19 |
|  | IGHV4-39 | IGKV1-27 | 0.19 |
|  | IGHV4-59 | IGKV3-11 | 0.19 |
|  | IGHV5-51 | IGKV1-5 | 0.19 |
|  | IGHV5-51 | IGKV2-28/2D-28 | 0.19 |
|  | IGHV3-7 | IGKV3-11 | 0.19 |
|  | IGHV3-7 | IGKV2-30 | 0.19 |
|  | IGHV1-18 | IGKV3-15 | 0.19 |
|  | IGHV1-18 | IGKV3-11 | 0.19 |
|  | IGHV3-21 | IGKV4-1 | 0.19 |
|  | IGHV3-15 | IGKV3-15 | 0.19 |
|  | IGHV3-15 | IGKV4-1 | 0.19 |
|  | IGHV3-15 | IGKV1-33/1D-33 | 0.19 |
|  | IGHV4-31 | IGKV1-39/1D-39 | 0.19 |
|  | IGHV4-31 | IGKV1-5 | 0.19 |
|  | IGHV4-31 | IGKV3-15 | 0.19 |
|  | IGHV4-31 | IGKV2-28/2D-28 | 0.19 |
|  | IGHV3-33 | IGKV2-28/2D-28 | 0.19 |
|  | IGHV3-53 | IGKV4-1 | 0.19 |
|  | IGHV3-53 | IGKV3-11 | 0.19 |
|  | IGHV3-74 | IGKV3-20 | 0.19 |
|  | IGHV4-4 | IGKV1-5 | 0.19 |
|  | IGHV1-46 | IGKV1-9 | 0.19 |
|  | IGHV1-8 | IGKV3-15 | 0.19 |
|  | IGHV1-24 | IGKV3-11 | 0.19 |
|  | IGHV1-3 | IGKV1-39/1D-39 | 0.19 |
|  | IGHV3-49 | IGKV1-39/1D-39 | 0.19 |
|  | IGHV3-23 | IGLV2-23 | 0.19 |
|  | IGHV3-30 | IGLV1-44 | 0.19 |
|  | IGHV4-59 | IGLV2-14 | 0.19 |
|  | IGHV4-59 | IGLV1-44 | 0.19 |
|  | IGHV4-59 | IGLV1-51 | 0.19 |
|  | IGHV4-34 | IGLV2-8 | 0.19 |
|  | IGHV5-51 | IGLV1-47 | 0.19 |
|  | IGHV1-69 | IGLV2-8 | 0.19 |
|  | IGHV3-7 | IGLV1-40 | 0.19 |
|  | IGHV3-15 | IGLV1-44 | 0.19 |
|  | IGHV4-31 | IGLV2-23 | 0.19 |
|  | IGHV3-33 | IGLV2-14 | 0.19 |
|  | IGHV3-33 | IGLV1-47 | 0.19 |
|  | IGHV3-33 | IGLV2-23 | 0.19 |
|  | IGHV3-33 | IGLV3-21 | 0.19 |
|  | IGHV3-9 | IGLV1-44 | 0.19 |
|  | IGHV4-4 | IGLV2-14 | 0.19 |
|  | IGHV1-46 | IGLV1-51 | 0.19 |
|  | IGHV4-61 | IGLV1-44 | 0.19 |
|  | IGHV1-8 | IGLV2-14 | 0.19 |
|  | IGHV4-28 | IGLV2-23 | 0.19 |
| 20 | IGHV3-23 | IGKV1-9 | 0.14 |
|  | IGHV3-23 | IGKV1-16 | 0.14 |
|  | IGHV4-39 | IGKV1-6 | 0.14 |
|  | IGHV4-59 | IGKV1-5 | 0.14 |
|  | IGHV4-59 | IGKV1-27 | 0.14 |
|  | IGHV4-34 | IGKV1-33/1D-33 | 0.14 |
|  | IGHV5-51 | IGKV1-33/1D-33 | 0.14 |
|  | IGHV1-69 | IGKV2-28/2D-28 | 0.14 |
|  | IGHV1-69 | IGKV1-33/1D-33 | 0.14 |
|  | IGHV3-7 | IGKV2-28/2D-28 | 0.14 |
|  | IGHV3-7 | IGKV1-8 | 0.14 |
|  | IGHV3-48 | IGKV2-28/2D-28 | 0.14 |
|  | IGHV3-48 | IGKV1-8 | 0.14 |
|  | IGHV3-15 | IGKV3-11 | 0.14 |
|  | IGHV3-15 | IGKV2-28/2D-28 | 0.14 |
|  | IGHV3-15 | IGKV1-9 | 0.14 |
|  | IGHV4-31 | IGKV1-33/1D-33 | 0.14 |
|  | IGHV1-2 | IGKV1-5 | 0.14 |
|  | IGHV1-2 | IGKV4-1 | 0.14 |
|  | IGHV3-11 | IGKV3-20 | 0.14 |
|  | IGHV3-11 | IGKV3-11 | 0.14 |
|  | IGHV3-11 | IGKV2-28/2D-28 | 0.14 |
|  | IGHV3-9 | IGKV1-39/1D-39 | 0.14 |
|  | IGHV3-9 | IGKV1-5 | 0.14 |
|  | IGHV3-9 | IGKV4-1 | 0.14 |
|  | IGHV3-9 | IGKV2D-29 | 0.14 |
|  | IGHV3-74 | IGKV1-39/1D-39 | 0.14 |
|  | IGHV3-74 | IGKV1-5 | 0.14 |
|  | IGHV3-74 | IGKV3-15 | 0.14 |
|  | IGHV3-74 | IGKV4-1 | 0.14 |
|  | IGHV4-4 | IGKV3-15 | 0.14 |
|  | IGHV4-4 | IGKV4-1 | 0.14 |
|  | IGHV4-4 | IGKV3-11 | 0.14 |
|  | IGHV1-46 | IGKV1-5 | 0.14 |
|  | IGHV1-46 | IGKV3-15 | 0.14 |
|  | IGHV4-61 | IGKV1-39/1D-39 | 0.14 |
|  | IGHV1-24 | IGKV1-39/1D-39 | 0.14 |
|  | IGHV1-24 | IGKV3-15 | 0.14 |
|  | IGHV1-3 | IGKV3-15 | 0.14 |
|  | IGHV3-49 | IGKV1-17 | 0.14 |
|  | IGHV3-43 | IGKV1-5 | 0.14 |
|  | IGHV7-81 | IGKV3-20 | 0.14 |
|  | IGHV3-13 | IGKV1-39/1D-39 | 0.14 |
|  | IGHV3-23 | IGLV1-51 | 0.14 |
|  | IGHV3-30 | IGLV3-21 | 0.14 |
|  | IGHV3-30 | IGLV3-1 | 0.14 |
|  | IGHV4-39 | IGLV1-47 | 0.14 |
|  | IGHV4-39 | IGLV2-18 | 0.14 |
|  | IGHV4-59 | IGLV1-47 | 0.14 |
|  | IGHV5-51 | IGLV2-23 | 0.14 |
|  | IGHV5-51 | IGLV3-21 | 0.14 |
|  | IGHV1-69 | IGLV2-23 | 0.14 |
|  | IGHV3-7 | IGLV1-44 | 0.14 |
|  | IGHV3-7 | IGLV1-51 | 0.14 |
|  | IGHV3-7 | IGLV1-47 | 0.14 |
|  | IGHV3-7 | IGLV3-21 | 0.14 |
|  | IGHV1-18 | IGLV1-44 | 0.14 |

TABLE 23-continued

The 400 VH/VL germline gene pairs functional tested are representative of the VH/VL germline gene pairs identified in the human immune repertoire

| pos | V heavy | V light | % |
|---|---|---|---|
| | IGHV1-18 | IGLV1-51 | 0.14 |
| | IGHV3-48 | IGLV3-1 | 0.14 |
| | IGHV3-21 | IGLV1-47 | 0.14 |
| | IGHV3-15 | IGLV7-46 | 0.14 |
| | IGHV4-31 | IGLV1-40 | 0.14 |
| | IGHV4-31 | IGLV1-51 | 0.14 |
| | IGHV4-31 | IGLV1-47 | 0.14 |
| | IGHV1-2 | IGLV1-51 | 0.14 |
| | IGHV1-2 | IGLV2-23 | 0.14 |
| | IGHV1-2 | IGLV3-1 | 0.14 |
| | IGHV3-11 | IGLV2-14 | 0.14 |
| | IGHV3-11 | IGLV1-44 | 0.14 |
| | IGHV3-11 | IGLV2-11 | 0.14 |
| | IGHV3-11 | IGLV3-1 | 0.14 |
| | IGHV3-9 | IGLV1-47 | 0.14 |
| | IGHV3-9 | IGLV2-11 | 0.14 |
| | IGHV3-74 | IGLV2-23 | 0.14 |
| | IGHV3-74 | IGLV3-21 | 0.14 |
| | IGHV4-4 | IGLV1-40 | 0.14 |
| | IGHV1-46 | IGLV2-14 | 0.14 |
| | IGHV1-46 | IGLV1-44 | 0.14 |
| | IGHV4-61 | IGLV2-14 | 0.14 |
| 21 | IGHV3-23 | IGKV2D-29 | 0.09 |
| | IGHV3-23 | IGKV2-29 | 0.09 |
| | IGHV3-23 | IGKV2-40/2D-40 | 0.09 |
| | IGHV3-30 | IGKV1-33/1D-33 | 0.09 |
| | IGHV3-30 | IGKV2-30 | 0.09 |
| | IGHV3-30 | IGKV1-8 | 0.09 |
| | IGHV3-30 | IGKV1-6 | 0.09 |
| | IGHV3-30 | IGKV2-24 | 0.09 |
| | IGHV3-30 | IGKV1D-8 | 0.09 |
| | IGHV4-39 | IGKV2-30 | 0.09 |
| | IGHV4-59 | IGKV1-33/1D-33 | 0.09 |
| | IGHV4-59 | IGKV1-12 | 0.09 |
| | IGHV4-34 | IGKV1-9 | 0.09 |
| | IGHV4-34 | IGKV1-17 | 0.09 |
| | IGHV4-34 | IGKV1-16 | 0.09 |
| | IGHV5-51 | IGKV2-30 | 0.09 |
| | IGHV1-69 | IGKV1-27 | 0.09 |
| | IGHV1-69 | IGKV1-8 | 0.09 |
| | IGHV1-69 | IGKV3D-15 | 0.09 |
| | IGHV3-7 | IGKV1-9 | 0.09 |
| | IGHV3-7 | IGKV1-17 | 0.09 |
| | IGHV3-7 | IGKV1-27 | 0.09 |
| | IGHV3-7 | IGKV1-13 | 0.09 |
| | IGHV1-18 | IGKV4-1 | 0.09 |
| | IGHV1-18 | IGKV2-30 | 0.09 |
| | IGHV3-48 | IGKV1-9 | 0.09 |
| | IGHV3-48 | IGKV1-17 | 0.09 |
| | IGHV3-48 | IGKV1-16 | 0.09 |
| | IGHV3-48 | IGKV3-11 | 0.09 |
| | IGHV3-21 | IGKV2-28/2D-28 | 0.09 |
| | IGHV3-21 | IGKV1-27 | 0.09 |
| | IGHV3-21 | IGKV1-8 | 0.09 |
| | IGHV3-21 | IGKV1-6 | 0.09 |
| | IGHV4-31 | IGKV4-1 | 0.09 |
| | IGHV4-31 | IGKV1-17 | 0.09 |
| | IGHV4-31 | IGKV1-27 | 0.09 |
| | IGHV1-2 | IGKV3-15 | 0.09 |
| | IGHV1-2 | IGKV2-28/2D-28 | 0.09 |
| | IGHV1-2 | IGKV1-27 | 0.09 |
| | IGHV3-33 | IGKV3-11 | 0.09 |
| | IGHV3-33 | IGKV1-33/1D-33 | 0.09 |
| | IGHV3-33 | IGKV1-9 | 0.09 |
| | IGHV3-53 | IGKV3-20 | 0.09 |
| | IGHV3-53 | IGKV1-27 | 0.09 |
| | IGHV3-53 | IGKV1-8 | 0.09 |
| | IGHV3-11 | IGKV4-1 | 0.09 |
| | IGHV3-11 | IGKV1-6 | 0.09 |
| | IGHV3-9 | IGKV3-15 | 0.09 |
| | IGHV3-9 | IGKV3-11 | 0.09 |
| | IGHV3-9 | IGKV1-16 | 0.09 |
| | IGHV3-74 | IGKV3-11 | 0.09 |
| | IGHV3-74 | IGKV2-30 | 0.09 |
| | IGHV4-4 | IGKV2-28/2D-28 | 0.09 |
| | IGHV4-4 | IGKV2D-29 | 0.09 |
| | IGHV1-46 | IGKV3-11 | 0.09 |
| | IGHV1-46 | IGKV1-27 | 0.09 |
| | IGHV1-46 | IGKV1-16 | 0.09 |
| | IGHV4-61 | IGKV3-15 | 0.09 |
| | IGHV1-8 | IGKV3-20 | 0.09 |
| | IGHV1-8 | IGKV4-1 | 0.09 |
| | IGHV1-24 | IGKV2-28/2D-28 | 0.09 |
| | IGHV1-24 | IGKV2-30 | 0.09 |
| | IGHV1-3 | IGKV3-20 | 0.09 |
| | IGHV3-49 | IGKV3-20 | 0.09 |
| | IGHV3-49 | IGKV1-5 | 0.09 |
| | IGHV3-43 | IGKV3-11 | 0.09 |
| | IGHV3-64 | IGKV1-5 | 0.09 |
| | IGHV3-64 | IGKV3-11 | 0.09 |
| | IGHV7-81 | IGKV1-39/1D-39 | 0.09 |
| | IGHV3-13 | IGKV4-1 | 0.09 |
| | IGHV3-72 | IGKV1-5 | 0.09 |
| | IGHV3-72 | IGKV3-15 | 0.09 |
| | IGHV1-58 | IGKV3-20 | 0.09 |
| | IGHV3-66 | IGKV1-39/1D-39 | 0.09 |
| | IGHV3-23 | IGLV1-36 | 0.09 |
| | IGHV3-30 | IGLV2-23 | 0.09 |
| | IGHV3-30 | IGLV2-11 | 0.09 |
| | IGHV3-30 | IGLV9-49 | 0.09 |
| | IGHV3-30 | IGLV3-10 | 0.09 |
| | IGHV4-39 | IGLV3-1 | 0.09 |
| | IGHV4-39 | IGLV6-57 | 0.09 |
| | IGHV4-59 | IGLV2-23 | 0.09 |
| | IGHV4-59 | IGLV3-21 | 0.09 |
| | IGHV4-59 | IGLV2-11 | 0.09 |
| | IGHV4-34 | IGLV1-44 | 0.09 |
| | IGHV4-34 | IGLV2-23 | 0.09 |
| | IGHV4-34 | IGLV3-21 | 0.09 |
| | IGHV4-34 | IGLV3-25 | 0.09 |
| | IGHV5-51 | IGLV1-36 | 0.09 |
| | IGHV5-51 | IGLV3-25 | 0.09 |
| | IGHV1-69 | IGLV1-47 | 0.09 |
| | IGHV1-69 | IGLV3-21 | 0.09 |
| | IGHV1-69 | IGLV3-1 | 0.09 |
| | IGHV3-7 | IGLV2-14 | 0.09 |
| | IGHV1-18 | IGLV2-8 | 0.09 |
| | IGHV1-18 | IGLV6-57 | 0.09 |
| | IGHV3-48 | IGLV2-11 | 0.09 |
| | IGHV3-21 | IGLV1-40 | 0.09 |
| | IGHV3-21 | IGLV1-44 | 0.09 |
| | IGHV3-21 | IGLV3-21 | 0.09 |
| | IGHV3-21 | IGLV2-11 | 0.09 |
| | IGHV3-21 | IGLV4-69 | 0.09 |
| | IGHV3-15 | IGLV1-40 | 0.09 |
| | IGHV3-15 | IGLV1-51 | 0.09 |
| | IGHV3-15 | IGLV3-1 | 0.09 |
| | IGHV3-15 | IGLV2-8 | 0.09 |
| | IGHV3-15 | IGLV7-43 | 0.09 |
| | IGHV4-31 | IGLV3-21 | 0.09 |
| | IGHV1-2 | IGLV2-8 | 0.09 |
| | IGHV1-2 | IGLV7-46 | 0.09 |
| | IGHV3-33 | IGLV6-57 | 0.09 |
| | IGHV3-53 | IGLV2-14 | 0.09 |
| | IGHV3-11 | IGLV2-23 | 0.09 |
| | IGHV3-11 | IGLV3-21 | 0.09 |
| | IGHV3-11 | IGLV4-69 | 0.09 |
| | IGHV3-9 | IGLV3-21 | 0.09 |
| | IGHV3-9 | IGLV2-8 | 0.09 |
| | IGHV3-74 | IGLV2-14 | 0.09 |
| | IGHV4-4 | IGLV1-51 | 0.09 |
| | IGHV4-4 | IGLV2-23 | 0.09 |
| | IGHV4-4 | IGLV2-8 | 0.09 |
| | IGHV1-46 | IGLV2-11 | 0.09 |
| | IGHV4-61 | IGLV2-11 | 0.09 |
| | IGHV1-8 | IGLV1-47 | 0.09 |
| | IGHV1-24 | IGLV2-23 | 0.09 |
| | IGHV1-3 | IGLV2-14 | 0.09 |

TABLE 23-continued

The 400 VH/VL germline gene pairs functional tested are representative of the VH/VL germline gene pairs identified in the human immune repertoire

| pos | V heavy | V light | % |
|---|---|---|---|
|  | IGHV1-3 | IGLV2-23 | 0.09 |
|  | IGHV1-3 | IGLV3-1 | 0.09 |
|  | IGHV3-49 | IGLV3-21 | 0.09 |
|  | IGHV4-28 | IGLV1-44 | 0.09 |
|  | IGHV4-28 | IGLV1-51 | 0.09 |
|  | IGHV4-28 | IGLV1-36 | 0.09 |
|  | IGHV3-43 | IGLV1-51 | 0.09 |
|  | IGHV3-64 | IGLV3-21 | 0.09 |
|  | IGHV7-81 | IGLV2-14 | 0.09 |
|  | IGHV7-81 | IGLV3-21 | 0.09 |
| 22 | IGHV3-23 | IGKV2-30 | 0.05 |
|  | IGHV3-23 | IGKV1-12 | 0.05 |
|  | IGHV3-23 | IGKV3D-20 | 0.05 |
|  | IGHV3-23 | IGKV1D-12 | 0.05 |
|  | IGHV3-23 | IGKV1D-13 | 0.05 |
|  | IGHV3-30 | IGKV1-17 | 0.05 |
|  | IGHV3-30 | IGKV1-27 | 0.05 |
|  | IGHV3-30 | IGKV1-16 | 0.05 |
|  | IGHV3-30 | IGKV2D-29 | 0.05 |
|  | IGHV3-30 | IGKV1-13 | 0.05 |
|  | IGHV3-30 | IGKV5-2 | 0.05 |
|  | IGHV3-30 | IGKV2D-30 | 0.05 |
|  | IGHV4-39 | IGKV1-17 | 0.05 |
|  | IGHV4-39 | IGKV3D-15 | 0.05 |
|  | IGHV4-59 | IGKV2-30 | 0.05 |
|  | IGHV4-59 | IGKV1-17 | 0.05 |
|  | IGHV4-59 | IGKV1-8 | 0.05 |
|  | IGHV4-59 | IGKV1-16 | 0.05 |
|  | IGHV4-59 | IGKV1D-43 | 0.05 |
|  | IGHV4-59 | IGKV2D-30 | 0.05 |
|  | IGHV4-59 | IGKV1D-17 | 0.05 |
|  | IGHV4-34 | IGKV1-27 | 0.05 |
|  | IGHV4-34 | IGKV1-8 | 0.05 |
|  | IGHV4-34 | IGKV1-12 | 0.05 |
|  | IGHV5-51 | IGKV1-9 | 0.05 |
|  | IGHV5-51 | IGKV1-17 | 0.05 |
|  | IGHV5-51 | IGKV1-27 | 0.05 |
|  | IGHV5-51 | IGKV1-12 | 0.05 |
|  | IGHV1-69 | IGKV2-30 | 0.05 |
|  | IGHV1-69 | IGKV1-16 | 0.05 |
|  | IGHV1-69 | IGKV1-6 | 0.05 |
|  | IGHV1-69 | IGKV2D-29 | 0.05 |
|  | IGHV1-69 | IGKV2D-30 | 0.05 |
|  | IGHV1-69 | IGKV1D-16 | 0.05 |
|  | IGHV3-7 | IGKV1-6 | 0.05 |
|  | IGHV3-7 | IGKV1D-8 | 0.05 |
|  | IGHV3-7 | IGKV1D-17 | 0.05 |
|  | IGHV1-18 | IGKV1-17 | 0.05 |
|  | IGHV1-18 | IGKV1-8 | 0.05 |
|  | IGHV1-18 | IGKV1-16 | 0.05 |
|  | IGHV1-18 | IGKV1-12 | 0.05 |
|  | IGHV1-18 | IGKV1-13 | 0.05 |
|  | IGHV1-18 | IGKV2-40/2D-40 | 0.05 |
|  | IGHV3-48 | IGKV1-5 | 0.05 |
|  | IGHV3-48 | IGKV1-27 | 0.05 |
|  | IGHV3-48 | IGKV1-6 | 0.05 |
|  | IGHV3-48 | IGKV2D-29 | 0.05 |
|  | IGHV3-48 | IGKV3D-20 | 0.05 |
|  | IGHV3-48 | IGKV1D-12 | 0.05 |
|  | IGHV3-21 | IGKV2D-29 | 0.05 |
|  | IGHV3-15 | IGKV2-30 | 0.05 |
|  | IGHV3-15 | IGKV1-27 | 0.05 |
|  | IGHV3-15 | IGKV2D-29 | 0.05 |
|  | IGHV3-15 | IGKV1-13 | 0.05 |
|  | IGHV3-15 | IGKV1D-43 | 0.05 |
|  | IGHV4-31 | IGKV1-6 | 0.05 |
|  | IGHV4-31 | IGKV2-29 | 0.05 |
|  | IGHV4-31 | IGKV2-40/2D-40 | 0.05 |
|  | IGHV1-2 | IGKV1-33/1D-33 | 0.05 |
|  | IGHV1-2 | IGKV2-30 | 0.05 |
|  | IGHV1-2 | IGKV1-8 | 0.05 |
|  | IGHV1-2 | IGKV1-6 | 0.05 |
|  | IGHV3-33 | IGKV1-17 | 0.05 |
|  | IGHV3-33 | IGKV1-8 | 0.05 |
|  | IGHV3-33 | IGKV1-16 | 0.05 |
|  | IGHV3-33 | IGKV2-24 | 0.05 |
|  | IGHV3-53 | IGKV2-28/2D-28 | 0.05 |
|  | IGHV3-53 | IGKV1-9 | 0.05 |
|  | IGHV3-53 | IGKV1-17 | 0.05 |
|  | IGHV3-53 | IGKV1-12 | 0.05 |
|  | IGHV3-53 | IGKV2-29 | 0.05 |
|  | IGHV3-53 | IGKV1D-16 | 0.05 |
|  | IGHV3-11 | IGKV1-33/1D-33 | 0.05 |
|  | IGHV3-11 | IGKV1-9 | 0.05 |
|  | IGHV3-11 | IGKV1-17 | 0.05 |
|  | IGHV3-11 | IGKV1-12 | 0.05 |
|  | IGHV3-11 | IGKV1D-8 | 0.05 |
|  | IGHV3-9 | IGKV3-20 | 0.05 |
|  | IGHV3-9 | IGKV2-28/2D-28 | 0.05 |
|  | IGHV3-9 | IGKV1-17 | 0.05 |
|  | IGHV3-9 | IGKV1-27 | 0.05 |
|  | IGHV3-9 | IGKV1-8 | 0.05 |
|  | IGHV3-9 | IGKV1-12 | 0.05 |
|  | IGHV3-9 | IGKV1D-8 | 0.05 |
|  | IGHV4-4 | IGKV1-17 | 0.05 |
|  | IGHV4-4 | IGKV1-27 | 0.05 |
|  | IGHV4-4 | IGKV1-6 | 0.05 |
|  | IGHV4-4 | IGKV1D-8 | 0.05 |
|  | IGHV1-46 | IGKV4-1 | 0.05 |
|  | IGHV1-46 | IGKV1-33/1D-33 | 0.05 |
|  | IGHV1-46 | IGKV1-8 | 0.05 |
|  | IGHV4-61 | IGKV3-11 | 0.05 |
|  | IGHV4-61 | IGKV2-28/2D-28 | 0.05 |
|  | IGHV4-61 | IGKV1-16 | 0.05 |
|  | IGHV4-61 | IGKV1-12 | 0.05 |
|  | IGHV4-61 | IGKV1-13 | 0.05 |
|  | IGHV1-8 | IGKV1-39/1D-39 | 0.05 |
|  | IGHV1-8 | IGKV1-5 | 0.05 |
|  | IGHV1-8 | IGKV3-11 | 0.05 |
|  | IGHV1-8 | IGKV2-28/2D-28 | 0.05 |
|  | IGHV1-8 | IGKV1-33/1D-33 | 0.05 |
|  | IGHV1-8 | IGKV1-9 | 0.05 |
|  | IGHV1-8 | IGKV2-29 | 0.05 |
|  | IGHV1-24 | IGKV3-20 | 0.05 |
|  | IGHV1-24 | IGKV4-1 | 0.05 |
|  | IGHV1-24 | IGKV1-33/1D-33 | 0.05 |
|  | IGHV1-24 | IGKV2-24 | 0.05 |
|  | IGHV1-24 | IGKV2-40/2D-40 | 0.05 |
|  | IGHV1-3 | IGKV1-5 | 0.05 |
|  | IGHV1-3 | IGKV1-33/1D-33 | 0.05 |
|  | IGHV1-3 | IGKV2-30 | 0.05 |
|  | IGHV1-3 | IGKV1-6 | 0.05 |
|  | IGHV1-3 | IGKV2D-29 | 0.05 |
|  | IGHV3-49 | IGKV3-15 | 0.05 |
|  | IGHV3-49 | IGKV3-11 | 0.05 |
|  | IGHV3-49 | IGKV2-28/2D-28 | 0.05 |
|  | IGHV4-28 | IGKV3-20 | 0.05 |
|  | IGHV4-28 | IGKV1-39/1D-39 | 0.05 |
|  | IGHV3-43 | IGKV3-15 | 0.05 |
|  | IGHV3-43 | IGKV4-1 | 0.05 |
|  | IGHV3-43 | IGKV2-28/2D-28 | 0.05 |
|  | IGHV3-43 | IGKV1-33/1D-33 | 0.05 |
|  | IGHV3-64 | IGKV3-15 | 0.05 |
|  | IGHV3-64 | IGKV1-9 | 0.05 |
|  | IGHV3-64 | IGKV2D-29 | 0.05 |
|  | IGHV7-81 | IGKV1-5 | 0.05 |
|  | IGHV7-81 | IGKV4-1 | 0.05 |
|  | IGHV7-81 | IGKV2-28/2D-28 | 0.05 |
|  | IGHV3-13 | IGKV1-5 | 0.05 |
|  | IGHV3-13 | IGKV1-33/1D-33 | 0.05 |
|  | IGHV3-13 | IGKV1-9 | 0.05 |
|  | IGHV3-13 | IGKV2-30 | 0.05 |
|  | IGHV3-72 | IGKV3-20 | 0.05 |
|  | IGHV3-72 | IGKV1-9 | 0.05 |
|  | IGHV3-72 | IGKV1-17 | 0.05 |
|  | IGHV3-72 | IGKV1-16 | 0.05 |
|  | IGHV3-73 | IGKV2-28/2D-28 | 0.05 |
|  | IGHV3-73 | IGKV1-9 | 0.05 |

TABLE 23-continued

The 400 VH/VL germline gene pairs functional tested are representative of the VH/VL germline gene pairs identified in the human immune repertoire

| pos | V heavy | V light | % |
|---|---|---|---|
| | IGHV1-58 | IGKV1-5 | 0.05 |
| | IGHV1-58 | IGKV4-1 | 0.05 |
| | IGHV1-58 | IGKV3-11 | 0.05 |
| | IGHV4-30.2 | IGKV1-39/1D-39 | 0.05 |
| | IGHV4-30.2 | IGKV4-1 | 0.05 |
| | IGHV7-4.1 | IGKV1-39/1D-39 | 0.05 |
| | IGHV7-4.1 | IGKV1-5 | 0.05 |
| | IGHV3-20 | IGKV1-39/1D-39 | 0.05 |
| | IGHV3-23 | IGLV1-47 | 0.05 |
| | IGHV3-23 | IGLV2-8 | 0.05 |
| | IGHV3-23 | IGLV7-43 | 0.05 |
| | IGHV3-23 | IGLV2-18 | 0.05 |
| | IGHV3-23 | IGLV3-19 | 0.05 |
| | IGHV3-30 | IGLV1-47 | 0.05 |
| | IGHV3-30 | IGLV2-8 | 0.05 |
| | IGHV3-30 | IGLV6-57 | 0.05 |
| | IGHV3-30 | IGLV3-27 | 0.05 |
| | IGHV4-39 | IGLV7-46 | 0.05 |
| | IGHV4-39 | IGLV3-9 | 0.05 |
| | IGHV4-59 | IGLV2-8 | 0.05 |
| | IGHV4-59 | IGLV6-57 | 0.05 |
| | IGHV4-59 | IGLV3-12 | 0.05 |
| | IGHV4-34 | IGLV2-11 | 0.05 |
| | IGHV4-34 | IGLV1-36 | 0.05 |
| | IGHV4-34 | IGLV7-43 | 0.05 |
| | IGHV4-34 | IGLV9-49 | 0.05 |
| | IGHV5-51 | IGLV7-43 | 0.05 |
| | IGHV1-69 | IGLV6-57 | 0.05 |
| | IGHV1-69 | IGLV3-25 | 0.05 |
| | IGHV1-69 | IGLV3-10 | 0.05 |
| | IGHV3-7 | IGLV2-23 | 0.05 |
| | IGHV3-7 | IGLV3-1 | 0.05 |
| | IGHV3-7 | IGLV2-8 | 0.05 |
| | IGHV3-7 | IGLV7-46 | 0.05 |
| | IGHV3-7 | IGLV3-27 | 0.05 |
| | IGHV1-18 | IGLV2-23 | 0.05 |
| | IGHV1-18 | IGLV2-11 | 0.05 |
| | IGHV1-18 | IGLV1-36 | 0.05 |
| | IGHV1-18 | IGLV3-25 | 0.05 |
| | IGHV1-18 | IGLV3-10 | 0.05 |
| | IGHV3-48 | IGLV1-40 | 0.05 |
| | IGHV3-48 | IGLV1-44 | 0.05 |
| | IGHV3-48 | IGLV1-51 | 0.05 |
| | IGHV3-48 | IGLV2-23 | 0.05 |
| | IGHV3-48 | IGLV3-21 | 0.05 |
| | IGHV3-48 | IGLV3-25 | 0.05 |
| | IGHV3-48 | IGLV7-46 | 0.05 |
| | IGHV3-48 | IGLV9-49 | 0.05 |
| | IGHV3-21 | IGLV2-23 | 0.05 |
| | IGHV3-21 | IGLV3-1 | 0.05 |
| | IGHV3-21 | IGLV2-8 | 0.05 |
| | IGHV3-21 | IGLV6-57 | 0.05 |
| | IGHV3-21 | IGLV3-25 | 0.05 |
| | IGHV3-21 | IGLV7-46 | 0.05 |
| | IGHV3-15 | IGLV2-14 | 0.05 |
| | IGHV3-15 | IGLV1-47 | 0.05 |
| | IGHV3-15 | IGLV2-23 | 0.05 |
| | IGHV3-15 | IGLV3-21 | 0.05 |
| | IGHV3-15 | IGLV6-57 | 0.05 |
| | IGHV3-15 | IGLV3-25 | 0.05 |
| | IGHV3-15 | IGLV2-18 | 0.05 |
| | IGHV3-15 | IGLV3-22 | 0.05 |
| | IGHV4-31 | IGLV1-44 | 0.05 |
| | IGHV4-31 | IGLV2-11 | 0.05 |
| | IGHV4-31 | IGLV3-1 | 0.05 |
| | IGHV4-31 | IGLV4-69 | 0.05 |
| | IGHV4-31 | IGLV7-43 | 0.05 |
| | IGHV1-2 | IGLV3-21 | 0.05 |
| | IGHV1-2 | IGLV2-11 | 0.05 |
| | IGHV1-2 | IGLV3-27 | 0.05 |
| | IGHV3-33 | IGLV1-40 | 0.05 |
| | IGHV3-33 | IGLV1-44 | 0.05 |
| | IGHV3-33 | IGLV1-51 | 0.05 |
| | IGHV3-33 | IGLV2-11 | 0.05 |
| | IGHV3-33 | IGLV3-1 | 0.05 |
| | IGHV3-33 | IGLV4-69 | 0.05 |
| | IGHV3-33 | IGLV3-27 | 0.05 |
| | IGHV3-33 | IGLV9-49 | 0.05 |
| | IGHV3-33 | IGLV3-9 | 0.05 |
| | IGHV3-53 | IGLV1-51 | 0.05 |
| | IGHV3-53 | IGLV1-47 | 0.05 |
| | IGHV3-53 | IGLV2-23 | 0.05 |
| | IGHV3-53 | IGLV2-11 | 0.05 |
| | IGHV3-53 | IGLV3-1 | 0.05 |
| | IGHV3-53 | IGLV2-8 | 0.05 |
| | IGHV3-53 | IGLV7-46 | 0.05 |
| | IGHV3-11 | IGLV1-40 | 0.05 |
| | IGHV3-11 | IGLV1-51 | 0.05 |
| | IGHV3-11 | IGLV1-47 | 0.05 |
| | IGHV3-11 | IGLV2-8 | 0.05 |
| | IGHV3-11 | IGLV3-25 | 0.05 |
| | IGHV3-11 | IGLV7-46 | 0.05 |
| | IGHV3-11 | IGLV9-49 | 0.05 |
| | IGHV3-11 | IGLV8-61 | 0.05 |
| | IGHV3-9 | IGLV1-40 | 0.05 |
| | IGHV3-9 | IGLV1-51 | 0.05 |
| | IGHV3-9 | IGLV4-69 | 0.05 |
| | IGHV3-9 | IGLV4-60 | 0.05 |
| | IGHV3-74 | IGLV1-47 | 0.05 |
| | IGHV3-74 | IGLV2-11 | 0.05 |
| | IGHV3-74 | IGLV3-1 | 0.05 |
| | IGHV3-74 | IGLV2-8 | 0.05 |
| | IGHV3-74 | IGLV7-43 | 0.05 |
| | IGHV3-74 | IGLV7-46 | 0.05 |
| | IGHV4-4 | IGLV2-11 | 0.05 |
| | IGHV4-4 | IGLV3-1 | 0.05 |
| | IGHV4-4 | IGLV3-25 | 0.05 |
| | IGHV4-4 | IGLV9-49 | 0.05 |
| | IGHV1-46 | IGLV1-40 | 0.05 |
| | IGHV1-46 | IGLV1-47 | 0.05 |
| | IGHV1-46 | IGLV2-23 | 0.05 |
| | IGHV1-46 | IGLV3-21 | 0.05 |
| | IGHV1-46 | IGLV6-57 | 0.05 |
| | IGHV4-61 | IGLV2-23 | 0.05 |
| | IGHV4-61 | IGLV3-21 | 0.05 |
| | IGHV4-61 | IGLV3-1 | 0.05 |
| | IGHV4-61 | IGLV7-43 | 0.05 |
| | IGHV1-8 | IGLV1-51 | 0.05 |
| | IGHV1-8 | IGLV2-11 | 0.05 |
| | IGHV1-8 | IGLV2-8 | 0.05 |
| | IGHV1-8 | IGLV9-49 | 0.05 |
| | IGHV1-24 | IGLV2-14 | 0.05 |
| | IGHV1-24 | IGLV1-40 | 0.05 |
| | IGHV1-24 | IGLV1-44 | 0.05 |
| | IGHV1-24 | IGLV3-21 | 0.05 |
| | IGHV1-24 | IGLV2-11 | 0.05 |
| | IGHV1-3 | IGLV1-40 | 0.05 |
| | IGHV3-49 | IGLV2-14 | 0.05 |
| | IGHV3-49 | IGLV1-40 | 0.05 |
| | IGHV3-49 | IGLV2-23 | 0.05 |
| | IGHV3-49 | IGLV2-8 | 0.05 |
| | IGHV4-28 | IGLV2-14 | 0.05 |
| | IGHV3-43 | IGLV2-14 | 0.05 |
| | IGHV3-43 | IGLV2-11 | 0.05 |
| | IGHV3-43 | IGLV3-1 | 0.05 |
| | IGHV3-43 | IGLV1-36 | 0.05 |
| | IGHV3-43 | IGLV9-49 | 0.05 |
| | IGHV3-64 | IGLV2-14 | 0.05 |
| | IGHV3-64 | IGLV7-43 | 0.05 |
| | IGHV7-81 | IGLV1-40 | 0.05 |
| | IGHV3-13 | IGLV1-40 | 0.05 |
| | IGHV3-13 | IGLV1-47 | 0.05 |
| | IGHV3-72 | IGLV1-51 | 0.05 |
| | IGHV3-72 | IGLV4-69 | 0.05 |
| | IGHV3-73 | IGLV1-40 | 0.05 |
| | IGHV3-73 | IGLV1-51 | 0.05 |

TABLE 23-continued

The 400 VH/VL germline gene pairs functional tested are representative of the VH/VL germline gene pairs identified in the human immune repertoire

| pos | V heavy | V light | % |
|---|---|---|---|
| | IGHV3-73 | IGLV1-47 | 0.05 |
| | IGHV3-73 | IGLV2-11 | 0.05 |
| | IGHV3-73 | IGLV6-57 | 0.05 |
| | IGHV1-58 | IGLV2-14 | 0.05 |
| | IGHV3-66 | IGLV1-44 | 0.05 |
| | IGHV3-66 | IGLV1-47 | 0.05 |
| | IGHV3-66 | IGLV3-25 | 0.05 |
| | IGHV4-30.2 | IGLV3-21 | 0.05 |
| | IGHV7-4.1 | IGLV1-51 | 0.05 |
| | IGHV3-20 | IGLV2-14 | 0.05 |

Example 4.2

As discussed in Example 2.4, it was felt to be important to differentiate between the naïve, antigen inexperienced, and the antigen experienced B cell populations. Therefore, Table 19, which shows the ranking of the VH/VL germline gene pairs identified in the naïve human immune repertoire is reproduced below as Table 24, wherein the 400 VH/VL germline gene pairs that were synthesized, and combined for further functional testing are bolded and underlined.

TABLE 24

The 400 VH/VL germline gene pairs functional tested are representative of the VH/VL germline gene pairs identified in the naïve human immune repertoire

| pos | V heavy | V light | % |
|---|---|---|---|
| 1 | IGHV4-34 | IGKV3-20 | 1.56 |
| 2 | IGHV4-39 | IGKV3-15 | 1.19 |
| 3 | IGHV4-34 | IGKV1-39/1D-39 | 0.97 |
| 4 | IGHV3-23 | IGKV3-20 | 0.89 |
| | IGHV4-59 | IGKV1-39/1D-39 | 0.89 |
| | IGHV1-69 | IGKV1-39/1D-39 | 0.89 |
| 5 | IGHV4-39 | IGKV1-39/1D-39 | 0.82 |
| | IGHV1-18 | IGKV3-20 | 0.82 |
| | IGHV5-51 | IGLV1-40 | 0.82 |
| 6 | IGHV4-39 | IGKV3-20 | 0.74 |
| | IGHV4-39 | IGKV1-5 | 0.74 |
| | IGHV4-59 | IGKV3-20 | 0.74 |
| 7 | IGHV3-23 | IGKV1-5 | 0.67 |
| | IGHV3-23 | IGKV3-15 | 0.67 |
| | IGHV3-30 | IGKV1-39/1D-39 | 0.67 |
| | IGHV3-30 | IGKV3-11 | 0.67 |
| | IGHV1-69 | IGKV3-20 | 0.67 |
| | IGHV4-39 | IGLV 2-8 | 0.67 |
| 8 | IGHV3-23 | IGKV1-39/1D-39 | 0.59 |
| | IGHV3-30 | IGKV1-5 | 0.59 |
| | IGHV3-7 | IGKV1-39/1D-39 | 0.59 |
| | IGHV1-2 | IGKV3-20 | 0.59 |
| | IGHV4-59 | IGLV 1-40 | 0.59 |
| | IGHV4-34 | IGLV 2-14 | 0.59 |
| 9 | IGHV3-23 | IGKV4-1 | 0.52 |
| | IGHV5-51 | IGKV3-20 | 0.52 |
| | IGHV5-51 | IGKV4-1 | 0.52 |
| | IGHV3-53 | IGKV1-5 | 0.52 |
| | IGHV3-23 | IGLV2-14 | 0.52 |
| | IGHV4-34 | IGLV 1-51 | 0.52 |
| | IGHV1-69 | IGLV2-14 | 0.52 |
| | IGHV1-69 | IGLV1-40 | 0.52 |
| 10 | IGHV3-23 | IGKV1-33/1D-33 | 0.45 |
| | IGHV3-30 | IGKV3-20 | 0.45 |
| | IGHV3-30 | IGKV4-1 | 0.45 |
| | IGHV3-30 | IGKV1-9 | 0.45 |
| | IGHV4-59 | IGKV4-1 | 0.45 |
| | IGHV4-34 | IGKV3-15 | 0.45 |
| | IGHV4-34 | IGKV4-1 | 0.45 |
| | IGHV1-18 | IGKV1-33/1D-33 | 0.45 |
| | IGHV3-48 | IGKV3-20 | 0.45 |
| | IGHV3-48 | IGKV3-11 | 0.45 |
| | IGHV3-21 | IGKV1-39/1D-39 | 0.45 |
| | IGHV3-21 | IGKV3-15 | 0.45 |
| | IGHV3-15 | IGKV3-20 | 0.45 |
| | IGHV3-15 | IGKV1-39/1D-39 | 0.45 |
| | IGHV3-30 | IGLV2-14 | 0.45 |
| | IGHV5-51 | IGLV2-14 | 0.45 |
| | IGHV3-21 | IGLV1-51 | 0.45 |
| | IGHV1-2 | IGLV2-14 | 0.45 |
| 11 | IGHV3-23 | IGKV2-28/2D-28 | 0.37 |
| | IGHV3-30 | IGKV3-15 | 0.37 |
| | IGHV4-39 | IGKV3-11 | 0.37 |
| | IGHV1-69 | IGKV4-1 | 0.37 |
| | IGHV1-18 | IGKV1-39/1D-39 | 0.37 |
| | IGHV1-18 | IGKV1-5 | 0.37 |
| | IGHV1-18 | IGKV2-28/2D-28 | 0.37 |
| | IGHV3-48 | IGKV1-39/1D-39 | 0.37 |
| | IGHV3-48 | IGKV3-15 | 0.37 |
| | IGHV3-48 | IGKV1-33/1D-33 | 0.37 |
| | IGHV3-21 | IGKV1-5 | 0.37 |
| | IGHV3-15 | IGKV1-5 | 0.37 |
| | IGHV4-31 | IGKV3-11 | 0.37 |
| | IGHV3-33 | IGKV3-20 | 0.37 |
| | IGHV3-53 | IGKV1-33/1D-33 | 0.37 |
| | IGHV3-23 | IGLV1-40 | 0.37 |
| | IGHV3-30 | IGLV1-51 | 0.37 |
| | IGHV4-39 | IGLV2-14 | 0.37 |
| | IGHV4-59 | IGLV 3-1 | 0.37 |
| | IGHV1-18 | IGLV1-40 | 0.37 |
| | IGHV3-48 | IGLV2-14 | 0.37 |
| | IGHV4-31 | IGLV2-14 | 0.37 |
| 12 | IGHV3-23 | IGKV3-11 | 0.30 |
| | IGHV3-23 | IGKV1-17 | 0.30 |
| | IGHV3-23 | IGKV1-27 | 0.30 |
| | IGHV4-39 | IGKV1-33/1D-33 | 0.30 |
| | IGHV4-59 | IGKV3-11 | 0.30 |
| | IGHV4-34 | IGKV1-5 | 0.30 |
| | IGHV4-34 | IGKV3-11 | 0.30 |
| | IGHV4-34 | IGKV2-28/2D-28 | 0.30 |
| | IGHV5-51 | IGKV3-15 | 0.30 |
| | IGHV5-51 | IGKV3-11 | 0.30 |
| | IGHV5-51 | IGKV2-28/2D-28 | 0.30 |
| | IGHV1-69 | IGKV1-5 | 0.30 |
| | IGHV3-7 | IGKV3-15 | 0.30 |
| | IGHV3-48 | IGKV4-1 | 0.30 |
| | IGHV3-21 | IGKV3-20 | 0.30 |
| | IGHV3-21 | IGKV4-1 | 0.30 |
| | IGHV3-15 | IGKV3-15 | 0.30 |
| | IGHV3-33 | IGKV1-39/1D-39 | 0.30 |
| | IGHV3-53 | IGKV1-39/1D-39 | 0.30 |
| | IGHV3-53 | IGKV3-15 | 0.30 |
| | IGHV3-53 | IGKV4-1 | 0.30 |
| | IGHV3-11 | IGKV1-39/1D-39 | 0.30 |
| | IGHV4-4 | IGKV3-20 | 0.30 |
| | IGHV1-46 | IGKV3-20 | 0.30 |
| | IGHV1-46 | IGKV1-39/1D-39 | 0.30 |
| | IGHV3-23 | IGLV3-21 | 0.30 |
| | IGHV3-23 | IGLV3-1 | 0.30 |
| | IGHV4-39 | IGLV1-40 | 0.30 |
| | IGHV4-39 | IGLV 1-44 | 0.30 |
| | IGHV4-39 | IGLV1-51 | 0.30 |
| | IGHV4-59 | IGLV 1-51 | 0.30 |
| | IGHV4-34 | IGLV 1-40 | 0.30 |
| | IGHV4-34 | IGLV 1-47 | 0.30 |
| | IGHV4-34 | IGLV 2-8 | 0.30 |
| | IGHV5-51 | IGLV 1-44 | 0.30 |
| | IGHV1-69 | IGLV1-51 | 0.30 |
| | IGHV1-69 | IGLV 2-8 | 0.30 |
| | IGHV3-9 | IGLV 2-14 | 0.30 |
| | IGHV3-9 | IGLV 2-23 | 0.30 |
| | IGHV4-4 | IGLV 1-44 | 0.30 |
| | IGHV4-61 | IGLV 1-44 | 0.30 |

TABLE 24-continued

The 400 VH/VL germline gene pairs functional tested are representative of the VH/VL germline gene pairs identified in the naïve human immune repertoire

| pos | V heavy | V light | % |
|---|---|---|---|
| 13 | IGHV3-23 | IGKV1-8 | 0.22 |
|  | IGHV3-30 | IGKV2-28/2D-28 | 0.22 |
|  | IGHV4-39 | IGKV4-1 | 0.22 |
|  | IGHV4-39 | IGKV1-27 | 0.22 |
|  | IGHV5-51 | IGKV1-39/1D-39 | 0.22 |
|  | IGHV1-69 | IGKV1-33/1D-33 | 0.22 |
|  | IGHV3-7 | IGKV3-20 | 0.22 |
|  | IGHV3-7 | IGKV3-11 | 0.22 |
|  | IGHV3-7 | IGKV1-8 | 0.22 |
|  | IGHV1-18 | IGKV3-11 | 0.22 |
|  | IGHV3-48 | IGKV1-8 | 0.22 |
|  | IGHV3-15 | IGKV3-11 | 0.22 |
|  | IGHV3-15 | IGKV1-33/1D-33 | 0.22 |
|  | IGHV4-31 | IGKV1-39/1D-39 | 0.22 |
|  | IGHV4-31 | IGKV3-15 | 0.22 |
|  | IGHV4-31 | IGKV1-33/1D-33 | 0.22 |
|  | IGHV1-2 | IGKV1-39/1D-39 | 0.22 |
|  | IGHV1-2 | IGKV1-5 | 0.22 |
|  | IGHV3-33 | IGKV3-15 | 0.22 |
|  | IGHV3-33 | IGKV4-1 | 0.22 |
|  | IGHV3-11 | IGKV1-5 | 0.22 |
|  | IGHV3-11 | IGKV3-15 | 0.22 |
|  | IGHV3-9 | IGKV1-39/1D-39 | 0.22 |
|  | IGHV4-4 | IGKV3-15 | 0.22 |
|  | IGHV4-4 | IGKV3-11 | 0.22 |
|  | IGHV1-46 | IGKV1-9 | 0.22 |
|  | IGHV4-61 | IGKV1-39/1D-39 | 0.22 |
|  | IGHV4-61 | IGKV4-1 | 0.22 |
|  | IGHV1-3 | IGKV1-39/1D-39 | 0.22 |
|  | IGHV3-49 | IGKV1-39/1D-39 | 0.22 |
|  | IGHV3-49 | IGKV1-17 | 0.22 |
|  | IGHV3-43 | IGKV1-5 | 0.22 |
|  | IGHV7-81 | IGKV3-20 | 0.22 |
|  | IGHV3-23 | IGLV2-23 | 0.22 |
|  | IGHV3-23 | IGLV2-11 | 0.22 |
|  | IGHV4-39 | IGLV2-23 | 0.22 |
|  | IGHV1-69 | IGLV2-23 | 0.22 |
|  | IGHV1-18 | IGLV2-14 | 0.22 |
|  | IGHV3-48 | IGLV3-1 | 0.22 |
|  | IGHV3-15 | IGLV 1-44 | 0.22 |
|  | IGHV4-31 | IGLV1-40 | 0.22 |
|  | IGHV1-2 | IGLV1-40 | 0.22 |
|  | IGHV1-2 | IGLV3-1 | 0.22 |
|  | IGHV3-33 | IGLV2-14 | 0.22 |
|  | IGHV3-33 | IGLV1-47 | 0.22 |
|  | IGHV3-33 | IGLV3-21 | 0.22 |
|  | IGHV3-9 | IGLV 1-44 | 0.22 |
|  | IGHV3-9 | IGLV 1-47 | 0.22 |
|  | IGHV3-9 | IGLV 2-11 | 0.22 |
|  | IGHV1-46 | IGLV 1-44 | 0.22 |
|  | IGHV1-8 | IGLV 2-14 | 0.22 |
| 14 | IGHV3-23 | IGKV1-16 | 0.15 |
|  | IGHV3-23 | IGKV2D-29 | 0.15 |
|  | IGHV3-23 | IGKV2-40/2D-40 | 0.15 |
|  | IGHV3-30 | IGKV1-33/1D-33 | 0.15 |
|  | IGHV3-30 | IGKV1D-8 | 0.15 |
|  | IGHV4-39 | IGKV2-28/2D-28 | 0.15 |
|  | IGHV4-39 | IGKV2-30 | 0.15 |
|  | IGHV4-39 | IGKV1-6 | 0.15 |
|  | IGHV4-59 | IGKV1-5 | 0.15 |
|  | IGHV4-59 | IGKV3-15 | 0.15 |
|  | IGHV4-59 | IGKV1-33/1D-33 | 0.15 |
|  | IGHV4-34 | IGKV1-33/1D-33 | 0.15 |
|  | IGHV4-34 | IGKV1-17 | 0.15 |
|  | IGHV4-34 | IGKV1-16 | 0.15 |
|  | IGHV5-51 | IGKV1-5 | 0.15 |
|  | IGHV5-51 | IGKV1-33/1D-33 | 0.15 |
|  | IGHV1-69 | IGKV3-15 | 0.15 |
|  | IGHV1-69 | IGKV3-11 | 0.15 |
|  | IGHV1-69 | IGKV1-8 | 0.15 |
|  | IGHV3-7 | IGKV1-5 | 0.15 |
|  | IGHV3-7 | IGKV4-1 | 0.15 |
|  | IGHV3-7 | IGKV2-28/2D-28 | 0.15 |
|  | IGHV3-7 | IGKV1-9 | 0.15 |
|  | IGHV3-7 | IGKV1-17 | 0.15 |
|  | IGHV3-7 | IGKV1-13 | 0.15 |
|  | IGHV1-18 | IGKV4-1 | 0.15 |
|  | IGHV1-18 | IGKV2-30 | 0.15 |
|  | IGHV3-48 | IGKV2-28/2D-28 | 0.15 |
|  | IGHV3-48 | IGKV1-17 | 0.15 |
|  | IGHV3-21 | IGKV2-28/2D-28 | 0.15 |
|  | IGHV3-21 | IGKV1-8 | 0.15 |
|  | IGHV3-15 | IGKV4-1 | 0.15 |
|  | IGHV3-15 | IGKV2-28/2D-28 | 0.15 |
|  | IGHV3-15 | IGKV1-9 | 0.15 |
|  | IGHV4-31 | IGKV3-20 | 0.15 |
|  | IGHV4-31 | IGKV2-28/2D-28 | 0.15 |
|  | IGHV1-2 | IGKV3-15 | 0.15 |
|  | IGHV1-2 | IGKV4-1 | 0.15 |
|  | IGHV1-2 | IGKV1-27 | 0.15 |
|  | IGHV3-33 | IGKV2-28/2D-28 | 0.15 |
|  | IGHV3-33 | IGKV1-9 | 0.15 |
|  | IGHV3-53 | IGKV3-20 | 0.15 |
|  | IGHV3-53 | IGKV3-11 | 0.15 |
|  | IGHV3-53 | IGKV1-8 | 0.15 |
|  | IGHV3-11 | IGKV3-20 | 0.15 |
|  | IGHV3-11 | IGKV4-1 | 0.15 |
|  | IGHV3-11 | IGKV3-11 | 0.15 |
|  | IGHV3-11 | IGKV2-28/2D-28 | 0.15 |
|  | IGHV3-11 | IGKV1-6 | 0.15 |
|  | IGHV3-9 | IGKV1-5 | 0.15 |
|  | IGHV3-9 | IGKV1-16 | 0.15 |
|  | IGHV3-9 | IGKV2D-29 | 0.15 |
|  | IGHV3-74 | IGKV1-39/1D-39 | 0.15 |
|  | IGHV3-74 | IGKV1-5 | 0.15 |
|  | IGHV3-74 | IGKV4-1 | 0.15 |
|  | IGHV4-4 | IGKV1-39/1D-39 | 0.15 |
|  | IGHV4-4 | IGKV1-5 | 0.15 |
|  | IGHV4-4 | IGKV4-1 | 0.15 |
|  | IGHV4-4 | IGKV2D-29 | 0.15 |
|  | IGHV1-46 | IGKV3-15 | 0.15 |
|  | IGHV1-46 | IGKV1-16 | 0.15 |
|  | IGHV4-61 | IGKV3-15 | 0.15 |
|  | IGHV1-24 | IGKV3-15 | 0.15 |
|  | IGHV1-24 | IGKV3-11 | 0.15 |
|  | IGHV1-24 | IGKV2-28/2D-28 | 0.15 |
|  | IGHV3-49 | IGKV3-20 | 0.15 |
|  | IGHV3-64 | IGKV1-5 | 0.15 |
|  | IGHV3-64 | IGKV3-11 | 0.15 |
|  | IGHV7-81 | IGKV1-39/1D-39 | 0.15 |
|  | IGHV3-13 | IGKV1-39/1D-39 | 0.15 |
|  | IGHV3-13 | IGKV4-1 | 0.15 |
|  | IGHV3-72 | IGKV3-15 | 0.15 |
|  | IGHV3-30 | IGLV1-40 | 0.15 |
|  | IGHV3-30 | IGLV 1-44 | 0.15 |
|  | IGHV3-30 | IGLV2-23 | 0.15 |
|  | IGHV3-30 | IGLV3-21 | 0.15 |
|  | IGHV3-30 | IGLV 9-49 | 0.15 |
|  | IGHV4-39 | IGLV 2-18 | 0.15 |
|  | IGHV4-59 | IGLV 2-23 | 0.15 |
|  | IGHV4-59 | IGLV 2-11 | 0.15 |
|  | IGHV4-34 | IGLV 1-44 | 0.15 |
|  | IGHV4-34 | IGLV 2-23 | 0.15 |
|  | IGHV4-34 | IGLV 3-25 | 0.15 |
|  | IGHV5-51 | IGLV1-47 | 0.15 |
|  | IGHV5-51 | IGLV2-23 | 0.15 |
|  | IGHV5-51 | IGLV3-21 | 0.15 |
|  | IGHV5-51 | IGLV 1-36 | 0.15 |
|  | IGHV5-51 | IGLV 3-25 | 0.15 |
|  | IGHV1-69 | IGLV 1-44 | 0.15 |
|  | IGHV1-69 | IGLV2-11 | 0.15 |
|  | IGHV1-69 | IGLV3-1 | 0.15 |
|  | IGHV1-18 | IGLV 1-44 | 0.15 |
|  | IGHV1-18 | IGLV 2-8 | 0.15 |
|  | IGHV1-18 | IGLV 6-57 | 0.15 |
|  | IGHV3-48 | IGLV1-47 | 0.15 |
|  | IGHV3-21 | IGLV2-14 | 0.15 |
|  | IGHV3-21 | IGLV1-47 | 0.15 |

TABLE 24-continued

The 400 VH/VL germline gene pairs functional tested are representative of the VH/VL germline gene pairs identified in the naïve human immune repertoire

| pos | V heavy | V light | % |
|---|---|---|---|
|  | IGHV3-21 | IGLV2-11 | 0.15 |
|  | IGHV3-15 | IGLV 7-46 | 0.15 |
|  | IGHV4-31 | IGLV1-51 | 0.15 |
|  | IGHV4-31 | IGLV1-47 | 0.15 |
|  | IGHV4-31 | IGLV2-23 | 0.15 |
|  | IGHV1-2 | IGLV 1-44 | 0.15 |
|  | IGHV1-2 | IGLV1-51 | 0.15 |
|  | IGHV1-2 | IGLV2-23 | 0.15 |
|  | IGHV1-2 | IGLV 2-8 | 0.15 |
|  | IGHV3-11 | IGLV3-21 | 0.15 |
|  | IGHV3-11 | IGLV3-1 | 0.15 |
|  | IGHV3-9 | IGLV 3-21 | 0.15 |
|  | IGHV3-74 | IGLV3-21 | 0.15 |
|  | IGHV4-4 | IGLV2-14 | 0.15 |
|  | IGHV4-4 | IGLV1-51 | 0.15 |
|  | IGHV1-46 | IGLV1-51 | 0.15 |
|  | IGHV4-61 | IGLV 2-11 | 0.15 |
|  | IGHV1-24 | IGLV 2-23 | 0.15 |
|  | IGHV1-3 | IGLV 2-14 | 0.15 |
|  | IGHV1-3 | IGLV 3-1 | 0.15 |
|  | IGHV4-28 | IGLV 1-44 | 0.15 |
|  | IGHV4-28 | IGLV 1-36 | 0.15 |
|  | IGHV3-43 | IGLV 1-51 | 0.15 |
| 15 | IGHV3-23 | IGKV1-9 | 0.07 |
|  | IGHV3-23 | IGKV2-30 | 0.07 |
|  | IGHV3-23 | IGKV1-12 | 0.07 |
|  | IGHV3-23 | IGKV2-29 | 0.07 |
|  | IGHV3-23 | IGKV3D-20 | 0.07 |
|  | IGHV3-23 | IGKV1D-12 | 0.07 |
|  | IGHV3-30 | IGKV2-30 | 0.07 |
|  | IGHV3-30 | IGKV1-27 | 0.07 |
|  | IGHV3-30 | IGKV1-16 | 0.07 |
|  | IGHV3-30 | IGKV1-6 | 0.07 |
|  | IGHV3-30 | IGKV2D-29 | 0.07 |
|  | IGHV3-30 | IGKV2-24 | 0.07 |
|  | IGHV3-30 | IGKV2D-30 | 0.07 |
|  | IGHV4-39 | IGKV1-17 | 0.07 |
|  | IGHV4-59 | IGKV2-30 | 0.07 |
|  | IGHV4-59 | IGKV1-17 | 0.07 |
|  | IGHV4-59 | IGKV1-27 | 0.07 |
|  | IGHV4-59 | IGKV1-8 | 0.07 |
|  | IGHV4-59 | IGKV1-16 | 0.07 |
|  | IGHV4-59 | IGKV1-12 | 0.07 |
|  | IGHV4-59 | IGKV1D-17 | 0.07 |
|  | IGHV4-34 | IGKV1-9 | 0.07 |
|  | IGHV4-34 | IGKV1-27 | 0.07 |
|  | IGHV4-34 | IGKV1-8 | 0.07 |
|  | IGHV4-34 | IGKV1-12 | 0.07 |
|  | IGHV5-51 | IGKV1-17 | 0.07 |
|  | IGHV5-51 | IGKV1-27 | 0.07 |
|  | IGHV1-69 | IGKV2-28/2D-28 | 0.07 |
|  | IGHV1-69 | IGKV2-30 | 0.07 |
|  | IGHV1-69 | IGKV1-16 | 0.07 |
|  | IGHV1-69 | IGKV2D-29 | 0.07 |
|  | IGHV1-69 | IGKV2D-30 | 0.07 |
|  | IGHV1-69 | IGKV1D-16 | 0.07 |
|  | IGHV1-69 | IGKV3D-15 | 0.07 |
|  | IGHV3-7 | IGKV2-30 | 0.07 |
|  | IGHV3-7 | IGKV1-27 | 0.07 |
|  | IGHV3-7 | IGKV1D-8 | 0.07 |
|  | IGHV3-7 | IGKV1D-17 | 0.07 |
|  | IGHV1-18 | IGKV3-15 | 0.07 |
|  | IGHV1-18 | IGKV1-8 | 0.07 |
|  | IGHV1-18 | IGKV1-16 | 0.07 |
|  | IGHV1-18 | IGKV1-12 | 0.07 |
|  | IGHV1-18 | IGKV1-13 | 0.07 |
|  | IGHV1-18 | IGKV2-40/2D-40 | 0.07 |
|  | IGHV3-48 | IGKV1-5 | 0.07 |
|  | IGHV3-48 | IGKV1-9 | 0.07 |
|  | IGHV3-48 | IGKV1-27 | 0.07 |
|  | IGHV3-48 | IGKV1-16 | 0.07 |
|  | IGHV3-48 | IGKV1-6 | 0.07 |
|  | IGHV3-48 | IGKV2D-29 | 0.07 |
|  | IGHV3-48 | IGKV3D-20 | 0.07 |
|  | IGHV3-48 | IGKV1D-12 | 0.07 |
|  | IGHV3-21 | IGKV3-11 | 0.07 |
|  | IGHV3-21 | IGKV1-27 | 0.07 |
|  | IGHV3-21 | IGKV2D-29 | 0.07 |
|  | IGHV3-15 | IGKV1-27 | 0.07 |
|  | IGHV3-15 | IGKV2D-29 | 0.07 |
|  | IGHV3-15 | IGKV1D-43 | 0.07 |
|  | IGHV4-31 | IGKV1-5 | 0.07 |
|  | IGHV4-31 | IGKV4-1 | 0.07 |
|  | IGHV4-31 | IGKV1-17 | 0.07 |
|  | IGHV4-31 | IGKV1-27 | 0.07 |
|  | IGHV4-31 | IGKV1-6 | 0.07 |
|  | IGHV4-31 | IGKV2-40/2D-40 | 0.07 |
|  | IGHV1-2 | IGKV2-28/2D-28 | 0.07 |
|  | IGHV1-2 | IGKV1-33/1D-33 | 0.07 |
|  | IGHV1-2 | IGKV2-30 | 0.07 |
|  | IGHV1-2 | IGKV1-8 | 0.07 |
|  | IGHV1-2 | IGKV1-6 | 0.07 |
|  | IGHV3-33 | IGKV1-5 | 0.07 |
|  | IGHV3-33 | IGKV1-33/1D-33 | 0.07 |
|  | IGHV3-33 | IGKV1-8 | 0.07 |
|  | IGHV3-53 | IGKV2-28/2D-28 | 0.07 |
|  | IGHV3-53 | IGKV1-9 | 0.07 |
|  | IGHV3-53 | IGKV1-17 | 0.07 |
|  | IGHV3-53 | IGKV1-27 | 0.07 |
|  | IGHV3-53 | IGKV1-12 | 0.07 |
|  | IGHV3-53 | IGKV2-29 | 0.07 |
|  | IGHV3-53 | IGKV1D-16 | 0.07 |
|  | IGHV3-11 | IGKV1-33/1D-33 | 0.07 |
|  | IGHV3-11 | IGKV1-9 | 0.07 |
|  | IGHV3-11 | IGKV1-17 | 0.07 |
|  | IGHV3-11 | IGKV1D-8 | 0.07 |
|  | IGHV3-9 | IGKV3-15 | 0.07 |
|  | IGHV3-9 | IGKV4-1 | 0.07 |
|  | IGHV3-9 | IGKV3-11 | 0.07 |
|  | IGHV3-9 | IGKV2-28/2D-28 | 0.07 |
|  | IGHV3-9 | IGKV1-27 | 0.07 |
|  | IGHV3-9 | IGKV1-8 | 0.07 |
|  | IGHV3-9 | IGKV1D-8 | 0.07 |
|  | IGHV3-74 | IGKV3-20 | 0.07 |
|  | IGHV3-74 | IGKV3-15 | 0.07 |
|  | IGHV3-74 | IGKV3-11 | 0.07 |
|  | IGHV3-74 | IGKV2-30 | 0.07 |
|  | IGHV4-4 | IGKV2-28/2D-28 | 0.07 |
|  | IGHV4-4 | IGKV1-17 | 0.07 |
|  | IGHV4-4 | IGKV1-27 | 0.07 |
|  | IGHV4-4 | IGKV1D-8 | 0.07 |
|  | IGHV1-46 | IGKV1-5 | 0.07 |
|  | IGHV1-46 | IGKV4-1 | 0.07 |
|  | IGHV1-46 | IGKV1-33/1D-33 | 0.07 |
|  | IGHV1-46 | IGKV1-8 | 0.07 |
|  | IGHV4-61 | IGKV2-28/2D-28 | 0.07 |
|  | IGHV4-61 | IGKV1-16 | 0.07 |
|  | IGHV4-61 | IGKV1-12 | 0.07 |
|  | IGHV1-8 | IGKV1-39/1D-39 | 0.07 |
|  | IGHV1-8 | IGKV3-15 | 0.07 |
|  | IGHV1-8 | IGKV4-1 | 0.07 |
|  | IGHV1-8 | IGKV3-11 | 0.07 |
|  | IGHV1-8 | IGKV2-28/2D-28 | 0.07 |
|  | IGHV1-8 | IGKV1-9 | 0.07 |
|  | IGHV1-8 | IGKV2-29 | 0.07 |
|  | IGHV1-24 | IGKV3-20 | 0.07 |
|  | IGHV1-24 | IGKV1-39/1D-39 | 0.07 |
|  | IGHV1-24 | IGKV4-1 | 0.07 |
|  | IGHV1-24 | IGKV1-33/1D-33 | 0.07 |
|  | IGHV1-24 | IGKV2-30 | 0.07 |
|  | IGHV1-24 | IGKV2-24 | 0.07 |
|  | IGHV1-3 | IGKV1-5 | 0.07 |
|  | IGHV1-3 | IGKV3-15 | 0.07 |
|  | IGHV1-3 | IGKV1-33/1D-33 | 0.07 |
|  | IGHV1-3 | IGKV2-30 | 0.07 |
|  | IGHV1-3 | IGKV2D-29 | 0.07 |
|  | IGHV3-49 | IGKV1-5 | 0.07 |
|  | IGHV3-49 | IGKV3-15 | 0.07 |
|  |  | IGKV1D-12 | 0.07 |
|  | IGHV3-48 | IGKV1D-12 | 0.07 |

TABLE 24-continued

The 400 VH/VL germline gene pairs functional tested are representative of the VH/VL germline gene pairs identified in the naïve human immune repertoire

| pos | V heavy | V light | % |
|---|---|---|---|
| | IGHV3-49 | IGKV3-11 | 0.07 |
| | IGHV3-49 | IGKV2-28/2D-28 | 0.07 |
| | IGHV3-43 | IGKV4-1 | 0.07 |
| | IGHV3-43 | IGKV3-11 | 0.07 |

Example 5

Generation of Germline Genes for Functional Analysis

As a next step, the VH, Vλ, and Vκ germline genes selected for combination and subsequent testing, as shown in Table 25, were sent to Geneart (Regensburg, Germany) for codon optimization respective to E. coli expression (neutral to mammalian expression), and synthesis.

TABLE 25

VH, Vλ, and Vκ germline genes sent for synthesis

| VH | Vκ | Vλ |
|---|---|---|
| 1. IGHV3-23 | 1. IGKV3-20 | 1. IGLV2-14 |
| 2. IGHV3-30 | 2. IGKV1-39/1D-39 | 2. IGLV1-40 |
| 3. IGHV4-39 | 3. IGKV1-5 | 3. IGLV1-51 |
| 4. IGHV1-69 | 4. IGKV3-15 | 4. IGLV2-23 |
| 5. IGHV5-51 | 5. IGKV3-11 | 5. IGLV3-21 |
| 6. IGHV3-7 | 6. IGKV2-30 | 6. IGLV1-47 |
| 7. IGHV1-18 | 7. IGKV1-9 | 7. IGLV3-1 |
| 8. IGHV3-48 | 8. IGKV1-17 | 8. IGLV2-11 |
| 9. IGHV3-15 | 9. IGKV1-27 | |
| 10. IGHV3-21 | 10. IGKV1-16 | |
| 11. IGHV1-2 | 11. IGKV1-6 | |
| 12. IGHV3-33 | 12. IGKV1-12 | |
| 13. IGHV4-31 | | |
| 14. IGHV3-53 | | |
| 15. IGHV3-11 | | |
| 16. IGHV4-4 | | |
| 17. IGHV1-46 | | |
| 18. IGHV3-74 | | |
| 19. IGHV3-73 | | |
| 20. IGHV6-1 | | |

The germline gene sequences of each of the VH, Vλ, and Vκ germline genes are shown in FIGS. 45-47. Each germline gene sequence was synthesized to include the following:

a) for VH: leader sequence (modified phoA signal sequence incorporating a NheI restriction site as shown in FIG. 3); germline FR1, CDR1, FR2, CDR2 and FR3 (incorporating a BssHII restriction site as shown in FIG. 3); CDR-H3 (WGGDGFYAMDY)(SEQ ID NO:1) of the 4D5 antibody as used in Ewert S. et al., J. Mol. Biol. (2003) 325, 531-553; and the JH4 FR4 (incorporating a XhoI/SalI RE site as shown in FIG. 3);

b) for Vk: leader sequence (modified ompA signal sequence incorporating the NdeI restriction site as shown in FIG. 3); germline FR1, CDR1, FR2, CDR2 and FR3 (incorporating a BbsI restriction site as shown in FIG. 3), kappa-like CDR-L3 (QQHYTTPPT)(SEQ ID NO:2)) according to Ewert S. et al., J. Mol. Biol. (2003) 325, 531-553; and the Jk1 FR4 (incorporating a KpnI RE site as shown in FIG. 3);

c) for Vλ: leader sequence (modified ompA signal sequence incorporating the NdeI restriction site as shown in FIG. 3); germline FR1, CDR1, FR2, CDR2 and FR3 (incorporating a BbsI restriction site as shown in FIG. 3), lambda-like CDR-L3 (QSYDSSLSGVV) (SEQ ID No:3)) according to Ewert S. et al., J. Mol. Biol. (2003) 325, 531-553; and the J12/3 FR4 (incorporating a KpnI RE site as shown in FIG. 3).

Example 6

Functional Testing of VH/VL Germline Gene Pairs Representative of the Human Immune Repertoire The 400 VH/VL germline gene pairs were then tested for the following properties: a) relative display after phage production and phage ELISA in Fab format; b) relative Fab expression levels after Fab production in E. coli, E. coli cell lysis and ELISA detection of produced Fab; c) temperature stability of Fab after Fab production in E. coli, E. coli cell lysis and ELISA detection of non-denatured Fab after incubation at increased temperatures; d) bovine/mouse serum stability of Fab from E. coli lysates by ELISA detection of non-denatured Fab after incubation in bovine/mouse serum; e) relative human IgG1 expression levels after IgG1 production in mammalian cells and ELISA detection of secreted IgG1 from cell culture supernatants; and f) bovine serum stability of human IgG1 by ELISA detection of non-denatured Fab after incubation in bovine/mouse serum.

Example 6.1

Generation of Fab Pool Displayed on Phage for Functional Characterization

The antibody or antibody fragments synthesized in Example 5, shown in Table 25, were cloned into the tricistronic Fab display vector pJPd1 (FIG. 48) for functional testing. Fab pools were generated that contained combinations of each of the master genes, the 20 VH, combined with the 8 Vλ and 12 Vκ, which yields 400 combinations, which represent the vast majority of the most prominent VH/VL germline gene pairs from the human immune repertoire, as shown in Tables 18 and FIGS. 39-40.

Figure 51:
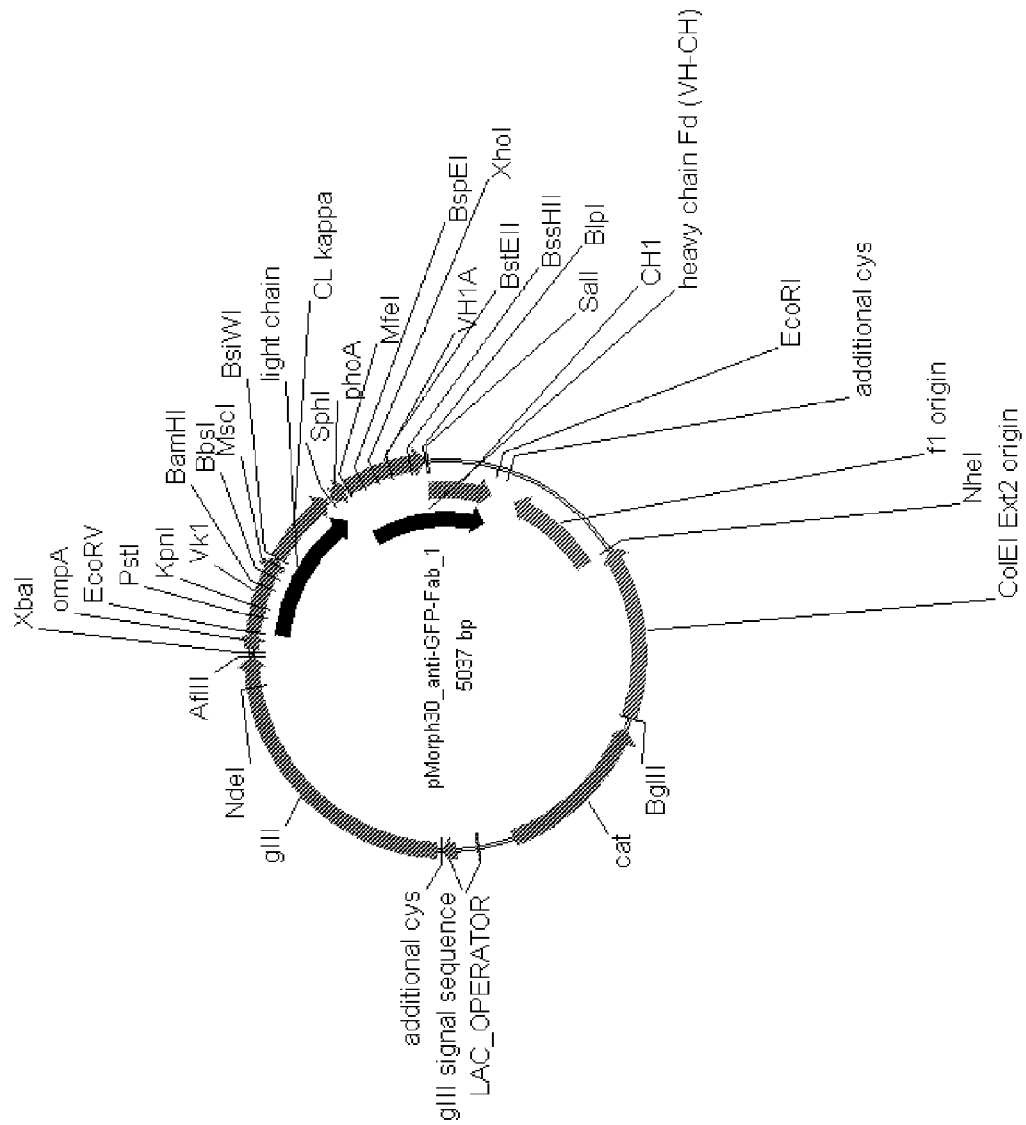
FIG. 51 shows the pMORPH30 Fab display vector.

Phage comprising the above gene pairs were produced in a small scale using 96 well plates. A master plate was generated by filling each of the wells with 2xYT/CAM/TET/Gluc medium and inoculating with clones from the 400 VH/VL combinations wherein pMORPH30_Vk3-11_AQA/VH3-23_TKA or pMORPH30_Vk3-11_AYA/VH3-23_VLA (pMORPH30 is shown in FIG. 51) were used as a control. The plates incubated overnight at 37° C. while shaking. The master plates were stored in a final concentration of 15% glycerol, and frozen at −80° C.

Additional 96 well plates were produced for phage production using 2xYT/CAM/TET/Gluc as medium and inoculated with clones from the master plates described above. The plates were incubated at 37° C. for ~2-4 h while shaking at 400 rpm, until an OD600 nm of ~0.5 was reached.

The plates were infected with 5 μl helper phage per well (Hyperphage; PROGEN; 1×10^12 pfu/ml). The plates were incubated at 37° C. for 45 min without shaking and then for 60 min while shaking at 400 rpm. The bacteria were spun down at 2200 g for 5 min at 4° C.

The helper phage containing supernatants were discarded and the infected E. coli pellets were re-suspended with 2xYT/Cam/TET/Kan/IPTG without glucose. The re-suspended pellets were transferred into a new 96 deep well plate pre-filled with 2xYT/Cm/TET/Kan/IPTG. The plates were incubated overnight at 22° C., while shaking. The phage containing supernatants were harvested by spinning down and discarding E. coli cells and debris.

Example 6.2

Evaluation of Fab Phage Display Ranking Using ELISA

The phage supernatants prepared as described in Example 6.1 were used for Fab phage display ranking in phage ELISAs.
Display of the Fab fragments was evaluated in a phage ELISA using two different capture antibodies:
(1) The anti-M13 antibody (Amersham #27-9420-01) was used for capture of phage particles via the major coat protein g8p; therefore, phage titer can be determined.
(2) An anti-Fd antibody (The Binding Site #PC075) was used, which binds to the displayed Fab; therefore, only phage displaying Fabs comprising the master genes, are captured.

The respective capture antibodies were immobilized on black 96-well Maxisorp™ plates by dispensing 100 µl antibody solution at a concentration of 7.5 µg/ml for the anti-M13 antibody and a 1.0 µg/ml concentration for the anti-Fd antibody into different wells, sealing the plate with laminated foil and incubating overnight at 4° C. The next day, the plates were washed twice with TBST, and each well was blocked with 300 µl CTBST for 1 h at room temperature.

Both the phage supernatants and reference samples were transferred for detection as follows. The blocked ELISA plates were washed twice with TBST. 100 µl of appropriately diluted phage supernatants in CTBST was transferred from the dilution plates to the coated ELISA plates, incubated for 1-2 h at room temperature, and washed 5× with TBST. 100 µl/well of anti-M13 peroxidase conjugate (Amersham) diluted 1:5000 in CTBST was added, and incubated for 1-2 h at room temperature. The Quanta Blu (Pierce) working solution was prepared by mixing 1 part (e.g. 0.5 ml) peroxide solution with 9 parts (e.g. 4.5 ml) substrate solution and equilibrating it to room temperature for at least 30 min. The ELISA plates were washed 5× with TBST, 100 µl/well of the QuantaBlu working solution was added. The fluorescence was measured after an incubation time of ~2 min (excitation: 320 nm, emission: 430 nm) and subsequently at intervals of 5 min.

The evaluation of the ELISA data was completed as follows: calibration curves were created by using a HuCAL GOLD reference phage preparation (VH3 kappa+lambda) and the titers of the phage supernatants and controls were calculated. For each sample, the titer on anti-Fd was divided by the titer on anti-M13 (anti-pVIII), the resulting ratio is the relative display rate.

As the relative display rate in Fab was calculated using an internal standard (HuCAL GOLD phage preparation VH3 kappa+lambda), which is not pubically available. The relative display rate was evaluated as a ranking. By ranking the relative display values, one of skill in the art can reproduce the above method using any control. For example, each germline protein pair displays an amount relative to a control. Therefore, the germline protein pairs having the highest relative display rate as compared to our control will also have the highest relative display rate compared to any control, despite the fact that the specific relative display rates would likely differ. Therefore, a ranking of the values was created using the relative display data shown in FIG. 55, also shown in Table 32, where the data was ranked from highest value to lowest. This ranking is shown in Table 26. From this the germline protein pairs comprising a relative display rate within the top 10%, 20%, 30%, 45%, 50%, 55%, 60%, 70%, 75%, 80%, and 90% of Fabs sampled can be identified.

Specifically, from the 400 pairs tested, relative display values were obtained for 196 pairs, see Table 26. Therefore, one of skill in the art can determine exactly which germline protein pairs fall within the top 10%, 20%, 30%, 45%, 50%, 55%, 60%, 70%, 75%, 80%, or 90% of Fabs sampled. For example, the top 75% includes the germline protein pairs ranked as Nos. 1-147 in Table 26.

TABLE 26

Ranking of relative Fab display values

| No. | VH | VL | Relative Fab Display (CysDisplay) |
|---|---|---|---|
| 1 | hVH_3_11 | hVK_1_39 | 29.0 |
| 2 | hVH_3_07 | hVK_1_39 | 27.3 |
| 3 | hVH_3_15 | hVK_3_11 | 19.4 |
| 4 | hVH_3_23 | hVK_1_27 | 17.1 |
| 5 | hVH_3_33 | hVL_2-23 | 17.1 |
| 6 | hVH_3_15 | hVL_1-40 | 16.7 |
| 7 | hVH_3_30 | hVL_3-21 | 16.6 |
| 8 | hVH_3_21 | hVK_1_06 | 16.1 |
| 9 | hVH_3_53 | hVK_1_12 | 14.8 |
| 10 | hVH_3_15 | hVK_1_16 | 14.5 |
| 11 | hVH_3_07 | hVK_3_15 | 14.5 |
| 12 | hVH_3_07 | hVK_1_27 | 14.5 |
| 13 | hVH_3_15 | hVK_1_39 | 14.2 |
| 14 | hVH_3_23 | hVL_2-11 | 13.6 |
| 15 | hVH_3_23 | hVK_3_20 | 13.3 |
| 16 | hVH_3_30 | hVK_1_39 | 13.1 |
| 17 | hVH_3_15 | hVL_1-47 | 13.0 |
| 18 | hVH_3_07 | hVK_2_30 | 13.0 |
| 19 | hVH_3_11 | hVL_1-40 | 12.4 |
| 20 | hVH_3_33 | hVK_3_15 | 12.3 |
| 21 | hVH_3_15 | hVK_3_15 | 12.1 |
| 22 | hVH_3_48 | hVK_3_15 | 12.1 |
| 23 | hVH_3_21 | hVL_3-21 | 11.8 |
| 24 | hVH_3_15 | hVK_1_06 | 11.7 |
| 25 | hVH_3_21 | hVK_1_39 | 11.6 |
| 26 | hVH_3_15 | hVK_1_12 | 11.5 |
| 27 | hVH_3_07 | hVL_2-14 | 11.3 |
| 28 | hVH_3_21 | hVK_1_12 | 11.3 |
| 29 | hVH_3_53 | hVK_1_05 | 11.1 |
| 30 | hVH_3_15 | hVL_1-51 | 11.0 |
| 31 | hVH_3_23 | hVK_1_39 | 10.8 |
| 32 | hVH_3_53 | hVK_1_16 | 10.7 |
| 33 | hVH_3_07 | hVK_1_12 | 10.6 |
| 34 | hVH_3_15 | hVL_2-11 | 10.5 |
| 35 | hVH_3_07 | hVK_1_17 | 10.5 |
| 36 | hVH_3_11 | hVK_1_16 | 10.3 |
| 37 | hVH_3_48 | hVL_1-47 | 10.3 |
| 38 | hVH_3_23 | hVL_1-51 | 10.2 |
| 39 | hVH_3_15 | hVL_2-23 | 10.1 |
| 40 | hVH_3_21 | hVK_1_05 | 10.0 |
| 41 | hVH_3_15 | hVK_1_09 | 10.0 |
| 42 | hVH_3_74 | hVK_3_15 | 10.0 |
| 43 | hVH_3_11 | hVL_3-21 | 9.8 |
| 44 | hVH_3_15 | hVL_2-14 | 9.7 |
| 45 | hVH_3_53 | hVK_3_15 | 9.6 |
| 46 | hVH_3_30 | hVL_2-23 | 9.5 |
| 47 | hVH_3_74 | hVK_1_06 | 9.5 |
| 48 | hVH_3_15 | hVL_3-1 | 9.4 |
| 49 | hVH_3_48 | hVL_2-23 | 9.3 |
| 50 | hVH_3_15 | hVL_3-21 | 9.2 |
| 51 | hVH_3_30 | hVK_1_27 | 9.1 |
| 52 | hVH_3_23 | hVL_2-14 | 9.1 |
| 53 | hVH_3_48 | hVK_1_27 | 8.9 |
| 54 | hVH_3_15 | hVK_3_20 | 8.9 |
| 55 | hVH_3_11 | hVL_2-23 | 8.9 |
| 56 | hVH_3_21 | hVL_2-23 | 8.8 |
| 57 | hVH_3_74 | hVL_1-40 | 8.8 |
| 58 | hVH_3_30 | hVL_3-1 | 8.8 |
| 59 | hVH_3_74 | hVK_1_39 | 8.7 |
| 60 | hVH_3_48 | hVK_1_16 | 8.7 |

TABLE 26-continued

Ranking of relative Fab display values

| No. | VH | VL | Relative Fab Display (CysDisplay) |
|---|---|---|---|
| 61 | hVH_3_74 | hVK_1_09 | 8.7 |
| 62 | hVH_3_21 | hVK_1_27 | 8.7 |
| 63 | hVH_3_74 | hVK_1_12 | 8.4 |
| 64 | hVH_3_11 | hVL_2-11 | 8.4 |
| 65 | hVH_3_23 | hVK_1_16 | 8.4 |
| 66 | hVH_3_53 | hVK_1_09 | 8.3 |
| 67 | hVH_4_04*03 | hVL_1-47 | 8.3 |
| 68 | hVH_3_11 | hVK_1_12 | 8.2 |
| 69 | hVH_3_07 | hVL_1-40 | 8.2 |
| 70 | hVH_3_15 | hVK_1_05 | 8.1 |
| 71 | hVH_3_11 | hVL_1-47 | 8.1 |
| 72 | hVH_3_74 | hVK_1_16 | 8.0 |
| 73 | hVH_3_15 | hVK_1_27 | 7.8 |
| 74 | hVH_3_23 | hVL_2-23 | 7.4 |
| 75 | hVH_3_23 | hVL_3-21 | 7.4 |
| 76 | hVH_3_53 | hVL_2-11 | 7.2 |
| 77 | hVH_6_1 | hVL_1-40 | 7.2 |
| 78 | hVH_3_74 | hVL_1-51 | 7.1 |
| 79 | hVH_3_74 | hVL_3-1 | 7.0 |
| 80 | hVH_3_07 | hVK_1_16 | 7.0 |
| 81 | hVH_3_07 | hVL_2-23 | 6.9 |
| 82 | hVH_3_53 | hVK_1_27 | 6.9 |
| 83 | hVH_3_11 | hVK_1_09 | 6.7 |
| 84 | hVH_3_07 | hVK_1_09 | 6.7 |
| 85 | hVH_3_21 | hVL_2-14 | 6.5 |
| 86 | hVH_3_74 | hVK_1_05 | 6.4 |
| 87 | hVH_3_11 | hVL_2-14 | 6.4 |
| 88 | hVH_3_15 | hVK_1_17 | 6.4 |
| 89 | hVH_3_53 | hVL_1-51 | 6.4 |
| 90 | hVH_3_53 | hVL_2-23 | 6.3 |
| 91 | hVH_3_07 | hVL_1-47 | 6.3 |
| 92 | hVH_3_23 | hVK_1_09 | 6.1 |
| 93 | hVH_3_48 | hVL_3-1 | 6.0 |
| 94 | hVH_3_11 | hVK_1_27 | 6.0 |
| 95 | hVH_6_1 | hVK_1_09 | 5.9 |
| 96 | hVH_1_46 | hVL_1-51 | 5.7 |
| 97 | hVH_3_11 | hVK_1_05 | 5.5 |
| 98 | hVH_3_30 | hVK_1_12 | 5.4 |
| 99 | hVH_1_46 | hVL_3-21 | 5.2 |
| 100 | hVH_4_04*03 | hVL_3-21 | 5.2 |
| 101 | hVH_3_53 | hVL_3-1 | 5.1 |
| 102 | hVH_3_07 | hVL_3-1 | 5.0 |
| 103 | hVH_3_74 | hVK_1_27 | 5.0 |
| 104 | hVH_3_21 | hVK_1_17 | 5.0 |
| 105 | hVH_3_74 | hVL_2-14 | 4.7 |
| 106 | hVH_3_11 | hVK_3_15 | 4.6 |
| 107 | hVH_3_23 | hVL_3-1 | 4.6 |
| 108 | hVH_1_69*01 | hVL_3-21 | 4.6 |
| 109 | hVH_4_04*03 | hVK_1_09 | 4.5 |
| 110 | hVH_1_18 | hVL_3-1 | 4.4 |
| 111 | hVH_1_18 | hVL_2-23 | 4.3 |
| 112 | hVH_1_46 | hVL_3-1 | 4.3 |
| 113 | hVH_3_11 | hVK_1_06 | 4.3 |
| 114 | hVH_3_23 | hVK_2_30 | 4.1 |
| 115 | hVH_5_51 | hVL_3-1 | 3.8 |
| 116 | hVH_1_18 | hVK_1_39 | 3.7 |
| 117 | hVH_5_51 | hVK_1_39 | 3.7 |
| 118 | hVH_3_73 | hVK_1_27 | 3.6 |
| 119 | hVH_4_39 | hVL_3-1 | 3.6 |
| 120 | hVH_1_69*01 | hVK_1_39 | 3.5 |
| 121 | hVH_1_69*01 | hVL_3-1 | 3.4 |
| 122 | hVH_1_18 | hVL_3-21 | 3.4 |
| 123 | hVH_6_1 | hVK_1_06 | 3.3 |
| 124 | hVH_4_04*03 | hVK_1_16 | 3.2 |
| 125 | hVH_3_74 | hVL_1-47 | 3.2 |
| 126 | hVH_1_46 | hVK_3_15 | 3.0 |
| 127 | hVH_5_51 | hVL_2-23 | 3.0 |
| 128 | hVH_1_46 | hVK_1_09 | 3.0 |
| 129 | hVH_1_69*01 | hVK_1_06 | 2.9 |
| 130 | hVH_3_53 | hVK_1_17 | 2.9 |
| 131 | hVH_1_46 | hVL_2-23 | 2.7 |
| 132 | hVH_4_04*03 | hVL_2-23 | 2.7 |
| 133 | hVH_5_51 | hVK_1_09 | 2.6 |
| 134 | hVH_1_18 | hVK_3_15 | 2.6 |
| 135 | hVH_1_46 | hVK_1_39 | 2.5 |
| 136 | hVH_1_18 | hVL_2-14 | 2.5 |
| 137 | hVH_1_18 | hVL_1-40 | 2.4 |
| 138 | hVH_4_04*03 | hVL_3-1 | 2.2 |
| 139 | hVH_1_18 | hVK_3_20 | 2.2 |
| 140 | hVH_4_39 | hVK_1_39 | 2.1 |
| 141 | hVH_1_69*01 | hVK_1_05 | 2.1 |
| 142 | hVH_5_51 | hVL_2-14 | 2.1 |
| 143 | hVH_1_69*01 | hVK_1_12 | 2.1 |
| 144 | hVH_6_1 | hVL_2-23 | 2.1 |
| 145 | hVH_4_39 | hVL_2-14 | 2.0 |
| 146 | hVH_1_18 | hVK_1_05 | 2.0 |
| 147 | hVH_1_18 | hVK_1_16 | 2.0 |
| 148 | hVH_1_18 | hVL_2-11 | 1.9 |
| 149 | hVH_1_18 | hVK_2_30 | 1.9 |
| 150 | hVH_5_51 | hVK_3_15 | 1.9 |
| 151 | hVH_5_51 | hVK_1_12 | 1.8 |
| 152 | hVH_1_69*01 | hVL_2-23 | 1.8 |
| 153 | hVH_3_74 | hVL_3-21 | 1.8 |
| 154 | hVH_4_39 | hVK_1_06 | 1.6 |
| 155 | hVH_1_46 | hVL_2-11 | 1.6 |
| 156 | hVH_1_69*01 | hVK_3_15 | 1.6 |
| 157 | hVH_1_18 | hVK_1_12 | 1.6 |
| 158 | hVH_6_1 | hVK_1_12 | 1.5 |
| 159 | hVH_4_31 | hVL_3-1 | 1.4 |
| 160 | hVH_1_46 | hVK_1_16 | 1.3 |
| 161 | hVH_3_53 | hVK_2_30 | 1.3 |
| 162 | hVH_5_51 | hVK_1_16 | 1.3 |
| 163 | hVH_1_46 | hVK_1_17 | 1.3 |
| 164 | hVH_1_69*01 | hVK_1_16 | 1.2 |
| 165 | hVH_1_18 | hVK_1_27 | 1.2 |
| 166 | hVH_6_1 | hVL_2-11 | 1.0 |
| 167 | hVH_1_69*01 | hVK_1_17 | 0.9 |
| 168 | hVH_4_39 | hVL_2-23 | 0.9 |
| 169 | hVH_5_51 | hVK_2_30 | 0.9 |
| 170 | hVH_1_69*01 | hVL_2-11 | 0.8 |
| 171 | hVH_3_73 | hVL_2-23 | 0.8 |
| 172 | hVH_4_39 | hVK_1_17 | 0.7 |
| 173 | hVH_4_39 | hVL_1-40 | 0.6 |
| 174 | hVH_1_18 | hVK_1_06 | 0.6 |
| 175 | hVH_3_73 | hVK_3_11 | 0.5 |
| 176 | hVH_3_73 | hVK_1_05 | 0.4 |
| 177 | hVH_5_51 | hVK_1_27 | 0.4 |
| 178 | hVH_6_1 | hVL_3-21 | 0.4 |
| 179 | hVH_3_73 | hVL_3-21 | 0.4 |
| 180 | hVH_1_2 | hVL_3-1 | 0.4 |
| 181 | hVH_4_04*03 | hVK_2_30 | 0.3 |
| 182 | hVH_3_73 | hVK_1_06 | 0.3 |
| 183 | hVH_3_73 | hVL_1-51 | 0.3 |
| 184 | hVH_3_73 | hVK_1_09 | 0.3 |
| 185 | hVH_3_73 | hVK_1_12 | 0.3 |
| 186 | hVH_3_73 | hVK_1_16 | 0.3 |
| 187 | hVH_3_73 | hVK_1_39 | 0.2 |
| 188 | hVH_3_73 | hVK_3_15 | 0.2 |
| 189 | hVH_3_73 | hVL_2-11 | 0.2 |
| 190 | hVH_1_69*01 | hVK_1_27 | 0.2 |
| 191 | hVH_1_2 | hVL_2-11 | 0.1 |
| 192 | hVH_1_2 | hVK_1_05 | 0.1 |
| 193 | hVH_1_2 | hVK_1_16 | 0.1 |
| 194 | hVH_3_73 | hVK_1_17 | 0.1 |
| 195 | hVH_1_2 | hVK_1_06 | 0.1 |
| 196 | hVH_1_2 | hVL_2-14 | 0.1 |

FIG. 55 shows the relative display rates for most of the 400 VH/VL germline gene pairs.

Example 6.3

Figure 49:
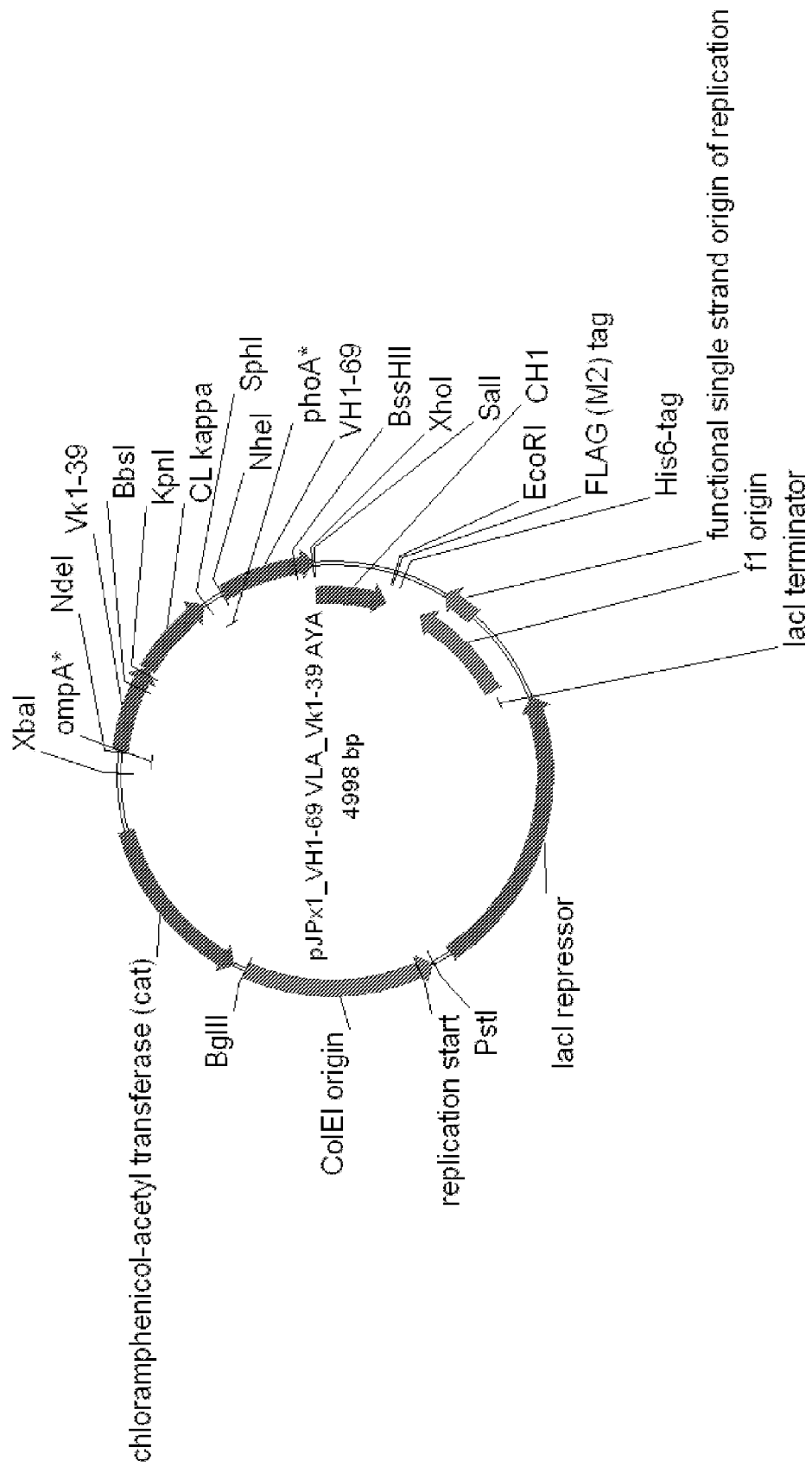
FIG. 49 shows the pJPx1 Fab expression vector.

Screening ELISA of 400 VH/VL Combinations to Determine the Fab Expression Level in E. coli Lysates Masterplates (MP) were inoculated by picking clones transformed by pools of VH/VL combinations in the Fab expression vector pJPx1 (shown in FIG. 49) into 2YT/Cam/ 1% Gluc medium per well. These plates were incubated at 37° C. over night while shaking. Expression plates (EP) were inoculated with 2.5 µl of the cultures from MPs into 2YT/ Cam/0.1% Glucose per well. Controls (see Table 27) were inoculated from glycerol stocks. These plates were incubated for 6 hours at 37° C. and shaking, then Fab expression was induced by adding IPTG and incubated at 22° C. over night while shaking. E. coli cell lysates were produced by adding boric/acid/EDTA/lysozyme-buffer to the EPs (1 h incubation at 22° C., shaking), and bacterial lysates were subsequently blocked with 12.5% MPBST, shaking at least for 30 min at room temperature. E. coli lysates from expression plates were diluted appropriately in 0.5% MPBS and used in the following assay.

Table 27 shows the unlabeled coating antibodies and AP-labeled detection antibodies which were used.

TABLE 27

| | MOR Name | Label | Host | Antibody | Company | Number | Concentration | Dilution | Lot |
|---|---|---|---|---|---|---|---|---|---|
| Coating Ab | 15 | unlabeled | sheep | anti-Human IgG (Fd) | Binding Site | pc075 | 12.1 mg/ml | 1:1000 | 236366, Exp 2009 October |
| detection Ab | AP27 | AP | mouse | anti-FlagM2 | Sigma | A9469 | 1.1 mg/ml | 1:5000 | 048K6143, new lot |

Table 28 describes the controls used.

TABLE 28

| # | Construct name |
|---|---|
| 3 | pMx11_FH VH1-69 VLA_Vl1-40 AYA |
| 5 | pMx11_FH VH3-23 VLA_Vk3-11 AYA |
| empty | pMx9_APStuffer_FHClone1 |
| BEL | (not containing Fab molecules!) |

The screening ELISA comprised the following steps: Coating 384 wells of a MaxiSorp plate with anti-human IgG Fd specific antibodies diluted in PBS, and incubating over night at 4° C. The next day, the plates were washed 2× with PBST and blocked by adding (5% Milkpowder in PBS) to each well and incubating for 1-2 h at RT, while shaking. Then the plates were washed again with PBST, and preblocked E. coli-lysates, diluted in 0.5% MPBS, were added and incubated for 1 h while shaking at RT. Also the controls #3 and #5, were added. The plates were then washed with PBST and the AP-labeled detection antibody was diluted in 0.5% MPBS. The diluted detection antibody was added and then incubated for 1 h at RT while shaking gently. The signal was identified by the following: washing the wells with TBST and adding 20 µl of AttoPhos (1:5 diluted in ddH2O), and reading at 5 min and 7-8 min using Tecan (infiniTe F200), program Prime-Screen.

Relative Fab expression levels are calculated by dividing the ELISA signal of the respective VH/VL pair through the ELISA signal of the reference Fab pMx11_FH VH1-69 VLA_Vl1-40 AYA. Thereby equally high ELISA signals result in a relative Fab expression level of 1. The reference Fab is expressed in a pMORPHX11 plasmids (shown in FIG. 50) comprising a) a modified phoA heavy chain signal sequence comprising the C-terminal NheI restriction site; b) a modified ompA light chain signal sequence comprising the C-terminal NdeI restriction site; c) the variable heavy germ-line protein sequences of the VH1-69*01 germline gene as shown in FIG. 45A, d) the variable light germline protein sequences of the IGLV1-40 germline gene as shown in FIG. 47A; e) incorporating the CDR-H3 (WGGDGFYAMDY) (SEQ ID NO: 1))of the hu4D5-8 antibody, and the JH4 germline protein sequence for heavy chain FR4; f) incorporating the CDR-L3 region (QSYDSSLSGVV (SEQ ID NO: 3)) and the Jl2/3 germline protein sequence for light chain FR4. The hu4D5-8 is described in Carter P. et al. (1992) "Humanization of an anti-p185Her2 antibody for human cancer therapy" Proc. Natl. Acad. Sci. USA 89, 4285-4289). All genes were generated at Geneart (Regensburg, Germany).

The results are shown in FIG. 56.

Example 6.4

Screening ELISA of 400 VH/VL Combinations to Determine the Temperature Stability of Fab in BEL Lysates Expression plates were generated as in Example 6.3. Diluted E. coli lysates from expression plates were incubated at different temperatures for 45 minutes and used in the following assay.

Table 29 shows the unlabeled coating antibodies and AP-labeled detection antibodies which were used.

TABLE 29

|  | MOR Name | Label | Host | Antibody | Company | Number | Concentration | Dilution | Lot |
|---|---|---|---|---|---|---|---|---|---|
| coating Ab | 57 | unlabeled | Mouse | monoclonal Anti poly Histidine Antibody IgG1 (anti 6x-Histidine); polypeptides containing a polyhistidine tag | R&D Systems | MAB050 | 500 µg/ml | 1:250 | AEJ1708111 |
| detection Ab | AP30 | AP | goat | anti-human kappa light chains | Sigma | A3813 | 2.3 mg/ml | 1:2300 | 018K6069 |
| detection Ab | AP5 | AP | goat | anti-human lambda light chains | Sigma | A2904 | 0.8 mg/ml | 1:800 | 096K6030 |

The screening ELISA comprised the following steps: 384 wells of a MaxiSorp plate were coated with coating antibody (see table above) diluted in PBS. The plates were incubated over night at 4° C. The next day, the plates were washed with PBST and blocked by adding 5% MPBS to each well and incubated for 1-2 h at RT while shaking. Then the diluted *E. coli* lysates from the expression plates were distributed into four 96 well PCR-plates (each about 40 µl) and exposed to different temperatures (4° C. (on ice), 60° C., 70° C., 80° C. and then on ice) in a PCR-Cycler, each temperature for 45 min. The blocked 384 well plates were washed with PBST, then the pre-incubated Fab lysates, were added to the plates. The plates were then incubated 1 h at RT while shaking. The plates were washed with PBST, the AP-labeled detection antibodies were diluted in 0.5% MPBS. 20 µl/well of the diluted detection antibodies were added and incubated for 1 h at RT while shaking gently. The signal was identified by the following: washing the wells with TBST and adding AttoPhos (1:5 diluted in ddH2O) to all wells. The signal was read at different timepoints (5 min to 10 min) using Tecan (infiniTe F200), program PimeScreen.

The results are shown in FIG. 57.

Example 6.5

Screening ELISA of 400 VH/VL Combinations to Determine the Serum Stabilty of Fab in *E. coli* Lysates Expression plates were generated as in Example 6.3. The Fab containing *E. coli* lysates were diluted and incubated in bovine and mouse serum using the following steps: *E. coli* lysates from the expression plates were diluted in 50% serum (total volume of 100 µl), 1:1000 Cam was added to prevent growth of bacteria, and the lysates were split into two 96 well plates and both plates were frozen. The first plate was thawed and incubated at 37° C. for 12-13 days. The second plate was stored at −80° C. until performing the ELISA (0 days incubation at 37° C.). Table 30 shows the unlabeled coating antibodies and AP-labeled detection antibodies which were used.

PBST. *E. coli* lysates in serum from the −80° C. and 37° C. samples were transferred to the coated ELISA plates and incubated for 1 hour at RT while shaking. The plates were washed with PBST, and the AP-labeled detection antibodies were diluted in 0.5% MPBS. AP-labeled detection antibody was added and the plate was incubated for 1 h at RT while shaking. The signal was identified by the following: washing the wells with TBST and adding AttoPhos (1:5 diluted in ddH2O) to all wells. The signal was read at different timepoints (5 min to 10 min) using Tecan (infiniTe F200), program PrimeScreen.

The results of the bovine serum stability testing are shown in FIG. 58.

The results of the mouse serum stability testing are shown in FIG. 59.

Example 7

Generation of IQGs for Evaluation of Biophysical Properties

Figure 52:
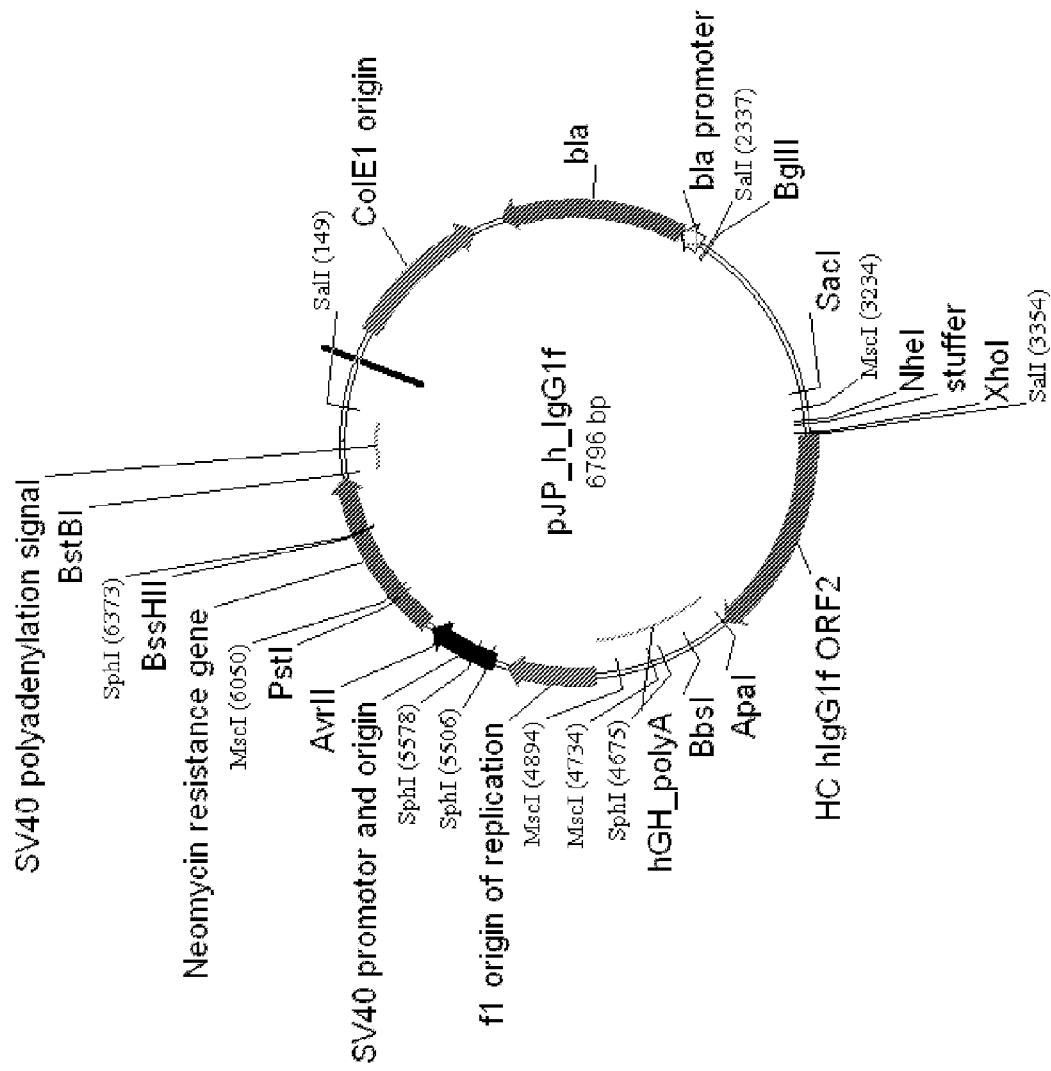
FIG. 52 shows the pJP_h_IgG1f variable heavy chain IgG expression vector.

For generation of the 400 VH/VL germline gene pairs, the 20 variable region heavy chain genes were sub-cloned into the human IgG1 expression vector pJP_hIgG1 shown in FIG. 52. In parallel the 12 variable region kappa genes were sub-cloned into the mammalian kappa light chain expression vector pJP_hIgkappa shown in FIG. 53 and the 8 variable region lambda genes were sub-cloned into the mammalian lambda light chain expression vector pJP_hIglambda shown in FIG. 54.

By co-transfection of each, a heavy chain and a light chain expression plasmid all 400 VH/VL pairs can be produced separately by only cloning 40 expression constructs. Thus, all 20 heavy chain constructs were co-transfected with each of the light chain expression constructs in HEK.EBNA cells. Human IgG1 was harvested or detected several days post transfection from the cell culture supernatants.

TABLE 30

|  | MOR Name | Label | Host | Antibody | Company | Number | Concentration | Dilution | Lot |
|---|---|---|---|---|---|---|---|---|---|
| coating Ab | 36 | Fab | Goat | anti-Human IgG (H + L) | Jackson Immuno Research | 109-006-088 | 1.3 mg/ml | 1:1000 | 80299 |
| detection Ab | AP30 | AP | goat | anti-human kappa light chains | Sigma | A3813 | 2.3 mg/ml | 1:2300 | 018K6069 |
| detection Ab | AP5 | AP | Goat | anti-Human lambda-light chain; bound + free | Sigma | A2904 | 0.8 mg/ml | 1:800 | 096K6030 |

On day 11 or 12, the 384 wells of a MaxiSorp plate were coated with 20 µl coating antibody diluted in PBS. The plates were incubated over night at 4° C. The following day, the plates were washed with PBST and blocked by adding 5% MPBS to each well and incubating for 1-2 h at RT while shaking. Then the blocked 384 well plates were washed with Example 7.1

IgG Expression Ranking

One of the criteria for the selection of the VH/VL pairings to be included in a library is the level of expression of the 400 different VH/VL pairings in the IgG format. The expression level of each VH/VL pairing in human IgG1 format was assessed by sandwich ELISA. Therefore all 400 VH/VL combinations in human IgG1 format were transfected into HEK-.EBNA cells and expressed in small scale. The cell culture supernatants were harvested after few days and IgG levels assessed.

The following procedure was performed. 384-well Max-iSorp™ plates were coated with Fcγ-pan R10Z8E9 mouse anti-human IgG at 2.5 µg/ml in PBS. The plates were incubated overnight at 4° C. The plates were washed with PBST. The plates were blocked with 5% BSA or 1× Chemiblocker in PBST and incubated for 1 h at room temperature while shaking and again washed with PBST. The IgG expression supernatants were diluted in 2.5% BSA-PBST and the diluted samples were added to the blocked and washed ELISA plate. The following controls were used: empty supernatant and supernatants with a low expressing antibody, moderate expressing antibody and a high expressing antibody. The plates were incubated for 2 h at room temperature while shaking. The plates were then washed with TBST. Appropriately diluted Fcγ-pan R10Z8E9 mouse anti-human IgG Biotin conjugate in 1% BSA-TBST was added. The plates were incubated for 1 h at room temperature. The plates were washed with TBST. Streptavidin-AP diluted 1:2000 in 0.5% BSA-TBST was added and the plates were incubated for 1 h at room temperature while shaking. The plates were washed with TBST. AttoPhos™ fluorescence substrate (prepared according to manufacturer's instructions) diluted in TBST directly before use was added. After 5 and 10 min, the fluorescence was measured via Tecan microplate reader.

Relative IgG1 expression levels were calculated by dividing the ELISA signal of the respective VH/VL pair through the ELISA signal of the reference IgG1 MOR03080 (shown in Table 31). Thereby equally high ELISA signals result in a relative IgG1 expression level of 1.

TABLE 31

The amino acid sequence of MOR03080 is as follows:

03080 Variable heavy chain with CDRs in bold:

(1) QVQLVESGGGLVQPGGSLRLSCAASGFTFSSYGMHWVRQAPGKGLEWVSN
(51) IYSDGSNTFYADSVKGRFTISRDNSKNTLYLQMNSLRAEDTAVYYCARNM
(101) YRWPFHYFFDYWGQGTLVTVSS (SEQ ID NO: 60)

03080 Variable light chain with CDRs in bold (1) DIELTQPPSV SVAPGQTARISCSGDNIGNKYVSWYQQKPGQAPVVVIYGD
(51) NNRPSGIPERFSGSNSGNTATLTISGTQAEDEADYYCSSYDSSYFVFGGG
(101) TKLTVLGQ (SEQ ID NO: 61)

The results are shown in FIG. 60.

Example 7.2

IgG1 Serum Stability Ranking

One of the criteria for the selection of the variable heavy and variable light chain pairings to be included in a library is the serum stability of the 400 different variable heavy and variable light chain pairings in IgG format. Serum stability of each IgG antibody supernatant was assessed by incubation in 50% mouse serum for 14 days and subsequent sandwich ELISA with mouse anti-human IgG (CH2) clone R10Z8E9. Again all 400 VH/VL combinations in human IgG1 format were transfected into HEK.EBNA cells and expressed in small scale. The cell culture supernatants were harvested after few days and the IgGs in the supernatant tested for serum stability.

The following procedure was performed. 384-well Max-iSorp™ plate were coated with Fcγ-pan R10Z8E9 mouse anti-human IgG at 2.5 µg/ml in PBS. The plates were incubated overnight at 4° C. The plates were washed with PBST and then blocked with 5% BSA-PBST or 1× Chemiblocker for 1 h at room temperature while shaking. The plates were washed with PBST. The IgG1 containing cell culture supernatants were diluted a) in 2.5% BSA-PBST and b) in 50% mouse serum and incubated at 37° C. for at least 14 days and these samples were added to the blocked and washed ELISA plate. The following controls were used: empty supernatant and supernatants a low expressing antibody, a moderate expressing antibody, and a high expressing antibody. The plates were incubated for 2 h at room temperature while shaking. The plates were washed with TBST. Fcγ-pan R10Z8E9 mouse anti-human IgG Biotin conjugate diluted to 0.8 µg/ml in 1% BSA-TBST was added. The plates were incubated for 1 h at room temperature. The plates were washed with TBST. Streptavidin-AP diluted 1:2000 in 0.5% BSA-TBST was added. The plates were incubated for 1 h at room temperature while shaking. The plates were washed with TBST. AttoPhos™ fluorescence substrate (prepared according to manufacturer's instructions) diluted 1:5 in TBST directly before use was added. After 5 and 10 min, the fluorescence was measured via Tecan microplate reader.

The results are shown in FIG. 61.

Example 8

Selection of the VH/VL Pairs with Favorable Bio-physical Properties for Incorporation into Collection Once the 400 VH/VL germline gene pairs were tested for the following properties: a) relative display after phage production and phage ELISA in Fab format; b) relative Fab expression levels after Fab production in *E. coli, E. coli* cell lysis and ELISA detection of produced Fab; c) temperature stability of Fab after Fab production in *E. coli, E. coli* cell lysis and ELISA detection of non-denatured Fab after incubation at increased temperatures; d) bovine/mouse serum stability of Fab from *E. coli* lysates by ELISA detection of non-denatured Fab after incubation in bovine/mouse serum; e) relative human IgG1 expression levels after IgG1 production in mammalian cells and ELISA detection of secreted IgG1 from cell culture supernatants; and f) bovine serum stability of human IgG1 by ELISA detection of non-denatured Fab after incubation in bovine/mouse serum; then the next step was to select which VH/VL germline pairs were to be incorporated into the collection.

The results of the functional testing for each VH/VL germline protein pairs are shown in Table 32.

TABLE 32

Compilation of functional data for each of the 400 VH/VL germline gene pairs

| No. | VH | VL | Relative Fab Display (CysDisplay) | Relative Fab expression | Fab thermo-stability | Fab stability in mouse serum | Fab stability in bovine serum | Fab ranking-value | Relative IgG1 expression | IgG1 stability in bovine serum |
|---|---|---|---|---|---|---|---|---|---|---|
| 1 | hVH_1_2 | hVK_1_05 | 0.1 | 0.0 | bg | U | S | 10 | 0.0 | bg |
| 2 | hVH_1_2 | hVK_1_06 | 0.1 | 0.2 | 60 | S | S | 42 | 0.0 | bg |
| 3 | hVH_1_2 | hVK_1_09 | 0.0 | 0.0 | bg | U | S | 11 | 0.0 | bg |
| 4 | hVH_1_2 | hVK_1_12 | 0.0 | 0.0 | bg | S | S | 20 | 0.0 | bg |
| 5 | hVH_1_2 | hVK_1_16 | 0.1 | 0.0 | bg | S | S | 20 | 0.0 | bg |
| 6 | hVH_1_2 | hVK_1_17 | 0.0 | 0.0 | bg | S | S | 21 | 0.0 | bg |
| 7 | hVH_1_2 | hVK_1_27 | 0.0 | 0.1 | bg | S | S | 22 | 0.0 | bg |
| 8 | hVH_1_2 | hVK_1_39 | 0.0 | 0.0 | bg | S | S | 21 | 0.0 | bg |
| 9 | hVH_1_2 | hVK_2_30 |  | 0.0 | bg | S | S | 20 | 0.0 | bg |
| 10 | hVH_1_2 | hVK_3_11 | 0.0 | 0.0 | bg | S | S | 20 | 0.0 | bg |
| 11 | hVH_1_2 | hVK_3_15 | 0.0 | 0.0 | bg | U | S | 10 | 0.0 | bg |
| 12 | hVH_1_2 | hVK_3_20 |  | 0.0 | bg | S | S | 21 | 0.0 | bg |
| 13 | hVH_1_2 | hVL_1-40 |  |  |  |  |  | 0 | 0.3 | bg |
| 14 | hVH_1_2 | hVL_1-47 | 0.0 | 0.0 | 4 | U | U | 2 | 0.0 | bg |
| 15 | hVH_1_2 | hVL_1-51 | 0.0 | 0.0 | 4 | U | U | 0 | 0.4 | bg |
| 16 | hVH_1_2 | hVL_2-11 | 0.1 | 0.0 | 4 | S | S | 22 | 0.3 | bg |
| 17 | hVH_1_2 | hVL_2-14 | 0.1 | 0.0 | 4 | U | U | 0 | 0.1 | bg |
| 18 | hVH_1_2 | hVL_2-23 | 0.0 | 0.0 | 4 | U | U | 0 | 0.0 | bg |
| 19 | hVH_1_2 | hVL_3-1 | 0.4 | 0.0 | 4 | U | U | 1 | 0.0 | bg |
| 20 | hVH_1_2 | hVL_3-21 | 0.0 | 0.0 | 4 | U | U | 0 | 0.0 | bg |
| 21 | hVH_1_18 | hVK_1_05 | 2.0 | 0.4 | 60 | S | S | 54 | 0.4 | S |
| 22 | hVH_1_18 | hVK_1_06 | 0.6 | 0.5 | 60 | S | S | 56 | 0.2 | S |
| 23 | hVH_1_18 | hVK_1_09 |  |  |  |  |  | 0 | 0.1 | S |
| 24 | hVH_1_18 | hVK_1_12 | 1.6 | 0.5 | 60 | S | S | 56 | 0.1 | bg |
| 25 | hVH_1_18 | hVK_1_16 | 2.0 |  |  |  |  | 3 | 0.2 | S |
| 26 | hVH_1_18 | hVK_1_17 |  | 0.5 |  | S | S | 38 | 0.3 | S |
| 27 | hVH_1_18 | hVK_1_27 | 1.2 | 0.4 | 70 | S | S | 62 | 0.5 | S |
| 28 | hVH_1_18 | hVK_1_39 | 3.7 | 0.3 | 60 | S | S | 53 | 0.1 | S |
| 29 | hVH_1_18 | hVK_2_30 | 1.9 | 0.5 | 60 | S | S | 56 | 0.0 | S |
| 30 | hVH_1_18 | hVK_3_11 |  | 0.6 | 60 | S | S | 56 | 0.0 | S |
| 31 | hVH_1_18 | hVK_3_15 | 2.6 | 0.5 | 70 | S | S | 67 | 0.3 | S |
| 32 | hVH_1_18 | hVK_3_20 | 2.2 | 0.9 | 60 | S | S | 72 | 0.0 | S |
| 33 | hVH_1_18 | hVL_1-40 | 2.4 |  |  |  |  | 4 | 0.5 | S |
| 34 | hVH_1_18 | hVL_1-47 |  | 0.8 | 60 | S | S | 66 | 0.4 | U |
| 35 | hVH_1_18 | hVL_1-51 |  |  |  |  |  | 0 | 0.5 | S |
| 36 | hVH_1_18 | hVL_2-11 | 1.9 |  |  |  |  | 3 | 0.5 | U |
| 37 | hVH_1_18 | hVL_2-14 | 2.5 | 0.6 | 60 | S | S | 64 | 0.5 | U |
| 38 | hVH_1_18 | hVL_2-23 | 4.3 | 0.7 | 60 | S | S | 70 | 0.4 | S |
| 39 | hVH_1_18 | hVL_3-1 | 4.4 | 0.6 | 60 | S | S | 65 | 0.2 | U |
| 40 | hVH_1_18 | hVL_3-21 | 3.4 | 0.6 | 60 | S | S | 64 | 0.2 | S |
| 41 | hVH_1_46 | hVK_1_05 |  | 0.4 | 60 | S | S | 51 | 0.9 | S |
| 42 | hVH_1_46 | hVK_1_06 |  |  |  |  |  | 0 | 0.9 | S |
| 43 | hVH_1_46 | hVK_1_09 | 3.0 | 0.6 | 60 | S | S | 63 | 0.4 | S |
| 44 | hVH_1_46 | hVK_1_12 |  | 0.5 | 60 | S | S | 55 | 0.2 | S |
| 45 | hVH_1_46 | hVK_1_16 | 1.3 | 0.6 | 60 | S | S | 61 | 0.3 | S |
| 46 | hVH_1_46 | hVK_1_17 | 1.3 |  |  |  |  | 2 | 0.5 | S |
| 47 | hVH_1_46 | hVK_1_27 |  |  |  |  |  | 0 | 0.6 | S |
| 48 | hVH_1_46 | hVK_1_39 | 2.5 | 0.4 | 60 | S | S | 55 | 0.5 | S |
| 49 | hVH_1_46 | hVK_2_30 |  | 0.2 | 4 | U | S | 16 | 0.0 | S |
| 50 | hVH_1_46 | hVK_3_11 |  |  |  |  |  | 0 | 0.1 | S |
| 51 | hVH_1_46 | hVK_3_15 | 3.0 | 0.7 | 60 | S | S | 68 | 0.4 | S |
| 52 | hVH_1_46 | hVK_3_20 |  |  |  |  |  | 0 | 0.1 | S |
| 53 | hVH_1_46 | hVL_1-40 |  | 1.0 | 60 | S | S | 73 | 0.9 | S |
| 54 | hVH_1_46 | hVL_1-47 |  |  |  |  |  | 0 | 0.6 | U |
| 55 | hVH_1_46 | hVL_1-51 | 5.7 |  |  |  |  | 10 | 0.3 | S |
| 56 | hVH_1_46 | hVL_2-11 | 1.6 |  |  |  |  | 3 | 0.3 | S |
| 57 | hVH_1_46 | hVL_2-14 |  |  |  |  |  | 0 | 0.3 | U |
| 58 | hVH_1_46 | hVL_2-23 | 2.7 | 1.0 | 60 | S | S | 79 | 0.3 | S |
| 59 | hVH_1_46 | hVL_3-1 | 4.3 |  |  |  |  | 7 | 0.4 | S |
| 60 | hVH_1_46 | hVL_3-21 | 5.2 |  |  |  |  | 9 | 0.3 | S |
| 61 | **hVH_1_69*01 | hVK_1_05 | 2.1 | 0.5 | 60 | S | S | 59 | 0.9 | S** |
| 62 | hVH_1_69*01 | hVK_1_06 | 2.9 |  |  |  |  | 5 | 0.5 | S |
| 63 | hVH_1_69*01 | hVK_1_09 |  | 0.3 | 60 | S | U | 37 | 0.4 | S |
| 64 | hVH_1_69*01 | hVK_1_12 | 2.1 | 0.4 | 60 | S | S | 53 | 0.3 | S |
| 65 | hVH_1_69*01 | hVK_1_16 | 1.2 |  |  |  |  | 2 | 0.4 | S |
| 66 | hVH_1_69*01 | hVK_1_17 | 0.9 | 0.3 | 4 | S | S | 31 | 0.3 | S |
| 67 | hVH_1_69*01 | hVK_1_27 | 0.2 | 0.3 | 70 | S | S | 56 | 0.4 | S |
| 68 | hVH_1_69*01 | hVK_1_39 | 3.5 | 0.1 | 4 | S | S | 31 | 0.4 | U |
| 69 | hVH_1_69*01 | hVK_2_30 |  |  |  |  |  | 0 | 0.0 | S |
| 70 | hVH_1_69*01 | hVK_3_11 |  | 0.7 | 60 | S | S | 60 | 0.0 | S |
| 71 | hVH_1_69*01 | hVK_3_15 | 1.6 | 0.5 | 70 | S | S | 66 | 0.5 | S |

TABLE 32-continued

Compilation of functional data for each of the 400 VH/VL germline gene pairs

| No. | VH | VL | Relative Fab Display (CysDisplay) | Relative Fab expression | Fab thermo-stability | Fab stability in mouse serum | Fab stability in bovine serum | Fab ranking-value | Relative IgG1 expression | IgG1 stability in bovine serum |
|---|---|---|---|---|---|---|---|---|---|---|
| 72 | hVH_1_69*01 | hVK_3_20 | | 0.5 | 60 | S | S | 54 | 0.0 | S |
| 73 | hVH_1_69*01 | hVL_1-40 | | 1.0 | 60 | S | S | 72 | 0.2 | S |
| 74 | hVH_1_69*01 | hVL_1-47 | | | | | | 0 | 0.2 | U |
| 75 | hVH_1_69*01 | hVL_1-51 | | 0.8 | 60 | S | S | 64 | 0.3 | S |
| 76 | hVH_1_69*01 | hVL_2-11 | 0.8 | 0.7 | 60 | S | S | 65 | 0.2 | S |
| 77 | hVH_1_69*01 | hVL_2-14 | | 0.8 | 60 | S | S | 64 | 0.3 | U |
| 78 | hVH_1_69*01 | hVL_2-23 | 1.8 | | | | | 3 | 0.3 | S |
| 79 | hVH_1_69*01 | hVL_3-1 | 3.4 | 0.7 | | S | S | 52 | 0.2 | S |
| 80 | hVH_1_69*01 | hVL_3-21 | 4.6 | 0.7 | 60 | S | S | 71 | 0.1 | S |
| 81 | hVH_3_07 | hVK_1_05 | | 0.7 | 60 | S | S | 63 | 0.9 | U |
| 82 | hVH_3_07 | hVK_1_06 | | 0.9 | 60 | S | S | 69 | 1.3 | S |
| 83 | hVH_3_07 | hVK_1_09 | 6.7 | 0.4 | 60 | S | S | 50 | 1.5 | S |
| 84 | hVH_3_07 | hVK_1_12 | 10.6 | 0.9 | 70 | S | S | 97 | 0.9 | S |
| 85 | hVH_3_07 | hVK_1_16 | 7.0 | | | | | 12 | 1.5 | S |
| 86 | hVH_3_07 | hVK_1_17 | 10.5 | 0.5 | 4 | S | S | 40 | 0.9 | S |
| 87 | hVH_3_07 | hVK_1_27 | 14.5 | 0.5 | 70 | S | S | 87 | 1.8 | S |
| 88 | hVH_3_07 | hVK_1_39 | 27.3 | 0.3 | 60 | U | S | 85 | 1.2 | S |
| 89 | hVH_3_07 | hVK_2_30 | 13.0 | | | | | 0 | 0.3 | S |
| 90 | hVH_3_07 | hVK_3_11 | | | | | | 0 | 0.4 | S |
| 91 | hVH_3_07 | hVK_3_15 | 14.5 | 0.7 | 70 | S | S | 95 | 1.8 | S |
| 92 | hVH_3_07 | hVK_3_20 | | | | | | 0 | 0.4 | S |
| 93 | hVH_3_07 | hVL_1-40 | 8.2 | | | | | 14 | 0.3 | S |
| 94 | hVH_3_07 | hVL_1-47 | 6.3 | 1.2 | 60 | S | S | 90 | 0.8 | U |
| 95 | hVH_3_07 | hVL_1-51 | | 1.0 | 60 | S | S | 74 | 0.9 | S |
| 96 | hVH_3_07 | hVL_2-11 | | | | | | 0 | 1.2 | S |
| 97 | hVH_3_07 | hVL_2-14 | 11.3 | | | | | 19 | 0.8 | U |
| 98 | hVH_3_07 | hVL_2-23 | 6.9 | 0.8 | 60 | S | S | 76 | 0.7 | S |
| 99 | hVH_3_07 | hVL_3-1 | 5.0 | 0.5 | 60 | S | S | 64 | 1.2 | S |
| 100 | hVH_3_07 | hVL_3-21 | | 0.7 | 60 | S | S | 61 | 0.3 | S |
| 101 | hVH_3_11 | hVK_1_05 | 5.5 | 0.5 | 60 | S | S | 65 | 0.5 | S |
| 102 | hVH_3_11 | hVK_1_06 | 4.3 | 0.6 | 60 | S | S | 64 | 1.4 | S |
| 103 | hVH_3_11 | hVK_1_09 | 6.7 | | | | | 0 | 0.9 | S |
| 104 | hVH_3_11 | hVK_1_12 | 8.2 | 0.6 | 60 | S | S | 73 | 0.9 | S |
| 105 | hVH_3_11 | hVK_1_16 | 10.3 | 0.6 | 60 | S | U | 61 | 1.2 | S |
| 106 | hVH_3_11 | hVK_1_17 | | | | | | 0 | 0.9 | S |
| 107 | hVH_3_11 | hVK_1_27 | 6.0 | | | | | 0 | 1.7 | S |
| 108 | hVH_3_11 | hVK_1_39 | 29.0 | | | | | 50 | 1.8 | S |
| 109 | hVH_3_11 | hVK_2_30 | | 0.4 | 4 | S | S | 34 | 1.1 | U |
| 110 | hVH_3_11 | hVK_3_11 | 0.0 | | | | | 0 | 0.6 | S |
| 111 | hVH_3_11 | hVK_3_15 | 4.6 | 0.7 | 60 | S | S | 68 | 1.6 | S |
| 112 | hVH_3_11 | hVK_3_20 | | | | | | 0 | 0.2 | S |
| 113 | hVH_3_11 | hVL_1-40 | 12.4 | | | | | 21 | 0.3 | S |
| 114 | hVH_3_11 | hVL_1-47 | 8.1 | 0.8 | 60 | S | S | 80 | 1.3 | U |
| 115 | hVH_3_11 | hVL_1-51 | | 1.1 | 60 | S | S | 77 | 1.9 | S |
| 116 | hVH_3_11 | hVL_2-11 | 8.4 | | | | | 14 | 1.1 | S |
| 117 | hVH_3_11 | hVL_2-14 | 6.4 | 0.9 | 60 | S | S | 81 | 0.4 | U |
| 118 | hVH_3_11 | hVL_2-23 | 8.9 | 1.0 | 60 | S | S | 88 | 0.4 | S |
| 119 | hVH_3_11 | hVL_3-1 | | 0.5 | 60 | S | S | 53 | 1.6 | S |
| 120 | hVH_3_11 | hVL_3-21 | 9.8 | | | | | 17 | 0.3 | S |
| 121 | hVH_3_15 | hVK_1_05 | 8.1 | 0.5 | 60 | S | S | 68 | 0.4 | S |
| 122 | hVH_3_15 | hVK_1_06 | 11.7 | 0.6 | 60 | S | S | 79 | 0.8 | S |
| 123 | hVH_3_15 | hVK_1_09 | 10.0 | 0.5 | 70 | S | S | 80 | 0.9 | S |
| 124 | hVH_3_15 | hVK_1_12 | 11.5 | 0.7 | 70 | S | S | 90 | 0.7 | S |
| 125 | hVH_3_15 | hVK_1_16 | 14.5 | 0.7 | 60 | S | S | 86 | 1.5 | S |
| 126 | hVH_3_15 | hVK_1_17 | 6.4 | 0.6 | 4 | U | U | 30 | 0.8 | S |
| 127 | hVH_3_15 | hVK_1_27 | 7.8 | 0.5 | 70 | S | S | 77 | 1.7 | S |
| 128 | hVH_3_15 | hVK_1_39 | 14.2 | 0.4 | 60 | S | S | 76 | 1.8 | S |
| 129 | hVH_3_15 | hVK_2_30 | | 0.3 | 4 | S | U | 23 | 0.6 | S |
| 130 | hVH_3_15 | hVK_3_11 | 19.4 | | | | | 33 | 0.8 | S |
| 131 | hVH_3_15 | hVK_3_15 | 12.1 | 0.6 | 70 | S | S | 70 | 1.9 | S |
| 132 | hVH_3_15 | hVK_3_20 | 8.9 | | | | | 0 | 0.5 | S |
| 133 | hVH_3_15 | hVL_1-40 | 16.7 | 0.9 | 60 | S | S | 98 | 0.1 | S |
| 134 | hVH_3_15 | hVL_1-47 | 13.0 | 1.2 | 60 | S | S | 102 | 0.2 | U |
| 135 | hVH_3_15 | hVL_1-51 | 11.0 | 1.1 | 60 | S | S | 94 | 0.9 | S |
| 136 | hVH_3_15 | hVL_2-11 | 10.5 | 0.9 | 60 | S | S | 88 | 0.8 | S |
| 137 | hVH_3_15 | hVL_2-14 | 9.7 | 0.8 | 60 | S | S | 83 | 0.9 | U |
| 138 | hVH_3_15 | hVL_2-23 | 10.1 | | | | | 17 | 0.4 | S |
| 139 | hVH_3_15 | hVL_3-1 | 9.4 | 0.3 | 4 | S | S | 46 | 1.0 | S |
| 140 | hVH_3_15 | hVL_3-21 | 9.2 | 0.8 | | S | S | 65 | 0.2 | S |
| 141 | hVH_3_21 | hVK_1_05 | 10.0 | | | | | 17 | 0.8 | S |
| 142 | hVH_3_21 | hVK_1_06 | 16.1 | 1.0 | 60 | S | S | 99 | 0.9 | S |
| 143 | hVH_3_21 | hVH_1_09 | | | | | | 0 | 0.4 | S |
| 144 | hVH_3_21 | hVK_1_12 | 11.3 | 0.6 | 60 | S | S | 77 | 0.5 | S |
| 145 | hVH_3_21 | hVK_1_16 | | 0.9 | 60 | S | S | 68 | 0.0 | S |

TABLE 32-continued

Compilation of functional data for each of the 400 VH/VL germline gene pairs

| No. | VH | VL | Relative Fab Display (CysDisplay) | Relative Fab expression | Fab thermo-stability | Fab stability in mouse serum | Fab stability in bovine serum | Fab ranking-value | Relative IgG1 expression | IgG1 stability in bovine serum |
|---|---|---|---|---|---|---|---|---|---|---|
| 146 | hVH_3_21 | hVK_1_17 | 5.0 | | | | | 9 | 0.0 | S |
| 147 | hVH_3_21 | hVK_1_27 | 8.7 | 0.6 | 60 | S | S | 78 | 0.5 | S |
| 148 | hVH_3_21 | hVK_1_39 | 11.6 | 0.5 | 60 | S | S | 54 | 0.8 | S |
| 149 | hVH_3_21 | hVK_2_30 | | 0.6 | 4 | S | S | 44 | 0.1 | U |
| 150 | hVH_3_21 | hVK_3_11 | | | | | | 0 | 0.2 | S |
| 151 | hVH_3_21 | hVK_3_15 | | 0.8 | 60 | S | S | 65 | 0.3 | S |
| 152 | hVH_3_21 | hVK_3_20 | | | | | | 0 | 0.5 | S |
| 153 | hVH_3_21 | hVL_1-40 | | 1.0 | 60 | S | S | 12 | 0.5 | S |
| 154 | hVH_3_21 | hVL_1-47 | 0.0 | 1.2 | 60 | S | S | 81 | 0.3 | S |
| 155 | hVH_3_21 | hVL_1-51 | | | | | | 0 | 0.9 | S |
| 156 | hVH_3_21 | hVL_2-11 | | 0.9 | 60 | S | S | 68 | 0.7 | S |
| 157 | hVH_3_21 | hVL_2-14 | 6.5 | 0.9 | 60 | S | S | 81 | 1.2 | S |
| 158 | hVH_3_21 | hVL_2-23 | 8.8 | 1.0 | 60 | S | S | 90 | 0.9 | S |
| 159 | hVH_3_21 | hVL_3-1 | | 0.7 | 60 | S | S | 60 | 0.4 | S |
| 160 | hVH_3_21 | hVL_3-21 | 11.8 | 0.9 | 60 | S | S | 88 | 0.1 | S |
| 161 | hVH_3_23 | hVK_1_05 | | 0.8 | 60 | S | S | 64 | 0.2 | S |
| 162 | hVH_3_23 | hVK_1_06 | | 0.7 | 60 | S | S | 61 | 0.2 | S |
| 163 | hVH_3_23 | hVK_1_09 | 6.1 | 0.8 | 70 | S | S | 86 | 0.1 | S |
| 164 | hVH_3_23 | hVK_1_12 | | 0.9 | 60 | S | S | 68 | 0.1 | S |
| 165 | hVH_3_23 | hVK_1_16 | 8.4 | 0.6 | 60 | S | S | 72 | 0.2 | S |
| 166 | hVH_3_23 | hVK_1_17 | | 0.6 | 4 | S | U | 31 | 0.1 | S |
| 167 | hVH_3_23 | hVK_1_27 | 17.1 | | | | | 29 | 0.2 | S |
| 168 | hVH_3_23 | hVK_1_39 | 10.8 | | | | | 19 | 0.3 | S |
| 169 | hVH_3_23 | hVK_2_30 | 4.1 | 0.3 | 4 | S | S | 39 | 0.0 | bg |
| 170 | hVH_3_23 | hVK_3_11 | | | | | | 0 | 0.0 | bg |
| 171 | hVH_3_23 | hVK_3_15 | | 0.7 | 70 | S | S | 73 | 0.4 | S |
| 172 | hVH_3_23 | hVK_3_20 | 13.3 | | | | | 0 | 0.2 | S |
| 173 | hVH_3_23 | hVL_1-40 | | | | | | 0 | 0.1 | S |
| 174 | hVH_3_23 | hVL_1-47 | | | | | | 0 | 0.1 | S |
| 175 | hVH_3_23 | hVL_1-51 | 10.2 | 1.1 | 60 | S | S | 94 | 0.2 | S |
| 176 | hVH_3_23 | hVL_2-11 | 13.6 | | | | | 23 | 0.1 | S |
| 177 | hVH_3_23 | hVL_2-14 | 9.1 | | | | | 16 | 0.3 | S |
| 178 | hVH_3_23 | hVL_2-23 | 7.4 | 0.9 | 60 | S | S | 82 | 0.3 | S |
| 179 | hVH_3_23 | hVL_3-1 | 4.6 | 0.4 | 60 | S | S | 60 | 0.1 | S |
| 180 | hVH_3_23 | hVL_3-21 | 7.4 | 0.8 | 60 | S | S | 78 | 0.1 | S |
| 181 | hVH_3_30 | hVK_1_05 | | | | | | 0 | 0.7 | S |
| 182 | hVH_3_30 | hVK_1_06 | | 1.0 | 60 | S | S | 75 | 0.6 | S |
| 183 | hVH_3_30 | hVK_1_09 | | | | | | 0 | 0.3 | S |
| 184 | hVH_3_30 | hVK_1_12 | 5.4 | 0.8 | 60 | S | S | 73 | 0.3 | S |
| 185 | hVH_3_30 | hVK_1_16 | | 0.9 | 60 | S | S | 69 | 0.4 | S |
| 186 | hVH_3_30 | hVK_1_17 | | | | | | 0 | 0.5 | S |
| 187 | hVH_3_30 | hVK_1_27 | 9.1 | 0.4 | 60 | S | U | 38 | 0.5 | S |
| 188 | hVH_3_30 | hVK_1_39 | 13.1 | 0.0 | bg | U | U | 19 | 1.0 | S |
| 189 | hVH_3_30 | hVK_2_30 | | 0.4 | 4 | S | U | 23 | 0.1 | bg |
| 190 | hVH_3_30 | hVK_3_11 | | 0.4 | 60 | S | S | 50 | 0.1 | S |
| 191 | hVH_3_30 | hVK_3_15 | | 0.7 | 60 | S | S | 61 | 0.9 | S |
| 192 | hVH_3_30 | hVK_3_20 | | 0.7 | 60 | S | S | 63 | 0.4 | S |
| 193 | hVH_3_30 | hVL_1-40 | | | | | | 0 | 0.8 | S |
| 194 | hVH_3_30 | hVL_1-47 | | 1.1 | 60 | S | S | 78 | 0.3 | S |
| 195 | hVH_3_30 | hVL_1-51 | | | | | | 0 | 0.4 | S |
| 196 | hVH_3_30 | hVL_2-11 | | 0.7 | 60 | S | S | 62 | 0.4 | S |
| 197 | hVH_3_30 | hVL_2-14 | | 0.8 | 60 | S | S | 66 | 1.0 | S |
| 198 | hVH_3_30 | hVL_2-23 | 9.5 | 1.0 | 60 | S | S | 89 | 0.5 | S |
| 199 | hVH_3_30 | hVL_3-1 | 8.8 | 0.6 | 60 | S | S | 73 | 0.5 | S |
| 200 | hVH_3_30 | hVL_3-21 | 16.6 | 0.8 | 60 | S | S | 93 | 0.2 | S |
| 201 | hVH_3_33 | hVK_1_05 | | 0.3 | 60 | S | S | 46 | 0.0 | S |
| 202 | hVH_3_33 | hVK_1_06 | | | | | | 0 | 0.6 | S |
| 203 | hVH_3_33 | hVK_1_09 | | 0.7 | 60 | S | S | 60 | 0.2 | S |
| 204 | hVH_3_33 | hVK_1_12 | | 0.2 | 60 | S | U | 34 | 0.2 | S |
| 205 | hVH_3_33 | hVK_1_16 | | | | | | 0 | 0.4 | S |
| 206 | hVH_3_33 | hVK_1_17 | | | | | | 0 | 0.5 | S |
| 207 | hVH_3_33 | hVK_1_27 | | 0.6 | 60 | S | S | 57 | 0.2 | S |
| 208 | hVH_3_33 | hVK_1_39 | | | | | | 0 | 0.8 | S |
| 209 | hVH_3_33 | hVK_2_30 | | | | | | 0 | 0.3 | S |
| 210 | hVH_3_33 | hVK_3_11 | | | | | | 0 | 0.6 | S |
| 211 | hVH_3_33 | hVK_3_15 | 12.3 | 0.6 | 60 | S | S | 77 | 0.9 | S |
| 212 | hVH_3_33 | hVK_3_20 | | 1.0 | 60 | S | S | 72 | 0.3 | S |
| 213 | hVH_3_33 | hVL_1-40 | | | | | | 0 | 1.0 | S |
| 214 | hVH_3_33 | hVL_1-47 | | 1.1 | 60 | S | S | 77 | 0.4 | S |
| 215 | hVH_3_33 | hVL_1-51 | | | | | | 0 | 0.6 | S |
| 216 | hVH_3_33 | hVL_2-11 | | 0.5 | 60 | S | S | 54 | 0.5 | S |
| 217 | hVH_3_33 | hVL_2-14 | | 0.9 | 4 | S | S | 53 | 0.9 | S |
| 218 | hVH_3_33 | hVL_2-23 | 17.1 | 0.5 | 60 | S | S | 82 | 0.5 | S |
| 219 | hVH_3_33 | hVL_3-1 | | 0.2 | 60 | S | S | 44 | 0.7 | S |

TABLE 32-continued

Compilation of functional data for each of the 400 VH/VL germline gene pairs

| No. | VH | VL | Relative Fab Display (CysDisplay) | Relative Fab expression | Fab thermo-stability | Fab stability in mouse serum | Fab stability in bovine serum | Fab ranking-value | Relative IgG1 expression | IgG1 stability in bovine serum |
|---|---|---|---|---|---|---|---|---|---|---|
| 220 | hVH_3_33 | hVL_3-21 |  | 0.8 | 60 | S | S | 67 | 0.5 | S |
| 221 | hVH_3_48 | hVK_1_05 |  |  |  |  |  | 0 | 0.6 | S |
| 222 | hVH_3_48 | hVK_1_06 |  |  |  |  |  | 0 | 0.7 | S |
| 223 | hVH_3_48 | hVK_1_09 |  |  |  |  |  | 0 | 0.2 | S |
| 224 | hVH_3_48 | hVK_1_12 |  |  |  |  |  | 0 | 0.3 | S |
| 225 | hVH_3_48 | hVK_1_16 | 8.7 |  |  |  |  | 15 | 0.5 | S |
| 226 | hVH_3_48 | hVK_1_17 |  |  |  |  |  | 0 | 0.5 | S |
| 227 | hVH_3_48 | hVK_1_27 | 8.9 | 0.7 | 60 | S | S | 74 | 0.9 | S |
| 228 | hVH_3_48 | hVK_1_39 |  |  |  |  |  | 0 | 0.5 | S |
| 229 | hVH_3_48 | hVK_2_30 |  |  |  |  |  | 0 | 0.3 | S |
| 230 | hVH_3_48 | hVK_3_11 |  |  |  |  |  | 0 | 0.7 | S |
| 231 | hVH_3_48 | hVK_3_15 | 12.1 |  |  |  |  | 21 | 0.3 | S |
| 232 | hVH_3_48 | hVK_3_20 |  | 0.8 | 60 | S | S | 65 | 0.4 | S |
| 233 | hVH_3_48 | hVL_1-40 |  | 0.8 |  | S | S | 51 | 0.6 | S |
| 234 | hVH_3_48 | hVL_1-47 | 10.3 |  |  |  |  | 18 | 0.4 | S |
| 235 | hVH_3_48 | hVL_1-51 |  | 1.2 | 60 | S | S | 80 | 0.7 | S |
| 236 | hVH_3_48 | hVL_2-11 |  |  |  |  |  | 0 | 0.6 | S |
| 237 | hVH_3_48 | hVL_2-14 |  |  |  |  |  | 0 | 0.6 | S |
| 238 | hVH_3_48 | hVL_2-23 | 9.3 |  |  |  |  | 16 | 0.5 | S |
| 239 | hVH_3_48 | hVL_3-1 | 6.0 | 0.8 |  | S | S | 61 | 0.5 | S |
| 240 | hVH_3_48 | hVL_3-21 |  |  |  |  |  | 0 | 0.3 | S |
| 241 | hVH_3_53 | hVK_1_05 | 11.1 | 0.7 | 4 | U | S | 60 | 0.8 | S |
| 242 | hVH_3_53 | hVK_1_06 |  | 0.7 | 60 | S | S | 63 | 0.7 | S |
| 243 | hVH_3_53 | hVK_1_09 | 8.3 | 0.9 | 60 | S | S | 83 | 0.4 | S |
| 244 | hVH_3_53 | hVK_1_12 | 14.8 | 0.7 | 60 | S | S | 60 | 0.2 | S |
| 245 | hVH_3_53 | hVK_1_16 | 10.7 | 0.0 | bg | bg | U | 20 | 0.3 | S |
| 246 | hVH_3_53 | hVK_1_17 | 2.9 | 0.5 | 4 | S | S | 42 | 0.5 | S |
| 247 | hVH_3_53 | hVK_1_27 | 6.9 | 0.4 | 60 | S | S | 62 | 0.2 | S |
| 248 | hVH_3_53 | hVK_1_39 |  | 0.6 | 60 | S | S | 56 | 0.2 | S |
| 249 | hVH_3_53 | hVK_2_30 | 1.3 | 0.3 | 4 | S | S | 32 | 0.0 | bg |
| 250 | hVH_3_53 | hVK_3_11 |  | 0.8 | 60 | S | S | 64 | 0.3 | S |
| 251 | hVH_3_53 | hVK_3_15 | 9.6 | 0.7 | 60 | S | S | 63 | 0.5 | S |
| 252 | hVH_3_53 | hVK_3_20 |  | 0.3 | 4 | S | S | 32 | 0.3 | S |
| 253 | hVH_3_53 | hVL_1-40 |  | 1.1 | 4 | S | S | 60 | 1.1 | S |
| 254 | hVH_3_53 | hVL_1-47 |  | 1.1 | 60 | S | S | 79 | 0.2 | S |
| 255 | hVH_3_53 | hVL_1-51 | 6.4 | 1.3 | 60 | S | S | 96 | 0.4 | S |
| 256 | hVH_3_53 | hVL_2-11 | 7.2 | 0.8 | 60 | S | S | 78 | 0.3 | S |
| 257 | hVH_3_53 | hVL_2-14 |  | 1.0 | 60 | S | S | 75 | 0.8 | S |
| 258 | hVH_3_53 | hVL_2-23 | 6.3 | 1.1 | 60 | S | S | 86 | 0.6 | S |
| 259 | hVH_3_53 | hVL_3-1 | 5.1 | 0.6 | 60 | S | S | 67 | 0.5 | S |
| 260 | hVH_3_53 | hVL_3-21 |  | 0.8 | 60 | S | S | 66 | 0.5 | S |
| 261 | hVH_3_73 | hVK_1_05 | 0.4 | 0.2 | 60 | S | S | 45 | 1.1 | S |
| 262 | hVH_3_73 | hVK_1_06 | 0.3 | 0.2 | 60 | S | S | 45 | 1.0 | S |
| 263 | hVH_3_73 | hVK_1_09 | 0.3 | 0.1 | 60 | S | S | 39 | 0.9 | S |
| 264 | hVH_3_73 | hVK_1_12 | 0.3 | 0.1 | 60 | S | S | 38 | 0.5 | S |
| 265 | hVH_3_73 | hVK_1_16 | 0.3 | 0.2 | 60 | S | S | 44 | 1.1 | S |
| 266 | hVH_3_73 | hVK_1_17 | 0.1 |  |  |  |  | 0 | 1.0 | S |
| 267 | hVH_3_73 | hVK_1_27 | 3.6 | 0.1 | 4 | S | S | 24 | 0.9 | S |
| 268 | hVH_3_73 | hVK_1_39 | 0.2 | 0.2 | 4 | S | S | 27 | 0.8 | S |
| 269 | hVH_3_73 | hVK_2_30 |  | 0.1 | bg | S | S | 22 | 0.3 | S |
| 270 | hVH_3_73 | hVK_3_11 | 0.5 |  |  |  |  | 0 | 0.2 | S |
| 271 | hVH_3_73 | hVK_3_15 | 0.2 | 0.1 | 60 | S | S | 39 | 0.1 | S |
| 272 | hVH_3_73 | hVK_3_20 |  |  |  |  |  | 0 | 1.1 | S |
| 273 | hVH_3_73 | hVL_1-40 |  | 0.1 | 60 | S | S | 40 | 1.2 | S |
| 274 | hVH_3_73 | hVL_1-47 | 0.0 | 0.3 | 4 | S | S | 31 | 0.8 | S |
| 275 | hVH_3_73 | hVL_1-51 | 0.3 | 0.2 | 60 | S | S | 44 | 0.7 | S |
| 276 | hVH_3_73 | hVL_2-11 | 0.2 | 0.2 | 4 | S | S | 26 | 0.8 | S |
| 277 | hVH_3_73 | hVL_2-14 |  |  |  |  |  | 0 | 0.4 | S |
| 278 | hVH_3_73 | hVL_2-23 | 0.8 |  |  |  |  | 1 | 0.1 | S |
| 279 | hVH_3_73 | hVL_3-1 | 0.0 | 0.1 | 60 | S | S | 39 | 1.0 | S |
| 280 | hVH_3_73 | hVL_3-21 | 0.4 | 0.2 | 60 | S | S | 43 | 1.1 | S |
| 281 | hVH_3_74 | hVK_1_05 | 6.4 |  |  |  |  | 11 | 0.6 | S |
| 282 | hVH_3_74 | hVK_1_06 | 9.5 | 0.9 | 60 | S | S | 86 | 1.0 | S |
| 283 | hVH_3_74 | hVK_1_09 | 8.7 | 0.6 | 60 | S | S | 74 | 0.5 | S |
| 284 | hVH_3_74 | hVK_1_12 | 8.4 | 0.6 | 60 | S | S | 74 | 0.0 | S |
| 285 | hVH_3_74 | hVK_1_16 | 8.0 |  |  |  |  | 11 | 0.8 | S |
| 286 | hVH_3_74 | hVK_1_17 |  | 0.6 | 60 | S | S | 58 | 0.2 | S |
| 287 | hVH_3_74 | hVK_1_27 | 5.0 | 0.6 | 70 | S | S | 77 | 1.1 | S |
| 288 | hVH_3_74 | hVK_1_39 | 8.7 |  |  |  |  | 15 | 0.3 | S |
| 289 | hVH_3_74 | hVK_2_30 |  | 0.4 |  | S | S | 37 | 0.7 | S |
| 290 | hVH_3_74 | hVK_3_11 |  |  |  |  |  | 0 | 0.1 | S |
| 291 | hVH_3_74 | hVK_3_15 | 10.0 | 0.8 | 70 | S | S | 94 | 1.0 | S |
| 292 | hVH_3_74 | hVK_3_20 |  | 0.7 | 60 | S | S | 62 | 0.6 | S |
| 293 | hVH_3_74 | hVL_1-40 | 8.8 | 0.4 | 4 | S | S | 51 | 1.3 | S |

TABLE 32-continued

Compilation of functional data for each of the 400 VH/VL germline gene pairs

| No. | VH | VL | Relative Fab Display (CysDisplay) | Relative Fab expression | Fab thermo-stability | Fab stability in mouse serum | Fab stability in bovine serum | Fab ranking-value | Relative IgG1 expression | IgG1 stability in bovine serum |
|---|---|---|---|---|---|---|---|---|---|---|
| 294 | hVH_3_74 | hVL_1-47 | 3.2 | 1.2 |  | S | S | 12 | 0.6 | S |
| 295 | hVH_3_74 | hVL_1-51 | 7.1 | 1.1 | 60 | S | S | 91 | 1.2 | S |
| 296 | hVH_3_74 | hVL_2-11 |  | 0.6 | 60 | S | S | 59 | 0.8 | S |
| 297 | hVH_3_74 | hVL_2-14 | 4.7 |  |  |  |  | 8 | 0.6 | S |
| 298 | hVH_3_74 | hVL_2-23 |  |  |  |  |  | 0 | 1.0 | S |
| 299 | hVH_3_74 | hVL_3-1 | 7.0 | 0.6 | 60 | S | S | 70 | 0.3 | S |
| 300 | hVH_3_74 | hVL_3-21 | 1.8 | 0.6 | 60 | S | S | 60 | 0.3 | S |
| 301 | hVH_4_04*03 | hVK_1_05 |  | 0.8 | 60 | S | S | 67 | 0.6 | S |
| 302 | hVH_4_04*03 | hVK_1_06 |  | 0.8 | 60 | S | S | 64 | 1.1 | S |
| 303 | hVH_4_04*03 | hVK_1_09 | 4.5 | 0.1 | bg | S | S | 30 | 0.6 | S |
| 304 | hVH_4_04*03 | hVK_1_12 |  | 0.7 | 60 | S | S | 61 | 0.8 | S |
| 305 | hVH_4_04*03 | hVK_1_16 | 3.2 | 0.2 | 60 | S | S | 48 | 0.4 | S |
| 306 | hVH_4_04*03 | hVK_1_17 |  | 0.4 | 4 | S | S | 34 | 0.8 | S |
| 307 | hVH_4_04*03 | hVK_1_27 |  | 0.4 | 60 | S | S | 48 | 0.9 | S |
| 308 | hVH_4_04*03 | hVK_1_39 |  | 0.2 | bg | S | S | 26 | 1.0 | S |
| 309 | hVH_4_04*03 | hVK_2_30 | 0.3 | 0.5 | 4 | S | S | 38 | 0.2 | U |
| 310 | hVH_4_04*03 | hVK_3_11 |  | 0.6 | bg | S | S | 43 | 0.3 | S |
| 311 | hVH_4_04*03 | hVK_3_15 |  | 0.6 | 60 | S | S | 58 | 1.1 | S |
| 312 | hVH_4_04*03 | hVK_3_20 |  | 1.1 | 60 | S | U | 65 | 1.1 | S |
| 313 | hVH_4_04*03 | hVL_1-40 |  | 1.0 | 60 | S | S | 75 | 0.9 | S |
| 314 | hVH_4_04*03 | hVL_1-47 | 8.3 |  |  |  |  | 14 | 0.4 | S |
| 315 | hVH_4_04*03 | hVL_1-51 |  | 0.9 | 60 | S | S | 71 | 0.6 | S |
| 316 | hVH_4_04*03 | hVL_2-11 |  | 1.0 | 60 | S | S | 73 | 0.7 | S |
| 317 | hVH_4_04*03 | hVL_2-14 |  | 0.7 | 60 | S | S | 63 | 0.4 | S |
| 318 | **hVH_4_04*03 | hVL_2-23 | 2.7 | 1.0 | 60 | S | S | 77 | 0.7 | S** |
| 319 | **hVH_4_04*03 | hVL_3-1 | 2.2 | 0.6 | 60 | S | S | 63 | 1.3 | S** |
| 320 | **hVH_4_04*03 | hVL_3-21 | 5.2 | 0.7 | 60 | S | S | 69 | 0.5 | S** |
| 321 | hVH_4_31 | hVK_1_05 |  | 0.0 | bg | S | S | 21 | 0.0 | bg |
| 322 | hVH_4_31 | hVK_1_06 |  |  |  |  |  | 0 | 0.2 | bg |
| 323 | hVH_4_31 | hVK_1_09 |  | 0.1 | 4 | S | S | 23 | 0.6 | S |
| 324 | hVH_4_31 | hVK_1_12 |  | 0.1 | 60 | S | S | 37 | 0.4 | S |
| 325 | hVH_4_31 | hVK_1_16 |  | 0.0 | bg | S | S | 20 | 0.0 | bg |
| 326 | hVH_4_31 | hVK_1_17 |  | 0.0 | bg | U | bg | 1 | 0.2 | bg |
| 327 | hVH_4_31 | hVK_1_27 |  | 0.0 | bg | S | S | 20 | 0.0 | bg |
| 328 | hVH_4_31 | hVK_1_39 |  | 0.8 | 60 | S | S | 65 | 0.5 | S |
| 329 | hVH_4_31 | hVK_2_30 |  | 0.0 | bg | S | S | 20 | 0.0 | bg |
| 330 | hVH_4_31 | hVK_3_11 |  |  |  |  |  | 0 | 0.0 | bg |
| 331 | hVH_4_31 | hVK_3_15 |  | 0.1 | bg | S | S | 24 | 0.1 | S |
| 332 | hVH_4_31 | hVK_3_20 |  |  |  |  |  | 0 | 0.4 | S |
| 333 | hVH_4_31 | hVL_1-40 | 0.0 | 0.6 | 60 | S | S | 57 | 0.8 | S |
| 334 | hVH_4_31 | hVL_1-47 | 0.0 | 0.7 | 60 | S | S | 62 | 0.1 | S |
| 335 | hVH_4_31 | hVL_1-51 |  | 0.9 | 60 | S | S | 70 | 0.3 | S |
| 336 | hVH_4_31 | hVL_2-11 |  | 0.5 | 60 | S | S | 55 | 0.2 | S |
| 337 | hVH_4_31 | hVL_2-14 | 0.0 |  |  |  |  | 0 | 0.5 | S |
| 338 | hVH_4_31 | hVL_2-23 |  | 0.0 | 60 | S | S | 37 | 0.3 | S |
| 339 | hVH_4_31 | hVL_3-1 | 1.4 | 0.3 | 60 | S | S | 50 | 1.3 | S |
| 340 | hVH_4_31 | hVL_3-21 |  | 0.4 | 60 | S | S | 50 | 0.4 | bg |
| 341 | hVH_4_39 | hVK_1_05 | 0.0 | 0.3 | 60 | S | S | 45 | 0.3 | S |
| 342 | hVH_4_39 | hVK_1_06 | 1.6 |  |  |  |  | 3 | 0.8 | S |
| 343 | hVH_4_39 | hVK_1_09 |  | 0.5 | 4 | S | S | 37 | 0.7 | S |
| 344 | hVH_4_39 | hVK_1_12 |  |  |  |  |  | 0 | 0.9 | S |
| 345 | hVH_4_39 | hVK_1_16 |  |  |  |  |  | 0 | 0.5 | S |
| 346 | hVH_4_39 | hVK_1_17 | 0.7 | 0.3 | 4 | S | S | 33 | 1.0 | S |
| 347 | hVH_4_39 | hVK_1_27 |  |  |  |  |  | 0 | 0.4 | S |
| 348 | hVH_4_39 | hVK_1_39 | 2.1 | 0.3 | 60 | S | S | 48 | 1.2 | S |
| 349 | hVH_4_39 | hVK_2_30 |  | 0.2 | 4 | S | S | 27 | 0.2 | S |
| 350 | hVH_4_39 | hVK_3_11 |  | 0.3 | 60 | S | S | 48 | 0.2 | S |
| 351 | hVH_4_39 | hVK_3_15 |  | 0.6 | 70 | S | S | 68 | 1.0 | S |
| 352 | hVH_4_39 | hVK_3_20 |  | 0.6 | 60 | S | S | 49 | 1.2 | S |
| 353 | hVH_4_39 | hVL_1-40 | 0.6 | 0.9 | 70 | S | S | 81 | 1.1 | S |
| 354 | hVH_4_39 | hVL_1-47 |  | 0.7 | 70 | S | S | 72 | 0.3 | S |
| 355 | hVH_4_39 | hVL_1-51 |  | 0.8 | 60 | S | S | 65 | 0.5 | S |
| 356 | hVH_4_39 | hVL_2-11 |  |  |  |  |  | 0 | 0.3 | S |
| 357 | hVH_4_39 | hVL_2-14 | 2.0 | 0.6 | 60 | S | S | 63 | 0.5 | S |
| 358 | hVH_4_39 | hVL_2-23 | 0.9 | 0.7 | 60 | S | S | 62 | 0.4 | S |
| 359 | hVH_4_39 | hVL_3-1 | 3.6 | 0.5 | 60 | S | S | 59 | 0.9 | S |
| 360 | hVH_4_39 | hVL_3-21 |  | 0.6 | 60 | S | S | 57 | 0.6 | S |
| 361 | hVH_5_51 | hVK_1_05 |  | 0.5 | 60 | S | S | 52 | 0.4 | S |
| 362 | hVH_5_51 | hVK_1_06 |  | 0.5 | 60 | S | S | 54 | 0.9 | S |
| 363 | hVH_5_51 | hVK_1_09 | 2.6 | 0.5 | 60 | S | S | 57 | 0.5 | S |
| 364 | hVH_5_51 | hVK_1_12 | 1.8 |  |  |  |  | 3 | 0.8 | S |
| 365 | hVH_5_51 | hVK_1_16 | 1.3 |  |  |  |  | 2 | 0.5 | S |
| 366 | hVH_5_51 | hVK_1_17 |  | 0.3 | 4 | S | S | 32 | 0.6 | S |
| 367 | hVH_5_51 | hVK_1_27 | 0.4 | 0.2 | 60 | S | S | 43 | 1.0 | S |

TABLE 32-continued

Compilation of functional data for each of the 400 VH/VL germline gene pairs

| No. | VH | VL | Relative Fab Display (CysDisplay) | Relative Fab expression | Fab thermo-stability | Fab stability in mouse serum | Fab stability in bovine serum | Fab ranking-value | Relative IgG1 expression | IgG1 stability in bovine serum |
|---|---|---|---|---|---|---|---|---|---|---|
| 368 | hVH_5_51 | hVK_1_39 | 3.7 | 0.3 | 60 | S | S | 51 | 1.2 | S |
| 369 | hVH_5_51 | hVK_2_30 | 0.9 | 0.2 | 4 | S | S | 19 | 0.7 | S |
| 370 | hVH_5_51 | hVK_3_11 |  |  | 1.0 | 60 | S |  | 62 | 0.6 | S |
| 371 | hVH_5_51 | hVK_3_15 | 1.9 |  |  |  |  | 3 | 1.2 | S |
| 372 | hVH_5_51 | hVK_3_20 |  |  |  |  |  | 0 | 1.1 | S |
| 373 | hVH_5_51 | hVL_1-40 |  | 1.0 | 60 | S | S | 72 | 1.3 | S |
| 374 | hVH_5_51 | hVL_1-47 |  | 1.0 | 60 | S | S | 73 | 0.8 | S |
| 375 | hVH_5_51 | hVL_1-51 |  | 1.1 | 60 | S | S | 77 | 0.5 | S |
| 376 | hVH_5_51 | hVL_2-11 | 0.0 | 0.7 | 60 | S | S | 63 | 0.3 | S |
| 377 | hVH_5_51 | hVL_2-14 | 2.1 |  |  |  |  | 4 | 0.8 | S |
| 378 | hVH_5_51 | hVL_2-23 | 3.0 | 1.0 | 60 | S | S | 79 | 0.7 | S |
| 379 | hVH_5_51 | hVL_3-1 | 3.8 | 0.7 | 60 | S | S | 67 | 1.3 | S |
| 380 | hVH_5_51 | hVL_3-21 |  |  |  |  |  | 0 | 0.7 | S |
| 381 | hVH_6_1 | hVK_1_05 |  | 0.7 | 60 | S | S | 62 | 0.0 | S |
| 382 | hVH_6_1 | hVK_1_06 | 3.3 | 0.6 | 60 | S | S | 64 | 1.2 | S |
| 383 | hVH_6_1 | hVK_1_09 | 5.9 |  |  |  |  | 10 | 1.3 | S |
| 384 | hVH_6_1 | hVK_1_12 | 1.5 | 0.0 | bg | U | S | 13 | 1.1 | S |
| 385 | hVH_6_1 | hVK_1_16 |  |  |  |  |  | 0 | 1.4 | S |
| 386 | hVH_6_1 | hVK_1_17 |  | 0.5 | 60 | S | S | 54 | 1.3 | S |
| 387 | hVH_6_1 | hVK_1_27 |  | 0.5 | 70 | S | S | 63 | 1.2 | S |
| 388 | hVH_6_1 | hVK_1_39 |  | 0.3 | 60 | S | S | 45 | 1.1 | S |
| 389 | hVH_6_1 | hVK_2_30 |  | 0.3 | 4 | S | S | 32 | 0.3 | S |
| 390 | hVH_6_1 | hVK_3_11 |  |  |  |  |  | 0 | 0.9 | S |
| 391 | hVH_6_1 | hVK_3_15 |  | 0.7 | 70 | S | S | 70 | 1.3 | S |
| 392 | hVH_6_1 | hVK_3_20 |  | 0.9 | 60 | S | S | 70 | 1.3 | S |
| 393 | hVH_6_1 | hVL_1-40 | 7.2 |  |  |  |  | 12 | 1.4 | S |
| 394 | hVH_6_1 | hVL_1-47 |  | 1.1 | 60 | S | S | 75 | 0.2 | S |
| 395 | hVH_6_1 | hVL_1-51 |  | 1.1 | 60 | S | S | 75 | 0.5 | S |
| 396 | hVH_6_1 | hVL_2-11 | 1.0 | 1.0 | 60 | S | S | 73 | 0.2 | S |
| 397 | hVH_6_1 | hVL_2-14 |  |  |  |  |  | 0 | 0.4 | S |
| 398 | hVH_6_1 | hVL_2-23 | 2.1 | 0.8 | 60 | S | S | 69 | 0.4 | S |
| 399 | hVH_6_1 | hVL_3-1 |  | 0.5 | 60 | S | S | 55 | 1.4 | S |
| 400 | hVH_6_1 | hVL_3-21 | 0.4 | 0.8 | 60 | S | S | 66 | 0.5 | S |

As described in the previous examples, the predominant VH and VL germline genes and the predominant VH/VL germline gene pairs were identified from the human immune repertoire and naïve human immune repertoire, then the predominant VH and VL germline protein sequences were analysed in silico in order to select identify variable heavy chain and variable light chain germline protein sequences having favorable biophysical properties. As shown in Tables 21, and FIGS. 37-38, generally, the top 20VH, top 8VA and top 12 Vκ were selected for synthesis, combination and subsequent functional analysis. The germline gene sequences were synthesized and then combined in order to generate a 400 germline protein pairs that are representative of the abundant germline gene pairs found in the immune repertoire, wherein each of the variable regions has favorable biophysical properties as identified in silico. The 400 VH/VL germline protein pairs were tested for the following properties: a) relative display after phage production and phage ELISA in Fab format; b) relative Fab expression levels after Fab production in *E. coli*, *E. coli* cell lysis and ELISA detection of produced Fab; c) temperature stability of Fab after Fab production in *E. coli*, *E. coli* cell lysis and ELISA detection of non-denatured Fab after incubation at increased temperatures; d) bovine/mouse serum stability of Fab from *E. coli* lysates by ELISA detection of non-denatured Fab after incubation in bovine/mouse serum; e) relative human IgG1 expression levels after IgG1 production in mammalian cells and ELISA detection of secreted IgG1 from cell culture supernatants; and f) bovine serum stability of human IgG1 by ELISA detection of non-denatured Fab after incubation in bovine/mouse serum.

Using the data provided in Table 32, one of skill in the art could readily identify the germline protein pairs having favorable biophysical properties.

Generally, the germline protein pairs having a threshold value in each functional property were selected for incorporation in the collections. For example, in some embodiments, the germline protein pairs comprising all of the following properties were selected for incorporation into a collection: i) a relative display rate in Fab format comprising a value within the top 75% of Fabs sampled; ii) an expression level in Fab format of at least 0.4 as compared to Fab VH1-69 VLA_Vl1-40 AYA; iii) thermal stability at 60° C. or more for at least 45 minutes in Fab format; iv) stability in bovine or mouse serum in Fab format for greater than ten days at 37° C.; v) an expression level in IgG format of at least 0.4 as compared to MOR03080; and vi) stability in serum in IgG format for fourteen days at 37° C. Table 32 shows in bold and underline the germline protein pairs comprising all of these functional properties.

As described above, however, germline protein pairs having one or more of the functional properties may be selected for incorporation into collections. Here, an aggregate ranking of the 400 germline protein pairs tested was created, so that each germline protein pair could be ranked against the other giving weight to each of the functional properties tested. This allowed the inventors to select one or more germline protein pairs having one or more or all of the listed functional properties. In some embodiments, the collections comprise all of the germline protein pairs having the above characteristics. In some embodiments, the collection comprises the germline protein pairs having the highest aggregate score of the 400 pairs tested. In some embodiments, the germline protein pairs having aggregate scores within the top 10%, top 20%, or top 30% of the 400 pairs tested were selected for incorporation into collections.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

We claim:

1. A collection of synthetic antibodies or functional fragments thereof, wherein the antibodies or fragments thereof comprise variable heavy chain and variable light chain pairs, wherein the variable heavy chains comprise framework regions and the variable light chains comprise framework regions, wherein the framework regions of the variable heavy chain and variable light chain pairs comprise germline protein sequence pairs of germline protein pairs, wherein said germline protein pairs comprise the following properties:

i) a relative display rate in Fab format comprising a value within the top 75% of Fabs sampled;

ii) an expression level in Fab format of at least 0.4 as compared to Fab VH1-69 VLA_VL1-40 AYA the sequences of which are depicted in Table 5, Table 9, FIG. 45A and FIG. 47A;

iii) thermal stability at 60° C. or more for at least 45 minutes in Fab format;

iv) stability in bovine or mouse serum in Fab format for greater than ten days at 37° C.;

v) an expression level in IgG format of at least 0.4 as compared to MOR03080 the CDR sequences of which are depicted in Table 31; and vi) stability in serum in IgG format for fourteen days at 37° C.;

wherein said collection of antibodies or functional fragments thereof further comprises the frawework regions of at least two different germline protein sequence pairs;
wherein the at least two different germline protein sequence pairs are selected from the following variable heavy chain and variable light chain pairs: SEQ ID NO: 65/ SEQ ID NO: 118; SEQ ID NO: 65/SEQ ID NO: 174; SEQ ID NO: 68/SEQ ID NO: 121; SEQ ID NO: 68/ SEQ ID NO: 129; SEQ ID NO: 68/SEQ ID NO: 153; SEQ ID NO: 70/SEQ ID NO: 118; SEQ ID NO: 77/SEQ ID NO: 121; SEQ ID NO: 77/SEQ ID NO: 122; SEQ ID NO: 77/SEQ ID NO: 126; SEQ ID NO: 77/SEQ ID NO: 153; SEQ ID NO: 77/SEQ ID NO: 167; SEQ ID NO: 77/SEQ ID NO: 174; SEQ ID NO: 77/SEQ ID NO: 176; SEQ ID NO: 79/SEQ ID NO: 118; SEQ ID NO: 79/SEQ ID NO: 119; SEQ ID NO: 79/SEQ ID NO: 122/SEQ ID NO: 79/SEQ ID NO: 124; SEQ ID NO: 79/SEQ ID NO: 153; SEQ ID NO: 79/SEQ ID NO: 167; SEQ ID NO: 79/SEQ ID NO: 174; SEQ ID NO: 81/SEQ ID NO: 118; SEQ ID NO: 81/SEQ ID NO: 119; SEQ ID NO: 81/SEQ ID NO: 121; SEQ ID NO: 81/SEQ ID NO: 122; SEQ ID NO: 81/SEQ ID NO: 124; SEQ ID NO: 81/SEQ ID NO: 126; SEQ ID NO: 81/SEQ ID NO: 129; SEQ ID NO: 81/SEQ ID NO: 153; SEQ ID NO: 81/SEQ ID NO: 165; SEQ ID NO: 81/SEQ ID NO: 169; SEQ ID NO: 81/SEQ ID NO: 171; SEQ ID NO: 84/SEQ ID NO: 119; SEQ ID NO: 84/SEQ ID NO: 122; SEQ ID NO: 84/SEQ ID NO: 126; SEQ ID NO: 84/SEQ ID NO: 129; SEQ ID NO: 84/SEQ ID NO: 172; SEQ ID NO: 84/SEQ ID NO: 174; SEQ ID NO: 86/SEQ ID NO: 174; SEQ ID NO: 86/SEQ ID NO: 176; SEQ ID NO: 89/SEQ ID NO: 153; SEQ ID NO: 89/ SEQ ID NO: 174; SEQ ID NO: 93/SEQ ID NO: 126; SEQ ID NO: 95/SEQ ID NO: 121; SEQ ID NO: 95/ SEQ ID NO: 122; SEQ ID NO: 95/SEQ ID NO: 169; SEQ ID NO: 95/SEQ ID NO: 174; SEQ ID NO: 95/ SEQ ID NO: 176; SEQ ID NO: 100/SEQ ID NO: 119; SEQ ID NO: 100/SEQ ID NO: 121; SEQ ID NO: 100/SEQ ID NO: 126; SEQ ID NO: 100/SEQ ID NO: 153; SEQ ID NO: 100/SEQ ID NO: 169; SEQ ID NO: 102/SEQ ID NO: 174; SEQ ID NO: 102/SEQ ID NO: 176; SEQ ID NO: 102/SEQ ID NO: 182; SEQ ID NO: 109/SEQ ID NO: 172; SEQ ID NO: 109/ SEQ ID NO: 176; SEQ ID NO: 113/SEQ ID NO: 121; SEQ ID NO: 113/SEQ ID NO: 174; SEQ ID NO: 113/SEQ ID NO: 176; SID ID NO: 115/SEQ ID NO: 119; and SEQ ID NO: 115/SEQ ID NO: 174, wherein the variable heavy chain and variable light chain pairs are listed together.

2. The collection according to claim 1, wherein said antibodies or functional fragments thereof comprise human sequences.

3. The collection according to 1, wherein said collection of antibodies or functional fragments thereof comprises the framework regions of at least eight different germline protein sequence pairs,
wherein the at least eight different germline protein pairs are selected from the following variable heavy chain and variable light chain pairs: SEQ ID NO: 65/SEQ ID NO: 118; SEQ ID NO: 65/ SEQ ID NO: 174; SEQ ID NO: 68/SEQ ID NO: 121; SEQ ID NO: 68/SEQ ID NO: 129; SEQ ID NO: 68/SEQ ID NO: 153; SEQ ID NO: 70/SEQ ID NO: 118; SEQ ID NO: 77/ SEQ ID NO: 121; SEQ ID NO: 77/SEQ ID NO: 122; SEQ ID NO: 77/SEQ ID NO: 126; SEQ ID NO: 77/ SEQ ID NO: 153; SEQ ID NO: 77/SEQ ID NO: 167; SEQ ID NO: 77/SEQ ID NO: 174; SEQ ID NO: 77/SEQ ID NO: 176; SEQ ID NO: 79/SEQ ID NO: 118; SEQ ID NO: 79/SEQ ID NO: 119; SEQ ID NO: 79/SEQ ID NO: 122; SEQ ID NO: 79/ SEQ ID NO: 124; SEQ ID NO: 79/SEQ ID NO: 153; SEQ ID NO: 79/SEQ ID NO: 167; SEQ ID NO: 79/SEQ ID NO: 174; SEQ ID NO: 81/SEQ ID NO: 118; SEQ ID NO: 81/ SEQ ID NO: 119; SEQ ID NO: 81/SEQ ID NO: 121; SEQ ID NO: 81/SEQ ID NO: 122; SEQ ID NO: 81/SEQ ID NO: 124; SEQ ID NO: 81/SEQ ID NO: 126; SEQ ID NO: 81/ SEQ ID NO: 129; SEQ ID NO: 81/SEQ ID NO: 153; SEQ ID NO: 81/SEQ ID NO: 165; SEQ ID NO: 81/SEQ ID NO: 169; SEQ ID NO: 87/SEQ ID NO: 171; SEQ ID NO: 84/ SEQ ID NO: 119; SEQ ID NO: 84/SEQ ID NO: 122; SEQ ID NO: 84/SEQ ID NO: 126; SEQ ID NO: 84/SEQ ID NO: 129; SEQ ID NO: 84/SEQ ID NO: 172; SEQ ID NO: 84/ SEQ ID NO: 174; SEQ ID NO: 86/SEQ ID NO: 174; SEQ ID NO: 86/SEQ ID NO: 176; SEQ ID NO: 89/SEQ ID NO: 153; SEQ ID NO: 89/SEQ ID NO: 174; SEQ ID NO: 93/ SEQ ID NO: 126; SEQ ID NO: 95/SEQ ID NO: 121; SEQ ID NO: 95/SEQ ID NO: 122; SEQ ID NO: 95/SEQ ID NO: 169; SEQ ID NO: 93/SEQ ID NO: 174; SEQ ID NO: 95/ SEQ ID NO: 176; SEQ ID NO: 100/SEQ ID NO: 119; SEQ ID NO: 100/SEQ ID NO: 121; SEQ ID NO: 100/SEQ ID NO: 126; SEQ ID NO: 100/SEQ ID NO: 153; SEQ ID NO: 100/ SEQ ID NO: 169; SEQ ID NO: 102/SEQ ID NO: 174; SEQ ID NO: 102/SEQ ID NO: 176; SEQ ID NO: 102/SEQ ID NO: 182; SEQ ID NO: 109/SEQ ID NO: 172; SEQ ID NO: 109/ SEQ ID NO: 176; SEQ ID NO: 113/SEQ ID NO: 121; SEQ ID NO: 113/SEQ ID NO: 174; SEQ ID NO: 113/SEQ ID NO: 176; SID ID NO: 115/SEQ ID NO: 119; and SEQ ID NO: 115/SEQ ID NO: 174, wherein the variable heavy chain and variable light chain pairs are listed together.

4. The collection according to claims 1, wherein said antibodies or functional fragments thereof comprise one or more complementarity determining regions comprising germline protein sequences.

5. The collection according to claim 4, wherein said antibodies or functional fragments thereof comprise FR1, CDR1, FR2, CDR2, and FR3 regions comprising germline protein sequences.

6. The collection according to claim 1, wherein said antibodies or functional fragments thereof comprise a FR4 region selected from the group consisting of: JH4, Jκ1, and Jλ2/3.

7. The collection according to claim 1, wherein said antibodies or functional fragments thereof comprise a diversified HCDR3 region.

8. The collection according to claim 1, wherein said antibodies or functional fragments thereof comprise a diversified LEDR3 region.

9. The collection according to claim 1, wherein the collection comprises $1 \times 10^4$ antibodies or functional fragments thereof.

10. The collection according to claim 1, wherein said fragments of said antibodies are selected from the group consisting of Fab, F(ab')2, Fab', Fv, and scFv.

11. The collection according to claim 3, wherein said collection of antibodies or functional fragments thereof comprises the frawework regions of at least ten different germline protein sequence pairs, wherein the at least ten different germline protein pairs are selected from the following variable heavy chain and variable light chain pairs: SEQ ID NO: 65/SEQ ID NO: 118; SEQ ID NO: 65/SEQ ID NO: 174; SEQ ID NO: 68/SEQ ID NO: 121; SEQ ID NO: 68/SEQ ID NO: 129; SEQ ID NO: 68/SEQ ID NO: 153; SEQ ID NO: 70/SEQ ID NO: 118; SEQ ID NO: 77/SEQ ID NO: 121; SEQ ID NO: 77/SEQ ID NO: 122; SEQ ID NO: 77/SEQ ID NO: 126; SEQ ID NO: 77/SEQ ID NO: 153; SEQ ID NO: 77/SEQ ID NO: 167; SEQ ID NO: 77/SEQ ID NO: 174; SEQ ID NO: 77/SEQ ID NO: 176; SEQ ID NO: 79/SEQ ID NO: 118; SEQ ID NO: 79/SEQ ID NO: 119; SEQ ID NO: 79/SEQ ID NO: 122; SEQ ID NO: 79/SEQ ID NO: 124; SEQ ID NO: 79/SEQ ID NO: 153; SEQ ID NO: 79/SEQ ID NO: 167; SEQ ID NO: 79/SEQ ID NO: 174; SEQ ID NO: 81/SEQ ID NO: 118; SEQ ID NO: 81/SEQ ID NO: 119; SEQ ID NO: 81/SEQ ID NO: 121; SEQ ID NO: 81/SEQ ID NO: 122; SEQ ID NO: 81/SEQ ID NO: 124; SEQ ID NO: 81/SEQ ID NO: 126; SEQ ID NO: 81/SEQ ID NO: 129; SEQ ID NO: 81/SEQ ID NO: 153; SEQ ID NO: 81/SEQ ID NO: 165; SEQ ID NO: 81/SEQ ID NO: 169; SEQ ID NO: 81/SEQ ID NO: 171; SEQ ID NO: 84/SEQ ID NO: 119; SEQ ID NO: 84/SEQ ID NO: 122; SEQ ID NO: 84/SEQ ID NO: 126; SEQ ID NO: 84/SEQ ID NO: 129; SEQ ID NO: 84/SEQ ID NO: 172; SEQ ID NO: 84/SEQ ID NO: 174; SEQ ID NO: 86/SEQ ID NO: 174; SEQ ID NO: 86/SEQ ID NO: 176; SEQ ID NO: 89/SEQ ID NO: 153; SEQ ID NO: 89/SEQ ID NO: 174; SEQ ID NO: 93/SEQ ID NO: 126; SEQ ID NO: 95/SEQ ID NO: 121; SEQ ID NO: 95/SEQ ID NO: 122; SEQ ID NO: 95/SEQ ID NO: 169; SEQ ID NO: 95/SEQ ID NO: 174; SEQ ID NO: 95/SEQ ID NO: 176; SEQ ID NO: 100/SEQ ID NO: 119; SEQ ID NO: 100/SEQ ID NO: 121; SEQ ID NO: 100/SEQ ID NO: 126; SEQ ID NO: 100/SEQ ID NO: 153; SEQ ID NO: 100/SEQ ID NO: 169; SEQ ID NO: 102/SEQ ID NO: 174; SEQ ID NO: 102/SEQ ID NO: 176; SEQ ID NO: 102/SEQ ID NO: 182; SEQ ID NO: 109/SEQ ID NO: 172; SEQ ID NO: 109/SEQ ID NO: 176; SEQ ID NO: 113/SEQ ID NO: 121; SEQ ID NO: 113/SEQ ID NO: 174; SEQ ID NO: 113/SEQ ID NO: 176; SEQ ID NO: 115/SEQ ID NO: 119; and SEQ ID NO: 115/SEQ ID NO: 174, wherein the variable heavy chain and variable light chain pairs are listed together.

12. The collection according to claim 11, wherein said collection of antibodies or functional fragments thereof comprises the frawework regions of at least fifteen different germline protein sequence pairs, wherein the at least fifteen different germline protein pairs are selected from the following variable heavy chain and variable light chain pairs: SEQ ID NO: 65/SEQ ID NO: 118; SEQ ID NO: 65/SEQ ID NO: 174; SEQ ID NO: 68/SEQ ID NO: 121; SEQ ID NO: 68/SEQ ID NO: 129; SEQ ID NO: 68/SEQ ID NO: 153; SEQ ID NO: 70/SEQ ID NO: 118; SEQ ID NO: 77/SEQ ID NO: 121; SEQ ID NO: 77/SEQ ID NO: 122; SEQ ID NO: 77/SEQ ID NO: 126; SEQ ID NO: 77/SEQ ID NO: 153; SEQ ID NO: 77/SEQ ID NO: 167; SEQ ID NO: 77/SEQ ID NO: 174; SEQ ID NO: 77/ SEQ ID NO: 176; SEQ ID NO: 79/SEQ ID NO: 118; SEQ ID NO: 79/SEQ ID NO: 119; SEQ ID NO: 79/SEQ ID NO: 122; SEQ ID NO: 79/SEQ ID NO: 124; SEQ ID NO: 79/ SEQ ID NO: 153; SEQ ID NO: 79/SEQ ID NO: 167; SEQ ID NO: 79/SEQ ID NO: 174; SEQ ID NO: 81/SEQ ID NO: 118; SEQ ID NO: 81/SEQ ID NO: 119; SEQ ID NO: 81/ SEQ ID NO: 121; SEQ ID NO: 81/SEQ ID NO: 122; SEQ ID NO: 81/SEQ ID NO: 124; SEQ ID NO: 81/SEQ ID NO: 126; SEQ ID NO: 81/SEQ ID NO: 129; SEQ ID NO: 81/ SEQ ID NO: 153; SEQ ID NO: 81/SEQ ID NO: 165; SEQ ID NO: 81/SEQ ID NO: 169; SEQ ID NO: 81/SEQ ID NO: 171; SEQ ID NO: 84/SEQ ID NO: 119; SEQ ID NO: 84/ SEQ ID NO: 122; SEQ ID NO: 84/SEQ ID NO: 126; SEQ ID NO: 84/SEQ ID NO: 129; SEQ ID NO: 84/SEQ ID NO: 172; SEQ ID NO: 84/SEQ ID NO: 174; SEQ ID NO: 86/ SEQ ID NO: 174; SEQ ID NO: 86/SEQ ID NO: 176; SEQ ID NO: 89/SEQ ID NO: 153; SEQ ID NO: 89/SEQ ID NO: 174; SEQ ID NO: 93/SEQ ID NO: 126; SEQ ID NO: 95/ SEQ ID NO: 121; SEQ ID NO: 95/SEQ ID NO: 122; SEQ ID NO: 95/SEQ ID NO: 169; SEQ ID NO: 95/SEQ ID NO: 174; SEQ ID NO: 95/SEQ ID NO: 176; SEQ ID NO: 100/ SEQ ID NO: 119; SEQ ID NO: 100/SEQ ID NO: 121; SEQ ID NO: 100/SEQ ID NO: 126; SEQ ID NO: 100/SEQ ID NO: 153; SEQ ID NO: 100/SEQ ID NO: 169; SEQ ID NO: 102 / SEQ ID NO: 174; SEQ ID NO: 102/SEQ ID NO: 176; SEQ ID NO: 102/SEQ ID NO: 182; SEQ ID NO: 109/SEQ ID NO: 172; SEQ ID NO: 109/SEQ ID NO: 176; SEQ ID NO: 113/ SEQ ID NO: 121; SEQ ID NO: 113/SEQ ID NO: 174; SEQ ID NO: 113/SEQ ID NO: 176; SEQ ID NO: 115/SEQ ID NO: 119; and SEQ ID NO: 115/SEQ ID NO: 174, wherein the variable heavy chain and variable light chain pairs are listed together.

13. The collection according to claim 12, wherein said collection of antibodies or functional fragments thereof comprises the frawework regions of at least twenty different germline protein sequence pairs, wherein the at least twenty different germline protein pairs are selected from the following variable heavy chain and variable light chain pairs: SEQ ID NO: 65/SEQ ID NO: 118; SEQ ID NO: 65/SEQ ID NO: 174; SEQ ID NO: 68/SEQ ID NO: 121; SEQ ID NO: 68/SEQ ID NO: 129; SEQ ID NO: 68/SEQ ID NO: 153; SEQ ID NO: 70/SEQ ID NO: 118; SEQ ID NO: 77/SEQ ID NO: 121; SEQ ID NO: 77/SEQ ID NO: 122; SEQ ID NO: 77/SEQ ID NO: 126; SEQ ID ND: 77/SEQ ID NO: 153; SEQ ID NO: 77/SEQ ID NO: 167; SEQ ID NO: 77/SEQ ID NO: 174; SEQ ID NO: 77/ SEQ ID NO: 176; SEQ ID NO: 79/SEQ ID NO: 118; SEQ ID NO: 79/SEQ ID NO: 119; SEQ ID NO: 79/SEQ ID NO: 122; SEQ ID NO: 79/SEQ ID NO: 124; SEQ ID NO: 79/ SEQ ID NO: 153; SEQ ID NO: 79/SEQ ID NO: 167; SEQ ID NO: 79/SEQ ID NO: 174; SEQ ID NO: 81/SEQ ID NO: 118; SEQ ID NO: 81/SEQ ID NO: 119; SEQ ID NO: 81/ SEQ ID NO: 121; SEQ ID NO: 81/SEQ ID NO: 122; SEQ ID NO: 81/SEQ ID NO: 124; SEQ ID NO: 81/SEQ ID NO: 126; SEQ ID NO: 81/SEQ ID NO: 129; SEQ ID NO: 81; SEQ ID NO: 153; SEQ ID NO: 81/SEQ ID NO: 165; SEQ ID NO: 81/SEQ ID NO: 169; SEQ ID NO: 81/SEQ ID NO: 171; SEQ ID NO: 84/SEQ ID NO: 119; SEQ ID NO: 84/ SEQ ID NO: 122; SEQ ID NO: 84/SEQ ID NO: 126; SEQ ID NO: 84/SEQ ID NO: 129; SEQ ID NO: 84/SEQ ID NO: 172; SEQ ID NO: 84/SEQ ID NO: 174; SEQ ID NO: 86/ SEQ ID NO: 174; SEQ ID NO: 86/SEQ ID NO: 176; SEQ ID NO: 89/SEQ ID NO: 153; SEQ ID NO: 89/SEQ ID NO: 174; SEQ ID NO: 93/SEQ ID NO: 126; SEQ ID NO: 95/ SEQ ID NO: 121; SEQ ID NO: 95/SEQ ID NO: 122; SEQ ID NO: 95/SEQ ID NO: 169; SEQ ID NO: 95/SEQ ID NO: 174; SEQ ID NO: 95/SEQ ID NO: 176; SEQ ID NO: 100/ SEQ ID NO: 119; SEQ ID NO: 100/SEQ ID NO: 121; SEQ ID NO: 100/SEQ ID NO: 126; SEQ ID NO: 100/SEQ ID NO: 153; SEQ ID NO: 100/SEQ ID NO: 169; SEQ ID NO: 102/ SEQ ID NO: 174; SEQ ID NO: 102/SEQ ID NO: 176; SEQ ID NO: 102/SEQ ID NO: 182; SEQ ID NO: 109/SEQ ID NO: 172; SEQ ID NO: 109/SEQ ID NO: 176; SEQ ID NO: 113/ SEQ ID NO: 121; SEQ ID NO: 113/SEQ ID NO: 174; SEQ ID NO: 113/SEQ ID NO: 176; SEQ ID NO: 115/SEQ ID NO: 119; and SEQ ID NO: 115/SEQ ID NO: 174, wherein the variable heavy chain and variable light chain pairs are listed together.

14. The collection according to claim 13, wherein said collection of antibodies or functional fragments thereof comprises the frawework regions of at least twenty five different germline protein sequence pairs, wherein the at least twenty five different germline protein pairs are selected from the following variable heavy chain and variable light chain pairs: SEQ ID NO: 65/SEQ ID NO: 118; SEQ ID NO: 65, SEQ ID NO: 174; SEQ ID NO: 68/SEQ ID NO: 121; SEQ ID NO: 68/SEQ ID NO: 129; SEQ ID NO: 68/SEQ ID NO: 153; SEQ ID NO: 70/SEQ ID NO: 118; SEQ ID NO: 77/SEQ ID NO: 121; SEQ ID NO: 77/SEQ ID NO: 122; SEQ ID NO: 77/SEQ ID NO: 126; SEQ ID NO: 77/SEQ ID NO: 153; SEQ ID NO: 77/SEQ ID NO: 167; SEQ ID NO: 77/SEQ ID NO: 174; SEQ ID NO: 77/SEQ ID NO: 176; SEQ ID NO: 79/SEQ ID NO: 118; SEQ ID NO: 79/SEQ ID NO: 119; SEQ ID NO: 79/SEQ ID NO: 122; SEQ ID NO: 79/SEQ ID NO: 124; SEQ ID NO: 79/SEQ ID NO: 153; SEQ ID NO: 79/SEQ ID NO: 167; SEQ ID NO: 79/SEQ ID NO: 174; SEQ ID NO: 81/SEQ ID NO: 118; SEQ ID NO: 81/SEQ ID NO: 119; SEQ ID NO: 81/SEQ ID NO: 121; SEQ ID NO: 81/SEQ ID NO: 122; SEQ ID NO: 81/SEQ ID NO: 124; SEQ ID NO: 81/SEQ ID NO: 126; SEQ ID NO: 81/SEQ ID NO: 129; SEQ ID NO: 81/SEQ ID NO: 153; SEQ ID NO: 81/SEQ ID NO: 165; SEQ ID NO: 81/SEQ ID NO: 169; SEQ ID NO: 81/SEQ ID NO: 171; SEQ ID NO: 84/SEQ ID NO: 119; SEQ ID NO: 84/SEQ ID NO: 122; SEQ ID NO: 84/SEQ ID NO: 126; SEQ ID NO: 84/SEQ ID NO: 129; SEQ ID NO: 84/SEQ ID NO: 172; SEQ ID NO: 84/SEQ ID NO: 174; SEQ ID NO: 86/SEQ ID NO: 174; SEQ ID NO: 86/SEQ ID NO: 176; SEQ ID NO: 89/SEQ ID NO: 153; SEQ ID NO: 89/SEQ ID NO: 174; SEQ ID NO: 93/SEQ ID NO: 126; SEQ ID NO: 95/SEQ ID NO: 121; SEQ ID NO: 95/SEQ ID NO: 122; SEQ ID NO: 95/SEQ ID NO: 169; SEQ ID NO: 95/SEQ ID NO: 174; SEQ ID NO: 95/SEQ ID NO: 176; SEQ ID NO: 100/SEQ ID NO: 119; SEQ ID NO: 100/SEQ ID NO: 121; SEQ ID NO: 100/SEQ ID NO: 126; SEQ ID NO: 100/SEQ ID NO: 153; SEQ ID NO: 100/SEQ ID NO: 169; SEQ ID NO: 102/SEQ ID NO: 174; SEQ ID NO: 102/SEQ ID NO: 176; SEQ ID NO: 102/SEQ NO: 182; SEQ ID NO: 109/SEQ ID NO: 172; SEQ ID NO: 109/SEQ ID NO: 176; SEQ ID NO: 113/SEQ ID NO: 121; SEQ ID NO: 113/SEQ ID NO: 174; SEQ ID NO: 113/SEQ ID NO: 176; SEQ ID NO: 115/SEQ ID NO: 119; and SEQ ID NO: 115/SEQ ID NO: 174, wherein the variable heavy chain and variable light chain pairs are listed together.

15. The collection according to claim 14, wherein said collection of antibodies or functional fragments thereof comprises the frawework regions of at least thirty different germline protein sequence pairs, wherein the at least thirty different germline protein pairs are selected from the following variable heavy chain and variable light chain pairs: SEQ ID NO: 65/SEQ ID NO: 118; SEQ ID NO: 65/SEQ ID NO: 174; SEQ ID NO: 68/SEQ ID NO: 121; SEQ ID NO: 68/SEQ ID NO: 129; SEQ ID NO: 68/SEQ ID NO: 153; SEQ ID NO: 70/SEQ ID NO: 118; SEQ ID NO: 77/SEQ ID NO: 121; SEQ ID NO: 77/SEQ ID NO: 122; SEQ ID NO: 77/SEQ ID NO: 126; SEQ ID NO: 77/SEQ ID NO: 153; SEQ ID NO: 77/ SEQ ID NO: 167; SEQ ID NO: 77/SEQ ID NO: 174; SEQ ID NO: 77/SEQ ID NO: 176; SEQ ID NO: 79/SEQ ID NO: 118; SEQ ID NO: 79/SEQ ID NO: 119; SEQ ID NO: 79/ SEQ ID NO: 122; SEQ ID NO: 79/SEQ ID NO: 124; SEQ ID NO: 79/SEQ ID NO: 153; SEQ ID NO: 79/SEQ ID NO: 167; SEQ ID NO: 79/SEQ ID NO: 174; SEQ ID NO: 81/ SEQ ID NO: 118; SEQ ID NO: 81/SEQ ID NO: 119; SEQ ID NO: 81/SEQ ID NO: 121; SEQ ID NO: 81/SEQ ID NO: 122; SEQ ID NO: 81/SEQ ID NO: 124; SEQ ID NO: 81/ SEQ ID NO: 126; SEQ ID NO: 81/SEQ ID NO: 129; SEQ ID NO: 81/SEQ ID NO: 153; SEQ ID NO: 81/SEQ ID NO: 165; SEQ ID NO: 81/SEQ ID NO: 169; SEQ ID NO: 81/ SEQ ID NO: 171; SEQ ID NO: 84/SEQ ID NO: 119; SEQ ID NO: 84/SEQ ID NO: 122; SEQ ID NO: 84/SEQ ID NO: 126; SEQ ID NO: 84/SEQ ID NO: 129; SEQ ID NO: 84/ SEQ ID NO: 172; SEQ ID NO: 84/SEQ ID NO: 174; SEQ ID NO: 86/SEQ ID NO: 174; SEQ ID NO: 86/SEQ ID NO: 176; SEQ ID NO: 89/SEQ ID NO: 153; SEQ ID NO: 89/ SEQ ID NO: 174; SEQ ID NO: 93/SEQ ID NO: 126; SEQ ID NO: 95/SEQ ID NO: 121; SEQ ID NO: 95/SEQ ID NO: 122; SEQ ID NO: 95/SEQ ID NO: 169; SEQ ID NO: 95/ SEQ ID NO: 174; SEQ ID NO: 95/SEQ ID NO: 176; SEQ ID NO: 100/SEQ ID NO: 119; SEQ ID NO: 100/SEQ ID NO: 121; SEQ ID NO: 100/SEQ ID NO: 126; SEQ ID NO: 100/ SEQ ID NO: 153; SEQ ID NO: 100/SEQ ID NO: 169; SEQ ID NO: 102/SEQ ID NO: 174; SEQ ID NO: 102/SEQ ID NO: 176; SEQ ID NO: 102/SEQ ID NO: 182; SEQ ID NO: 109/ SEQ ID NO: 172; SEQ ID NO: 109/SEQ ID NO: 176; SEQ ID NO: 113/SEQ ID NO: 121; SEQ ID NO: 113/SEQ ID NO: 174; SEQ ID NO: 113/SEQ ID NO: 176; SEQ ID NO: 115/ SEQ ID NO: 119; and SEQ ID NO: 115/SEQ ID NO: 174, wherein the variable heavy chain and variable light chain pairs are listed together.

16. The collection according to claim 15, wherein said collection of antibodies or functional fragments thereof comprises the frawework regions of at least thirty five different germline protein sequence pairs, wherein the at least thirty five different germline protein pairs are selected from the following variable heavy chain and variable light chain pairs: SEQ ID NO: 65/SEQ ID NO: 118; SEQ ID NO: 65/SEQ ID NO: 174; SEQ ID NO: 68/SEQ ID NO: 121; SEQ ID NO: 68/SEQ ID NO: 129; SEQ ID NO: 68/SEQ ID NO: 153; SEQ ID NO: 70/SEQ ID NO: 118; SEQ ID NO: 77/SEQ ID NO: 121; SEQ ID NO: 77/SEQ ID NO: 122; SEQ ID NO: 77/SEQ ID NO: 126; SEQ ID NO: 77/SEQ ID NO: 153; SEQ ID NO: 77/SEQ ID NO: 167; SEQ ID NO: 77/SEQ ID NO: 174; SEQ ID NO: 77/SEQ ID NO: 176; SEQ ID NO: 79/SEQ ID NO: 118; SEQ ID NO: 79/SEQ ID NO: 119; SEQ ID NO: 79/SEQ ID NO: 122; SEQ ID NO: 79/SEQ ID NO: 124; SEQ ID NO: 79/SEQ ID NO: 153; SEQ ID NO: 79/SEQ ID NO: 167; SEQ ID NO: 79/SEQ ID NO: 174; SEQ ID NO: 81/SEQ ID NO: 118; SEQ ID NO: 81/SEQ ID NO: 119; SEQ ID NO: 81/SEQ ID NO: 121; SEQ ID NO: 81/SEQ ID NO: 122; SEQ ID NO: 81/SEQ ID NO: 124; SEQ ID NO: 81/SEQ ID NO: 126; SEQ ID NO: 81/SEQ ID NO: 129; SEQ ID NO: 81/SEQ ID NO: 153; SEQ ID NO: 81/SEQ ID NO: 165; SEQ ID NO: 81/SEQ ID NO: 169; SEQ ID NO: 81/SEQ ID NO: 171; SEQ ID NO: 84/SEQ ID NO: 119; SEQ ID NO: 84/SEQ ID NO: 122; SEQ ID NO: 84/SEQ ID NO: 126; SEQ ID NO: 84/SEQ ID NO: 129; SEQ ID NO: 84/SEQ ID NO: 172; SEQ ID NO: 84/SEQ ID NO: 174; SEQ ID NO: 86/SEQ ID NO: 174; SEQ ID NO: 86/SEQ ID NO: 176; SEQ ID NO: 89/SEQ ID NO: 153; SEQ ID NO: 89/SEQ ID NO: 174; SEQ ID NO: 93/SEQ ID NO: 126; SEQ ID NO: 95/SEQ ID NO: 121; SEQ ID NO: 95/SEQ ID NO: 122; SEQ ID NO: 95/SEQ ID NO: 169; SEQ ID NO: 95/SEQ ID NO: 174; SEQ ID NO: 95/SEQ ID NO: 176; SEQ ID NO: 100/SEQ ID NO: 119; SEQ ID NO: 100/SEQ ID NO: 121; SEQ ID NO: 100/SEQ ID NO: 126; SEQ ID NO: 100/ SEQ ID NO: 153; SEQ ID NO: 100/SEQ ID NO: 169; SEQ ID NO: 102/SEQ ID NO: 174; SEQ ID NO: 102/SEQ ID NO: 176; SEQ ID NO: 102/SEQ ID NO: 182; SEQ ID NO: 109/ SEQ ID NO: 172; SEQ ID NO: 109/SEQ ID NO: 176; SEQ ID NO: 113/SEQ ID NO: 121; SEQ ID NO: 113/SEQ ID NO: 174; SEQ ID NO: 113/SEQ ID NO: 176; SEQ ID NO: 115/ SEQ ID NO: 119; and SEQ ID NO: 115/SEQ ID NO: 174, wherein the variable heavy chain and variable light chain pairs are listed together.

17. The collection according to claim 16, wherein said collection of antibodies or functional fragments thereof comprises the frawework regions of at least forty different germline protein sequence pairs, wherein the at least forty different germline protein pairs are selected from the following variable heavy chain and variable light chain pairs: SEQ ID NO: 65/SEQ ID NO: 118; SEQ ID NO: 65/SEQ ID NO: 174; SEQ ID NO: 68/SEQ ID NO: 121; SEQ ID NO: 68/SEQ ID NO: 129; SEQ ID NO: 68/SEQ ID NO: 153; SEQ ID NO: 70/SEQ ID NO: 118; SEQ ID NO: 77/SEQ ID NO: 121; SEQ ID NO: 77/SEQ ID NO: 122; SEQ ID NO: 77/SEQ ID NO: 126; SEQ ID NO: 77/SEQ ID NO: 153; SEQ ID NO: 77/ SEQ ID NO: 167; SEQ ID NO: 77/SEQ ID NO: 174; SEQ ID NO: 77/SEQ ID NO: 176; SEQ ID NO: 79/SEQ ID NO: 118; SEQ ID NO: 79/SEQ ID NO: 119; SEQ ID NO: 79/ SEQ ID NO: 122; SEQ ID NO: 79/SEQ ID NO: 124; SEQ ID NO: 79/SEQ ID NO: 153; SEQ ID NO: 79/SEQ ID NO: 167; SEQ ID NO: 79/SEQ ID NO: 174; SEQ ID NO: 81/ SEQ ID NO: 118; SEQ ID NO: 81/SEQ ID NO: 119; SEQ ID NO: 81/SEQ ID NO: 121; SEQ ID NO: 81/SEQ ID NO: 122; SEQ ID NO: 81/SEQ ID NO: 124; SEQ ID NO: 81/ SEQ ID NO: 126; SEQ ID NO: 81/SEQ ID NO: 129; SEQ ID NO: 81/SEQ ID NO: 153; SEQ ID NO: 81/SEQ ID NO: 165; SEQ ID NO: 81/SEQ ID NO: 169; SEQ ID NO: 81/ SEQ ID NO: 171; SEQ ID NO: 84/SEQ ID NO: 119; SEQ ID NO: 84/SEQ ID NO: 122; SEQ ID NO: 84/SEQ ID NO: 126; SEQ ID NO: 84/SEQ ID NO: 129; SEQ ID NO: 84/ SEQ ID NO: 172; SEQ ID NO: 84/SEQ ID NO: 174; SEQ ID NO: 86/SEQ ID NO: 174; SEQ ID NO: 86/SEQ ID NO: 176; SEQ ID NO: 89/SEQ ID NO: 153; SEQ ID NO: 89/ SEQ ID NO: 174; SEQ ID NO: 93/SEQ ID NO: 126; SEQ ID NO: 95/SEQ ID NO: 121; SEQ ID NO: 95/SEQ ID NO: 122; SEQ ID NO: 95/SEQ ID NO: 169; SEQ ID NO: 95/ SEQ ID NO: 174; SEQ ID NO: 95/SEQ ID NO: 176; SEQ ID NO: 100/ SEQ ID NO: 119; SEQ ID NO: 100/SEQ ID NO: 121; SEQ ID NO: 100/SEQ ID NO: 126; SEQ ID NO: 100/ SEQ ID NO: 153; SEQ ID NO: 100/SEQ ID NO: 169; SEQ ID NO: 102/ SEQ ID NO: 174; SEQ ID NO: 102/SEQ ID NO: 176; SEQ ID NO: 102/SEQ ID NO: 182; SEQ ID NO: 109/ SEQ ID NO: 172; SEQ ID NO: 109/SEQ ID NO: 176; SEQ ID NO: 113/ SEQ ID NO: 121; SEQ ID NO: 113/SEQ ID NO: 174; SEQ ID NO: 113/SEQ ID NO: 176; SEQ ID NO: 115/ SEQ ID NO: 119; and SEQ ID NO: 115/SEQ ID NO: 174, wherein the variable heavy chain and variable light chain pairs are listed together.

18. The collection according to claim 17, wherein said collection of antibodies or functional fragments thereof comprises the frawework regions of at least forty five different germline protein sequence pairs, wherein the at least forty five different germline protein pairs are selected from the following variable heavy chain and variable light chain pairs: SEQ ID NO: 65/SEQ ID NO: 118; SEQ ID NO: 65/SEQ ID NO: 174; SEQ ID NO: 68/SEQ ID NO: 121; SEQ ID NO: 68/SEQ ID NO: 129; SEQ ID NO: 68/SEQ ID NO: 153; SEQ ID NO: 70/SEQ ID NO: 118; SEQ ID NO: 77/SEQ ID NO: 121; SEQ ID NO: 77/SEQ ID NO: 122; SEQ ID NO: 77/SEQ ID NO: 126; SEQ ID NO: 77/SEQ ID NO: 153; SEQ ID NO: 77/SEQ ID NO: 167; SEQ ID NO: 77/SEQ ID NO: 174; SEQ ID NO: 77/SEQ ID NO: 176; SEQ ID NO: 79/SEQ ID NO: 118; SEQ ID NO: 79/SEQ ID NO: 119; SEQ ID NO: 79/SEQ ID NO: 122; SEQ ID NO: 79/SEQ ID NO: 124; SEQ ID NO: 79/SEQ ID NO: 153; SEQ ID NO: 79/SEQ ID NO: 167; SEQ ID NO: 79/SEQ ID NO: 174; SEQ ID NO: 81/SEQ ID NO: 118; SEQ ID NO: 81/SEQ ID NO: 119; SEQ ID NO: 81/SEQ ID NO: 121; SEQ ID NO: 81/SEQ ID NO: 122; SEQ ID NO: 81/SEQ ID NO: 124; SEQ ID NO: 81/ SEQ ID NO: 126; SEQ ID NO: 81/SEQ ID NO: 129; SEQ ID NO: 81/SEQ ID NO: 153; SEQ ID NO: 81/SEQ ID NO: 165; SEQ ID NO: 81/SEQ ID NO: 169; SEQ ID NO: 81/ SEQ ID NO: 171; SEQ ID NO: 84/SEQ ID NO: 119; SEQ ID NO: 84/SEQ ID NO: 122; SEQ ID NO: 84/SEQ ID NO: 126; SEQ ID NO: 84/SEQ ID NO: 129; SEQ ID NO: 84/ SEQ ID NO: 172; SEQ ID NO: 84/SEQ ID NO: 174; SEQ ID NO: 86/SEQ ID NO: 174; SEQ ID NO: 86/SEQ ID NO: 176; SEQ ID NO: 89/SEQ ID NO: 153; SEQ ID NO: 89/ SEQ ID NO: 174; SEQ ID NO: 93)/SEQ ID NO: 126; SEQ ID NO: 95/SEQ ID NO: 121; SEQ ID NO: 95/SEQ ID NO: 122; SEQ ID NO: 95/SEQ ID NO: 169; SEQ ID NO: 95/ SEQ ID NO: 174; SEQ ID NO: 95)/SEQ ID NO: 176; SEQ ID NO: 100/ SEQ ID NO: 119; SEQ ID NO: 100/SEQ ID NO: 121; SEQ ID NO: 100/SEQ ID NO: 126; SEQ ID NO: 100/ SEQ ID NO: 153; SEQ ID NO: 100/SEQ ID NO: 169; SEQ ID NO: 102/ SEQ ID NO: 174; SEQ ID NO: 102/SEQ ID NO: 176; SEQ ID NO: 102/SEQ ID NO: 182; SEQ ID NO: 109/ SEQ ID NO: 172; SEQ ID NO: 109/SEQ ID NO: 176; SEQ ID NO: 113/ SEQ ID NO: 121; SEQ ID NO: 113/SEQ ID NO: 174; SEQ ID NO: 113/SEQ ID NO: 176; SEQ ID NO: 115/ SEQ ID NO: 119; and SEQ ID NO: 115/SEQ ID NO: 174, wherein the variable heavy chain and variable light chain pairs are listed together.

19. The collection according to claim 18, wherein said collection of antibodies or functional fragments thereof comprises the frawework regions of at least fifty different germline protein sequence pairs, wherein the at least fifty different germline protein pairs are selected from the following variable heavy chain and variable light chain pairs SEQ ID NO: 65/SEQ ID NO: 118; SEQ ID NO: 65/SEQ ID NO: 174; SEQ ID NO: 68/SEQ ID NO: 121; SEQ ID NO: 68/SEQ ID NO: 129; SEQ ID NO: 68/SEQ ID NO: 153; SEQ ID NO: 70/SEQ ID NO: 118; SEQ ID NO: 77/SEQ ID NO: 121; SEQ ID NO: 77/SEQ ID NO: 122; SEQ ID NO: 77/SEQ ID NO: 126; SEQ ID NO: 77/SEQ ID NO: 153; SEQ ID NO: 77/ SEQ ID NO: 167; SEQ ID NO: 77/SEQ ID NO: 174; SEQ ID NO: 77/SEQ ID NO: 176; SEQ ID NO: 79/SEQ ID NO: 118; SEQ ID NO: 79/SEQ ID NO: 119; SEQ ID NO: 79/ SEQ ID NO: 122; SEQ ID NO: 79/SEQ ID NO: 124; SEQ ID NO: 79/SEQ ID NO: 153; SEQ ID NO: 79/SEQ ID NO: 167; SEQ ID NO: 79/SEQ ID NO: 174; SEQ ID NO: 81/ SEQ ID NO: 118; SEQ ID NO: 81/SEQ ID NO: 119; SEQ ID NO: 81/SEQ ID NO: 121; SEQ ID NO: 81/SEQ ID NO: 122; SEQ ID NO: 81/SEQ ID NO: 124; SEQ ID NO: 81/ SEQ ID NO: 126; SEQ ID NO: 81/SEQ ID NO: 129; SEQ ID NO: 81/SEQ ID NO: 153; SEQ ID NO: 81/SEQ ID NO: 165; SEQ ID NO: 81/SEQ ID NO: 169; SEQ ID NO: 81/ SEQ ID NO: 171; SEQ ID NO: 84/SEQ ID NO: 119; SEQ ID NO: 84/SEQ ID NO: 122; SEQ ID NO: 84/SEQ ID NO: 126; SEQ ID NO: 84/SEQ ID NO: 129; SEQ ID NO: 84/ SEQ ID NO: 172; SEQ ID NO: 84/SEQ ID NO: 174; SEQ ID NO: 86/SEQ ID NO: 174; SEQ ID NO: 86/SEQ ID NO: 176; SEQ ID NO: 89/SEQ ID NO: 153; SEQ ID NO: 89/ SEQ ID NO: 174; SEQ ID NO: 93)/SEQ ID NO: 126; SEQ ID NO: 95/SEQ ID NO: 121; SEQ ID NO: 95/SEQ ID NO: 122; SEQ ID NO: 95/SEQ ID NO: 169; SEQ ID NO: 95/ SEQ ID NO: 174; SEQ ID NO: 95)/SEQ ID NO: 176; SEQ ID NO: 100/ SEQ ID NO: 119; SEQ ID NO: 100/SEQ ID NO: 121; SEQ ID NO: 100/SEQ ID NO: 126; SEQ ID NO: 100/ SEQ ID NO: 153; SEQ ID NO: 100/SEQ ID NO: 169; SEQ ID NO: 102/ SEQ ID NO: 174; SEQ ID NO: 102/SEQ ID NO: 176; SEQ ID NO: 102/SEQ ID NO: 182; SEQ ID NO: 109/ SEQ ID NO: 172; SEQ ID NO: 109/SEQ ID NO: 176; SEQ ID NO: 113/ SEQ ID NO: 121; SEQ ID NO: 113/SEQ ID NO: 174; SEQ ID NO: 113/SEQ ID NO: 176; SEQ ID NO: 115/ SEQ ID NO: 119; and SEQ ID NO: 115/SEQ ID NO: 174, wherein the variable heavy chain and variable light chain pairs are listed together.

\* \* \* \* \*